US011752155B2

(12) United States Patent
Shapiro et al.

(10) Patent No.: US 11,752,155 B2
(45) **Date of Patent: *Sep. 12, 2023**

(54) TREATMENT OF AUTISM SPECTRUM DISORDERS, OBSESSIVE-COMPULSIVE DISORDER AND ANXIETY DISORDERS

(71) Applicant: Rugen Holdings (Cayman) Limited, Grand Cayman (KY)

(72) Inventors: Gideon Shapiro, Gainesville, FL (US); Dorothy G. Flood, West Chester, PA (US)

(73) Assignee: Rugen Holdings (Cayman) Limited, Grand Cayman (KY)

( * ) Notice: Subject to any disclaimer, the term of this patent is extended or adjusted under 35 U.S.C. 154(b) by 240 days.

This patent is subject to a terminal disclaimer.

(21) Appl. No.: 17/204,648

(22) Filed: Mar. 17, 2021

(65) Prior Publication Data

US 2021/0220365 A1 Jul. 22, 2021

Related U.S. Application Data

(63) Continuation of application No. 16/462,832, filed as application No. PCT/US2017/062726 on Nov. 21, 2017, now Pat. No. 11,000,526.
(Continued)

(51) Int. Cl.

| | |
|---|---|
| ***A61K 31/519*** | (2006.01) |
| ***A61P 25/20*** | (2006.01) |
| ***A61P 25/22*** | (2006.01) |
| ***A61K 9/00*** | (2006.01) |
| ***A61K 31/444*** | (2006.01) |

(Continued)

(52) U.S. Cl.
CPC .......... *A61K 31/519* (2013.01); *A61K 9/0019* (2013.01); *A61K 31/444* (2013.01); *A61K 31/497* (2013.01); *A61K 31/4985* (2013.01); *A61K 31/501* (2013.01); *A61K 31/506* (2013.01); *A61K 45/06* (2013.01);
(Continued)

(58) Field of Classification Search
CPC .............. A61K 31/444; A61K 31/4545; A61K 31/497; A61K 31/4985; A61K 31/501; A61K 31/506; A61K 31/519; A61K 45/06; A61K 9/0019; A61P 25/20; A61P 25/22
See application file for complete search history.

(56) References Cited

U.S. PATENT DOCUMENTS 6,008,233 A 12/1999 Andino et al.
7,592,360 B2 9/2009 Liverton et al.
(Continued)

FOREIGN PATENT DOCUMENTS

CN 1503793 A 6/2004
CN 1798744 A 7/2006
(Continued)

OTHER PUBLICATIONS

U.S. Appl. No. 15/513,112, Liu et al.
(Continued)

*Primary Examiner* — Savitha M Rao
(74) *Attorney, Agent, or Firm* — Choate, Hall & Stewart LLP; Brenda Herschbach Jarrell; Kristen C. Buteau

(57) ABSTRACT

Disclosed are methods for treating NMDA receptor-mediated disorders by administering certain NR2B subunit-selective NMDA (N methyl-D aspartate) antagonists. NMDA receptor-mediated disorders include autism spectrum disorders, obsessive-compulsive disorder and anxiety disorders.

23 Claims, 9 Drawing Sheets

Related U.S. Application Data

(60) Provisional application No. 62/425,269, filed on Nov. 22, 2016.

(51) Int. Cl.

| | |
|---|---|
| ***A61K 31/497*** | (2006.01) |
| ***A61K 31/501*** | (2006.01) |
| ***A61K 31/506*** | (2006.01) |
| ***A61K 45/06*** | (2006.01) |
| ***A61K 31/4985*** | (2006.01) |
| ***A61K 31/4545*** | (2006.01) |

(52) U.S. Cl.
CPC ............... *A61P 25/20* (2018.01); *A61P 25/22* (2018.01); *A61K 31/4545* (2013.01)

(56) References Cited

U.S. PATENT DOCUMENTS

| | | | |
|---|---|---|---|
| 9,387,212 | B2 | 7/2016 | Michel et al. |
| 9,567,341 | B2 | 2/2017 | Shapiro |
| 9,968,610 | B2 | 5/2018 | Shapiro |
| 10,030,026 | B2 | 7/2018 | Shapiro |
| 10,221,182 | B2 | 3/2019 | Shapiro |
| 10,294,230 | B2 | 5/2019 | Shapiro |
| 10,420,768 | B2 | 9/2019 | Shapiro |
| 10,584,127 | B2 | 3/2020 | Shapiro |
| 11,000,526 | B2 | 5/2021 | Shapiro et al. |
| 11,136,328 | B2 | 10/2021 | Shapiro |
| 2002/0165241 | A1 | 11/2002 | Claiborne et al. |
| 2003/0018038 | A1 | 1/2003 | Thompson et al. |
| 2007/0149568 | A1 | 6/2007 | Liverton et al. |
| 2007/0293515 | A1 | 12/2007 | Layton et al. |
| 2008/0086006 | A1 | 4/2008 | Nelson |
| 2009/0062261 | A1 | 3/2009 | Masui et al. |
| 2010/0105650 | A1 | 4/2010 | Plettenburg et al. |
| 2011/0172415 | A1 | 7/2011 | Masui et al. |
| 2011/0280808 | A1 | 11/2011 | Kroth et al. |
| 2013/0096115 | A1 | 4/2013 | Lichter et al. |
| 2013/0225575 | A1 | 8/2013 | Lichter et al. |
| 2013/0231348 | A1 | 9/2013 | Campbell et al. |
| 2014/0018348 | A1 | 1/2014 | Javitt |
| 2014/0336185 | A1 | 11/2014 | Boehm et al. |
| 2016/0075713 | A1 | 3/2016 | Shapiro |
| 2017/0101412 | A1 | 4/2017 | Shapiro |
| 2017/0209449 | A1 | 7/2017 | Shapiro |
| 2018/0030055 | A1 | 2/2018 | Shapiro |
| 2018/0170935 | A1 | 6/2018 | Shapiro |
| 2018/0271869 | A1 | 9/2018 | Liu et al. |
| 2018/0303834 | A1 | 10/2018 | Shapiro |
| 2018/0346476 | A1 | 12/2018 | Shapiro |
| 2019/0298725 | A1 | 10/2019 | Shapiro et al. |
| 2020/0299300 | A1 | 9/2020 | Shapiro |
| 2022/0024937 | A1 | 1/2022 | Shapiro |

FOREIGN PATENT DOCUMENTS

| | | | |
|---|---|---|---|
| CN | 101163482 | A | 4/2008 |
| EP | 2933247 | A1 | 10/2015 |
| EP | 3194403 | A1 | 7/2017 |
| JP | 2006-526650 | A | 11/2006 |
| JP | 2010-502704 | A | 1/2010 |
| RU | 2271361 | C2 | 3/2006 |
| RU | 2499598 | C2 | 11/2013 |
| TW | 200510378 | A | 3/2005 |
| WO | WO-2002/034718 | A1 | 5/2002 |
| WO | WO-02068409 | A1 | 9/2002 |
| WO | WO-2004/108705 | A1 | 12/2004 |
| WO | WO-2005/102390 | A2 | 11/2005 |
| WO | WO-2006/113471 | A2 | 10/2006 |
| WO | WO-2007/061868 | A2 | 5/2007 |
| WO | WO-2008/030391 | A2 | 3/2008 |
| WO | WO-2009/118187 | A1 | 10/2009 |
| WO | WO-2010/015637 | A1 | 2/2010 |
| WO | WO-2012/123312 | A1 | 9/2012 |
| WO | WO-2013/156614 | A1 | 10/2013 |
| WO | WO-2014/092100 | A1 | 6/2014 |
| WO | WO-2014/120800 | A1 | 8/2014 |
| WO | WO-2015/069593 | A1 | 5/2015 |
| WO | WO-2015/171770 | A1 | 11/2015 |
| WO | WO-2015/187845 | A1 | 12/2015 |
| WO | WO-2016/044323 | A1 | 3/2016 |
| WO | WO-2016/049048 | A1 | 3/2016 |
| WO | WO-2016/100349 | A2 | 6/2016 |
| WO | WO-2016/126869 | A1 | 8/2016 |
| WO | WO-2016/196513 | A1 | 12/2016 |
| WO | WO-2018/098128 | A1 | 5/2018 |

OTHER PUBLICATIONS

U.S. Appl. No. 15/961,553, Shapiro.

U.S. Appl. No. 16/100,596, Shapiro.

Addy, C. et al., Single-dose administration of MK-0657, an NR2B-selective NMDA antagonist, does not result in clinically meaningful improvement in motor function in patients with moderate Parkinson's disease, J Clin Pharmacol, 49(7):856-864 (2009).

Ayata, C. et al., Suppression of cortical spreading depression in migraine prophylaxis, Ann Neurol, 59(4):652-661 (2006).

Bandyopadhyay, S. and Hablitz, J., NR2B antagonists restrict spatiotemporal spread of activity in a rat model of cortical dysplasia, Epilepsy Research, 72:127-139 (2006).

Barton, M. et al., Pharmacological characterization of the 6 Hz psychomotor seizure model of partial epilepsy, Epilepsy Res, 47(3):217-227 (2001).

Bausch, S. et al., Inverse relationship between seizure expression and extrasynaptic NMDAR function following chronic NMDAR inhibition, Epilepsia, 51(Suppl 3):102-105 (2010).

Beinat, C. et al., Insights into Structure-Activity Relationships and CNS Therapeutic Applications of NR2B Selective Antagonists, Current Medicinal Chemistry, 17:4166-4190 (2010).

Berge, S. et al., Pharmaceutical salts, J Pharm Sci, 66(1):1-19 (1977).

Bezzard et al., Neuroscience Disease Models, Neuroscience, 211:1 (2012).

Bogdanova, O. et al., Factors influencing behavior in the forced swim test, Physiol Behav, 118:227-239 (2013).

Borza, I. and Domány, G., NR2B selective NMDA antagonists: the evolution of the ifenprodil-type pharmacophore, Curr Top Med Chem, 6(7):687-695 (2006).

Boyce-Rustay, J.M. and Holmes, A., Functional Roles of NMDA Receptor NR2A and NR2B Subunits in the Acute Intoxicating Effects of Ethanol in Mice, Synapse, 56:222-225 (2005).

Brown, D. et al., 2,6-Disubstituted pyrazines and related analogs as NR2B site antagonists of the NMDA receptor with anti-depressant activity, Bioorg Med Chem Lett, 21(11):3399-3403 (2011).

Brown, W. et al., Comparative assay of an antiepileptic drugs by psychomotor seizure test and minimal electroshock threshold test, J Pharmacol Exp Ther, 107(3):273-283 (1953).

Can, A. et al., The mouse forced swim test, J Vis Exp, (59):e3638 (2012).

Castel-Branco, M. et al., The maximal electroshock seizure (MES) model in the preclinical assessment of potential new antiepileptic drugs, Methods Find Exp Clin Pharmacol, 31(2):101-106 (2009).

Chen, M. et al., Differential Roles of NMDA Receptor Subtypes in Ischemic Neuronal Cell Death and Ischemic Tolerance, Stroke, 39:3042-3048 (2008).

Chenard, B. et al., (1S,2S)-1-(4-hydroxyphenyl)-2-(4-hydroxy-4-phenylpiperidino)-1-propanol: a potent new neuroprotectant which blocks N-methyl-D-aspartate responses, J Med Chem, 38(16):3138-3145 (1995).

Chermat and Simon, Fiche Technique, Journal of Pharmacology, 6:494-496 (1975).

Claiborne, C. et al., Orally efficacious NR2B-selective NMDA receptor antagonists, Bioorg Med Chem Lett, 13(4):697-700 (2003).

Cull-Candy, S. et al., NMDA receptor diversity in the cerebellum: identification of subunits contributing to functional receptors, Neuropharmacology, 37(10-11):1369-1380 (1998).

(56) References Cited

OTHER PUBLICATIONS

Curran, H. and Morgan, C., Cognitive, dissociative and psychotogenic effects of ketamine in recreational users on the night of drug use and 3 days later, Addiction, 95(4):575-590 (2000).
Curtis, N. et al., Novel N1-(benzyl)cinnamamidine derived NR2B subtype-selective NMDA receptor antagonists, Bioorg Med Chem Lett, 13(4):693-696 (2003).
Dalby, N. and Nielsen, E., Comparison of the preclinical anticonvulsant profiles of tiagabine, lamotrigine, gabapentin and vigabatrin, Epilepsy Res, 28(1):63-72 (1997).
Damasio, Antonio R., Alzheimer's Disease and Related Dementias, Cecil Textbook of Medicine, 20th Edition, 2:1992-1996 (1996).
Dubuisson, D. and Dennis, S., The formalin test: a quantitative study of the analgesic effects of morphine, meperidine, and brain stem stimulation in rats and cats, Pain, 4(2):161-74 (1977).
Duman, C., Models of depression, Vitam Horm, 82:1-21 (2010).
Esneault, E. et al., Evaluation of pro-convulsant risk in the rat: spontaneous and provoked convulsions, J Pharmacol Toxicol Methods, 72:59-66 (2015).
Fischer, G. et al., Ro 25-6981, a highly potent and selective blocker of N-methyl-D-aspartate receptors containing the NR2B subunit, Characterization in vitro, J Pharmacol Exp Ther, 283(3):1285-1292 (1997).
Fisher, R. et al., Epileptic seizures and epilepsy: definitions proposed by the International League Against Epilepsy (ILAE) and the International Bureau for Epilepsy (IBE), Epilepsia, 46(4):470-472 (2005).
Garner, R. et al., Preclinical pharmacology and pharmacokinetics of CERC-301, a GluN2B-selective N-methyl-D-aspartate receptor antagonist, Pharmacology Research & Perspectives, 3(6):e00198 (2015).
Ghasemi, M. and Schachter, S.C., The NMDA receptor complex as a therapeutic target in epilepsy: a review, Epilepsy & Behavior, 22:617-640 (2011).
Giannini, A. James et al., Phencyclidine and the Dissociatives, Psychiatric Medicine, 3:197-217 (1985).
Haas, D. and Harper, D., Ketamine: a review of its pharmacologic properties and use in ambulatory anesthesia, Anesth Prog, 39(3):61-68 (1992).
Hancox, J. and James, A., Refining insights into high-affinity drug binding to the human ether-à-go-go-related gene potassium channel, Mol Pharmacol, 73(6):1592-1595 (2008).
Hansen, K. et al., Pharmacological characterization of ligands at recombinant NMDA receptor subtypes by electrophysiological recordings and intracellular calcium measurements, Comb Chem High Throughput Screen, 11(4):304-315 (2008).
Hardy, J. et al., Randomized, double-blind, placebo-controlled study to assess the efficacy and toxicity of subcutaneous ketamine in the management of cancer pain, J Clin Oncol, 30(29):3611-3617 (2012).
Hooft, R. et al., Determination of absolute structure using Bayesian statistics on Bijvoet differences, J Appl Crystallogr, 41(Pt 1):96-103 (2008).
Ibrahim, L. et al., Randomized, placebo-controlled, crossover pilot trial of the oral selective NR2B antagonist MK-0657 in patients with treatment-resistant major depressive disorder, J Clin Psychopharmacol, 32(4):551-557 (2012).
International Search Report for PCT/US2015/034009, 3 pages (dated Sep. 30, 2015).
International Search Report for PCT/US2015/050267, 4 pages (dated Dec. 9, 2015).
International Search Report for PCT/US2015/051488, 4 pages (dated Jan. 27, 2016).
International Search Report for PCT/US2015/65829 (Bicyclic Azaheterocyclic Compounds as NR2B NMDA Receptor Antagonists, filed Dec. 15, 2015), issued by ISA/US, 3 pages (dated Feb. 25, 2016).
International Search Report for PCT/US2016/16442 (3,3-Difluoro-Piperidine Derivatives as NR2B NMDA Receptor Antagonists, filed Feb. 3, 2016), issued by ISA/US, 3 pages (dated Apr. 8, 2016).
International Search Report for PCT/US2016/35098, 3 pages (dated Aug. 31, 2016).
International Search Report for PCT/US2017/062726 (Treatment of Autism Spectrum Disorders, Obsessive-Compulsive Disorder and Anxiety Disorders, filed Nov. 21, 2017), issued by ISA/EP, 7 pages (dated Apr. 3, 2018).
Jimenez-Sanchez, L. et al., The Role of GluN2A and GluN2B Subunits on the Effect of NMDA Receptor Antagonists in Modeling Schizophrenia and Treating Refractory Depression, Neuropsychopharmacology, 39:2673-2680 (2014).
Jordan, V. Craig, Tamoxifen: A Most Unlikely Pioneering Medicine, Nature Reviews: Drug Discovery, 2(3):205-213 (2003).
Kao, J. et al., NR2B subunit of NMDA receptor at nucleus accumbens is involved in morphine rewarding effect by siRNA study, Drug and Alcohol Dependence, 118:366-374 (2011).
Katalinic, N. et al., Ketamine as a new treatment for depression: a review of its efficacy and adverse effects, Aust N Z J Psychiatry, 47(8):710-727 (2013).
Kawai, M. et al., Discovery of novel and orally active NR2B-selective N-methyl-D-aspartate (NMDA) antagonists, pyridinol derivatives with reduced HERG binding affinity, Bioorg Med Chem Lett, 17(20):5533-5536 (2007).
Khisti, R. et al., Haloperidol-induced catalepsy: a model for screening antidepressants effective in treatment of depression with Parkinson's disease, Indian J Exp Biol, 35(12):1297-1301 (1997).
Kiss, L. et al., In vitro characterization of novel NR2B selective NMDA receptor antagonists, Neurochem Int, 46(6):453-464 (2005).
Kong, M. et al., NR2B antagonist CP-101,606 inhibits NR2B phosphorylation at tyrosine-1472 and its interactions with Fyn in levodopa-induced dyskinesia rat model, Behavioural Brain Research, 282:46-53 (2015).
Konitsiotis, S. et al., Effects of N-methyl-D-aspartate receptor antagonism on neuroleptic-indeuced orofacial dyskinesias, Physchopharmacology, 185:369-377 (2006).
Koudih, R. et al., Synthesis and in vitro characterization of trans- and cis-[(18)F]-4-methylbenzyl 4-[(pyrimidin-2-ylamino)methyl]-3-fluoropiperidine-1-carboxylates as new potential PET radiotracer candidates for the NR2B subtype N-methyl-D-aspartate receptor, Eur J Med Chem, 53:408-415 (2012).
Krall, R. et al., Antiepileptic drug development: II. Anticonvulsant drug screening, Epilepsia, 19(4):409-428 (1978).
Krska, S. et al., Enantioselective synthesis of a chiral fluoropiperidine via asymmetric hydrogenation of a vinyl fluoride, Tetrahedron, 65:8987-8994 (2009).
Layton, M. et al., Recent advances in the development of NR2B subtype-selective NMDA receptor antagonists, Curr Top Med Chem, 6(7):697-709 (2006).
Layton, M.E. et al., Discovery of 3-Substituted Aminocyclopentances as Potent and Orally Bioavailable NR2B Subtype-Selective NMDA Antagonists, ACS Chem. Neurosci., 2:352-362 (2011).
Lemke, J. et al., GRIN2B Mutations in West Syndrome and Intellectual Disability with Focal Epilepsy, Ann Neurol, 75:147-154 (2014).
Li, L. et al., Role of NR2B-type NMDA receptors in selective neurodegeneration in Huntington disease, Neurobiology of Aging, 24:1113-1121 (2003).
Lima-Ojeda, J.M. et al., Pharmacological blockade of GluN2B-containing NMDA receptors induces antidepressant-like effects lacking psychotomimetic action and neurotoxicity in the perinatal and adult rodent brain, Progress in Neuro-Psychopharmacology & Biological Psychiatry, 45:28-33 (2013).
Liverton, N. et al., Identification and characterization of 4-methylbenzyl 4-[(pyrimidin-2-ylamino)methyl]piperidine-1-carboxylate, an orally bioavailable, brain penetrant NR2B selective N-methyl-D-aspartate receptor antagonist, J Med Chem, 50(4):807-819 (2007).
Loscher, Wolfgang, Critical review of current animal models of seizures and epilepsy used in the discovery and development of new antiepileptic drugs, Seizure, 20(5):359-368 (2011).
Lucki, I. et al., Sensitivity to the effects of pharmacologically selective antidepressants in different strains of mice, Psychopharmacology (Berl), 155(3):315-322 (2001).
Mares, P. and Mikulecka, A., Different effects of two N-methyl-D-aspartate receptor antagonists on seizures, spontaneous behavior, and motor performance in immature rats, Epilepsy & Behavior, 14:32-39 (2009).

(56) References Cited

OTHER PUBLICATIONS

Mares, P., Age and activation determines the anticonvulsant effect in ifenprodil in rats, Naunyn-Schmiedeberg's Arch Pharmacol, 387:753-761 (2014).
Mathews, D. and Zarate, C., Current status of ketamine and related compounds for depression, J Clin Psychiatry, 74(5):516-517 (2013).
Menniti, F. et al., CP-101,606: An NR2B-Selective NMDA Receptor Antagonist, CNS Drug Reviews, 4(4):307-322 (1998).
Menniti, F.S. et al., CP-101,606, an NR2B subunit selective NMDA receptor antagonist, inhibits NMDA and injury induced c-fos expression and corticol spreading depression in rodents, Neurpharmacology, 39:1147-1155 (2000).
Mony, L. et al., Allosteric modulators of NR2B-containing NMDA receptors: molecular mechanisms and therapeutic potential, Br J Pharmacol, 157(8):1301-1317 (2009).
Murrough, J. et al., Antidepressant efficacy of ketamine in treatment-resistant major depression: a two-site randomized controlled trial, Am J Psychiatry, 170(10):1134-1142 (2013).
Naspolini, A.P. et al., Traxoprodil decreases pentylenetetrazol-induced seizures, Epilepsy Research, 100:12-19 (2012).
Neligan, et al., The epidemiology ofthe epilepsies, Handb Clin Neurol, 107:113-133 (2012).
Nielsen, D. et al., Antidepressant-like activity of corticotropin-releasing factor type-1 receptor antagonists in mice, European Journal of Pharmacology, 499:135-146 (2004).
Niesters, M. et al., Ketamine for chronic pain: risks and benefits, British Journal of Clinical Pharmacology, 77(2):357-367 (2013).
Noppers, I. et al., Drug-induced liver injury following a repeated course of ketamine treatment for chronic pain in CRPS type 1 patients: a report of 3 cases, Pain, 152(9):2173-2178 (2011).
Nutt, J.G. et al., Effects of NR2B Selective NMDA Glutamate Antagonist, CP-101,606, on Dyskinesia and Parkinsonism, Movement Disorders, 23(13):1860-1866 (2008).
Paoletti, P. et al., NMDA receptor subunit diversity: impact on receptor properties, synaptic plasticity and disease, Nat Rev Neurosci, 14(6):383-400 (2013).
Patani, G. and Lavoie, E., Bioisosterism: A Rational Approach in Drug Design, Chem. Rev., 96:3147-3176 (1996).
Paterson, B., et al., A randomized, double-blind, placebo-controlled, parallel-group, three-part safety, pharmacokinetic, and pharmacodynamic study of CERC-301 in healthy subjects, Presented at the 2015 National Network of Depression Centers Annual Conference, Nov. 2015, Ann Arbor, MI, USA, Poster (2015).
Paterson, B., et al., A Randomized, double-blind, placebo-controlled, sequential parallel study of CERC-301 in the adjunctive treatment of subjects with severe depression and recent active suicidal ideation despite antidepressant treatment, Presented at the 2015 National Network of Depression Centers Annual Conference, Nov. 2015, Ann Arbor, MI, USA, Poster (2015).
Peeters, M. et al., Effects of Pan- and Subtype-Selective N-Methyl-D-aspartate Receptor Antagonists on Cortical Spreading Depression in the Rat: Therapeutic Potential for Migraine, The Journal of Pharmacology and Experimental Therapeutics, 321(2):564-572 (2007).
Porsolt, et al., Behavioral Despair in Rats: A New Model Sensitive to Antidepressant Treatments, Eur. J. Pharmacol., 47:379-391 (1978).
Porsolt, R. et al., Behavioral despair in mice: a primary screening test for antidepressants, Arch Int Pharmacodyn Ther, 229(2):327-336 (1977).
Porsolt, R. et al., Depression: a new animal model sensitive to antidepressant treatments, Nature, 266(5604):730-732 (1977).
Preskorn, S. et al., An innovative design to establish proof of concept of the antidepressant effects of the NR2B subunit selective N-methyl-D-aspartate antagonist, CP-101,606, in patients with treatment-refractory major depressive disorder, J Clin Psychopharmacol, 28(6):631-637 (2008).
Reynolds, I. and Miller, R., Ifenprodil is a novel type of N-methyl-D-aspartate receptor antagonist: interaction with polyamines, Mol Pharmacol, 36(5):758-765 (1989).
Rodriguez, C. et al., Randomized Controlled Crossover Trial of Ketamine in Obsessive-Compulsive Disorder: Proof-of-Concept, Neuropsychopharmacology, 38:2475-2483 (2013).
Ruppa, K. et al., NMDA Antagonists of GluN2B Subtype and Modulators of GluN2A, GluN2C, and GluN2D Subtypes—Recent Results and Developments, Annual Reports in Medicinal Chemistry, 47:89-103 (2012).
Sanacora, G. et al., Targeting the glutamatergic system to develop novel, improved therapeutics for mood disorders, Nat Rev Drug Discov, 7(5):426-437 (2008).
Sang, C.N. et al., The NR2B subunit-selective NMDA receptor antagonist, CP-101,606, reduces spontaneous pain intensity in patients with central and peripheral neuropathic pain, Society for Neuroscience, Abstract 814.9 (2003).
Shatillo, A., et al., Involvement of NMDA receptor subtypes in cortical spreading depression in rats assessed by fMRI, Neuropharmacology, 93:164-170 (2015).
Shehadeh, J. et al., Striatal neuronal apoptosis is preferentially enhanced by NMDA receptor activation in YAC transgenic mouse model of Huntington disease, Neurobiology of Disease, 21:392-403 (2006).
Slattery, D. and Cryan, J., Using the rat forced swim test to assess antidepressant-like activity in rodents, Nat Protoc, 7(6):1009-1014 (2012).
Steece-Collier, K. et al., Antiparkinsonian actions of CP-101,606, an antagonist of NR2B subunit-containing N-methyl-d-aspartate receptors, Exp Neurol, 163(1):239-243 (2000).
Swinyard, E. et al., Comparative assays of antiepileptic drugs in mice and rats, J Pharmacol Exp Ther, 106(3):319-330 (1952).
Szczurowska, E. and Mares, P., Different action of a specific NR2B/NMDA antagonist Ro 25-6981 on cortical evoked potentials and epileptic afterdischarges in immature rats, Brain Research Bulletin, 111:1-8 (2015).
Tahirovic, Y.A. et al., Enantiomeric Propanolamines as selective N-Methyl-D-aspartate 2B Receptor Antagonists, J. Med. Chem., 51:5506-5521 (2008).
Tang, W. and Zhang, X., New chiral phosphorus ligands for enantioselective hydrogenation, Chem Rev, 103(8):3029-3070 (2003).
Taniguchi, K. et al., Antinociceptive activity of CP-101,606 an NMDA receptor NR2B subunit antagonist, British Journal of Pharmacology, 122:809-812 (1997).
Traynelis, S. et al., Glutamate receptor ion channels: structure, regulation, and function, Pharmacol Rev, 62(3):405-496 (2010).
Tudge, M. et al., Development of a Kilogram-Scale Asymmetric Synthesis of a Potent DP Receptor Antagonist, Organic Process Research and Development, 14:787-798 (2010).
Vengeliene, V. et al., The role of the NMDA receptor in alcohol relapse: a pharmacological mapping study using the alcohol deprivation effect, Neuropharmacology, 48:822-829 (2005).
Wang, H. et al., pH-Sensitive NMDA Inhibitors Improve Outcome in a Murine Model of SAH, Neurocrit Care, 21:119-131 (2014).
Wang, X.M. and Bausch, S.B., Effects of distinct classes of N-methyl-D-aspartate receptor antagonists on seizures, axonal sprouting and neuronal loss in vitro: suppression by NR2B-selective antagonists, Neuropharmacology, 47:1008-1020 (2004).
Warraich, S.T. et al., Evaluation of behavioural effects of a selective NMDA NR1A/2B receptor antagonist in the unilateral 6-OHDA lesion rat model, Brain Research Bulletin, 79:85-90 (2009).
Wessel, R.H. et al., NR2B selective NMDA receptor antagonist CP-101,606 prevents levodopa-induced motor response alterations in hemi-parkinsonian rats, Neuropharmacology, 47:184-194 (2004).
Written Opinion for PCT/US2015/034009, 6 pages (dated Sep. 30, 2015).
Written Opinion for PCT/US2015/050267, 5 pages (dated Dec. 9, 2015).
Written Opinion for PCT/US2015/051488, 9 pages (dated Jan. 27, 2016).
Written Opinion for PCT/US2015/65829 (Bicyclic Azaheterocyclic Compounds as NR2B NMDA Receptor Antagonists, filed Dec. 15, 2015), issued by ISA/US, 9 pages (dated Feb. 25, 2016).
Written Opinion for PCT/US2016/16442 (3,3-Difluoro-Piperidine Derivatives as NR2B NMDA Receptor Antagonists, filed Feb. 3, 2016), issued by ISA/US, 9 pages (dated Apr. 8, 2016).

(56) References Cited

OTHER PUBLICATIONS

Written Opinion for PCT/US2016/35098, 8 pages (dated Aug. 31, 2016).
Written Opinion for PCT/US2017/062726 (Treatment of Autism Spectrum Disorders, Obsessive-Compulsive Disorder and Anxiety Disorders, filed Nov. 21, 2017), issued by ISA/EP, 11 pages (dated Apr. 3, 2018).
Xie, X. et al., Role of a Hippocampal Src-Family Kinase-Mediated Glutamatergic Mechanism in Drug Context-Induced Cocaine Seeking, Neuropsychopharmacology, 38:2657-2665 (2013).
Yuan, H. et al., Context-Dependent GluN2B-Selective Inhibitors of NMDA Receptor Function are Neuroprotective with Minimal Side Effects, Neuron, 85:1305-1318 (2015).
Zarate, C. et al., A randomized trial of an N-methyl-D-aspartate antagonist in treatment-resistant major depression, Arch Gen Psychiatry, 63(8):856-864 (2006).
Zarate, C. et al., Replication of ketamine's antidepressant efficacy in bipolar depression: a randomized controlled add-on trial, Biol Psychiatry, 71(11):939-946 (2012).
Zeron, M.M. et al., Increased Sensitivity to N-Methyl-D-Aspartate Receptor-Mediated Excitotoxicity in a Mouse Model of Huntington's Disease, Neuron, 33:849-860 (2002).
Zhou, Q. and Sheng, M., NMDA receptors in nervous system diseases, Neuropharmacology, 74:69-75 (2013).

TREATMENT OF AUTISM SPECTRUM DISORDERS, OBSESSIVE-COMPULSIVE DISORDER AND ANXIETY DISORDERS

CROSS REFERENCE TO RELATED APPLICATIONS

The present application is a continuation of U.S. patent application Ser. No. 16/462,832, filed on May 21, 2019, which is a National Stage Entry of PCT/US2017/062726, filed on Nov. 21, 2017, which claims priority to U.S. Provisional Application No. 62/425,269, filed Nov. 22, 2016, the entirety of each of which is hereby incorporated by reference.

BACKGROUND

Neuropsychiatric and neurogenetic disorders are chronic, disabling conditions that impose enormous costs both on individuals and on society. Among neuropsychiatric diseases, anxiety disorder syndromes including obsessive-compulsive disorder (OCD) are among the most frequently diagnosed neuropsychiatric diseases in adults in Western countries.

SUMMARY

Among neurogenetic disorders, autism spectrum disorders (ASDs) refer to a series of pervasive developmental disorders that cause severe and ubiquitous impairment in thinking, feeling, language, and the ability to relate to others. These patients typically exhibit restricted, repetitive patterns of behavior, interests, or activities, as manifested by stereotyped or repetitive motor movements, inflexible adherence to routines, or ritualized patterns of verbal or nonverbal behavior. The onset is generally before the age of 3 years, and an ASD is usually first diagnosed in early childhood. ASDs can range from a severe form, called autistic disorder, through pervasive development disorder not otherwise specified (PDD-NOS), to a much milder form, commonly known as Asperger's syndrome. ASDs have a prevalence of 0.6% in the population, affecting many more boys than girls (Bertrand et al. *Pediatrics* 2001, 108:1155-1161; Yeargin et al. *JAMA* 2003, 289:49-55; Newschaffer et al. *Pediatrics* 2005, 115:e277-282). Twin and family studies have estimated the heritability of autism as being up to 90%, making it one of the most heritable complex disorders. Rare genetic syndromes and known chromosomal anomalies explain roughly 10% of cases of audsm, including Fragile X, tuberous sclerosis, Smith-Lemli-Opitz syndrome, and maternally-inherited duplications of the Prader-Willi/Angelman syndrome region (chromosome 15qll-13). However, despite high heritability, genetic studies to date have not provided substantial insight into the 90% of ASDs with idiopathic etiology. Emerging science suggests that circuit-level explanations of ASD pathogenesis are appealing because they most directly account for the emergence of clinical symptoms. The role of cortiostriatal circuit activity is implicated in the behavioral flexibility, motivational state, goal-directed learning, and attention (Dolen and Sahin *Front. Neurosci.* 2016, 10:182). From the neuronal circuit-level perspective, ASD might be thought of as a "synaptopathy" as many ASD risk genes known at this time encode synaptic proteins, and could be linked together by biochemical signaling pathways that regulate synaptic pruning and plasticity during early postnatal development. For example, deletions, duplications and coding mutations in the three SH3 and multiple ankyrin repeat domains of SHANK genes have been recurrently reported in individuals with ASD (Leblond et al. *PLoS Genet.* 2014, 10(9):e1004580).

Current therapeutic strategies for the diverse forms of autistic syndromes are mainly targeted to the correction of the most severe behavioral problems or symptoms associated with the main disorder. A number of psychopharmacological agents have been utilized in children with autism, but only to address specific psychiatric or behavioral symptoms, and with mixed results. These agents include: serotonin-related drugs, dopamine-related agents, epinephrine- and norepinephrine-related compounds, and a variety of other agents such as opiate antagonists, ACTH, atypical antipsychotics (e.g., clozapine and risperidone), vitamins B6 and B12 and melatonin. Thus, while children with ASDs are prescribed a number of drugs, there is still no accepted rational therapeutic regimen designed to address autism or its causes.

Anxiety disorders include a variety of psychological disorders that involve excess fear, worry, avoidance, and compulsive behaviors. Anxiety disorders are among the most common psychiatric diseases in the United States and are responsible for significant morbidity, functional impairment, and excessive use of healthcare services. Anxiety disorders have been formally classified into specific conditions including agoraphobia (with or without panic disorder), generalized anxiety disorder (GAD), social anxiety disorder (SAD), panic disorder (PD), and post-traumatic stress disorder (PTSD). Patients may suffer from a single specific disorder or a combination of them.

In the past, OCD was grouped together with anxiety disorders; however, the new edition of the Diagnostic and Statistical Manual of Mental Disorders, Fifth Edition (DSM-5; American Psychiatric Association, Arlington, Va., 2013), includes a new chapter for OCD and related disorders, including body dysmorphic disorder (e.g., anorexia nervosa), hoarding disorder, trichotillomania, and excoriation disorder. The DSM-5 defines OCD as the presence of obsessions, compulsions, or both. An individual with OCD experiences exaggerated concerns about danger, hygiene or harm that result in persistent conscious attention to the perceived threat or threats—referred to as "obsessions". It has been proposed that OCD symptoms occur in response to cues that activate a normal, biologically primal motivational system that protects people from potential danger. However, security-related behaviors that for most people would readily shut down these primal concerns do not work well in people with OCD. Thus, from a pathophysiological perspective, OCD patients repeat these behaviors in an attempt to overcome their weak internal stop signal (Hinds et al. *PLos ONE* 2012, 7(1):e30586).

Although exposure with response prevention (ERP), the prevailing psychotherapeutic treatment for OCD, is quite effective, a sizeable proportion of patients do not comply with or find they cannot tolerate ERP. Pharmacologic treatment of OCD and related anxiety disorders currently relies on drugs that modulate the gamma-aminobutyric acid (GABA) and/or serotonin receptor systems. Benzodiazepines are a class of drug that increase the tone of inhibitory GABA receptors and have profound anxiolytic effects in humans. Benzodiazepines are most often used in cases of GAD but also have found use in the other forms of anxiety disorders including PD, SAD, and PTSD. Selective serotonin reuptake inhibitors (SSRIs) have been widely prescribed as stand-alone or adjunct therapy for all of the anxiety disorders, particularly PD, agoraphobia, and social phobia. Buspirone, a selective 5-$HT_{1A}$ partial agonist has been approved by the United States Food and Drug Administration as an anxiolytic agent and is often used in the treatment of GAD in combination with SSRIs.

Numerous early studies involving SSRIs led to the hypothesis that OCD may be associated with dysregulation of serotonergic neurotransmission. Indeed, SSRIs have been established as the first-line pharmacotherapy of OCD. However, approximately one-half of the patients who receive an adequate trial with these agents remain clinically unchanged. In addition, SSRIs can have undesirable side effects, such as nausea; nervousness, agitation or restlessness; dizziness; erectile dysfunction or reduced sexual desire; drowsiness; insomnia; weight gain or loss; headache; dry mouth; vomiting; diarrhea; indigestion; blurred vision; or excessive sweating. Dopamine antagonists have similarly been used to augment treatment of patients resistant to SSRIs, but these agents have drawbacks in terms of side effects, such as acute dystonias, akathisia, parkinsonian symptoms, and neuroleptic malignant syndrome.

No single drug or protocol has been proven to be entirely satisfactory for addressing the behavioral and psychological symptoms associated with ASDs, OCD and/or anxiety disorders as chronically administered therapies. In addition, currently used drugs display limiting side effects. While benzodiazepine drugs can be effective, side effects that circumscribe their chronic use include sedation, memory loss, and addiction. SSRIs are amenable to chronic use but still have a high incidence of side effects that limit quality of life, such as impeded sexual function.

Research in both ASD and OCD has moved from genetic, epigenetic, and neuronal studies to animal models and, currently, to case reports and early exploratory open label clinical studies with oxytocin and various therapies targeting the glutamatergic system. While findings are preliminary, there are indications that there could be potential benefits in the social communication and repetitive behavioral difficulties with these medications (Sung et al. *Neuropsychiatr. Dis. Treat.* 2014, 10:371-381). More recently, glutamate-modulating interventions, such as with memantine and ketamine, have been considered as potential novel OCD treatments (Pittenger and Bloch *Psychiatr. Clin. North Am.* 2014, 37(3):375-391). Two small ketamine studies (total N=25), one open-label study (Rodriguez et al. *Neuropsychopharmacology* 2013, 38(12):2475-2483) and one study using a double-blind crossover design (Bloch et al. Biol. Psychiatry 2012, 72(11):964-970), investigating the efficacy of ketamine to treat OCD have produced conflicting results. In both studies, significant dissociative side effects of ketamine were reported by the study participants. More recently, a pair of blinded, placebo-controlled studies examined memantine augmentation or monotherapy and found a surprisingly substantial benefit (Haghighi et al. *Psychopharmacology* (*Berl.*) 2013, 228(4):633-640). The effects reported were substantially more robust than what has been suggested by the previously reported open-label studies, reaching 100% response and 89% remission after 8 weeks of treatment. These studies are promising, but replication in other populations is needed to increase confidence in the generalizability of the results. In summary, no single drug or protocol has proven entirely satisfactory for addressing the behavioral and psychological symptoms associated with ASDs, OCD and/or anxiety disorders as chronically administered therapies.

In a retrospective open-label study of 18 pediatric and adolescent patients (6-19 years of age) with ASD, who were treated with memantine, eleven out of 18 responded with improvements in social withdrawal and inattention. However, in the same study, seven out of 18 patients developed adverse effects, which included sedation, irritability, rash, emesis, and increased seizure frequency (Erickson et al. *Psychopharmacology* (*Berl.*) 2007, 191(1):141-147).

In another 12-week prospective open-label study in adults with ASD, memantine treatment was generally well tolerated and was not associated with any serious adverse events. However, the efficacy in this intellectually capable and high-functioning adult population was quite modest (Joshi et al. *J. Clin. Psychopharmacol.* 2016, 36(3):262-271).

Accordingly, there is a continuing need in the art for compounds that can address the underlying causes of ASDs, OCD and/or anxiety disorders and alleviate the associated behavioral abnormalities common to these conditions. The present invention encompasses the insight that certain NR2B subunit-selective N-methyl-D-aspartate (NMDA) receptor antagonists are effective for the treatment of ASDs, OCD and/or anxiety disorders.

In some embodiments, the NR2B subunit-selective NMDA antagonist is a chemical entity of formula $I^{A'}$:

$I^{A'}$

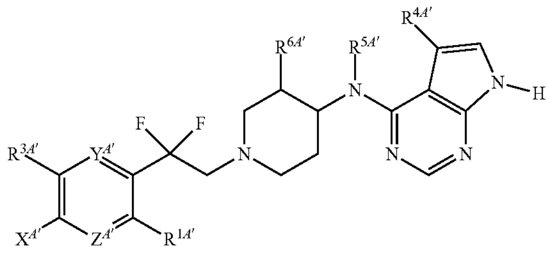

wherein $X^{A'}$, $Y^{A'}$, $Z^{A'}$ $R^{1A'}$, $R^{3A'}$, $R^{4A'}$ $R^{A5'}$, and $R^{6A'}$ are defined herein.

In some embodiments, the NR2B subunit-selective NMDA antagonist is a chemical entity of formula $I^{B'}$.

$I^{B'}$

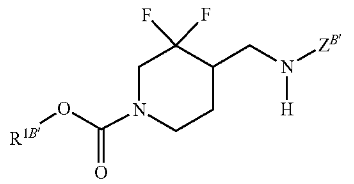

wherein $Z^{B'}$ and $R^{1B'}$ are defined herein.

Significance comparing vehicle-treated Shank3 complete knockout and wild type mice was determined by repeated measures analysis of variance followed by Bonferroni's post-hoc test; $^{\#\#}$p<0.01. The within-subjects measure was pre- vs. post-spray periods. The Shank3 complete knockout mice treated with vehicle groomed significantly longer than the vehicle-treated wild type littermates, confirming the ASD-like deficit. The NR2B antagonists reduced the amount of grooming in Shank3 complete knockout mice to a level similar to or below that observed in the vehicle-treated wild type littermates. The NR2B antagonists at 3 mg/kg also reduced the amount of grooming in wild type mice. N=6 mice per group.

Figure 7:
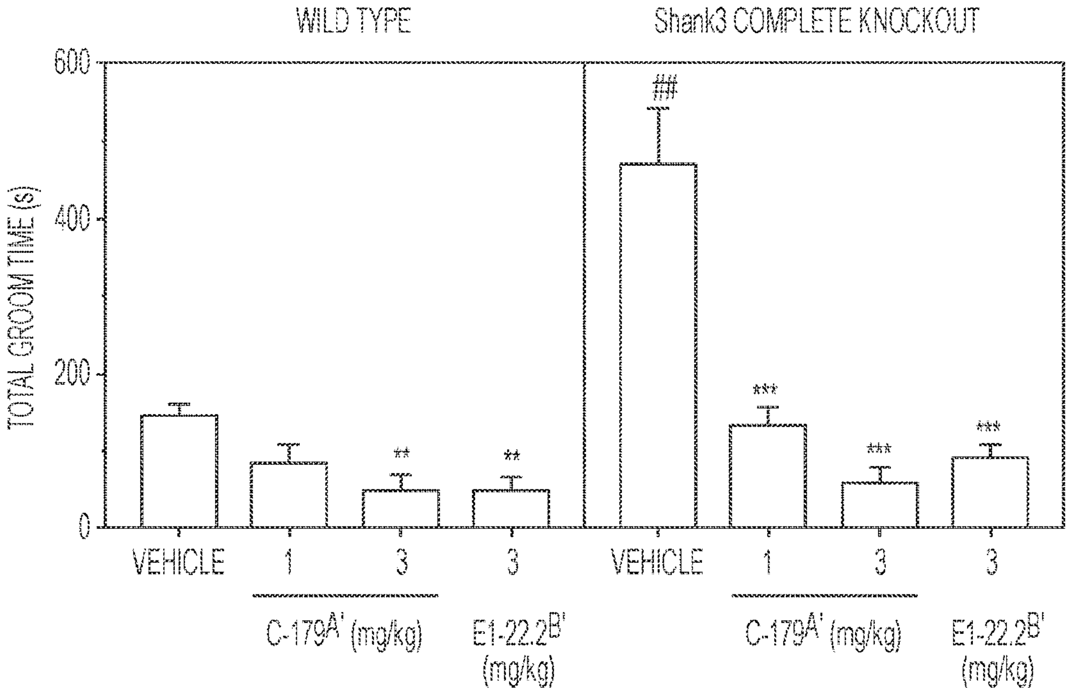
FIG. 7. Acute administration of NR2B antagonists reduces self-grooming in Shank3 complete knockout mice and their wild type littermates. The effect of C-179$^{A'}$ at 1 and 3 mg/kg and of E1-22.2$^{B'}$ at 3 mg/kg administered intraperitoneally 20 minutes before testing on time spent grooming (seconds) in an unfamiliar environment for the entire 20-minute test period (before and after being sprayed with water midway through the test period). Significance comparing compound treatments with vehicle within each genotype was determined by one-way analysis of variance followed by Bonferroni's post-hoc test; p<0.01, and *p<0.001.
Figure 8:
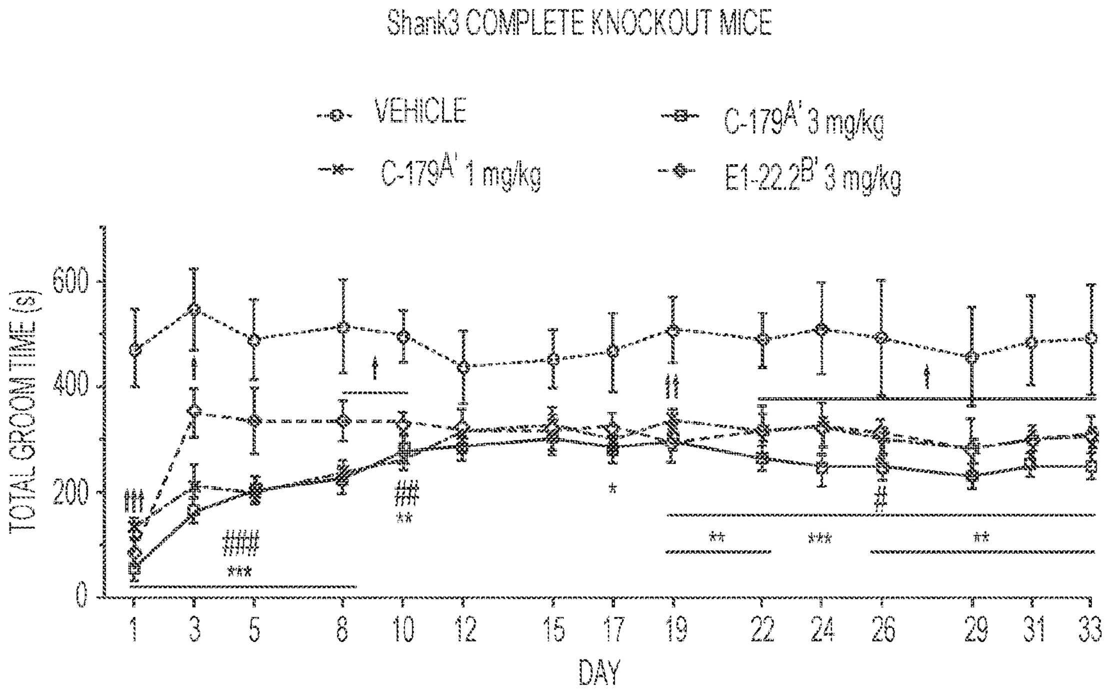

FIG. 8. Sustained effects of a single dose of an NR2B antagonist on reducing self-grooming in Shank3 complete knockout mice. The effect of single doses of two NR2B antagonists administered intraperitoneally 20 minutes before testing on Day 1 on time spent grooming (seconds) for Shank3 complete knockout mice. (See FIG. 7 for Day 1 data alone.) Significance comparing compound treatment and vehicle was determined by repeated measures analysis of variance followed by Bonferroni's post-hoc test. The repeated measure was test day. Compound C-179$^{A'}$: 3 mg/kg, *p<0.05, p<0.01, and *p<0.001; and 1 mg/kg, $^{\#}$p<0.05, $^{\#\#}$p<0.01, and $^{\#\#\#}$p<0.001. Compound E1-22.2$^{B'}$: 3 mg/kg, p<0.05, $^{\dagger}$p<0.01, and $^{\dagger\dagger}$p<0.001.

The compounds reduced grooming through Day 33. The compounds were cleared from plasma in about 8 hours. The sustained effect on grooming in the Shank3 complete knockout mice lasted for a longer time period than in the Sapap3 knockout mice. N=6 mice per group.

Figure 9:
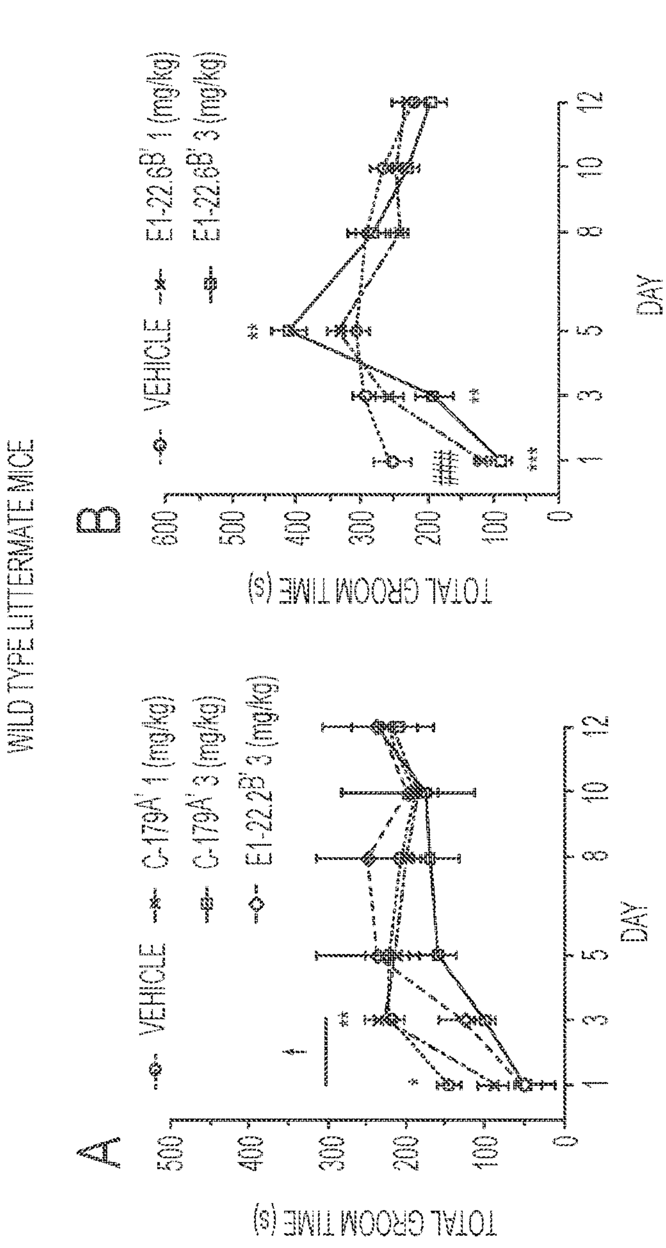

FIG. 9. Sustained effects of a single dose of an NR2B antagonist on reducing self-grooming in the wild type littermates of Sapap3 and Shank3 complete knockout mice. The effect of single doses of three NR2B antagonists administered intraperitoneally 20 minutes before testing on Day 1 on time spent grooming (seconds) for wild type littermate mice. Significance comparing compound treatment and vehicle was determined by repeated measures analysis of variance followed by Bonferroni's post-hoc test. The repeated measure was test day. A, Compound C-179$^{A'}$: 3 mg/kg, *p<0.05 and p<0.01; and Compound E1-22.2$^{B'}$: 3 mg/kg, $^{\dagger}$p<0.05 in wild type littermates of Shank3 complete knockout mice. B, E1-22.6$^{B'}$: 3 mg/kg, p<0.01 and ***p<0.001; and 1 mg/kg, $^{\#\#\#}$p<0.001 in wild type littermates of Sapap3 knockout mice. Compounds C-179$^{A'}$, E1-22.2$^{B'}$, and E1-22.6$^{B'}$ at 3 mg/kg reduced grooming on Day 3 after dosing on Day 1. The sustained effects on grooming in wild type mice lasted for a shorter period of time than in the Sapap3 and Shank3 complete knockout mice. N=6-10 mice per group.

DETAILED DESCRIPTION OF CERTAIN EMBODIMENTS

In some embodiments, the present invention encompasses the insight that certain NR2B subtype-selective NMDA receptor antagonists are useful in the treatment of ASDs, OCD, and/or anxiety disorders. More particularly, it has been discovered that certain antagonists of NR2B subtype-selective NMDA receptors can correct behavioral abnormalities in animals genetically engineered to model human symptoms associated with ASDs, OCD, and/or anxiety. Among other things, the present disclosure establishes that administration of these compounds to subjects suffering from or susceptible to (e.g., diagnosed with, displaying one or more symptoms associated with, genetically related to one or more subjects diagnosed with or displaying one or more symptoms associated with, etc.) one or more ASDs, OCD, or anxiety disorders has the potential to treat (e.g., reduce frequency and/or severity of, and/or delay onset of, etc.) at least one of the behavioral or psychological symptoms associated with such conditions.

Definitions

As used herein, the term "NMDA-receptor-mediated disorder" means a disease or disorder in which the NMDA receptor is known or suspected to play a role. A variety of disorders are associated with altered N/DA-receptor signaling in the process of synaptic neurotransmission. An early report of synaptic scaling at central synapses revealed that activity blockade increased excitatory, glutamatergic synaptic transmission through a simple change in the accumulation of postsynaptic NMDA receptors, with no changes in presynaptic function (Turrigiano et al. *Nature* 1998, 391: 892-896). More recently, reduction of the firing of NMDA-receptor-dependent current excitatory circuits in the anterior cingulate gyrus was shown to be helpful in treating depressive symptoms. Interrupting the activity of these circuits might underlie the immediate beneficial effects of the NMDA receptor antagonist ketamine in some patients and may also underlie more prolonged beneficial actions. More specific to ASD and OCD, specific deletions of ASD- and OCD-related genes associated with glutamatergic excitatory neurotransmission at interneurons result in neurodevelopmental deficits as well as in repetitive grooming behavior in mice. For example, loss of MeCP2 from excitatory postsynaptic protein complexes in GABAergic interneurons leads to autistic-like repetitive movements, seizures, and deficits in auditory event-related potentials (Chao et al. *Nature* 2010, 468:263-269). Deficits in inhibitory neurotransmission, along with altered balance of excitation and inhibition have been consistently observed in cortical and hippocampal neuronal circuitries in diverse mouse models (Dani et al. *Proc. Natl. Acad. Sci. USA* 2005, 102:12560-12565). Mice with a deletion of the Sapap3 gene exhibit excessive self-grooming, increased anxiety-like behavior, and corticostriatal synaptic defects (Welch et al. *Nature* 2007, 448:894-900). Without wishing to be bound by theory, in some patients with ASD and OCD, the process of synaptic homeostasis might not be able to counter the effects of the mutations on synaptic activity, leading to neuronal activity that is too high or too low. Abnormal sprouting (or pruning) of synapses, as a result of the mutations, could therefore lead to abnormal coordination and competition among neuronal networks.

Unless otherwise indicated, the word "includes" (or any variation thereon, e.g., "include", "including", etc.) is intended to be open-ended. For example, "A includes 1, 2 and 3" means that A includes but is not limited to 1, 2, and 3.

Unless otherwise indicated, the phrase "such as" is intended to be open-ended. For example, "A can be a halogen, such as chloro or bromo" means that A can be, but is not limited to, chloro or bromo.

As used herein, an "effective dosage" or "effective amount" of drug, compound, or pharmaceutical composition is an amount sufficient to effect beneficial or desired results. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In the case of an ASD, OCD, or anxiety disorder, an effective amount of the drug may have the effect in reducing and/or relieving to some extent one or more of the symptoms associated with the disorder. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As used herein, "in conjunction with" or "in combination with" refers to administration of one treatment modality in addition to another treatment modality. As such, "in conjunction with" or "in combination with" refers to administration of one treatment modality before, during or after administration of the other treatment modality to the subject.

As used herein, "treatment" or "treating" is an approach for obtaining beneficial or desired results including clinical results. For purposes of this invention, beneficial or desired clinical results include one or more of the following: decreasing the severity and/or frequency of one or more symptoms resulting from or otherwise associated with the disease, increasing the quality of life of those suffering from the disease, decreasing the dose of one or more other medications required to treat the disease, delaying the development of the disease, and/or prolonging survival of subjects.

As used herein, "delaying development of a disease" means to defer, hinder, slow, retard, stabilize, and/or postpone development of the disease (such as an ASD, OCD, or anxiety disorder). This delay can be of varying lengths of time, depending on the history of the disease and/or subject being treated. As is evident to one skilled in the art, a sufficient or significant delay can, in effect, encompass prevention, in that the subject does not develop the disease.

The term "pharmaceutically acceptable" means a material which is not biologically or otherwise undesirable, i.e., the material may be administered to a subject without causing any undesirable biological effects or interacting in a deleterious manner with any of the components of the composition in which it is contained.

It is understood that aspects and variations of the invention described herein include "consisting" and/or "consisting essentially of" aspects and variations.

As used herein, the singular form "a", "an", and "the" includes plural references unless indicated otherwise.

As used herein, the term "subject" includes a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is someone to whom diagnosis and/or therapy is and/or has been administered. In some embodiments, a subject is a fetus, an infant, a child, a teenager, an adult, or a senior citizen (i.e., the subject is of advanced age, such as older than 50). In some embodiments, a child refers to a human between 2 and 18 years of age. In some embodiments, an adult refers to a human 18 years of age or older.

Chemical entities of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, *Handbook of Chemistry and Physics,* 75th Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry,* 5th Ed., John Wiley & Sons, Inc., New York, 2001; Larock, *Comprehensive Organic Transformations*, VCH Publishers, Inc., New York, 1989; and Carruthers, *Some Modern Methods of Organic Synthesis,* 3rd Ed., Cambridge University Press, Cambridge, 1987.

The term "alkyl", used alone or as part of a larger moiety, means a substituted or unsubstituted, linear or branched, univalent hydrocarbon chain that is completely saturated or that contains one or more units of unsaturation. Unless otherwise specified, alkyl groups contain 1 to 7 carbon atoms ("$C_1$-$C_7$ alkyl"). In some embodiments, alkyl groups contain 1 to 6 carbon atoms ("$C_1$-$C_6$ alkyl"). In some embodiments, alkyl groups contain 1 to 5 carbon atoms ("$C_1$-$C_5$ alkyl"). In some embodiments, alkyl groups contain 1 to 4 carbon atoms ("$C_1$-$C_4$ alkyl"). In some embodiments, alkyl groups contain 3 to 7 carbon atoms ("$C_3$-$C_7$ alkyl"). Examples of saturated alkyl groups include methyl, ethyl, n-propyl, i-propyl, n-butyl, t-butyl, i-butyl, s-butyl, homologs and isomers of, for example, n-pentyl, n-hexyl, n-heptyl, n-octyl, and the like. An unsaturated alkyl group is one having one or more carbon-carbon double bonds or carbon-carbon triple bonds. Examples of unsaturated alkyl groups include allyl, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the like. The term "lower alkyl" refers to alkyl groups having 1 to 4 (if saturated) or 2 to 4 (if unsaturated) carbon atoms. Exemplary lower alkyl groups include methyl, ethyl, n-propyl, i-propyl, n-butyl, s-butyl, i-butyl, t-butyl, and the like. The term "alkenyl" refers to alkyl groups having at least two carbon atoms and at least one carbon-carbon double bond. The term "alkynyl" refers to alkyl groups having at least two carbon atoms and at least one carbon-carbon triple bond.

The term "cycloalkyl", used alone or as part of a larger moiety, e.g., "(cycloalkyl)alkyl", refers to a univalent monocyclic hydrocarbon that is completely saturated or that contains one or more units of unsaturation, but which is not aromatic; or bicyclo[2.2.1]heptanyl (also called norbornyl) or bicyclo[2.2.2]octanyl. In some embodiments, cycloalkyl groups contain 3 to 8 ring carbon atoms ("$C_3$-$C_8$ cycloalkyl"). Examples of cycloalkyl include cyclopropyl, cyclobutyl, cyclopentyl, cyclohexyl, 1-cyclohexenyl, 3-cyclohexenyl, cycloheptyl, and the like, as well as bicyclo[2.2.1]heptanyl and bicyclo[2.2.2]octanyl. In some embodiments, the term "cycloalkyl" includes a monocyclic hydrocarbon that is completely saturated or that contains one or more units of unsaturation, but which is not aromatic, that is fused to one or more aryl rings and the point of attachment is located on the cycloalkyl ring. In some such embodiments, a cycloalkyl is indanyl.

The term "alkoxy", used alone or as part of a larger moiety, refers to the group —O-alkyl.

The term "halogen" or "halo", used alone or as part of a larger moiety, refers to fluoro, chloro, bromo, or iodo.

The term "aryl", used alone or as part of a larger moiety, e.g., "(aryl)alkyl", refers to a univalent monocyclic or bicyclic carbocyclic aromatic ring system. Unless otherwise specified, aryl groups contain 6 or 10 ring members. Examples of aryl include phenyl, naphthyl, and the like. In some embodiments, the term "aryl" includes a monocyclic or bicyclic carbocyclic aromatic ring system that is fused to at least one ring that is completely saturated or that contains one or more units of unsaturation, but which is not aromatic, wherein the point of attachment is located on the aryl ring.

The term "heteroaryl", used alone or as part of a larger moiety, e.g., "(heteroaryl)alkyl", refers to a univalent monocyclic or bicyclic group having 5 to 10 ring atoms, preferably 5, 6, 9, or 10 ring atoms, having 6, 10, or 14 $\pi$ electrons shared in a cyclic array, and having, in addition to ring carbon atoms, from one to four ring heteroatoms. Examples of heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, and the like.

The term "heterocyclyl", used alone or as part of a larger moiety, e.g., "(heterocyclyl)alkyl", refers to a univalent stable 5- to 7-membered monocyclic or 7- to 10-membered bicyclic heterocyclic moiety that is either saturated or partially unsaturated, and having, in addition to ring carbon atoms, one to four heteroatoms. Examples of heterocycyl groups include tetrahydrofuranyl, pyrrolidinyl, tetrahydropyranyl, piperidinyl, morpholinyl, and the like.

As used herein, the term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in J. Pharm. Sci. 1977, 66:1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}\ alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement hydrogen, carbon, nitrogen, oxygen, chlorine, or fluorine with $^2H$, $^3H$, $^{11}C$, $^{13}C$, $^{14}C$, $^{13}N$, $^{15}N$, O, $^{18}O$, $^{36}Cl$, or $^{18}F$, respectively, are within the scope of this invention. Such compounds are useful, for example, as analytical tools, as probes in biological assays, or as therapeutic agents in accordance with the present invention.

Additionally, incorporation of heavier isotopes such as deuterium ($^2H$) can afford certain therapeutic advantages resulting from greater metabolic stability, for example, increased in vivo half-life, or reduced dosage requirements.

Unless otherwise specified or clear from context, the term "chemical entity" refers to a compound having the indicated structure, whether in its "free" form (e.g., "free compound" or "free base" or "free acid" form, as applicable), or in a salt form, particularly a pharmaceutically acceptable salt form, and furthermore whether in solid-state form or otherwise. In some embodiments, a solid-state form is an amorphous (i.e., non-crystalline) form; in some embodiments, a solid-state form is a crystalline form. In some embodiments, a crystalline form (e.g., a polymorph, pseudohydrate, or hydrate). Similarly, the term encompasses the compound whether provided in solid form or otherwise. Unless otherwise specified, all statements made herein regarding "compounds" apply to the associated chemical entities, as defined.

General Description of Chemical Entities

Formula $I^{A'}$

In some embodiments, the present invention provides chemical entities of formula $I^{A'}$:

$I^{A'}$

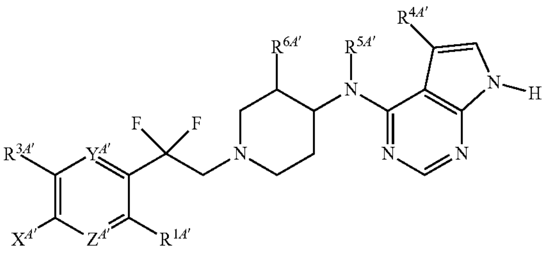

wherein:

$Y^{A'}$ and $Z^{A'}$ are independently N or $C(R^{2A'})$;

$X^{A'}$ is —H; halo; $C_1$-$C_6$ alkyl optionally substituted with 1 to 6 fluoro; $C_3$-$C_6$ cycloalkyl; $C_1$-$C_4$ alkoxy optionally substituted with 1 to 6 fluoro; —CN; —$NO_2$; —$N(R^{7A'})(R^{8A'})$; —$SR^{7A'}$; —$S(O)_2R^{9A'}$; or —$C(O)OR^{7A'}$.

$R^{1A'}$ is —H; halo; $C_1$-$C_4$ alkyl optionally substituted with 1 to 3 fluoro; $C_3$-$C_6$ cycloalkyl; $C_1$-$C_4$ alkoxy optionally substituted with 1 to 3 fluoro; —CN; —$NO_2$; —$N(R^{7A'})(R^{8A'})$; —$C(O)OR^{7A'}$; or —$C(O)N(R^{7A'})(R^{A8'})$;

$R^{2A'}$ is —H; halo; $C_1$-$C_4$ alkyl optionally substituted with 1 to 3 fluoro; cyclopropyl; or $C_1$-$C_4$ alkoxy optionally substituted with 1 to 3 fluoro;

$R^{3A'}$ is —H, —F, —Cl, —$CH_3$, —$CF_3$, or —$OCH_3$;

$R^{4A'}$ is —H; —F; —Cl; $C_1$-$C_3$ alkyl optionally substituted with 1 to 3 fluoro; or cyclopropyl;

$R^{5A'}$ is —H or —$CH_3$;

$R^{6A'}$ is —H, —F, or —$CH_3$;

each instance of $R^{7A'}$ independently is $C_1$-$C_4$ alkyl;

each instance of $R^{8A'}$ independently is —H or $C_1$-$C_4$ alkyl; and $R^{9A'}$ is $C_1$-$C_4$ alkyl optionally substituted with 1 to 3 fluoro.

Formula $I^{B'}$

In some embodiments, the present invention provides chemical entities of Formula $I^{B'}$:

$I^{B'}$

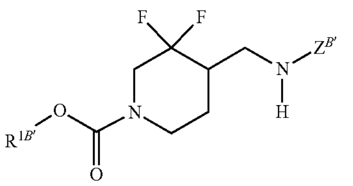

wherein:

$R^{1B'}$ is alkyl, cycloalkyl, (cycloalkyl)alkyl, heterocyclyl, (heterocyclyl)alkyl, aryl, (aryl)alkyl, heteroaryl or (heteroaryl)alkyl, wherein each of cycloalkyl, (cycloalkyl) alkyl, heterocyclyl, (heterocyclyl)alkyl, aryl, (aryl)alkyl, heteroaryl, and (heteroaryl)alkyl is independently optionally substituted with 1 to 3 groups independently selected from —F, —Cl, $C_1$-$C_4$ alkyl, cyclopropyl, —C≡CH, —$CFH_2$, —$CF_2H$, —$CF_3$, —$CF_2CH_3$, —$CH_2CF_3$, $C_1$-$C_4$ alkoxy, —$OCFH_2$, —$OCF_2H$, —$OCF_3$, —CN, —N($R^{2B'}$)($R^{3B'}$), —$NO_2$, $C_1$-$C_4$ alkylthio, $C_1$-$C_4$ alkylsulfonyl, and —$S(O)_2CF_3$;

wherein each instance of $R^{2B'}$ and $R^{3B'}$ independently is —H or $C_1$-$C_4$ alkyl, or —N($R^{2B'}$)($R^{3B'}$) is

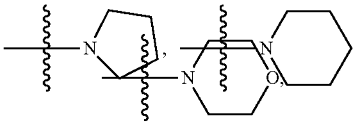

$Z^{B'}$ is 5- or 6-membered monocyclic or 9- or 10-membered bicyclic heteroaryl having ring carbon atoms, 1 nitrogen ring atom and 0-3 additional ring heteroatoms independently selected from N, O, and S, which is optionally substituted with 1 or 2 $R^{xB'}$ groups and optionally substituted with 1 $R^{aB'}$ group, wherein each $R^{xB'}$ is attached to a ring carbon atom and $R^{aB'}$ is attached to a ring nitrogen atom;

wherein:

each instance of $R^{xB'}$ independently is —F, —Cl, —$CH_3$, —$CFH_2$, —$CF_2H$, —$CF_3$, —OH, —$OCH_3$, —$OCF_3$, or —CN; and $R^{aB'}$ is hydrogen, $C_{1-4}$ alkyl, $C_{3-4}$ cycloalkyl, or —$S(O)_2$—$C_{1-4}$ alkyl.

Exemplary Embodiments of Chemical Entities

Formula $I^{A'}$

In some embodiments, the present invention provides chemical entities of formula $I^{A'}$:

$I^{A'}$

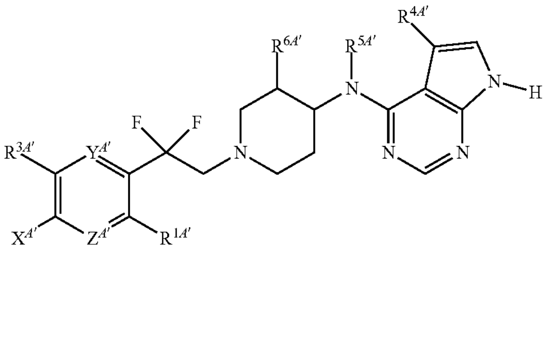

wherein:

$Y^{A'}$ and $Z^{A'}$ are independently N or C($R^{2A'}$);

$X^{A'}$ is —H; halo; $C_1$-$C_6$ alkyl optionally substituted with 1 to 6 fluoro; $C_3$-$C_6$ cycloalkyl; $C_1$-$C_4$ alkoxy optionally substituted with 1 to 6 fluoro; —CN; —$NO_2$; —N($R^{7A'}$)($R^{8A'}$); —$SR^{7A'}$. —$S(O)_2R^{9A'}$; or —C(O)$OR^{7A'}$.

$R^{1A'}$ is —H; halo; $C_1$-$C_4$ alkyl optionally substituted with 1 to 3 fluoro; $C_3$-$C_6$ cycloalkyl; $C_1$-$C_4$ alkoxy optionally substituted with 1 to 3 fluoro; —CN; —$NO_2$; —N($R^{7A'}$)($R^{8A'}$); —C(O)$OR^{7A'}$; or —C(O)N($R^{7A'}$)($R^{8A'}$);

$R^{2A'}$ is —H; halo; $C_1$-$C_4$ alkyl optionally substituted with 1 to 3 fluoro; cyclopropyl; or $C_1$-$C_4$ alkoxy optionally substituted with 1 to 3 fluoro;

$R^{3A'}$ is —H, —F, —Cl, —$CH_3$, —$CF_3$, or —$OCH_3$;

$R^{4A'}$ is —H; —F; —Cl; $C_1$-$C_3$ alkyl optionally substituted with 1 to 3 fluoro; or cyclopropyl;

$R^{5A'}$ is —H or —$CH_3$;

$R^{6A'}$ is —H, —F, or —$CH_3$;

each instance of $R^{7A'}$ independently is $C_1$-$C_4$ alkyl;

each instance of $R^{8A'}$ independently is —H or $C_1$-$C_4$ alkyl; and $R^{9A'}$ is $C_1$-$C_4$ alkyl optionally substituted with 1 to 3 fluoro.

In some such embodiments, at least one of $Y^{A'}$ and $Z^{A'}$ is N.

In some embodiments, $Y^{A'}$ and $Z^{A'}$ are independently N or C($R^{2A'}$);

$X^{A'}$ is —H; halo; $C_1$-$C_4$ alkyl optionally substituted with 1 to 6 fluoro; cyclopropyl; $C_1$-$C_2$ alkoxy optionally substituted with 1 to 3 fluoro; —CN; —$NO_2$; —N($R^{7A'}$)($R^{8A'}$); —$SR^{7A'}$; or —$S(O)_2R^{9A'}$.

$R^{1A'}$ is —H; halo; $C_1$-$C_4$ alkyl optionally substituted with 1 to 3 fluoro; cyclopropyl; $C_1$-$C_2$ alkoxy optionally substituted with 1 to 3 fluoro; —CN; —$NO_2$; —N($R^{7A'}$)($R^{8A'}$); —C(O)$OR^{7A'}$; or —C(O)N($R^{7A'}$)($R^{8A'}$);

$R^{2A'}$ is —H; halo; $C_1$-$C_4$ alkyl optionally substituted with 1 to 3 fluoro; cyclopropyl; or $C_1$-$C_2$ alkoxy optionally substituted with 1 to 3 fluoro;

$R^{3A'}$ is —H, —F, —Cl, —$CH_3$, —$CF_3$, or —$OCH_3$;

$R^{4A'}$ is —H; —F; —Cl; $C_1$-$C_3$ alkyl optionally substituted with 1 to 3 fluoro; or cyclopropyl;

$R^{5A'}$ is —H or —$CH_3$;

$R^{6A'}$ is —H, —F, or —$CH_3$;

each instance of $R^{7A'}$ independently is $C_1$-$C_2$ alkyl;

each instance of $R^{8A'}$ independently is —H or $C_1$-$C_2$ alkyl; and $R^{9A'}$ is $C_1$-$C_2$ alkyl optionally substituted with 1 to 3 fluoro.

In some such embodiments, at least one of $Y^{A'}$ and $Z^{A'}$ is N.

In some embodiments, $Y^{A'}$ and $Z^{A'}$ are independently N or C($R^{2A'}$);

$X^{A'}$ is —H, —F, —Cl, —$CH_3$, —$CH_2CH_3$, —$CH(CH_3)_2$, —$CF_3$, —$CHF_2$, —$CH_2F$, —$CF_2CF_3$, —$CH_2CF_2CF_3$, —$CH(CF_3)_2$, cyclopropyl, —$OCH_3$, —$OCF_3$, —$OCHF_2$, —$OCFH_2$, —CN, —$NO_2$, —NH($CH_3$), —$N(CH_3)_2$, —N($CH_3$)($CH_2CH_3$), —$SCH_3$, —$SCH_2CH_3$, —$SO_2CH_3$, —$SO_2CH_2CH_3$, or —$SO_2CF_3$;

$R^{1A'}$ is —H, —F, —Cl, —$CH_3$, —$CH_2CH_3$, —$CH(CH_3)_2$, —$CF_3$, cyclopropyl, —$OCH_3$, —$OCF_3$, —$OCHF_2$, —$OCFH_2$, —CN, —$NO_2$, —$CO_2CH_3$, —$CO_2CH_2CH_3$, —C(O)$N(CH_3)_2$, —C(O)NH($CH_3$), or —C(O)N($CH_3$)($CH_2CH_3$);

$R^{2A'}$ is —H, —F, —Cl, —$CH_3$, —$CH_2CH_3$, —$CH(CH_3)_2$, —$CF_3$, cyclopropyl, —$OCH_3$, —$OCF_3$, —$OCHF_2$, or —$OCFH_2$;

$R^{3A'}$ is —H, —F, —Cl, —$CH_3$, —$CF_3$, or —$OCH_3$;

$R^{4A'}$ is —H, —F, —Cl, —$CH_3$, or cyclopropyl;

$R^{5A'}$ is —H or —$CH_3$; and $R^{6A'}$ is —H, —F, or —$CH_3$.

In some such embodiments, at least one of $Y^{A'}$ and $Z^{A'}$ is N.

In some embodiments, $Y^{A'}$ and $Z^{A'}$ are independently N or $C(R^{2A'})$;

$X^{A'}$ is —H, —F, —Cl, —$CH_3$, —$CH_2CH_3$, —$CH(CH_3)_2$, —$CF_3$, —$CHF_2$, —$CH_2F$, —$CF_2CF_3$, —$CH_2CF_2CF_3$, —$CH(CF_3)_2$, cyclopropyl, —$OCH_3$, —$OCF_3$, —$OCHF_2$, —$OCFH_2$, —CN, —$NO_2$, —$N(CH_3)_2$, —$SCH_3$, —$SO_2CH_3$, or —$SO_2CF_3$;

$R^{1A'}$ is —H, —F, —Cl, —$CH_3$, —$CH_2CH_3$, —$CH(CH_3)_2$, —$CF_3$, cyclopropyl, —$OCH_3$, —$OCF_3$, —$OCHF_2$, —$OCFH_2$, —CN, —$NO_2$, —$CO_2CH_3$, —$CO_2CH_2CH_3$, —$C(O)N(CH_3)_2$, or —$C(O)NH(CH_3)$;

$R^{2A'}$ is —H, —F, —Cl, —$CH_3$, —$CH_2CH_3$, —$CH(CH_3)_2$, —$CF_3$, cyclopropyl, —$OCH_3$, —$OCF_3$, —$OCHF_2$, or —$OCFH_2$;

$R^{3A'}$ is —H, —F, —Cl, —$CH_3$, —$CF_3$, or —$OCH_3$;

$R^{4A'}$ is —H, —F, —Cl, —$CH_3$, or cyclopropyl;

$R^{5A'}$ is —H or —$CH_3$; and $R^{6A'}$ is —H, —F, or —$CH_3$.

In some such embodiments, at least one of $Y^{A'}$ and $Z^{A'}$ is N.

In some embodiments, $Y^{A'}$ and $Z^{A'}$ are independently N or $C(R^{2A'})$;

$X^{A'}$ is —H, —F, —Cl, —$CH_3$, —$CH_2CH_3$, —$CH(CH_3)_2$, —$CF_3$, —$CHF_2$, —$CH_2F$, cyclopropyl, —$OCH_3$, —$OCF_3$, —$OCHF_2$, —CN, or —$SCH_3$;

$R^{1A'}$ is —H, —F, —Cl, —$CH_3$, or —$CF_3$;

$R^{2A'}$ is —H, —F, —Cl, —$CH_3$, or —$CF_3$;

$R^{3A'}$ is —H, —F, —Cl, —$CH_3$, or —$CF_3$;

$R^{4A'}$ is —H, —Cl, or —$CH_3$;

$R^{5A'}$ is —H or —$CH_3$; and $R^{6A'}$ is —H, —F, or —$CH_3$.

In some such embodiments, at least one of $Y^{A'}$ and $Z^{A'}$ is N.

In some embodiments, $X^{A'}$ is —H; halo; $C_1$-$C_4$ alkyl optionally substituted with 1 to 6 fluoro; cyclopropyl; $C_1$-$C_2$ alkoxy optionally substituted with 1 to 3 fluoro; —CN; —$NO_2$; —$N(R^{7A'})(R^{8A'})$; —$SR^{7A'}$; or —$S(O)_2R^{9A'}$. In some embodiments, $X^{A'}$ is —H, —F, —Cl, —$CH_3$, —$CH_2CH_3$, —$CH(CH_3)_2$, —$CF_3$, —$CHF_2$, —$CH_2F$, —$CF_2CF_3$, —$CH_2CF_2CF_3$, —$CH(CF_3)_2$, cyclopropyl, —$OCH_3$, —$OCF_3$, —$OCHF_2$, —$OCFH_2$, —CN, —$NO_2$, —$NH(CH_3)$, —$N(CH_3)_2$, —$N(CH_3)(CH_2CH_3)$, —$SCH_3$, —$SCH_2CH_3$, —$SO_2CH_3$, —$SO_2CH_2CH_3$, or —$SO_2CF_3$. In some embodiments, $X^{A'}$ is —H, —F, —Cl, —$CH_3$, —$CH_2CH_3$, —$CH(CH_3)_2$, —$CF_3$, —$CHF_2$, —$CH_2F$, —$CF_2CF_3$, —$CH_2CF_2CF_3$, —$CH(CF_3)_2$, cyclopropyl, —$OCH_3$, —$OCF_3$, —$OCHF_2$, —$OCFH_2$, —CN, —$NO_2$, —$N(CH_3)_2$, —$SCH_3$, —$SO_2CH_3$, or —$SO_2CF_3$. In some embodiments, $X^{A'}$ is —H, —F, —Cl, —$CH_3$, —$CH_2CH_3$, —$CH(CH_3)_2$, —$CF_3$, —$CHF_2$, —$CH_2F$, cyclopropyl, —$OCH_3$, —$OCF_3$, —$OCHF_2$, —CN, or —$SCH_3$.

In some embodiments, $X^{A'}$ is —H.

In some embodiments, $X^{A'}$ is halo. In some embodiments, $X^{A'}$ is —F or —Cl.

In some embodiments, $X^{A'}$ is $C_1$-$C_6$ alkyl optionally substituted with 1 to 6 fluoro. In some embodiments, $X^{A'}$ is $C_1$-$C_4$ alkyl optionally substituted with 1 to 6 fluoro. In some embodiments, $X^{A'}$ is —$CH_3$, —$CH_2CH_3$, —$CH(CH_3)_2$, —$CF_3$, —$CHF_2$, —$CH_2F$, —$CF_2CF_3$, —$CH_2CF_2CF_3$, or —$CH(CF_3)_2$. In some embodiments, $X^{A'}$ is-$CH_3$, —$CH_2CH_3$, —$CH(CH_3)_2$, —$CF_3$, —$CHF_2$, or —$CH_2F$.

In some embodiments, $X^{A'}$ is $C_3$-$C_6$ cycloalkyl. In some embodiments $X^{A'}$ is cyclopropyl.

In some embodiments, $X^{A'}$ is $C_1$-$C_4$ alkoxy optionally substituted with 1 to 6 fluoro. In some embodiments, $X^{A'}$ is $C_1$-$C_2$ alkoxy optionally substituted with 1 to 3 fluoro. In some embodiments, $X^{A'}$ is —$OCH_3$, —$OCF_3$, —$OCHF_2$, or —$OCFH_2$. In some embodiments, $X^{A'}$ is —$OCH_3$, —$OCF_3$ or —$OCHF_2$, In some embodiments, $X^{A'}$ is —CN.

In some embodiments, $X^{A'}$ is —$NO_2$.

In some embodiments, $X^{A'}$ is —$N(R^{7A'})(R^{8A'})$. In some embodiments, $X^{A'}$ is —$NH(CH_3)$, —$N(CH_3)_2$, or —$N(CH_3)(CH_2CH_3)$. In some embodiments, $X^{A'}$ is —$N(CH_3)_2$.

In some embodiments, $X^{A'}$ is —$SR^{7A'}$. In some embodiments, $X^{A'}$ is —$SCH_3$ or —$SCH_2CH_3$.

In some embodiments, $X^{A'}$ is —$SCH_3$.

In some embodiments, $X^{A'}$ is —$S(O)_2R$ A'. In some embodiments, $X^{A'}$ is —$SO_2CH_3$, —$SO_2CH_2CH_3$, or —$SO_2CF_3$. In some embodiments, $X^{A'}$ is -(2$CH_3$ or —$SO_2CF_3$.

In some embodiments, $R^{1A'}$ is —H; halo; $C_1$-$C_4$ alkyl optionally substituted with 1 to 3 fluoro; cyclopropyl; $C_1$-$C_2$ alkoxy optionally substituted with 1 to 3 fluoro; —CN; —$NO_2$; —$N(R^{7A'})(R^{8A'})$; —$C(O)OR^{7A'}$; or —$C(O)N(R^{7A'})(R^{8A'})$. In some embodiments, $R^{5A'}$ is —H, —F, —Cl, —$CH_3$, —$CH_2CH_3$, —$CH(CH_3)_2$, —$CF_3$, cyclopropyl, —$OCH_3$, —$OCF_3$, —$OCHF_2$, —$OCFH_2$, —CN, —$NO_2$, —$CO_2CH_3$, —$CO_2CH_2CH_3$, —$C(O)N(CH_3)_2$, —$C(O)NH(CH_3)$, or —$C(O)N(CH_3)(CH_2CH_3)$. In some embodiments, $R^{1A'}$ is —H, —F, —Cl, —$CH_3$, —$CH_2CH_3$, —$CH(CH_3)_2$, —$CF_3$, cyclopropyl, —$OCH_3$, —$OCF_3$, —$OCHF_2$, —$OCFH_2$, —CN, —$NO_2$, —$CO_2CH_3$, —$CO_2CH_2CH_3$, —$C(O)N(CH_3)_2$, or —$C(O)NH(CH_3)$. In some embodiments, $R^{1A'}$ is —H, —F, —Cl, —$CH_3$, or —$CF_3$.

In some embodiments, $R^{1A'}$ is —H.

In some embodiments, $R^{1A'}$ is halo. In some embodiments, $R^{1A'}$ is —F or —Cl.

In some embodiments, $R^{1A'}$ is $C_1$-$C_4$ alkyl optionally substituted with 1 to 3 fluoro. In some embodiments, $R^{1A'}$ is —$CH_3$, —$CH_2CH_3$, —$CH(CH_3)_2$, or —$CF_3$. In some embodiments, $R^{1A'}$ is —$CH_3$ or —$CF_3$.

In some embodiments, $R^{1A'}$ is $C_3$-$C_6$ cycloalkyl. In some embodiments, $R^{1A'}$ is cyclopropyl.

In some embodiments, $R^{1A'}$ is $C_1$-$C_4$ alkoxy optionally substituted with 1 to 3 fluoro. In some embodiments, $R^{2A'}$ is $C_1$-$C_2$ alkoxy optionally substituted with 1 to 3 fluoro. In some embodiments, $R^{1A'}$ is —$OCH_3$, —$OCF_3$, —$OCHF_2$, or —$OCFH_2$.

In some embodiments, $R^{1A'}$ is —CN.

In some embodiments, $R^{1A'}$ is —$NO_2$.

In some embodiments, $R^{1A'}$ is —$N(R^{7A'})(R^{8A'})$.

In some embodiments, $R^{1A'}$ is —$C(O)OR^{7A'}$. In some embodiments, $R^{1A'}$ is —$CO_2CH_3$, or —$CO_2CH_2CH_3$.

In some embodiments, $R^{1A'}$ is —$C(O)N(R^{7A'})(R^{8A'})$. In some embodiments, $R^{1A'}$ is —$C(O)N(CH_3)_2$, —$C(O)NH(CH_3)$, or —$C(O)N(CH_3)(CH_2CH_3)$. In some embodiments, $R^{1A'}$ is —$C(O)N(CH_3)_2$ or —$C(O)NH(CH_3)$.

In some embodiments, $R^{2A'}$ is —H; halo; $C_1$-$C_4$ alkyl optionally substituted with 1 to 3 fluoro; cyclopropyl; or $C_1$-$C_2$ alkoxy optionally substituted with 1 to 3 fluoro. In some embodiments, $R^{2A'}$ is —H, —F, —Cl, —$CH_3$, —$CH_2CH_3$, —$CH(CH_3)_2$, —$CF_3$, cyclopropyl, —$OCH_3$, —$OCF_3$, —$OCHF_2$, or —$OCFH_2$. In some embodiments, $R^{2A'}$ is —H, —F, —Cl, —$CH_3$, or —$CF_3$.

In some embodiments, $R^{2A'}$ is —H.

In some embodiments, $R^{2A'}$ is halo. In some embodiments, $R^{2A'}$ is —F or —Cl.

In some embodiments, $R^{2A'}$ is $C_1$-$C_4$ alkyl optionally substituted with 1 to 3 fluoro. In some embodiments, $R^{2A'}$ is —$CH_3$, —$CH_2CH_3$, —$CH(CH_3)_2$, or —$CF_3$. In some embodiments, $R^{2A'}$ is —$CH_3$ or —$CF_3$.

In some embodiments, $R^{2A'}$ is cyclopropyl.

In some embodiments, $R^{2A'}$ is $C_1$-$C_4$ alkoxy optionally substituted with 1 to 3 fluoro. In some embodiments, $R^{2A'}$ is $C_1$-$C_2$ alkoxy optionally substituted with 1 to 3 fluoro. In some embodiments, $R^{2A'}$ is —$OCH_3$, —$OCF_3$, —$OCHF_2$, or —$OCFH_2$.

In some embodiments, $R^{3A'}$ is —H, —F, —Cl, —$CH_3$, —$CF_3$, or —$OCH_3$. In some embodiments, $R^{3A'}$ is —H, —F, —Cl, —$CH_3$, or —$CF_3$.

In some embodiments, $R^{3A'}$ is —H.

In some embodiments, $R^{3A'}$ is —F or —Cl.

In some embodiments, $R^{3A'}$ is —$CH_3$ or —$CF_3$.

In some embodiments, $R^{3A'}$ is —$OCH_3$.

In some embodiments, $R^{4A'}$ is —H; —F; —Cl; $C_1$-$C_3$ alkyl optionally substituted with 1 to 3 fluoro; or cyclopropyl. In some embodiments, $R^{4A'}$ is —H, —F, —Cl, —$CH_3$, or cyclopropyl. In some embodiments, $R^{4A'}$ is —H, —Cl, or —$CH_3$.

In some embodiments, $R^{4A'}$ is —H.

In some embodiments, $R^{4A'}$ is —F or —Cl.

In some embodiments, $R^{4A'}$ is $C_1$-$C_3$ alkyl optionally substituted with 1 to 3 fluoro. In some embodiments, $R^{4A'}$ is —$CH_3$.

In some embodiments, $R^{4A'}$ is cyclopropyl.

In some embodiments, $R^{5A'}$ is —H or —$CH_3$.

In some embodiments, $R^{5A'}$ is —H.

In some embodiments, $R^{5A'}$ is —$CH_3$.

In some embodiments, $R^{6A'}$ is —H, —F, or —$CH_3$.

In some embodiments, $R^{6A'}$ is —H.

In some embodiments, $R^{6A'}$ is —F.

In some embodiments, $R^{6A'}$ is —$CH_3$.

In some embodiments, a chemical entity of formula $I^{A'}$ is a chemical entity of formula $Ia^{A'}$:

$Ia^{A'}$

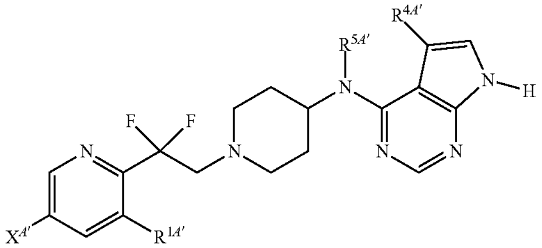

wherein each of $R^{1A'}$, $X^{A'}$, $R^{4A'}$, and $R^{5A'}$ is as described in embodiments of formula $I^{A'}$, supra, or described in embodiments herein, both singly and in combination.

In some embodiments of formula $Ia^{A'}$:

$X^{A'}$ is —H, —F, —Cl, —$CH_3$, —$CH_2CH_3$, —$CH(CH_3)_2$, —$CF_3$, —$CHF_2$, —$CH_2F$, —$CF_2CF_3$, —$CH_2CF_2CF_3$, —$CH(CF_3)_2$, cyclopropyl, —$OCH_3$, —$OCF_3$, —$OCHF_2$, —$OCFH_2$, —CN, —$NO_2$, —$N(CH_3)_2$, —$SCH_3$, —$SO_2CH_3$, or —$SO_2CF_3$;

$R^{1A'}$ is —H, —F, —Cl, —$CH_3$, —$CH_2CH_3$, —$CH(CH_3)_2$, —$CF_3$, cyclopropyl, —$OCH_3$, —$OCF_3$, —$OCHF_2$, —$OCFH_2$, —CN, —$NO_2$, —$CO_2CH_3$, —$CO_2CH_2CH_3$, —$C(O)N(CH_3)_2$, or —$C(O)NH(CH_3)$;

$R^{4A'}$ is —H, —F, —Cl, —$CH_3$, or cyclopropyl; and $R^{5A'}$ is —H or —$CH_3$.

In some embodiments of formula $Ia^{A'}$:

$X^{A'}$ is —H, —F, —Cl, —$CH_3$, —$CH_2CH_3$, —$CH(CH_3)_2$, —$CF_3$, —$CHF_2$, —$CH_2F$, cyclopropyl, —$OCH_3$, —$OCF_3$, —$OCHF_2$, —CN, or —$SCH_3$;

$R^{1A'}$ is —H, —F, —Cl, —$CH_3$, or —$CF_3$;

$R^{4A'}$ is —H, —Cl, or —$CH_3$; and $R^{5A'}$ is —H or —$CH_3$.

In some embodiments of formula $Ia^{A'}$:

$X^{A'}$ is —Cl, —$CH_3$, or —$CF_3$;

$R^{1A'}$ is —H or —F;

$R^{4A'}$ is —Cl or —$CH_3$; and $R^{5A'}$ is —H.

In some embodiments of formula $Ia^{A'}$:

$X^{A'}$ is —Cl, —$CH_3$, or —$CF_3$;

$R^{1A'}$ is —H;

$R^{4A'}$ is —H; and $R^{5A'}$ is —$CH_3$.

In some embodiments, a chemical entity of formula $I^{A'}$ is a chemical entity of formula $II^{A'}$.

$II^{A'}$

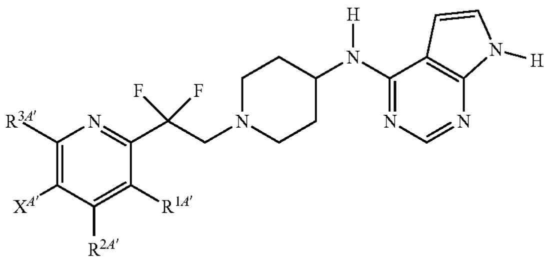

wherein each of $R^{1A'}$, $R^{2A'}$, $X^{A'}$, and $R^{3A'}$ is as described in embodiments of formula $I^{A'}$, supra, or described in embodiments herein, both singly and in combination.

In some embodiments of formula $II^{A'}$.

$X^{A'}$ is —H, —F, —Cl, —$CH_3$, —$CH_2CH_3$, —$CH(CH_3)_2$, —$CF_3$, —$CHF_2$, —$CH_2F$, —$CF_2CF_3$, —$CH_2CF_2CF_3$, —$CH(CF_3)_2$, cyclopropyl, —$OCH_3$, —$OCF_3$, —$OCHF_2$, —$OCFH_2$, —CN, —$NO_2$, —$N(CH_3)_2$, —$SCH_3$, —$SO_2CH_3$, or —$SO_2CF_3$;

$R^{1A'}$ is —H, —F, —Cl, —$CH_3$, —$CH_2CH_3$, —$CH(CH_3)_2$, —$CF_3$, cyclopropyl, —$OCH_3$, —$OCF_3$, —$OCHF_2$, —$OCFH_2$, —CN, —$NO_2$, —$CO_2CH_3$, —$CO_2CH_2CH_3$, —$C(O)N(CH_3)_2$, or —$C(O)NH(CH_3)$;

$R^{2A'}$ is —H, —F, —Cl, —$CH_3$, —$CH_2CH_3$, —$CH(CH_3)_2$, —$CF_3$, cyclopropyl, —$OCH_3$, —$OCF_3$, —$OCHF_2$, or —$OCFH_2$; and $R^{3A'}$ is —H, —F, —Cl, —$CH_3$, —$CF_3$, or —$OCH_3$.

In some embodiments of formula $II^{A'}$.

$X^{A'}$ is —H, —F, —Cl, —$CH_3$, —$CH_2CH_3$, —$CH(CH_3)_2$, —$CF_3$, —$CHF_2$, —$CH_2F$, cyclopropyl, —$OCH_3$, —$OCF_3$, —$OCHF_2$, —CN, or —$SCH_3$;

$R^{5A'}$ is —H, —F, —Cl, —$CH_3$, or —$CF_3$;

$R^{2A'}$ is —H, —F, —Cl, —$CH_3$, or —$CF_3$; and $R^{3A'}$ is —H, —F, —Cl, —$CH_3$, or —$CF_3$.

In some embodiments of formula $II^{A'}$.

$X^{A'}$ is —F, —Cl, —$CH_3$, or —$CF_3$;

$R^{1A'}$ is —H;

$R^{2A'}$ is —H, —F, —Cl, or —$CH_3$; and $R^{3A'}$ is —H, —F, —Cl, or —$CH_3$.

In some embodiments, a chemical entity of formula $I^{A'}$ is a chemical entity of formula $IIa^{A'}$:

$IIa^{A'}$

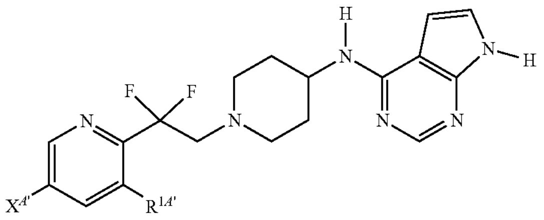

wherein each of $R^{1A'}$ and $X^{A'}$ is as described in embodiments of formula $I^{A'}$, supra, or described in embodiments herein, both singly and in combination.

In some embodiments of formula $IIa^{A'}$:

$X^{A'}$ is —H, —F, —Cl, —$CH_3$, —$CH_2CH_3$, —$CH(CH_3)_2$, —$CF_3$, —$CHF_2$, —$CH_2F$, —$CF_2CF_3$, —$CH_2CF_2CF_3$, —$CH(CF_3)_2$, cyclopropyl, —$OCH_3$, —$OCF_3$, —$OCHF_2$, —$OCFH_2$, —CN, —$NO_2$, —$N(CH_3)_2$, —$SCH_3$, —$SO_2CH_3$, or —$SO_2CF_3$; and $R^{1A'}$ is —H, —F, —Cl, —$CH_3$, —$CH_2CH_3$, —$CH(CH_3)_2$, —$CF_3$, cyclopropyl, —$OCH_3$, —$OCF_3$, —$OCHF_2$, —$OCFH_2$, —CN, —$NO_2$, —$CO_2CH_3$, —$CO_2CH_2CH_3$, —$C(O)N(CH_3)_2$, or —$C(O)NH(CH_3)$.

In some embodiments of formula $IIa^{A'}$:

$X^{A'}$ is —H, —F, —Cl, —$CH_3$, —$CH_2CH_3$, —$CH(CH_3)_2$, —$CF_3$, —$CHF_2$, —$CH_2F$, cyclopropyl, —$OCH_3$, —$OCF_3$, —$OCHF_2$, —CN, or —$SCH_3$; and $R^{1A'}$ is —H, —F, —Cl, —$CH_3$, or —$CF_3$.

In some embodiments of formula $IIa^{A'}$:

$X^{A'}$ is —H, —F, —Cl, —$CH_3$, —$CH_2CH_3$, —$CF_3$, —$CHF_2$, —$CH_2F$, cyclopropyl, —$OCH_3$, —$OCF_3$, —$OCHF_2$, —CN, or —$SCH_3$; and $R^{1A'}$ is —H, —F, —Cl, or —$CH_3$.

In some embodiments, a chemical entity of formula $I^{A'}$ is a chemical entity of formula $III^{A'}$.

$III^{A'}$

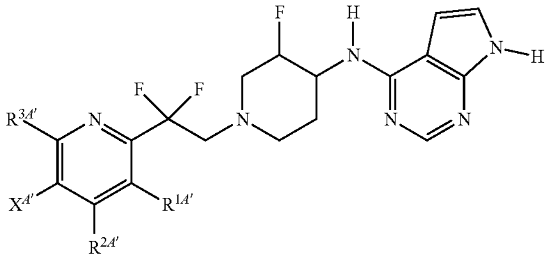

wherein each of $R^{1A'}$, $R^{2A'}$, $X^{A'}$, and $R^{3A'}$ is as described in embodiments of formula $I^{A'}$, supra, or described in embodiments herein, both singly and in combination.

In some embodiments of formula $III^{A'}$.

$X^{A'}$ is —H, —F, —Cl, —$CH_3$, —$CH_2CH_3$, —$CH(CH_3)_2$, —$CF_3$, —$CHF_2$, —$CH_2F$, —$CF_2CF_3$, —$CH_2CF_2CF_3$, —$CH(CF_3)_2$, cyclopropyl, —$OCH_3$, —$OCF_3$, —$OCHF_2$, —$OCFH_2$, —CN, —$NO_2$, —$N(CH_3)_2$, —$SCH_3$, —$SO_2CH_3$, or —$SO_2CF_3$;

$R^{1A'}$ is —H, —F, —Cl, —$CH_3$, —$CH_2CH_3$, —$CH(CH_3)_2$, —$CF_3$, cyclopropyl, —$OCH_3$, —$OCF_3$, —$OCHF_2$, —$OCFH_2$, —CN, —$NO_2$, —$CO_2CH_3$, —$CO_2CH_2CH_3$, —$C(O)N(CH_3)_2$, or —$C(O)NH(CH_3)$;

$R^{2A'}$ is —H, —F, —Cl, —$CH_3$, —$CH_2CH_3$, —$CH(CH_3)_2$, —$CF_3$, cyclopropyl, —$OCH_3$, —$OCF_3$, —$OCHF_2$, or —$OCFH_2$; and $R^{3A'}$ is —H, —F, —Cl, —$CH_3$, —$CF_3$, or —$OCH_3$.

In some embodiments of formula $III^{A'}$.

$X^{A'}$ is —H, —F, —Cl, —$CH_3$, —$CH_2CH_3$, —$CH(CH_3)_2$, —$CF_3$, —$CHF_2$, —$CH_2F$, cyclopropyl, —$OCH_3$, —$OCF_3$, —$OCHF_2$, —CN, or —$SCH_3$;

$R^{5A'}$ is —H, —F, —Cl, —$CH_3$, or —$CF_3$;

$R^{2A'}$ is —H, —F, —Cl, —$CH_3$, or —$CF_3$; and $R^{3A'}$ is —H, —F, —Cl, —$CH_3$, or —$CF_3$.

In some embodiments, a chemical entity of formula $I^{A'}$ is a chemical entity of formula $IIIa^{A'}$:

$IIIa^{A'}$

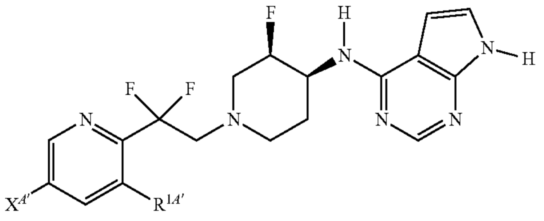

wherein each of $R^{1A'}$ and $X^{A'}$ is as described in embodiments for formula $I^{A'}$, supra, or described in embodiments herein, both singly and in combination.

In some embodiments of formula $IIIa^{A'}$:

$X^{A'}$ is —H, —F, —Cl, —$CH_3$, —$CH_2CH_3$, —$CH(CH_3)_2$, —$CF_3$, —$CHF_2$, —$CH_2F$, —$CF_2CF_3$, —$CH_2CF_2CF_3$, —$CH(CF_3)_2$, cyclopropyl, —$OCH_3$, —$OCF_3$, —$OCHF_2$, —$OCFH_2$, —CN, —$NO_2$, —$N(CH_3)_2$, —$SCH_3$, —$SO_2CH_3$, or —$SO_2CF_3$; and $R^{1A'}$ is —H, —F, —Cl, —$CH_3$, —$CH_2CH_3$, —$CH(CH_3)_2$, —$CF_3$, cyclopropyl, —$OCH_3$, —$OCF_3$, —$OCHF_2$, —$OCFH_2$, —CN, —$NO_2$, —$CO_2CH_3$, —$CO_2CH_2CH_3$, —$C(O)N(CH_3)_2$, or —$C(O)NH(CH_3)$.

In some embodiments of formula $IIIa^{A'}$:

$X^{A'}$ is —H, —F, —Cl, —$CH_3$, —$CH_2CH_3$, —$CH(CH_3)_2$, —$CF_3$, —$CHF_2$, —$CH_2F$, cyclopropyl, —$OCH_3$, —$OCF_3$, —$OCHF_2$, —CN, or —$SCH_3$; and $R^{1A'}$ is —H, —F, —Cl, —$CH_3$, or —$CF_3$.

In some embodiments of formula $IIIa^{A'}$:

$X^{A'}$ is —F, —Cl, —$CH_3$, —$CH_2CH_3$, —$CF_3$, —$CHF_2$, —$CH_2F$, cyclopropyl, —$OCF_3$, or —$OCHF_2$; and $R^{1A'}$ is —H or —F.

In some embodiments, a chemical entity of formula $I^{A'}$ is a chemical entity of formula $IIIb^{A'}$.

$IIIb^{A'}$

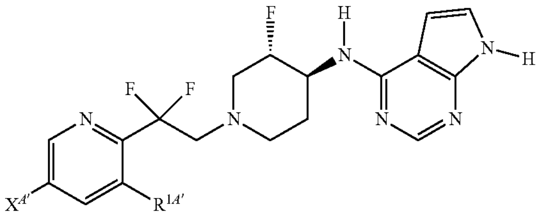

wherein each of $R^{1A'}$ and $X^{A'}$ is as described in embodiments for formula $I^{A'}$ supra, or described in embodiments herein, both singly and in combination.

In some embodiments of formula $IIIb^{A'}$, $X^{A'}$ is —H, —F, —Cl, —$CH_3$, —$CH_2CH_3$, —$CH(CH_3)_2$, —$CF_3$, —$CHF_2$, —$CH_2F$, —$CF_2CF_3$, —$CH_2CF_2CF_3$, —$CH(CF_3)_2$, cyclopropyl, —$OCH_3$, —$OCF_3$, —$OCHF_2$, —$OCFH_2$, —CN, —$NO_2$, —$N(CH_3)_2$, —$SCH_3$, —$SO_2CH_3$, or —$SO_2CF_3$; and $R^{1A'}$ is —H, —F, —Cl, —$CH_3$, —$CH_2CH_3$, —$CH(CH_3)_2$, —$CF_3$, cyclopropyl, —$OCH_3$, —$OCF_3$, —$OCHF_2$, —$OCFH_2$, —CN, —$NO_2$, —$CO_2CH_3$, —$CO_2CH_2CH_3$, —$C(O)N(CH_3)_2$, or —$C(O)NH(CH_3)$.

In some embodiments of formula $IIIb^{A'}$:

$X^{A'}$ is —H, —F, —Cl, —$CH_3$, —$CH_2CH_3$, —$CH(CH_3)_2$, —$CF_3$, —$CHF_2$, —$CH_2F$, cyclopropyl, —$OCH_3$, —$OCF_3$, —$OCHF_2$, —CN, or —$SCH_3$; and $R^{1A'}$ is —H, —F, —Cl, —$CH_3$, or —$CF_3$.

In some embodiments of formula $IIIb^{A'}$:

$X^{A'}$ is —F, —Cl, —$CH_3$, —$CH_2CH_3$, —$CF_3$, —$CHF_2$, —$CH_2F$, cyclopropyl, —$OCF_3$, or —$OCHF_2$; and $R^{1A'}$ is —H or —F.

In some embodiments, a chemical entity of formula $I^{A'}$ is a chemical entity of formula $IV^{A'}$:

$IV^{A'}$

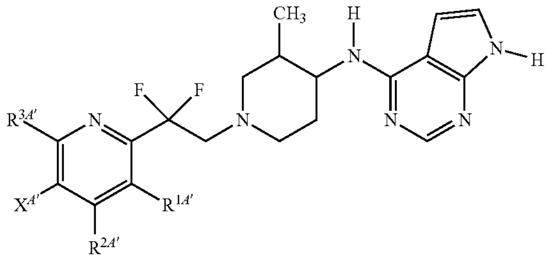

wherein each of $R^{1A'}$, $R^{2A'}$, $X^{A'}$, and $R^{3A'}$ is as described in embodiments of formula $I^{A'}$, supra, or described in embodiments herein, both singly and in combination.

In some embodiments of formula $IV^{A'}$:

$X^{A'}$ is —H, —F, —Cl, —$CH_3$, —$CH_2CH_3$, —$CH(CH_3)_2$, —$CF_3$, —$CHF_2$, —$CH_2F$, —$CF_2CF_3$, —$CH_2CF_2CF_3$, —$CH(CF_3)_2$, cyclopropyl, —$OCH_3$, —$OCF_3$, —$OCHF_2$, —$OCFH_2$, —CN, —$NO_2$, —$N(CH_3)_2$, —$SCH_3$, —$SO_2CH_3$, or —$SO_2CF_3$;

$R^{1A'}$ is —H, —F, —Cl, —$CH_3$, —$CH_2CH_3$, —$CH(CH_3)_2$, —$CF_3$, cyclopropyl, —$OCH_3$, —$OCF_3$, —$OCHF_2$, —$OCFH_2$, —CN, —$NO_2$, —$CO_2CH_3$, —$CO_2CH_2CH_3$, —$C(O)N(CH_3)_2$, or —$C(O)NH(CH_3)$;

$R^{2A'}$ is —H, —F, —Cl, —$CH_3$, —$CH_2CH_3$, —$CH(CH_3)_2$, —$CF_3$, cyclopropyl, —$OCH_3$, —$OCF_3$, —$OCHF_2$, or —$OCFH_2$; and $R^{3A'}$ is —H, —F, —Cl, —$CH_3$, —$CF_3$, or —$OCH_3$.

In some embodiments of formula $IV^{A'}$:

$X^{A'}$ is —H, —F, —Cl, —$CH_3$, —$CH_2CH_3$, —$CH(CH_3)_2$, —$CF_3$, —$CHF_2$, —$CH_2F$, cyclopropyl, —$OCH_3$, —$OCF_3$, —$OCHF_2$, —CN, or —$SCH_3$;

$R^{1A'}$ is —H, —F, —Cl, —$CH_3$, or —$CF_3$;

$R^{2A'}$ is —H, —F, —Cl, —$CH_3$, or —$CF_3$; and $R^{3A'}$ is —H, —F, —Cl, —$CH_3$, or —$CF_3$.

In some embodiments, a chemical entity of formula $I^{A'}$ is a chemical entity of formula $IVa^{A'}$:

$IVa^{A'}$

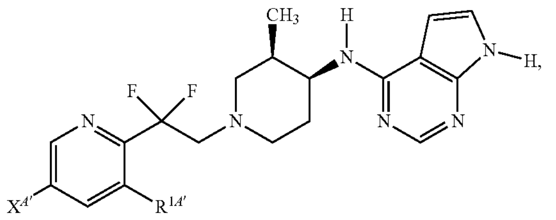

wherein each of $R^{1A'}$ and $X^{A'}$ is as described in embodiments for formula $I^{A'}$, supra, or described in embodiments herein, both singly and in combination.

In some embodiments of formula $IVa^{A'}$:

$X^{A'}$ is —H, —F, —Cl, —$CH_3$, —$CH_2CH_3$, —$CH(CH_3)_2$, —$CF_3$, —$CHF_2$, —$CH_2F$, —$CF_2CF_3$, —$CH_2CF_2CF_3$, —$CH(CF_3)_2$, cyclopropyl, —$OCH_3$, —$OCF_3$, —$OCHF_2$, —$OCFH_2$, —CN, —$NO_2$, —$N(CH_3)_2$, —$SCH_3$, —$SO_2CH_3$, or —$SO_2CF_3$; and $R^{1A'}$ is —H, —F, —Cl, —$CH_3$, —$CH_2CH_3$, —$CH(CH_3)_2$, —$CF_3$, cyclopropyl, —$OCH_3$, —$OCF_3$, —$OCHF_2$, —$OCFH_2$, —CN, —$NO_2$, —$CO_2CH_3$, —$CO_2CH_2CH_3$, —$C(O)N(CH_3)_2$, or —$C(O)NH(CH_3)$.

In some embodiments of formula $IVa^{A'}$:

$X^{A'}$ is —H, —F, —Cl, —$CH_3$, —$CH_2CH_3$, —$CH(CH_3)_2$, —$CF_3$, —$CHF_2$, —$CH_2F$, cyclopropyl, —$OCH_3$, —$OCF_3$, —$OCHF_2$, —CN, or —$SCH_3$; and $R^{1A'}$ is —H, —F, —Cl, —$CH_3$, or —$CF_3$.

In some embodiments of formula $IVa^{A'}$:

$X^{A'}$ is —F, —Cl, —$CH_3$, —$CH_2CH_3$, —$CF_3$, —$CHF_2$, —$CH_2F$, cyclopropyl, —$OCF_3$, or —$OCHF_2$; and $R^{1A'}$ is —H or —F.

In some embodiments, a chemical entity of formula $I^{A'}$ is a chemical entity of formula $IVb^{A'}$:

$IVb^{A'}$

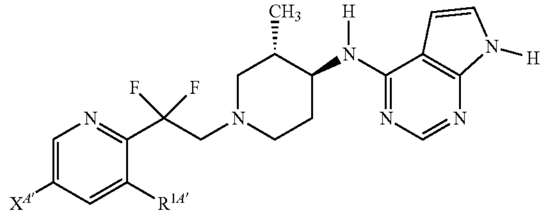

wherein each of $R^{1A'}$ and $X^{A'}$ is as described in embodiments for formula $I^{A'}$, supra, or described in embodiments herein, both singly and in combination.

In some embodiments of formula $IVb^{A'}$:

$X^{A'}$ is —H, —F, —Cl, —$CH_3$, —$CH_2CH_3$, —$CH(CH_3)_2$, —$CF_3$, —$CHF_2$, —$CH_2F$, —$CF_2CF_3$, —$CH_2CF_2CF_3$, —$CH(CF_3)_2$, cyclopropyl, —$OCH_3$, —$OCF_3$, —$OCHF_2$, —$OCFH_2$, —CN, —$NO_2$, —$N(CH_3)_2$, —$SCH_3$, —$SO_2CH_3$, or —$SO_2CF_3$; and $R^{1A'}$ is —H, —F, —Cl, —$CH_3$, —$CH_2CH_3$, —$CH(CH_3)_2$, —$CF_3$, cyclopropyl, —$OCH_3$, —$OCF_3$, —$OCHF_2$, —$OCFH_2$, —CN, —$NO_2$, —$CO_2CH_3$, —$CO_2CH_2CH_3$, —$C(O)N(CH_3)_2$, or —$C(O)NH(CH_3)$.

In some embodiments of formula $IVb^{A'}$:

$X^{A'}$ is —H, —F, —Cl, —$CH_3$, —$CH_2CH_3$, —$CH(CH_3)_2$, —$CF_3$, —$CHF_2$, —$CH_2F$, cyclopropyl, —$OCH_3$, —$OCF_3$, —$OCHF_2$, —CN, or —$SCH_3$; and $R^{1A'}$ is —H, —F, —Cl, —$CH_3$, or —$CF_3$.

In some embodiments of formula $IVb^{A'}$:

$X^{A'}$ is —F, —Cl, —$CH_3$, —$CH_2CH_3$, —$CF_3$, —$CHF_2$, —$CH_2F$, cyclopropyl, —$OCF_3$, or —$OCHF_2$; and $R^{1A'}$ is —H or —F.

In some embodiments, a chemical entity of formula $I^{A'}$ is a chemical entity of formula $V^{A'}$:

$V^{A'}$

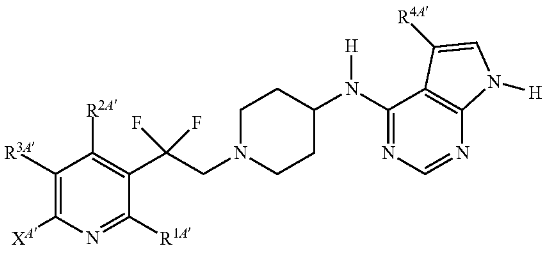

wherein each of $R^{1A'}$, $R^{2A'}$, $X^{A'}$, $R^{3A'}$ and $R^{4A'}$ is as described in embodiments of formula $I^{A'}$, supra, or described in embodiments herein, both singly and in combination.

In some embodiments of formula $V^{A'}$:

$X^{A'}$ is —H, —F, —Cl, —$CH_3$, —$CH_2CH_3$, —$CH(CH_3)_2$, —$CF_3$, —$CHF_2$, —$CH_2F$, —$CF_2CF_3$, —$CH_2CF_2CF_3$, —$CH(CF_3)_2$, cyclopropyl, —$OCH_3$, —$OCF_3$, —$OCHF_2$, —$OCFH_2$, —CN, —$NO_2$, —$N(CH_3)_2$, —$SCH_3$, —$SO_2CH_3$, or —$SO_2CF_3$;

$R^{1A'}$ is —H, —F, —Cl, —$CH_3$, —$CH_2CH_3$, —$CH(CH_3)_2$, —$CF_3$, cyclopropyl, —$OCH_3$, —$OCF_3$, —$OCHF_2$, —$OCFH_2$, —CN, —$NO_2$, —$CO_2CH_3$, —$CO_2CH_2CH_3$, —$C(O)N(CH_3)_2$, or —$C(O)NH(CH_3)$;

$R^{2A'}$ is —H, —F, —Cl, —$CH_3$, —$CH_2CH_3$, —$CH(CH_3)_2$, —$CF_3$, cyclopropyl, —$OCH_3$, —$OCF_3$, —$OCHF_2$, or —$OCFH_2$;

$R^{3A'}$ is —H, —F, —Cl, —$CH_3$, —$CF_3$, or —$OCH_3$; and $R^{4A'}$ is —H, —F, —Cl, —$CH_3$, or cyclopropyl.

In some embodiments of formula $V^{A'}$:

$X^{A'}$ is —H, —F, —Cl, —$CH_3$, —$CH_2CH_3$, —$CH(CH_3)_2$, —$CF_3$, —$CHF_2$, —$CH_2F$, cyclopropyl, —$OCH_3$, —$OCF_3$, —$OCHF_2$, —CN, or —$SCH_3$;

$R^{5A'}$ is —H, —F, —Cl, —$CH_3$, or —$CF_3$;

$R^{1A'}$ is —H, —F, —Cl, —$CH_3$, or —$CF_3$;

$R^{3A'}$ is —H, —F, —Cl, —$CH_3$, or —$CF_3$; and $R^{4A'}$ is —H, —Cl, or —$CH_3$.

In some embodiments of formula $V^{A'}$:

$X^{A'}$ is —H, —$CH_3$, or —$CF_3$;

$R^{1A'}$ is —H, —F, or —$CF_3$;

$R^{2A'}$ is —H;

$R^{3A'}$ is —H or —$CF_3$; and $R^{4A'}$ is —Cl or —$CH_3$.

In some embodiments, a chemical entity of formula $I^{A'}$ is a chemical entity of formula $Va^{A'}$:

$Va^{A'}$

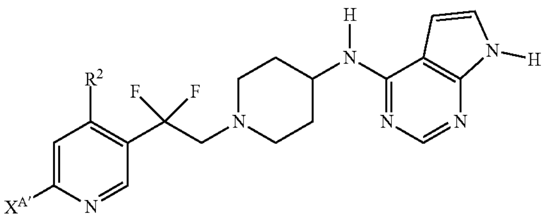

wherein each of $R^{2A'}$ and $X^{A'}$ is as described in embodiments of formula $I^{A'}$, supra, or described in embodiments herein, both singly and in combination.

In some embodiments of formula $Va^{A'}$:

$X^{A'}$ is —H, —F, —Cl, —$CH_3$, —$CH_2CH_3$, —$CH(CH_3)_2$, —$CF_3$, —$CHF_2$, —$CH_2F$, —$CF_2CF_3$, —$CH_2CF_2CF_3$, —$CH(CF_3)_2$, cyclopropyl, —$OCH_3$, —$OCF_3$, —$OCHF_2$, —$OCFH_2$, —CN, —$NO_2$, —$N(CH_3)_2$, —$SCH_3$, —$SO_2CH_3$, or —$SO_2CF_3$; and $R^{2A'}$ is —H, —F, —Cl, —$CH_3$, —$CH_2CH_3$, —$CH(CH_3)_2$, —$CF_3$, cyclopropyl, —$OCH_3$, —$OCF_3$, —$OCHF_2$, or —$OCFH_2$.

In some embodiments of formula $Va^{A'}$:

$X^{A'}$ is —H, —F, —Cl, —$CH_3$, —$CH_2CH_3$, —$CH(CH_3)_2$, —$CF_3$, —$CHF_2$, —$CH_2F$, cyclopropyl, —$OCH_3$, —$OCF_3$, —$OCHF_2$, —CN, or —$SCH_3$; and $R^{1A'}$ is —H, —F, —Cl, —$CH_3$, or —$CF_3$.

In some embodiments of formula $Va^{A'}$:

$X^{A'}$ is —H, —F, —Cl, —$CH_3$, —$CH_2CH_3$, —$CF_3$, cyclopropyl, —$OCH_3$, —$OCF_3$, or —$SCH_3$; and $R^{2A'}$ is —H, —F, or —$CF_3$.

In some embodiments, a chemical entity of formula $I^{A'}$ is a chemical entity of formula $VI^{A'}$:

$VI^{A'}$

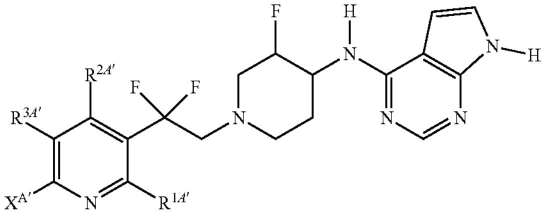

wherein each of $R^{1A'}$, $R^{2A'}$, $X^{A'}$, and $R^{3A'}$ is as described in embodiments of formula $I^{A'}$, supra, or described in embodiments herein, both singly and in combination.

In some embodiments of formula $VI^{A'}$:

$X^{A'}$ is —H, —F, —Cl, —$CH_3$, —$CH_2CH_3$, —$CH(CH_3)_2$, —$CF_3$, —$CHF_2$, —$CH_2F$, —$CF_2CF_3$, —$CH_2CF_2CF_3$, —$CH(CF_3)_2$, cyclopropyl, —$OCH_3$, —$OCF_3$, —$OCHF_2$, —$OCFH_2$, —CN, —$NO_2$, —$N(CH_3)_2$, —$SCH_3$, —$SO_2CH_3$, or —$SO_2CF_3$;

$R^{1A'}$ is —H, —F, —Cl, —$CH_3$, —$CH_2CH_3$, —$CH(CH_3)_2$, —$CF_3$, cyclopropyl, —$OCH_3$, —$OCF_3$, —$OCHF_2$, —$OCFH_2$, —CN, —$NO_2$, —$CO_2CH_3$, —$CO_2CH_2CH_3$, —$C(O)N(CH_3)_2$, or —$C(O)NH(CH_3)$;

$R^{2A'}$ is —H, —F, —Cl, —$CH_3$, —$CH_2CH_3$, —$CH(CH_3)_2$, —$CF_3$, cyclopropyl, —$OCH_3$, —$OCF_3$, —$OCHF_2$, or —$OCFH_2$; and $R^{3A'}$ is —H, —F, —Cl, —$CH_3$, —$CF_3$, or —$OCH_3$.

In some embodiments of formula $VI^{A'}$:

$X^{A'}$ is —H, —F, —Cl, —$CH_3$, —$CH_2CH_3$, —$CH(CH_3)_2$, —$CF_3$, —$CHF_2$, —$CH_2F$, cyclopropyl, —$OCH_3$, —$OCF_3$, —$OCHF_2$, —CN, or —$SCH_3$;

$R^{5A'}$ is —H, —F, —Cl, —$CH_3$, or —$CF_3$;

$R^{2A'}$ is —H, —F, —Cl, —$CH_3$, or —$CF_3$; and $R^{3A'}$ is —H, —F, —Cl, —$CH_3$, or —$CF_3$.

In some embodiments, a chemical entity of formula $I^{A'}$ is a chemical entity of formula $VIa^{A'}$:

$VIa^{A'}$

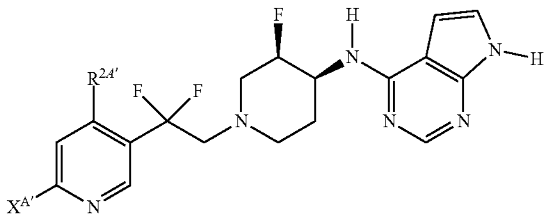

wherein each of $R^{2A'}$ and $X^{A'}$ is as described in embodiments for formula $I^{A'}$ supra, or described in embodiments herein, both singly and in combination.

In some embodiments of formula $VIa^{A'}$:

$X^{A'}$ is —H, —F, —Cl, —$CH_3$, —$CH_2CH_3$, —$CH(CH_3)_2$, —$CF_3$, —$CHF_2$, —$CH_2F$, —$CF_2CF_3$, —$CH_2CF_2CF_3$, —$CH(CF_3)_2$, cyclopropyl, —$OCH_3$, —$OCF_3$, —$OCHF_2$, —$OCFH_2$, —CN, —$NO_2$, —$N(CH_3)_2$, —$SCH_3$, —$SO_2CH_3$, or —$SO_2CF_3$; and $R^{2A'}$ is —H, —F, —Cl, —$CH_3$, —$CH_2CH_3$, —$CH(CH_3)_2$, —$CF_3$, cyclopropyl, —$OCH_3$, —$OCF_3$, —$OCHF_2$, or —$OCFH_2$.

In some embodiments of formula $VIa^{A'}$:

$X^{A'}$ is —H, —F, —Cl, —$CH_3$, —$CH_2CH_3$, —$CH(CH_3)_2$, —$CF_3$, —$CHF_2$, —$CH_2F$, cyclopropyl, —$OCH_3$, —$OCF_3$, —$OCHF_2$, —CN, or —$SCH_3$; and $R^{2A'}$ is —H, —F, —Cl, —$CH_3$, or —$CF_3$.

In some embodiments of formula $VIa^{A'}$:

$X^{A'}$ is —$CH_3$, —$CH_2CH_3$, —$CF_3$, cyclopropyl, —$OCH_3$, —$OCF_3$, or —$SCH_3$; and $R^{2A'}$ is —H.

In some embodiments, a chemical entity of formula $I^{A'}$ is a chemical entity of formula $VIb^{A'}$:

$VIb^{A'}$

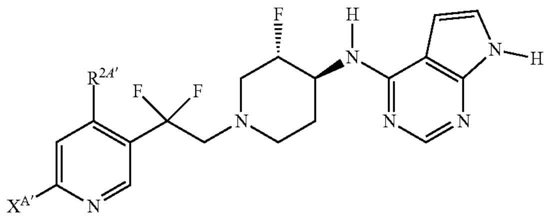

wherein each of $R^{2A'}$ and $X^{A'}$ is as described in embodiments for formula $I^{A'}$ supra, or described in embodiments herein, both singly and in combination.

In some embodiments of formula $VIb^{A'}$:

$X^{A'}$ is —H, —F, —Cl, —$CH_3$, —$CH_2CH_3$, —$CH(CH_3)_2$, —$CF_3$, —$CHF_2$, —$CH_2F$, —$CF_2CF_3$, —$CH_2CF_2CF_3$, —$CH(CF_3)_2$, cyclopropyl, —$OCH_3$, —$OCF_3$, —$OCHF_2$, —$OCFH_2$, —CN, —$NO_2$, —$N(CH_3)_2$, —$SCH_3$, —$SO_2CH_3$, or —$SO_2CF_3$; and $R^{2A'}$ is —H, —F, —Cl, —$CH_3$, —$CH_2CH_3$, —$CH(CH_3)_2$, —$CF_3$, cyclopropyl, —$OCH_3$, —$OCF_3$, —$OCHF_2$, or —$OCFH_2$.

In some embodiments of formula $VIb^{A'}$:

$X^{A'}$ is —H, —F, —Cl, —$CH_3$, —$CH_2CH_3$, —$CH(CH_3)_2$, —$CF_3$, —$CHF_2$, —$CH_2F$, cyclopropyl, —$OCH_3$, —$OCF_3$, —$OCHF_2$, —CN, or —$SCH_3$; and $R^{2A'}$ is —H, —F, —Cl, —$CH_3$, or —$CF_3$.

In some embodiments of formula $VIb^{A'}$:

$X^{A'}$ is —$CH_3$, —$CH_2CH_3$, —$CF_3$, cyclopropyl, —$OCH_3$, —$OCF_3$, or —$SCH_3$; and $R^{2A'}$ is —H.

In some embodiments, a chemical entity of formula $I^{A'}$ is a chemical entity of formula $VII^{A'}$:

$VII^{A'}$

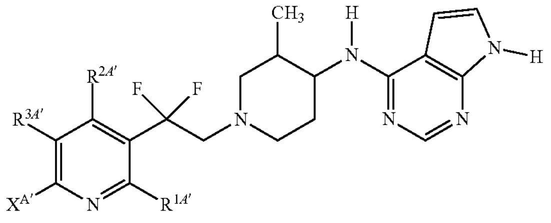

wherein each of $R^{1A'}$, $R^{2A'}$, $X^{A'}$, and $R^{3A'}$ is as described in embodiments of formula $I^{A'}$, supra, or described in embodiments herein, both singly and in combination.

In some embodiments of formula $VII^{A'}$:

$X^{A'}$ is —H, —F, —Cl, —$CH_3$, —$CH_2CH_3$, —$CH(CH_3)_2$, —$CF_3$, —$CHF_2$, —$CH_2F$, —$CF_2CF_3$, —$CH_2CF_2CF_3$, —$CH(CF_3)_2$, cyclopropyl, —$OCH_3$, —$OCF_3$, —$OCHF_2$, —$OCFH_2$, —CN, —$NO_2$, —$N(CH_3)_2$, —$SCH_3$, —$SO_2CH_3$, or —$SO_2CF_3$;

$R^{1A'}$ is —H, —F, —Cl, —$CH_3$, —$CH_2CH_3$, —$CH(CH_3)_2$, —$CF_3$, cyclopropyl, —$OCH_3$, —$OCF_3$, —$OCHF_2$, —$OCFH_2$, —CN, —$NO_2$, —$CO_2CH_3$, —$CO_2CH_2CH_3$, —$C(O)N(CH_3)_2$ or —$C(O)NH(CH_3)$;

$R^{1A'}$ is —H, —F, —Cl, —$CH_3$, —$CH_2CH_3$, —$CH(CH_3)_2$, —$CF_3$, cyclopropyl, —$OCH_3$, —$OCF_3$, —$OCHF_2$, or —$OCFH_2$; and $R^{3A'}$ is —H, —F, —Cl, —$CH_3$, —$CF_3$, or —$OCH_3$.

In some embodiments of formula $VII^{A'}$:

$X^{A'}$ is —H, —F, —Cl, —$CH_3$, —$CH_2CH_3$, —$CH(CH_3)_2$, —$CF_3$, —$CHF_2$, —$CH_2F$, cyclopropyl, —$OCH_3$, —$OCF_3$, —$OCHF_2$, —CN, or —$SCH_3$;

$R^{5A'}$ is —H, —F, —Cl, —$CH_3$, or —$CF_3$;

$R^{2A'}$ is —H, —F, —Cl, —$CH_3$, or —$CF_3$; and $R^{3A'}$ is —H, —F, —Cl, —$CH_3$, or —$CF_3$.

In some embodiments, a chemical entity of formula $I^{A'}$ is a chemical entity of formula $VIIa^{A'}$.

$VIIa^{A'}$

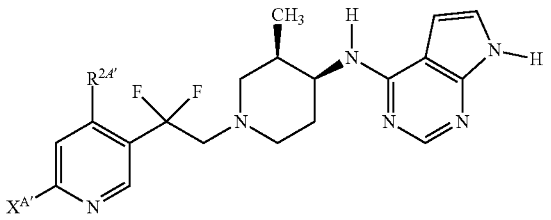

wherein each of $R^{2A'}$ and $X^{A'}$ is as described in embodiments for formula $I^{A'}$ supra, or described in embodiments herein, both singly and in combination.

In some embodiments of formula $VIIa^{A'}$:

$X^{A'}$ is —H, —F, —Cl, $—CH_3$, $—CH_2CH_3$, $—CH(CH_3)_2$, $—CF_3$, $—CHF_2$, $—CH_2F$, $—CF_2CF_3$, $—CH_2CF_2CF_3$, $—CH(CF_3)_2$, cyclopropyl, $—OCH_3$, $—OCF_3$, $—OCHF_2$, $—OCFH_2$, —CN, $—NO_2$, $—N(CH_3)_2$, $—SCH_3$, $—SO_2CH_3$, or $—SO_2CF_3$; and $R^{2A'}$ is —H, —F, —Cl, $—CH_3$, $—CH_2CH_3$, $—CH(CH_3)_2$, $—CF_3$, cyclopropyl, $—OCH_3$, $—OCF_3$, $—OCHF_2$, or $—OCFH_2$.

In some embodiments of formula $VIIa^{A'}$:

$X^{A'}$ is —H, —F, —Cl, $—CH_3$, $—CH_2CH_3$, $—CH(CH_3)_2$, $—CF_3$, $—CHF_2$, $—CH_2F$, cyclopropyl, $—OCH_3$, $—OCF_3$, $—OCHF_2$, —CN, or $—SCH_3$; and $R^{2A'}$ is —H, —F, —Cl, $—CH_3$, or $—CF_3$.

In some embodiments of formula $VIIa^{A'}$:

$X^{A'}$ is $—CH_3$, $—CH_2CH_3$, $—CF_3$, cyclopropyl, $—OCH_3$, $—OCF_3$, or $—SCH_3$; and $R^{2A'}$ is —H.

In some embodiments, a chemical entity of formula $I^{A'}$ is a chemical entity of formula $VIIb^{A'}$:

$VIIb^{A'}$

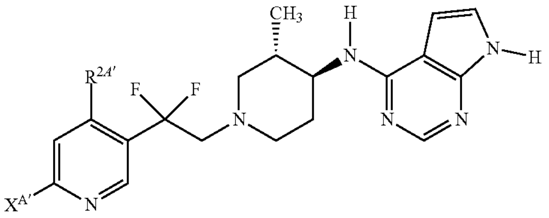

wherein each of $R^{2A'}$ and $X^{A'}$ is as described in embodiments for formula $I^{A'}$ supra, or described in embodiments herein, both singly and in combination.

In some embodiments of formula $VIIb^{A'}$, $X^{A'}$ is —H, —F, —Cl, $—CH_3$, $—CH_2CH_3$, $—CH(CH_3)_2$, $—CF_3$, $—CHF_2$, $—CH_2F$, $—CF_2CF_3$, $—CH_2CF_2CF_3$, $—CH(CF_3)_2$, cyclopropyl, $—OCH_3$, $—OCF_3$, $—OCHF_2$, $—OCFH_2$, —CN, $—NO_2$, $—N(CH_3)_2$, $—SCH_3$, $—SO_2CH_3$, or $—SO_2CF_3$; and $R^{2A'}$ is —H, —F, —Cl, $—CH_3$, $—CH_2CH_3$, $—CH(CH_3)_2$, $—CF_3$, cyclopropyl, $—OCH_3$, $—OCF_3$, $—OCHF_2$, or $—OCFH_2$.

In some embodiments of formula $VIIb^{A'}$:

$X^{A'}$ is —H, —F, —Cl, $—CH_3$, $—CH_2CH_3$, $—CH(CH_3)_2$, $—CF_3$, $—CHF_2$, $—CH_2F$, cyclopropyl, $—OCH_3$, $—OCF_3$, $—OCHF_2$, —CN, or $—SCH_3$; and $R^{2A'}$ is —H, —F, —Cl, $—CH_3$, or $—CF_3$.

In some embodiments of formula $VIIb^{A'}$:

$X^{A'}$ is $—CH_3$, $—CH_2CH_3$, $—CF_3$, cyclopropyl, $—OCH_3$, $—OCF_3$, or $—SCH_3$; and $R^{2A'}$ is —H.

In some embodiments, a chemical entity of formula $I^{A'}$ is a chemical entity of formula $VIII^{A'}$:

$VIII^{A'}$

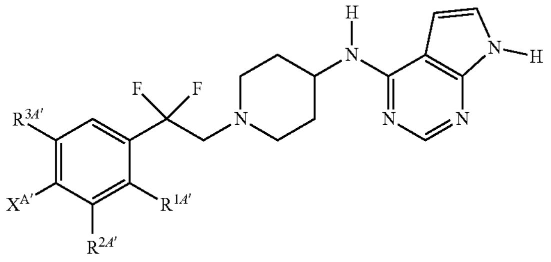

wherein each of $R^{1A'}$, $R^{2A'}$, $X^{A'}$, and $R^{3A'}$ is as described in embodiments of formula $I^{A'}$, supra, or described in embodiments herein, both singly and in combination.

In some embodiments of formula $VIII^{A'}$:

$X^{A'}$ is —H, —F, —Cl, $—CH_3$, $—CH_2CH_3$, $—CH(CH_3)_2$, $—CF_3$, $—CHF_2$, $—CH_2F$, $—CF_2CF_3$, $—CH_2CF_2CF_3$, $—CH(CF_3)_2$, cyclopropyl, $—OCH_3$, $—OCF_3$, $—OCHF_2$, $—OCFH_2$, —CN, $—NO_2$, $—N(CH_3)_2$, $—SCH_3$, $—SO_2CH_3$, or $—SO_2CF_3$;

$R^{1A'}$ is —H, —F, —Cl, $—CH_3$, $—CH_2CH_3$, $—CH(CH_3)_2$, $—CF_3$, cyclopropyl, $—OCH_3$, $—OCF_3$, $—OCHF_2$, $—OCFH_2$, —CN, $—NO_2$, $—CO_2CH_3$, $—CO_2CH_2CH_3$, $—C(O)N(CH_3)_2$, or $—C(O)NH(CH_3)$;

$R^{2A'}$ is —H, —F, —Cl, $—CH_3$, $—CH_2CH_3$, $—CH(CH_3)_2$, $—CF_3$, cyclopropyl, $—OCH_3$, $—OCF_3$, $—OCHF_2$, or $—OCFH_2$; and $R^{3A'}$ is —H, —F, —Cl, $—CH_3$, $—CF_3$, or $—OCH_3$.

In some embodiments of formula $VIII^{A'}$:

$X^{A'}$ is —H, —F, —Cl, $—CH_3$, $—CH_2CH_3$, $—CH(CH_3)_2$, $—CF_3$, $—CHF_2$, $—CH_2F$, cyclopropyl, $—OCH_3$, $—OCF_3$, $—OCHF_2$, —CN, or $—SCH_3$;

$R^{1A'}$ is —H, —F, —Cl, $—CH_3$, or $—CF_3$;

$R^{2A'}$ is —H, —F, —Cl, $—CH_3$, or $—CF_3$; and $R^{3A'}$ is —H, —F, —Cl, $—CH_3$, or $—CF_3$.

In some embodiments of formula $VIII^{A'}$:

$X^{A'}$ is —F, —Cl, $—CH_3$, or $—CF_3$;

$R^{1A'}$ is —H;

$R^{2A'}$ is —H, —F, —Cl, or $—CH_3$; and $R^{3A'}$ is —H, —F, —Cl, or $—CH_3$.

In some embodiments, a chemical entity of formula $I^{A'}$ is a chemical entity of formula $VIIIa^{A'}$:

$VIIIa^{A'}$

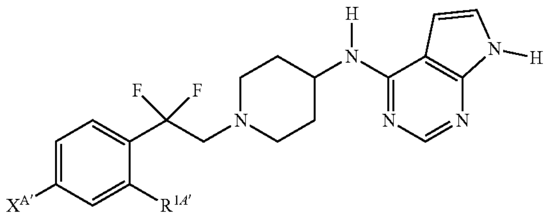

wherein each of $R^{1A'}$ and $X^{A'}$ is as described in embodiments of formula $I^{A'}$ supra, or described in embodiments herein, both singly and in combination.

In some embodiments of formula $VIIIa^{A'}$:

$X^{A'}$ is —H, —F, —Cl, $—CH_3$, $—CH_2CH_3$, $—CH(CH_3)_2$, $—CF_3$, $—CHF_2$, $—CH_2F$, $—CF_2CF_3$, $—CH_2CF_2CF_3$,

—CH($CF_3$)$_2$, cyclopropyl, —$OCH_3$, —$OCF_3$, —$OCHF_2$, —$OCFH_2$, —CN, —$NO_2$, —N($CH_3$)$_2$, —$SCH_3$, —$SO_2CH_3$, or —$SO_2CF_3$; and $R^{1A'}$ is —H, —F, —Cl, —$CH_3$, —$CH_2CH_3$, —CH($CH_3$)$_2$, —$CF_3$, cyclopropyl, —$OCH_3$, —$OCF_3$, —$OCHF_2$, —$OCFH_2$, —CN, —$NO_2$, —$CO_2CH_3$, —$CO_2CH_2CH_3$, —C(O)N($CH_3$)$_2$, or —C(O)NH($CH_3$).

In some embodiments of formula VIIIa$^{A'}$:

$X^{A'}$ is —H, —F, —Cl, —$CH_3$, —$CH_2CH_3$, —CH($CH_3$)$_2$, —$CF_3$, —$CHF_2$, —$CH_2F$, cyclopropyl, —$OCH_3$, —$OCF_3$, —$OCHF_2$, —CN, or —$SCH_3$; and $R^{1A'}$ is —H, —F, —Cl, —$CH_3$, or —$CF_3$.

In some embodiments of formula VIIIa$^{A'}$:

$X^{A'}$ is —H, —F, —Cl, —$CH_3$, —$CH_2CH_3$, —$CF_3$, —$CHF_2$, —$CH_2F$, cyclopropyl, —$OCH_3$, —$OCF_3$, —$OCHF_2$, —CN, or —$SCH_3$; and $R^{1A'}$ is —H, —F, —Cl, or —$CH_3$.

In some embodiments, a chemical entity of formula $I^{A'}$ is a chemical entity of formula $IX^{A'}$:

$IX^{A'}$

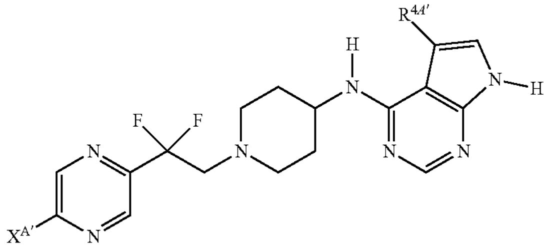

wherein each of $X^{A'}$, and $R^{4A'}$ is as described in embodiments of formula $I^{A'}$ supra, or described in embodiments herein, both singly and in combination.

In some embodiments of formula $IX^{A'}$.

$X^{A'}$ is —H, —F, —Cl, —$CH_3$, —$CH_2CH_3$, —CH($CH_3$)$_2$, —$CF_3$, —$CHF_2$, —$CH_2F$, —$CF_2CF_3$, —$CH_2CF_2CF_3$, —CH($CF_3$)$_2$, cyclopropyl, —$OCH_3$, —$OCF_3$, —$OCHF_2$, —$OCFH_2$, —CN, —$NO_2$, —N($CH_3$)$_2$, —$SCH_3$, —$SO_2CH_3$, or —$SO_2CF_3$; and $R^{4A'}$ is —H, —F, —Cl, —$CH_3$, or cyclopropyl.

In some embodiments of formula $IX^{A'}$:

$X^{A'}$ is —H, —F, —Cl, —$CH_3$, —$CH_2CH_3$, —CH($CH_3$)$_2$, —$CF_3$, —$CHF_2$, —$CH_2F$, cyclopropyl, —$OCH_3$, —$OCF_3$, —$OCHF_2$, —CN, or —$SCH_3$; and $R^{4A'}$ is —H, —Cl, or —$CH_3$.

In some embodiments of formula $IX^{A'}$:

$X^{A'}$ is —F, —Cl, —$CH_3$, —$CH_2CH_3$, —CH($CH_3$)$_2$, —$CF_3$, —$CHF_2$, cyclopropyl, —$OCF_3$, or —$OCHF_2$; and $R^{4A'}$ is —H or —$CH_3$.

Exemplary chemical entities of formula I are shown in Tables 1.C to 11.C, below.

TABLE 1.C

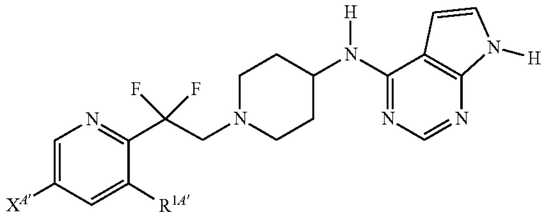

| compound | $X^{A'}$ | $R^{1A'}$ |
|---|---|---|
| C-1$^{A'}$ | H | H |
| C-2$^{A'}$ | F | H |
| C-3$^{A'}$ | Cl | H |
| C-4$^{A'}$ | $CH_3$ | H |
| C-5$^{A'}$ | $CF_3$ | H |
| C-6$^{A'}$ | $CF_2H$ | H |
| C-7$^{A'}$ | $CH_2F$ | H |
| C-8$^{A'}$ | $CH_2CH_3$ | H |
| C-9$^{A'}$ | cyclopropyl | H |
| C-10$^{A'}$ | $CH_3O$ | H |
| C-11$^{A'}$ | $CF_3O$ | H |
| C-12$^{A'}$ | $CHF_2O$ | H |
| C-13$^{A'}$ | $SCH_3$ | H |
| C-14$^{A'}$ | CN | H |
| C-15$^{A'}$ | F | F |
| C-16$^{A'}$ | Cl | F |
| C-17$^{A'}$ | $CH_3$ | F |
| C-18$^{A'}$ | $CF_3$ | F |
| C-19$^{A'}$ | $CF_2H$ | F |
| C-20$^{A'}$ | $CH_2F$ | F |
| C-21$^{A'}$ | $CH_2CH_3$ | F |
| C-22$^{A'}$ | cyclopropyl | F |
| C-23$^{A'}$ | F | Cl |
| C-24$^{A'}$ | Cl | Cl |
| C-25$^{A'}$ | $CH_3$ | Cl |
| C-26$^{A'}$ | $CF_3$ | Cl |
| C-27$^{A'}$ | cyclopropyl | Cl |
| C-28$^{A'}$ | F | $CH_3$ |
| C-29$^{A'}$ | Cl | $CH_3$ |
| C-30$^{A'}$ | $CH_3$ | $CH_3$ |
| C-31$^{A'}$ | $CF_3$ | $CH_3$ |
| C-32$^{A'}$ | cyclopropyl | $CH_3$ |

TABLE 2.C

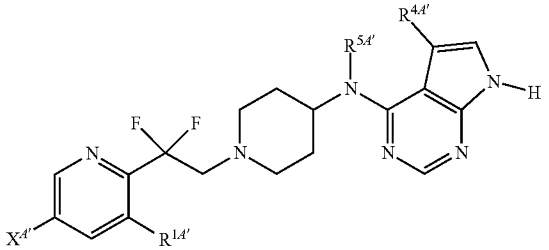

| compound | $X^{A'}$ | $r^{1A'}$ | $R^{4A'}$ | $R^{5A'}$ |
|---|---|---|---|---|
| C-33$^{A'}$ | CF | H | $CH_3$ | H |
| C-34$^{A'}$ | Cl | H | $CH_3$ | H |
| C-35$^{A'}$ | $CH_3$ | H | $CH_3$ | H |
| C-36$^{A'}$ | CF | H | Cl | H |
| C-37$^{A'}$ | Cl | H | Cl | H |
| C-38$^{A'}$ | $CH_3$ | H | Cl | H |
| C-39$^{A'}$ | CF | F | $CH_3$ | H |
| C-40$^{A'}$ | Cl | F | $CH_3$ | H |
| C-41$^{A'}$ | $CH_3$ | F | $CH_3$ | H |
| C-42$^{A'}$ | CF | F | Cl | H |
| C-43$^{A'}$ | Cl | F | Cl | H |

TABLE 2.C-continued

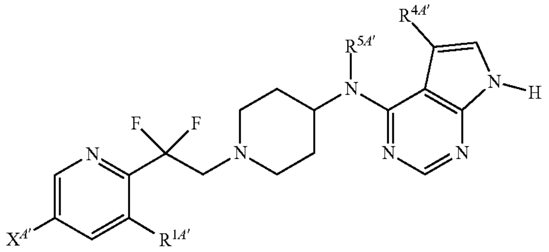

| compound | $X^{4'}$ | $r^{1A'}$ | $R^{4A'}$ | $R^{5A'}$ |
|---|---|---|---|---|
| C-$44^{4'}$ | $CH_3$ | F | Cl | H |
| C-$45^{4'}$ | CF | H | H | $CH_3$ |
| C-$46^{4'}$ | Cl | H | H | $CH_3$ |
| C-$47^{4'}$ | $CH_3$ | H | H | $CH_3$ |

TABLE 3.C

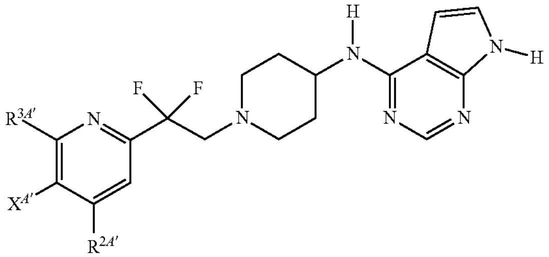

| compound | $X^{4'}$ | $R^{2A'}$ | $R^{3A'}$ |
|---|---|---|---|
| C-$48^{4'}$ | F | F | H |
| C-$49^{4'}$ | Cl | F | H |
| C-$50^{4'}$ | $CH_3$ | F | H |
| C-$51^{4'}$ | $CF_3$ | F | H |
| C-$52^{4'}$ | F | $CH_3$ | H |
| C-$53^{4'}$ | Cl | $CH_3$ | H |
| C-$54^{4'}$ | $CH_3$ | $CH_3$ | H |
| C-$55^{4'}$ | $CF_3$ | $CH_3$ | H |
| C-$56^{4'}$ | F | Cl | H |
| C-$57^{4'}$ | Cl | Cl | H |
| C-$58^{4'}$ | $CH_3$ | Cl | H |
| C-$59^{4'}$ | $CF_3$ | Cl | F |
| C-$60^{4'}$ | F | H | F |
| C-$61^{4'}$ | Cl | H | F |
| C-$62^{4'}$ | $CH_3$ | H | F |
| C-$63^{4'}$ | $CF_3$ | H | Cl |
| C-$64^{4'}$ | F | H | Cl |
| C-$65^{4'}$ | Cl | H | Cl |
| C-$66^{4'}$ | $CH_3$ | H | Cl |
| C-$67^{4'}$ | $CF_3$ | H | $CH_3$ |
| C-$68^{4'}$ | F | H | $CH_3$ |
| C-$69^{4'}$ | Cl | H | $CH_3$ |
| C-$70^{4'}$ | $CH_3$ | H | $CH_3$ |

TABLE 4.C

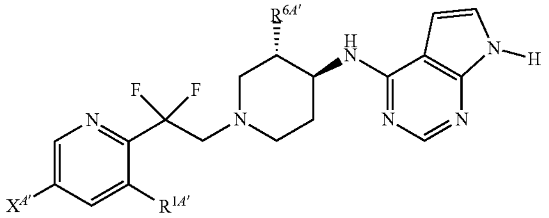

| compound | $X^{4'}$ | $R^{1A'}$ | $R^{6A'}$ |
|---|---|---|---|
| C-$71^{4'}$ | F | H | $CH_3$ |
| C-$72^{4'}$ | Cl | H | $CH_3$ |
| C-$73^{4'}$ | $CH_3$ | H | $CH_3$ |
| C-$74^{4'}$ | $CF_3$ | H | $CH_3$ |
| C-$75^{4'}$ | $CF_2H$ | H | $CH_3$ |
| C-$76^{4'}$ | $CH_2F$ | H | $CH_3$ |
| C-$77^{4'}$ | $OCF_3$ | H | $CH_3$ |
| C-$78^{4'}$ | $OCF_2H$ | H | $CH_3$ |
| C-$79^{4'}$ | $CH_2CH_3$ | H | $CH_3$ |
| C-$80^{4'}$ | cyclopropyl | H | $CH_3$ |
| C-$81^{4'}$ | F | H | F |
| C-$82^{4'}$ | Cl | H | F |
| C-$83^{4'}$ | $CH_3$ | H | F |
| C-$84^{4'}$ | $CF_3$ | H | F |
| C-$85^{4'}$ | $CF_2H$ | H | F |
| C-$86^{4'}$ | $CH_2F$ | H | F |
| C-$87^{4'}$ | $OCF_3$ | H | F |
| C-$88^{4'}$ | $OCF_2H$ | H | F |
| C-$89^{4'}$ | $CH_2CH_3$ | H | F |
| C-$90^{4'}$ | cyclopropyl | H | F |
| C-$91^{4'}$ | F | F | $CH_3$ |
| C-$92^{4'}$ | Cl | F | $CH_3$ |
| C-$93^{4'}$ | $CH_3$ | F | $CH_3$ |
| C-$94^{4'}$ | $CF_3$ | F | $CH_3$ |
| C-$95^{4'}$ | F | F | F |
| C-$96^{4'}$ | Cl | F | F |
| C-$97^{4'}$ | $CH_3$ | F | F |
| C-$98^{4'}$ | $CF_3$ | F | F |

TABLE 5.C

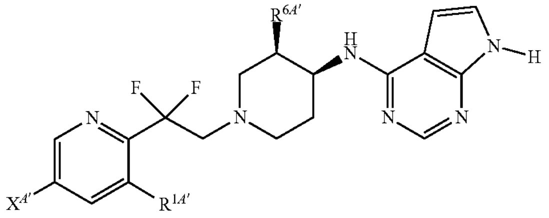

| compound | $X^{4'}$ | $R^{1A'}$ | $R^{6A'}$ |
|---|---|---|---|
| C-$99^{4'}$ | F | H | $CH_3$ |
| C-$100^{4'}$ | Cl | H | $CH_3$ |
| C-$101^{4'}$ | $CH_3$ | H | $CH_3$ |
| C-$102^{4'}$ | $CF_3$ | H | $CH_3$ |
| C-$103^{4'}$ | $CF_2H$ | H | $CH_3$ |
| C-$104^{4'}$ | $CH_2F$ | H | $CH_3$ |
| C-$105^{4'}$ | $OCF_3$ | H | $CH_3$ |
| C-$106^{4'}$ | $OCF_2H$ | H | $CH_3$ |
| C-$107^{4'}$ | $CH_2CH_3$ | H | $CH_3$ |
| C-$108^{4'}$ | cyclopropyl | H | $CH_3$ |
| C-$109^{4'}$ | F | H | F |
| C-$110^{4'}$ | Cl | H | F |
| C-$111^{4'}$ | $CH_3$ | H | F |
| C-$112^{4'}$ | $CF_3$ | H | F |
| C-$113^{4'}$ | $CF_2H$ | H | F |
| C-$114^{4'}$ | $CH_2F$ | H | F |
| C-$115^{4'}$ | $OCF_3$ | H | F |
| C-$116^{4'}$ | $OCF_2H$ | H | F |
| C-$117^{4'}$ | $CH_2CH_3$ | H | F |
| C-$118^{4'}$ | cyclopropyl | H | F |

TABLE 5.C-continued

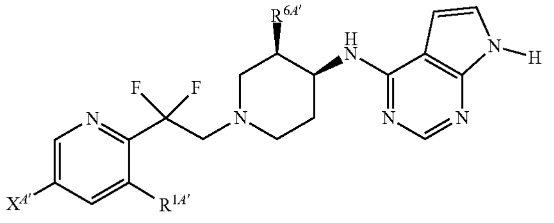

| compound | X$^{4'}$ | R$^{1A'}$ | R$^{6A'}$ |
|---|---|---|---|
| C-119$^{4'}$ | F | F | $CH_3$ |
| C-120$^{4'}$ | Cl | F | $CH_3$ |
| C-121$^{4'}$ | $CH_3$ | F | $CH_3$ |
| C-122$^{4'}$ | $CF_3$ | F | $CH_3$ |
| C-123$^{4'}$ | F | F | F |
| C-124$^{4'}$ | Cl | F | F |
| C-125$^{4'}$ | $CH_3$ | F | F |
| C-126$^{4'}$ | $CF_3$ | F | F |

TABLE 6.C

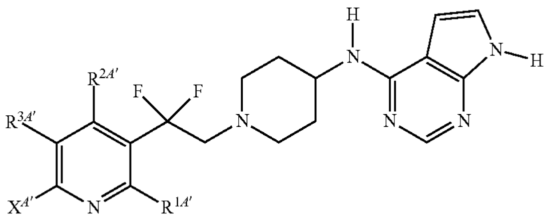

| compound | X$^{4'}$ | R$^{1A'}$ | R$^{2A'}$ | R$^{3A'}$ |
|---|---|---|---|---|
| C-127$^{4'}$ | $CF_3$ | H | H | H |
| C-128$^{4'}$ | $CH_3$ | H | H | H |
| C-129$^{4'}$ | F | H | H | H |
| C-130$^{4'}$ | Cl | H | H | H |
| C-131$^{4'}$ | $OCH_3$ | H | H | H |
| C-132$^{4'}$ | $OCF_3$ | H | H | H |
| C-133$^{4'}$ | $SCH_3$ | H | H | H |
| C-134$^{4'}$ | $CH_2CH_3$ | H | H | H |
| C-135$^{4'}$ | cyclopropyl | H | H | H |
| C-136$^{4'}$ | $CF_3$ | F | H | H |
| C-137$^{4'}$ | $CF_3$ | H | F | H |
| C-138$^{4'}$ | $CF_3$ | H | H | F |
| C-139$^{4'}$ | H | $CF_3$ | H | H |
| C-140$^{4'}$ | H | H | $CF_3$ | H |
| C-141$^{4'}$ | H | H | H | $CF_3$ |

TABLE 7.C

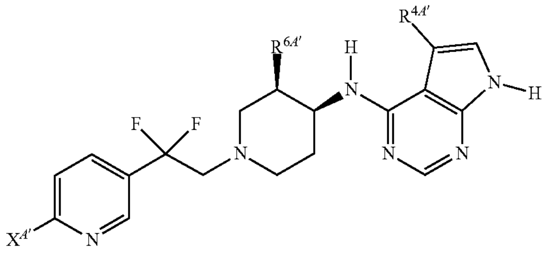

| compound | X$^{4'}$ | r$^{4A'}$ | R$^{6A'}$ |
|---|---|---|---|
| C-142$^{4'}$ | $CF_3$ | $CH_3$ | H |
| C-143$^{4'}$ | $CH_3$ | $CH_3$ | H |
| C-144$^{4'}$ | $CF_3$ | H | F |
| C-145$^{4'}$ | $CH_3$ | H | F |
| C-146$^{4'}$ | $CH_2CH_3$ | H | F |

TABLE 7.C-continued

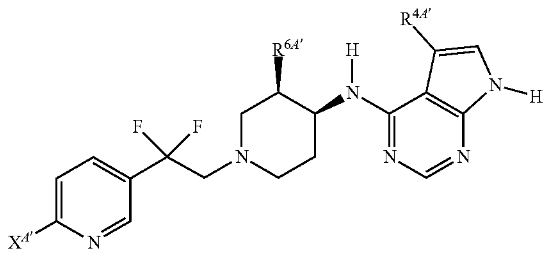

| compound | X$^{4'}$ | r$^{4A'}$ | R$^{6A'}$ |
|---|---|---|---|
| C-147$^{4'}$ | $SCH_3$ | H | F |
| C-148$^{4'}$ | cyclopropyl | H | F |
| C-149$^{4'}$ | $OCF_3$ | H | F |
| C-150$^{4'}$ | $OCH_3$ | H | F |
| C-151$^{4'}$ | $CF_3$ | H | $CH_3$ |
| C-152$^{4'}$ | $CH_3$ | H | $CH_3$ |
| C-153$^{4'}$ | $CH_2CH_3$ | H | $CH_3$ |
| C-154$^{4'}$ | $SCH_3$ | H | $CH_3$ |
| C-155$^{4'}$ | cyclopropyl | H | $CH_3$ |
| C-156$^{4'}$ | $OCF_3$ | H | $CH_3$ |
| C-157$^{4'}$ | $OCH_3$ | H | $CH_3$ |

TABLE 8.C

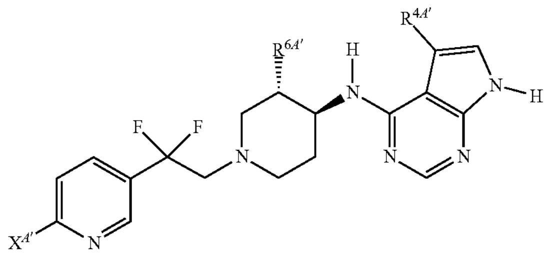

| compound | X$^{4'}$ | r$^{4A'}$ | R$^{6A'}$ |
|---|---|---|---|
| C-158$^{4'}$ | $CF_3$ | Cl | H |
| C-159$^{4'}$ | $CH_3$ | Cl | H |
| C-160$^{4'}$ | $CF_3$ | H | F |
| C-161$^{4'}$ | $CH_3$ | H | F |
| C-162$^{4'}$ | $CH_2CH_3$ | H | F |
| C-163$^{4'}$ | $SCH_3$ | H | F |
| C-164$^{4'}$ | cyclopropyl | H | F |
| C-165$^{4'}$ | $OCF_3$ | H | F |
| C-166$^{4'}$ | $OCH_3$ | H | F |
| C-167$^{4'}$ | $CF_3$ | H | $CH_3$ |
| C-168$^{4'}$ | $CH_3$ | H | $CH_3$ |
| C-169$^{4'}$ | $CH_2CH_3$ | H | $CH_3$ |
| C-170$^{4'}$ | $SCH_3$ | H | $CH_3$ |
| C-171$^{4'}$ | cyclopropyl | H | $CH_3$ |
| C-172$^{4'}$ | $OCF_3$ | H | $CH_3$ |
| C-173$^{4'}$ | $OCH_3$ | H | $CH_3$ |

TABLE 9.C

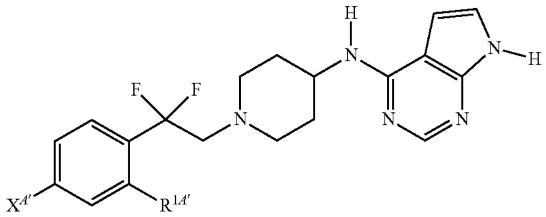

| compound | $X^{A'}$ | $R^{1A'}$ |
|---|---|---|
| C-174$^{A'}$ | H | H |
| C-175$^{A'}$ | F | H |
| C-176$^{A'}$ | Cl | H |
| C-177$^{A'}$ | $CH_3$ | H |
| C-178$^{A'}$ | $CF_3$ | H |
| C-179$^{A'}$ | $CF_2H$ | H |
| C-180$^{A'}$ | $CH_2F$ | H |
| C-181$^{A'}$ | $CH_2CH_3$ | H |
| C-182$^{A'}$ | cyclopropyl | H |
| C-183$^{A'}$ | $CH_3O$ | H |
| C-184$^{A'}$ | $CF_3O$ | H |
| C-185$^{A'}$ | $CHF_2O$ | H |
| C-186$^{A'}$ | $SCH_3$ | H |
| C-187$^{A'}$ | CN | H |
| C-188$^{A'}$ | F | F |
| C-189$^{A'}$ | Cl | F |
| C-190$^{A'}$ | $CH_3$ | F |
| C-191$^{A'}$ | $CF_3$ | F |
| C-192$^{A'}$ | $CF_2H$ | F |
| C-193$^{A'}$ | $CH_2F$ | F |
| C-194$^{A'}$ | $CH_2CH_3$ | F |
| C-195$^{A'}$ | cyclopropyl | F |
| C-196$^{A'}$ | F | Cl |
| C-197$^{A'}$ | Cl | Cl |
| C-198$^{A'}$ | $CH_3$ | Cl |
| C-199$^{A'}$ | $CF_3$ | Cl |
| C-200$^{A'}$ | cyclopropyl | Cl |
| C-201$^{A'}$ | F | $CH_3$ |
| C-202$^{A'}$ | Cl | $CH_3$ |
| C-203$^{A'}$ | $CH_3$ | $CH_3$ |
| C-204$^{A'}$ | $CF_3$ | $CH_3$ |
| C-205$^{A'}$ | cyclopropyl | $CH_3$ |

TABLE 10.C

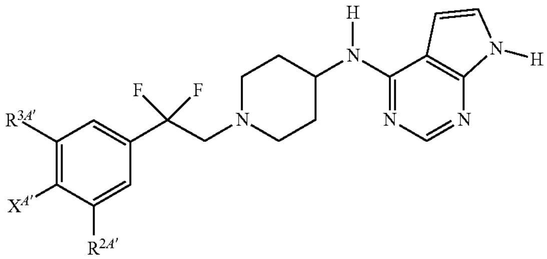

| compound | $X^{A'}$ | $R^{2A'}$ | $R^{3A'}$ |
|---|---|---|---|
| C-206$^{A'}$ | F | F | H |
| C-207$^{A'}$ | Cl | F | H |
| C-208$^{A'}$ | $CH_3$ | F | H |
| C-209$^{A'}$ | $CF_3$ | F | H |
| C-210$^{A'}$ | F | $CH_3$ | H |
| C-211$^{A'}$ | Cl | $CH_3$ | H |
| C-212$^{A'}$ | $CH_3$ | $CH_3$ | H |
| C-213$^{A'}$ | $CF_3$ | $CH_3$ | H |
| C-214$^{A'}$ | F | Cl | H |
| C-215$^{A'}$ | Cl | Cl | H |
| C-216$^{A'}$ | $CH_3$ | Cl | H |
| C-217$^{A'}$ | $CF_3$ | Cl | F |
| C-218$^{A'}$ | F | H | F |
| C-219$^{A'}$ | Cl | H | F |

TABLE 10.C-continued

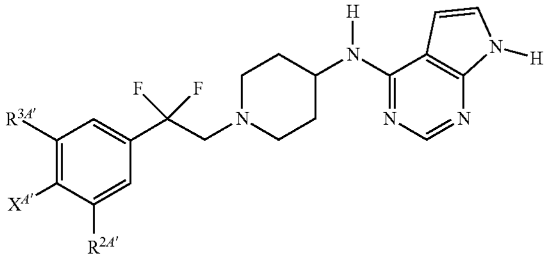

| compound | $X^{A'}$ | $R^{2A'}$ | $R^{3A'}$ |
|---|---|---|---|
| C-220$^{A'}$ | $CH_3$ | H | F |
| C-221$^{A'}$ | $CF_3$ | H | Cl |
| C-222$^{A'}$ | F | H | Cl |
| C-223$^{A'}$ | Cl | H | Cl |
| C-224$^{A'}$ | $CH_3$ | H | Cl |
| C-225$^{A'}$ | $CF_3$ | H | $CH_3$ |
| C-226$^{A'}$ | F | H | $CH_3$ |
| C-227$^{A'}$ | Cl | H | $CH_3$ |
| C-228$^{A'}$ | $CH_3$ | H | $CH_3$ |

TABLE 11.C

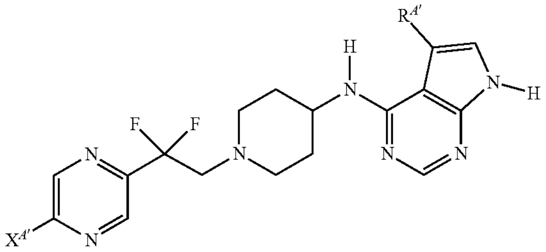

| compound | $X^{A'}$ | $R^{4A'}$ |
|---|---|---|
| C-229$^{A'}$ | $CF_3$ | H |
| C-230$^{A'}$ | $CH_3$ | H |
| C-231$^{A'}$ | Cl | H |
| C-232$^{A'}$ | F | H |
| C-233$^{A'}$ | $CF_2H$ | H |
| C-234$^{A'}$ | $OCF_3$ | H |
| C-235$^{A'}$ | $OCF_2H$ | H |
| C-236$^{A'}$ | $CH_2CH_3$ | H |
| C-237$^{A'}$ | cyclopropyl | H |
| C-238$^{A'}$ | isopropyl | H |
| C-239$^{A'}$ | $CF_3$ | $CH_3$ |
| C-240$^{A'}$ | $CH_3$ | $CH_3$ |
| C-241$^{A'}$ | $CH_2CH_3$ | $CH_3$ |
| C-242$^{A'}$ | cyclopropyl | $CH_3$ |
| C-243$^{A'}$ | isopropyl | $CH_3$ |
| C-244$^{A'}$ | $OCF_3$ | $CH_3$ |

Formula $I^{B'}$

In some embodiments, the present invention provides chemical entities of Formula $I^{B'}$:

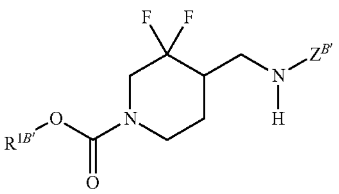

$I^{B'}$ wherein $R^{1B'}$ and $Z^{B'}$ are as described above.

In some embodiments, $R^{1B'}$ is optionally substituted alkyl.

In some embodiments, $R^{1B'}$ is optionally substituted cycloalkyl or optionally substituted (cycloalkyl)alkyl. In some embodiments, $R^{1B'}$ is optionally substituted cycloalkyl. In some embodiments, $R^{1B'}$ is optionally substituted cyclohexyl. In some embodiments, $R^{1B'}$ is cyclohexyl. In some embodiments, $R^{1B'}$ is 4,4-difluorocyclohexyl. In some embodiments, $R^{1B'}$ is 4,4-dimethylcyclohexyl. In some embodiments, $R^{1B'}$ is 4-methylcyclohexyl. In some embodiments, $R^{1B'}$ is 4-ethylcyclohexyl. In some embodiments, $R^{1B'}$ is 4-cyclopropylcyclohexyl. In some embodiments, $R^{1B'}$ is optionally substituted norbornanyl. In some embodiments, $R^{1B'}$ is indanyl. In some embodiments, $R^{1B'}$ is optionally substituted (cycloalkyl)alkyl. In some embodiments, $R^{1B'}$ is bicyclo[2.2.1]heptan-2-ylmethyl. In some embodiments, $R^{1B'}$ is optionally substituted cyclohexylmethyl. In some embodiments, $R^{1B'}$ is cyclohexylmethyl. In some embodiments, $R^{1B'}$ is (4,4-dimethylcyclohexyl)methyl. In some embodiments, $R^{1B'}$ is (4,4-difluorocyclohexyl)methyl.

In some embodiments, $R^{1B'}$ is optionally substituted heterocyclyl or optionally substituted (heterocyclyl)alkyl. In some embodiments, $R^{1B'}$ is optionally substituted heterocyclyl. In some embodiments, $R^{1B'}$ is optionally substituted tetrahydropyranyl. In some embodiments, $R^{1B'}$ is tetrahydropyran-4-yl. In some embodiments, $R^{1B'}$ is optionally substituted (heterocyclyl)alkyl.

In some embodiments, $R^{1B'}$ is optionally substituted tetrahydropyranylmethyl. In some embodiments, $R^{1B'}$ is tetrahydropyran-4-ylmethyl.

In some embodiments, $R^{1B'}$ is optionally substituted aryl or optionally substituted (aryl)alkyl. In some embodiments, $R^{1B'}$ is optionally substituted (aryl)alkyl. In some embodiments, $R^{1B'}$ is optionally substituted benzyl. In some embodiments, $R^{1B'}$ is 4-methylbenzyl. In some embodiments, $R^{1B'}$ is 4-ethylbenzyl. In some embodiments, $R^{1B'}$ is 4-isopropylbenzyl. In some embodiments, $R^{1B'}$ is 4-(2,2,2-trifluoroethyl)benzyl. In some embodiments, $R^{1B'}$ is 4-(1,1-difluoroethyl)benzyl. In some embodiments, $R^{1B'}$ is 4-t-butylbenzyl. In some embodiments, $R^{1B'}$ is 4-chlorobenzyl. In some embodiments, $R^{1B'}$ is 4-fluorobenzyl. In some embodiments, $R^{1B'}$ is 4-difluoromethylbenzyl. In some embodiments, $R^{1B'}$ is 4-trifluoromethylbenzyl. In some embodiments, $R^{1B'}$ is 4-difluoromethoxybenzyl. In some embodiments, $R^{1B'}$ is 4-trifluoromethoxybenzyl. In some embodiments, $R^{1B'}$ is 4-methylthiobenzyl. In some embodiments, $R^{1B'}$ is 4-ethylthiobenzyl. In some embodiments, $R^{1B'}$ is 4-methylsulfonylbenzyl. In some embodiments $R^{1B'}$ is 4-ethylsulfonylbenzyl. In some embodiments, $R^{1B'}$ is 4-trifluoromethylsulfonylbenzyl.

In some embodiments, $R^{1B'}$ is optionally substituted heteroaryl or optionally substituted (heteroaryl)alkyl. In some embodiments, $R^{1B'}$ is optionally substituted (heteroaryl) alkyl. In some embodiments, $R^{1B'}$ is optionally substituted (pyridin-2-yl)methyl. In some embodiments, $R^{1B'}$ is optionally (5-chloro-pyridin-2-yl)methyl. In some embodiments, $R^{1B'}$ is optionally (5-methyl-pyridin-2-yl)methyl. In some embodiments, $R^{1B'}$ is optionally substituted (pyridin-3-yl) methyl. In some embodiments, $R^{1B'}$ is (5-methyl-pyridin-3-yl)methyl.

In some embodiments, $Z^{B'}$ is 5- or 6-membered monocyclic or 9- or 10-membered bicyclic heteroaryl having ring carbon atoms, 1 ring nitrogen atom and 0-3 additional ring heteroatoms independently selected from N, O, and S, which is optionally substituted with 1 or 2 $R^{xB'}$ groups and optionally substituted with 1 Re group, wherein each $R^{xB'}$ is attached to a ring carbon atom and Re is attached to a ring nitrogen atom.

In some embodiments, $Z^{B'}$ is 9-membered optionally substituted bicyclic heteroaromatic ring system having ring carbon atoms, 1 ring nitrogen atom and 0-3 additional ring heteroatoms independently selected from N, O, and S.

In some embodiments, $Z^{B'}$ is a 9-membered optionally substituted bicyclic heteraromatic ring system having ring carbon atoms, 1 ring nitrogen heteroatom and 1 oxygen ring heteroatom.

In some embodiments, $Z^{B'}$ is a 9-membered optionally substituted bicyclic heteraromatic ring system having ring carbon atoms and 2 ring nitrogen heteroatoms.

In some embodiments, $Z^{B'}$ is a 9-membered optionally substituted bicyclic heteraromatic ring system having ring carbon atoms and 3 ring nitrogen heteroatoms.

In some embodiments, $Z^{B'}$ is a 9-membered optionally substituted bicyclic heteraromatic ring system having ring carbon atoms and 4 ring nitrogen heteroatoms.

In some embodiments, $Z^{B'}$ is a 5- or 6-membered optionally substituted monocyclic heteraromatic ring system having ring carbon atoms, 1 ring nitrogen atom and 0-2 additional ring heteroatoms independently selected from N, O, and S.

In some embodiments, $Z^{B'}$ is a 6-membered optionally substituted monocyclic heteraromatic ring system having ring carbon atoms, 1 ring nitrogen atom and 0 or 1 additional ring nitrogen atoms. In some embodiments, $Z^{B'}$ is pyridyl. In some embodiments, $Z^{B'}$ is pyrimidinyl. In some embodiments, $Z^{B'}$ is pyridazinyl.

In some embodiments, $Z^{B'}$ is a 6-membered optionally substituted monocyclic heteraromatic ring system having ring carbon atoms and 2 ring nitrogen atoms.

In some embodiments, $Z^{B'}$ is a 6-membered monocyclic heteraromatic ring system having ring carbon atoms and 2 ring nitrogen atoms, wherein $Z^{B'}$ is substituted with 1 or 2 $R^{X}$ groups.

In certain embodiments, $Z^{B'}$ is a 6-membered monocyclic heteraromatic ring system having ring carbon atoms and 2 ring nitrogen atoms, wherein $Z^{B'}$ is substituted with 1 $R^{xB'}$ group.

Thus, in some embodiments, $Z^{B'}$ is a 6-membered monocyclic heteraromatic ring system having ring carbon atoms and 2 ring nitrogen atoms, wherein $Z^{B'}$ is monosubstituted with $R^{xB'}$.

In some embodiments, $Z^{B'}$ is pyridyl monosubstituted with R. In some embodiments, $Z^{B'}$ is pyrimidinyl monosubstituted with $R^{xB'}$. In some embodiments, $Z^{B'}$ is pyridazinyl monosubstituted with $R^{B}$.

In some embodiments, $Z^{B'}$ is a 5-membered optionally substituted monocyclic heteraromatic ring system having ring carbon atoms, 1 ring nitrogen atom and 0-2 additional ring heteroatoms independently selected from N, O, and S.

In some embodiments, $Z^{B'}$ is a 5-membered optionally substituted monocyclic heteraromatic ring system having ring carbon atoms, 1 ring nitrogen atom and 0 or 1 additional ring heteroatoms independently selected from N, O, and S. In some embodiments, $Z^{B'}$ is imidazolyl or thiazolyl. In some embodiments, $Z^{B'}$ is imidazolyl. In some embodiments, $Z^{B'}$ is thiazolyl.

In some embodiments, $Z^{B'}$ is a 5-membered optionally substituted monocyclic heteraromatic ring system having ring carbon atoms, 1 ring nitrogen atom and 0-2 additional ring heteroatoms independently selected from N, O, and S. In some embodiments, $Z^{B'}$ is thiazolyl, oxadiazolyl, or thiadiazolyl. In some embodiments, $Z^{B'}$ is triazolyl. In some embodiments, $Z^{B'}$ is oxadiazolyl. In some embodiments, $Z^{B'}$ is thiadiazolyl.

In some embodiments, $Z^{B'}$ is optionally substituted with 1 or 2 $R^{xB'}$ groups and optionally substituted with 1 $R^{aB'}$ group, wherein each $R^{xB'}$ is attached to a ring carbon atom and $R^{aB'}$ is attached to a ring nitrogen atom. In some embodiments, each $R^{xB'}$ is independently selected from —F, —Cl, —$CH_3$, —$CFH_2$, —$CF_2H$, —$CF_3$, —OH, —$OCH_3$, —$OCF_3$, or —CN. In some embodiments, each $R^{xB'}$ is independently selected from —F, —Cl, —$CH_3$, —$CF_3$, or —CN. In some embodiments, $R^{xB'}$ is —F or —Cl. In some embodiments, $R^{xB'}$ is —F, —Cl, or —CN. In some embodiments, Re is —$CH_3$, —$CFH_2$, —$CF_2H$ or —$CF_3$. In some such embodiments, $R^{xB'}$ is —$CFH_2$, —$CF_2H$, or —$CF_3$. In some embodiments, $R^{xB'}$ is —$CH_3$ or —$CF_3$. In some embodiments, $R^{aB'}$ is —OH, —$OCH_3$, or —$OCF_3$.

In some embodiments, each $R^{aB'}$ is independently selected from hydrogen, $C_{1-4}$ alkyl, $C_{3-4}$ cycloalkyl, or —$S(O)_2$—$C_{1-4}$ alkyl. In some embodiments, Ra is hydrogen. In some embodiments, $R^{aB'}$ is $C_{1-4}$ alkyl or $C_{3-4}$ cycloalkyl. In some embodiments, $R^{aB'}$ is $C_{1-4}$ alkyl. In some embodiments, $R^{aB'}$ is —$S(O)_2$—$C_{1-4}$ alkyl.

In some embodiments, $Z^{B'}$ is one of Formulas $Z1^{B'}$—$Z36^{B'}$, wherein $Z^{B'}$ is optionally substituted with 1 or 2 $R^{B'}$ groups, wherein each $R^{B'}$ is attached to a ring carbon atom:

$Z1^{B'}$

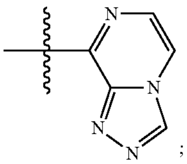

$Z2^{B'}$

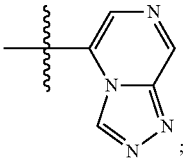

$Z3^{B'}$

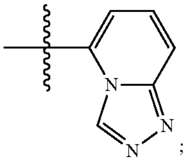

$Z4^{B'}$

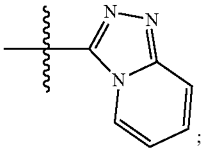

$Z5^{B'}$

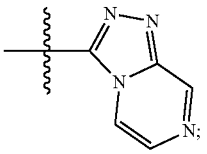

$Z6^{B'}$

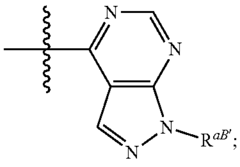

-continued $Z7^{B'}$

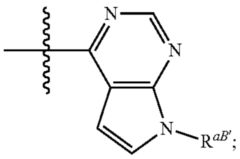

$Z8^{B'}$

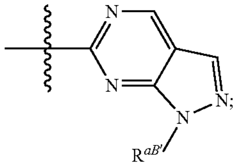

$Z9^{B'}$

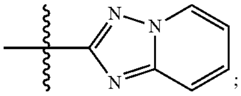

$Z10^{B'}$

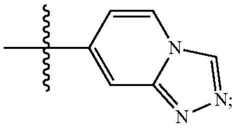

$Z11^{B'}$

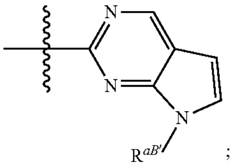

$Z12^{B'}$

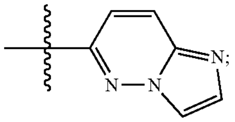

$Z13^{B'}$

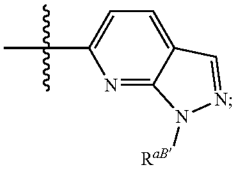

$Z14^{B'}$

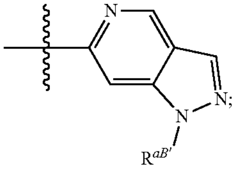

$Z15^{B'}$

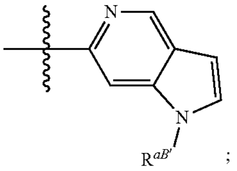

-continued $Z16^{B'}$

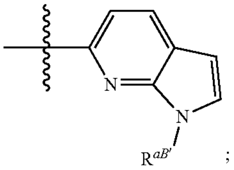

$Z17^{B'}$

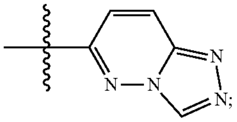

$Z18^{B'}$

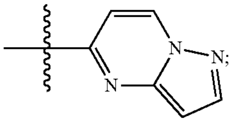

$Z19^{B'}$

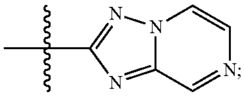

$Z20^{B'}$

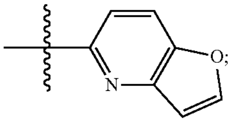

$Z21^{B'}$

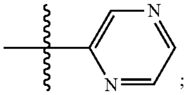

$Z22^{B'}$

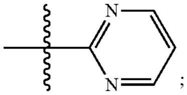

$Z23^{B'}$

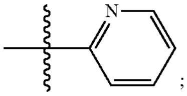

$Z24^{B'}$

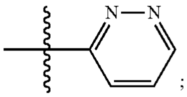

$Z25^{B'}$

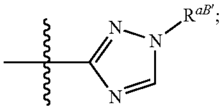

$Z26^{B'}$

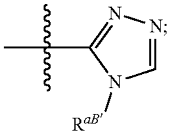

$Z27^{B'}$

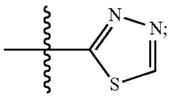

-continued $Z28^{B'}$

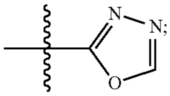

$Z29^{B'}$

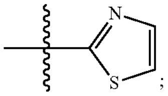

$Z30^{B'}$

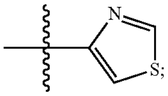

$Z31^{B'}$

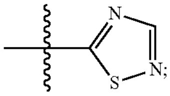

$Z32^{B'}$

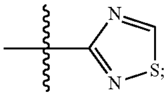

$Z33^{B'}$

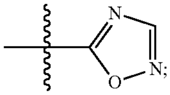

$Z34^{B'}$

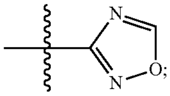

$Z35^{B'}$

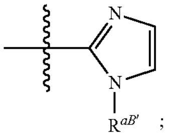

$Z36^{B'}$

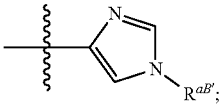

$Z37^{B'}$

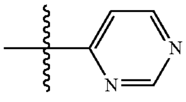

$Z38^{B'}$

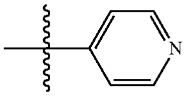

each instance of R independently is —F, —Cl, —$CH_3$, —$CFH_2$, —$CF_2H$, —$CF_3$, —OH, —$OCH_3$, —$OCF_3$, or —CN; and $R^{aB'}$ is hydrogen, $C_{1-4}$ alkyl, $C_{3-4}$ cycloalkyl, or —$S(O)_2$—$C_{1-4}$ alkyl.

In some embodiments, $Z^{B'}$ is $Z1^{B'}$, $Z2^{B'}$, $Z3^{B'}$, $Z4^{B'}$, $Z5^{B'}$, $Z6^{B'}$, $Z7^{B'}$, $Z8^{B'}$, $Z9^{B'}$, $Z10^{B'}$, $Z11^{B'}$, $Z12^{B'}$, $Z13^{B'}$, $Z14^{B'}$, $Z15^{B'}$, $Z16^{B'}$, $Z17^{B'}$, $Z18^{B'}$, $Z19^{B'}$, $Z20^{B'}$, $Z21^{B'}$, $Z22^{B'}$, $Z23^{B'}$, $Z24^{B'}$, $Z25^{B'}$, $Z26^{B'}$, $Z27^{B'}$, $Z28^{B'}$, $Z29^{B'}$, $Z30^{B'}$, $Z31^{B'}$, $Z32^{B'}$, $Z33^{B'}$, $Z34^{B'}$, $Z35^{B'}$ or $Z36^{B'}$. In some embodiments, $Z^{B'}$ is $Z1^{B'}$, $Z2^{B'}$, $Z3^{B'}$, $Z4^{B'}$, $Z5^{B'}$, $Z6^{B'}$, $Z7^{B'}$, $Z8^{B'}$, $Z9^{B'}$, $Z10^{B'}$, $Z12^{B'}$, $Z12^{B'}$, $Z13^{B'}$, $Z14^{B'}$, $Z15^{B'}$, $Z16^{B'}$, $Z17^{B'}$, Z18$^{B'}$, Z19$^{B'}$, Z20$^{B'}$, Z21$^{B'}$, Z22$^{B'}$, Z23$^{B'}$, Z24$^{B'}$, Z25$^{B'}$, Z26$^{B'}$, Z27$^{B'}$, Z28$^{B'}$, Z29$^{B'}$, Z30$^{B'}$, Z31$^{B'}$, Z32$^{B'}$, Z33$^{B'}$, Z34$^{B'}$, Z35$^{B'}$, Z36$^{B'}$, Z37$^{B'}$ or Z38$^{B'}$.

In some embodiments, Z$^{B'}$ is Z1$^{B'}$, Z2$^{B'}$, Z3$^{B'}$, Z4$^{B'}$, Z5$^{B'}$, Z6$^{B'}$, Z7$^{B'}$, Z8$^{B'}$, Z9$^{B'}$, Z10$^{B'}$, Z11$^{B'}$, Z12$^{B'}$, Z13$^{B'}$, Z14$^{B'}$, Z15$^{B'}$, Z16$^{B'}$, Z17$^{B'}$, Z18$^{B'}$, Z19$^{B'}$ or Z20$^{B'}$.

In some embodiments, Z$^{B'}$ is Z1$^{B'}$, Z2$^{B'}$, Z5$^{B'}$, Z6$^{B'}$, Z8$^{B'}$, Z17$^{B'}$, or Z19$^{B'}$. In some embodiments, Z$^{B'}$ is Z1$^{B'}$ or Z2$^{B'}$. In some embodiments, Z$^{B'}$ is Z1$^{B'}$. In some embodiments, Z$^{B'}$ is Z2$^{B'}$. In some embodiments, Z is Z6$^{B'}$ or Z8$^{B'}$. In some embodiments, Z$^{B'}$ is Z6$^{B'}$. In some embodiments, Z$^{B'}$ is Z8$^{B'}$.

In some embodiments, Z$^{B'}$ is Z3$^{B'}$, Z4$^{B'}$, Z7$^{B'}$, Z9$^{B'}$, Z10$^{B'}$, Z11$^{B'}$, Z12$^{B'}$, Z13$^{B'}$, Z14$^{B'}$, or Z18$^{B'}$. In some embodiments, Z$^{B'}$ is Z7$^{B'}$ or Z9$^{B'}$. In some embodiments, Z$^{B'}$ is Z7$^{B'}$. In some embodiments, Z$^{B'}$ is Z9$^{B'}$.

In some embodiments, Z$^{B'}$ is Z15$^{B'}$, Z16$^{B'}$, or Z20$^{B'}$. In some embodiments, Z$^{B'}$ is Z15$^{B'}$ or Z16$^{B'}$. In some embodiments, Z$^{B'}$ is Z15$^{B'}$. In some embodiments, Z$^{B'}$ is Z16$^{B'}$. In some embodiments, Z$^{B'}$ is Z20$^{B'}$.

In some embodiments, Z$^{B'}$ is Z21$^{B'}$, Z22$^{B'}$, Z23$^{B'}$, Z24$^{B'}$, Z25$^{B'}$, Z26$^{B'}$, Z27$^{B'}$, Z28$^{B'}$, Z29$^{B'}$, Z30$^{B'}$, Z31$^{B'}$, Z32$^{B'}$, Z33$^{B'}$, Z34$^{B'}$, Z35$^{B'}$, or Z36$^{B'}$. In some embodiments, Z$^{B'}$ is Z21$^{B'}$, Z22$^{B'}$, Z23$^{B'}$, or Z24$^{B'}$. In some embodiments, Z$^{B'}$ is Z25$^{B'}$, Z26$^{B'}$, Z27$^{B'}$, Z28$^{B'}$, Z29$^{B'}$, Z30$^{B'}$, Z31$^{B'}$, Z32$^{B'}$, Z33$^{B'}$, Z34$^{B'}$, Z35$^{B'}$ or Z36$^{B'}$.

In some embodiments, Z$^{B'}$ is Z23$^{B'}$. In some embodiments, Z$^{B'}$ is Z24$^{B'}$. In some embodiments, Z$^{B'}$ is Z21$^{B'}$, Z22$^{B'}$, Z24$^{B'}$, Z29$^{B'}$, Z30$^{B'}$, Z35$^{B'}$, or Z36$^{B'}$. In some embodiments, Z$^{B'}$ is Z21$^{B'}$, Z22$^{B'}$, Z24$^{B'}$, Z35$^{B'}$, or Z36$^{B'}$. In some embodiments, Z$^{B'}$ is Z21$^{B'}$ or Z22$^{B'}$. In some embodiments, Z$^{B'}$ is Z21$^{B'}$. In some embodiments, Z$^{B'}$ is Z22$^{B'}$. In some embodiments, Z$^{B'}$ is Z29$^{B'}$ or Z30$^{B'}$.

In some embodiments, Z$^{B'}$ is Z25$^{B'}$, Z26$^{B'}$, Z27$^{B'}$, Z28$^{B'}$, Z31$^{B'}$, Z32$^{B'}$, Z33$^{B'}$, or Z34$^{B'}$ In some embodiments, Z$^{B'}$ is Z25$^{B'}$ or Z26$^{B'}$. In some embodiments, Z$^{B'}$ is Z25$^{B'}$. In some embodiments, Z$^{B'}$ is Z26$^{B'}$. In some embodiments, Z$^{B'}$ is Z27$^{B'}$, Z31$^{B'}$, or Z32$^{B'}$. In some embodiments, Z$^{B'}$ is Z28$^{B'}$, Z33$^{B'}$, or Z34$^{B'}$.

In some embodiments, Z$^{B'}$ is Z27$^{B'}$, Z29$^{B'}$, Z30$^{B'}$, Z31$^{B'}$, or Z32$^{B'}$. In some embodiments, Z$^{B'}$ is Z29$^{B'}$ or Z30$^{B'}$. In some embodiments, Z$^{B'}$ is Z27$^{B'}$, Z31$^{B'}$, or Z32$^{B'}$.

In some embodiments, Z$^{B'}$ is Z28$^{B'}$, Z33$^{B'}$, or Z34$^{B'}$. In some embodiments, Z$^{B'}$ is Z28$^{B'}$ In some embodiments, each instance of R$^{xB'}$ independently is —F, —Cl, —$CH_3$, —$CF_3$, or —CN. In some embodiments, each instance of R$^{xB'}$ independently is —$CH_3$ or —$CF_3$.

In some embodiments, Z$^{B'}$ is Z21$^{B'}$, Z22$^{B'}$, Z23$^{B'}$, Z24$^{B'}$, Z25$^{B'}$, Z26$^{B'}$, Z27$^{B'}$, Z28$^{B'}$, Z29$^{B'}$, Z30$^{B'}$, Z31$^{B'}$, Z32$^{B'}$, Z33$^{B'}$, Z34$^{B'}$, Z35$^{B'}$, or Z36$^{B'}$. In some embodiments, Z$^{B'}$ is Z21$^{B'}$, Z22$^{B'}$, Z23$^{B'}$, Z24$^{B'}$, Z25$^{B'}$, Z26$^{B'}$, Z27$^{B'}$, Z28$^{B'}$, Z29$^{B'}$, Z30$^{B'}$, Z31$^{B'}$, Z32$^{B'}$, Z33$^{B'}$, Z34$^{B'}$, Z35$^{B'}$, or Z36$^{B'}$ and each instance of R$^{xB'}$ independently is —F, —Cl, —$CH_3$, —$CFH_2$, —$CF_2H$, —$CF_3$, —OH, —$OCH_3$, —$OCF_3$, or —CN. In some embodiments, Z$^{B'}$ is Z21$^{B'}$, Z22$^{B'}$, Z23$^{B'}$, Z24$^{B'}$, Z25$^{B'}$, Z26$^{B'}$, Z27$^{B'}$, Z28$^{B'}$, Z29$^{B'}$, Z30$^{B'}$, Z31$^{B'}$, Z32$^{B'}$, Z33$^{B'}$, Z34$^{B'}$, Z35$^{B'}$, or Z36$^{B'}$ and each instance of R$^{xB'}$ independently is —F, —Cl, —$CH_3$, —$CF_3$, or —CN.

In some embodiments, Z$^{B'}$ is Z21$^{B'}$, Z22$^{B'}$, Z23$^{B'}$, or Z24$^{B'}$. In some embodiments, Z$^{B'}$ is Z21$^{B'}$, Z22$^{B'}$, Z23$^{B'}$, Z24$^{B'}$, Z37$^{B'}$, or Z38$^{B'}$. In some embodiments, Z$^{B'}$ is Z21$^{B'}$, Z22$^{B'}$, Z24$^{B'}$, or Z37$^{B'}$. In some embodiments, Z$^{B'}$ is Z23$^{B'}$ or Z38$^{B'}$. In some embodiments, Z$^{B'}$ is Z21$^{B'}$, Z22$^{B'}$, Z23$^{B'}$, or Z24$^{B'}$ and each instance of R$^{xB'}$ independently is —F, —Cl, —$CH_3$, —$CFH_2$, —$CF_2H$, —$CF_3$, —OH, —$OCH_3$, —$OCF_3$ or —CN. In some embodiments, Z$^{B'}$ is Z21$^{B'}$, Z22$^{B'}$, Z23$^{B'}$, Z24$^{B'}$, Z37$^{B'}$, or Z38$^{B'}$ and each instance of R$^{xB'}$ independently is —F, —Cl, —$CH_3$, —$CFH_2$, —$CF_2H$, —$CF_3$, —OH, —$OCH_3$, —$OCF_3$, or —CN. In some embodiments, Z$^{B'}$ is Z21$^{B'}$, Z22$^{B'}$, Z23$^{B'}$ or Z24$^{B'}$ and each instance of R$^{xB'}$ independently is —F, —Cl, —$CH_3$, —$CF_3$ or —CN. In some embodiments, Z$^{B'}$ is Z21$^{B'}$, Z22$^{B'}$, Z23$^{B'}$, Z24$^{B'}$, Z37$^{B'}$, or Z38$^{B'}$ and each instance of R$^{xB'}$ independently is —F, —Cl, —$CH_3$, —$CF_3$, or —CN.

In some embodiments, R$^{aB'}$ is hydrogen.

In some embodiments, R$^{aB'}$ is —$CH_3$.

In some embodiments, a chemical entity of Formula I$^{B'}$ is a chemical entity of Formula II$^{B'}$:

II$^{B'}$

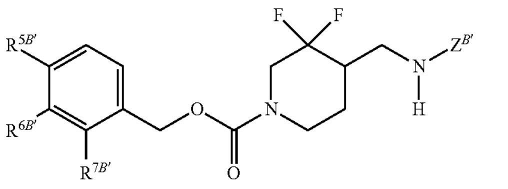

wherein Z$^{B'}$ is as described in embodiments of Formula I$^{B'}$, supra, or described in embodiments herein, both singly and in combination; and wherein R$^{5B'}$, R$^{6B'}$, and R$^{7B'}$ independently are —H, —F, —Cl, $C_1$-$C_4$ alkyl, cyclopropyl, —C≡CH, —$CFH_2$, —$CF_2H$, —$CF_3$, —$CF_2CH_3$, —$CH_2CF_3$, $C_1$-$C_4$ alkoxy, —$OCFH_2$, —$OCF_2H$, —$OCF_3$, —CN, —N(R$^{2B'}$)(R$^{3B'}$), —$NO_2$, $C_1$-$C_4$ alkylthio, $C_1$-$C_4$ alkylsulfonyl, or —$S(O)_2CF_3$;

wherein each instance of R$^{2B'}$ and R$^{3B'}$ independently is —H or $C_1$-$C_4$ alkyl, or —N(R$^{2B'}$)(R$^{3B'}$) is

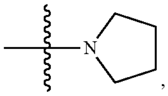
,
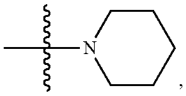
, or
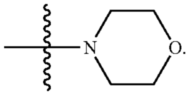

In some embodiments, Z$^{B'}$ is selected from formulas Z1$^{B'}$—Z36$^{B'}$, wherein: R$^{xB'}$ and R$^{aB'}$ are as described in embodiments of formulas Z1$^{B'}$-Z36$^{B'}$, supra, or described in embodiments herein, both singly and in combination.

In some embodiments, Z$^{B'}$ is selected from formulas Z1$^{B'}$—Z38$^{B'}$, wherein: R$^{xB'}$ and R$^{aB'}$ are as described in embodiments of formulas Z1$^{B'}$—Z38$^{B'}$, supra, or described in embodiments herein, both singly and in combination.

In some embodiments, a provided chemical entity is a chemical entity of Formula II$^{B'}$, wherein each of R$^{5B'}$, R$^{6B'}$, and R$^{7B'}$ independently is —H, —F, —Cl, —$CH_3$, —$CFH_2$, —$CF_2H$, —$CF_3$, —$CH_2CH_3$, —$CF_2CH_3$, —$CH_2CF_3$, isopropyl, tert-butyl, cyclopropyl, —$OCF_3$, —$OCF_2H$, —$SCH_3$, —$SCH_2CH_3$, —$S(O)_2CH_3$, —$S(O)_2CH_2CH_3$, —$S(O)_2CF_3$, or —C≡CH.

In some embodiments, a provided chemical entity is a chemical entity of Formula II$^{B'}$, wherein each of R$^{5B'}$, R$^{6B'}$, and R$^{7B'}$ independently is —H, —F, —Cl, —$CH_3$, —$CFH_2$, —$CF_2H$, —$CF_3$, —$CH_2CH_3$, —$CF_2CH_3$, —$CH_2CF_3$, cyclopropyl, —$OCF_3$, —$OCF_2H$, —$SCH_3$, —$S(O)_2CH_3$, or —C≡CH.

In some embodiments, a provided chemical entity is a chemical entity of Formula II$^{B'}$, wherein:

R$^{5B'}$ is —H, —F, —Cl, —$CH_3$, —$CFH_2$, —$CF_2H$, —$CF_3$, —$CH_2CH_3$, —$CF_2CH_3$, —$CH_2CF_3$, cyclopropyl, —$OCF_3$, —$OCF_2H$, —$SCH_3$, —$S(O)_2CH_3$, or —C≡CH;

$R^{6B'}$ is —H or —F; and $R^{7B'}$ is —H, —F, —Cl, or —$CH_3$.

In some embodiments, a provided chemical entity is a chemical entity of Formula $II^{B'}$, wherein each of $R^{5B'}$, $R^{6B'}$, and $R^{7B'}$ independently is —H, —F, —Cl, —$CH_3$, —$CFH_2$, —$CF_2H$, —$CF_3$, —$CH_2CH_3$, —$CF_2CH_3$, —$CH_2CF_3$, isopropyl, tert-butyl, cyclopropyl, —$OCF_3$, —$OCF_2H$, —$SCH_3$, —$SCH_2CH_3$, —$S(O)_2CH_3$, —$S(O)_2CH_2CH_3$, —$S(O)_2CF_3$, or —C≡CH; and $Z^{B'}$ is $Z1^{B'}$, $Z2^{B'}$, $Z6^{B'}$, $Z7^{B'}$, $Z8^{B'}$, $Z9^{B'}$, $Z21^{B'}$, or $Z22^{B'}$. In some such embodiments, $Z^{B'}$ is $Z1^{B'}$, $Z2^{B'}$, $Z8^{B'}$, $Z9^{B'}$, $Z21^{B'}$, or $Z22^{B'}$. In some embodiments, $Z^{B'}$ is $Z1^{B'}$ or $Z2^{B'}$. In some embodiments, $Z^{B'}$ is $Z1^{B'}$. In some embodiments, $Z^{B'}$ is $Z2^{B'}$. In some embodiments, $Z^{B'}$ is $Z21^{B'}$. In some embodiments, $Z^{B'}$ is $Z22^{B'}$.

In some embodiments, a provided chemical entity is a chemical entity of Formula $II^{B'}$, wherein each of $R^{5B'}$, $R^{6B'}$, and $R^{7B'}$ independently is —H, —F, —Cl, —$CH_3$, —$CFH_2$, —$CF_2H$, —$CF_3$, —$CH_2CH_3$, —$CF_2CH_3$, —$CH_2CF_3$, cyclopropyl, —$OCF_3$, —$OCF_2H$, —$SCH_3$, —$S(O)_2CH_3$, or —C≡CH; and $Z^{B'}$ is $Z1^{B'}$, $Z2^{B'}$, $Z8^{B'}$, $Z9^{B'}$, $Z21^{B'}$, or $Z22^{B'}$. In some such embodiments, $Z^{B'}$ is $Z^{B'}$ or $Z2^{B'}$. In some embodiments, $Z^{B'}$ is $Z1^{B'}$. In some embodiments, $Z^{B'}$ is $Z2^{B'}$. In some embodiments, $Z^{B'}$ is $Z21^{B'}$ In some embodiments, $Z^{B'}$ is $Z22^{B'}$.

In some embodiments, a provided chemical entity is a chemical entity of Formula $II^{B'}$, wherein:

$R^{5B'}$ is —H, —F, —Cl, —$CH_3$, —$CFH_2$, —$CF_2H$, —$CF_3$, —$CH_2CH_3$, —$CF_2CH_3$, —$CH_2CF_3$, cyclopropyl, —$OCF_3$, —$OCF_2H$, —$SCH_3$, —$S(O)_2CH_3$, or —C≡CH;

$R^{6B'}$ is —H or —F;

$R^{7B'}$ is —H, —F, —Cl, or —$CH_3$; and $Z^{B'}$ is $Z1^{B'}$, $Z2^{B'}$, $Z8^{B'}$, $Z9^{B'}$, $Z21^{B'}$ or $Z22^{B'}$.

In some embodiments, $Z^{B'}$ is $Z1^{B'}$ or $Z2^{B'}$. In some embodiments, $Z^{B'}$ is Z1B. In some embodiments, $Z^{B'}$ is $Z2^{B'}$. In some embodiments, $Z^{B'}$ is $Z21^{B'}$. In some embodiments, $Z^{B'}$ is $Z22^{B'}$.

In some embodiments, a chemical entity of Formula $I^{B'}$ is a chemical entity of Formula $III^{B'}$:

$III^{B'}$

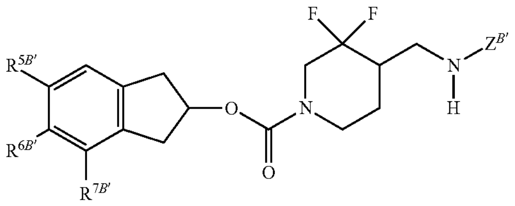

wherein $Z^{B'}$ is as described in embodiments of Formula $I^{B'}$, supra, or described in embodiments herein, both singly and in combination; and wherein $R^{5B'}$, $R^{6B'}$, and $R^{7B'}$ independently are —H, —F, —Cl, $C_1$-$C_4$ alkyl, cyclopropyl, —C≡CH, —$CFH_2$, —$CF_2H$, —$CF_3$, —$CF_2CH_3$, —$CH_2CF_3$, $C_1$-$C_4$ alkoxy, —$OCFH_2$, —$OCF_2H$, —$OCF_3$, —CN, —$N(R^{2B'})(R^{3B'})$, —$NO_2$, $C_1$-$C_4$ alkylthio, $C_1$-$C_4$ alkylsulfonyl, or —$S(O)_2CF_3$;

wherein each instance of $R^{2B'}$ and $R^{3B'}$ independently is —H or $C_1$-$C_4$ alkyl, or —$N(R^{2B'})(R^{3B'})$ is

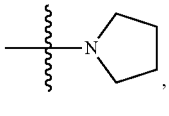
,
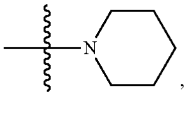
, or

-continued

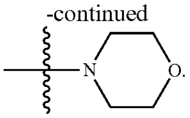
.

In some embodiments, $Z^{B'}$ is selected from formulas $Z1^{B'}$—$Z38^{B'}$, wherein: $R^{xB'}$ and $R^{aB'}$ are as described in embodiments of formulas $Z1^{B'}$—$Z38^{B'}$, supra, or described in embodiments herein, both singly and in combination. In some embodiments, a provided chemical entity is a chemical entity of Formula $III^{B'}$, wherein each of $R^{5B'}$, $R^{6B'}$, and $R^{7B'}$ independently is —H, —F, —Cl, —$CH_3$, —$CFH_2$, —$CF_2H$, —$CF_3$, —$CH_2CH_3$, —$CF_2CH_3$, —$CH_2CF_3$, isopropyl, tert-butyl, cyclopropyl, —$OCF_3$, —$OCF_2H$, —$SCH_3$, —$SCH_2CH_3$, —$S(O)_2CH_3$, —$S(O)_2CH_2CH_3$, —$S(O)_2CF_3$, or —C≡CH.

In some embodiments, a provided chemical entity is a chemical entity of Formula $III^{B'}$, wherein each of $R^{5B'}$, $R^{6B'}$, and $R^{7B'}$ independently is —H, —F, —Cl, —$CH_3$, —$CFH_2$, —$CF_2H$, —$CF_3$, —$CH_2CH_3$, —$CF_2CH_3$, —$CH_2CF_3$, cyclopropyl, —$OCF_3$, —$OCF_2H$, —$SCH_3$, —$S(O)_2CH_3$, or —C≡CH.

In some embodiments, a provided chemical entity is a chemical entity of Formula $II^{B'}$, wherein each of $R^{5B'}$, $R^{6B'}$, and $R^{7B'}$ independently is —H, —F, —Cl, —$CH_3$, —$CFH_2$, —$CF_2H$, —$CF_3$, —$CH_2CH_3$, —$CF_2CH_3$, —$CH_2CF_3$, isopropyl, tert-butyl, cyclopropyl, —$OCF_3$, —$OCF_2H$, —$SCH_3$, —$SCH_2CH_3$, —$S(O)_2CH_3$, —$S(O)_2CH_2CH_3$, —$S(O)_2CF_3$, or —C≡CH; and $Z^{B'}$ is $Z21^{B'}$, $Z22^{B'}$, $Z24^{B'}$, $Z37^{B'}$, or $Z38^{B'}$. In some embodiments, $Z^{B'}$ is $Z21^{B'}$. In some embodiments, $Z^{B'}$ is $Z22^{B'}$. In some embodiments, $Z^{B'}$ is $Z24^{B'}$. In some embodiments, $Z^{B'}$ is $Z37^{B'}$. In some embodiments, $Z^{B'}$ is $Z38^{B'}$.

In some embodiments, a provided chemical entity is a chemical entity of Formula $II^{B'}$, wherein each of $R^{5B'}$, $R^{6B'}$, and $R^{7B'}$ independently is —H, —F, —Cl, —$CH_3$, —$CFH_2$, —$CF_2H$, —$CF_3$, —$CH_2CH_3$, —$CF_2CH_3$, —$CH_2CF_3$, cyclopropyl, —$OCF_3$, —$OCF_2H$, —$SCH_3$, —$S(O)_2CH_3$, or —C≡CH; and $Z^{B'}$ is $Z21^{B'}$, $Z22^{B'}$, $Z24^{B'}$, $Z37^{B'}$, or $Z38^{B'}$. In some embodiments, $Z^{B'}$ is $Z21^{B'}$. In some embodiments, $Z^{B'}$ is $Z22^{B'}$. In some embodiments, $Z^{B'}$ is $Z24^{B'}$. In some embodiments, $Z^{B'}$ is $Z37^{B'}$. In some embodiments, $Z^{B'}$ is $Z38^{B'}$.

Designation of the stereocenter as R indicates that the R isomer is present in greater amount than the corresponding S isomer. For example, the R isomer can be present in an enantiomeric excess of 50%, 60%, 70%, 80%, 85%, 90%, 92%, 94%, 96%, or 98% relative to the S isomer. Similarly, in synthetic intermediates in which more than one stereocenter may be indicated, the R isomer can be present in a diastereomeric excess of 50%, 60%, 70%, 80%, 85%, 90%, 92%, 94%, 96%, or 98% relative to the S isomer.

Designation of the stereocenter as S indicates that the S isomer is present in greater amount than the corresponding R isomer. For example, the S isomer can be present in an enantiomeric excess of 50%, 60%, 70%, 80%, 85%, 90%, 92%, 94%, 96%, or 98% relative to the R isomer. Similarly, in synthetic intermediates in which more than one stereocenter may be indicated, the S isomer can be present in a diastereomeric excess of 50%, 60%, 70%, 80%, 85%, 90%, 92%, 94%, 96%, or 98% relative to the R isomer.

Designation of the optical rotation of a chemical entity indicates that the indicated enantiomer is present in greater amount than the opposite enantiomer. For example, the (−) isomer can be present in an enantiomeric excess of 50%, 60%, 70%, 80%, 85%, 90%, 92%, 94%, 96%, or 98% relative to the (+) isomer. Similarly, the (+) isomer can be present in an enantiomeric excess of 50%, 60%, 70%, 80%, 85%, 90%, 92%, 94%, 96%, or 98% relative to the (−) isomer.

Exemplary chemical entities of Formula $I^{B'}$ are shown in Tables 12.C, 13.E1, 14.E2, 15.III-C and 16.III-E1 below.

TABLE 12.C

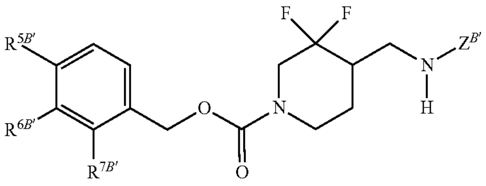

(racemic)

| compound | $Z^{B'}$ | $R^{5B'}$ | $R^{6B'}$ | $R^{7B'}$ |
|---|---|---|---|---|
| C-1.1$^{B'}$ | $Z1^{B'}$ | H | H | H |
| C-1.2$^{B'}$ | $Z1^{B'}$ | $CH_3$ | H | H |
| C-1.3$^{B'}$ | $Z1^{B'}$ | Cl | H | H |
| C-1.4$^{B'}$ | $Z1^{B'}$ | F | H | H |
| C-1.5$^{B'}$ | $Z1^{B'}$ | $CH_2CH_3$ | H | H |
| C-1.6$^{B'}$ | $Z1^{B'}$ | $CF_2H$ | H | H |
| C-1.7$^{B'}$ | $Z1^{B'}$ | $CH_2F$ | H | H |
| C-1.8$^{B'}$ | $Z1^{B'}$ | $CF_3$ | H | H |
| C-1.9$^{B'}$ | $Z1^{B'}$ | $CF_2CH_3$ | H | H |
| C-1.10$^{B'}$ | $Z1^{B'}$ | $CH_2CF_3$ | H | H |
| C-1.11$^{B'}$ | $Z1^{B'}$ | cyclopropyl | H | H |
| C-1.12$^{B'}$ | $Z1^{B'}$ | $OCF_3$ | H | H |
| C-1.13$^{B'}$ | $Z1^{B'}$ | $OCF_2H$ | H | H |
| C-1.14$^{B'}$ | $Z1^{B'}$ | Cl | H | F |
| C-1.15$^{B'}$ | $Z1^{B'}$ | $CH_3$ | H | F |
| C-1.16$^{B'}$ | $Z1^{B'}$ | $CH_3$ | F | H |
| C-1.17$^{B'}$ | $Z1^{B'}$ | Cl | F | H |
| C-1.18$^{B'}$ | $Z1^{B'}$ | F | F | H |
| C-1.19$^{B'}$ | $Z1^{B'}$ | F | H | F |
| C-1.20$^{B'}$ | $Z1^{B'}$ | F | H | Cl |
| C-1.21$^{B'}$ | $Z1^{B'}$ | F | H | $CH_3$ |
| C-1.22$^{B'}$ | $Z1^{B'}$ | Cl | H | $CH_3$ |
| C-1.23$^{B'}$ | $Z1^{B'}$ | $SCH_3$ | H | H |
| C-1.24$^{B'}$ | $Z1^{B'}$ | $SO_2CH_3$ | H | H |
| C-1.25$^{B'}$ | $Z1^{B'}$ | ethynyl | H | H |
| C-2.1$^{B'}$ | $Z2^{B'}$ | H | H | H |
| C-2.2$^{B'}$ | $Z2^{B'}$ | $CH_3$ | H | H |
| C-2.3$^{B'}$ | $Z2^{B'}$ | Cl | H | H |
| C-2.4$^{B'}$ | $Z2^{B'}$ | F | H | H |
| C-2.5$^{B'}$ | $Z2^{B'}$ | $CH_2CH_3$ | H | H |
| C-2.6$^{B'}$ | $Z2^{B'}$ | $CF_2H$ | H | H |
| C-2.7$^{B'}$ | $Z2^{B'}$ | $CH_2F$ | H | H |
| C-2.8$^{B'}$ | $Z2^{B'}$ | $CF_3$ | H | H |
| C-2.9$^{B'}$ | $Z2^{B'}$ | $CF_2CH_3$ | H | H |
| C-2.10$^{B'}$ | $Z2^{B'}$ | $CH_2CF_3$ | H | H |
| C-2.11$^{B'}$ | $Z2^{B'}$ | cyclopropyl | H | H |
| C-2.12$^{B'}$ | $Z2^{B'}$ | $OCF_3$ | H | H |
| C-2.13$^{B'}$ | $Z2^{B'}$ | $OCF_2H$ | H | H |
| C-2.14$^{B'}$ | $Z2^{B'}$ | Cl | H | F |
| C-2.15$^{B'}$ | $Z2^{B'}$ | $CH_3$ | H | F |
| C-2.16$^{B'}$ | $Z2^{B'}$ | $CH_3$ | F | H |
| C-2.17$^{B'}$ | $Z2^{B'}$ | Cl | F | H |
| C-2.18$^{B'}$ | $Z2^{B'}$ | F | F | H |
| C-2.19$^{B'}$ | $Z2^{B'}$ | F | H | F |
| C-2.20$^{B'}$ | $Z2^{B'}$ | F | H | Cl |
| C-2.21$^{B'}$ | $Z2^{B'}$ | F | H | $CH_3$ |
| C-2.22$^{B'}$ | $Z2^{B'}$ | Cl | H | $CH_3$ |
| C-2.23$^{B'}$ | $Z2^{B'}$ | $SCH_3$ | H | H |
| C-2.24$^{B'}$ | $Z2^{B'}$ | $SO_2CH_3$ | H | H |
| C-2.25$^{B'}$ | $Z2^{B'}$ | ethynyl | H | H |
| C-3.1$^{B'}$ | $Z3^{B'}$ | H | H | H |
| C-3.2$^{B'}$ | $Z3^{B'}$ | $CH_3$ | H | H |
| C-3.3$^{B'}$ | $Z3^{B'}$ | Cl | H | H |
| C-3.4$^{B'}$ | $Z3^{B'}$ | F | H | H |
| C-3.5$^{B'}$ | $Z3^{B'}$ | $CH_2CH_3$ | H | H |
| C-3.6$^{B'}$ | $Z3^{B'}$ | $CF_2H$ | H | H |
| C-3.7$^{B'}$ | $Z3^{B'}$ | $CH_2F$ | H | H |
| C-3.8$^{B'}$ | $Z3^{B'}$ | $CF_3$ | H | H |

TABLE 12.C-continued

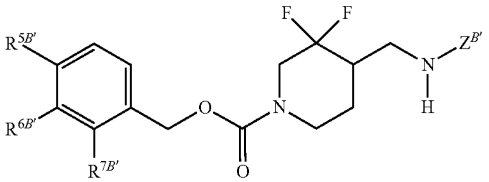

(racemic)

| compound | $Z^{B'}$ | $R^{5B'}$ | $R^{6B'}$ | $R^{7B'}$ |
|---|---|---|---|---|
| C-3.9$^{B'}$ | $Z3^{B'}$ | $CF_2CH_3$ | H | H |
| C-3.10$^{B'}$ | $Z3^{B'}$ | $CH_2CF_3$ | H | H |
| C-3.11$^{B'}$ | $Z3^{B'}$ | cyclopropyl | H | H |
| C-3.12$^{B'}$ | $Z3^{B'}$ | $OCF_3$ | H | H |
| C-3.13$^{B'}$ | $Z3^{B'}$ | $OCF_2H$ | H | H |
| C-3.14$^{B'}$ | $Z3^{B'}$ | Cl | H | F |
| C-3.15$^{B'}$ | $Z3^{B'}$ | $CH_3$ | H | F |
| C-3.16$^{B'}$ | $Z3^{B'}$ | $CH_3$ | F | H |
| C-3.17$^{B'}$ | $Z3^{B'}$ | Cl | F | H |
| C-3.18$^{B'}$ | $Z3^{B'}$ | F | F | H |
| C-3.19$^{B'}$ | $Z3^{B'}$ | F | H | F |
| C-3.20$^{B'}$ | $Z3^{B'}$ | F | H | Cl |
| C-3.21$^{B'}$ | $Z3^{B'}$ | F | H | $CH_3$ |
| C-3.22$^{B'}$ | $Z3^{B'}$ | Cl | H | $CH_3$ |
| C-3.23$^{B'}$ | $Z3^{B'}$ | $SCH_3$ | H | H |
| C-3.24$^{B'}$ | $Z3^{B'}$ | $SO_2CH_3$ | H | H |
| C-3.25$^{B'}$ | $Z3^{B'}$ | ethynyl | H | H |
| C-4.1$^{B'}$ | $Z4^{B'}$ | H | H | H |
| C-4.2$^{B'}$ | $Z4^{B'}$ | $CH_3$ | H | H |
| C-4.3$^{B'}$ | $Z4^{B'}$ | Cl | H | H |
| C-4.4$^{B'}$ | $Z4^{B'}$ | F | H | H |
| C-4.5$^{B'}$ | $Z4^{B'}$ | $CH_2CH_3$ | H | H |
| C-4.6$^{B'}$ | $Z4^{B'}$ | $CF_2H$ | H | H |
| C-4.7$^{B'}$ | $Z4^{B'}$ | $CH_2F$ | H | H |
| C-4.8$^{B'}$ | $Z4^{B'}$ | $CF_3$ | H | H |
| C-4.9$^{B'}$ | $Z4^{B'}$ | $CF_2CH_3$ | H | H |
| C-4.10$^{B'}$ | $Z4^{B'}$ | $CH_2CF_3$ | H | H |
| C-4.11$^{B'}$ | $Z4^{B'}$ | cyclopropyl | H | H |
| C-4.12$^{B'}$ | $Z4^{B'}$ | $OCF_3$ | H | H |
| C-4.13$^{B'}$ | $Z4^{B'}$ | $OCF_2H$ | H | H |
| C-4.14$^{B'}$ | $Z4^{B'}$ | Cl | H | F |
| C-4.15$^{B'}$ | $Z4^{B'}$ | $CH_3$ | H | F |
| C-4.16$^{B'}$ | $Z4^{B'}$ | $CH_3$ | F | H |
| C-4.17$^{B'}$ | $Z4^{B'}$ | Cl | F | H |
| C-4.18$^{B'}$ | $Z4^{B'}$ | F | F | H |
| C-4.19$^{B'}$ | $Z4^{B'}$ | F | H | F |
| C-4.20$^{B'}$ | $Z4^{B'}$ | F | H | Cl |
| C-4.21$^{B'}$ | $Z4^{B'}$ | F | H | $CH_3$ |
| C-4.22$^{B'}$ | $Z4^{B'}$ | Cl | H | $CH_3$ |
| C-4.23$^{B'}$ | $Z4^{B'}$ | $SCH_3$ | H | H |
| C-4.24$^{B'}$ | $Z4^{B'}$ | $SO_2CH_3$ | H | H |
| C-4.25$^{B'}$ | $Z4^{B'}$ | ethynyl | H | H |
| C-5.1$^{B'}$ | $Z5^{B'}$ | H | H | H |
| C-5.2$^{B'}$ | $Z5^{B'}$ | $CH_3$ | H | H |
| C-5.3$^{B'}$ | $Z5^{B'}$ | Cl | H | H |
| C-5.4$^{B'}$ | $Z5^{B'}$ | F | H | H |
| C-5.5$^{B'}$ | $Z5^{B'}$ | $CH_2CH_3$ | H | H |
| C-5.6$^{B'}$ | $Z5^{B'}$ | $CF_2H$ | H | H |
| C-5.7$^{B'}$ | $Z5^{B'}$ | $CH_2F$ | H | H |
| C-5.8$^{B'}$ | $Z5^{B'}$ | $CF_3$ | H | H |
| C-5.9$^{B'}$ | $Z5^{B'}$ | $CF_2CH_3$ | H | H |
| C-5.10$^{B'}$ | $Z5^{B'}$ | $CH_2CF_3$ | H | H |
| C-5.11$^{B'}$ | $Z5^{B'}$ | cyclopropyl | H | H |
| C-5.12$^{B'}$ | $Z5^{B'}$ | $OCF_3$ | H | H |
| C-5.13$^{B'}$ | $Z5^{B'}$ | $OCF_2H$ | H | H |
| C-5.14$^{B'}$ | $Z5^{B'}$ | Cl | H | F |
| C-5.15$^{B'}$ | $Z5^{B'}$ | $CH_3$ | H | F |
| C-5.16$^{B'}$ | $Z5^{B'}$ | $CH_3$ | F | H |
| C-5.17$^{B'}$ | $Z5^{B'}$ | Cl | F | H |
| C-5.18$^{B'}$ | $Z5^{B'}$ | F | F | H |
| C-5.19$^{B'}$ | $Z5^{B'}$ | F | H | F |
| C-5.20$^{B'}$ | $Z5^{B'}$ | F | H | Cl |
| C-5.21$^{B'}$ | $Z5^{B'}$ | F | H | $CH_3$ |
| C-5.22$^{B'}$ | $Z5^{B'}$ | Cl | H | $CH_3$ |
| C-5.23$^{B'}$ | $Z5^{B'}$ | $SCH_3$ | H | H |
| C-5.24$^{B'}$ | $Z5^{B'}$ | $SO_2CH_3$ | H | H |

TABLE 12.C-continued

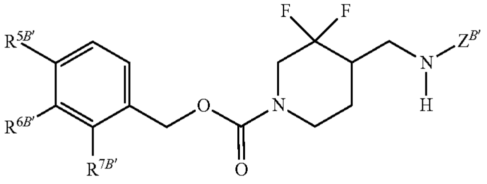

(racemic)

| compound | $Z^{B'}$ | $R^{5B'}$ | $R^{6B'}$ | $R^{7B'}$ |
|---|---|---|---|---|
| C-5.25$^{B'}$ | Z5$^{B'}$ | ethynyl | H | H |
| C-6.1$^{B'}$ | Z6$^{B'}$, $R^{aB'}$ is H | H | H | H |
| C-6.2$^{B'}$ | Z6$^{B'}$, $R^{aB'}$ is H | $CH_3$ | H | H |
| C-6.3$^{B'}$ | Z6$^{B'}$, $R^{aB'}$ is H | Cl | H | H |
| C-6.4$^{B'}$ | Z6$^{B'}$, $R^{aB'}$ is H | F | H | H |
| C-6.5$^{B'}$ | Z6$^{B'}$, $R^{aB'}$ is H | $CH_2CH_3$ | H | H |
| C-6.6$^{B'}$ | Z6$^{B'}$, $R^{aB'}$ is H | $CF_2H$ | H | H |
| C-6.7$^{B'}$ | Z6$^{B'}$, $R^{aB'}$ is H | $CH_2F$ | H | H |
| C-6.8$^{B'}$ | Z6$^{B'}$, $R^{aB'}$ is H | $CF_3$ | H | H |
| C-6.9$^{B'}$ | Z6$^{B'}$, $R^{aB'}$ is H | $CF_2CH_3$ | H | H |
| C-6.10$^{B'}$ | Z6$^{B'}$, $R^{aB'}$ is H | $CH_2CF_3$ | H | H |
| C-6.11$^{B'}$ | Z6$^{B'}$, $R^{aB'}$ is H | cyclopropyl | H | H |
| C-6.12$^{B'}$ | Z6$^{B'}$, $R^{aB'}$ is H | $OCF_3$ | H | H |
| C-6.13$^{B'}$ | Z6$^{B'}$, $R^{aB'}$ is H | $OCF_2H$ | H | H |
| C-6.14$^{B'}$ | Z6$^{B'}$, $R^{aB'}$ is H | Cl | H | F |
| C-6.15$^{B'}$ | Z6$^{B'}$, $R^{aB'}$ is H | $CH_3$ | H | F |
| C-6.16$^{B'}$ | Z6$^{B'}$, $R^{aB'}$ is H | $CH_3$ | F | H |
| C-6.17$^{B'}$ | Z6$^{B'}$, $R^{aB'}$ is H | Cl | F | H |
| C-6.18$^{B'}$ | Z6$^{B'}$, $R^{aB'}$ is H | F | F | H |
| C-6.19$^{B'}$ | Z6$^{B'}$, $R^{aB'}$ is H | F | H | F |
| C-6.20$^{B'}$ | Z6$^{B'}$, $R^{aB'}$ is H | F | H | Cl |
| C-6.21$^{B'}$ | Z6$^{B'}$, $R^{aB'}$ is H | F | H | $CH_3$ |
| C-6.22$^{B'}$ | Z6$^{B'}$, $R^{aB'}$ is H | Cl | H | $CH_3$ |
| C-6.23$^{B'}$ | Z6$^{B'}$, $R^{aB'}$ is H | $SCH_3$ | H | H |
| C-6.24$^{B'}$ | Z6$^{B'}$, $R^{aB'}$ is H | $SO_2CH_3$ | H | H |
| C-6.25$^{B'}$ | Z6$^{B'}$, $R^{aB'}$ is H | ethynyl | H | H |
| C-7.1$^{B'}$ | Z7$^{B'}$, $R^{aB'}$ is H | H | H | H |
| C-7.2$^{B'}$ | Z7$^{B'}$, $R^{aB'}$ is H | $CH_3$ | H | H |
| C-7.3$^{B'}$ | Z7$^{B'}$, $R^{aB'}$ is H | Cl | H | H |
| C-7.4$^{B'}$ | Z7$^{B'}$, $R^{aB'}$ is H | F | H | H |
| C-7.5$^{B'}$ | Z7$^{B'}$, $R^{aB'}$ is H | $CH_2CH_3$ | H | H |
| C-7.6$^{B'}$ | Z7$^{B'}$, $R^{aB'}$ is H | $CF_2H$ | H | H |
| C-7.7$^{B'}$ | Z7$^{B'}$, $R^{aB'}$ is H | $CH_2F$ | H | H |
| C-7.8$^{B'}$ | Z7$^{B'}$, $R^{aB'}$ is H | $CF_3$ | H | H |
| C-7.9$^{B'}$ | Z7$^{B'}$, $R^{aB'}$ is H | $CF_2CH_3$ | H | H |
| C-7.10$^{B'}$ | Z7$^{B'}$, $R^{aB'}$ is H | $CH_2CF_3$ | H | H |
| C-7.11$^{B'}$ | Z7$^{B'}$, $R^{aB'}$ is H | cyclopropyl | H | H |
| C-7.12$^{B'}$ | Z7$^{B'}$, $R^{aB'}$ is H | $OCF_3$ | H | H |
| C-7.13$^{B'}$ | Z7$^{B'}$, $R^{aB'}$ is H | $OCF_2H$ | H | H |
| C-7.14$^{B'}$ | Z7$^{B'}$, $R^{aB'}$ is H | Cl | H | F |
| C-7.15$^{B'}$ | Z7$^{B'}$, $R^{aB'}$ is H | $CH_3$ | H | F |
| C-7.16$^{B'}$ | Z7$^{B'}$, $R^{aB'}$ is H | $CH_3$ | F | H |
| C-7.17$^{B'}$ | Z7$^{B'}$, $R^{aB'}$ is H | Cl | F | H |
| C-7.18$^{B'}$ | Z7$^{B'}$, $R^{aB'}$ is H | F | F | H |
| C-7.19$^{B'}$ | Z7$^{B'}$, $R^{aB'}$ is H | F | H | F |
| C-7.20$^{B'}$ | Z7$^{B'}$, $R^{aB'}$ is H | F | H | Cl |
| C-7.21$^{B'}$ | Z7$^{B'}$, $R^{aB'}$ is H | F | H | $CH_3$ |
| C-7.22$^{B'}$ | Z7$^{B'}$, $R^{aB'}$ is H | Cl | H | $CH_3$ |
| C-7.23$^{B'}$ | Z7$^{B'}$, $R^{aB'}$ is H | $SCH_3$ | H | H |
| C-7.24$^{B'}$ | Z7$^{B'}$, $R^{aB'}$ is H | $SO_2CH_3$ | H | H |
| C-7.25$^{B'}$ | Z7$^{B'}$, $R^{aB'}$ is H | ethynyl | H | H |
| C-8.1$^{B'}$ | Z8$^{B'}$, $R^{aB'}$ is H | H | H | H |
| C-8.2$^{B'}$ | Z8$^{B'}$, $R^{aB'}$ is H | $CH_3$ | H | H |
| C-8.3$^{B'}$ | Z8$^{B'}$, $R^{aB'}$ is H | Cl | H | H |
| C-8.4$^{B'}$ | Z8$^{B'}$, $R^{aB'}$ is H | F | H | H |
| C-8.5$^{B'}$ | Z8$^{B'}$, $R^{aB'}$ is H | $CH_2CH_3$ | H | H |
| C-8.6$^{B'}$ | Z8$^{B'}$, $R^{aB'}$ is H | $CF_2H$ | H | H |
| C-8.7$^{B'}$ | Z8$^{B'}$, $R^{aB'}$ is H | $CH_2F$ | H | H |
| C-8.8$^{B'}$ | Z8$^{B'}$, $R^{aB'}$ is H | $CF_3$ | H | H |
| C-8.9$^{B'}$ | Z8$^{B'}$, $R^{aB'}$ is H | $CF_2CH_3$ | H | H |
| C-8.10$^{B'}$ | Z8$^{B'}$, $R^{aB'}$ is H | $CH_2CF_3$ | H | H |
| C-8.11$^{B'}$ | Z8$^{B'}$, $R^{aB'}$ is H | cyclopropyl | H | H |
| C-8.12$^{B'}$ | Z8$^{B'}$, $R^{aB'}$ is H | $OCF_3$ | H | H |
| C-8.13$^{B'}$ | Z8$^{B'}$, $R^{aB'}$ is H | $OCF_2H$ | H | H |
| C-8.14$^{B'}$ | Z8$^{B'}$, $R^{aB'}$ is H | Cl | H | F |
| C-8.15$^{B'}$ | Z8$^{B'}$, $R^{aB'}$ is H | $CH_3$ | H | F |

TABLE 12.C-continued

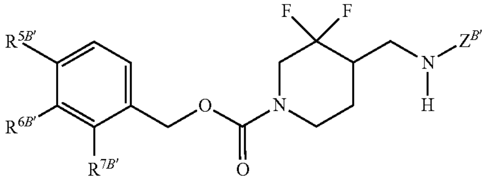

(racemic)

| compound | $Z^{B'}$ | $R^{5B'}$ | $R^{6B'}$ | $R^{7B'}$ |
|---|---|---|---|---|
| C-8.16$^{B'}$ | Z8$^{B'}$, $R^{aB'}$ is H | $CH_3$ | F | H |
| C-8.17$^{B'}$ | Z8$^{B'}$, $R^{aB'}$ is H | Cl | F | H |
| C-8.18$^{B'}$ | Z8$^{B'}$, $R^{aB'}$ is H | F | F | H |
| C-8.19$^{B'}$ | Z8$^{B'}$, $R^{aB'}$ is H | F | H | F |
| C-8.20$^{B'}$ | Z8$^{B'}$, $R^{aB'}$ is H | F | H | Cl |
| C-8.21$^{B'}$ | Z8$^{B'}$, $R^{aB'}$ is H | F | H | $CH_3$ |
| C-8.22$^{B'}$ | Z8$^{B'}$, $R^{aB'}$ is H | Cl | H | $CH_3$ |
| C-8.23$^{B'}$ | Z8$^{B'}$, $R^{aB'}$ is H | $SCH_3$ | H | H |
| C-8.24$^{B'}$ | Z8$^{B'}$, $R^{aB'}$ is H | $SO_2CH_3$ | H | H |
| C-8.25$^{B'}$ | Z8$^{B'}$, $R^{aB'}$ is H | ethynyl | H | H |
| C-9.1$^{B'}$ | Z9$^{B'}$ | H | H | H |
| C-9.2$^{B'}$ | Z9$^{B'}$ | $CH_3$ | H | H |
| C-9.3$^{B'}$ | Z9$^{B'}$ | Cl | H | H |
| C-9.4$^{B'}$ | Z9$^{B'}$ | F | H | H |
| C-9.5$^{B'}$ | Z9$^{B'}$ | $CH_2CH_3$ | H | H |
| C-9.6$^{B'}$ | Z9$^{B'}$ | $CF_2H$ | H | H |
| C-9.7$^{B'}$ | Z9$^{B'}$ | $CH_2F$ | H | H |
| C-9.8$^{B'}$ | Z9$^{B'}$ | $CF_3$ | H | H |
| C-9.9$^{B'}$ | Z9$^{B'}$ | $CF_2CH_3$ | H | H |
| C-9.10$^{B'}$ | Z9$^{B'}$ | $CH_2CF_3$ | H | H |
| C-9.11$^{B'}$ | Z9$^{B'}$ | cyclopropyl | H | H |
| C-9.12$^{B'}$ | Z9$^{B'}$ | $OCF_3$ | H | H |
| C-9.13$^{B'}$ | Z9$^{B'}$ | $OCF_2H$ | H | H |
| C-9.14$^{B'}$ | Z9$^{B'}$ | Cl | H | F |
| C-9.15$^{B'}$ | Z9$^{B'}$ | $CH_3$ | H | F |
| C-9.16$^{B'}$ | Z9$^{B'}$ | $CH_3$ | F | H |
| C-9.17$^{B'}$ | Z9$^{B'}$ | Cl | F | H |
| C-9.18$^{B'}$ | Z9$^{B'}$ | F | F | H |
| C-9.19$^{B'}$ | Z9$^{B'}$ | F | H | F |
| C-9.20$^{B'}$ | Z9$^{B'}$ | F | H | Cl |
| C-9.21$^{B'}$ | Z9$^{B'}$ | F | H | $CH_3$ |
| C-9.22$^{B'}$ | Z9$^{B'}$ | Cl | H | $CH_3$ |
| C-9.23$^{B'}$ | Z9$^{B'}$ | $SCH_3$ | H | H |
| C-9.24$^{B'}$ | Z9$^{B'}$ | $SO_2CH_3$ | H | H |
| C-9.25$^{B'}$ | Z9$^{B'}$ | ethynyl | H | H |
| C-10.1$^{B'}$ | Z10$^{B'}$ | H | H | H |
| C-10.2$^{B'}$ | Z10$^{B'}$ | $CH_3$ | H | H |
| C-10.3$^{B'}$ | Z10$^{B'}$ | Cl | H | H |
| C-10.4$^{B'}$ | Z10$^{B'}$ | F | H | H |
| C-10.5$^{B'}$ | Z10$^{B'}$ | $CH_2CH_3$ | H | H |
| C-10.6$^{B'}$ | Z10$^{B'}$ | $CF_2H$ | H | H |
| C-10.7$^{B'}$ | Z10$^{B'}$ | $CH_2F$ | H | H |
| C-10.8$^{B'}$ | Z10$^{B'}$ | $CF_3$ | H | H |
| C-10.9$^{B'}$ | Z10$^{B'}$ | $CF_2CH_3$ | H | H |
| C-10.10$^{B'}$ | Z10$^{B'}$ | $CH_2CF_3$ | H | H |
| C-10.11$^{B'}$ | Z10$^{B'}$ | cyclopropyl | H | H |
| C-10.12$^{B'}$ | Z10$^{B'}$ | $OCF_3$ | H | H |
| C-10.13$^{B'}$ | Z10$^{B'}$ | $OCF_2H$ | H | H |
| C-10.14$^{B'}$ | Z10$^{B'}$ | Cl | H | F |
| C-10.15$^{B'}$ | Z10$^{B'}$ | $CH_3$ | H | F |
| C-10.16$^{B'}$ | Z10$^{B'}$ | $CH_3$ | F | H |
| C-10.17$^{B'}$ | Z10$^{B'}$ | Cl | F | H |
| C-10.18$^{B'}$ | Z10$^{B'}$ | F | F | H |
| C-10.19$^{B'}$ | Z10$^{B'}$ | F | H | F |
| C-10.20$^{B'}$ | Z10$^{B'}$ | F | H | Cl |
| C-10.21$^{B'}$ | Z10$^{B'}$ | F | H | $CH_3$ |
| C-10.22$^{B'}$ | Z10$^{B'}$ | Cl | H | $CH_3$ |
| C-10.23$^{B'}$ | Z10$^{B'}$ | $SCH_3$ | H | H |
| C-10.24$^{B'}$ | Z10$^{B'}$ | $SO_2CH_3$ | H | H |
| C-10.25$^{B'}$ | Z10$^{B'}$ | ethynyl | H | H |
| C-11.1$^{B'}$ | Z11$^{B'}$, $R^{aB'}$ is H | H | H | H |
| C-11.2$^{B'}$ | Z11$^{B'}$, $R^{aB'}$ is H | $CH_3$ | H | H |
| C-11.3$^{B'}$ | Z11$^{B'}$, $R^{aB'}$ is H | Cl | H | H |
| C-11.4$^{B'}$ | Z11$^{B'}$, $R^{aB'}$ is H | F | H | H |
| C-11.5$^{B'}$ | Z11$^{B'}$, $R^{aB'}$ is H | $CH_2CH_3$ | H | H |
| C-11.6$^{B'}$ | Z11$^{B'}$, $R^{aB'}$ is H | $CF_2H$ | H | H |

TABLE 12.C-continued

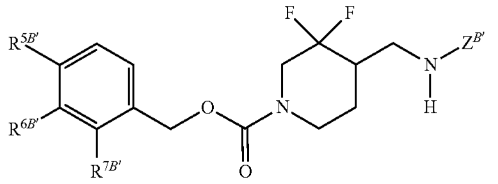

(racemic)

| compound | $Z^{B'}$ | $R^{5B'}$ | $R^{6B'}$ | $R^{7B'}$ |
|---|---|---|---|---|
| C-11.7$^{B'}$ | Z11$^{B'}$, $R^{aB'}$ is H | $CH_2F$ | H | H |
| C-11.8$^{B'}$ | Z11$^{B'}$, $R^{aB'}$ is H | $CF_3$ | H | H |
| C-11.9$^{B'}$ | Z11$^{B'}$, $R^{aB'}$ is H | $CF_2CH_3$ | H | H |
| C-11.10$^{B'}$ | Z11$^{B'}$, $R^{aB'}$ is H | $CH_2CF_3$ | H | H |
| C-11.11$^{B'}$ | Z11$^{B'}$, $R^{aB'}$ is H | cyclopropyl | H | H |
| C-11.12$^{B'}$ | Z11$^{B'}$, $R^{aB'}$ is H | $OCF_3$ | H | H |
| C-11.13$^{B'}$ | Z11$^{B'}$, $R^{aB'}$ is H | $OCF_2H$ | H | H |
| C-11.14$^{B'}$ | Z11$^{B'}$, $R^{aB'}$ is H | Cl | H | F |
| C-11.15$^{B'}$ | Z11$^{B'}$, $R^{aB'}$ is H | $CH_3$ | H | F |
| C-11.16$^{B'}$ | Z11$^{B'}$, $R^{aB'}$ is H | $CH_3$ | F | H |
| C-11.17$^{B'}$ | Z11$^{B'}$, $R^{aB'}$ is H | Cl | F | H |
| C-11.18$^{B'}$ | Z11$^{B'}$, $R^{aB'}$ is H | F | F | H |
| C-11.19$^{B'}$ | Z11$^{B'}$, $R^{aB'}$ is H | F | H | F |
| C-11.20$^{B'}$ | Z11$^{B'}$, $R^{aB'}$ is H | F | H | Cl |
| C-11.21$^{B'}$ | Z11$^{B'}$, $R^{aB'}$ is H | F | H | $CH_3$ |
| C-11.22$^{B'}$ | Z11$^{B'}$, $R^{aB'}$ is H | Cl | H | $CH_3$ |
| C-11.23$^{B'}$ | Z11$^{B'}$, $R^{aB'}$ is H | $SCH_3$ | H | H |
| C-11.24$^{B'}$ | Z11$^{B'}$, $R^{aB'}$ is H | $SO_2CH_3$ | H | H |
| C-11.25$^{B'}$ | Z11$^{B'}$, $R^{aB'}$ is H | ethynyl | H | H |
| C-12.1$^{B'}$ | Z12$^{B'}$ | H | H | H |
| C-12.2$^{B'}$ | Z12$^{B'}$ | $CH_3$ | H | H |
| C-12.3$^{B'}$ | Z12$^{B'}$ | Cl | H | H |
| C-12.4$^{B'}$ | Z12$^{B'}$ | F | H | H |
| C-12.5$^{B'}$ | Z12$^{B'}$ | $CH_2CH_3$ | H | H |
| C-12.6$^{B'}$ | Z12$^{B'}$ | $CF_2H$ | H | H |
| C-12.7$^{B'}$ | Z12$^{B'}$ | $CH_2F$ | H | H |
| C-12.8$^{B'}$ | Z12$^{B'}$ | $CF_3$ | H | H |
| C-12.9$^{B'}$ | Z12$^{B'}$ | $CF_2CH_3$ | H | H |
| C-12.10$^{B'}$ | Z12$^{B'}$ | $CH_2CF_3$ | H | H |
| C-12.11$^{B'}$ | Z12$^{B'}$ | cyclopropyl | H | H |
| C-12.12$^{B'}$ | Z12$^{B'}$ | $OCF_3$ | H | H |
| C-12.13$^{B'}$ | Z12$^{B'}$ | $OCF_2H$ | H | H |
| C-12.14$^{B'}$ | Z12$^{B'}$ | Cl | H | F |
| C-12.15$^{B'}$ | Z12$^{B'}$ | $CH_3$ | H | F |
| C-12.16$^{B'}$ | Z12$^{B'}$ | $CH_3$ | F | H |
| C-12.17$^{B'}$ | Z12$^{B'}$ | Cl | F | H |
| C-12.18$^{B'}$ | Z12$^{B'}$ | F | F | H |
| C-12.19$^{B'}$ | Z12$^{B'}$ | F | H | F |
| C-12.20$^{B'}$ | Z12$^{B'}$ | F | H | Cl |
| C-12.21$^{B'}$ | Z12$^{B'}$ | F | H | $CH_3$ |
| C-12.22$^{B'}$ | Z12$^{B'}$ | Cl | H | $CH_3$ |
| C-12.23$^{B'}$ | Z12$^{B'}$ | $SCH_3$ | H | H |
| C-12.24$^{B'}$ | Z12$^{B'}$ | $SO_2CH_3$ | H | H |
| C-12.25$^{B'}$ | Z12$^{B'}$ | ethynyl | H | H |
| C-13.1$^{B'}$ | Z13$^{B'}$, $R^{aB'}$ is H | H | H | H |
| C-13.2$^{B'}$ | Z13$^{B'}$, $R^{aB'}$ is H | $CH_3$ | H | H |
| C-13.3$^{B'}$ | Z13$^{B'}$, $R^{aB'}$ is H | Cl | H | H |
| C-13.4$^{B'}$ | Z13$^{B'}$, $R^{aB'}$ is H | F | H | H |
| C-13.5$^{B'}$ | Z13$^{B'}$, $R^{aB'}$ is H | $CH_2CH_3$ | H | H |
| C-13.6$^{B'}$ | Z13$^{B'}$, $R^{aB'}$ is H | $CF_2H$ | H | H |
| C-13.7$^{B'}$ | Z13$^{B'}$, $R^{aB'}$ is H | $CH_2F$ | H | H |
| C-13.8$^{B'}$ | Z13$^{B'}$, $R^{aB'}$ is H | $CF_3$ | H | H |
| C-13.9$^{B'}$ | Z13$^{B'}$, $R^{aB'}$ is H | $CF_2CH_3$ | H | H |
| C-13.10$^{B'}$ | Z13$^{B'}$, $R^{aB'}$ is H | $CH_2CF_3$ | H | H |
| C-13.11$^{B'}$ | Z13$^{B'}$, $R^{aB'}$ is H | cyclopropyl | H | H |
| C-13.12$^{B'}$ | Z13$^{B'}$, $R^{aB'}$ is H | $OCF_3$ | H | H |
| C-13.13$^{B'}$ | Z13$^{B'}$, $R^{aB'}$ is H | $OCF_2H$ | H | H |
| C-13.14$^{B'}$ | Z13$^{B'}$, $R^{aB'}$ is H | Cl | H | F |
| C-13.15$^{B'}$ | Z13$^{B'}$, $R^{aB'}$ is H | $CH_3$ | H | F |
| C-13.16$^{B'}$ | Z13$^{B'}$, $R^{aB'}$ is H | $CH_3$ | F | H |
| C-13.17$^{B'}$ | Z13$^{B'}$, $R^{aB'}$ is H | Cl | F | H |
| C-13.18$^{B'}$ | Z13$^{B'}$, $R^{aB'}$ is H | F | F | H |
| C-13.19$^{B'}$ | Z13$^{B'}$, $R^{aB'}$ is H | F | H | F |
| C-13.20$^{B'}$ | Z13$^{B'}$, $R^{aB'}$ is H | F | H | Cl |
| C-13.21$^{B'}$ | Z13$^{B'}$, $R^{aB'}$ is H | F | H | $CH_3$ |
| C-13.22$^{B'}$ | Z13$^{B'}$, $R^{aB'}$ is H | Cl | H | $CH_3$ |

TABLE 12.C-continued

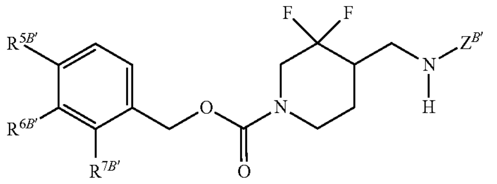

(racemic)

| compound | $Z^{B'}$ | $R^{5B'}$ | $R^{6B'}$ | $R^{7B'}$ |
|---|---|---|---|---|
| C-13.23$^{B'}$ | Z13$^{B'}$, $R^{aB'}$ is H | $SCH_3$ | H | H |
| C-13.24$^{B'}$ | Z13$^{B'}$, $R^{aB'}$ is H | $SO_2CH_3$ | H | H |
| C-13.25$^{B'}$ | Z13$^{B'}$, $R^{aB'}$ is H | ethynyl | H | H |
| C-14.1$^{B'}$ | Z14$^{B'}$, $R^{aB'}$ is H | H | H | H |
| C-14.2$^{B'}$ | Z14$^{B'}$, $R^{aB'}$ is H | $CH_3$ | H | H |
| C-14.3$^{B'}$ | Z14$^{B'}$, $R^{aB'}$ is H | Cl | H | H |
| C-14.4$^{B'}$ | Z14$^{B'}$, $R^{aB'}$ is H | F | H | H |
| C-14.5$^{B'}$ | Z14$^{B'}$, $R^{aB'}$ is H | $CH_2CH_3$ | H | H |
| C-14.6$^{B'}$ | Z14$^{B'}$, $R^{aB'}$ is H | $CF_2H$ | H | H |
| C-14.7$^{B'}$ | Z14$^{B'}$, $R^{aB'}$ is H | $CH_2F$ | H | H |
| C-14.8$^{B'}$ | Z14$^{B'}$, $R^{aB'}$ is H | $CF_3$ | H | H |
| C-14.9$^{B'}$ | Z14$^{B'}$, $R^{aB'}$ is H | $CF_2CH_3$ | H | H |
| C-14.10$^{B'}$ | Z14$^{B'}$, $R^{aB'}$ is H | $CH_2CF_3$ | H | H |
| C-14.11$^{B'}$ | Z14$^{B'}$, $R^{aB'}$ is H | cyclopropyl | H | H |
| C-14.12$^{B'}$ | Z14$^{B'}$, $R^{aB'}$ is H | $OCF_3$ | H | H |
| C-14.13$^{B'}$ | Z14$^{B'}$, $R^{aB'}$ is H | $OCF_2H$ | H | H |
| C-14.14$^{B'}$ | Z14$^{B'}$, $R^{aB'}$ is H | Cl | H | F |
| C-14.15$^{B'}$ | Z14$^{B'}$, $R^{aB'}$ is H | $CH_3$ | H | F |
| C-14.16$^{B'}$ | Z14$^{B'}$, $R^{aB'}$ is H | $CH_3$ | F | H |
| C-14.17$^{B'}$ | Z14$^{B'}$, $R^{aB'}$ is H | Cl | F | H |
| C-14.18$^{B'}$ | Z14$^{B'}$, $R^{aB'}$ is H | F | F | H |
| C-14.19$^{B'}$ | Z14$^{B'}$, $R^{aB'}$ is H | F | H | F |
| C-14.20$^{B'}$ | Z14$^{B'}$, $R^{aB'}$ is H | F | H | Cl |
| C-14.21$^{B'}$ | Z14$^{B'}$, $R^{aB'}$ is H | F | H | $CH_3$ |
| C-14.22$^{B'}$ | Z14$^{B'}$, $R^{aB'}$ is H | Cl | H | $CH_3$ |
| C-14.23$^{B'}$ | Z14$^{B'}$, $R^{aB'}$ is H | $SCH_3$ | H | H |
| C-14.24$^{B'}$ | Z14$^{B'}$, $R^{aB'}$ is H | $SO_2CH_3$ | H | H |
| C-14.25$^{B'}$ | Z14$^{B'}$, $R^{aB'}$ is H | ethynyl | H | H |
| C-15.1$^{B'}$ | Z15$^{B'}$, $R^{aB'}$ is H | H | H | H |
| C-15.2$^{B'}$ | Z15$^{B'}$, $R^{aB'}$ is H | $CH_3$ | H | H |
| C-15.3$^{B'}$ | Z15$^{B'}$, $R^{aB'}$ is H | Cl | H | H |
| C-15.4$^{B'}$ | Z15$^{B'}$, $R^{aB'}$ is H | F | H | H |
| C-15.5$^{B'}$ | Z15$^{B'}$, $R^{aB'}$ is H | $CH_2CH_3$ | H | H |
| C-15.6$^{B'}$ | Z15$^{B'}$, $R^{aB'}$ is H | $CF_2H$ | H | H |
| C-15.7$^{B'}$ | Z15$^{B'}$, $R^{aB'}$ is H | $CH_2F$ | H | H |
| C-15.8$^{B'}$ | Z15$^{B'}$, $R^{aB'}$ is H | $CF_3$ | H | H |
| C-15.9$^{B'}$ | Z15$^{B'}$, $R^{aB'}$ is H | $CF_2CH_3$ | H | H |
| C-15.10$^{B'}$ | Z15$^{B'}$, $R^{aB'}$ is H | $CH_2CF_3$ | H | H |
| C-15.11$^{B'}$ | Z15$^{B'}$, $R^{aB'}$ is H | cyclopropyl | H | H |
| C-15.12$^{B'}$ | Z15$^{B'}$, $R^{aB'}$ is H | $OCF_3$ | H | H |
| C-15.13$^{B'}$ | Z15$^{B'}$, $R^{aB'}$ is H | $OCF_2H$ | H | H |
| C-15.14$^{B'}$ | Z15$^{B'}$, $R^{aB'}$ is H | Cl | H | F |
| C-15.15$^{B'}$ | Z15$^{B'}$, $R^{aB'}$ is H | $CH_3$ | H | F |
| C-15.16$^{B'}$ | Z15$^{B'}$, $R^{aB'}$ is H | $CH_3$ | F | H |
| C-15.17$^{B'}$ | Z15$^{B'}$, $R^{aB'}$ is H | Cl | F | H |
| C-15.18$^{B'}$ | Z15$^{B'}$, $R^{aB'}$ is H | F | F | H |
| C-15.19$^{B'}$ | Z15$^{B'}$, $R^{aB'}$ is H | F | H | F |
| C-15.20$^{B'}$ | Z15$^{B'}$, $R^{aB'}$ is H | F | H | Cl |
| C-15.21$^{B'}$ | Z15$^{B'}$, $R^{aB'}$ is H | F | H | $CH_3$ |
| C-15.22$^{B'}$ | Z15$^{B'}$, $R^{aB'}$ is H | Cl | H | $CH_3$ |
| C-15.23$^{B'}$ | Z15$^{B'}$, $R^{aB'}$ is H | $SCH_3$ | H | H |
| C-15.24$^{B'}$ | Z15$^{B'}$, $R^{aB'}$ is H | $SO_2CH_3$ | H | H |
| C-15.25$^{B'}$ | Z15$^{B'}$, $R^{aB'}$ is H | ethynyl | H | H |
| C-16.1$^{B'}$ | Z16$^{B'}$, $R^{aB'}$ is H | H | H | H |
| C-16.2$^{B'}$ | Z16$^{B'}$, $R^{aB'}$ is H | $CH_3$ | H | H |
| C-16.3$^{B'}$ | Z16$^{B'}$, $R^{aB'}$ is H | Cl | H | H |
| C-16.4$^{B'}$ | Z16$^{B'}$, $R^{aB'}$ is H | F | H | H |
| C-16.5$^{B'}$ | Z16$^{B'}$, $R^{aB'}$ is H | $CH_2CH_3$ | H | H |
| C-16.6$^{B'}$ | Z16$^{B'}$, $R^{aB'}$ is H | $CF_2H$ | H | H |
| C-16.7$^{B'}$ | Z16$^{B'}$, $R^{aB'}$ is H | $CH_2F$ | H | H |
| C-16.8$^{B'}$ | Z16$^{B'}$, $R^{aB'}$ is H | $CF_3$ | H | H |
| C-16.9$^{B'}$ | Z16$^{B'}$, $R^{aB'}$ is H | $CF_2CH_3$ | H | H |
| C-16.10$^{B'}$ | Z16$^{B'}$, $R^{aB'}$ is H | $CH_2CF_3$ | H | H |
| C-16.11$^{B'}$ | Z16$^{B'}$, $R^{aB'}$ is H | cyclopropyl | H | H |
| C-16.12$^{B'}$ | Z16$^{B'}$, $R^{aB'}$ is H | $OCF_3$ | H | H |
| C-16.13$^{B'}$ | Z16$^{B'}$, $R^{aB'}$ is H | $OCF_2H$ | H | H |

TABLE 12.C-continued

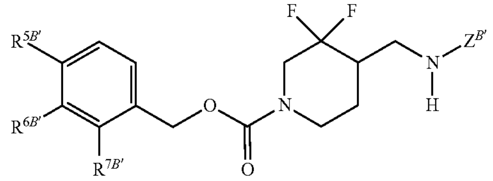

(racemic)

| compound | $Z^{B'}$ | $R^{5B'}$ | $R^{6B'}$ | $R^{7B'}$ |
|---|---|---|---|---|
| C-16.14$^{B'}$ | Z16$^{B'}$, $R^{aB'}$ is H | Cl | H | F |
| C-16.15$^{B'}$ | Z16$^{B'}$, $R^{aB'}$ is H | $CH_3$ | H | F |
| C-16.16$^{B'}$ | Z16$^{B'}$, $R^{aB'}$ is H | $CH_3$ | F | H |
| C-16.17$^{B'}$ | Z16$^{B'}$, $R^{aB'}$ is H | Cl | F | H |
| C-16.18$^{B'}$ | Z16$^{B'}$, $R^{aB'}$ is H | F | F | H |
| C-16.19$^{B'}$ | Z16$^{B'}$, $R^{aB'}$ is H | F | H | F |
| C-16.20$^{B'}$ | Z16$^{B'}$, $R^{aB'}$ is H | F | H | Cl |
| C-16.21$^{B'}$ | Z16$^{B'}$, $R^{aB'}$ is H | F | H | $CH_3$ |
| C-16.22$^{B'}$ | Z16$^{B'}$, $R^{aB'}$ is H | Cl | H | $CH_3$ |
| C-16.23$^{B'}$ | Z16$^{B'}$, $R^{aB'}$ is H | $SCH_3$ | H | H |
| C-16.24$^{B'}$ | Z16$^{B'}$, $R^{aB'}$ is H | $SO_2CH_3$ | H | H |
| C-16.25$^{B'}$ | Z16$^{B'}$, $R^{aB'}$ is H | ethynyl | H | H |
| C-17.1$^{B'}$ | Z17$^{B'}$ | H | H | H |
| C-17.2$^{B'}$ | Z17$^{B'}$ | $CH_3$ | H | H |
| C-17.3$^{B'}$ | Z17$^{B'}$ | Cl | H | H |
| C-17.4$^{B'}$ | Z17$^{B'}$ | F | H | H |
| C-17.5$^{B'}$ | Z17$^{B'}$ | $CH_2CH_3$ | H | H |
| C-17.6$^{B'}$ | Z17$^{B'}$ | $CF_2H$ | H | H |
| C-17.7$^{B'}$ | Z17$^{B'}$ | $CH_2F$ | H | H |
| C-17.8$^{B'}$ | Z17$^{B'}$ | $CF_3$ | H | H |
| C-17.9$^{B'}$ | Z17$^{B'}$ | $CF_2CH_3$ | H | H |
| C-17.10$^{B'}$ | Z17$^{B'}$ | $CH_2CF_3$ | H | H |
| C-17.11$^{B'}$ | Z17$^{B'}$ | cyclopropyl | H | H |
| C-17.12$^{B'}$ | Z17$^{B'}$ | $OCF_3$ | H | H |
| C-17.13$^{B'}$ | Z17$^{B'}$ | $OCF_2H$ | H | H |
| C-17.14$^{B'}$ | Z17$^{B'}$ | Cl | H | F |
| C-17.15$^{B'}$ | Z17$^{B'}$ | $CH_3$ | H | F |
| C-17.16$^{B'}$ | Z17$^{B'}$ | $CH_3$ | F | H |
| C-17.17$^{B'}$ | Z17$^{B'}$ | Cl | F | H |
| C-17.18$^{B'}$ | Z17$^{B'}$ | F | F | H |
| C-17.19$^{B'}$ | Z17$^{B'}$ | F | H | F |
| C-17.20$^{B'}$ | Z17$^{B'}$ | F | H | Cl |
| C-17.21$^{B'}$ | Z17$^{B'}$ | F | H | $CH_3$ |
| C-17.22$^{B'}$ | Z17$^{B'}$ | Cl | H | $CH_3$ |
| C-17.23$^{B'}$ | Z17$^{B'}$ | $SCH_3$ | H | H |
| C-17.24$^{B'}$ | Z17$^{B'}$ | $SO_2CH_3$ | H | H |
| C-17.25$^{B'}$ | Z17$^{B'}$ | ethynyl | H | H |
| C-18.1$^{B'}$ | Z18$^{B'}$ | H | H | H |
| C-18.2$^{B'}$ | Z18$^{B'}$ | $CH_3$ | H | H |
| C-18.3$^{B'}$ | Z18$^{B'}$ | Cl | H | H |
| C-18.4$^{B'}$ | Z18$^{B'}$ | F | H | H |
| C-18.5$^{B'}$ | Z18$^{B'}$ | $CH_2CH_3$ | H | H |
| C-18.6$^{B'}$ | Z18$^{B'}$ | $CF_2H$ | H | H |
| C-18.7$^{B'}$ | Z18$^{B'}$ | $CH_2F$ | H | H |
| C-18.8$^{B'}$ | Z18$^{B'}$ | $CF_3$ | H | H |
| C-18.9$^{B'}$ | Z18$^{B'}$ | $CF_2CH_3$ | H | H |
| C-18.10$^{B'}$ | Z18$^{B'}$ | $CH_2CF_3$ | H | H |
| C-18.11$^{B'}$ | Z18$^{B'}$ | cyclopropyl | H | H |
| C-18.12$^{B'}$ | Z18$^{B'}$ | $OCF_3$ | H | H |
| C-18.13$^{B'}$ | Z18$^{B'}$ | $OCF_2H$ | H | H |
| C-18.14$^{B'}$ | Z18$^{B'}$ | Cl | H | F |
| C-18.15$^{B'}$ | Z18$^{B'}$ | $CH_3$ | H | F |
| C-18.16$^{B'}$ | Z18$^{B'}$ | $CH_3$ | F | H |
| C-18.17$^{B'}$ | Z18$^{B'}$ | Cl | F | H |
| C-18.18$^{B'}$ | Z18$^{B'}$ | F | F | H |
| C-18.19$^{B'}$ | Z18$^{B'}$ | F | H | F |
| C-18.20$^{B'}$ | Z18$^{B'}$ | F | H | Cl |
| C-18.21$^{B'}$ | Z18$^{B'}$ | F | H | $CH_3$ |
| C-18.22$^{B'}$ | Z18$^{B'}$ | Cl | H | $CH_3$ |
| C-18.23$^{B'}$ | Z18$^{B'}$ | $SCH_3$ | H | H |
| C-18.24$^{B'}$ | Z18$^{B'}$ | $SO_2CH_3$ | H | H |
| C-18.25$^{B'}$ | Z18$^{B'}$ | ethynyl | H | H |
| C-19.1$^{B'}$ | Z19$^{B'}$ | H | H | H |
| C-19.2$^{B'}$ | Z19$^{B'}$ | $CH_3$ | H | H |
| C-19.3$^{B'}$ | Z19$^{B'}$ | Cl | H | H |
| C-19.4$^{B'}$ | Z19$^{B'}$ | F | H | H |

TABLE 12.C-continued

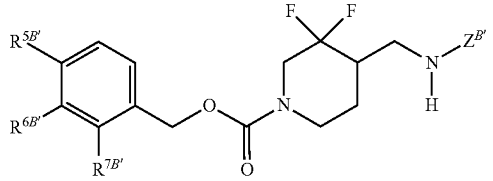

(racemic)

| compound | $Z^{B'}$ | $R^{5B'}$ | $R^{6B'}$ | $R^{7B'}$ |
|---|---|---|---|---|
| C-19.5$^{B'}$ | Z19$^{B'}$ | $CH_2CH_3$ | H | H |
| C-19.6$^{B'}$ | Z19$^{B'}$ | $CF_2H$ | H | H |
| C-19.7$^{B'}$ | Z19$^{B'}$ | $CH_2F$ | H | H |
| C-19.8$^{B'}$ | Z19$^{B'}$ | $CF_3$ | H | H |
| C-19.9$^{B'}$ | Z19$^{B'}$ | $CF_2CH_3$ | H | H |
| C-19.10$^{B'}$ | Z19$^{B'}$ | $CH_2CF_3$ | H | H |
| C-19.11$^{B'}$ | Z19$^{B'}$ | cyclopropyl | H | H |
| C-19.12$^{B'}$ | Z19$^{B'}$ | $OCF_3$ | H | H |
| C-19.13$^{B'}$ | Z19$^{B'}$ | $OCF_2H$ | H | H |
| C-19.14$^{B'}$ | Z19$^{B'}$ | Cl | H | F |
| C-19.15$^{B'}$ | Z19$^{B'}$ | $CH_3$ | H | F |
| C-19.16$^{B'}$ | Z19$^{B'}$ | $CH_3$ | F | H |
| C-19.17$^{B'}$ | Z19$^{B'}$ | Cl | F | H |
| C-19.18$^{B'}$ | Z19$^{B'}$ | F | F | H |
| C-19.19$^{B'}$ | Z19$^{B'}$ | F | H | F |
| C-19.20$^{B'}$ | Z19$^{B'}$ | F | H | Cl |
| C-19.21$^{B'}$ | Z19$^{B'}$ | F | H | $CH_3$ |
| C-19.22$^{B'}$ | Z19$^{B'}$ | Cl | H | $CH_3$ |
| C-19.23$^{B'}$ | Z19$^{B'}$ | $SCH_3$ | H | H |
| C-19.24$^{B'}$ | Z19$^{B'}$ | $SO_2CH_3$ | H | H |
| C-19.25$^{B'}$ | Z19$^{B'}$ | ethynyl | H | H |
| C-19.26$^{B'}$ | Z19$^{B'}$ | $CH_3$ | H | H |
| C-20.1$^{B'}$ | Z20$^{B'}$ | H | H | H |
| C-20.2$^{B'}$ | Z20$^{B'}$ | $CH_3$ | H | H |
| C-20.3$^{B'}$ | Z20$^{B'}$ | Cl | H | H |
| C-20.4$^{B'}$ | Z20$^{B'}$ | F | H | H |
| C-20.5$^{B'}$ | Z20$^{B'}$ | $CH_2CH_3$ | H | H |
| C-20.6$^{B'}$ | Z20$^{B'}$ | $CF_2H$ | H | H |
| C-20.7$^{B'}$ | Z20$^{B'}$ | $CH_2F$ | H | H |
| C-20.8$^{B'}$ | Z20$^{B'}$ | $CF_3$ | H | H |
| C-20.9$^{B'}$ | Z20$^{B'}$ | $CF_2CH_3$ | H | H |
| C-20.10$^{B'}$ | Z20$^{B'}$ | $CH_2CF_3$ | H | H |
| C-20.11$^{B'}$ | Z20$^{B'}$ | cyclopropyl | H | H |
| C-20.12$^{B'}$ | Z20$^{B'}$ | $OCF_3$ | H | H |
| C-20.13$^{B'}$ | Z20$^{B'}$ | $OCF_2H$ | H | H |
| C-20.14$^{B'}$ | Z20$^{B'}$ | Cl | H | F |
| C-20.15$^{B'}$ | Z20$^{B'}$ | $CH_3$ | H | F |
| C-20.16$^{B'}$ | Z20$^{B'}$ | $CH_3$ | F | H |
| C-20.17$^{B'}$ | Z20$^{B'}$ | Cl | F | H |
| C-20.18$^{B'}$ | Z20$^{B'}$ | F | F | H |
| C-20.19$^{B'}$ | Z20$^{B'}$ | F | H | F |
| C-20.20$^{B'}$ | Z20$^{B'}$ | F | H | Cl |
| C-20.21$^{B'}$ | Z20$^{B'}$ | F | H | $CH_3$ |
| C-20.22$^{B'}$ | Z20$^{B'}$ | Cl | H | $CH_3$ |
| C-20.23$^{B'}$ | Z20$^{B'}$ | $SCH_3$ | H | H |
| C-20.24$^{B'}$ | Z20$^{B'}$ | $SO_2CH_3$ | H | H |
| C-20.25$^{B'}$ | Z20$^{B'}$ | ethynyl | H | H |
| C-21.1$^{B'}$ | Z21$^{B'}$ | H | H | H |
| C-21.2$^{B'}$ | Z21$^{B'}$ | $CH_3$ | H | H |
| C-21.3$^{B'}$ | Z21$^{B'}$ | Cl | H | H |
| C-21.4$^{B'}$ | Z21$^{B'}$ | F | H | H |
| C-21.5$^{B'}$ | Z21$^{B'}$ | $CH_2CH_3$ | H | H |
| C-21.6$^{B'}$ | Z21$^{B'}$ | $CF_2H$ | H | H |
| C-21.7$^{B'}$ | Z21$^{B'}$ | $CH_2F$ | H | H |
| C-21.8$^{B'}$ | Z21$^{B'}$ | $CF_3$ | H | H |
| C-21.9$^{B'}$ | Z21$^{B'}$ | $CF_2CH_3$ | H | H |
| C-21.10$^{B'}$ | Z21$^{B'}$ | $CH_2CF_3$ | H | H |
| C-21.11$^{B'}$ | Z21$^{B'}$ | cyclopropyl | H | H |
| C-21.12$^{B'}$ | Z21$^{B'}$ | $OCF_3$ | H | H |
| C-21.13$^{B'}$ | Z21$^{B'}$ | $OCF_2H$ | H | H |
| C-21.14$^{B'}$ | Z21$^{B'}$ | Cl | H | F |
| C-21.15$^{B'}$ | Z21$^{B'}$ | $CH_3$ | H | F |
| C-21.16$^{B'}$ | Z21$^{B'}$ | $CH_3$ | F | H |
| C-21.17$^{B'}$ | Z21$^{B'}$ | Cl | F | H |
| C-21.18$^{B'}$ | Z21$^{B'}$ | F | F | H |
| C-21.19$^{B'}$ | Z21$^{B'}$ | F | H | F |

TABLE 12.C-continued

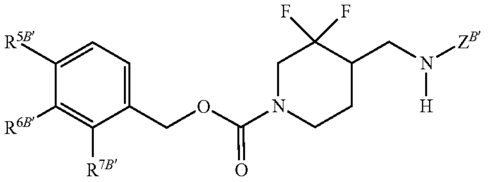

(racemic)

| compound | $Z^{B'}$ | $R^{5B'}$ | $R^{6B'}$ | $R^{7B'}$ |
|---|---|---|---|---|
| C-21.20$^{B'}$ | Z21$^{B'}$ | F | H | Cl |
| C-21.21$^{B'}$ | Z21$^{B'}$ | F | H | $CH_3$ |
| C-21.22$^{B'}$ | Z21$^{B'}$ | Cl | H | $CH_3$ |
| C-21.23$^{B'}$ | Z21$^{B'}$ | $SCH_3$ | H | H |
| C-21.24$^{B'}$ | Z21$^{B'}$ | $SO_2CH_3$ | H | H |
| C-21.25$^{B'}$ | Z21$^{B'}$ | ethynyl | H | H |
| C-21.26$^{B'}$ | 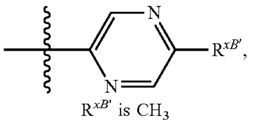 $R^{xB'}$ is $CH_3$ | $CH_3$ | H | H |
| C-21.27$^{B'}$ | 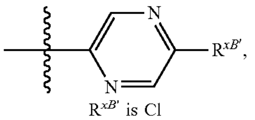 $R^{xB'}$ is Cl | $CH_3$ | H | H |
| C-21.28$^{B'}$ | 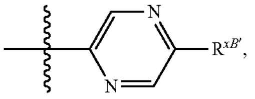 $R^{xB'}$ is F | $CH_3$ | H | H |
| C-21.29$^{B'}$ | 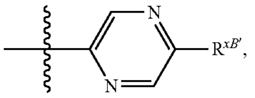 $R^{xB'}$ is $CF_3$ | $CH_3$ | H | H |
| C-21.30$^{B'}$ | 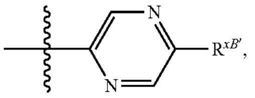 $R^{xB'}$ is CN | $CH_3$ | H | H |
| C-21.31$^{B'}$ | 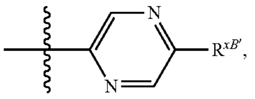 $R^{xB'}$ is $CH_3$ | H | H | H |
| C-21.32$^{B'}$ | 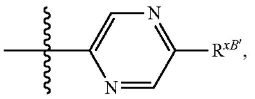 $R^{xB'}$ is $CH_3$ | $CH_3$ | H | H |
| C-21.33$^{B'}$ | 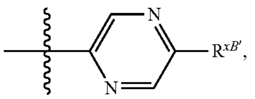 $R^{xB'}$ is $CH_3$ | Cl | H | H |
| C-21.34$^{B'}$ | 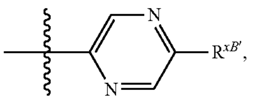 $R^{xB'}$ is $CH_3$ | F | H | H |

TABLE 12.C-continued

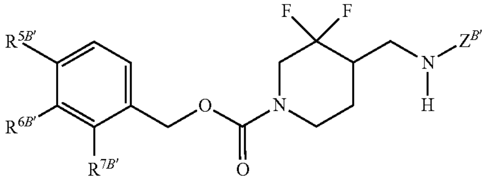

(racemic)

| compound | $Z^{B'}$ | $R^{5B'}$ | $R^{6B'}$ | $R^{7B'}$ |
|---|---|---|---|---|
| C-21.35$^{B'}$ | 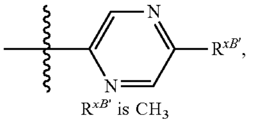 $R^{xB'}$ is $CH_3$ | $CH_2CH_3$ | H | H |
| C-21.36$^{B'}$ | 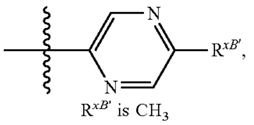 $R^{xB'}$ is $CH_3$ | $CF_2H$ | H | H |
| C-22.1$^{B'}$ | Z22$^{B'}$ | H | H | H |
| C-22.2$^{B'}$ | Z22$^{B'}$ | $CH_3$ | H | H |
| C-22.3$^{B'}$ | Z22$^{B'}$ | Cl | H | H |
| C-22.4$^{B'}$ | Z22$^{B'}$ | F | H | H |
| C-22.5$^{B'}$ | Z22$^{B'}$ | $CH_2CH_3$ | H | H |
| C-22.6$^{B'}$ | Z22$^{B'}$ | $CF_2H$ | H | H |
| C-22.7$^{B'}$ | Z22$^{B'}$ | $CH_2F$ | H | H |
| C-22.8$^{B'}$ | Z22$^{B'}$ | $CF_3$ | H | H |
| C-22.9$^{B'}$ | Z22$^{B'}$ | $CF_2CH_3$ | H | H |
| C-22.10$^{B'}$ | Z22$^{B'}$ | $CH_2CF_3$ | H | H |
| C-22.11$^{B'}$ | Z22$^{B'}$ | cyclopropyl | H | H |
| C-22.12$^{B'}$ | Z22$^{B'}$ | $OCF_3$ | H | H |
| C-22.13$^{B'}$ | Z22$^{B'}$ | $OCF_2H$ | H | H |
| C-22.14$^{B'}$ | Z22$^{B'}$ | Cl | H | F |
| C-22.15$^{B'}$ | Z22$^{B'}$ | $CH_3$ | H | F |
| C-22.16$^{B'}$ | Z22$^{B'}$ | $CH_3$ | F | H |
| C-22.17$^{B'}$ | Z22$^{B'}$ | Cl | F | H |
| C-22.18$^{B'}$ | Z22$^{B'}$ | F | F | H |
| C-22.19$^{B'}$ | Z22$^{B'}$ | F | H | F |
| C-22.20$^{B'}$ | Z22$^{B'}$ | F | H | Cl |
| C-22.21$^{B'}$ | Z22$^{B'}$ | F | H | $CH_3$ |
| C-22.22$^{B'}$ | Z22$^{B'}$ | Cl | H | $CH_3$ |
| C-22.23$^{B'}$ | Z22$^{B'}$ | $SCH_3$ | H | H |
| C-22.24$^{B'}$ | Z22$^{B'}$ | $SO_2CH_3$ | H | H |
| C-22.25$^{B'}$ | Z22$^{B'}$ | ethynyl | H | H |
| C-22.26$^{B'}$ | 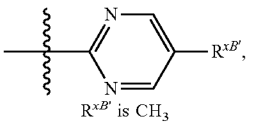 $R^{xB'}$ is $CH_3$ | $CH_3$ | H | H |
| C-22.27$^{B'}$ | 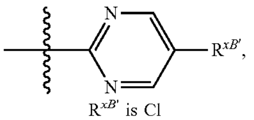 $R^{xB'}$ is Cl | $CH_3$ | H | H |
| C-22.28$^{B'}$ | 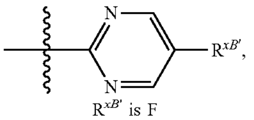 $R^{xB'}$ is F | $CH_3$ | H | H |
| C-22.29$^{B'}$ | 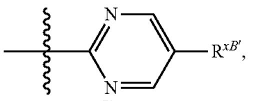 $R^{xB'}$ is $CF_3$ | $CH_3$ | H | H |

TABLE 12.C-continued

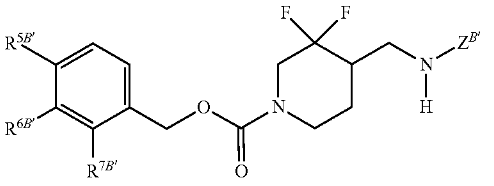

(racemic)

| compound | $Z^{B'}$ | $R^{5B'}$ | $R^{6B'}$ | $R^{7B'}$ |
|---|---|---|---|---|
| C-22.30$^{B'}$ | 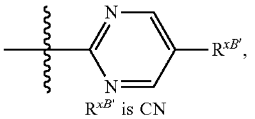 $R^{xB'}$ is CN | $CH_3$ | H | H |
| C-23.1$^{B'}$ | Z23$^{B'}$ | H | H | H |
| C-23.2$^{B'}$ | Z23$^{B'}$ | $CH_3$ | H | H |
| C-23.3$^{B'}$ | Z23$^{B'}$ | Cl | H | H |
| C-23.4$^{B'}$ | Z23$^{B'}$ | F | H | H |
| C-23.5$^{B'}$ | Z23$^{B'}$ | $CH_2CH_3$ | H | H |
| C-23.6$^{B'}$ | Z23$^{B'}$ | $CF_2H$ | H | H |
| C-23.7$^{B'}$ | Z23$^{B'}$ | $CH_2F$ | H | H |
| C-23.8$^{B'}$ | Z23$^{B'}$ | $CF_3$ | H | H |
| C-23.9$^{B'}$ | Z23$^{B'}$ | $CF_2CH_3$ | H | H |
| C-23.10$^{B'}$ | Z23$^{B'}$ | $CH_2CF_3$ | H | H |
| C-23.11$^{B'}$ | Z23$^{B'}$ | cyclopropyl | H | H |
| C-23.12$^{B'}$ | Z23$^{B'}$ | $OCF_3$ | H | H |
| C-23.13$^{B'}$ | Z23$^{B'}$ | $OCF_2H$ | H | H |
| C-23.14$^{B'}$ | Z23$^{B'}$ | Cl | H | F |
| C-23.15$^{B'}$ | Z23$^{B'}$ | $CH_3$ | H | F |
| C-23.16$^{B'}$ | Z23$^{B'}$ | $CH_3$ | F | H |
| C-23.17$^{B'}$ | Z23$^{B'}$ | Cl | F | H |
| C-23.18$^{B'}$ | Z23$^{B'}$ | F | F | H |
| C-23.19$^{B'}$ | Z23$^{B'}$ | F | H | F |
| C-23.20$^{B'}$ | Z23$^{B'}$ | F | H | Cl |
| C-23.21$^{B'}$ | Z23$^{B'}$ | F | H | $CH_3$ |
| C-23.22$^{B'}$ | Z23$^{B'}$ | Cl | H | $CH_3$ |
| C-23.23$^{B'}$ | Z23$^{B'}$ | $SCH_3$ | H | H |
| C-23.24$^{B'}$ | Z23$^{B'}$ | $SO_2CH_3$ | H | H |
| C-23.25$^{B'}$ | Z23$^{B'}$ | ethynyl | H | H |
| C-23.26$^{B'}$ | 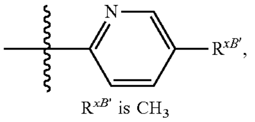 $R^{xB'}$ is $CH_3$ | $CH_3$ | H | H |
| C-23.27$^{B'}$ | 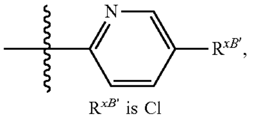 $R^{xB'}$ is Cl | $CH_3$ | H | H |
| C-23.28$^{B'}$ | 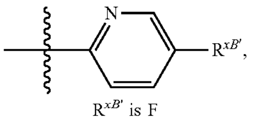 $R^{xB'}$ is F | $CH_3$ | H | H |
| C-23.29$^{B'}$ | 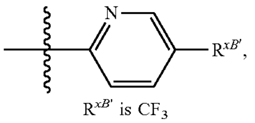 $R^{xB'}$ is $CF_3$ | $CH_3$ | H | H |
| C-23.30$^{B'}$ | 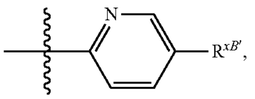 $R^{xB'}$ is CN | $CH_3$ | H | H |

TABLE 12.C-continued

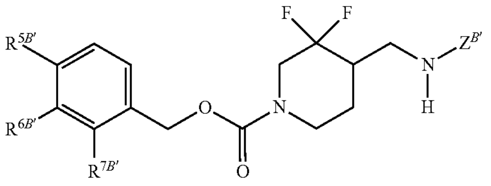

(racemic)

| compound | $Z^{B'}$ | $R^{5B'}$ | $R^{6B'}$ | $R^{7B'}$ |
|---|---|---|---|---|
| C-23.31$^{B'}$ | 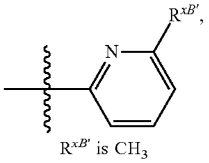 $R^{xB'}$ is $CH_3$ | H | H | H |
| C-23.32$^{B'}$ | 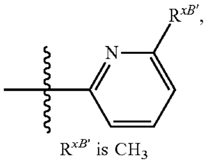 $R^{xB'}$ is $CH_3$ | $CH_3$ | H | H |
| C-23.33$^{B'}$ | 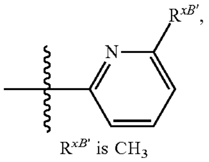 $R^{xB'}$ is $CH_3$ | Cl | H | H |
| C-23.34$^{B'}$ | 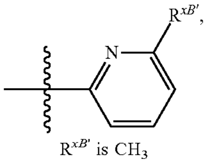 $R^{xB'}$ is $CH_3$ | F | H | H |
| C-23.35$^{B'}$ | 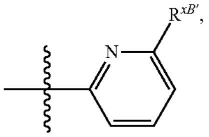 $R^{xB'}$ is $CH_3$ | $CH_2CH_3$ | H | H |
| C-23.36$^{B'}$ | 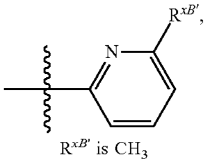 $R^{xB'}$ is $CH_3$ | $CF_2H$ | H | H |
| C-24.1$^{B'}$ | Z24$^{B'}$ | H | H | H |
| C-24.2$^{B'}$ | Z24$^{B'}$ | $CH_3$ | H | H |
| C-24.3$^{B'}$ | Z24$^{B'}$ | Cl | H | H |
| C-24.4$^{B'}$ | Z24$^{B'}$ | F | H | H |
| C-24.5$^{B'}$ | Z24$^{B'}$ | $CH_2CH_3$ | H | H |
| C-24.6$^{B'}$ | Z24$^{B'}$ | $CF_2H$ | H | H |
| C-24.7$^{B'}$ | Z24$^{B'}$ | $CH_2F$ | H | H |
| C-24.8$^{B'}$ | Z24$^{B'}$ | $CF_3$ | H | H |
| C-24.9$^{B'}$ | Z24$^{B'}$ | $CF_2CH_3$ | H | H |
| C-24.10$^{B'}$ | Z24$^{B'}$ | $CH_2CF_3$ | H | H |
| C-24.11$^{B'}$ | Z24$^{B'}$ | cyclopropyl | H | H |
| C-24.12$^{B'}$ | Z24$^{B'}$ | $OCF_3$ | H | H |
| C-24.13$^{B'}$ | Z24$^{B'}$ | $OCF_2H$ | H | H |
| C-24.14$^{B'}$ | Z24$^{B'}$ | Cl | H | F |
| C-24.15$^{B'}$ | Z24$^{B'}$ | $CH_3$ | H | F |
| C-24.16$^{B'}$ | Z24$^{B'}$ | $CH_3$ | F | H |
| C-24.17$^{B'}$ | Z24$^{B'}$ | Cl | F | H |

TABLE 12.C-continued

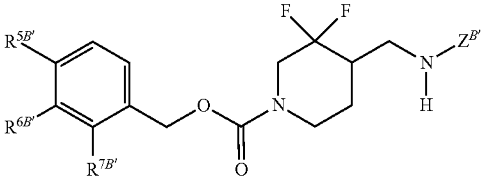

(racemic)

| compound | $Z^{B'}$ | $R^{5B'}$ | $R^{6B'}$ | $R^{7B'}$ |
|---|---|---|---|---|
| C-24.18$^{B'}$ | Z24$^{B'}$ | F | F | H |
| C-24.19$^{B'}$ | Z24$^{B'}$ | F | H | F |
| C-24.20$^{B'}$ | Z24$^{B'}$ | F | H | Cl |
| C-24.21$^{B'}$ | Z24$^{B'}$ | F | H | $CH_3$ |
| C-24.22$^{B'}$ | Z24$^{B'}$ | Cl | H | $CH_3$ |
| C-24.23$^{B'}$ | Z24$^{B'}$ | $SCH_3$ | H | H |
| C-24.24$^{B'}$ | Z24$^{B'}$ | $SO_2CH_3$ | H | H |
| C-24.25$^{B'}$ | Z24$^{B'}$ | ethynyl | H | H |
| C-24.26$^{B'}$ | 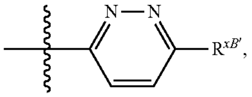 $R^{xB'}$ is $CH_3$ | $CH_3$ | H | H |
| C-24.27$^{B'}$ | 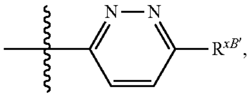 $R^{xB'}$ is Cl | $CH_3$ | H | H |
| C-24.28$^{B'}$ | 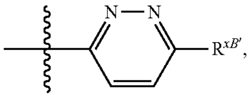 $R^{xB'}$ is F | $CH_3$ | H | H |
| C-24.29$^{B'}$ | 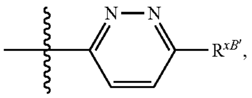 $R^{xB'}$ is $CF_3$ | $CH_3$ | H | H |
| C-24.30$^{B'}$ | 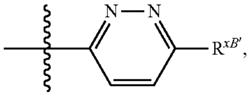 $R^{xB'}$ is CN | $CH_3$ | H | H |
| C-25.1$^{B'}$ | Z25$^{B'}$, $R^{aB'}$ is H | H | H | H |
| C-25.2$^{B'}$ | Z25$^{B'}$, $R^{aB'}$ is H | $CH_3$ | H | H |
| C-25.3$^{B'}$ | Z25$^{B'}$, $R^{aB'}$ is H | Cl | H | H |
| C-25.4$^{B'}$ | Z25$^{B'}$, $R^{aB'}$ is H | F | H | H |
| C-25.5$^{B'}$ | Z25$^{B'}$, $R^{aB'}$ is H | $CH_2CH_3$ | H | H |
| C-25.6$^{B'}$ | Z25$^{B'}$, $R^{aB'}$ is H | $CF_2H$ | H | H |
| C-25.7$^{B'}$ | Z25$^{B'}$, $R^{aB'}$ is H | $CH_2F$ | H | H |
| C-25.8$^{B'}$ | Z25$^{B'}$, $R^{aB'}$ is H | $CF_3$ | H | H |
| C-25.9$^{B'}$ | Z25$^{B'}$, $R^{aB'}$ is H | $CF_2CH_3$ | H | H |
| C-25.10$^{B'}$ | Z25$^{B'}$, $R^{aB'}$ is H | $CH_2CF_3$ | H | H |
| C-25.11$^{B'}$ | Z25$^{B'}$, $R^{aB'}$ is H | cyclopropyl | H | H |
| C-25.12$^{B'}$ | Z25$^{B'}$, $R^{aB'}$ is H | $OCF_3$ | H | H |
| C-25.13$^{B'}$ | Z25$^{B'}$, $R^{aB'}$ is H | $OCF_2H$ | H | H |
| C-25.14$^{B'}$ | Z25$^{B'}$, $R^{aB'}$ is H | Cl | H | F |
| C-25.15$^{B'}$ | Z25$^{B'}$, $R^{aB'}$ is H | $CH_3$ | H | F |
| C-25.16$^{B'}$ | Z25$^{B'}$, $R^{aB'}$ is H | $CH_3$ | F | H |
| C-25.17$^{B'}$ | Z25$^{B'}$, $R^{aB'}$ is H | Cl | F | H |
| C-25.18$^{B'}$ | Z25$^{B'}$, $R^{aB'}$ is H | F | F | H |
| C-25.19$^{B'}$ | Z25$^{B'}$, $R^{aB'}$ is H | F | H | F |
| C-25.20$^{B'}$ | Z25$^{B'}$, $R^{aB'}$ is H | F | H | Cl |
| C-25.21$^{B'}$ | Z25$^{B'}$, $R^{aB'}$ is H | F | H | $CH_3$ |
| C-25.22$^{B'}$ | Z25$^{B'}$, $R^{aB'}$ is H | Cl | H | $CH_3$ |
| C-25.23$^{B'}$ | Z25$^{B'}$, $R^{aB'}$ is H | $SCH_3$ | H | H |
| C-25.24$^{B'}$ | Z25$^{B'}$, $R^{aB'}$ is H | $SO_2CH_3$ | H | H |
| C-25.25$^{B'}$ | Z25$^{B'}$, $R^{aB'}$ is H | ethynyl | H | H |

TABLE 12.C-continued

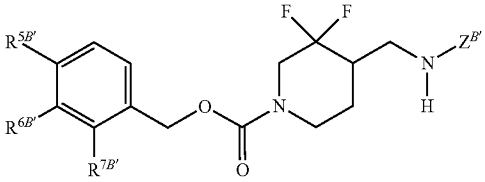

(racemic)

| compound | $Z^{B'}$ | $R^{5B'}$ | $R^{6B'}$ | $R^{7B'}$ |
|---|---|---|---|---|
| C-25.26$^{B'}$ | 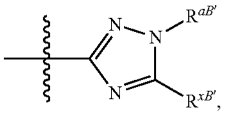 $R^{aB'}$, is H; $R^{xB'}$ is $CH_3$ | $CH_3$ | H | H |
| C-25.27$^{B'}$ | 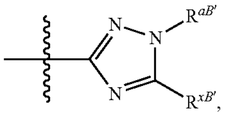 $R^{aB'}$, is H; $R^{xB'}$ is Cl | $CH_3$ | H | H |
| C-25.28$^{B'}$ | 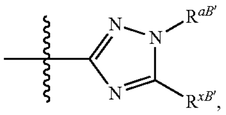 $R^{aB'}$, is H; $R^{xB'}$ is F | $CH_3$ | H | H |
| C-25.29$^{B'}$ | 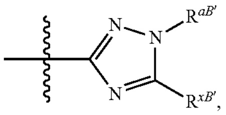 $R^{aB'}$, is H; $R^{xB'}$ is $CF_3$ | $CH_3$ | H | H |
| C-25.30$^{B'}$ | 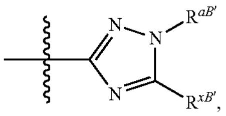 $R^{aB'}$, is H; $R^{xB'}$ is CN | $CH_3$ | H | H |
| C-26.1$^{B'}$ | Z26$^{B'}$, $R^{aB'}$ is H | H | H | H |
| C-26.2$^{B'}$ | Z26$^{B'}$, $R^{aB'}$ is H | $CH_3$ | H | H |
| C-26.3$^{B'}$ | Z26$^{B'}$, $R^{aB'}$ is H | Cl | H | H |
| C-26.4$^{B'}$ | Z26$^{B'}$, $R^{aB'}$ is H | F | H | H |
| C-26.5$^{B'}$ | Z26$^{B'}$, $R^{aB'}$ is H | $CH_2CH_3$ | H | H |
| C-26.6$^{B'}$ | Z26$^{B'}$, $R^{aB'}$ is H | $CF_2H$ | H | H |
| C-26.7$^{B'}$ | Z26$^{B'}$, $R^{aB'}$ is H | $CH_2F$ | H | H |
| C-26.8$^{B'}$ | Z26$^{B'}$, $R^{aB'}$ is H | $CF_3$ | H | H |
| C-26.9$^{B'}$ | Z26$^{B'}$, $R^{aB'}$ is H | $CF_2CH_3$ | H | H |
| C-26.10$^{B'}$ | Z26$^{B'}$, $R^{aB'}$ is H | $CH_2CF_3$ | H | H |
| C-26.11$^{B'}$ | Z26$^{B'}$, $R^{aB'}$ is H | cyclopropyl | H | H |
| C-26.12$^{B'}$ | Z26$^{B'}$, $R^{aB'}$ is H | $OCF_3$ | H | H |
| C-26.13$^{B'}$ | Z26$^{B'}$, $R^{aB'}$ is H | $OCF_2H$ | H | H |
| C-26.14$^{B'}$ | Z26$^{B'}$, $R^{aB'}$ is H | Cl | H | F |
| C-26.15$^{B'}$ | Z26$^{B'}$, $R^{aB'}$ is H | $CH_3$ | H | F |
| C-26.16$^{B'}$ | Z26$^{B'}$, $R^{aB'}$ is H | $CH_3$ | F | H |
| C-26.17$^{B'}$ | Z26$^{B'}$, $R^{aB'}$ is H | Cl | F | H |
| C-26.18$^{B'}$ | Z26$^{B'}$, $R^{aB'}$ is H | F | F | H |
| C-26.19$^{B'}$ | Z26$^{B'}$, $R^{aB'}$ is H | F | H | F |
| C-26.20$^{B'}$ | Z26$^{B'}$, $R^{aB'}$ is H | F | H | Cl |
| C-26.21$^{B'}$ | Z26$^{B'}$, $R^{aB'}$ is H | F | H | $CH_3$ |
| C-26.22$^{B'}$ | Z26$^{B'}$, $R^{aB'}$ is H | Cl | H | $CH_3$ |
| C-26.23$^{B'}$ | Z26$^{B'}$, $R^{aB'}$ is H | $SCH_3$ | H | H |
| C-26.24$^{B'}$ | Z26$^{B'}$, $R^{aB'}$ is H | $SO_2CH_3$ | H | H |
| C-26.25$^{B'}$ | Z26$^{B'}$, $R^{aB'}$ is H | ethynyl | H | H |

TABLE 12.C-continued

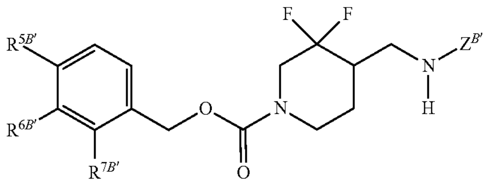

(racemic)

| compound | $Z^{B'}$ | $R^{5B'}$ | $R^{6B'}$ | $R^{7B'}$ |
|---|---|---|---|---|
| C-26.26$^{B'}$ | 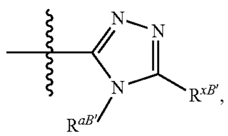 $R^{aB'}$, is H; $R^{xB'}$ is $CH_3$ | $CH_3$ | H | H |
| C-26.27$^{B'}$ | 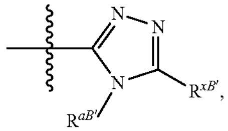 $R^{aB'}$, is H; $R^{xB'}$ is Cl | $CH_3$ | H | H |
| C-26.28$^{B'}$ | 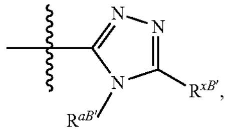 $R^{aB'}$, is H; $R^{xB'}$ is F | $CH_3$ | H | H |
| C-26.29$^{B'}$ | 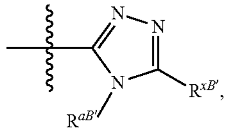 $R^{aB'}$, is H; $R^{xB'}$ is $CF_3$ | $CH_3$ | H | H |
| C-26.30$^{B'}$ | 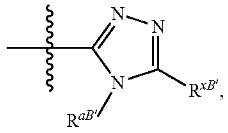 $R^{aB'}$, is H; $R^{xB'}$ is CN | $CH_3$ | H | H |
| C-27.1$^{B'}$ | Z27$^{B'}$ | H | H | H |
| C-27.2$^{B'}$ | Z27$^{B'}$ | $CH_3$ | H | H |
| C-27.3$^{B'}$ | Z27$^{B'}$ | Cl | H | H |
| C-27.4$^{B'}$ | Z27$^{B'}$ | F | H | H |
| C-27.5$^{B'}$ | Z27$^{B'}$ | $CH_2CH_3$ | H | H |
| C-27.6$^{B'}$ | Z27$^{B'}$ | $CF_2H$ | H | H |
| C-27.7$^{B'}$ | Z27$^{B'}$ | $CH_2F$ | H | H |
| C-27.8$^{B'}$ | Z27$^{B'}$ | $CF_3$ | H | H |
| C-27.9$^{B'}$ | Z27$^{B'}$ | $CF_2CH_3$ | H | H |
| C-27.10$^{B'}$ | Z27$^{B'}$ | $CH_2CF_3$ | H | H |
| C-27.11$^{B'}$ | Z27$^{B'}$ | cyclopropyl | H | H |
| C-27.12$^{B'}$ | Z27$^{B'}$ | $OCF_3$ | H | H |
| C-27.13$^{B'}$ | Z27$^{B'}$ | $OCF_2H$ | H | H |
| C-27.14$^{B'}$ | Z27$^{B'}$ | Cl | H | F |
| C-27.15$^{B'}$ | Z27$^{B'}$ | $CH_3$ | H | F |
| C-27.16$^{B'}$ | Z27$^{B'}$ | $CH_3$ | F | H |
| C-27.17$^{B'}$ | Z27$^{B'}$ | Cl | F | H |
| C-27.18$^{B'}$ | Z27$^{B'}$ | F | F | H |
| C-27.19$^{B'}$ | Z27$^{B'}$ | F | H | F |
| C-27.20$^{B'}$ | Z27$^{B'}$ | F | H | Cl |
| C-27.21$^{B'}$ | Z27$^{B'}$ | F | H | $CH_3$ |
| C-27.22$^{B'}$ | Z27$^{B'}$ | Cl | H | $CH_3$ |
| C-27.23$^{B'}$ | Z27$^{B'}$ | $SCH_3$ | H | H |
| C-27.24$^{B'}$ | Z27$^{B'}$ | $SO_2CH_3$ | H | H |
| C-27.25$^{B'}$ | Z27$^{B'}$ | ethynyl | H | H |

TABLE 12.C-continued

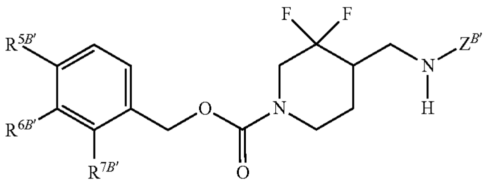

(racemic)

| compound | $Z^{B'}$ | $R^{5B'}$ | $R^{6B'}$ | $R^{7B'}$ |
|---|---|---|---|---|
| C-27.26$^{B'}$ | 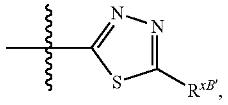 $R^{xB'}$ is $CH_3$ | $CH_3$ | H | H |
| C-27.27$^{B'}$ | 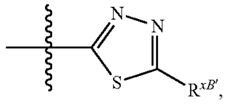 $R^{xB'}$ is Cl | $CH_3$ | H | H |
| C-27.28$^{B'}$ | 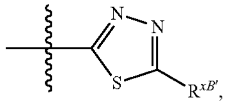 $R^{xB'}$ is F | $CH_3$ | H | H |
| C-27.29$^{B'}$ | 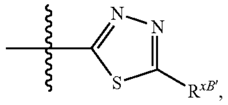 $R^{xB'}$ is $CF_3$ | $CH_3$ | H | H |
| C-27.30$^{B'}$ | 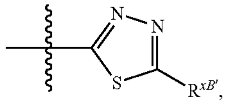 $R^{xB'}$ is CN | $CH_3$ | H | H |
| C-28.1$^{B'}$ | Z28$^{B'}$ | H | H | H |
| C-28.2$^{B'}$ | Z28$^{B'}$ | $CH_3$ | H | H |
| C-28.3$^{B'}$ | Z28$^{B'}$ | Cl | H | H |
| C-28.4$^{B'}$ | Z28$^{B'}$ | F | H | H |
| C-28.5$^{B'}$ | Z28$^{B'}$ | $CH_2CH_3$ | H | H |
| C-28.6$^{B'}$ | Z28$^{B'}$ | $CF_2H$ | H | H |
| C-28.7$^{B'}$ | Z28$^{B'}$ | $CH_2F$ | H | H |
| C-28.8$^{B'}$ | Z28$^{B'}$ | $CF_3$ | H | H |
| C-28.9$^{B'}$ | Z28$^{B'}$ | $CF_2CH_3$ | H | H |
| C-28.10$^{B'}$ | Z28$^{B'}$ | $CH_2CF_3$ | H | H |
| C-28.11$^{B'}$ | Z28$^{B'}$ | cyclopropyl | H | H |
| C-28.12$^{B'}$ | Z28$^{B'}$ | $OCF_3$ | H | H |
| C-28.13$^{B'}$ | Z28$^{B'}$ | $OCF_2H$ | H | H |
| C-28.14$^{B'}$ | Z28$^{B'}$ | Cl | H | F |
| C-28.15$^{B'}$ | Z28$^{B'}$ | $CH_3$ | H | F |
| C-28.16$^{B'}$ | Z28$^{B'}$ | $CH_3$ | F | H |
| C-28.17$^{B'}$ | Z28$^{B'}$ | Cl | F | H |
| C-28.18$^{B'}$ | Z28$^{B'}$ | F | F | H |
| C-28.19$^{B'}$ | Z28$^{B'}$ | F | H | F |
| C-28.20$^{B'}$ | Z28$^{B'}$ | F | H | Cl |
| C-28.21$^{B'}$ | Z28$^{B'}$ | F | H | $CH_3$ |
| C-28.22$^{B'}$ | Z28$^{B'}$ | Cl | H | $CH_3$ |
| C-28.23$^{B'}$ | Z28$^{B'}$ | $SCH_3$ | H | H |
| C-28.24$^{B'}$ | Z28$^{B'}$ | $SO_2CH_3$ | H | H |
| C-28.25$^{B'}$ | Z28$^{B'}$ | ethynyl | H | H |
| C-28.26$^{B'}$ | 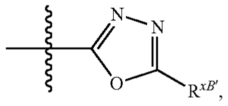 $R^{xB'}$ is $CH_3$ | $CH_3$ | H | H |

TABLE 12.C-continued

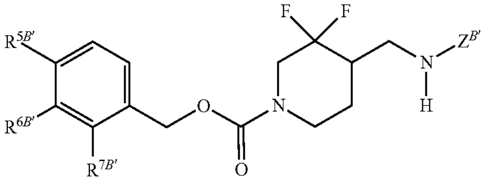

(racemic)

| compound | $Z^{B'}$ | $R^{5B'}$ | $R^{6B'}$ | $R^{7B'}$ |
|---|---|---|---|---|
| C-28.27$^{B'}$ | 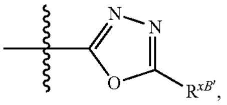 $R^{xB'}$ is Cl | $CH_3$ | H | H |
| C-28.28$^{B'}$ | 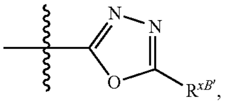 $R^{xB'}$ isF | $CH_3$ | H | H |
| C-28.29$^{B'}$ | 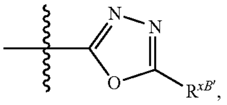 $R^{xB'}$ is $CF_3$ | $CH_3$ | H | H |
| C-28.30$^{B'}$ | 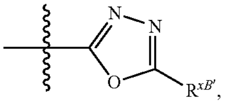 $R^{xB'}$ is CN | $CH_3$ | H | H |
| C-29.1$^{B'}$ | Z29$^{B'}$ | H | H | H |
| C-29.2$^{B'}$ | Z29$^{B'}$ | $CH_3$ | H | H |
| C-29.3$^{B'}$ | Z29$^{B'}$ | Cl | H | H |
| C-29.4$^{B'}$ | Z29$^{B'}$ | F | H | H |
| C-29.5$^{B'}$ | Z29$^{B'}$ | $CH_2CH_3$ | H | H |
| C-29.6$^{B'}$ | Z29$^{B'}$ | $CF_2H$ | H | H |
| C-29.7$^{B'}$ | Z29$^{B'}$ | $CH_2F$ | H | H |
| C-29.8$^{B'}$ | Z29$^{B'}$ | $CF_3$ | H | H |
| C-29.9$^{B'}$ | Z29$^{B'}$ | $CF_2CH_3$ | H | H |
| C-29.10$^{B'}$ | Z29$^{B'}$ | $CH_2CF_3$ | H | H |
| C-29.11$^{B'}$ | Z29$^{B'}$ | cyclopropyl | H | H |
| C-29.12$^{B'}$ | Z29$^{B'}$ | $OCF_3$ | H | H |
| C-29.13$^{B'}$ | Z29$^{B'}$ | $OCF_2H$ | H | H |
| C-29.14$^{B'}$ | Z29$^{B'}$ | Cl | H | F |
| C-29.15$^{B'}$ | Z29$^{B'}$ | $CH_3$ | H | F |
| C-29.16$^{B'}$ | Z29$^{B'}$ | $CH_3$ | F | H |
| C-29.17$^{B'}$ | Z29$^{B'}$ | Cl | F | H |
| C-29.18$^{B'}$ | Z29$^{B'}$ | F | F | H |
| C-29.19$^{B'}$ | Z29$^{B'}$ | F | H | F |
| C-29.20$^{B'}$ | Z29$^{B'}$ | F | H | Cl |
| C-29.21$^{B'}$ | Z29$^{B'}$ | F | H | $CH_3$ |
| C-29.22$^{B'}$ | Z29$^{B'}$ | Cl | H | $CH_3$ |
| C-29.23$^{B'}$ | Z29$^{B'}$ | $SCH_3$ | H | H |
| C-29.24$^{B'}$ | Z29$^{B'}$ | $SO_2CH_3$ | H | H |
| C-29.25$^{B'}$ | Z29$^{B'}$ | ethynyl | H | H |
| C-29.26$^{B'}$ | 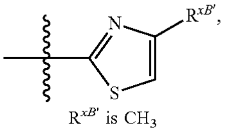 $R^{xB'}$ is $CH_3$ | $CH_3$ | H | H |

TABLE 12.C-continued

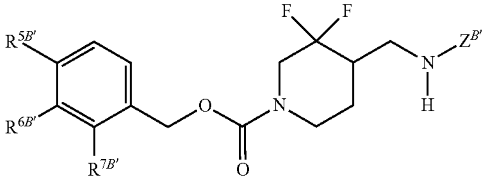

(racemic)

| compound | $Z^{B'}$ | $R^{5B'}$ | $R^{6B'}$ | $R^{7B'}$ |
|---|---|---|---|---|
| C-29.27$^{B'}$ | 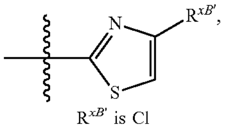 $R^{xB'}$ is Cl | $CH_3$ | H | H |
| C-29.28$^{B'}$ | 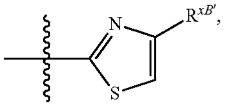 $R^{xB'}$ is F | $CH_3$ | H | H |
| C-29.29$^{B'}$ | 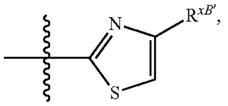 $R^{xB'}$ is $CF_3$ | $CH_3$ | H | H |
| C-29.30$^{B'}$ | 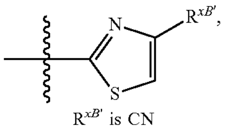 $R^{xB'}$ is CN | $CH_3$ | H | H |
| C-29.31$^{B'}$ | 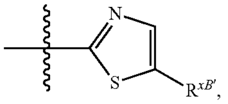 $R^{xB'}$ is $CH_3$ | $CH_3$ | H | H |
| C-29.32$^{B'}$ | 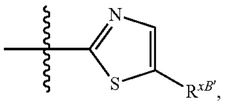 $R^{xB'}$ is Cl | $CH_3$ | H | H |
| C-29.33$^{B'}$ | 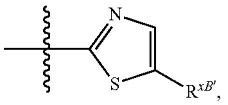 $R^{xB'}$ is F | $CH_3$ | H | H |
| C-29.34$^{B'}$ | 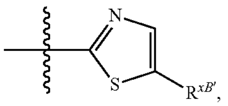 $R^{xB'}$ is $CF_3$ | $CH_3$ | H | H |
| C-29.35$^{B'}$ | 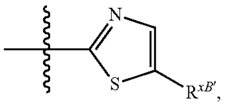 $R^{xB'}$ is CN | $CH_3$ | H | H |
| C-30.1$^{B'}$ | Z30$^{B'}$ | H | H | H |
| C-30.2$^{B'}$ | Z30$^{B'}$ | $CH_3$ | H | H |
| C-30.3$^{B'}$ | Z30$^{B'}$ | Cl | H | H |
| C-30.4$^{B'}$ | Z30$^{B'}$ | F | H | H |

TABLE 12.C-continued

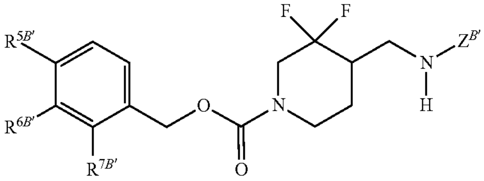

(racemic)

| compound | $Z^{B'}$ | $R^{5B'}$ | $R^{6B'}$ | $R^{7B'}$ |
|---|---|---|---|---|
| C-30.5$^{B'}$ | Z30$^{B'}$ | $CH_2CH_3$ | H | H |
| C-30.6$^{B'}$ | Z30$^{B'}$ | $CF_2H$ | H | H |
| C-30.7$^{B'}$ | Z30$^{B'}$ | $CH_2F$ | H | H |
| C-30.8$^{B'}$ | Z30$^{B'}$ | $CF_3$ | H | H |
| C-30.9$^{B'}$ | Z30$^{B'}$ | $CF_2CH_3$ | H | H |
| C-30.10$^{B'}$ | Z30$^{B'}$ | $CH_2CF_3$ | H | H |
| C-30.11$^{B'}$ | Z30$^{B'}$ | cyclopropyl | H | H |
| C-30.12$^{B'}$ | Z30$^{B'}$ | $OCF_3$ | H | H |
| C-30.13$^{B'}$ | Z30$^{B'}$ | $OCF_2H$ | H | H |
| C-30.14$^{B'}$ | Z30$^{B'}$ | Cl | H | F |
| C-30.15$^{B'}$ | Z30$^{B'}$ | $CH_3$ | H | F |
| C-30.16$^{B'}$ | Z30$^{B'}$ | $CH_3$ | F | H |
| C-30.17$^{B'}$ | Z30$^{B'}$ | Cl | F | H |
| C-30.18$^{B'}$ | Z30$^{B'}$ | F | F | H |
| C-30.19$^{B'}$ | Z30$^{B'}$ | F | H | F |
| C-30.20$^{B'}$ | Z30$^{B'}$ | F | H | Cl |
| C-30.21$^{B'}$ | Z30$^{B'}$ | F | H | $CH_3$ |
| C-30.22$^{B'}$ | Z30$^{B'}$ | Cl | H | $CH_3$ |
| C-30.23$^{B'}$ | Z30$^{B'}$ | $SCH_3$ | H | H |
| C-30.24$^{B'}$ | Z30$^{B'}$ | $SO_2CH_3$ | H | H |
| C-30.25$^{B'}$ | Z30$^{B'}$ | ethynyl | H | H |
| C-30.26$^{B'}$ | 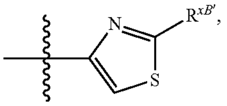 , $R^{xB'}$ is $CH_3$ | $CH_3$ | H | H |
| C-30.27$^{B'}$ | 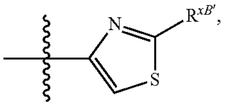 , $R^{xB'}$ is Cl | $CH_3$ | H | H |
| C-30.28$^{B'}$ | 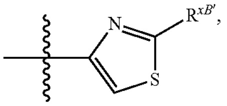 , $R^{xB'}$ is F | $CH_3$ | H | H |
| C-30.29$^{B'}$ | 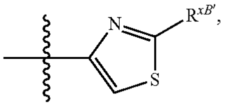 , $R^{xB'}$ is $CF_3$ | $CH_3$ | H | H |
| C-30.30$^{B'}$ | 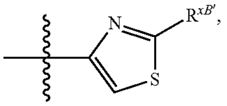 , $R^{xB'}$ is CN | $CH_3$ | H | H |
| C-30.31$^{B'}$ | 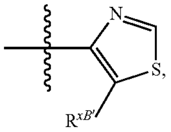 , $R^{xB'}$ is $CH_3$ | $CH_3$ | H | H |

TABLE 12.C-continued

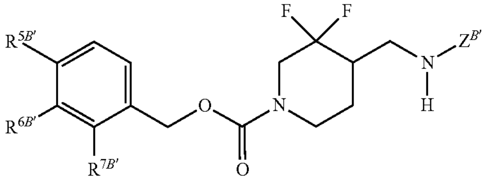

(racemic)

| compound | $Z^{B'}$ | $R^{5B'}$ | $R^{6B'}$ | $R^{7B'}$ |
|---|---|---|---|---|
| C-30.32$^{B'}$ | 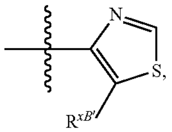 , $R^{xB'}$ is Cl | $CH_3$ | H | H |
| C-30.33$^{B'}$ | 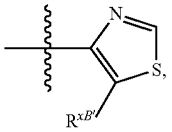 , $R^{xB'}$ is F | $CH_3$ | H | H |
| C-30.34$^{B'}$ | 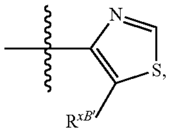 , $R^{xB'}$ is $CF_3$ | $CH_3$ | H | H |
| C-30.35$^{B'}$ | 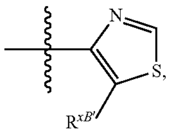 , $R^{xB'}$ is CN | $CH_3$ | H | H |
| C-31.1$^{B'}$ | Z31$^{B'}$ | H | H | H |
| C-31.2$^{B'}$ | Z31$^{B'}$ | $CH_3$ | H | H |
| C-31.3$^{B'}$ | Z31$^{B'}$ | Cl | H | H |
| C-31.4$^{B'}$ | Z31$^{B'}$ | F | H | H |
| C-31.5$^{B'}$ | Z31$^{B'}$ | $CH_2CH_3$ | H | H |
| C-31.6$^{B'}$ | Z31$^{B'}$ | $CF_2H$ | H | H |
| C-31.7$^{B'}$ | Z31$^{B'}$ | $CH_2F$ | H | H |
| C-31.8$^{B'}$ | Z31$^{B'}$ | $CF_3$ | H | H |
| C-31.9$^{B'}$ | Z31$^{B'}$ | $CF_2CH_3$ | H | H |
| C-31.10$^{B'}$ | Z31$^{B'}$ | $CH_2CF_3$ | H | H |
| C-31.11$^{B'}$ | Z31$^{B'}$ | cyclopropyl | H | H |
| C-31.12$^{B'}$ | Z31$^{B'}$ | $OCF_3$ | H | H |
| C-31.13$^{B'}$ | Z31$^{B'}$ | $OCF_2H$ | H | H |
| C-31.14$^{B'}$ | Z31$^{B'}$ | Cl | H | F |
| C-31.15$^{B'}$ | Z31$^{B'}$ | $CH_3$ | H | F |
| C-31.16$^{B'}$ | Z31$^{B'}$ | $CH_3$ | F | H |
| C-31.17$^{B'}$ | Z31$^{B'}$ | Cl | F | H |
| C-31.18$^{B'}$ | Z31$^{B'}$ | F | F | H |
| C-31.19$^{B'}$ | Z31$^{B'}$ | F | H | F |
| C-31.20$^{B'}$ | Z31$^{B'}$ | F | H | Cl |
| C-31.21$^{B'}$ | Z31$^{B'}$ | F | H | $CH_3$ |
| C-31.22$^{B'}$ | Z31$^{B'}$ | Cl | H | $CH_3$ |
| C-31.23$^{B'}$ | Z31$^{B'}$ | $SCH_3$ | H | H |
| C-31.24$^{B'}$ | Z31$^{B'}$ | $SO_2CH_3$ | H | H |
| C-31.25$^{B'}$ | Z31$^{B'}$ | ethynyl | H | H |
| C-31.26$^{B'}$ | 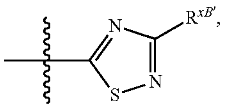 , $R^{xB'}$ is $CH_3$ | $CH_3$ | H | H |

TABLE 12.C-continued

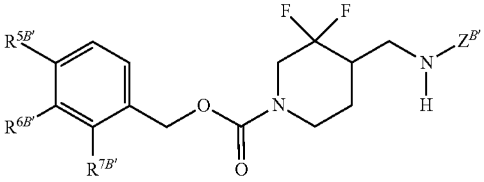

(racemic)

| compound | $Z^{B'}$ | $R^{5B'}$ | $R^{6B'}$ | $R^{7B'}$ |
|---|---|---|---|---|
| C-31.27$^{B'}$ | 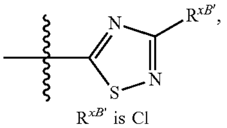 $R^{xB'}$ is Cl | $CH_3$ | H | H |
| C-31.28$^{B'}$ | 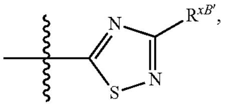 $R^{xB'}$ is F | $CH_3$ | H | H |
| C-31.29$^{B'}$ | 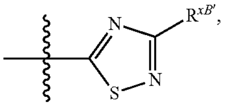 $R^{xB'}$ is $CF_3$ | $CH_3$ | H | H |
| C-31.30$^{B'}$ | 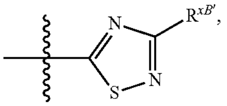 $R^{xB'}$ is CN | $CH_3$ | H | H |
| C-32.1$^{B'}$ | Z32$^{B'}$ | H | H | H |
| C-32.2$^{B'}$ | Z32$^{B'}$ | $CH_3$ | H | H |
| C-32.3$^{B'}$ | Z32$^{B'}$ | Cl | H | H |
| C-32.4$^{B'}$ | Z32$^{B'}$ | F | H | H |
| C-32.5$^{B'}$ | Z32$^{B'}$ | $CH_2CH_3$ | H | H |
| C-32.6$^{B'}$ | Z32$^{B'}$ | $CF_2H$ | H | H |
| C-32.7$^{B'}$ | Z32$^{B'}$ | $CH_2F$ | H | H |
| C-32.8$^{B'}$ | Z32$^{B'}$ | $CF_3$ | H | H |
| C-32.9$^{B'}$ | Z32$^{B'}$ | $CF_2CH_3$ | H | H |
| C-32.10$^{B'}$ | Z32$^{B'}$ | $CH_2CF_3$ | H | H |
| C-32.11$^{B'}$ | Z32$^{B'}$ | cyclopropyl | H | H |
| C-32.12$^{B'}$ | Z32$^{B'}$ | $OCF_3$ | H | H |
| C-32.13$^{B'}$ | Z32$^{B'}$ | $OCF_2H$ | H | H |
| C-32.14$^{B'}$ | Z32$^{B'}$ | Cl | H | F |
| C-32.15$^{B'}$ | Z32$^{B'}$ | $CH_3$ | H | F |
| C-32.16$^{B'}$ | Z32$^{B'}$ | $CH_3$ | F | H |
| C-32.17$^{B'}$ | Z32$^{B'}$ | Cl | F | H |
| C-32.18$^{B'}$ | Z32$^{B'}$ | F | F | H |
| C-32.19$^{B'}$ | Z32$^{B'}$ | F | H | F |
| C-32.20$^{B'}$ | Z32$^{B'}$ | F | H | Cl |
| C-32.21$^{B'}$ | Z32$^{B'}$ | F | H | $CH_3$ |
| C-32.22$^{B'}$ | Z32$^{B'}$ | Cl | H | $CH_3$ |
| C-32.23$^{B'}$ | Z32$^{B'}$ | $SCH_3$ | H | H |
| C-32.24$^{B'}$ | Z32$^{B'}$ | $SO_2CH_3$ | H | H |
| C-32.25$^{B'}$ | Z32$^{B'}$ | ethynyl | H | H |
| C-32.26$^{B'}$ | 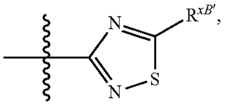 $R^{xB'}$ is $CH_3$ | $CH_3$ | H | H |
| C-32.27$^{B'}$ | 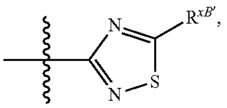 $R^{xB'}$ is Cl | $CH_3$ | H | H |

TABLE 12.C-continued

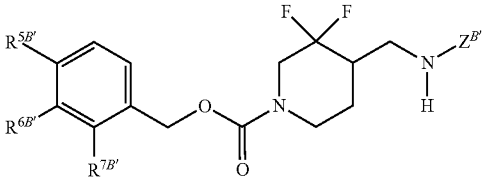

(racemic)

| compound | $Z^{B'}$ | $R^{5B'}$ | $R^{6B'}$ | $R^{7B'}$ |
|---|---|---|---|---|
| C-32.28$^{B'}$ | 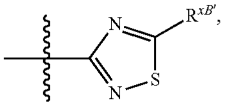 $R^{xB'}$ is F | $CH_3$ | H | H |
| C-32.29$^{B'}$ | 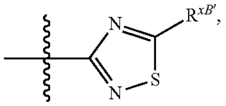 $R^{xB'}$ is $CF_3$ | $CH_3$ | H | H |
| C-32.30$^{B'}$ | 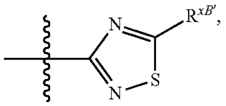 $R^{xB'}$ is CN | $CH_3$ | H | H |
| C-33.1$^{B'}$ | Z33$^{B'}$ | H | H | H |
| C-33.2$^{B'}$ | Z33$^{B'}$ | $CH_3$ | H | H |
| C-33.3$^{B'}$ | Z33$^{B'}$ | Cl | H | H |
| C-33.4$^{B'}$ | Z33$^{B'}$ | F | H | H |
| C-33.5$^{B'}$ | Z33$^{B'}$ | $CH_2CH_3$ | H | H |
| C-33.6$^{B'}$ | Z33$^{B'}$ | $CF_2H$ | H | H |
| C-33.7$^{B'}$ | Z33$^{B'}$ | $CH_2F$ | H | H |
| C-33.8$^{B'}$ | Z33$^{B'}$ | $CF_3$ | H | H |
| C-33.9$^{B'}$ | Z33$^{B'}$ | $CF_2CH_3$ | H | H |
| C-33.10$^{B'}$ | Z33$^{B'}$ | $CH_2CF_3$ | H | H |
| C-33.11$^{B'}$ | Z33$^{B'}$ | cyclopropyl | H | H |
| C-33.12$^{B'}$ | Z33$^{B'}$ | $OCF_3$ | H | H |
| C-33.13$^{B'}$ | Z33$^{B'}$ | $OCF_2H$ | H | H |
| C-33.14$^{B'}$ | Z33$^{B'}$ | Cl | H | F |
| C-33.15$^{B'}$ | Z33$^{B'}$ | $CH_3$ | H | F |
| C-33.16$^{B'}$ | Z33$^{B'}$ | $CH_3$ | F | H |
| C-33.17$^{B'}$ | Z33$^{B'}$ | Cl | F | H |
| C-33.18$^{B'}$ | Z33$^{B'}$ | F | F | H |
| C-33.19$^{B'}$ | Z33$^{B'}$ | F | H | F |
| C-33.20$^{B'}$ | Z33$^{B'}$ | F | H | Cl |
| C-33.21$^{B'}$ | Z33$^{B'}$ | F | H | $CH_3$ |
| C-33.22$^{B'}$ | Z33$^{B'}$ | Cl | H | $CH_3$ |
| C-33.23$^{B'}$ | Z33$^{B'}$ | $SCH_3$ | H | H |
| C-33.24$^{B'}$ | Z33$^{B'}$ | $SO_2CH_3$ | H | H |
| C-33.25$^{B'}$ | Z33$^{B'}$ | ethynyl | H | H |
| C-33.26$^{B'}$ | 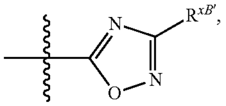 $R^{xB'}$ is $CH_3$ | $CH_3$ | H | H |
| C-33.27$^{B'}$ | 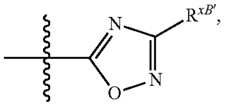 $R^{xB'}$ is Cl | $CH_3$ | H | H |

TABLE 12.C-continued

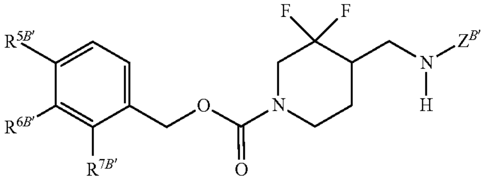

(racemic)

| compound | $Z^{B'}$ | $R^{5B'}$ | $R^{6B'}$ | $R^{7B'}$ |
|---|---|---|---|---|
| C-33.28$^{B'}$ | 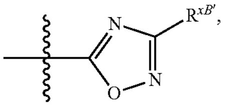 $R^{xB'}$ is F | $CH_3$ | H | H |
| C-33.29$^{B'}$ | 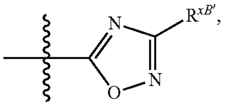 $R^{xB'}$ is $CF_3$ | $CH_3$ | H | H |
| C-33.30$^{B'}$ | 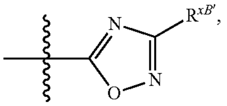 $R^{xB'}$ is CN | $CH_3$ | H | H |
| C-34.1$^{B'}$ | Z34$^{B'}$ | H | H | H |
| C-34.2$^{B'}$ | Z34$^{B'}$ | $CH_3$ | H | H |
| C-34.3$^{B'}$ | Z34$^{B'}$ | Cl | H | H |
| C-34.4$^{B'}$ | Z34$^{B'}$ | F | H | H |
| C-34.5$^{B'}$ | Z34$^{B'}$ | $CH_2CH_3$ | H | H |
| C-34.6$^{B'}$ | Z34$^{B'}$ | $CF_2H$ | H | H |
| C-34.7$^{B'}$ | Z34$^{B'}$ | $CH_2F$ | H | H |
| C-34.8$^{B'}$ | Z34$^{B'}$ | $CF_3$ | H | H |
| C-34.9$^{B'}$ | Z34$^{B'}$ | $CF_2CH_3$ | H | H |
| C-34.10$^{B'}$ | Z34$^{B'}$ | $CH_2CF_3$ | H | H |
| C-34.11$^{B'}$ | Z34$^{B'}$ | cyclopropyl | H | H |
| C-34.12$^{B'}$ | Z34$^{B'}$ | $OCF_3$ | H | H |
| C-34.13$^{B'}$ | Z34$^{B'}$ | $OCF_2H$ | H | H |
| C-34.14$^{B'}$ | Z34$^{B'}$ | Cl | H | F |
| C-34.15$^{B'}$ | Z34$^{B'}$ | $CH_3$ | H | F |
| C-34.16$^{B'}$ | Z34$^{B'}$ | $CH_3$ | F | H |
| C-34.17$^{B'}$ | Z34$^{B'}$ | Cl | F | H |
| C-34.18$^{B'}$ | Z34$^{B'}$ | F | F | H |
| C-34.19$^{B'}$ | Z34$^{B'}$ | F | H | F |
| C-34.20$^{B'}$ | Z34$^{B'}$ | F | H | Cl |
| C-34.21$^{B'}$ | Z34$^{B'}$ | F | H | $CH_3$ |
| C-34.22$^{B'}$ | Z34$^{B'}$ | Cl | H | $CH_3$ |
| C-34.23$^{B'}$ | Z34$^{B'}$ | $SCH_3$ | H | H |
| C-34.24$^{B'}$ | Z34$^{B'}$ | $SO_2CH_3$ | H | H |
| C-34.25$^{B'}$ | Z34$^{B'}$ | ethynyl | H | H |
| C-34.26$^{B'}$ | 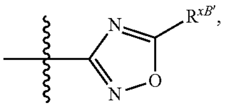 $R^{xB'}$ is $CH_3$ | $CH_3$ | H | H |
| C-34.27$^{B'}$ | 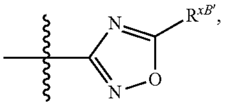 $R^{xB'}$ is Cl | $CH_3$ | H | H |
| C-34.28$^{B'}$ | 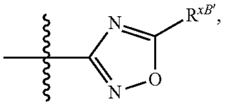 $R^{xB'}$ is F | $CH_3$ | H | H |

TABLE 12.C-continued

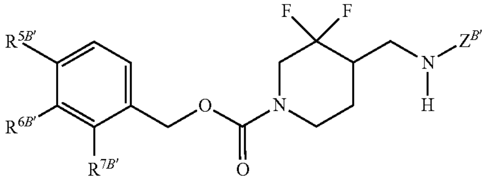

(racemic)

| compound | $Z^{B'}$ | $R^{5B'}$ | $R^{6B'}$ | $R^{7B'}$ |
|---|---|---|---|---|
| C-34.29$^{B'}$ | 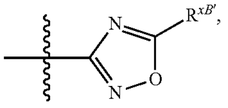 $R^{xB'}$ is $CF_3$ | $CH_3$ | H | H |
| C-34.30$^{B'}$ | 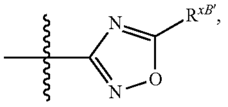 $R^{xB'}$ is CN | $CH_3$ | H | H |
| C-35.1$^{B'}$ | Z35$^{B'}$, $R^{aB'}$ is H | H | H | H |
| C-35.2$^{B'}$ | Z35$^{B'}$, $R^{aB'}$ is H | $CH_3$ | H | H |
| C-35.3$^{B'}$ | Z35$^{B'}$, $R^{aB'}$ is H | Cl | H | H |
| C-35.4$^{B'}$ | Z35$^{B'}$, $R^{aB'}$ is H | F | H | H |
| C-35.5$^{B'}$ | Z35$^{B'}$, $R^{aB'}$ is H | $CH_2CH_3$ | H | H |
| C-35.6$^{B'}$ | Z35$^{B'}$, $R^{aB'}$ is H | $CF_2H$ | H | H |
| C-35.7$^{B'}$ | Z35$^{B'}$, $R^{aB'}$ is H | $CH_2F$ | H | H |
| C-35.8$^{B'}$ | Z35$^{B'}$, $R^{aB'}$ is H | $CF_3$ | H | H |
| C-35.9$^{B'}$ | Z35$^{B'}$, $R^{aB'}$ is H | $CF_2CH_3$ | H | H |
| C-35.10$^{B'}$ | Z35$^{B'}$, $R^{aB'}$ is H | $CH_2CF_3$ | H | H |
| C-35.11$^{B'}$ | Z35$^{B'}$, $R^{aB'}$ is H | cyclopropyl | H | H |
| C-35.12$^{B'}$ | Z35$^{B'}$, $R^{aB'}$ is H | $OCF_3$ | H | H |
| C-35.13$^{B'}$ | Z35$^{B'}$, $R^{aB'}$ is H | $OCF_2H$ | H | H |
| C-35.14$^{B'}$ | Z35$^{B'}$, $R^{aB'}$ is H | Cl | H | F |
| C-35.15$^{B'}$ | Z35$^{B'}$, $R^{aB'}$ is H | $CH_3$ | H | F |
| C-35.16$^{B'}$ | Z35$^{B'}$, $R^{aB'}$ is H | $CH_3$ | F | H |
| C-35.17$^{B'}$ | Z35$^{B'}$, $R^{aB'}$ is H | Cl | F | H |
| C-35.18$^{B'}$ | Z35$^{B'}$, $R^{aB'}$ is H | F | F | H |
| C-35.19$^{B'}$ | Z35$^{B'}$, $R^{aB'}$ is H | F | H | F |
| C-35.20$^{B'}$ | Z35$^{B'}$, $R^{aB'}$ is H | F | H | Cl |
| C-35.21$^{B'}$ | Z35$^{B'}$, $R^{aB'}$ is H | F | H | $CH_3$ |
| C-35.22$^{B'}$ | Z35$^{B'}$, $R^{aB'}$ is H | Cl | H | $CH_3$ |
| C-35.23$^{B'}$ | Z35$^{B'}$, $R^{aB'}$ is H | $SCH_3$ | H | H |
| C-35.24$^{B'}$ | Z35$^{B'}$, $R^{aB'}$ is H | $SO_2CH_3$ | H | H |
| C-35.25$^{B'}$ | Z35$^{B'}$, $R^{aB'}$ is H | ethynyl | H | H |
| C-35.26$^{B'}$ | 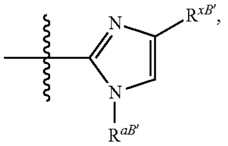 $R^{aB'}$ is H; $R^{xB'}$ is $CH_3$ | $CH_3$ | H | H |
| C-35.27$^{B'}$ | 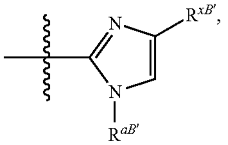 $R^{aB'}$ is H; $R^{xB'}$ is Cl | $CH_3$ | H | H |
| C-35.28$^{B'}$ | 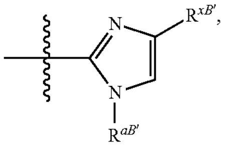 $R^{aB'}$ is H; $R^{xB'}$ is F | $CH_3$ | H | H |

TABLE 12.C-continued

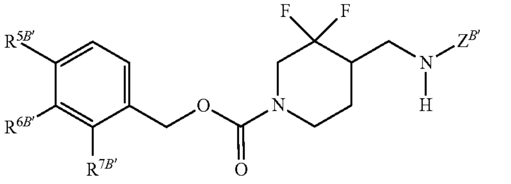

(racemic)

| compound | $Z^{B'}$ | $R^{5B'}$ | $R^{6B'}$ | $R^{7B'}$ |
|---|---|---|---|---|
| C-35.29$^{B'}$ | 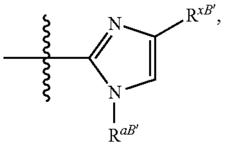 $R^{aB'}$ is H; $R^{xB'}$ is $CF_3$ | $CH_3$ | H | H |
| C-35.30$^{B'}$ | 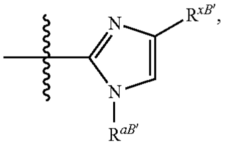 $R^{aB'}$ is H; $R^{xB'}$ is CN | $CH_3$ | H | H |
| C-35.31$^{B'}$ | 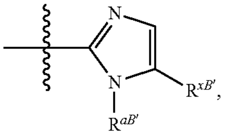 $R^{aB'}$ is H; $R^{xB'}$ is $CH_3$ | $CH_3$ | H | H |
| C-35.32$^{B'}$ | 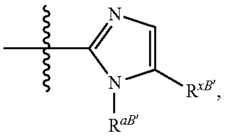 $R^{aB'}$ is H; $R^{xB'}$ is Cl | $CH_3$ | H | H |
| C-35.33$^{B'}$ | 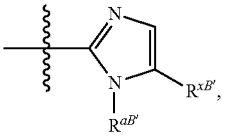 $R^{aB'}$ is H; $R^{xB'}$ is F | $CH_3$ | H | H |
| C-35.34$^{B'}$ | 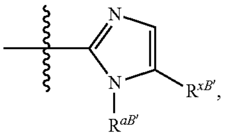 $R^{aB'}$ is H; $R^{xB'}$ is $CF_3$ | $CH_3$ | H | H |
| C-35.35$^{B'}$ | 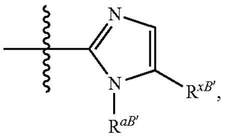 $R^{aB'}$ is H; $R^{xB'}$ is CN | $CH_3$ | H | H |
| C-36.1$^{B'}$ | Z36$^{B'}$, $R^{aB'}$ is H | H | H | H |
| C-36.2$^{B'}$ | Z36$^{B'}$, $R^{aB'}$ is H | $CH_3$ | H | H |
| C-36.3$^{B'}$ | Z36$^{B'}$, $R^{aB'}$ is H | Cl | H | H |
| C-36.4$^{B'}$ | Z36$^{B'}$, $R^{aB'}$ is H | F | H | H |
| C-36.5$^{B'}$ | Z36$^{B'}$, $R^{aB'}$ is H | $CH_2CH_3$ | H | H |
| C-36.6$^{B'}$ | Z36$^{B'}$, $R^{aB'}$ is H | $CF_2H$ | H | H |

TABLE 12.C-continued

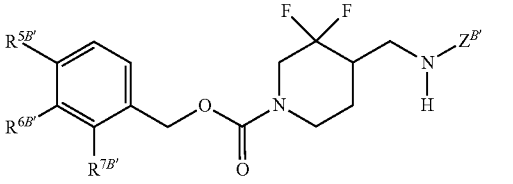

(racemic)

| compound | $Z^{B'}$ | $R^{5B'}$ | $R^{6B'}$ | $R^{7B'}$ |
|---|---|---|---|---|
| C-36.7$^{B'}$ | Z36$^{B'}$, $R^{aB'}$ is H | $CH_2F$ | H | H |
| C-36.8$^{B'}$ | Z36$^{B'}$, $R^{aB'}$ is H | $CF_3$ | H | H |
| C-36.9$^{B'}$ | Z36$^{B'}$, $R^{aB'}$ is H | $CF_2CH_3$ | H | H |
| C-36.10$^{B'}$ | Z36$^{B'}$, $R^{aB'}$ is H | $CH_2CF_3$ | H | H |
| C-36.11$^{B'}$ | Z36$^{B'}$, $R^{aB'}$ is H | cyclopropyl | H | H |
| C-36.12$^{B'}$ | Z36$^{B'}$, $R^{aB'}$ is H | $OCF_3$ | H | H |
| C-36.13$^{B'}$ | Z36$^{B'}$, $R^{aB'}$ is H | $OCF_2H$ | H | H |
| C-36.14$^{B'}$ | Z36$^{B'}$, $R^{aB'}$ is H | Cl | H | F |
| C-36.15$^{B'}$ | Z36$^{B'}$, $R^{aB'}$ is H | $CH_3$ | H | F |
| C-36.16$^{B'}$ | Z36$^{B'}$, $R^{aB'}$ is H | $CH_3$ | F | H |
| C-36.17$^{B'}$ | Z36$^{B'}$, $R^{aB'}$ is H | Cl | F | H |
| C-36.18$^{B'}$ | Z36$^{B'}$, $R^{aB'}$ is H | F | F | H |
| C-36.19$^{B'}$ | Z36$^{B'}$, $R^{aB'}$ is H | F | H | F |
| C-36.20$^{B'}$ | Z36$^{B'}$, $R^{aB'}$ is H | F | H | Cl |
| C-36.21$^{B'}$ | Z36$^{B'}$, $R^{aB'}$ is H | F | H | $CH_3$ |
| C-36.22$^{B'}$ | Z36$^{B'}$, $R^{aB'}$ is H | Cl | H | $CH_3$ |
| C-36.23$^{B'}$ | Z36$^{B'}$, $R^{aB'}$ is H | $SCH_3$ | H | H |
| C-36.24$^{B'}$ | Z36$^{B'}$, $R^{aB'}$ is H | $SO_2CH_3$ | H | H |
| C-36.25$^{B'}$ | Z36$^{B'}$, $R^{aB'}$ is H | ethynyl | H | H |
| C-36.26$^{B'}$ | 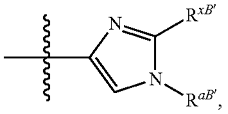 $R^{aB'}$ is H; $R^{xB'}$ is $CH_3$ | $CH_3$ | H | H |
| C-36.27$^{B'}$ | 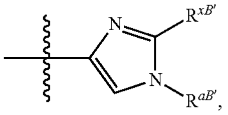 $R^{aB'}$ is H; $R^{xB'}$ is Cl | $CH_3$ | H | H |
| C-36.28$^{B'}$ | 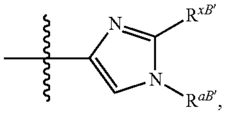 $R^{aB'}$ is H; $R^{xB'}$ is F | $CH_3$ | H | H |
| C-36.29$^{B'}$ | 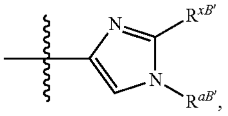 $R^{aB'}$ is H; $R^{xB'}$ is $CF_3$ | $CH_3$ | H | H |
| C-36.30$^{B'}$ | 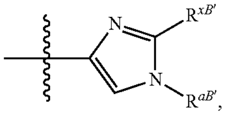 $R^{aB'}$ is H; $R^{xB'}$ is CN | $CH_3$ | H | H |
| C-37.1$^{B'}$ | Z37$^{B'}$ | H | H | H |
| C-37.2$^{B'}$ | Z37$^{B'}$ | $CH_3$ | H | H |
| C-37.3$^{B'}$ | Z37$^{B'}$ | Cl | H | H |
| C-37.4$^{B'}$ | Z37$^{B'}$ | F | H | H |
| C-37.5$^{B'}$ | Z37$^{B'}$ | $CH_2CH_3$ | H | H |
| C-37.6$^{B'}$ | Z37$^{B'}$ | $CF_2H$ | H | H |
| C-38.1$^{B'}$ | Z38$^{B'}$ | H | H | H |
| C-38.2$^{B'}$ | Z38$^{B'}$ | $CH_3$ | H | H |
| C-38.3$^{B'}$ | Z38$^{B'}$ | Cl | H | H |
| C-38.4$^{B'}$ | Z38$^{B'}$ | F | H | H |

TABLE 12.C-continued

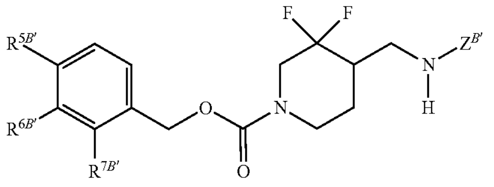

(racemic)

| compound | $Z^{B'}$ | $R^{5B'}$ | $R^{6B'}$ | $R^{7B'}$ |
|---|---|---|---|---|
| C-38.5$^{B'}$ | Z38$^{B'}$ | $CH_2CH_3$ | H | H |
| C-38.6$^{B'}$ | Z38$^{B'}$ | $CF_2H$ | H | H |
| C-38.7$^{B'}$ | 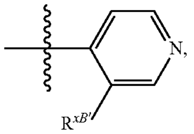 $R^{xB'}$ is F | H | H | H |
| C-38.8$^{B'}$ | 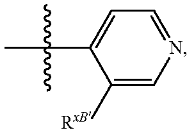 $R^{xB'}$ is F | $CH_3$ | H | H |
| C-38.9$^{B'}$ | 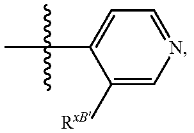 $R^{xB'}$ is F | Cl | H | H |
| C-38.10$^{B'}$ | 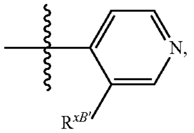 $R^{xB'}$ is F | F | H | H |
| C-38.11$^{B'}$ | 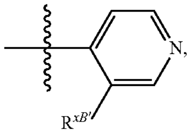 $R^{xB'}$ is F | $CH_2CH_3$ | H | H |
| C-38.12$^{B'}$ | 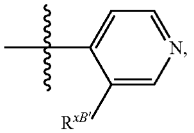 $R^{xB'}$ is F | $CF_2H$ | H | H |

TABLE 13

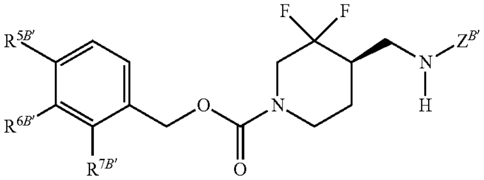

| compound | $Z^{B'}$ | $R^{5B'}$ | $R^{6B'}$ | $R^{7B'}$ |
|---|---|---|---|---|
| E1-1.1$^{B'}$ | Z1$^{B'}$ | H | H | H |
| E1-1.2$^{B'}$ | Z1$^{B'}$ | $CH_3$ | H | H |
| E1-1.3$^{B'}$ | Z1$^{B'}$ | Cl | H | H |
| E1-1.4$^{B'}$ | Z1$^{B'}$ | F | H | H |
| E1-1.5$^{B'}$ | Z1$^{B'}$ | $CH_2CH_3$ | H | H |
| E1-1.6$^{B'}$ | Z1$^{B'}$ | $CF_2H$ | H | H |
| E1-1.7$^{B'}$ | Z1$^{B'}$ | $CH_2F$ | H | H |
| E1-1.8$^{B'}$ | Z1$^{B'}$ | $CF_3$ | H | H |
| E1-1.9$^{B'}$ | Z1$^{B'}$ | $CF_2CH_3$ | H | H |
| E1-1.10$^{B'}$ | Z1$^{B'}$ | $CH_2CF_3$ | H | H |
| E1-1.11$^{B'}$ | Z1$^{B'}$ | cyclopropyl | H | H |
| E1-1.12$^{B'}$ | Z1$^{B'}$ | $OCF_3$ | H | H |
| E1-1.13$^{B'}$ | Z1$^{B'}$ | $OCF_2H$ | H | H |
| E1-1.14$^{B'}$ | Z1$^{B'}$ | Cl | H | F |
| E1-1.15$^{B'}$ | Z1$^{B'}$ | $CH_3$ | H | F |
| E1-1.16$^{B'}$ | Z1$^{B'}$ | $CH_3$ | F | H |
| E1-1.17$^{B'}$ | Z1$^{B'}$ | Cl | F | H |
| E1-1.18$^{B'}$ | Z1$^{B'}$ | F | F | H |
| E1-1.19$^{B'}$ | Z1$^{B'}$ | F | H | F |
| E1-1.20$^{B'}$ | Z1$^{B'}$ | F | H | Cl |
| E1-1.21$^{B'}$ | Z1$^{B'}$ | F | H | $CH_3$ |
| E1-1.22$^{B'}$ | Z1$^{B'}$ | Cl | H | $CH_3$ |
| E1-1.23$^{B'}$ | Z1$^{B'}$ | $SCH_3$ | H | H |
| E1-1.24$^{B'}$ | Z1$^{B'}$ | $SO_2CH_3$ | H | H |
| E1-1.25$^{B'}$ | Z1$^{B'}$ | ethynyl | H | H |
| E1-2.1$^{B'}$ | Z2$^{B'}$ | H | H | H |
| E1-2.2$^{B'}$ | Z2$^{B'}$ | $CH_3$ | H | H |
| E1-2.3$^{B'}$ | Z2$^{B'}$ | Cl | H | H |
| E1-2.4$^{B'}$ | Z2$^{B'}$ | F | H | H |
| E1-2.5$^{B'}$ | Z2$^{B'}$ | $CH_2CH_3$ | H | H |
| E1-2.6$^{B'}$ | Z2$^{B'}$ | $CF_2H$ | H | H |
| E1-2.7$^{B'}$ | Z2$^{B'}$ | $CH_2F$ | H | H |
| E1-2.8$^{B'}$ | Z2$^{B'}$ | $CF_3$ | H | H |
| E1-2.9$^{B'}$ | Z2$^{B'}$ | $CF_2CH_3$ | H | H |
| E1-2.10$^{B'}$ | Z2$^{B'}$ | $CH_2CF_3$ | H | H |
| E1-2.11$^{B'}$ | Z2$^{B'}$ | cyclopropyl | H | H |
| E1-2.12$^{B'}$ | Z2$^{B'}$ | $OCF_3$ | H | H |
| E1-2.13$^{B'}$ | Z2$^{B'}$ | $OCF_2H$ | H | H |
| E1-2.14$^{B'}$ | Z2$^{B'}$ | Cl | H | F |
| E1-2.15$^{B'}$ | Z2$^{B'}$ | $CH_3$ | H | F |
| E1-2.16$^{B'}$ | Z2$^{B'}$ | $CH_3$ | F | H |
| E1-2.17$^{B'}$ | Z2$^{B'}$ | Cl | F | H |
| E1-2.18$^{B'}$ | Z2$^{B'}$ | F | F | H |
| E1-2.19$^{B'}$ | Z2$^{B'}$ | F | H | F |
| E1-2.20$^{B'}$ | Z2$^{B'}$ | F | H | Cl |
| E1-2.21$^{B'}$ | Z2$^{B'}$ | F | H | $CH_3$ |
| E1-2.22$^{B'}$ | Z2$^{B'}$ | Cl | H | $CH_3$ |
| E1-2.23$^{B'}$ | Z2$^{B'}$ | $SCH_3$ | H | H |
| E1-2.24$^{B'}$ | Z2$^{B'}$ | $SO_2CH_3$ | H | H |
| E1-2.25$^{B'}$ | Z2$^{B'}$ | ethynyl | H | H |
| E1-3.1$^{B'}$ | Z3$^{B'}$ | H | H | H |
| E1-3.2$^{B'}$ | Z3$^{B'}$ | $CH_3$ | H | H |
| E1-3.3$^{B'}$ | Z3$^{B'}$ | Cl | H | H |
| E1-3.4$^{B'}$ | Z3$^{B'}$ | F | H | H |
| E1-3.5$^{B'}$ | Z3$^{B'}$ | $CH_2CH_3$ | H | H |
| E1-3.6$^{B'}$ | Z3$^{B'}$ | $CF_2H$ | H | H |
| E1-3.7$^{B'}$ | Z3$^{B'}$ | $CH_2F$ | H | H |
| E1-3.8$^{B'}$ | Z3$^{B'}$ | $CF_3$ | H | H |
| E1-3.9$^{B'}$ | Z3$^{B'}$ | $CF_2CH_3$ | H | H |
| E1-3.10$^{B'}$ | Z3$^{B'}$ | $CH_2CF_3$ | H | H |
| E1-3.11$^{B'}$ | Z3$^{B'}$ | cyclopropyl | H | H |
| E1-3.12$^{B'}$ | Z3$^{B'}$ | $OCF_3$ | H | H |
| E1-3.13$^{B'}$ | Z3$^{B'}$ | $OCF_2H$ | H | H |
| E1-3.14$^{B'}$ | Z3$^{B'}$ | Cl | H | F |
| E1-3.15$^{B'}$ | Z3$^{B'}$ | $CH_3$ | H | F |
| E1-3.16$^{B'}$ | Z3$^{B'}$ | $CH_3$ | F | H |
| E1-3.17$^{B'}$ | Z3$^{B'}$ | Cl | F | H |
| E1-3.18$^{B'}$ | Z3$^{B'}$ | F | F | H |

TABLE 13-continued

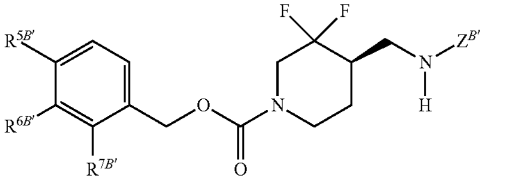

| compound | $Z^{B'}$ | $R^{5B'}$ | $R^{6B'}$ | $R^{7B'}$ |
|---|---|---|---|---|
| E1-3.19$^{B'}$ | Z3$^{B'}$ | F | H | F |
| E1-3.20$^{B'}$ | Z3$^{B'}$ | F | H | Cl |
| E1-3.21$^{B'}$ | Z3$^{B'}$ | F | H | $CH_3$ |
| E1-3.22$^{B'}$ | Z3$^{B'}$ | Cl | H | $CH_3$ |
| E1-3.23$^{B'}$ | Z3$^{B'}$ | $SCH_3$ | H | H |
| E1-3.24$^{B'}$ | Z3$^{B'}$ | $SO_2CH_3$ | H | H |
| E1-3.25$^{B'}$ | Z3$^{B'}$ | ethynyl | H | H |
| E1-4.1$^{B'}$ | Z4$^{B'}$ | H | H | H |
| E1-4.2$^{B'}$ | Z4$^{B'}$ | $CH_3$ | H | H |
| E1-4.3$^{B'}$ | Z4$^{B'}$ | Cl | H | H |
| E1-4.4$^{B'}$ | Z4$^{B'}$ | F | H | H |
| E1-4.5$^{B'}$ | Z4$^{B'}$ | $CH_2CH_3$ | H | H |
| E1-4.6$^{B'}$ | Z4$^{B'}$ | $CF_2H$ | H | H |
| E1-4.7$^{B'}$ | Z4$^{B'}$ | $CH_2F$ | H | H |
| E1-4.8$^{B'}$ | Z4$^{B'}$ | $CF_3$ | H | H |
| E1-4.9$^{B'}$ | Z4$^{B'}$ | $CF_2CH_3$ | H | H |
| E1-4.10$^{B'}$ | Z4$^{B'}$ | $CH_2CF_3$ | H | H |
| E1-4.11$^{B'}$ | Z4$^{B'}$ | cyclopropyl | H | H |
| E1-4.12$^{B'}$ | Z4$^{B'}$ | $OCF_3$ | H | H |
| E1-4.13$^{B'}$ | Z4$^{B'}$ | $OCF_2H$ | H | H |
| E1-4.14$^{B'}$ | Z4$^{B'}$ | Cl | H | F |
| E1-4.15$^{B'}$ | Z4$^{B'}$ | $CH_3$ | H | F |
| E1-4.16$^{B'}$ | Z4$^{B'}$ | $CH_3$ | F | H |
| E1-4.17$^{B'}$ | Z4$^{B'}$ | Cl | F | H |
| E1-4.18$^{B'}$ | Z4$^{B'}$ | F | F | H |
| E1-4.19$^{B'}$ | Z4$^{B'}$ | F | H | F |
| E1-4.20$^{B'}$ | Z4$^{B'}$ | F | H | Cl |
| E1-4.21$^{B'}$ | Z4$^{B'}$ | F | H | $CH_3$ |
| E1-4.22$^{B'}$ | Z4$^{B'}$ | Cl | H | $CH_3$ |
| E1-4.23$^{B'}$ | Z4$^{B'}$ | $SCH_3$ | H | H |
| E1-4.24$^{B'}$ | Z4$^{B'}$ | $SO_2CH_3$ | H | H |
| E1-4.25$^{B'}$ | Z4$^{B'}$ | ethynyl | H | H |
| E1-5.1$^{B'}$ | Z5$^{B'}$ | H | H | H |
| E1-5.2$^{B'}$ | Z5$^{B'}$ | $CH_3$ | H | H |
| E1-5.3$^{B'}$ | Z5$^{B'}$ | Cl | H | H |
| E1-5.4$^{B'}$ | Z5$^{B'}$ | F | H | H |
| E1-5.5$^{B'}$ | Z5$^{B'}$ | $CH_2CH_3$ | H | H |
| E1-5.6$^{B'}$ | Z5$^{B'}$ | $CF_2H$ | H | H |
| E1-5.7$^{B'}$ | Z5$^{B'}$ | $CH_2F$ | H | H |
| E1-5.8$^{B'}$ | Z5$^{B'}$ | $CF_3$ | H | H |
| E1-5.9$^{B'}$ | Z5$^{B'}$ | $CF_2CH_3$ | H | H |
| E1-5.10$^{B'}$ | Z5$^{B'}$ | $CH_2CF_3$ | H | H |
| E1-5.11$^{B'}$ | Z5$^{B'}$ | cyclopropyl | H | H |
| E1-5.12$^{B'}$ | Z5$^{B'}$ | $OCF_3$ | H | H |
| E1-5.13$^{B'}$ | Z5$^{B'}$ | $OCF_2H$ | H | H |
| E1-5.14$^{B'}$ | Z5$^{B'}$ | Cl | H | F |
| E1-5.15$^{B'}$ | Z5$^{B'}$ | $CH_3$ | H | F |
| E1-5.16$^{B'}$ | Z5$^{B'}$ | $CH_3$ | F | H |
| E1-5.17$^{B'}$ | Z5$^{B'}$ | Cl | F | H |
| E1-5.18$^{B'}$ | Z5$^{B'}$ | F | F | H |
| E1-5.19$^{B'}$ | Z5$^{B'}$ | F | H | F |
| E1-5.20$^{B'}$ | Z5$^{B'}$ | F | H | Cl |
| E1-5.21$^{B'}$ | Z5$^{B'}$ | F | H | $CH_3$ |
| E1-5.22$^{B'}$ | Z5$^{B'}$ | Cl | H | $CH_3$ |
| E1-5.23$^{B'}$ | Z5$^{B'}$ | $SCH_3$ | H | H |
| E1-5.24$^{B'}$ | Z5$^{B'}$ | $SO_2CH_3$ | H | H |
| E1-5.25$^{B'}$ | Z5$^{B'}$ | ethynyl | H | H |
| E1-6.1$^{B'}$ | Z6$^{B'}$, R$^{aB'}$ is H | H | H | H |
| E1-6.2$^{B'}$ | Z6$^{B'}$, R$^{aB'}$ is H | $CH_3$ | H | H |
| E1-6.3$^{B'}$ | Z6$^{B'}$, R$^{aB'}$ is H | Cl | H | H |
| E1-6.4$^{B'}$ | Z6$^{B'}$, R$^{aB'}$ is H | F | H | H |
| E1-6.5$^{B'}$ | Z6$^{B'}$, R$^{aB'}$ is H | $CH_2CH_3$ | H | H |
| E1-6.6$^{B'}$ | Z6$^{B'}$, R$^{aB'}$ is H | $CF_2H$ | H | H |
| E1-6.7$^{B'}$ | Z6$^{B'}$, R$^{aB'}$ is H | $CH_2F$ | H | H |
| E1-6.8$^{B'}$ | Z6$^{B'}$, R$^{aB'}$ is H | $CF_3$ | H | H |
| E1-6.9$^{B'}$ | Z6$^{B'}$, R$^{aB'}$ is H | $CF_2CH_3$ | H | H |
| E1-6.10$^{B'}$ | Z6$^{B'}$, R$^{aB'}$ is H | $CH_2CF_3$ | H | H |
| E1-6.11$^{B'}$ | Z6$^{B'}$, R$^{aB'}$ is H | cyclopropyl | H | H |

TABLE 13-continued

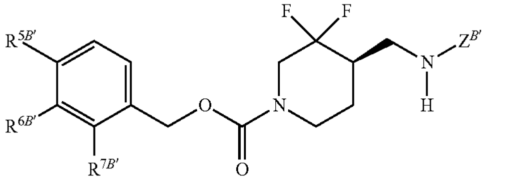

| compound | $Z^{B'}$ | $R^{5B'}$ | $R^{6B'}$ | $R^{7B'}$ |
|---|---|---|---|---|
| E1-6.12$^{B'}$ | Z6$^{B'}$, R$^{aB'}$ is H | $OCF_3$ | H | H |
| E1-6.13$^{B'}$ | Z6$^{B'}$, R$^{aB'}$ is H | $OCF_2H$ | H | H |
| E1-6.14$^{B'}$ | Z6$^{B'}$, R$^{aB'}$ is H | Cl | H | F |
| E1-6.15$^{B'}$ | Z6$^{B'}$, R$^{aB'}$ is H | $CH_3$ | H | F |
| E1-6.16$^{B'}$ | Z6$^{B'}$, R$^{aB'}$ is H | $CH_3$ | F | H |
| E1-6.17$^{B'}$ | Z6$^{B'}$, R$^{aB'}$ is H | Cl | F | H |
| E1-6.18$^{B'}$ | Z6$^{B'}$, R$^{aB'}$ is H | F | F | H |
| E1-6.19$^{B'}$ | Z6$^{B'}$, R$^{aB'}$ is H | F | H | F |
| E1-6.20$^{B'}$ | Z6$^{B'}$, R$^{aB'}$ is H | F | H | Cl |
| E1-6.21$^{B'}$ | Z6$^{B'}$, R$^{aB'}$ is H | F | H | $CH_3$ |
| E1-6.22$^{B'}$ | Z6$^{B'}$, R$^{aB'}$ is H | Cl | H | $CH_3$ |
| E1-6.23$^{B'}$ | Z6$^{B'}$, R$^{aB'}$ is H | $SCH_3$ | H | H |
| E1-6.24$^{B'}$ | Z6$^{B'}$, R$^{aB'}$ is H | $SO_2CH_3$ | H | H |
| E1-6.25$^{B'}$ | Z6$^{B'}$, R$^{aB'}$ is H | ethynyl | H | H |
| E1-7.1$^{B'}$ | Z7$^{B'}$, R$^{aB'}$ is H | H | H | H |
| E1-7.2$^{B'}$ | Z7$^{B'}$, R$^{aB'}$ is H | $CH_3$ | H | H |
| E1-7.3$^{B'}$ | Z7$^{B'}$, R$^{aB'}$ is H | Cl | H | H |
| E1-7.4$^{B'}$ | Z7$^{B'}$, R$^{aB'}$ is H | F | H | H |
| E1-7.5$^{B'}$ | Z7$^{B'}$, R$^{aB'}$ is H | $CH_2CH_3$ | H | H |
| E1-7.6$^{B'}$ | Z7$^{B'}$, R$^{aB'}$ is H | $CF_2H$ | H | H |
| E1-7.7$^{B'}$ | Z7$^{B'}$, R$^{aB'}$ is H | $CH_2F$ | H | H |
| E1-7.8$^{B'}$ | Z7$^{B'}$, R$^{aB'}$ is H | $CF_3$ | H | H |
| E1-7.9$^{B'}$ | Z7$^{B'}$, R$^{aB'}$ is H | $CF_2CH_3$ | H | H |
| E1-7.10$^{B'}$ | Z7$^{B'}$, R$^{aB'}$ is H | $CH_2CF_3$ | H | H |
| E1-7.11$^{B'}$ | Z7$^{B'}$, R$^{aB'}$ is H | cyclopropyl | H | H |
| E1-7.12$^{B'}$ | Z7$^{B'}$, R$^{aB'}$ is H | $OCF_3$ | H | H |
| E1-7.13$^{B'}$ | Z7$^{B'}$, R$^{aB'}$ is H | $OCF_2H$ | H | H |
| E1-7.14$^{B'}$ | Z7$^{B'}$, R$^{aB'}$ is H | Cl | H | F |
| E1-7.15$^{B'}$ | Z7$^{B'}$, R$^{aB'}$ is H | $CH_3$ | H | F |
| E1-7.16$^{B'}$ | Z7$^{B'}$, R$^{aB'}$ is H | $CH_3$ | F | H |
| E1-7.17$^{B'}$ | Z7$^{B'}$, R$^{aB'}$ is H | Cl | F | H |
| E1-7.18$^{B'}$ | Z7$^{B'}$, R$^{aB'}$ is H | F | F | H |
| E1-7.19$^{B'}$ | Z7$^{B'}$, R$^{aB'}$ is H | F | H | F |
| E1-7.20$^{B'}$ | Z7$^{B'}$, R$^{aB'}$ is H | F | H | Cl |
| E1-7.21$^{B'}$ | Z7$^{B'}$, R$^{aB'}$ is H | F | H | $CH_3$ |
| E1-7.22$^{B'}$ | Z7$^{B'}$, R$^{aB'}$ is H | Cl | H | $CH_3$ |
| E1-7.23$^{B'}$ | Z7$^{B'}$, R$^{aB'}$ is H | $SCH_3$ | H | H |
| E1-7.24$^{B'}$ | Z7$^{B'}$, R$^{aB'}$ is H | $SO_2CH_3$ | H | H |
| E1-7.25$^{B'}$ | Z7$^{B'}$, R$^{aB'}$ is H | ethynyl | H | H |
| E1-8.1$^{B'}$ | Z8$^{B'}$, R$^{aB'}$ is H | H | H | H |
| E1-8.2$^{B'}$ | Z8$^{B'}$, R$^{aB'}$ is H | $CH_3$ | H | H |
| E1-8.3$^{B'}$ | Z8$^{B'}$, R$^{aB'}$ is H | Cl | H | H |
| E1-8.4$^{B'}$ | Z8$^{B'}$, R$^{aB'}$ is H | F | H | H |
| E1-8.5$^{B'}$ | Z8$^{B'}$, R$^{aB'}$ is H | $CH_2CH_3$ | H | H |
| E1-8.6$^{B'}$ | Z8$^{B'}$, R$^{aB'}$ is H | $CF_2H$ | H | H |
| E1-8.7$^{B'}$ | Z8$^{B'}$, R$^{aB'}$ is H | $CH_2F$ | H | H |
| E1-8.8$^{B'}$ | Z8$^{B'}$, R$^{aB'}$ is H | $CF_3$ | H | H |
| E1-8.9$^{B'}$ | Z8$^{B'}$, R$^{aB'}$ is H | $CF_2CH_3$ | H | H |
| E1-8.10$^{B'}$ | Z8$^{B'}$, R$^{aB'}$ is H | $CH_2CF_3$ | H | H |
| E1-8.11$^{B'}$ | Z8$^{B'}$, R$^{aB'}$ is H | cyclopropyl | H | H |
| E1-8.12$^{B'}$ | Z8$^{B'}$, R$^{aB'}$ is H | $OCF_3$ | H | H |
| E1-8.13$^{B'}$ | Z8$^{B'}$, R$^{aB'}$ is H | $OCF_2H$ | H | H |
| E1-8.14$^{B'}$ | Z8$^{B'}$, R$^{aB'}$ is H | Cl | H | F |
| E1-8.15$^{B'}$ | Z8$^{B'}$, R$^{aB'}$ is H | $CH_3$ | H | F |
| E1-8.16$^{B'}$ | Z8$^{B'}$, R$^{aB'}$ is H | $CH_3$ | F | H |
| E1-8.17$^{B'}$ | Z8$^{B'}$, R$^{aB'}$ is H | Cl | F | H |
| E1-8.18$^{B'}$ | Z8$^{B'}$, R$^{aB'}$ is H | F | F | H |
| E1-8.19$^{B'}$ | Z8$^{B'}$, R$^{aB'}$ is H | F | H | F |
| E1-8.20$^{B'}$ | Z8$^{B'}$, R$^{aB'}$ is H | F | H | Cl |
| E1-8.21$^{B'}$ | Z8$^{B'}$, R$^{aB'}$ is H | F | H | $CH_3$ |
| E1-8.22$^{B'}$ | Z8$^{B'}$, R$^{aB'}$ is H | Cl | H | $CH_3$ |
| E1-8.23$^{B'}$ | Z8$^{B'}$, R$^{aB'}$ is H | $SCH_3$ | H | H |
| E1-8.24$^{B'}$ | Z8$^{B'}$, R$^{aB'}$ is H | $SO_2CH_3$ | H | H |
| E1-8.25$^{B'}$ | Z8$^{B'}$, R$^{aB'}$ is H | ethynyl | H | H |
| E1-9.1$^{B'}$ | Z9$^{B'}$ | H | H | H |
| E1-9.2$^{B'}$ | Z9$^{B'}$ | $CH_3$ | H | H |
| E1-9.3$^{B'}$ | Z9$^{B'}$ | Cl | H | H |
| E1-9.4$^{B'}$ | Z9$^{B'}$ | F | H | H |

TABLE 13-continued

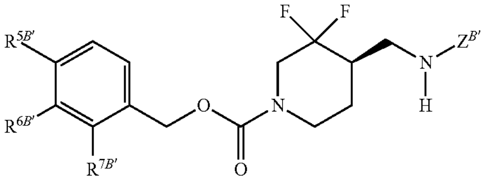

| compound | $Z^{B'}$ | $R^{5B'}$ | $R^{6B'}$ | $R^{7B'}$ |
|---|---|---|---|---|
| E1-9.5$^{B'}$ | Z9$^{B'}$ | $CH_2CH_3$ | H | H |
| E1-9.6$^{B'}$ | Z9$^{B'}$ | $CF_2H$ | H | H |
| E1-9.7$^{B'}$ | Z9$^{B'}$ | $CH_2F$ | H | H |
| E1-9.8$^{B'}$ | Z9$^{B'}$ | $CF_3$ | H | H |
| E1-9.9$^{B'}$ | Z9$^{B'}$ | $CF_2CH_3$ | H | H |
| E1-9.10$^{B'}$ | Z9$^{B'}$ | $CH_2CF_3$ | H | H |
| E1-9.11$^{B'}$ | Z9$^{B'}$ | cyclopropyl | H | H |
| E1-9.12$^{B'}$ | Z9$^{B'}$ | $OCF_3$ | H | H |
| E1-9.13$^{B'}$ | Z9$^{B'}$ | $OCF_2H$ | H | H |
| E1-9.14$^{B'}$ | Z9$^{B'}$ | Cl | H | F |
| E1-9.15$^{B'}$ | Z9$^{B'}$ | $CH_3$ | H | F |
| E1-9.16$^{B'}$ | Z9$^{B'}$ | $CH_3$ | F | H |
| E1-9.17$^{B'}$ | Z9$^{B'}$ | Cl | F | H |
| E1-9.18$^{B'}$ | Z9$^{B'}$ | F | F | H |
| E1-9.19$^{B'}$ | Z9$^{B'}$ | F | H | F |
| E1-9.20$^{B'}$ | Z9$^{B'}$ | F | H | Cl |
| E1-9.21$^{B'}$ | Z9$^{B'}$ | F | H | $CH_3$ |
| E1-9.22$^{B'}$ | Z9$^{B'}$ | Cl | H | $CH_3$ |
| E1-9.23$^{B'}$ | Z9$^{B'}$ | $SCH_3$ | H | H |
| E1-9.24$^{B'}$ | Z9$^{B'}$ | $SO_2CH_3$ | H | H |
| E1-9.25$^{B'}$ | Z9$^{B'}$ | ethynyl | H | H |
| E1-10.1$^{B'}$ | Z10$^{B'}$ | H | H | H |
| E1-10.2$^{B'}$ | Z10$^{B'}$ | $CH_3$ | H | H |
| E1-10.3$^{B'}$ | Z10$^{B'}$ | Cl | H | H |
| E1-10.4$^{B'}$ | Z10$^{B'}$ | F | H | H |
| E1-10.5$^{B'}$ | Z10$^{B'}$ | $CH_2CH_3$ | H | H |
| E1-10.6$^{B'}$ | Z10$^{B'}$ | $CF_2H$ | H | H |
| E1-10.7$^{B'}$ | Z10$^{B'}$ | $CH_2F$ | H | H |
| E1-10.8$^{B'}$ | Z10$^{B'}$ | $CF_3$ | H | H |
| E1-10.9$^{B'}$ | Z10$^{B'}$ | $CF_2CH_3$ | H | H |
| E1-10.10$^{B'}$ | Z10$^{B'}$ | $CH_2CF_3$ | H | H |
| E1-10.11$^{B'}$ | Z10$^{B'}$ | cyclopropyl | H | H |
| E1-10.12$^{B'}$ | Z10$^{B'}$ | $OCF_3$ | H | H |
| E1-10.13$^{B'}$ | Z10$^{B'}$ | $OCF_2H$ | H | H |
| E1-10.14$^{B'}$ | Z10$^{B'}$ | Cl | H | F |
| E1-10.15$^{B'}$ | Z10$^{B'}$ | $CH_3$ | H | F |
| E1-10.16$^{B'}$ | Z10$^{B'}$ | $CH_3$ | F | H |
| E1-10.17$^{B'}$ | Z10$^{B'}$ | Cl | F | H |
| E1-10.18$^{B'}$ | Z10$^{B'}$ | F | F | H |
| E1-10.19$^{B'}$ | Z10$^{B'}$ | F | H | F |
| E1-10.20$^{B'}$ | Z10$^{B'}$ | F | H | Cl |
| E1-10.21$^{B'}$ | Z10$^{B'}$ | F | H | $CH_3$ |
| E1-10.22$^{B'}$ | Z10$^{B'}$ | Cl | H | $CH_3$ |
| E1-10.23$^{B'}$ | Z10$^{B'}$ | $SCH_3$ | H | H |
| E1-10.24$^{B'}$ | Z10$^{B'}$ | $SO_2CH_3$ | H | H |
| E1-10.25$^{B'}$ | Z10$^{B'}$ | ethynyl | H | H |
| E1-11.1$^{B'}$ | Z11$^{B'}$, R$^{aB'}$ is H | H | H | H |
| E1-11.2$^{B'}$ | Z11$^{B'}$, R$^{aB'}$ is H | $CH_3$ | H | H |
| E1-11.3$^{B'}$ | Z11$^{B'}$, R$^{aB'}$ is H | Cl | H | H |
| E1-11.4$^{B'}$ | Z11$^{B'}$, R$^{aB'}$ is H | F | H | H |
| E1-11.5$^{B'}$ | Z11$^{B'}$, R$^{aB'}$ is H | $CH_2CH_3$ | H | H |
| E1-11.6$^{B'}$ | Z11$^{B'}$, R$^{aB'}$ is H | $CF_2H$ | H | H |
| E1-11.7$^{B'}$ | Z11$^{B'}$, R$^{aB'}$ is H | $CH_2F$ | H | H |
| E1-11.8$^{B'}$ | Z11$^{B'}$, R$^{aB'}$ is H | $CF_3$ | H | H |
| E1-11.9$^{B'}$ | Z11$^{B'}$, R$^{aB'}$ is H | $CF_2CH_3$ | H | H |
| E1-11.10$^{B'}$ | Z11$^{B'}$, R$^{aB'}$ is H | $CH_2CF_3$ | H | H |
| E1-11.11$^{B'}$ | Z11$^{B'}$, R$^{aB'}$ is H | cyclopropyl | H | H |
| E1-11.12$^{B'}$ | Z11$^{B'}$, R$^{aB'}$ is H | $OCF_3$ | H | H |
| E1-11.13$^{B'}$ | Z11$^{B'}$, R$^{aB'}$ is H | $OCF_2H$ | H | H |
| E1-11.14$^{B'}$ | Z11$^{B'}$, R$^{aB'}$ is H | Cl | H | F |
| E1-11.15$^{B'}$ | Z11$^{B'}$, R$^{aB'}$ is H | $CH_3$ | H | F |
| E1-11.16$^{B'}$ | Z11$^{B'}$, R$^{aB'}$ is H | $CH_3$ | F | H |
| E1-11.17$^{B'}$ | Z11$^{B'}$, R$^{aB'}$ is H | Cl | F | H |
| E1-11.18$^{B'}$ | Z11$^{B'}$, R$^{aB'}$ is H | F | F | H |
| E1-11.19$^{B'}$ | Z11$^{B'}$, R$^{aB'}$ is H | F | H | F |
| E1-11.20$^{B'}$ | Z11$^{B'}$, R$^{aB'}$ is H | F | H | Cl |
| E1-11.21$^{B'}$ | Z11$^{B'}$, R$^{aB'}$ is H | F | H | $CH_3$ |
| E1-11.22$^{B'}$ | Z11$^{B'}$, R$^{aB'}$ is H | Cl | H | $CH_3$ |

TABLE 13-continued

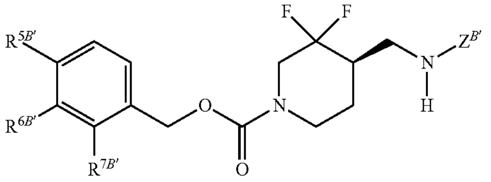

| compound | $Z^{B'}$ | $R^{5B'}$ | $R^{6B'}$ | $R^{7B'}$ |
|---|---|---|---|---|
| E1-11.23$^{B'}$ | Z11$^{B'}$, R$^{aB'}$ is H | $SCH_3$ | H | H |
| E1-11.24$^{B'}$ | Z11$^{B'}$, R$^{aB'}$ is H | $SO_2CH_3$ | H | H |
| E1-11.25$^{B'}$ | Z11$^{B'}$, R$^{aB'}$ is H | ethynyl | H | H |
| E1-12.1$^{B'}$ | Z12$^{B'}$ | H | H | H |
| E1-12.2$^{B'}$ | Z12$^{B'}$ | $CH_3$ | H | H |
| E1-12.3$^{B'}$ | Z12$^{B'}$ | Cl | H | H |
| E1-12.4$^{B'}$ | Z12$^{B'}$ | F | H | H |
| E1-12.5$^{B'}$ | Z12$^{B'}$ | $CH_2CH_3$ | H | H |
| E1-12.6$^{B'}$ | Z12$^{B'}$ | $CF_2H$ | H | H |
| E1-12.7$^{B'}$ | Z12$^{B'}$ | $CH_2F$ | H | H |
| E1-12.8$^{B'}$ | Z12$^{B'}$ | $CF_3$ | H | H |
| E1-12.9$^{B'}$ | Z12$^{B'}$ | $CF_2CH_3$ | H | H |
| E1-12.10$^{B'}$ | Z12$^{B'}$ | $CH_2CF_3$ | H | H |
| E1-12.11$^{B'}$ | Z12$^{B'}$ | cyclopropyl | H | H |
| E1-12.12$^{B'}$ | Z12$^{B'}$ | $OCF_3$ | H | H |
| E1-12.13$^{B'}$ | Z12$^{B'}$ | $OCF_2H$ | H | H |
| E1-12.14$^{B'}$ | Z12$^{B'}$ | Cl | H | F |
| E1-12.15$^{B'}$ | Z12$^{B'}$ | $CH_3$ | H | F |
| E1-12.16$^{B'}$ | Z12$^{B'}$ | $CH_3$ | F | H |
| E1-12.17$^{B'}$ | Z12$^{B'}$ | Cl | F | H |
| E1-12.18$^{B'}$ | Z12$^{B'}$ | F | F | H |
| E1-12.19$^{B'}$ | Z12$^{B'}$ | F | H | F |
| E1-12.20$^{B'}$ | Z12$^{B'}$ | F | H | Cl |
| E1-12.21$^{B'}$ | Z12$^{B'}$ | F | H | $CH_3$ |
| E1-12.22$^{B'}$ | Z12$^{B'}$ | Cl | H | $CH_3$ |
| E1-12.23$^{B'}$ | Z12$^{B'}$ | $SCH_3$ | H | H |
| E1-12.24$^{B'}$ | Z12$^{B'}$ | $SO_2CH_3$ | H | H |
| E1-12.25$^{B'}$ | Z12$^{B'}$ | ethynyl | H | H |
| E1-13.1$^{B'}$ | Z13$^{B'}$, R$^{aB'}$ is H | H | H | H |
| E1-13.2$^{B'}$ | Z13$^{B'}$, R$^{aB'}$ is H | $CH_3$ | H | H |
| E1-13.3$^{B'}$ | Z13$^{B'}$, R$^{aB'}$ is H | Cl | H | H |
| E1-13.4$^{B'}$ | Z13$^{B'}$, R$^{aB'}$ is H | F | H | H |
| E1-13.5$^{B'}$ | Z13$^{B'}$, R$^{aB'}$ is H | $CH_2CH_3$ | H | H |
| E1-13.6$^{B'}$ | Z13$^{B'}$, R$^{aB'}$ is H | $CF_2H$ | H | H |
| E1-13.7$^{B'}$ | Z13$^{B'}$, R$^{aB'}$ is H | $CH_2F$ | H | H |
| E1-13.8$^{B'}$ | Z13$^{B'}$, R$^{aB'}$ is H | $CF_3$ | H | H |
| E1-13.9$^{B'}$ | Z13$^{B'}$, R$^{aB'}$ is H | $CF_2CH_3$ | H | H |
| E1-13.10$^{B'}$ | Z13$^{B'}$, R$^{aB'}$ is H | $CH_2CF_3$ | H | H |
| E1-13.11$^{B'}$ | Z13$^{B'}$, R$^{aB'}$ is H | cyclopropyl | H | H |
| E1-13.12$^{B'}$ | Z13$^{B'}$, R$^{aB'}$ is H | $OCF_3$ | H | H |
| E1-13.13$^{B'}$ | Z13$^{B'}$, R$^{aB'}$ is H | $OCF_2H$ | H | H |
| E1-13.14$^{B'}$ | Z13$^{B'}$, R$^{aB'}$ is H | Cl | H | F |
| E1-13.15$^{B'}$ | Z13$^{B'}$, R$^{aB'}$ is H | $CH_3$ | H | F |
| E1-13.16$^{B'}$ | Z13$^{B'}$, R$^{aB'}$ is H | $CH_3$ | F | H |
| E1-13.17$^{B'}$ | Z13$^{B'}$, R$^{aB'}$ is H | Cl | F | H |
| E1-13.18$^{B'}$ | Z13$^{B'}$, R$^{aB'}$ is H | F | F | H |
| E1-13.19$^{B'}$ | Z13$^{B'}$, R$^{aB'}$ is H | F | H | F |
| E1-13.20$^{B'}$ | Z13$^{B'}$, R$^{aB'}$ is H | F | H | Cl |
| E1-13.21$^{B'}$ | Z13$^{B'}$, R$^{aB'}$ is H | F | H | $CH_3$ |
| E1-13.22$^{B'}$ | Z13$^{B'}$, R$^{aB'}$ is H | Cl | H | $CH_3$ |
| E1-13.23$^{B'}$ | Z13$^{B'}$, R$^{aB'}$ is H | $SCH_3$ | H | H |
| E1-13.24$^{B'}$ | Z13$^{B'}$, R$^{aB'}$ is H | $SO_2CH_3$ | H | H |
| E1-13.25$^{B'}$ | Z13$^{B'}$, R$^{aB'}$ is H | ethynyl | H | H |
| E1-14.1$^{B'}$ | Z14$^{B'}$, R$^{aB'}$ is H | H | H | H |
| E1-14.2$^{B'}$ | Z14$^{B'}$, R$^{aB'}$ is H | $CH_3$ | H | H |
| E1-14.3$^{B'}$ | Z14$^{B'}$, R$^{aB'}$ is H | Cl | H | H |
| E1-14.4$^{B'}$ | Z14$^{B'}$, R$^{aB'}$ is H | F | H | H |
| E1-14.5$^{B'}$ | Z14$^{B'}$, R$^{aB'}$ is H | $CH_2CH_3$ | H | H |
| E1-14.6$^{B'}$ | Z14$^{B'}$, R$^{aB'}$ is H | $CF_2H$ | H | H |
| E1-14.7$^{B'}$ | Z14$^{B'}$, R$^{aB'}$ is H | $CH_2F$ | H | H |
| E1-14.8$^{B'}$ | Z14$^{B'}$, R$^{aB'}$ is H | $CF_3$ | H | H |
| E1-14.9$^{B'}$ | Z14$^{B'}$, R$^{aB'}$ is H | $CF_2CH_3$ | H | H |
| E1-14.10$^{B'}$ | Z14$^{B'}$, R$^{aB'}$ is H | $CH_2CF_3$ | H | H |
| E1-14.11$^{B'}$ | Z14$^{B'}$, R$^{aB'}$ is H | cyclopropyl | H | H |
| E1-14.12$^{B'}$ | Z14$^{B'}$, R$^{aB'}$ is H | $OCF_3$ | H | H |
| E1-14.13$^{B'}$ | Z14$^{B'}$, R$^{aB'}$ is H | $OCF_2H$ | H | H |
| E1-14.14$^{B'}$ | Z14$^{B'}$, R$^{aB'}$ is H | Cl | H | F |
| E1-14.15$^{B'}$ | Z14$^{B'}$, R$^{aB'}$ is H | $CH_3$ | H | F |

TABLE 13-continued

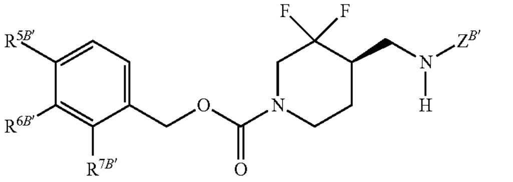

| compound | Z$^{B'}$ | R$^{5B'}$ | R$^{6B'}$ | R$^{7B'}$ |
|---|---|---|---|---|
| E1-14.16$^{B'}$ | Z14$^{B'}$, R$^{aB'}$ is H | $CH_3$ | F | H |
| E1-14.17$^{B'}$ | Z14$^{B'}$, R$^{aB'}$ is H | Cl | F | H |
| E1-14.18$^{B'}$ | Z14$^{B'}$, R$^{aB'}$ is H | F | F | H |
| E1-14.19$^{B'}$ | Z14$^{B'}$, R$^{aB'}$ is H | F | H | F |
| E1-14.20$^{B'}$ | Z14$^{B'}$, R$^{aB'}$ is H | F | H | Cl |
| E1-14.21$^{B'}$ | Z14$^{B'}$, R$^{aB'}$ is H | F | H | $CH_3$ |
| E1-14.22$^{B'}$ | Z14$^{B'}$, R$^{aB'}$ is H | Cl | H | $CH_3$ |
| E1-14.23$^{B'}$ | Z14$^{B'}$, R$^{aB'}$ is H | $SCH_3$ | H | H |
| E1-14.24$^{B'}$ | Z14$^{B'}$, R$^{aB'}$ is H | $SO_2CH_3$ | H | H |
| E1-14.25$^{B'}$ | Z14$^{B'}$, R$^{aB'}$ is H | ethynyl | H | H |
| E1-15.1$^{B'}$ | Z15$^{B'}$, R$^{aB'}$ is H | H | H | H |
| E1-15.2$^{B'}$ | Z15$^{B'}$, R$^{aB'}$ is H | $CH_3$ | H | H |
| E1-15.3$^{B'}$ | Z15$^{B'}$, R$^{aB'}$ is H | Cl | H | H |
| E1-15.4$^{B'}$ | Z15$^{B'}$, R$^{aB'}$ is H | F | H | H |
| E1-15.5$^{B'}$ | Z15$^{B'}$, R$^{aB'}$ is H | $CH_2CH_3$ | H | H |
| E1-15.6$^{B'}$ | Z15$^{B'}$, R$^{aB'}$ is H | $CF_2H$ | H | H |
| E1-15.7$^{B'}$ | Z15$^{B'}$, R$^{aB'}$ is H | $CH_2F$ | H | H |
| E1-15.8$^{B'}$ | Z15$^{B'}$, R$^{aB'}$ is H | $CF_3$ | H | H |
| E1-15.9$^{B'}$ | Z15$^{B'}$, R$^{aB'}$ is H | $CF_2CH_3$ | H | H |
| E1-15.10$^{B'}$ | Z15$^{B'}$, R$^{aB'}$ is H | $CH_2CF_3$ | H | H |
| E1-15.11$^{B'}$ | Z15$^{B'}$, R$^{aB'}$ is H | cyclopropyl | H | H |
| E1-15.12$^{B'}$ | Z15$^{B'}$, R$^{aB'}$ is H | $OCF_3$ | H | H |
| E1-15.13$^{B'}$ | Z15$^{B'}$, R$^{aB'}$ is H | $OCF_2H$ | H | H |
| E1-15.14$^{B'}$ | Z15$^{B'}$, R$^{aB'}$ is H | Cl | H | F |
| E1-15.15$^{B'}$ | Z15$^{B'}$, R$^{aB'}$ is H | $CH_3$ | H | F |
| E1-15.16$^{B'}$ | Z15$^{B'}$, R$^{aB'}$ is H | $CH_3$ | F | H |
| E1-15.17$^{B'}$ | Z15$^{B'}$, R$^{aB'}$ is H | Cl | F | H |
| E1-15.18$^{B'}$ | Z15$^{B'}$, R$^{aB'}$ is H | F | F | H |
| E1-15.19$^{B'}$ | Z15$^{B'}$, R$^{aB'}$ is H | F | H | F |
| E1-15.20$^{B'}$ | Z15$^{B'}$, R$^{aB'}$ is H | F | H | Cl |
| E1-15.21$^{B'}$ | Z15$^{B'}$, R$^{aB'}$ is H | F | H | $CH_3$ |
| E1-15.22$^{B'}$ | Z15$^{B'}$, R$^{aB'}$ is H | Cl | H | $CH_3$ |
| E1-15.23$^{B'}$ | Z15$^{B'}$, R$^{aB'}$ is H | $SCH_3$ | H | H |
| E1-15.24$^{B'}$ | Z15$^{B'}$, R$^{aB'}$ is H | $SO_2CH_3$ | H | H |
| E1-15.25$^{B'}$ | Z15$^{B'}$, R$^{aB'}$ is H | ethynyl | H | H |
| E1-16.1$^{B'}$ | Z16$^{B'}$, R$^{aB'}$ is H | H | H | H |
| E1-16.2$^{B'}$ | Z16$^{B'}$, R$^{aB'}$ is H | $CH_3$ | H | H |
| E1-16.3$^{B'}$ | Z16$^{B'}$, R$^{aB'}$ is H | Cl | H | H |
| E1-16.4$^{B'}$ | Z16$^{B'}$, R$^{aB'}$ is H | F | H | H |
| E1-16.5$^{B'}$ | Z16$^{B'}$, R$^{aB'}$ is H | $CH_2CH_3$ | H | H |
| E1-16.6$^{B'}$ | Z16$^{B'}$, R$^{aB'}$ is H | $CF_2H$ | H | H |
| E1-16.7$^{B'}$ | Z16$^{B'}$, R$^{aB'}$ is H | $CH_2F$ | H | H |
| E1-16.8$^{B'}$ | Z16$^{B'}$, R$^{aB'}$ is H | $CF_3$ | H | H |
| E1-16.9$^{B'}$ | Z16$^{B'}$, R$^{aB'}$ is H | $CF_2CH_3$ | H | H |
| E1-16.10$^{B'}$ | Z16$^{B'}$, R$^{aB'}$ is H | $CH_2CF_3$ | H | H |
| E1-16.11$^{B'}$ | Z16$^{B'}$, R$^{aB'}$ is H | cyclopropyl | H | H |
| E1-16.12$^{B'}$ | Z16$^{B'}$, R$^{aB'}$ is H | $OCF_3$ | H | H |
| E1-16.13$^{B'}$ | Z16$^{B'}$, R$^{aB'}$ is H | $OCF_2H$ | H | H |
| E1-16.14$^{B'}$ | Z16$^{B'}$, R$^{aB'}$ is H | Cl | H | F |
| E1-16.15$^{B'}$ | Z16$^{B'}$, R$^{aB'}$ is H | $CH_3$ | H | F |
| E1-16.16$^{B'}$ | Z16$^{B'}$, R$^{aB'}$ is H | $CH_3$ | F | H |
| E1-16.17$^{B'}$ | Z16$^{B'}$, R$^{aB'}$ is H | Cl | F | H |
| E1-16.18$^{B'}$ | Z16$^{B'}$, R$^{aB'}$ is H | F | F | H |
| E1-16.19$^{B'}$ | Z16$^{B'}$, R$^{aB'}$ is H | F | H | F |
| E1-16.20$^{B'}$ | Z16$^{B'}$, R$^{aB'}$ is H | F | H | Cl |
| E1-16.21$^{B'}$ | Z16$^{B'}$, R$^{aB'}$ is H | F | H | $CH_3$ |
| E1-16.22$^{B'}$ | Z16$^{B'}$, R$^{aB'}$ is H | Cl | H | $CH_3$ |
| E1-16.23$^{B'}$ | Z16$^{B'}$, R$^{aB'}$ is H | $SCH_3$ | H | H |
| E1-16.24$^{B'}$ | Z16$^{B'}$, R$^{aB'}$ is H | $SO_2CH_3$ | H | H |
| E1-16.25$^{B'}$ | Z16$^{B'}$, R$^{aB'}$ is H | ethynyl | H | H |
| E1-17.1$^{B'}$ | Z17$^{B'}$ | H | H | H |
| E1-17.2$^{B'}$ | Z17$^{B'}$ | $CH_3$ | H | H |
| E1-17.3$^{B'}$ | Z17$^{B'}$ | Cl | H | H |
| E1-17.4$^{B'}$ | Z17$^{B'}$ | F | H | H |
| E1-17.5$^{B'}$ | Z17$^{B'}$ | $CH_2CH_3$ | H | H |
| E1-17.6$^{B'}$ | Z17$^{B'}$ | $CF_2H$ | H | H |
| E1-17.7$^{B'}$ | Z17$^{B'}$ | $CH_2F$ | H | H |
| E1-17.8$^{B'}$ | Z17$^{B'}$ | $CF_3$ | H | H |

TABLE 13-continued

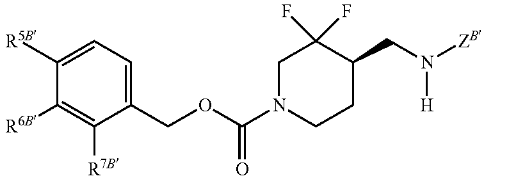

| compound | Z$^{B'}$ | R$^{5B'}$ | R$^{6B'}$ | R$^{7B'}$ |
|---|---|---|---|---|
| E1-17.9$^{B'}$ | Z17$^{B'}$ | $CF_2CH_3$ | H | H |
| E1-17.10$^{B'}$ | Z17$^{B'}$ | $CH_2CF_3$ | H | H |
| E1-17.11$^{B'}$ | Z17$^{B'}$ | cyclopropyl | H | H |
| E1-17.12$^{B'}$ | Z17$^{B'}$ | $OCF_3$ | H | H |
| E1-17.13$^{B'}$ | Z17$^{B'}$ | $OCF_2H$ | H | H |
| E1-17.14$^{B'}$ | Z17$^{B'}$ | Cl | H | F |
| E1-17.15$^{B'}$ | Z17$^{B'}$ | $CH_3$ | H | F |
| E1-17.16$^{B'}$ | Z17$^{B'}$ | $CH_3$ | F | H |
| E1-17.17$^{B'}$ | Z17$^{B'}$ | Cl | F | H |
| E1-17.18$^{B'}$ | Z17$^{B'}$ | F | F | H |
| E1-17.19$^{B'}$ | Z17$^{B'}$ | F | H | F |
| E1-17.20$^{B'}$ | Z17$^{B'}$ | F | H | Cl |
| E1-17.21$^{B'}$ | Z17$^{B'}$ | F | H | $CH_3$ |
| E1-17.22$^{B'}$ | Z17$^{B'}$ | Cl | H | $CH_3$ |
| E1-17.23$^{B'}$ | Z17$^{B'}$ | $SCH_3$ | H | H |
| E1-17.24$^{B'}$ | Z17$^{B'}$ | $SO_2CH_3$ | H | H |
| E1-17.25$^{B'}$ | Z17$^{B'}$ | ethynyl | H | H |
| E1-18.1$^{B'}$ | Z18$^{B'}$ | H | H | H |
| E1-18.2$^{B'}$ | Z18$^{B'}$ | $CH_3$ | H | H |
| E1-18.3$^{B'}$ | Z18$^{B'}$ | Cl | H | H |
| E1-18.4$^{B'}$ | Z18$^{B'}$ | F | H | H |
| E1-18.5$^{B'}$ | Z18$^{B'}$ | $CH_2CH_3$ | H | H |
| E1-18.6$^{B'}$ | Z18$^{B'}$ | $CF_2H$ | H | H |
| E1-18.7$^{B'}$ | Z18$^{B'}$ | $CH_2F$ | H | H |
| E1-18.8$^{B'}$ | Z18$^{B'}$ | $CF_3$ | H | H |
| E1-18.9$^{B'}$ | Z18$^{B'}$ | $CF_2CH_3$ | H | H |
| E1-18.10$^{B'}$ | Z18$^{B'}$ | $CH_2CF_3$ | H | H |
| E1-18.11$^{B'}$ | Z18$^{B'}$ | cyclopropyl | H | H |
| E1-18.12$^{B'}$ | Z18$^{B'}$ | $OCF_3$ | H | H |
| E1-18.13$^{B'}$ | Z18$^{B'}$ | $OCF_2H$ | H | H |
| E1-18.14$^{B'}$ | Z18$^{B'}$ | Cl | H | F |
| E1-18.15$^{B'}$ | Z18$^{B'}$ | $CH_3$ | H | F |
| E1-18.16$^{B'}$ | Z18$^{B'}$ | $CH_3$ | F | H |
| E1-18.17$^{B'}$ | Z18$^{B'}$ | Cl | F | H |
| E1-18.18$^{B'}$ | Z18$^{B'}$ | F | F | H |
| E1-18.19$^{B'}$ | Z18$^{B'}$ | F | H | F |
| E1-18.20$^{B'}$ | Z18$^{B'}$ | F | H | Cl |
| E1-18.21$^{B'}$ | Z18$^{B'}$ | F | H | $CH_3$ |
| E1-18.22$^{B'}$ | Z18$^{B'}$ | Cl | H | $CH_3$ |
| E1-18.23$^{B'}$ | Z18$^{B'}$ | $SCH_3$ | H | H |
| E1-18.24$^{B'}$ | Z18$^{B'}$ | $SO_2CH_3$ | H | H |
| E1-18.25$^{B'}$ | Z18$^{B'}$ | ethynyl | H | H |
| E1-19.1$^{B'}$ | Z19$^{B'}$ | H | H | H |
| E1-19.2$^{B'}$ | Z19$^{B'}$ | $CH_3$ | H | H |
| E1-19.3$^{B'}$ | Z19$^{B'}$ | Cl | H | H |
| E1-19.4$^{B'}$ | Z19$^{B'}$ | F | H | H |
| E1-19.5$^{B'}$ | Z19$^{B'}$ | $CH_2CH_3$ | H | H |
| E1-19.6$^{B'}$ | Z19$^{B'}$ | $CF_2H$ | H | H |
| E1-19.7$^{B'}$ | Z19$^{B'}$ | $CH_2F$ | H | H |
| E1-19.8$^{B'}$ | Z19$^{B'}$ | $CF_3$ | H | H |
| E1-19.9$^{B'}$ | Z19$^{B'}$ | $CF_2CH_3$ | H | H |
| E1-19.10$^{B'}$ | Z19$^{B'}$ | $CH_2CF_3$ | H | H |
| E1-19.11$^{B'}$ | Z19$^{B'}$ | cyclopropyl | H | H |
| E1-19.12$^{B'}$ | Z19$^{B'}$ | $OCF_3$ | H | H |
| E1-19.13$^{B'}$ | Z19$^{B'}$ | $OCF_2H$ | H | H |
| E1-19.14$^{B'}$ | Z19$^{B'}$ | Cl | H | F |
| E1-19.15$^{B'}$ | Z19$^{B'}$ | $CH_3$ | H | F |
| E1-19.16$^{B'}$ | Z19$^{B'}$ | $CH_3$ | F | H |
| E1-19.17$^{B'}$ | Z19$^{B'}$ | Cl | F | H |
| E1-19.18$^{B'}$ | Z19$^{B'}$ | F | F | H |
| E1-19.19$^{B'}$ | Z19$^{B'}$ | F | H | F |
| E1-19.20$^{B'}$ | Z19$^{B'}$ | F | H | Cl |
| E1-19.21$^{B'}$ | Z19$^{B'}$ | F | H | $CH_3$ |
| E1-19.22$^{B'}$ | Z19$^{B'}$ | Cl | H | $CH_3$ |
| E1-19.23$^{B'}$ | Z19$^{B'}$ | $SCH_3$ | H | H |
| E1-19.24$^{B'}$ | Z19$^{B'}$ | $SO_2CH_3$ | H | H |
| E1-19.25$^{B'}$ | Z19$^{B'}$ | ethynyl | H | H |
| E1-19.26$^{B'}$ | Z19$^{B'}$ | $CH_3$ | H | H |

TABLE 13-continued

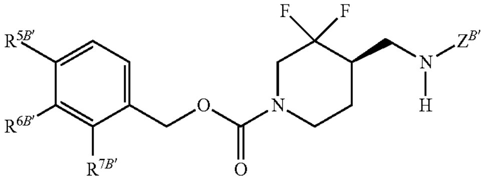

| compound | $Z^{B'}$ | $R^{5B'}$ | $R^{6B'}$ | $R^{7B'}$ |
|---|---|---|---|---|
| E1-20.1$^{B'}$ | Z20$^{B'}$ | H | H | H |
| E1-20.2$^{B'}$ | Z20$^{B'}$ | $CH_3$ | H | H |
| E1-20.3$^{B'}$ | Z20$^{B'}$ | Cl | H | H |
| E1-20.4$^{B'}$ | Z20$^{B'}$ | F | H | H |
| E1-20.5$^{B'}$ | Z20$^{B'}$ | $CH_2CH_3$ | H | H |
| E1-20.6$^{B'}$ | Z20$^{B'}$ | $CF_2H$ | H | H |
| E1-20.7$^{B'}$ | Z20$^{B'}$ | $CH_2F$ | H | H |
| E1-20.8$^{B'}$ | Z20$^{B'}$ | $CF_3$ | H | H |
| E1-20.9$^{B'}$ | Z20$^{B'}$ | $CF_2CH_3$ | H | H |
| E1-20.10$^{B'}$ | Z20$^{B'}$ | $CH_2CF_3$ | H | H |
| E1-20.11$^{B'}$ | Z20$^{B'}$ | cyclopropyl | H | H |
| E1-20.12$^{B'}$ | Z20$^{B'}$ | $OCF_3$ | H | H |
| E1-20.13$^{B'}$ | Z20$^{B'}$ | $OCF_2H$ | H | H |
| E1-20.14$^{B'}$ | Z20$^{B'}$ | Cl | H | F |
| E1-20.15$^{B'}$ | Z20$^{B'}$ | $CH_3$ | H | F |
| E1-20.16$^{B'}$ | Z20$^{B'}$ | $CH_3$ | F | H |
| E1-20.17$^{B'}$ | Z20$^{B'}$ | Cl | F | H |
| E1-20.18$^{B'}$ | Z20$^{B'}$ | F | F | H |
| E1-20.19$^{B'}$ | Z20$^{B'}$ | F | H | F |
| E1-20.20$^{B'}$ | Z20$^{B'}$ | F | H | Cl |
| E1-20.21$^{B'}$ | Z20$^{B'}$ | F | H | $CH_3$ |
| E1-20.22$^{B'}$ | Z20$^{B'}$ | Cl | H | $CH_3$ |
| E1-20.23$^{B'}$ | Z20$^{B'}$ | $SCH_3$ | H | H |
| E1-20.24$^{B'}$ | Z20$^{B'}$ | $SO_2CH_3$ | H | H |
| E1-20.25$^{B'}$ | Z20$^{B'}$ | ethynyl | H | H |
| E1-21.1$^{B'}$ | Z21$^{B'}$ | H | H | H |
| E1-21.2$^{B'}$ | Z21$^{B'}$ | $CH_3$ | H | H |
| E1-21.3$^{B'}$ | Z21$^{B'}$ | Cl | H | H |
| E1-21.4$^{B'}$ | Z21$^{B'}$ | F | H | H |
| E1-21.5$^{B'}$ | Z21$^{B'}$ | $CH_2CH_3$ | H | H |
| E1-21.6$^{B'}$ | Z21$^{B'}$ | $CF_2H$ | H | H |
| E1-21.7$^{B'}$ | Z21$^{B'}$ | $CH_2F$ | H | H |
| E1-21.8$^{B'}$ | Z21$^{B'}$ | $CF_3$ | H | H |
| E1-21.9$^{B'}$ | Z21$^{B'}$ | $CF_2CH_3$ | H | H |
| E1-21.10$^{B'}$ | Z21$^{B'}$ | $CH_2CF_3$ | H | H |
| E1-21.11$^{B'}$ | Z21$^{B'}$ | cyclopropyl | H | H |
| E1-21.12$^{B'}$ | Z21$^{B'}$ | $OCF_3$ | H | H |
| E1-21.13$^{B'}$ | Z21$^{B'}$ | $OCF_2H$ | H | H |
| E1-21.14$^{B'}$ | Z21$^{B'}$ | Cl | H | F |
| E1-21.15$^{B'}$ | Z21$^{B'}$ | $CH_3$ | H | F |
| E1-21.16$^{B'}$ | Z21$^{B'}$ | $CH_3$ | F | H |
| E1-21.17$^{B'}$ | Z21$^{B'}$ | Cl | F | H |
| E1-21.18$^{B'}$ | Z21$^{B'}$ | F | F | H |
| E1-21.19$^{B'}$ | Z21$^{B'}$ | F | H | F |
| E1-21.20$^{B'}$ | Z21$^{B'}$ | F | H | Cl |
| E1-21.21$^{B'}$ | Z21$^{B'}$ | F | H | $CH_3$ |
| E1-21.22$^{B'}$ | Z21$^{B'}$ | Cl | H | $CH_3$ |
| E1-21.23$^{B'}$ | Z21$^{B'}$ | $SCH_3$ | H | H |
| E1-21.24$^{B'}$ | Z21$^{B'}$ | $SO_2CH_3$ | H | H |
| E1-21.25$^{B'}$ | Z21$^{B'}$ | ethynyl | H | H |
| E1-21.26$^{B'}$ | 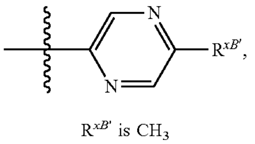 $R^{xB'}$ is $CH_3$ | $CH_3$ | H | H |
| E1-21.27$^{B'}$ | 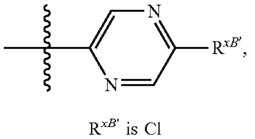 $R^{xB'}$ is Cl | $CH_3$ | H | H |

TABLE 13-continued

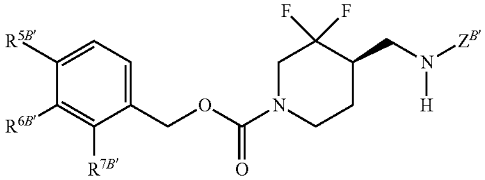

| compound | $Z^{B'}$ | $R^{5B'}$ | $R^{6B'}$ | $R^{7B'}$ |
|---|---|---|---|---|
| E1-21.28$^{B'}$ | 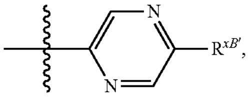 $R^{xB'}$ is F | $CH_3$ | H | H |
| E1-21.29$^{B'}$ | 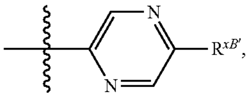 $R^{xB'}$ is $CF_3$ | $CH_3$ | H | H |
| E1-21.30$^{B'}$ | 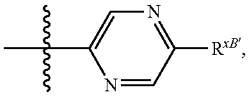 $R^{xB'}$ is CN | $CH_3$ | H | H |
| E1-21.31$^{B'}$ | 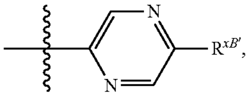 $R^{xB'}$ is $CH_3$ | H | H | H |
| E1-21.32$^{B'}$ | 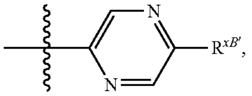 $R^{xB'}$ is $CH_3$ | $CH_3$ | H | H |
| E1-21.33$^{B'}$ | 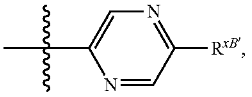 $R^{xB'}$ is $CH_3$ | Cl | H | H |
| E1-21.34$^{B'}$ | 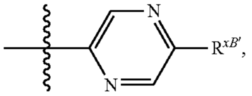 $R^{xB'}$ is $CH_3$ | F | H | H |
| E1-21.35$^{B'}$ | 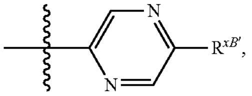 $R^{xB'}$ is $CH_3$ | $CH_2CH_3$ | H | H |
| E1-21.36$^{B'}$ | 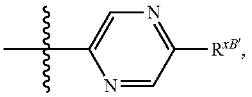 $R^{xB'}$ is $CH_3$ | $CF_2H$ | H | H |
| E1-22.1$^{B'}$ | Z22$^{B'}$ | H | H | H |
| E1-22.2$^{B'}$ | Z22$^{B'}$ | $CH_3$ | H | H |
| E1-22.3$^{B'}$ | Z22$^{B'}$ | Cl | H | H |

TABLE 13-continued

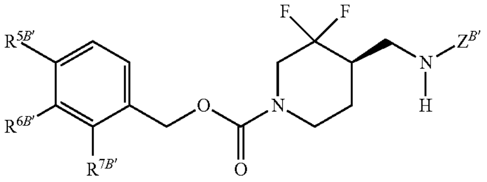

| compound | $Z^{B'}$ | $R^{5B'}$ | $R^{6B'}$ | $R^{7B'}$ |
|---|---|---|---|---|
| E1-22.4$^{B'}$ | Z22$^{B'}$ | F | H | H |
| E1-22.5$^{B'}$ | Z22$^{B'}$ | $CH_2CH_3$ | H | H |
| E1-22.6$^{B'}$ | Z22$^{B'}$ | $CF_2H$ | H | H |
| E1-22.7$^{B'}$ | Z22$^{B'}$ | $CH_2F$ | H | H |
| E1-22.8$^{B'}$ | Z22$^{B'}$ | $CF_3$ | H | H |
| E1-22.9$^{B'}$ | Z22$^{B'}$ | $CF_2CH_3$ | H | H |
| E1-22.10$^{B'}$ | Z22$^{B'}$ | $CH_2CF_3$ | H | H |
| E1-22.11$^{B'}$ | Z22$^{B'}$ | cyclopropyl | H | H |
| E1-22.12$^{B'}$ | Z22$^{B'}$ | $OCF_3$ | H | H |
| E1-22.13$^{B'}$ | Z22$^{B'}$ | $OCF_2H$ | H | H |
| E1-22.14$^{B'}$ | Z22$^{B'}$ | Cl | H | F |
| E1-22.15$^{B'}$ | Z22$^{B'}$ | $CH_3$ | H | F |
| E1-22.16$^{B'}$ | Z22$^{B'}$ | $CH_3$ | F | H |
| E1-22.17$^{B'}$ | Z22$^{B'}$ | Cl | F | H |
| E1-22.18$^{B'}$ | Z22$^{B'}$ | F | F | H |
| E1-22.19$^{B'}$ | Z22$^{B'}$ | F | H | F |
| E1-22.20$^{B'}$ | Z22$^{B'}$ | F | H | Cl |
| E1-22.21$^{B'}$ | Z22$^{B'}$ | F | H | $CH_3$ |
| E1-22.22$^{B'}$ | Z22$^{B'}$ | Cl | H | $CH_3$ |
| E1-22.23$^{B'}$ | Z22$^{B'}$ | $SCH_3$ | H | H |
| E1-22.24$^{B'}$ | Z22$^{B'}$ | $SO_2CH_3$ | H | H |
| E1-22.25$^{B'}$ | Z22$^{B'}$ | ethynyl | H | H |
| E1-22.26$^{B'}$ | 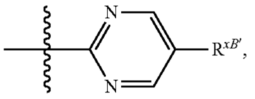 $R^{xB'}$ is $CH_3$ | $CH_3$ | H | H |
| E1-22.27$^{B'}$ | 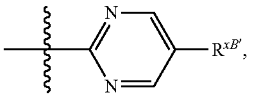 $R^{xB'}$ is Cl | $CH_3$ | H | H |
| E1-22.28$^{B'}$ | 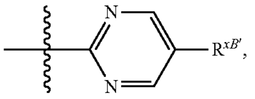 $R^{xB'}$ is F | $CH_3$ | H | H |
| E1-22.29$^{B'}$ | 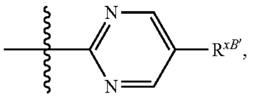 $R^{xB'}$ is $CF_3$ | $CH_3$ | H | H |
| E1-22.30$^{B'}$ | 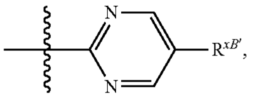 $R^{xB'}$ is CN | $CH_3$ | H | H |
| E1-23.1$^{B'}$ | Z23$^{B'}$ | H | H | H |
| E1-23.2$^{B'}$ | Z23$^{B'}$ | $CH_3$ | H | H |
| E1-23.3$^{B'}$ | Z23$^{B'}$ | Cl | H | H |
| E1-23.4$^{B'}$ | Z23$^{B'}$ | F | H | H |
| E1-23.5$^{B'}$ | Z23$^{B'}$ | $CH_2CH_3$ | H | H |
| E1-23.6$^{B'}$ | Z23$^{B'}$ | $CF_2H$ | H | H |
| E1-23.7$^{B'}$ | Z23$^{B'}$ | $CH_2F$ | H | H |
| E1-23.8$^{B'}$ | Z23$^{B'}$ | $CF_3$ | H | H |
| E1-23.9$^{B'}$ | Z23$^{B'}$ | $CF_2CH_3$ | H | H |

TABLE 13-continued

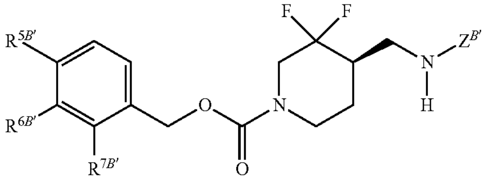

| compound | $Z^{B'}$ | $R^{5B'}$ | $R^{6B'}$ | $R^{7B'}$ |
|---|---|---|---|---|
| E1-23.10$^{B'}$ | Z23$^{B'}$ | $CH_2CF_3$ | H | H |
| E1-23.11$^{B'}$ | Z23$^{B'}$ | cyclopropyl | H | H |
| E1-23.12$^{B'}$ | Z23$^{B'}$ | $OCF_3$ | H | H |
| E1-23.13$^{B'}$ | Z23$^{B'}$ | $OCF_2H$ | H | H |
| E1-23.14$^{B'}$ | Z23$^{B'}$ | Cl | H | F |
| E1-23.15$^{B'}$ | Z23$^{B'}$ | $CH_3$ | H | F |
| E1-23.16$^{B'}$ | Z23$^{B'}$ | $CH_3$ | F | H |
| E1-23.17$^{B'}$ | Z23$^{B'}$ | Cl | F | H |
| E1-23.18$^{B'}$ | Z23$^{B'}$ | F | F | H |
| E1-23.19$^{B'}$ | Z23$^{B'}$ | F | H | F |
| E1-23.20$^{B'}$ | Z23$^{B'}$ | F | H | Cl |
| E1-23.21$^{B'}$ | Z23$^{B'}$ | F | H | $CH_3$ |
| E1-23.22$^{B'}$ | Z23$^{B'}$ | Cl | H | $CH_3$ |
| E1-23.23$^{B'}$ | Z23$^{B'}$ | $SCH_3$ | H | H |
| E1-23.24$^{B'}$ | Z23$^{B'}$ | $SO_2CH_3$ | H | H |
| E1-23.25$^{B'}$ | Z23$^{B'}$ | ethynyl | H | H |
| E1-23.26$^{B'}$ | 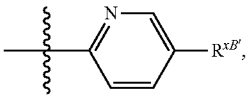 $R^{xB'}$ is $CH_3$ | $CH_3$ | H | H |
| E1-23.27$^{B'}$ | 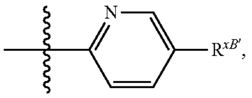 $R^{xB'}$ is Cl | $CH_3$ | H | H |
| E1-23.28$^{B'}$ | 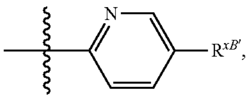 $R^{xB'}$ is F | $CH_3$ | H | H |
| E1-23.29$^{B'}$ | 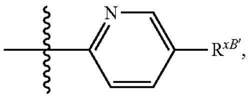 $R^{xB'}$ is $CF_3$ | $CH_3$ | H | H |
| E1-23.30$^{B'}$ | 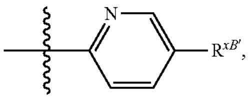 $R^{xB'}$ is CN | $CH_3$ | H | H |
| E1-23.31$^{B'}$ | 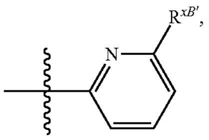 $R^{xB'}$ is $CH_3$ | H | H | H |

TABLE 13-continued

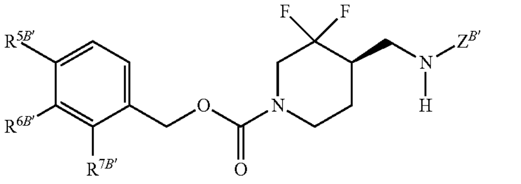

| compound | $Z^{B'}$ | $R^{5B'}$ | $R^{6B'}$ | $R^{7B'}$ |
|---|---|---|---|---|
| E1-23.32$^{B'}$ | 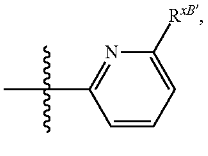 $R^{xB'}$ is $CH_3$ | $CH_3$ | H | H |
| E1-23.33$^{B'}$ | 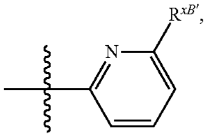 $R^{xB'}$ is $CH_3$ | Cl | H | H |
| E1-23.34$^{B'}$ | 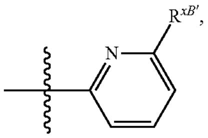 $R^{xB'}$ is $CH_3$ | F | H | H |
| E1-23.35$^{B'}$ | 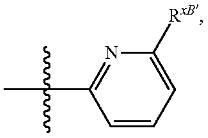 $R^{xB'}$ is $CH_3$ | $CH_2CH_3$ | H | H |
| E1-23.36$^{B'}$ | 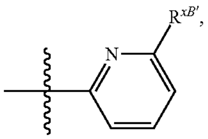 $R^{xB'}$ is $CH_3$ | $CF_2H$ | H | H |
| E1-24.1$^{B'}$ | Z24$^{B'}$ | H | H | H |
| E1-24.2$^{B'}$ | Z24$^{B'}$ | $CH_3$ | H | H |
| E1-24.3$^{B'}$ | Z24$^{B'}$ | Cl | H | H |
| E1-24.4$^{B'}$ | Z24$^{B'}$ | F | H | H |
| E1-24.5$^{B'}$ | Z24$^{B'}$ | $CH_2CH_3$ | H | H |
| E1-24.6$^{B'}$ | Z24$^{B'}$ | $CF_2H$ | H | H |
| E1-24.7$^{B'}$ | Z24$^{B'}$ | $CH_2F$ | H | H |
| E1-24.8$^{B'}$ | Z24$^{B'}$ | $CF_3$ | H | H |
| E1-24.9$^{B'}$ | Z24$^{B'}$ | $CF_2CH_3$ | H | H |
| E1-24.10$^{B'}$ | Z24$^{B'}$ | $CH_2CF_3$ | H | H |
| E1-24.11$^{B'}$ | Z24$^{B'}$ | cyclopropyl | H | H |
| E1-24.12$^{B'}$ | Z24$^{B'}$ | $OCF_3$ | H | H |
| E1-24.13$^{B'}$ | Z24$^{B'}$ | $OCF_2H$ | H | H |
| E1-24.14$^{B'}$ | Z24$^{B'}$ | Cl | H | F |
| E1-24.15$^{B'}$ | Z24$^{B'}$ | $CH_3$ | H | F |
| E1-24.16$^{B'}$ | Z24$^{B'}$ | $CH_3$ | F | H |
| E1-24.17$^{B'}$ | Z24$^{B'}$ | Cl | F | H |
| E1-24.18$^{B'}$ | Z24$^{B'}$ | F | F | H |
| E1-24.19$^{B'}$ | Z24$^{B'}$ | F | H | F |
| E1-24.20$^{B'}$ | Z24$^{B'}$ | F | H | Cl |
| E1-24.21$^{B'}$ | Z24$^{B'}$ | F | H | $CH_3$ |
| E1-24.22$^{B'}$ | Z24$^{B'}$ | Cl | H | $CH_3$ |

TABLE 13-continued

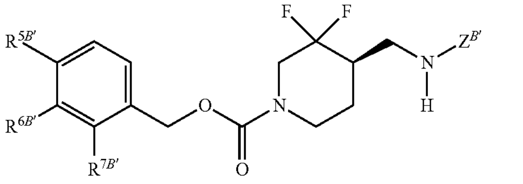

| compound | $Z^{B'}$ | $R^{5B'}$ | $R^{6B'}$ | $R^{7B'}$ |
|---|---|---|---|---|
| E1-24.23$^{B'}$ | Z24$^{B'}$ | $SCH_3$ | H | H |
| E1-24.24$^{B'}$ | Z24$^{B'}$ | $SO_2CH_3$ | H | H |
| E1-24.25$^{B'}$ | Z24$^{B'}$ | ethynyl | H | H |
| E1-24.26$^{B'}$ | 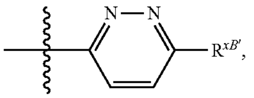 $R^{xB'}$ is $CH_3$ | $CH_3$ | H | H |
| E1-24.27$^{B'}$ | 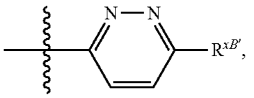 $R^{xB'}$ is Cl | $CH_3$ | H | H |
| E1-24.28$^{B'}$ | 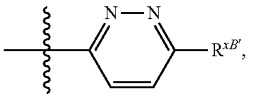 $R^{xB'}$ is F | $CH_3$ | H | H |
| E1-24.29$^{B'}$ | 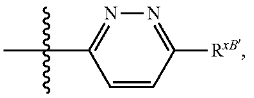 $R^{xB'}$ is $CF_3$ | $CH_3$ | H | H |
| E1-24.30$^{B'}$ | 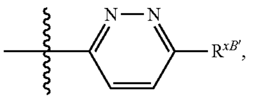 $R^{xB'}$ is CN | $CH_3$ | H | H |
| E1-25.1$^{B'}$ | Z25$^{B'}$, $R^{aB'}$ is H | H | H | H |
| E1-25.2$^{B'}$ | Z25$^{B'}$, $R^{aB'}$ is H | $CH_3$ | H | H |
| E1-25.3$^{B'}$ | Z25$^{B'}$, $R^{aB'}$ is H | Cl | H | H |
| E1-25.4$^{B'}$ | Z25$^{B'}$, $R^{aB'}$ is H | F | H | H |
| E1-25.5$^{B'}$ | Z25$^{B'}$, $R^{aB'}$ is H | $CH_2CH_3$ | H | H |
| E1-25.6$^{B'}$ | Z25$^{B'}$, $R^{aB'}$ is H | $CF_2H$ | H | H |
| E1-25.7$^{B'}$ | Z25$^{B'}$, $R^{aB'}$ is H | $CH_2F$ | H | H |
| E1-25.8$^{B'}$ | Z25$^{B'}$, $R^{aB'}$ is H | $CF_3$ | H | H |
| E1-25.9$^{B'}$ | Z25$^{B'}$, $R^{aB'}$ is H | $CF_2CH_3$ | H | H |
| E1-25.10$^{B'}$ | Z25$^{B'}$, $R^{aB'}$ is H | $CH_2CF_3$ | H | H |
| E1-25.11$^{B'}$ | Z25$^{B'}$, $R^{aB'}$ is H | cyclopropyl | H | H |
| E1-25.12$^{B'}$ | Z25$^{B'}$, $R^{aB'}$ is H | $OCF_3$ | H | H |
| E1-25.13$^{B'}$ | Z25$^{B'}$, $R^{aB'}$ is H | $OCF_2H$ | H | H |
| E1-25.14$^{B'}$ | Z25$^{B'}$, $R^{aB'}$ is H | Cl | H | F |
| E1-25.15$^{B'}$ | Z25$^{B'}$, $R^{aB'}$ is H | $CH_3$ | H | F |
| E1-25.16$^{B'}$ | Z25$^{B'}$, $R^{aB'}$ is H | $CH_3$ | F | H |
| E1-25.17$^{B'}$ | Z25$^{B'}$, $R^{aB'}$ is H | Cl | F | H |
| E1-25.18$^{B'}$ | Z25$^{B'}$, $R^{aB'}$ is H | F | F | H |
| E1-25.19$^{B'}$ | Z25$^{B'}$, $R^{aB'}$ is H | F | H | F |
| E1-25.20$^{B'}$ | Z25$^{B'}$, $R^{aB'}$ is H | F | H | Cl |
| E1-25.21$^{B'}$ | Z25$^{B'}$, $R^{aB'}$ is H | F | H | $CH_3$ |
| E1-25.22$^{B'}$ | Z25$^{B'}$, $R^{aB'}$ is H | Cl | H | $CH_3$ |
| E1-25.23$^{B'}$ | Z25$^{B'}$, $R^{aB'}$ is H | $SCH_3$ | H | H |
| E1-25.24$^{B'}$ | Z25$^{B'}$, $R^{aB'}$ is H | $SO_2CH_3$ | H | H |
| E1-25.25$^{B'}$ | Z25$^{B'}$, $R^{aB'}$ is H | ethynyl | H | H |

TABLE 13-continued

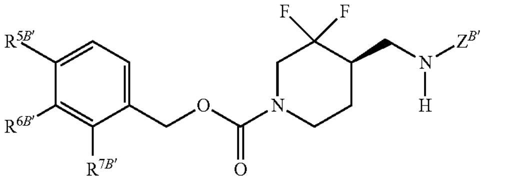

| compound | $Z^{B'}$ | $R^{5B'}$ | $R^{6B'}$ | $R^{7B'}$ |
|---|---|---|---|---|
| E1-25.26$^{B'}$ | 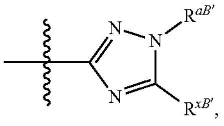 $R^{aB'}$ is H; $R^{xB'}$ is $CH_3$ | $CH_3$ | H | H |
| E1-25.27$^{B'}$ | 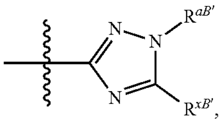 $R^{aB'}$ is H; $R^{xB'}$ is Cl | $CH_3$ | H | H |
| E1-25.28$^{B'}$ | 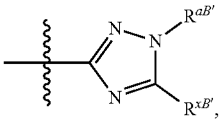 $R^{aB'}$ is H; $R^{xB'}$ is F | $CH_3$ | H | H |
| E1-25.29$^{B'}$ | 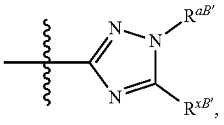 $R^{aB'}$ is H; $R^{xB'}$ is $CF_3$ | $CH_3$ | H | H |
| E1-25.30$^{B'}$ | 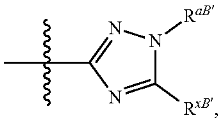 $R^{aB'}$ is H; $R^{xB'}$ is CN | $CH_3$ | H | H |
| E1-26.1$^{B'}$ | $Z26^{B'}$, $R^{aB'}$ is H | H | H | H |
| E1-26.2$^{B'}$ | $Z26^{B'}$, $R^{aB'}$ is H | $CH_3$ | H | H |
| E1-26.3$^{B'}$ | $Z26^{B'}$, $R^{aB'}$ is H | Cl | H | H |
| E1-26.4$^{B'}$ | $Z26^{B'}$, $R^{aB'}$ is H | F | H | H |
| E1-26.5$^{B'}$ | $Z26^{B'}$, $R^{aB'}$ is H | $CH_2CH_3$ | H | H |
| E1-26.6$^{B'}$ | $Z26^{B'}$, $R^{aB'}$ is H | $CF_2H$ | H | H |
| E1-26.7$^{B'}$ | $Z26^{B'}$, $R^{aB'}$ is H | $CH_2F$ | H | H |
| E1-26.8$^{B'}$ | $Z26^{B'}$, $R^{aB'}$ is H | $CF_3$ | H | H |
| E1-26.9$^{B'}$ | $Z26^{B'}$, $R^{aB'}$ is H | $CF_2CH_3$ | H | H |
| E1-26.10$^{B'}$ | $Z26^{B'}$, $R^{aB'}$ is H | $CH_2CF_3$ | H | H |
| E1-26.11$^{B'}$ | $Z26^{B'}$, $R^{aB'}$ is H | cyclopropyl | H | H |
| E1-26.12$^{B'}$ | $Z26^{B'}$, $R^{aB'}$ is H | $OCF_3$ | H | H |
| E1-26.13$^{B'}$ | $Z26^{B'}$, $R^{aB'}$ is H | $OCF_2H$ | H | H |
| E1-26.14$^{B'}$ | $Z26^{B'}$, $R^{aB'}$ is H | Cl | H | F |
| E1-26.15$^{B'}$ | $Z26^{B'}$, $R^{aB'}$ is H | $CH_3$ | H | F |
| E1-26.16$^{B'}$ | $Z26^{B'}$, $R^{aB'}$ is H | $CH_3$ | F | H |
| E1-26.17$^{B'}$ | $Z26^{B'}$, $R^{aB'}$ is H | Cl | F | H |
| E1-26.18$^{B'}$ | $Z26^{B'}$, $R^{aB'}$ is H | F | F | H |
| E1-26.19$^{B'}$ | $Z26^{B'}$, $R^{aB'}$ is H | F | H | F |
| E1-26.20$^{B'}$ | $Z26^{B'}$, $R^{aB'}$ is H | F | H | Cl |
| E1-26.21$^{B'}$ | $Z26^{B'}$, $R^{aB'}$ is H | F | H | $CH_3$ |
| E1-26.22$^{B'}$ | $Z26^{B'}$, $R^{aB'}$ is H | Cl | H | $CH_3$ |
| E1-26.23$^{B'}$ | $Z26^{B'}$, $R^{aB'}$ is H | $SCH_3$ | H | H |
| E1-26.24$^{B'}$ | $Z26^{B'}$, $R^{aB'}$ is H | $SO_2CH_3$ | H | H |
| E1-26.25$^{B'}$ | $Z26^{B'}$, $R^{aB'}$ is H | ethynyl | H | H |

TABLE 13-continued

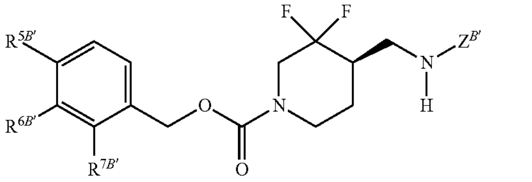

| compound | $Z^{B'}$ | $R^{5B'}$ | $R^{6B'}$ | $R^{7B'}$ |
|---|---|---|---|---|
| E1-26.26$^{B'}$ | 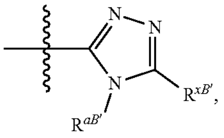 $R^{aB'}$ is H; $R^{xB'}$ is $CH_3$ | $CH_3$ | H | H |
| E1-26.27$^{B'}$ | 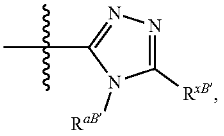 $R^{aB'}$ is H; $R^{xB'}$ is Cl | $CH_3$ | H | H |
| E1-26.28$^{B'}$ | 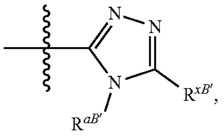 $R^{aB'}$ is H; $R^{xB'}$ is F | $CH_3$ | H | H |
| E1-26.29$^{B'}$ | 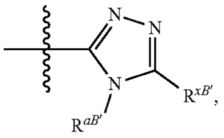 $R^{aB'}$ is H; $R^{xB'}$ is $CF_3$ | $CH_3$ | H | H |
| E1-26.30$^{B'}$ | 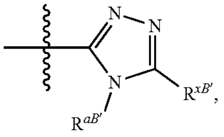 $R^{aB'}$ is H; $R^{xB'}$ is CN | $CH_3$ | H | H |
| E1-27.1$^{B'}$ | $Z27^{B'}$ | H | H | H |
| E1-27.2$^{B'}$ | $Z27^{B'}$ | $CH_3$ | H | H |
| E1-27.3$^{B'}$ | $Z27^{B'}$ | Cl | H | H |
| E1-27.4$^{B'}$ | $Z27^{B'}$ | F | H | H |
| E1-27.5$^{B'}$ | $Z27^{B'}$ | $CH_2CH_3$ | H | H |
| E1-27.6$^{B'}$ | $Z27^{B'}$ | $CF_2H$ | H | H |
| E1-27.7$^{B'}$ | $Z27^{B'}$ | $CH_2F$ | H | H |
| E1-27.8$^{B'}$ | $Z27^{B'}$ | $CF_3$ | H | H |
| E1-27.9$^{B'}$ | $Z27^{B'}$ | $CF_2CH_3$ | H | H |
| E1-27.10$^{B'}$ | $Z27^{B'}$ | $CH_2CF_3$ | H | H |
| E1-27.11$^{B'}$ | $Z27^{B'}$ | cyclopropyl | H | H |
| E1-27.12$^{B'}$ | $Z27^{B'}$ | $OCF_3$ | H | H |
| E1-27.13$^{B'}$ | $Z27^{B'}$ | $OCF_2H$ | H | H |
| E1-27.14$^{B'}$ | $Z27^{B'}$ | Cl | H | F |
| E1-27.15$^{B'}$ | $Z27^{B'}$ | $CH_3$ | H | F |
| E1-27.16$^{B'}$ | $Z27^{B'}$ | $CH_3$ | F | H |
| E1-27.17$^{B'}$ | $Z27^{B'}$ | Cl | F | H |
| E1-27.18$^{B'}$ | $Z27^{B'}$ | F | F | H |
| E1-27.19$^{B'}$ | $Z27^{B'}$ | F | H | F |
| E1-27.20$^{B'}$ | $Z27^{B'}$ | F | H | Cl |
| E1-27.21$^{B'}$ | $Z27^{B'}$ | F | H | $CH_3$ |
| E1-27.22$^{B'}$ | $Z27^{B'}$ | Cl | H | $CH_3$ |
| E1-27.23$^{B'}$ | $Z27^{B'}$ | $SCH_3$ | H | H |

TABLE 13-continued

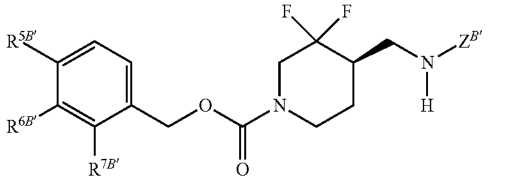

| compound | $Z^{B'}$ | $R^{5B'}$ | $R^{6B'}$ | $R^{7B'}$ |
|---|---|---|---|---|
| E1-27.24$^{B'}$ | Z27$^{B'}$ | $SO_2CH_3$ | H | H |
| E1-27.25$^{B'}$ | Z27$^{B'}$ | ethynyl | H | H |
| E1-27.26$^{B'}$ | 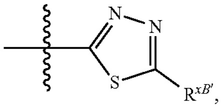<br>$R^{aB'}$ is H; $R^{xB'}$ is $CH_3$ | $CH_3$ | H | H |
| E1-27.27$^{B'}$ | 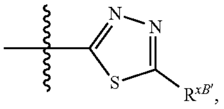<br>$R^{aB'}$ is H; $R^{xB'}$ is Cl | $CH_3$ | H | H |
| E1-27.28$^{B'}$ | 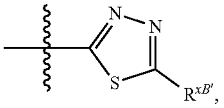<br>$R^{aB'}$ is H; $R^{xB'}$ is F | $CH_3$ | H | H |
| E1-27.29$^{B'}$ | 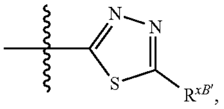<br>$R^{aB'}$ is H; $R^{xB'}$ is $CF_3$ | $CH_3$ | H | H |
| E1-27.30$^{B'}$ | 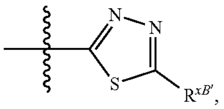<br>$R^{aB'}$ is H; $R^{xB'}$ is CN | $CH_3$ | H | H |
| E1-28.1$^{B'}$ | Z28$^{B'}$ | H | H | H |
| E1-28.2$^{B'}$ | Z28$^{B'}$ | $CH_3$ | H | H |
| E1-28.3$^{B'}$ | Z28$^{B'}$ | Cl | H | H |
| E1-28.4$^{B'}$ | Z28$^{B'}$ | F | H | H |
| E1-28.5$^{B'}$ | Z28$^{B'}$ | $CH_2CH_3$ | H | H |
| E1-28.6$^{B'}$ | Z28$^{B'}$ | $CF_2H$ | H | H |
| E1-28.7$^{B'}$ | Z28$^{B'}$ | $CH_2F$ | H | H |
| E1-28.8$^{B'}$ | Z28$^{B'}$ | $CF_3$ | H | H |
| E1-28.9$^{B'}$ | Z28$^{B'}$ | $CF_2CH_3$ | H | H |
| E1-28.10$^{B'}$ | Z28$^{B'}$ | $CH_2CF_3$ | H | H |
| E1-28.11$^{B'}$ | Z28$^{B'}$ | cyclopropyl | H | H |
| E1-28.12$^{B'}$ | Z28$^{B'}$ | $OCF_3$ | H | H |
| E1-28.13$^{B'}$ | Z28$^{B'}$ | $OCF_2H$ | H | H |
| E1-28.14$^{B'}$ | Z28$^{B'}$ | Cl | H | F |
| E1-28.15$^{B'}$ | Z28$^{B'}$ | $CH_3$ | H | F |
| E1-28.16$^{B'}$ | Z28$^{B'}$ | $CH_3$ | F | H |
| E1-28.17$^{B'}$ | Z28$^{B'}$ | Cl | F | H |
| E1-28.18$^{B'}$ | Z28$^{B'}$ | F | F | H |
| E1-28.19$^{B'}$ | Z28$^{B'}$ | F | H | F |
| E1-28.20$^{B'}$ | Z28$^{B'}$ | F | H | Cl |
| E1-28.21$^{B'}$ | Z28$^{B'}$ | F | H | $CH_3$ |
| E1-28.22$^{B'}$ | Z28$^{B'}$ | Cl | H | $CH_3$ |
| E1-28.23$^{B'}$ | Z28$^{B'}$ | $SCH_3$ | H | H |
| E1-28.24$^{B'}$ | Z28$^{B'}$ | $SO_2CH_3$ | H | H |
| E1-28.25$^{B'}$ | Z28$^{B'}$ | ethynyl | H | H |

TABLE 13-continued

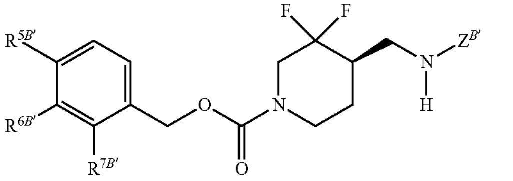

| compound | $Z^{B'}$ | $R^{5B'}$ | $R^{6B'}$ | $R^{7B'}$ |
|---|---|---|---|---|
| E1-28.26$^{B'}$ | 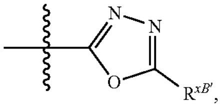<br>$R^{xB'}$ is $CH_3$ | $CH_3$ | H | H |
| E1-28.27$^{B'}$ | 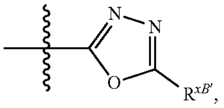<br>$R^{xB'}$ is Cl | $CH_3$ | H | H |
| E1-28.28$^{B'}$ | 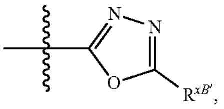<br>$R^{xB'}$ is F | $CH_3$ | H | H |
| E1-28.29$^{B'}$ | 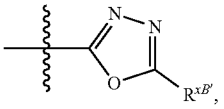<br>$R^{xB'}$ is $CF_3$ | $CH_3$ | H | H |
| E1-28.30$^{B'}$ | 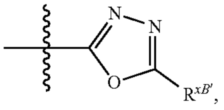<br>$R^{xB'}$ is CN | $CH_3$ | H | H |
| E1-29.1$^{B'}$ | Z29$^{B'}$ | H | H | H |
| E1-29.2$^{B'}$ | Z29$^{B'}$ | $CH_3$ | H | H |
| E1-29.3$^{B'}$ | Z29$^{B'}$ | Cl | H | H |
| E1-29.4$^{B'}$ | Z29$^{B'}$ | F | H | H |
| E1-29.5$^{B'}$ | Z29$^{B'}$ | $CH_2CH_3$ | H | H |
| E1-29.6$^{B'}$ | Z29$^{B'}$ | $CF_2H$ | H | H |
| E1-29.7$^{B'}$ | Z29$^{B'}$ | $CH_2F$ | H | H |
| E1-29.8$^{B'}$ | Z29$^{B'}$ | $CF_3$ | H | H |
| E1-29.9$^{B'}$ | Z29$^{B'}$ | $CF_2CH_3$ | H | H |
| E1-29.10$^{B'}$ | Z29$^{B'}$ | $CH_2CF_3$ | H | H |
| E1-29.11$^{B'}$ | Z29$^{B'}$ | cyclopropyl | H | H |
| E1-29.12$^{B'}$ | Z29$^{B'}$ | $OCF_3$ | H | H |
| E1-29.13$^{B'}$ | Z29$^{B'}$ | $OCF_2H$ | H | H |
| E1-29.14$^{B'}$ | Z29$^{B'}$ | Cl | H | F |
| E1-29.15$^{B'}$ | Z29$^{B'}$ | $CH_3$ | H | F |
| E1-29.16$^{B'}$ | Z29$^{B'}$ | $CH_3$ | F | H |
| E1-29.17$^{B'}$ | Z29$^{B'}$ | Cl | F | H |
| E1-29.18$^{B'}$ | Z29$^{B'}$ | F | F | H |
| E1-29.19$^{B'}$ | Z29$^{B'}$ | F | H | F |
| E1-29.20$^{B'}$ | Z29$^{B'}$ | F | H | Cl |
| E1-29.21$^{B'}$ | Z29$^{B'}$ | F | H | $CH_3$ |
| E1-29.22$^{B'}$ | Z29$^{B'}$ | Cl | H | $CH_3$ |
| E1-29.23$^{B'}$ | Z29$^{B'}$ | $SCH_3$ | H | H |
| E1-29.24$^{B'}$ | Z29$^{B'}$ | $SO_2CH_3$ | H | H |
| E1-29.25$^{B'}$ | Z29$^{B'}$ | ethynyl | H | H |

TABLE 13-continued

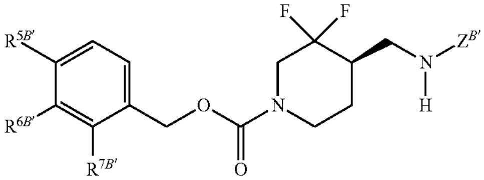

| compound | $Z^{B'}$ | $R^{5B'}$ | $R^{6B'}$ | $R^{7B'}$ |
|---|---|---|---|---|
| E1-29.26$^{B'}$ | 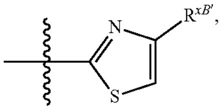 $R^{xB'}$ is $CH_3$ | $CH_3$ | H | H |
| E1-29.27$^{B'}$ | 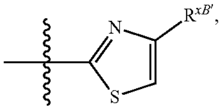 $R^{xB'}$ is Cl | $CH_3$ | H | H |
| E1-29.28$^{B'}$ | 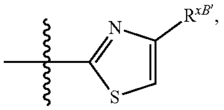 $R^{xB'}$ is F | $CH_3$ | H | H |
| E1-29.29$^{B'}$ | 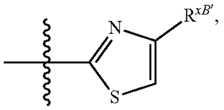 $R^{xB'}$ is $CF_3$ | $CH_3$ | H | H |
| E1-29.30$^{B'}$ | 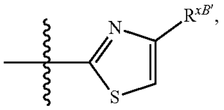 $R^{xB'}$ is CN | $CH_3$ | H | H |
| E1-29.31$^{B'}$ | 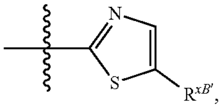 $R^{xB'}$ is $CH_3$ | $CH_3$ | H | H |
| E1-29.32$^{B'}$ | 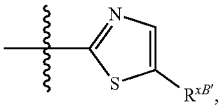 $R^{xB'}$ is Cl | $CH_3$ | H | H |
| E1-29.33$^{B'}$ | 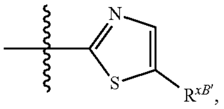 $R^{xB'}$ is F | $CH_3$ | H | H |

TABLE 13-continued

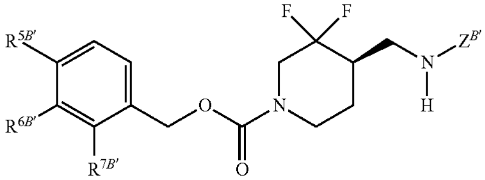

| compound | $Z^{B'}$ | $R^{5B'}$ | $R^{6B'}$ | $R^{7B'}$ |
|---|---|---|---|---|
| E1-29.34$^{B'}$ | 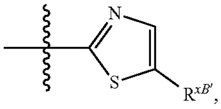 $R^{xB'}$ is $CF_3$ | $CH_3$ | H | H |
| E1-29.35$^{B'}$ | 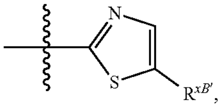 $R^{xB'}$ is CN | $CH_3$ | H | H |
| E1-30.1$^{B'}$ | Z30$^{B'}$ | H | H | H |
| E1-30.2$^{B'}$ | Z30$^{B'}$ | $CH_3$ | H | H |
| E1-30.3$^{B'}$ | Z30$^{B'}$ | Cl | H | H |
| E1-30.4$^{B'}$ | Z30$^{B'}$ | F | H | H |
| E1-30.5$^{B'}$ | Z30$^{B'}$ | $CH_2CH_3$ | H | H |
| E1-30.6$^{B'}$ | Z30$^{B'}$ | $CF_2H$ | H | H |
| E1-30.7$^{B'}$ | Z30$^{B'}$ | $CH_2F$ | H | H |
| E1-30.8$^{B'}$ | Z30$^{B'}$ | $CF_3$ | H | H |
| E1-30.9$^{B'}$ | Z30$^{B'}$ | $CF_2CH_3$ | H | H |
| E1-30.10$^{B'}$ | Z30$^{B'}$ | $CH_2CF_3$ | H | H |
| E1-30.11$^{B'}$ | Z30$^{B'}$ | cyclopropyl | H | H |
| E1-30.12$^{B'}$ | Z30$^{B'}$ | $OCF_3$ | H | H |
| E1-30.13$^{B'}$ | Z30$^{B'}$ | $OCF_2H$ | H | H |
| E1-30.14$^{B'}$ | Z30$^{B'}$ | Cl | H | F |
| E1-30.15$^{B'}$ | Z30$^{B'}$ | $CH_3$ | H | F |
| E1-30.16$^{B'}$ | Z30$^{B'}$ | $CH_3$ | F | H |
| E1-30.17$^{B'}$ | Z30$^{B'}$ | Cl | F | H |
| E1-30.18$^{B'}$ | Z30$^{B'}$ | F | F | H |
| E1-30.19$^{B'}$ | Z30$^{B'}$ | F | H | F |
| E1-30.20$^{B'}$ | Z30$^{B'}$ | F | H | Cl |
| E1-30.21$^{B'}$ | Z30$^{B'}$ | F | H | $CH_3$ |
| E1-30.22$^{B'}$ | Z30$^{B'}$ | Cl | H | $CH_3$ |
| E1-30.23$^{B'}$ | Z30$^{B'}$ | $SCH_3$ | H | H |
| E1-30.24$^{B'}$ | Z30$^{B'}$ | $SO_2CH_3$ | H | H |
| E1-30.25$^{B'}$ | Z30$^{B'}$ | ethynyl | H | H |
| E1-30.26$^{B'}$ | 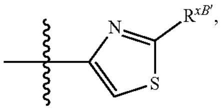 $R^{xB'}$ is $CH_3$ | $CH_3$ | H | H |
| E1-30.27$^{B'}$ | 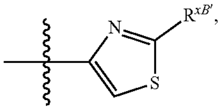 $R^{xB'}$ is Cl | $CH_3$ | H | H |
| E1-30.28$^{B'}$ | 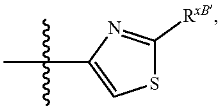 $R^{xB'}$ is F | $CH_3$ | H | H |

TABLE 13-continued

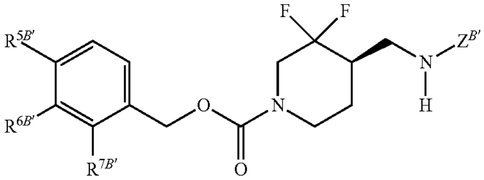

| compound | $Z^{B'}$ | $R^{5B'}$ | $R^{6B'}$ | $R^{7B'}$ |
|---|---|---|---|---|
| E1-30.29$^{B'}$ | 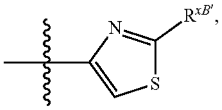 $R^{xB'}$ is $CF_3$ | $CH_3$ | H | H |
| E1-30.30$^{B'}$ | 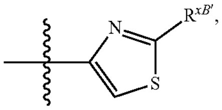 $R^{xB'}$ is CN | $CH_3$ | H | H |
| E1-30.31$^{B'}$ | 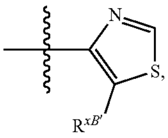 $R^{xB'}$ is $CH_3$ | $CH_3$ | H | H |
| E1-30.32$^{B'}$ | 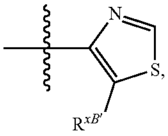 $R^{xB'}$ is Cl | $CH_3$ | H | H |
| E1-30.33$^{B'}$ | 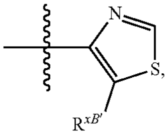 $R^{xB'}$ is F | $CH_3$ | H | H |
| E1-30.34$^{B'}$ | 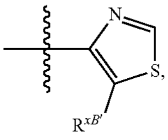 $R^{xB'}$ is $CF_3$ | $CH_3$ | H | H |
| E1-30.35$^{B'}$ | 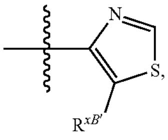 $R^{xB'}$ is CN | $CH_3$ | H | H |
| E1-31.1$^{B'}$ | Z31$^{B'}$ | H | H | H |
| E1-31.2$^{B'}$ | Z31$^{B'}$ | $CH_3$ | H | H |
| E1-31.3$^{B'}$ | Z31$^{B'}$ | Cl | H | H |
| E1-31.4$^{B'}$ | Z31$^{B'}$ | F | H | H |
| E1-31.5$^{B'}$ | Z31$^{B'}$ | $CH_2CH_3$ | H | H |
| E1-31.6$^{B'}$ | Z31$^{B'}$ | $CF_2H$ | H | H |
| E1-31.7$^{B'}$ | Z31$^{B'}$ | $CH_2F$ | H | H |

TABLE 13-continued

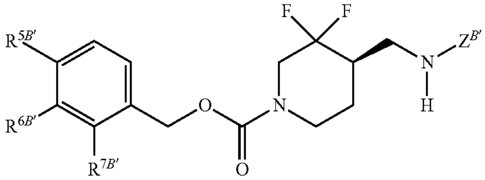

| compound | $Z^{B'}$ | $R^{5B'}$ | $R^{6B'}$ | $R^{7B'}$ |
|---|---|---|---|---|
| E1-31.8$^{B'}$ | Z31$^{B'}$ | $CF_3$ | H | H |
| E1-31.9$^{B'}$ | Z31$^{B'}$ | $CF_2CH_3$ | H | H |
| E1-31.10$^{B'}$ | Z31$^{B'}$ | $CH_2CF_3$ | H | H |
| E1-31.11$^{B'}$ | Z31$^{B'}$ | cyclopropyl | H | H |
| E1-31.12$^{B'}$ | Z31$^{B'}$ | $OCF_3$ | H | H |
| E1-31.13$^{B'}$ | Z31$^{B'}$ | $OCF_2H$ | H | H |
| E1-31.14$^{B'}$ | Z31$^{B'}$ | Cl | H | F |
| E1-31.15$^{B'}$ | Z31$^{B'}$ | $CH_3$ | H | F |
| E1-31.16$^{B'}$ | Z31$^{B'}$ | $CH_3$ | F | H |
| E1-31.17$^{B'}$ | Z31$^{B'}$ | Cl | F | H |
| E1-31.18$^{B'}$ | Z31$^{B'}$ | F | F | H |
| E1-31.19$^{B'}$ | Z31$^{B'}$ | F | H | F |
| E1-31.20$^{B'}$ | Z31$^{B'}$ | F | H | Cl |
| E1-31.21$^{B'}$ | Z31$^{B'}$ | F | H | $CH_3$ |
| E1-31.22$^{B'}$ | Z31$^{B'}$ | Cl | H | $CH_3$ |
| E1-31.23$^{B'}$ | Z31$^{B'}$ | $SCH_3$ | H | H |
| E1-31.24$^{B'}$ | Z31$^{B'}$ | $SO_2CH_3$ | H | H |
| E1-31.25$^{B'}$ | Z31$^{B'}$ | ethynyl | H | H |
| E1-31.26$^{B'}$ | 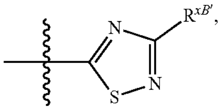 $R^{xB'}$ is $CH_3$ | $CH_3$ | H | H |
| E1-31.27$^{B'}$ | 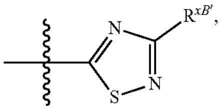 $R^{xB'}$ is Cl | $CH_3$ | H | H |
| E1-31.28$^{B'}$ | 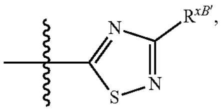 $R^{xB'}$ is F | $CH_3$ | H | H |
| E1-31.29$^{B'}$ | 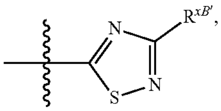 $R^{xB'}$ is $CF_3$ | $CH_3$ | H | H |
| E1-31.30$^{B'}$ | 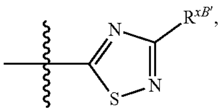 $R^{xB'}$ is CN | $CH_3$ | H | H |
| E1-32.1$^{B'}$ | Z32$^{B'}$ | H | H | H |
| E1-32.2$^{B'}$ | Z32$^{B'}$ | $CH_3$ | H | H |
| E1-32.3$^{B'}$ | Z32$^{B'}$ | Cl | H | H |
| E1-32.4$^{B'}$ | Z32$^{B'}$ | F | H | H |
| E1-32.5$^{B'}$ | Z32$^{B'}$ | $CH_2CH_3$ | H | H |
| E1-32.6$^{B'}$ | Z32$^{B'}$ | $CF_2H$ | H | H |
| E1-32.7$^{B'}$ | Z32$^{B'}$ | $CH_2F$ | H | H |
| E1-32.8$^{B'}$ | Z32$^{B'}$ | $CF_3$ | H | H |
| E1-32.9$^{B'}$ | Z32$^{B'}$ | $CF_2CH_3$ | H | H |
| E1-32.10$^{B'}$ | Z32$^{B'}$ | $CH_2CF_3$ | H | H |

TABLE 13-continued

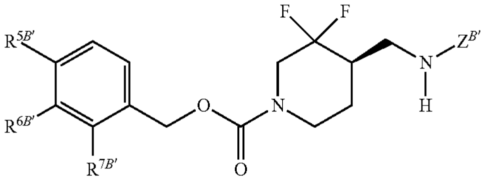

| compound | $Z^{B'}$ | $R^{5B'}$ | $R^{6B'}$ | $R^{7B'}$ |
|---|---|---|---|---|
| E1-32.11$^{B'}$ | Z32$^{B'}$ | cyclopropyl | H | H |
| E1-32.12$^{B'}$ | Z32$^{B'}$ | $OCF_3$ | H | H |
| E1-32.13$^{B'}$ | Z32$^{B'}$ | $OCF_2H$ | H | H |
| E1-32.14$^{B'}$ | Z32$^{B'}$ | Cl | H | F |
| E1-32.15$^{B'}$ | Z32$^{B'}$ | $CH_3$ | H | F |
| E1-32.16$^{B'}$ | Z32$^{B'}$ | $CH_3$ | F | H |
| E1-32.17$^{B'}$ | Z32$^{B'}$ | Cl | F | H |
| E1-32.18$^{B'}$ | Z32$^{B'}$ | F | F | H |
| E1-32.19$^{B'}$ | Z32$^{B'}$ | F | H | F |
| E1-32.20$^{B'}$ | Z32$^{B'}$ | F | H | Cl |
| E1-32.21$^{B'}$ | Z32$^{B'}$ | F | H | $CH_3$ |
| E1-32.22$^{B'}$ | Z32$^{B'}$ | Cl | H | $CH_3$ |
| E1-32.23$^{B'}$ | Z32$^{B'}$ | $SCH_3$ | H | H |
| E1-32.24$^{B'}$ | Z32$^{B'}$ | $SO_2CH_3$ | H | H |
| E1-32.25$^{B'}$ | Z32$^{B'}$ | ethynyl | H | H |
| E1-32.26$^{B'}$ | 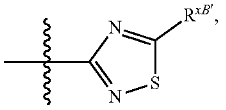 $R^{xB'}$ is $CH_3$ | $CH_3$ | H | H |
| E1-32.27$^{B'}$ | 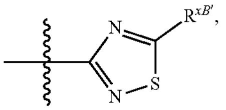 $R^{xB'}$ is Cl | $CH_3$ | H | H |
| E1-32.28$^{B'}$ | 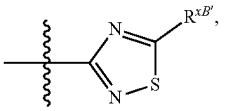 $R^{xB'}$ is F | $CH_3$ | H | H |
| E1-32.29$^{B'}$ | 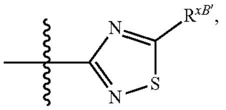 $R^{xB'}$ is $CF_3$ | $CH_3$ | H | H |
| E1-32.30$^{B'}$ | 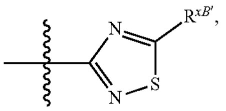 $R^{xB'}$ is CN | $CH_3$ | H | H |
| E1-33.1$^{B'}$ | Z33$^{B'}$ | H | H | H |
| E1-33.2$^{B'}$ | Z33$^{B'}$ | $CH_3$ | H | H |
| E1-33.3$^{B'}$ | Z33$^{B'}$ | Cl | H | H |
| E1-33.4$^{B'}$ | Z33$^{B'}$ | F | H | H |
| E1-33.5$^{B'}$ | Z33$^{B'}$ | $CH_2CH_3$ | H | H |
| E1-33.6$^{B'}$ | Z33$^{B'}$ | $CF_2H$ | H | H |
| E1-33.7$^{B'}$ | Z33$^{B'}$ | $CH_2F$ | H | H |
| E1-33.8$^{B'}$ | Z33$^{B'}$ | $CF_3$ | H | H |
| E1-33.9$^{B'}$ | Z33$^{B'}$ | $CF_2CH_3$ | H | H |
| E1-33.10$^{B'}$ | Z33$^{B'}$ | $CH_2CF_3$ | H | H |
| E1-33.11$^{B'}$ | Z33$^{B'}$ | cyclopropyl | H | H |
| E1-33.12$^{B'}$ | Z33$^{B'}$ | $OCF_3$ | H | H |
| E1-33.13$^{B'}$ | Z33$^{B'}$ | $OCF_2H$ | H | H |

TABLE 13-continued

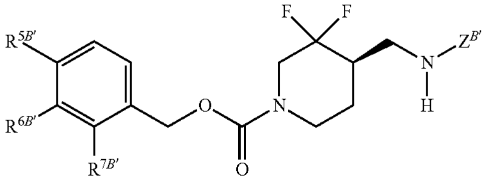

| compound | $Z^{B'}$ | $R^{5B'}$ | $R^{6B'}$ | $R^{7B'}$ |
|---|---|---|---|---|
| E1-33.14$^{B'}$ | Z33$^{B'}$ | Cl | H | F |
| E1-33.15$^{B'}$ | Z33$^{B'}$ | $CH_3$ | H | F |
| E1-33.16$^{B'}$ | Z33$^{B'}$ | $CH_3$ | F | H |
| E1-33.17$^{B'}$ | Z33$^{B'}$ | Cl | F | H |
| E1-33.18$^{B'}$ | Z33$^{B'}$ | F | F | H |
| E1-33.19$^{B'}$ | Z33$^{B'}$ | F | H | F |
| E1-33.20$^{B'}$ | Z33$^{B'}$ | F | H | Cl |
| E1-33.21$^{B'}$ | Z33$^{B'}$ | F | H | $CH_3$ |
| E1-33.22$^{B'}$ | Z33$^{B'}$ | Cl | H | $CH_3$ |
| E1-33.23$^{B'}$ | Z33$^{B'}$ | $SCH_3$ | H | H |
| E1-33.24$^{B'}$ | Z33$^{B'}$ | $SO_2CH_3$ | H | H |
| E1-33.25$^{B'}$ | Z33$^{B'}$ | ethynyl | H | H |
| E1-33.26$^{B'}$ | 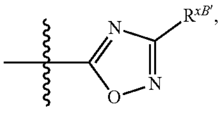 $R^{xB'}$ is $CH_3$ | $CH_3$ | H | H |
| E1-33.27$^{B'}$ | 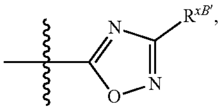 $R^{xB'}$ is Cl | $CH_3$ | H | H |
| E1-33.28$^{B'}$ | 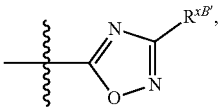 $R^{xB'}$ is F | $CH_3$ | H | H |
| E1-33.29$^{B'}$ | 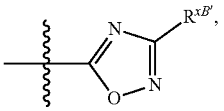 $R^{xB'}$ is $CF_3$ | $CH_3$ | H | H |
| E1-33.30$^{B'}$ | 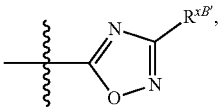 $R^{xB'}$ is CN | $CH_3$ | H | H |
| E1-34.1$^{B'}$ | Z34$^{B'}$ | H | H | H |
| E1-34.2$^{B'}$ | Z34$^{B'}$ | $CH_3$ | H | H |
| E1-34.3$^{B'}$ | Z34$^{B'}$ | Cl | H | H |
| E1-34.4$^{B'}$ | Z34$^{B'}$ | F | H | H |
| E1-34.5$^{B'}$ | Z34$^{B'}$ | $CH_2CH_3$ | H | H |
| E1-34.6$^{B'}$ | Z34$^{B'}$ | $CF_2H$ | H | H |
| E1-34.7$^{B'}$ | Z34$^{B'}$ | $CH_2F$ | H | H |
| E1-34.8$^{B'}$ | Z34$^{B'}$ | $CF_3$ | H | H |
| E1-34.9$^{B'}$ | Z34$^{B'}$ | $CF_2CH_3$ | H | H |
| E1-34.10$^{B'}$ | Z34$^{B'}$ | $CHCF_3$ | H | H |
| E1-34.11$^{B'}$ | Z34$^{B'}$ | cyclopropyl | H | H |
| E1-34.12$^{B'}$ | Z34$^{B'}$ | $OCF_3$ | H | H |
| E1-34.13$^{B'}$ | Z34$^{B'}$ | $OCF_2H$ | H | H |
| E1-34.14$^{B'}$ | Z34$^{B'}$ | Cl | H | F |
| E1-34.15$^{B'}$ | Z34$^{B'}$ | $CH_3$ | H | F |
| E1-34.16$^{B'}$ | Z34$^{B'}$ | $CH_3$ | F | H |

TABLE 13-continued

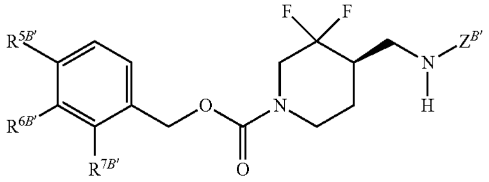

| compound | $Z^{B'}$ | $R^{5B'}$ | $R^{6B'}$ | $R^{7B'}$ |
|---|---|---|---|---|
| E1-34.17$^{B'}$ | Z34$^{B'}$ | Cl | F | H |
| E1-34.18$^{B'}$ | Z34$^{B'}$ | F | F | H |
| E1-34.19$^{B'}$ | Z34$^{B'}$ | F | H | F |
| E1-34.20$^{B'}$ | Z34$^{B'}$ | F | H | Cl |
| E1-34.21$^{B'}$ | Z34$^{B'}$ | F | H | $CH_3$ |
| E1-34.22$^{B'}$ | Z34$^{B'}$ | Cl | H | $CH_3$ |
| E1-34.23$^{B'}$ | Z34$^{B'}$ | $SCH_3$ | H | H |
| E1-34.24$^{B'}$ | Z34$^{B'}$ | $SO_2CH_3$ | H | H |
| E1-34.25$^{B'}$ | Z34$^{B'}$ | ethynyl | H | H |
| E1-34.26$^{B'}$ | 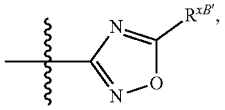 $R^{xB'}$ is $CH_3$ | $CH_3$ | H | H |
| E1-34.27$^{B'}$ | 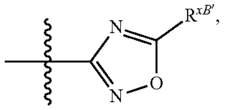 $R^{xB'}$ is Cl | $CH_3$ | H | H |
| E1-34.28$^{B'}$ | 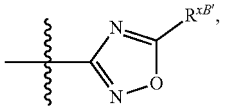 $R^{xB'}$ is F | $CH_3$ | H | H |
| E1-34.29$^{B'}$ | 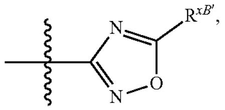 $R^{xB'}$ is $CF_3$ | $CH_3$ | H | H |
| E1-34.30$^{B'}$ | 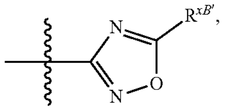 $R^{xB'}$ is CN | $CH_3$ | H | H |
| E1-35.1$^{B'}$ | Z35$^{B'}$, $R^{aB'}$ is H | H | H | H |
| E1-35.2$^{B'}$ | Z35$^{B'}$, $R^{aB'}$ is H | $CH_3$ | H | H |
| E1-35.3$^{B'}$ | Z35$^{B'}$, $R^{aB'}$ is H | Cl | H | H |
| E1-35.4$^{B'}$ | Z35$^{B'}$, $R^{aB'}$ is H | F | H | H |
| E1-35.5$^{B'}$ | Z35$^{B'}$, $R^{aB'}$ is H | $CH_2CH_3$ | H | H |
| E1-35.6$^{B'}$ | Z35$^{B'}$, $R^{aB'}$ is H | $CF_2H$ | H | H |
| E1-35.7$^{B'}$ | Z35$^{B'}$, $R^{aB'}$ is H | $CH_2F$ | H | H |
| E1-35.8$^{B'}$ | Z35$^{B'}$, $R^{aB'}$ is H | $CF_3$ | H | H |
| E1-35.9$^{B'}$ | Z35$^{B'}$, $R^{aB'}$ is H | $CF_2CH_3$ | H | H |
| E1-35.10$^{B'}$ | Z35$^{B'}$, $R^{aB'}$ is H | $CH_2CF_3$ | H | H |
| E1-35.11$^{B'}$ | Z35$^{B'}$, $R^{aB'}$ is H | cyclopropyl | H | H |
| E1-35.12$^{B'}$ | Z35$^{B'}$, $R^{aB'}$ is H | $OCF_3$ | H | H |
| E1-35.13$^{B'}$ | Z35$^{B'}$, $R^{aB'}$ is H | $OCF_2H$ | H | H |
| E1-35.14$^{B'}$ | Z35$^{B'}$, $R^{aB'}$ is H | Cl | H | F |
| E1-35.15$^{B'}$ | Z35$^{B'}$, $R^{aB'}$ is H | $CH_3$ | H | F |
| E1-35.16$^{B'}$ | Z35$^{B'}$, $R^{aB'}$ is H | $CH_3$ | F | H |
| E1-35.17$^{B'}$ | Z35$^{B'}$, $R^{aB'}$ is H | Cl | F | H |
| E1-35.18$^{B'}$ | Z35$^{B'}$, $R^{aB'}$ is H | F | F | H |
| E1-35.19$^{B'}$ | Z35$^{B'}$, $R^{aB'}$ is H | F | H | F |

TABLE 13-continued

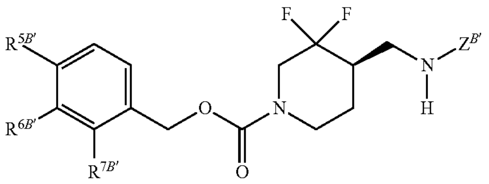

| compound | $Z^{B'}$ | $R^{5B'}$ | $R^{6B'}$ | $R^{7B'}$ |
|---|---|---|---|---|
| E1-35.20$^{B'}$ | Z35$^{B'}$, $R^{aB'}$ is H | F | H | Cl |
| E1-35.21$^{B'}$ | Z35$^{B'}$, $R^{aB'}$ is H | F | H | $CH_3$ |
| E1-35.22$^{B'}$ | Z35$^{B'}$, $R^{aB'}$ is H | Cl | H | $CH_3$ |
| E1-35.23$^{B'}$ | Z35$^{B'}$, $R^{aB'}$ is H | $SCH_3$ | H | H |
| E1-35.24$^{B'}$ | Z35$^{B'}$, $R^{aB'}$ is H | $SO_2CH_3$ | H | H |
| E1-35.25$^{B'}$ | Z35$^{B'}$, $R^{aB'}$ is H | ethynyl | H | H |
| E1-35.26$^{B'}$ | 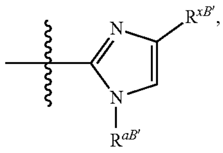 $R^{aB'}$ is H; $R^{xB'}$ is $CH_3$ | $CH_3$ | H | H |
| E1-35.27$^{B'}$ | 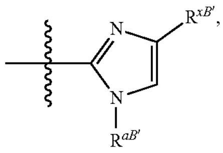 $R^{aB'}$ is H; $R^{xB'}$ is Cl | $CH_3$ | H | H |
| E1-35.28$^{B'}$ | 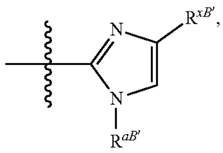 $R^{aB'}$ is H; $R^{xB'}$ is F | $CH_3$ | H | H |
| E1-35.29$^{B'}$ | 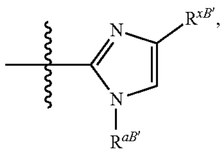 $R^{aB'}$ is H; $R^{xB'}$ is $CF_3$ | $CH_3$ | H | H |
| E1-35.30$^{B'}$ | 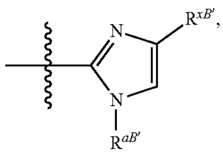 $R^{aB'}$ is H; $R^{xB'}$ is CN | $CH_3$ | H | H |
| E1-35.31$^{B'}$ | 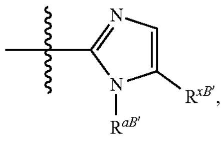 $R^{aB'}$ is H; $R^{xB'}$ is $CH_3$ | $CH_3$ | H | H |

TABLE 13-continued

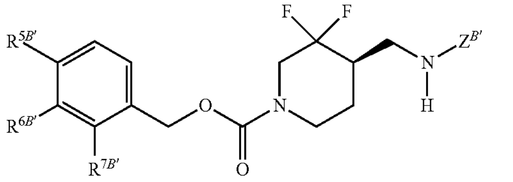

| compound | $Z^{B'}$ | $R^{5B'}$ | $R^{6B'}$ | $R^{7B'}$ |
|---|---|---|---|---|
| E1-35.32$^{B'}$ | 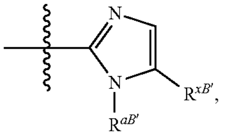 $R^{aB'}$ is H; $R^{xB'}$ is Cl | $CH_3$ | H | H |
| E1-35.33$^{B'}$ | 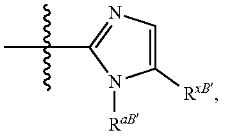 $R^{aB'}$ is H; $R^{xB'}$ is F | $CH_3$ | H | H |
| E1-35.34$^{B'}$ | 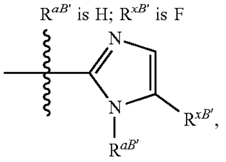 $R^{aB'}$ is H; $R^{xB'}$ is $CF_3$ | $CH_3$ | H | H |
| E1-35.35$^{B'}$ | 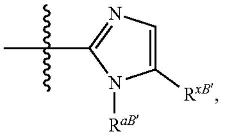 $R^{aB'}$ is H; $R^{xB'}$ is CN | $CH_3$ | H | H |
| E1-36.1$^{B'}$ | Z36$^{B'}$, $R^{aB'}$ is H | H | H | H |
| E1-36.2$^{B'}$ | Z36$^{B'}$, $R^{aB'}$ is H | $CH_3$ | H | H |
| E1-36.3$^{B'}$ | Z36$^{B'}$, $R^{aB'}$ is H | Cl | H | H |
| E1-36.4$^{B'}$ | Z36$^{B'}$, $R^{aB'}$ is H | F | H | H |
| E1-36.5$^{B'}$ | Z36$^{B'}$, $R^{aB'}$ is H | $CH_2CH_3$ | H | H |
| E1-36.6$^{B'}$ | Z36$^{B'}$, $R^{aB'}$ is H | $CF_2H$ | H | H |
| E1-36.7$^{B'}$ | Z36$^{B'}$, $R^{aB'}$ is H | $CH_2F$ | H | H |
| E1-36.8$^{B'}$ | Z36$^{B'}$, $R^{aB'}$ is H | $CF_3$ | H | H |
| E1-36.9$^{B'}$ | Z36$^{B'}$, $R^{aB'}$ is H | $CF_2CH_3$ | H | H |
| E1-36.10$^{B'}$ | Z36$^{B'}$, $R^{aB'}$ is H | $CH_2CF_3$ | H | H |
| E1-36.11$^{B'}$ | Z36$^{B'}$, $R^{aB'}$ is H | cyclopropyl | H | H |
| E1-36.12$^{B'}$ | Z36$^{B'}$, $R^{aB'}$ is H | $OCF_3$ | H | H |
| E1-36.13$^{B'}$ | Z36$^{B'}$, $R^{aB'}$ is H | $OCF_2H$ | H | H |
| E1-36.14$^{B'}$ | Z36$^{B'}$, $R^{aB'}$ is H | Cl | H | F |
| E1-36.15$^{B'}$ | Z36$^{B'}$, $R^{aB'}$ is H | $CH_3$ | H | F |
| E1-36.16$^{B'}$ | Z36$^{B'}$, $R^{aB'}$ is H | $CH_3$ | F | H |
| E1-36.17$^{B'}$ | Z36$^{B'}$, $R^{aB'}$ is H | Cl | F | H |
| E1-36.18$^{B'}$ | Z36$^{B'}$, $R^{aB'}$ is H | F | F | H |
| E1-36.19$^{B'}$ | Z36$^{B'}$, $R^{aB'}$ is H | F | H | F |
| E1-36.20$^{B'}$ | Z36$^{B'}$, $R^{aB'}$ is H | F | H | Cl |
| E1-36.21$^{B'}$ | Z36$^{B'}$, $R^{aB'}$ is H | F | H | $CH_3$ |
| E1-36.22$^{B'}$ | Z36$^{B'}$, $R^{aB'}$ is H | Cl | H | $CH_3$ |
| E1-36.23$^{B'}$ | Z36$^{B'}$, $R^{aB'}$ is H | $SCH_3$ | H | H |
| E1-36.24$^{B'}$ | Z36$^{B'}$, $R^{aB'}$ is H | $SO_2CH_3$ | H | H |
| E1-36.25$^{B'}$ | Z36$^{B'}$, $R^{aB'}$ is H | ethynyl | H | H |
| E1-36.26$^{B'}$ | 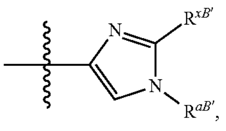 $R^{aB'}$ is H; $R^{xB'}$ is $CH_3$ | $CH_3$ | H | H |

TABLE 13-continued

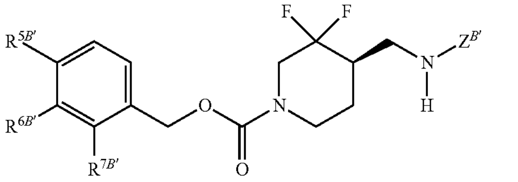

| compound | $Z^{B'}$ | $R^{5B'}$ | $R^{6B'}$ | $R^{7B'}$ |
|---|---|---|---|---|
| E1-36.27$^{B'}$ | 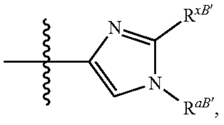 $R^{aB'}$ is H; $R^{xB'}$ is Cl | $CH_3$ | H | H |
| E1-36.28$^{B'}$ | 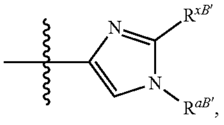 $R^{aB'}$ is H; $R^{xB'}$ is F | $CH_3$ | H | H |
| E1-36.29$^{B'}$ | 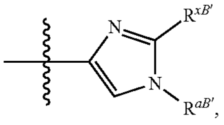 $R^{aB'}$ is H; $R^{xB'}$ is $CF_3$ | $CH_3$ | H | H |
| E1-36.30$^{B'}$ | 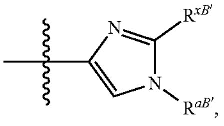 $R^{aB'}$ is H; $R^{xB'}$ is CN | $CH_3$ | H | H |
| E1-37.1$^{B'}$ | Z37$^{B'}$ | H | H | H |
| E1-37.2$^{B'}$ | Z37$^{B'}$ | $CH_3$ | H | H |
| E1-37.3$^{B'}$ | Z37$^{B'}$ | Cl | H | H |
| E1-37.4$^{B'}$ | Z37$^{B'}$ | F | H | H |
| E1-37.5$^{B'}$ | Z37$^{B'}$ | $CH_2CH_3$ | H | H |
| E1-37.6$^{B'}$ | Z37$^{B'}$ | $CF_2H$ | H | H |
| E1-38.1$^{B'}$ | Z38$^{B'}$ | H | H | H |
| E1-38.2$^{B'}$ | Z38$^{B'}$ | $CH_3$ | H | H |
| E1-38.3$^{B'}$ | Z38$^{B'}$ | Cl | H | H |
| E1-38.4$^{B'}$ | Z38$^{B'}$ | F | H | H |
| E1-38.5$^{B'}$ | Z38$^{B'}$ | $CH_2CH_3$ | H | H |
| E1-38.6$^{B'}$ | Z38$^{B'}$ | $CF_2H$ | H | H |
| E1-38.7$^{B'}$ | 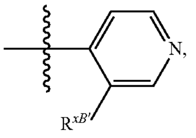 $R^{xB'}$ is F | H | H | H |
| E1-38.8$^{B'}$ | 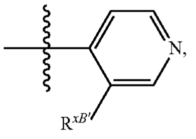 $R^{xB'}$ is F | $CH_3$ | H | H |

TABLE 13-continued

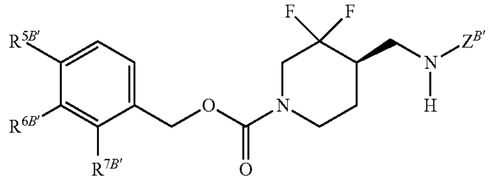

| compound | $Z^{B'}$ | $R^{5B'}$ | $R^{6B'}$ | $R^{7B'}$ |
|---|---|---|---|---|
| E1-38.9$^{B'}$ | 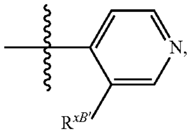 $R^{xB'}$ is F | Cl | H | H |
| E1-38.10$^{B'}$ | 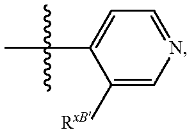 $R^{xB'}$ is F | F | H | H |
| E1-38.11$^{B'}$ | 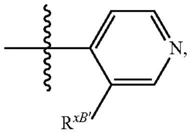 $R^{xB'}$ is F | $CH_2CH_3$ | H | H |
| E1-38.12$^{B'}$ | 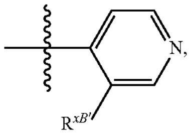 $R^{xB'}$ is F | $CF_2H$ | H | H |

TABLE 14.E2

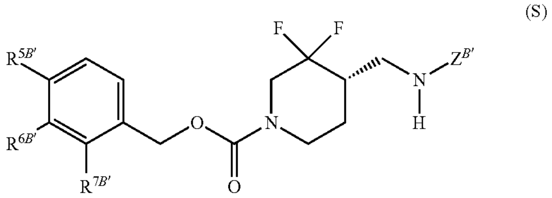

| compound | $Z^{B'}$ | $R^{5B'}$ | $R^{6B'}$ | $R^{7B'}$ |
|---|---|---|---|---|
| E2-1.1$^{B'}$ | Z1$^{B'}$ | H | H | H |
| E2-1.2$^{B'}$ | Z1$^{B'}$ | $CH_3$ | H | H |
| E2-1.3$^{B'}$ | Z1$^{B'}$ | Cl | H | H |
| E2-1.4$^{B'}$ | Z1$^{B'}$ | F | H | H |
| E2-1.5$^{B'}$ | Z1$^{B'}$ | $CH_2CH_3$ | H | H |
| E2-1.6$^{B'}$ | Z1$^{B'}$ | $CF_2H$ | H | H |
| E2-1.7$^{B'}$ | Z1$^{B'}$ | $CH_2F$ | H | H |
| E2-1.8$^{B'}$ | Z1$^{B'}$ | $CF_3$ | H | H |
| E2-1.9$^{B'}$ | Z1$^{B'}$ | $CF_2CH_3$ | H | H |
| E2-1.10$^{B'}$ | Z1$^{B'}$ | $CH_2CF_3$ | H | H |
| E2-1.11$^{B'}$ | Z1$^{B'}$ | cyclopropyl | H | H |
| E2-1.12$^{B'}$ | Z1$^{B'}$ | $OCF_3$ | H | H |
| E2-1.13$^{B'}$ | Z1$^{B'}$ | $OCF_2H$ | H | H |
| E2-1.14$^{B'}$ | Z1$^{B'}$ | Cl | H | F |
| E2-1.15$^{B'}$ | Z1$^{B'}$ | $CH_3$ | H | F |

TABLE 14.E2-continued

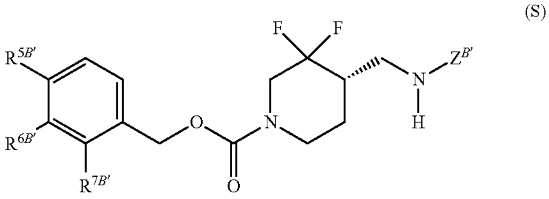

| compound | $Z^{B'}$ | $R^{5B'}$ | $R^{6B'}$ | $R^{7B'}$ |
|---|---|---|---|---|
| E2-1.16$^{B'}$ | Z1$^{B'}$ | $CH_3$ | F | H |
| E2-1.17$^{B'}$ | Z1$^{B'}$ | Cl | F | H |
| E2-1.18$^{B'}$ | Z1$^{B'}$ | F | F | H |
| E2-1.19$^{B'}$ | Z1$^{B'}$ | F | H | F |
| E2-1.20$^{B'}$ | Z1$^{B'}$ | F | H | Cl |
| E2-1.21$^{B'}$ | Z1$^{B'}$ | F | H | $CH_3$ |
| E2-1.22$^{B'}$ | Z1$^{B'}$ | Cl | H | $CH_3$ |
| E2-1.23$^{B'}$ | Z1$^{B'}$ | $SCH_3$ | H | H |
| E2-1.24$^{B'}$ | Z1$^{B'}$ | $SO_2CH_3$ | H | H |
| E2-1.25$^{B'}$ | Z1$^{B'}$ | ethynyl | H | H |
| E2-2.1$^{B'}$ | Z2$^{B'}$ | H | H | H |
| E2-2.2$^{B'}$ | Z2$^{B'}$ | $CH_3$ | H | H |
| E2-2.3$^{B'}$ | Z2$^{B'}$ | Cl | H | H |
| E2-2.4$^{B'}$ | Z2$^{B'}$ | F | H | H |
| E2-2.5$^{B'}$ | Z2$^{B'}$ | $CH_2CH_3$ | H | H |
| E2-2.6$^{B'}$ | Z2$^{B'}$ | $CF_2H$ | H | H |
| E2-2.7$^{B'}$ | Z2$^{B'}$ | $CH_2F$ | H | H |
| E2-2.8$^{B'}$ | Z2$^{B'}$ | $CF_3$ | H | H |
| E2-2.9$^{B'}$ | Z2$^{B'}$ | $CF_2CH_3$ | H | H |
| E2-2.10$^{B'}$ | Z2$^{B'}$ | $CH_2CF_3$ | H | H |
| E2-2.11$^{B'}$ | Z2$^{B'}$ | cyclopropyl | H | H |
| E2-2.12$^{B'}$ | Z2$^{B'}$ | $OCF_3$ | H | H |
| E2-2.13$^{B'}$ | Z2$^{B'}$ | $OCF_2H$ | H | H |
| E2-2.14$^{B'}$ | Z2$^{B'}$ | Cl | H | F |
| E2-2.15$^{B'}$ | Z2$^{B'}$ | $CH_3$ | H | F |
| E2-2.16$^{B'}$ | Z2$^{B'}$ | $CH_3$ | F | H |
| E2-2.17$^{B'}$ | Z2$^{B'}$ | Cl | F | H |
| E2-2.18$^{B'}$ | Z2$^{B'}$ | F | F | H |
| E2-2.19$^{B'}$ | Z2$^{B'}$ | F | H | F |
| E2-2.20$^{B'}$ | Z2$^{B'}$ | F | H | Cl |
| E2-2.21$^{B'}$ | Z2$^{B'}$ | F | H | $CH_3$ |
| E2-2.22$^{B'}$ | Z2$^{B'}$ | Cl | H | $CH_3$ |
| E2-2.23$^{B'}$ | Z2$^{B'}$ | $SCH_3$ | H | H |
| E2-2.24$^{B'}$ | Z2$^{B'}$ | $SO_2CH_3$ | H | H |
| E2-2.25$^{B'}$ | Z2$^{B'}$ | ethynyl | H | H |
| E2-3.1$^{B'}$ | Z3$^{B'}$ | H | H | H |
| E2-3.2$^{B'}$ | Z3$^{B'}$ | $CH_3$ | H | H |
| E2-3.3$^{B'}$ | Z3$^{B'}$ | Cl | H | H |
| E2-3.4$^{B'}$ | Z3$^{B'}$ | F | H | H |
| E2-3.5$^{B'}$ | Z3$^{B'}$ | $CH_2CH_3$ | H | H |
| E2-3.6$^{B'}$ | Z3$^{B'}$ | $CF_2H$ | H | H |
| E2-3.7$^{B'}$ | Z3$^{B'}$ | $CH_2F$ | H | H |
| E2-3.8$^{B'}$ | Z3$^{B'}$ | $CF_3$ | H | H |
| E2-3.9$^{B'}$ | Z3$^{B'}$ | $CF_2CH_3$ | H | H |
| E2-3.10$^{B'}$ | Z3$^{B'}$ | $CH_2CF_3$ | H | H |
| E2-3.11$^{B'}$ | Z3$^{B'}$ | cyclopropyl | H | H |
| E2-3.12$^{B'}$ | Z3$^{B'}$ | $OCF_3$ | H | H |
| E2-3.13$^{B'}$ | Z3$^{B'}$ | $OCF_2H$ | H | H |
| E2-3.14$^{B'}$ | Z3$^{B'}$ | Cl | H | F |
| E2-3.15$^{B'}$ | Z3$^{B'}$ | $CH_3$ | H | F |
| E2-3.16$^{B'}$ | Z3$^{B'}$ | $CH_3$ | F | H |
| E2-3.17$^{B'}$ | Z3$^{B'}$ | Cl | F | H |
| E2-3.18$^{B'}$ | Z3$^{B'}$ | F | F | H |
| E2-3.19$^{B'}$ | Z3$^{B'}$ | F | H | F |
| E2-3.20$^{B'}$ | Z3$^{B'}$ | F | H | Cl |
| E2-3.21$^{B'}$ | Z3$^{B'}$ | F | H | $CH_3$ |
| E2-3.22$^{B'}$ | Z3$^{B'}$ | Cl | H | $CH_3$ |
| E2-3.23$^{B'}$ | Z3$^{B'}$ | $SCH_3$ | H | H |
| E2-3.24$^{B'}$ | Z3$^{B'}$ | $SO_2CH_3$ | H | H |
| E2-3.25$^{B'}$ | Z3$^{B'}$ | ethynyl | H | H |
| E2-4.1$^{B'}$ | Z4$^{B'}$ | H | H | H |
| E2-4.2$^{B'}$ | Z4$^{B'}$ | $CH_3$ | H | H |
| E2-4.3$^{B'}$ | Z4$^{B'}$ | Cl | H | H |
| E2-4.4$^{B'}$ | Z4$^{B'}$ | F | H | H |
| E2-4.5$^{B'}$ | Z4$^{B'}$ | $CH_2CH_3$ | H | H |
| E2-4.6$^{B'}$ | Z4$^{B'}$ | $CF_2H$ | H | H |
| E2-4.7$^{B'}$ | Z4$^{B'}$ | $CH_2F$ | H | H |

TABLE 14.E2-continued

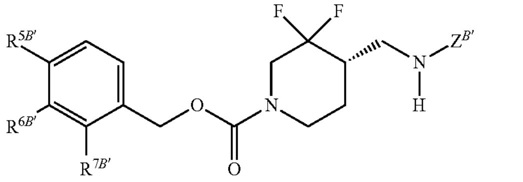

(S)

| compound | $Z^{B'}$ | $R^{5B'}$ | $R^{6B'}$ | $R^{7B'}$ |
|---|---|---|---|---|
| E2-4.8$^{B'}$ | Z4$^{B'}$ | $CF_3$ | H | H |
| E2-4.9$^{B'}$ | Z4$^{B'}$ | $CF_2CH_3$ | H | H |
| E2-4.10$^{B'}$ | Z4$^{B'}$ | $CH_2CF_3$ | H | H |
| E2-4.11$^{B'}$ | Z4$^{B'}$ | cyclopropyl | H | H |
| E2-4.12$^{B'}$ | Z4$^{B'}$ | $OCF_3$ | H | H |
| E2-4.13$^{B'}$ | Z4$^{B'}$ | $OCF_2H$ | H | H |
| E2-4.14$^{B'}$ | Z4$^{B'}$ | Cl | H | F |
| E2-4.15$^{B'}$ | Z4$^{B'}$ | $CH_3$ | H | F |
| E2-4.16$^{B'}$ | Z4$^{B'}$ | $CH_3$ | F | H |
| E2-4.17$^{B'}$ | Z4$^{B'}$ | Cl | F | H |
| E2-4.18$^{B'}$ | Z4$^{B'}$ | F | F | H |
| E2-4.19$^{B'}$ | Z4$^{B'}$ | F | H | F |
| E2-4.20$^{B'}$ | Z4$^{B'}$ | F | H | Cl |
| E2-4.21$^{B'}$ | Z4$^{B'}$ | F | H | $CH_3$ |
| E2-4.22$^{B'}$ | Z4$^{B'}$ | Cl | H | $CH_3$ |
| E2-4.23$^{B'}$ | Z4$^{B'}$ | $SCH_3$ | H | H |
| E2-4.24$^{B'}$ | Z4$^{B'}$ | $SO_2CH_3$ | H | H |
| E2-4.25$^{B'}$ | Z4$^{B'}$ | ethynyl | H | H |
| E2-5.1$^{B'}$ | Z5$^{B'}$ | H | H | H |
| E2-5.2$^{B'}$ | Z5$^{B'}$ | $CH_3$ | H | H |
| E2-5.3$^{B'}$ | Z5$^{B'}$ | Cl | H | H |
| E2-5.4$^{B'}$ | Z5$^{B'}$ | F | H | H |
| E2-5.5$^{B'}$ | Z5$^{B'}$ | $CH_2CH_3$ | H | H |
| E2-5.6$^{B'}$ | Z5$^{B'}$ | $CF_2H$ | H | H |
| E2-5.7$^{B'}$ | Z5$^{B'}$ | $CH_2F$ | H | H |
| E2-5.8$^{B'}$ | Z5$^{B'}$ | $CF_3$ | H | H |
| E2-5.9$^{B'}$ | Z5$^{B'}$ | $CF_2CH_3$ | H | H |
| E2-5.10$^{B'}$ | Z5$^{B'}$ | $CH_2CF_3$ | H | H |
| E2-5.11$^{B'}$ | Z5$^{B'}$ | cyclopropyl | H | H |
| E2-5.12$^{B'}$ | Z5$^{B'}$ | $OCF_3$ | H | H |
| E2-5.13$^{B'}$ | Z5$^{B'}$ | $OCF_2H$ | H | H |
| E2-5.14$^{B'}$ | Z5$^{B'}$ | Cl | H | F |
| E2-5.15$^{B'}$ | Z5$^{B'}$ | $CH_3$ | H | F |
| E2-5.16$^{B'}$ | Z5$^{B'}$ | $CH_3$ | F | H |
| E2-5.17$^{B'}$ | Z5$^{B'}$ | Cl | F | H |
| E2-5.18$^{B'}$ | Z5$^{B'}$ | F | F | H |
| E2-5.19$^{B'}$ | Z5$^{B'}$ | F | H | F |
| E2-5.20$^{B'}$ | Z5$^{B'}$ | F | H | Cl |
| E2-5.21$^{B'}$ | Z5$^{B'}$ | F | H | $CH_3$ |
| E2-5.22$^{B'}$ | Z5$^{B'}$ | Cl | H | $CH_3$ |
| E2-5.23$^{B'}$ | Z5$^{B'}$ | $SCH_3$ | H | H |
| E2-5.24$^{B'}$ | Z5$^{B'}$ | $SO_2CH_3$ | H | H |
| E2-5.25$^{B'}$ | Z5$^{B'}$ | ethynyl | H | H |
| E2-6.1$^{B'}$ | Z6$^{B'}$, R$^{aB'}$ is H | H | H | H |
| E2-6.2$^{B'}$ | Z6$^{B'}$, R$^{aB'}$ is H | $CH_3$ | H | H |
| E2-6.3$^{B'}$ | Z6$^{B'}$, R$^{aB'}$ is H | Cl | H | H |
| E2-6.4$^{B'}$ | Z6$^{B'}$, R$^{aB'}$ is H | F | H | H |
| E2-6.5$^{B'}$ | Z6$^{B'}$, R$^{aB'}$ is H | $CH_2CH_3$ | H | H |
| E2-6.6$^{B'}$ | Z6$^{B'}$, R$^{aB'}$ is H | $CF_2H$ | H | H |
| E2-6.7$^{B'}$ | Z6$^{B'}$, R$^{aB'}$ is H | $CH_2F$ | H | H |
| E2-6.8$^{B'}$ | Z6$^{B'}$, R$^{aB'}$ is H | $CF_3$ | H | H |
| E2-6.9$^{B'}$ | Z6$^{B'}$, R$^{aB'}$ is H | $CF_2CH_3$ | H | H |
| E2-6.10$^{B'}$ | Z6$^{B'}$, R$^{aB'}$ is H | $CH_2CF_3$ | H | H |
| E2-6.11$^{B'}$ | Z6$^{B'}$, R$^{aB'}$ is H | cyclopropyl | H | H |
| E2-6.12$^{B'}$ | Z6$^{B'}$, R$^{aB'}$ is H | $OCF_3$ | H | H |
| E2-6.13$^{B'}$ | Z6$^{B'}$, R$^{aB'}$ is H | $OCF_2H$ | H | H |
| E2-6.14$^{B'}$ | Z6$^{B'}$, R$^{aB'}$ is H | Cl | H | F |
| E2-6.15$^{B'}$ | Z6$^{B'}$, R$^{aB'}$ is H | $CH_3$ | H | F |
| E2-6.16$^{B'}$ | Z6$^{B'}$, R$^{aB'}$ is H | $CH_3$ | F | H |
| E2-6.17$^{B'}$ | Z6$^{B'}$, R$^{aB'}$ is H | Cl | F | H |
| E2-6.18$^{B'}$ | Z6$^{B'}$, R$^{aB'}$ is H | F | F | H |
| E2-6.19$^{B'}$ | Z6$^{B'}$, R$^{aB'}$ is H | F | H | F |
| E2-6.20$^{B'}$ | Z6$^{B'}$, R$^{aB'}$ is H | F | H | Cl |
| E2-6.21$^{B'}$ | Z6$^{B'}$, R$^{aB'}$ is H | F | H | $CH_3$ |
| E2-6.22$^{B'}$ | Z6$^{B'}$, R$^{aB'}$ is H | Cl | H | $CH_3$ |
| E2-6.23$^{B'}$ | Z6$^{B'}$, R$^{aB'}$ is H | $SCH_3$ | H | H |
| E2-6.24$^{B'}$ | Z6$^{B'}$, R$^{aB'}$ is H | $SO_2CH_3$ | H | H |

TABLE 14.E2-continued

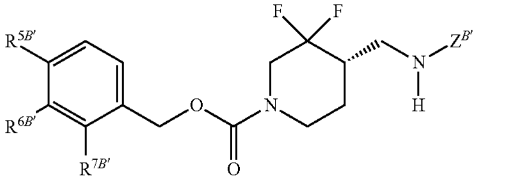

(S)

| compound | $Z^{B'}$ | $R^{5B'}$ | $R^{6B'}$ | $R^{7B'}$ |
|---|---|---|---|---|
| E2-6.25$^{B'}$ | Z6$^{B'}$, R$^{aB'}$ is H | ethynyl | H | H |
| E2-7.1$^{B'}$ | Z7$^{B'}$, R$^{aB'}$ is H | H | H | H |
| E2-7.2$^{B'}$ | Z7$^{B'}$, R$^{aB'}$ is H | $CH_3$ | H | H |
| E2-7.3$^{B'}$ | Z7$^{B'}$, R$^{aB'}$ is H | Cl | H | H |
| E2-7.4$^{B'}$ | Z7$^{B'}$, R$^{aB'}$ is H | F | H | H |
| E2-7.5$^{B'}$ | Z7$^{B'}$, R$^{aB'}$ is H | $CH_2CH_3$ | H | H |
| E2-7.6$^{B'}$ | Z7$^{B'}$, R$^{aB'}$ is H | $CF_2H$ | H | H |
| E2-7.7$^{B'}$ | Z7$^{B'}$, R$^{aB'}$ is H | $CH_2F$ | H | H |
| E2-7.8$^{B'}$ | Z7$^{B'}$, R$^{aB'}$ is H | $CF_3$ | H | H |
| E2-7.9$^{B'}$ | Z7$^{B'}$, R$^{aB'}$ is H | $CF_2CH_3$ | H | H |
| E2-7.10$^{B'}$ | Z7$^{B'}$, R$^{aB'}$ is H | $CH_2CF_3$ | H | H |
| E2-7.11$^{B'}$ | Z7$^{B'}$, R$^{aB'}$ is H | cyclopropyl | H | H |
| E2-7.12$^{B'}$ | Z7$^{B'}$, R$^{aB'}$ is H | $OCF_3$ | H | H |
| E2-7.13$^{B'}$ | Z7$^{B'}$, R$^{aB'}$ is H | $OCF_2H$ | H | H |
| E2-7.14$^{B'}$ | Z7$^{B'}$, R$^{aB'}$ is H | Cl | H | F |
| E2-7.15$^{B'}$ | Z7$^{B'}$, R$^{aB'}$ is H | $CH_3$ | H | F |
| E2-7.16$^{B'}$ | Z7$^{B'}$, R$^{aB'}$ is H | $CH_3$ | F | H |
| E2-7.17$^{B'}$ | Z7$^{B'}$, R$^{aB'}$ is H | Cl | F | H |
| E2-7.18$^{B'}$ | Z7$^{B'}$, R$^{aB'}$ is H | F | F | H |
| E2-7.19$^{B'}$ | Z7$^{B'}$, R$^{aB'}$ is H | F | H | F |
| E2-7.20$^{B'}$ | Z7$^{B'}$, R$^{aB'}$ is H | F | H | Cl |
| E2-7.21$^{B'}$ | Z7$^{B'}$, R$^{aB'}$ is H | F | H | $CH_3$ |
| E2-7.22$^{B'}$ | Z7$^{B'}$, R$^{aB'}$ is H | Cl | H | $CH_3$ |
| E2-7.23$^{B'}$ | Z7$^{B'}$, R$^{aB'}$ is H | $SCH_3$ | H | H |
| E2-7.24$^{B'}$ | Z7$^{B'}$, R$^{aB'}$ is H | $SO_2CH_3$ | H | H |
| E2-7.25$^{B'}$ | Z7$^{B'}$, R$^{aB'}$ is H | ethynyl | H | H |
| E2-8.1$^{B'}$ | Z8$^{B'}$, R$^{aB'}$ is H | H | H | H |
| E2-8.2$^{B'}$ | Z8$^{B'}$, R$^{aB'}$ is H | $CH_3$ | H | H |
| E2-8.3$^{B'}$ | Z8$^{B'}$, R$^{aB'}$ is H | Cl | H | H |
| E2-8.4$^{B'}$ | Z8$^{B'}$, R$^{aB'}$ is H | F | H | H |
| E2-8.5$^{B'}$ | Z8$^{B'}$, R$^{aB'}$ is H | $CH_2CH_3$ | H | H |
| E2-8.6$^{B'}$ | Z8$^{B'}$, R$^{aB'}$ is H | $CF_2H$ | H | H |
| E2-8.7$^{B'}$ | Z8$^{B'}$, R$^{aB'}$ is H | $CH_2F$ | H | H |
| E2-8.8$^{B'}$ | Z8$^{B'}$, R$^{aB'}$ is H | $CF_3$ | H | H |
| E2-8.9$^{B'}$ | Z8$^{B'}$, R$^{aB'}$ is H | $CF_2CH_3$ | H | H |
| E2-8.10$^{B'}$ | Z8$^{B'}$, R$^{aB'}$ is H | $CH_2CF_3$ | H | H |
| E2-8.11$^{B'}$ | Z8$^{B'}$, R$^{aB'}$ is H | cyclopropyl | H | H |
| E2-8.12$^{B'}$ | Z8$^{B'}$, R$^{aB'}$ is H | $OCF_3$ | H | H |
| E2-8.13$^{B'}$ | Z8$^{B'}$, R$^{aB'}$ is H | $OCF_2H$ | H | H |
| E2-8.14$^{B'}$ | Z8$^{B'}$, R$^{aB'}$ is H | Cl | H | F |
| E2-8.15$^{B'}$ | Z8$^{B'}$, R$^{aB'}$ is H | $CH_3$ | H | F |
| E2-8.16$^{B'}$ | Z8$^{B'}$, R$^{aB'}$ is H | $CH_3$ | F | H |
| E2-8.17$^{B'}$ | Z8$^{B'}$, R$^{aB'}$ is H | Cl | F | H |
| E2-8.18$^{B'}$ | Z8$^{B'}$, R$^{aB'}$ is H | F | F | H |
| E2-8.19$^{B'}$ | Z8$^{B'}$, R$^{aB'}$ is H | F | H | F |
| E2-8.20$^{B'}$ | Z8$^{B'}$, R$^{aB'}$ is H | F | H | Cl |
| E2-8.21$^{B'}$ | Z8$^{B'}$, R$^{aB'}$ is H | F | H | $CH_3$ |
| E2-8.22$^{B'}$ | Z8$^{B'}$, R$^{aB'}$ is H | Cl | H | $CH_3$ |
| E2-8.23$^{B'}$ | Z8$^{B'}$, R$^{aB'}$ is H | $SCH_3$ | H | H |
| E2-8.24$^{B'}$ | Z8$^{B'}$, R$^{aB'}$ is H | $SO_2CH_3$ | H | H |
| E2-8.25$^{B'}$ | Z8$^{B'}$, R$^{aB'}$ is H | ethynyl | H | H |
| E2-9.1$^{B'}$ | Z9$^{B'}$ | H | H | H |
| E2-9.2$^{B'}$ | Z9$^{B'}$ | $CH_3$ | H | H |
| E2-9.3$^{B'}$ | Z9$^{B'}$ | Cl | H | H |
| E2-9.4$^{B'}$ | Z9$^{B'}$ | F | H | H |
| E2-9.5$^{B'}$ | Z9$^{B'}$ | $CH_2CH_3$ | H | H |
| E2-9.6$^{B'}$ | Z9$^{B'}$ | $CF_2H$ | H | H |
| E2-9.7$^{B'}$ | Z9$^{B'}$ | $CH_2F$ | H | H |
| E2-9.8$^{B'}$ | Z9$^{B'}$ | $CF_3$ | H | H |
| E2-9.9$^{B'}$ | Z9$^{B'}$ | $CF_2CH_3$ | H | H |
| E2-9.10$^{B'}$ | Z9$^{B'}$ | $CH_2CF_3$ | H | H |
| E2-9.11$^{B'}$ | Z9$^{B'}$ | cyclopropyl | H | H |
| E2-9.12$^{B'}$ | Z9$^{B'}$ | $OCF_3$ | H | H |
| E2-9.13$^{B'}$ | Z9$^{B'}$ | $OCF_2H$ | H | H |
| E2-9.14$^{B'}$ | Z9$^{B'}$ | Cl | H | F |
| E2-9.15$^{B'}$ | Z9$^{B'}$ | $CH_3$ | H | F |
| E2-9.16$^{B'}$ | Z9$^{B'}$ | $CH_3$ | F | H |

TABLE 14.E2-continued (S)

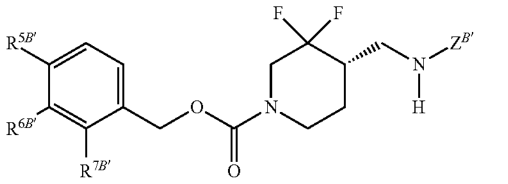

| compound | Z$^{B'}$ | R$^{5B'}$ | R$^{6B'}$ | R$^{7B'}$ |
|---|---|---|---|---|
| E2-9.17$^{B'}$ | Z9$^{B'}$ | Cl | F | H |
| E2-9.18$^{B'}$ | Z9$^{B'}$ | F | F | H |
| E2-9.19$^{B'}$ | Z9$^{B'}$ | F | H | F |
| E2-9.20$^{B'}$ | Z9$^{B'}$ | F | H | Cl |
| E2-9.21$^{B'}$ | Z9$^{B'}$ | F | H | $CH_3$ |
| E2-9.22$^{B'}$ | Z9$^{B'}$ | Cl | H | $CH_3$ |
| E2-9.23$^{B'}$ | Z9$^{B'}$ | $SCH_3$ | H | H |
| E2-9.24$^{B'}$ | Z9$^{B'}$ | $SO_2CH_3$ | H | H |
| E2-9.25$^{B'}$ | Z9$^{B'}$ | ethynyl | H | H |
| E2-10.1$^{B'}$ | Z10$^{B'}$ | H | H | H |
| E2-10.2$^{B'}$ | Z10$^{B'}$ | $CH_3$ | H | H |
| E2-10.3$^{B'}$ | Z10$^{B'}$ | Cl | H | H |
| E2-10.4$^{B'}$ | Z10$^{B'}$ | F | H | H |
| E2-10.5$^{B'}$ | Z10$^{B'}$ | $CH_2CH_3$ | H | H |
| E2-10.6$^{B'}$ | Z10$^{B'}$ | $CF_2H$ | H | H |
| E2-10.7$^{B'}$ | Z10$^{B'}$ | $CH_2F$ | H | H |
| E2-10.8$^{B'}$ | Z10$^{B'}$ | $CF_3$ | H | H |
| E2-10.9$^{B'}$ | Z10$^{B'}$ | $CF_2CH_3$ | H | H |
| E2-10.10$^{B'}$ | Z10$^{B'}$ | $CH_2CF_3$ | H | H |
| E2-10.11$^{B'}$ | Z10$^{B'}$ | cyclopropyl | H | H |
| E2-10.12$^{B'}$ | Z10$^{B'}$ | $OCF_3$ | H | H |
| E2-10.13$^{B'}$ | Z10$^{B'}$ | $OCF_2H$ | H | H |
| E2-10.14$^{B'}$ | Z10$^{B'}$ | Cl | H | F |
| E2-10.15$^{B'}$ | Z10$^{B'}$ | $CH_3$ | H | F |
| E2-10.16$^{B'}$ | Z10$^{B'}$ | $CH_3$ | F | H |
| E2-10.17$^{B'}$ | Z10$^{B'}$ | Cl | F | H |
| E2-10.18$^{B'}$ | Z10$^{B'}$ | F | F | H |
| E2-10.19$^{B'}$ | Z10$^{B'}$ | F | H | F |
| E2-10.20$^{B'}$ | Z10$^{B'}$ | F | H | Cl |
| E2-10.21$^{B'}$ | Z10$^{B'}$ | F | H | $CH_3$ |
| E2-10.22$^{B'}$ | Z10$^{B'}$ | Cl | H | $CH_3$ |
| E2-10.23$^{B'}$ | Z10$^{B'}$ | $SCH_3$ | H | H |
| E2-10.24$^{B'}$ | Z10$^{B'}$ | $SO_2CH_3$ | H | H |
| E2-10.25$^{B'}$ | Z10$^{B'}$ | ethynyl | H | H |
| E2-11.1$^{B'}$ | Z11$^{B'}$, R$^{aB'}$ is H | H | H | H |
| E2-11.2$^{B'}$ | Z11$^{B'}$, R$^{aB'}$ is H | $CH_3$ | H | H |
| E2-11.3$^{B'}$ | Z11$^{B'}$, R$^{aB'}$ is H | Cl | H | H |
| E2-11.4$^{B'}$ | Z11$^{B'}$, R$^{aB'}$ is H | F | H | H |
| E2-11.5$^{B'}$ | Z11$^{B'}$, R$^{aB'}$ is H | $CH_2CH_3$ | H | H |
| E2-11.6$^{B'}$ | Z11$^{B'}$, R$^{aB'}$ is H | $CF_2H$ | H | H |
| E2-11.7$^{B'}$ | Z11$^{B'}$, R$^{aB'}$ is H | $CH_2F$ | H | H |
| E2-11.8$^{B'}$ | Z11$^{B'}$, R$^{aB'}$ is H | $CF_3$ | H | H |
| E2-11.9$^{B'}$ | Z11$^{B'}$, R$^{aB'}$ is H | $CF_2CH_3$ | H | H |
| E2-11.10$^{B'}$ | Z11$^{B'}$, R$^{aB'}$ is H | $CH_2CF_3$ | H | H |
| E2-11.11$^{B'}$ | Z11$^{B'}$, R$^{aB'}$ is H | cyclopropyl | H | H |
| E2-11.12$^{B'}$ | Z11$^{B'}$, R$^{aB'}$ is H | $OCF_3$ | H | H |
| E2-11.13$^{B'}$ | Z11$^{B'}$, R$^{aB'}$ is H | $OCF_2H$ | H | H |
| E2-11.14$^{B'}$ | Z11$^{B'}$, R$^{aB'}$ is H | Cl | H | F |
| E2-11.15$^{B'}$ | Z11$^{B'}$, R$^{aB'}$ is H | $CH_3$ | H | F |
| E2-11.16$^{B'}$ | Z11$^{B'}$, R$^{aB'}$ is H | $CH_3$ | F | H |
| E2-11.17$^{B'}$ | Z11$^{B'}$, R$^{aB'}$ is H | Cl | F | H |
| E2-11.18$^{B'}$ | Z11$^{B'}$, R$^{aB'}$ is H | F | F | H |
| E2-11.19$^{B'}$ | Z11$^{B'}$, R$^{aB'}$ is H | F | H | F |
| E2-11.20$^{B'}$ | Z11$^{B'}$, R$^{aB'}$ is H | F | H | Cl |
| E2-11.21$^{B'}$ | Z11$^{B'}$, R$^{aB'}$ is H | F | H | $CH_3$ |
| E2-11.22$^{B'}$ | Z11$^{B'}$, R$^{aB'}$ is H | Cl | H | $CH_3$ |
| E2-11.23$^{B'}$ | Z11$^{B'}$, R$^{aB'}$ is H | $SCH_3$ | H | H |
| E2-11.24$^{B'}$ | Z11$^{B'}$, R$^{aB'}$ is H | $SO_2CH_3$ | H | H |
| E2-11.25$^{B'}$ | Z11$^{B'}$, R$^{aB'}$ is H | ethynyl | H | H |
| E2-12.1$^{B'}$ | Z12$^{B'}$ | H | H | H |
| E2-12.2$^{B'}$ | Z12$^{B'}$ | $CH_3$ | H | H |
| E2-12.3$^{B'}$ | Z12$^{B'}$ | Cl | H | H |
| E2-12.4$^{B'}$ | Z12$^{B'}$ | F | H | H |
| E2-12.5$^{B'}$ | Z12$^{B'}$ | $CH_2CH_3$ | H | H |
| E2-12.6$^{B'}$ | Z12$^{B'}$ | $CF_2H$ | H | H |
| E2-12.7$^{B'}$ | Z12$^{B'}$ | $CH_2F$ | H | H |
| E2-12.8$^{B'}$ | Z12$^{B'}$ | $CF_3$ | H | H |

TABLE 14.E2-continued (S)

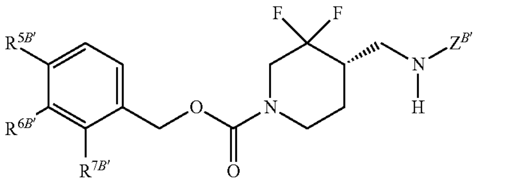

| compound | Z$^{B'}$ | R$^{5B'}$ | R$^{6B'}$ | R$^{7B'}$ |
|---|---|---|---|---|
| E2-12.9$^{B'}$ | Z12$^{B'}$ | $CF_2CH_3$ | H | H |
| E2-12.10$^{B'}$ | Z12$^{B'}$ | $CH_2CF_3$ | H | H |
| E2-12.11$^{B'}$ | Z12$^{B'}$ | cyclopropyl | H | H |
| E2-12.12$^{B'}$ | Z12$^{B'}$ | $OCF_3$ | H | H |
| E2-12.13$^{B'}$ | Z12$^{B'}$ | $OCF_2H$ | H | H |
| E2-12.14$^{B'}$ | Z12$^{B'}$ | Cl | H | F |
| E2-12.15$^{B'}$ | Z12$^{B'}$ | $CH_3$ | H | F |
| E2-12.16$^{B'}$ | Z12$^{B'}$ | $CH_3$ | F | H |
| E2-12.17$^{B'}$ | Z12$^{B'}$ | Cl | F | H |
| E2-12.18$^{B'}$ | Z12$^{B'}$ | F | F | H |
| E2-12.19$^{B'}$ | Z12$^{B'}$ | F | H | F |
| E2-12.20$^{B'}$ | Z12$^{B'}$ | F | H | Cl |
| E2-12.21$^{B'}$ | Z12$^{B'}$ | F | H | $CH_3$ |
| E2-12.22$^{B'}$ | Z12$^{B'}$ | Cl | H | $CH_3$ |
| E2-12.23$^{B'}$ | Z12$^{B'}$ | $SCH_3$ | H | H |
| E2-12.24$^{B'}$ | Z12$^{B'}$ | $SO_2CH_3$ | H | H |
| E2-12.25$^{B'}$ | Z12$^{B'}$ | ethynyl | H | H |
| E2-13.1$^{B'}$ | Z13$^{B'}$, R$^{aB'}$ is H | H | H | H |
| E2-13.2$^{B'}$ | Z13$^{B'}$, R$^{aB'}$ is H | $CH_3$ | H | H |
| E2-13.3$^{B'}$ | Z13$^{B'}$, R$^{aB'}$ is H | Cl | H | H |
| E2-13.4$^{B'}$ | Z13$^{B'}$, R$^{aB'}$ is H | F | H | H |
| E2-13.5$^{B'}$ | Z13$^{B'}$, R$^{aB'}$ is H | $CH_2CH_3$ | H | H |
| E2-13.6$^{B'}$ | Z13$^{B'}$, R$^{aB'}$ is H | $CF_2H$ | H | H |
| E2-13.7$^{B'}$ | Z13$^{B'}$, R$^{aB'}$ is H | $CH_2F$ | H | H |
| E2-13.8$^{B'}$ | Z13$^{B'}$, R$^{aB'}$ is H | $CF_3$ | H | H |
| E2-13.9$^{B'}$ | Z13$^{B'}$, R$^{aB'}$ is H | $CF_2CH_3$ | H | H |
| E2-13.10$^{B'}$ | Z13$^{B'}$, R$^{aB'}$ is H | $CH_2CF_3$ | H | H |
| E2-13.11$^{B'}$ | Z13$^{B'}$, R$^{aB'}$ is H | cyclopropyl | H | H |
| E2-13.12$^{B'}$ | Z13$^{B'}$, R$^{aB'}$ is H | $OCF_3$ | H | H |
| E2-13.13$^{B'}$ | Z13$^{B'}$, R$^{aB'}$ is H | $OCF_2H$ | H | H |
| E2-13.14$^{B'}$ | Z13$^{B'}$, R$^{aB'}$ is H | Cl | H | F |
| E2-13.15$^{B'}$ | Z13$^{B'}$, R$^{aB'}$ is H | $CH_3$ | H | F |
| E2-13.16$^{B'}$ | Z13$^{B'}$, R$^{aB'}$ is H | $CH_3$ | F | H |
| E2-13.17$^{B'}$ | Z13$^{B'}$, R$^{aB'}$ is H | Cl | F | H |
| E2-13.18$^{B'}$ | Z13$^{B'}$, R$^{aB'}$ is H | F | F | H |
| E2-13.19$^{B'}$ | Z13$^{B'}$, R$^{aB'}$ is H | F | H | F |
| E2-13.20$^{B'}$ | Z13$^{B'}$, R$^{aB'}$ is H | F | H | Cl |
| E2-13.21$^{B'}$ | Z13$^{B'}$, R$^{aB'}$ is H | F | H | $CH_3$ |
| E2-13.22$^{B'}$ | Z13$^{B'}$, R$^{aB'}$ is H | Cl | H | $CH_3$ |
| E2-13.23$^{B'}$ | Z13$^{B'}$, R$^{aB'}$ is H | $SCH_3$ | H | H |
| E2-13.24$^{B'}$ | Z13$^{B'}$, R$^{aB'}$ is H | $SO_2CH_3$ | H | H |
| E2-13.25$^{B'}$ | Z13$^{B'}$, R$^{aB'}$ is H | ethynyl | H | H |
| E2-14.1$^{B'}$ | Z14$^{B'}$, R$^{aB'}$ is H | H | H | H |
| E2-14.2$^{B'}$ | Z14$^{B'}$, R$^{aB'}$ is H | $CH_3$ | H | H |
| E2-14.3$^{B'}$ | Z14$^{B'}$, R$^{aB'}$ is H | Cl | H | H |
| E2-14.4$^{B'}$ | Z14$^{B'}$, R$^{aB'}$ is H | F | H | H |
| E2-14.5$^{B'}$ | Z14$^{B'}$, R$^{aB'}$ is H | $CH_2CH_3$ | H | H |
| E2-14.6$^{B'}$ | Z14$^{B'}$, R$^{aB'}$ is H | $CF_2H$ | H | H |
| E2-14.7$^{B'}$ | Z14$^{B'}$, R$^{aB'}$ is H | $CH_2F$ | H | H |
| E2-14.8$^{B'}$ | Z14$^{B'}$, R$^{aB'}$ is H | $CF_3$ | H | H |
| E2-14.9$^{B'}$ | Z14$^{B'}$, R$^{aB'}$ is H | $CF_2CH_3$ | H | H |
| E2-14.10$^{B'}$ | Z14$^{B'}$, R$^{aB'}$ is H | $CH_2CF_3$ | H | H |
| E2-14.11$^{B'}$ | Z14$^{B'}$, R$^{aB'}$ is H | cyclopropyl | H | H |
| E2-14.12$^{B'}$ | Z14$^{B'}$, R$^{aB'}$ is H | $OCF_3$ | H | H |
| E2-14.13$^{B'}$ | Z14$^{B'}$, R$^{aB'}$ is H | $OCF_2H$ | H | H |
| E2-14.14$^{B'}$ | Z14$^{B'}$, R$^{aB'}$ is H | Cl | H | F |
| E2-14.15$^{B'}$ | Z14$^{B'}$, R$^{aB'}$ is H | $CH_3$ | H | F |
| E2-14.16$^{B'}$ | Z14$^{B'}$, R$^{aB'}$ is H | $CH_3$ | F | H |
| E2-14.17$^{B'}$ | Z14$^{B'}$, R$^{aB'}$ is H | Cl | F | H |
| E2-14.18$^{B'}$ | Z14$^{B'}$, R$^{aB'}$ is H | F | F | H |
| E2-14.19$^{B'}$ | Z14$^{B'}$, R$^{aB'}$ is H | F | H | F |
| E2-14.20$^{B'}$ | Z14$^{B'}$, R$^{aB'}$ is H | F | H | Cl |
| E2-14.21$^{B'}$ | Z14$^{B'}$, R$^{aB'}$ is H | F | H | $CH_3$ |
| E2-14.22$^{B'}$ | Z14$^{B'}$, R$^{aB'}$ is H | Cl | H | $CH_3$ |
| E2-14.23$^{B'}$ | Z14$^{B'}$, R$^{aB'}$ is H | $SCH_3$ | H | H |
| E2-14.24$^{B'}$ | Z14$^{B'}$, R$^{aB'}$ is H | $SO_2CH_3$ | H | H |
| E2-14.25$^{B'}$ | Z14$^{B'}$, R$^{aB'}$ is H | ethynyl | H | H |

TABLE 14.E2-continued (S)

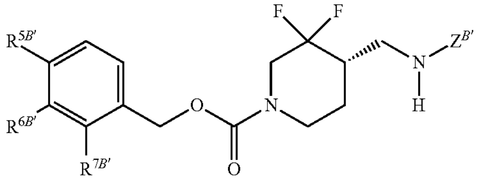

| compound | $Z^{B'}$ | $R^{5B'}$ | $R^{6B'}$ | $R^{7B'}$ |
|---|---|---|---|---|
| E2-15.1$^{B'}$ | Z15$^{B'}$, $R^{aB'}$ is H | H | H | H |
| E2-15.2$^{B'}$ | Z15$^{B'}$, $R^{aB'}$ is H | $CH_3$ | H | H |
| E2-15.3$^{B'}$ | Z15$^{B'}$, $R^{aB'}$ is H | Cl | H | H |
| E2-15.4$^{B'}$ | Z15$^{B'}$, $R^{aB'}$ is H | F | H | H |
| E2-15.5$^{B'}$ | Z15$^{B'}$, $R^{aB'}$ is H | $CH_2CH_3$ | H | H |
| E2-15.6$^{B'}$ | Z15$^{B'}$, $R^{aB'}$ is H | $CF_2H$ | H | H |
| E2-15.7$^{B'}$ | Z15$^{B'}$, $R^{aB'}$ is H | $CH_2F$ | H | H |
| E2-15.8$^{B'}$ | Z15$^{B'}$, $R^{aB'}$ is H | $CF_3$ | H | H |
| E2-15.9$^{B'}$ | Z15$^{B'}$, $R^{aB'}$ is H | $CF_2CH_3$ | H | H |
| E2-15.10$^{B'}$ | Z15$^{B'}$, $R^{aB'}$ is H | $CH_2CF_3$ | H | H |
| E2-15.11$^{B'}$ | Z15$^{B'}$, $R^{aB'}$ is H | cyclopropyl | H | H |
| E2-15.12$^{B'}$ | Z15$^{B'}$, $R^{aB'}$ is H | $OCF_3$ | H | H |
| E2-15.13$^{B'}$ | Z15$^{B'}$, $R^{aB'}$ is H | $OCF_2H$ | H | H |
| E2-15.14$^{B'}$ | Z15$^{B'}$, $R^{aB'}$ is H | Cl | H | F |
| E2-15.15$^{B'}$ | Z15$^{B'}$, $R^{aB'}$ is H | $CH_3$ | H | F |
| E2-15.16$^{B'}$ | Z15$^{B'}$, $R^{aB'}$ is H | $CH_3$ | F | H |
| E2-15.17$^{B'}$ | Z15$^{B'}$, $R^{aB'}$ is H | Cl | F | H |
| E2-15.18$^{B'}$ | Z15$^{B'}$, $R^{aB'}$ is H | F | F | H |
| E2-15.19$^{B'}$ | Z15$^{B'}$, $R^{aB'}$ is H | F | H | F |
| E2-15.20$^{B'}$ | Z15$^{B'}$, $R^{aB'}$ is H | F | H | Cl |
| E2-15.21$^{B'}$ | Z15$^{B'}$, $R^{aB'}$ is H | F | H | $CH_3$ |
| E2-15.22$^{B'}$ | Z15$^{B'}$, $R^{aB'}$ is H | Cl | H | $CH_3$ |
| E2-15.23$^{B'}$ | Z15$^{B'}$, $R^{aB'}$ is H | $SCH_3$ | H | H |
| E2-15.24$^{B'}$ | Z15$^{B'}$, $R^{aB'}$ is H | $SO_2CH_3$ | H | H |
| E2-15.25$^{B'}$ | Z15$^{B'}$, $R^{aB'}$ is H | ethynyl | H | H |
| E2-16.1$^{B'}$ | Z16$^{B'}$, $R^{aB'}$ is H | H | H | H |
| E2-16.2$^{B'}$ | Z16$^{B'}$, $R^{aB'}$ is H | $CH_3$ | H | H |
| E2-16.3$^{B'}$ | Z16$^{B'}$, $R^{aB'}$ is H | Cl | H | H |
| E2-16.4$^{B'}$ | Z16$^{B'}$, $R^{aB'}$ is H | F | H | H |
| E2-16.5$^{B'}$ | Z16$^{B'}$, $R^{aB'}$ is H | $CH_2CH_3$ | H | H |
| E2-16.6$^{B'}$ | Z16$^{B'}$, $R^{aB'}$ is H | $CF_2H$ | H | H |
| E2-16.7$^{B'}$ | Z16$^{B'}$, $R^{aB'}$ is H | $CH_2F$ | H | H |
| E2-16.8$^{B'}$ | Z16$^{B'}$, $R^{aB'}$ is H | $CF_3$ | H | H |
| E2-16.9$^{B'}$ | Z16$^{B'}$, $R^{aB'}$ is H | $CF_2CH_3$ | H | H |
| E2-16.10$^{B'}$ | Z16$^{B'}$, $R^{aB'}$ is H | $CH_2CF_3$ | H | H |
| E2-16.11$^{B'}$ | Z16$^{B'}$, $R^{aB'}$ is H | cyclopropyl | H | H |
| E2-16.12$^{B'}$ | Z16$^{B'}$, $R^{aB'}$ is H | $OCF_3$ | H | H |
| E2-16.13$^{B'}$ | Z16$^{B'}$, $R^{aB'}$ is H | $OCF_2H$ | H | H |
| E2-16.14$^{B'}$ | Z16$^{B'}$, $R^{aB'}$ is H | Cl | H | F |
| E2-16.15$^{B'}$ | Z16$^{B'}$, $R^{aB'}$ is H | $CH_3$ | H | F |
| E2-16.16$^{B'}$ | Z16$^{B'}$, $R^{aB'}$ is H | $CH_3$ | F | H |
| E2-16.17$^{B'}$ | Z16$^{B'}$, $R^{aB'}$ is H | Cl | F | H |
| E2-16.18$^{B'}$ | Z16$^{B'}$, $R^{aB'}$ is H | F | F | H |
| E2-16.19$^{B'}$ | Z16$^{B'}$, $R^{aB'}$ is H | F | H | F |
| E2-16.20$^{B'}$ | Z16$^{B'}$, $R^{aB'}$ is H | F | H | Cl |
| E2-16.21$^{B'}$ | Z16$^{B'}$, $R^{aB'}$ is H | F | H | $CH_3$ |
| E2-16.22$^{B'}$ | Z16$^{B'}$, $R^{aB'}$ is H | Cl | H | $CH_3$ |
| E2-16.23$^{B'}$ | Z16$^{B'}$, $R^{aB'}$ is H | $SCH_3$ | H | H |
| E2-16.24$^{B'}$ | Z16$^{B'}$, $R^{aB'}$ is H | $SO_2CH_3$ | H | H |
| E2-16.25$^{B'}$ | Z16$^{B'}$, $R^{aB'}$ is H | ethynyl | H | H |
| E2-17.1$^{B'}$ | Z17$^{B'}$ | H | H | H |
| E2-17.2$^{B'}$ | Z17$^{B'}$ | $CH_3$ | H | H |
| E2-17.3$^{B'}$ | Z17$^{B'}$ | Cl | H | H |
| E2-17.4$^{B'}$ | Z17$^{B'}$ | F | H | H |
| E2-17.5$^{B'}$ | Z17$^{B'}$ | $CH_2CH_3$ | H | H |
| E2-17.6$^{B'}$ | Z17$^{B'}$ | $CF_2H$ | H | H |
| E2-17.7$^{B'}$ | Z17$^{B'}$ | $CH_2F$ | H | H |
| E2-17.8$^{B'}$ | Z17$^{B'}$ | $CF_3$ | H | H |
| E2-17.9$^{B'}$ | Z17$^{B'}$ | $CF_2CH_3$ | H | H |
| E2-17.10$^{B'}$ | Z17$^{B'}$ | $CH_2CF_3$ | H | H |
| E2-17.11$^{B'}$ | Z17$^{B'}$ | cyclopropyl | H | H |
| E2-17.12$^{B'}$ | Z17$^{B'}$ | $OCF_3$ | H | H |
| E2-17.13$^{B'}$ | Z17$^{B'}$ | $OCF_2H$ | H | H |
| E2-17.14$^{B'}$ | Z17$^{B'}$ | Cl | H | F |
| E2-17.15$^{B'}$ | Z17$^{B'}$ | $CH_3$ | H | F |
| E2-17.16$^{B'}$ | Z17$^{B'}$ | $CH_3$ | F | H |
| E2-17.17$^{B'}$ | Z17$^{B'}$ | Cl | F | H |

TABLE 14.E2-continued (S)

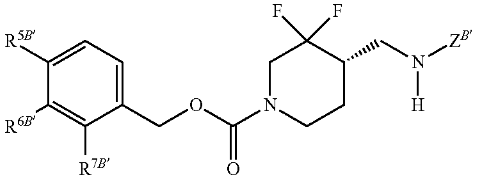

| compound | $Z^{B'}$ | $R^{5B'}$ | $R^{6B'}$ | $R^{7B'}$ |
|---|---|---|---|---|
| E2-17.18$^{B'}$ | Z17$^{B'}$ | F | F | H |
| E2-17.19$^{B'}$ | Z17$^{B'}$ | F | H | F |
| E2-17.20$^{B'}$ | Z17$^{B'}$ | F | H | Cl |
| E2-17.21$^{B'}$ | Z17$^{B'}$ | F | H | $CH_3$ |
| E2-17.22$^{B'}$ | Z17$^{B'}$ | Cl | H | $CH_3$ |
| E2-17.23$^{B'}$ | Z17$^{B'}$ | $SCH_3$ | H | H |
| E2-17.24$^{B'}$ | Z17$^{B'}$ | $SO_2CH_3$ | H | H |
| E2-17.25$^{B'}$ | Z17$^{B'}$ | ethynyl | H | H |
| E2-18.1$^{B'}$ | Z18$^{B'}$ | H | H | H |
| E2-18.2$^{B'}$ | Z18$^{B'}$ | $CH_3$ | H | H |
| E2-18.3$^{B'}$ | Z18$^{B'}$ | Cl | H | H |
| E2-18.4$^{B'}$ | Z18$^{B'}$ | F | H | H |
| E2-18.5$^{B'}$ | Z18$^{B'}$ | $CH_2CH_3$ | H | H |
| E2-18.6$^{B'}$ | Z18$^{B'}$ | $CF_2H$ | H | H |
| E2-18.7$^{B'}$ | Z18$^{B'}$ | $CH_2F$ | H | H |
| E2-18.8$^{B'}$ | Z18$^{B'}$ | $CF_3$ | H | H |
| E2-18.9$^{B'}$ | Z18$^{B'}$ | $CF_2CH_3$ | H | H |
| E2-18.10$^{B'}$ | Z18$^{B'}$ | $CH_2CF_3$ | H | H |
| E2-18.11$^{B'}$ | Z18$^{B'}$ | cyclopropyl | H | H |
| E2-18.12$^{B'}$ | Z18$^{B'}$ | $OCF_3$ | H | H |
| E2-18.13$^{B'}$ | Z18$^{B'}$ | $OCF_2H$ | H | H |
| E2-18.14$^{B'}$ | Z18$^{B'}$ | Cl | H | F |
| E2-18.15$^{B'}$ | Z18$^{B'}$ | $CH_3$ | H | F |
| E2-18.16$^{B'}$ | Z18$^{B'}$ | $CH_3$ | F | H |
| E2-18.17$^{B'}$ | Z18$^{B'}$ | Cl | F | H |
| E2-18.18$^{B'}$ | Z18$^{B'}$ | F | F | H |
| E2-18.19$^{B'}$ | Z18$^{B'}$ | F | H | F |
| E2-18.20$^{B'}$ | Z18$^{B'}$ | F | H | Cl |
| E2-18.21$^{B'}$ | Z18$^{B'}$ | F | H | $CH_3$ |
| E2-18.22$^{B'}$ | Z18$^{B'}$ | Cl | H | $CH_3$ |
| E2-18.23$^{B'}$ | Z18$^{B'}$ | $SCH_3$ | H | H |
| E2-18.24$^{B'}$ | Z18$^{B'}$ | $SO_2CH_3$ | H | H |
| E2-18.25$^{B'}$ | Z18$^{B'}$ | ethynyl | H | H |
| E2-19.1$^{B'}$ | Z19$^{B'}$ | H | H | H |
| E2-19.2$^{B'}$ | Z19$^{B'}$ | $CH_3$ | H | H |
| E2-19.3$^{B'}$ | Z19$^{B'}$ | Cl | H | H |
| E2-19.4$^{B'}$ | Z19$^{B'}$ | F | H | H |
| E2-19.5$^{B'}$ | Z19$^{B'}$ | $CH_2CH_3$ | H | H |
| E2-19.6$^{B'}$ | Z19$^{B'}$ | $CF_2H$ | H | H |
| E2-19.7$^{B'}$ | Z19$^{B'}$ | $CH_2F$ | H | H |
| E2-19.8$^{B'}$ | Z19$^{B'}$ | $CF_3$ | H | H |
| E2-19.9$^{B'}$ | Z19$^{B'}$ | $CF_2CH_3$ | H | H |
| E2-19.10$^{B'}$ | Z19$^{B'}$ | $CH_2CF_3$ | H | H |
| E2-19.11$^{B'}$ | Z19$^{B'}$ | cyclopropyl | H | H |
| E2-19.12$^{B'}$ | Z19$^{B'}$ | $OCF_3$ | H | H |
| E2-19.13$^{B'}$ | Z19$^{B'}$ | $OCF_2H$ | H | H |
| E2-19.14$^{B'}$ | Z19$^{B'}$ | Cl | H | F |
| E2-19.15$^{B'}$ | Z19$^{B'}$ | $CH_3$ | H | F |
| E2-19.16$^{B'}$ | Z19$^{B'}$ | $CH_3$ | F | H |
| E2-19.17$^{B'}$ | Z19$^{B'}$ | Cl | F | H |
| E2-19.18$^{B'}$ | Z19$^{B'}$ | F | F | H |
| E2-19.19$^{B'}$ | Z19$^{B'}$ | F | H | F |
| E2-19.20$^{B'}$ | Z19$^{B'}$ | F | H | Cl |
| E2-19.21$^{B'}$ | Z19$^{B'}$ | F | H | $CH_3$ |
| E2-19.22$^{B'}$ | Z19$^{B'}$ | Cl | H | $CH_3$ |
| E2-19.23$^{B'}$ | Z19$^{B'}$ | $SCH_3$ | H | H |
| E2-19.24$^{B'}$ | Z19$^{B'}$ | $SO_2CH_3$ | H | H |
| E2-19.25$^{B'}$ | Z19$^{B'}$ | ethynyl | H | H |
| E2-19.26$^{B'}$ | Z19$^{B'}$ | $CH_3$ | H | H |
| E2-20.1$^{B'}$ | Z20$^{B'}$ | H | H | H |
| E2-20.2$^{B'}$ | Z20$^{B'}$ | $CH_3$ | H | H |
| E2-20.3$^{B'}$ | Z20$^{B'}$ | Cl | H | H |
| E2-20.4$^{B'}$ | Z20$^{B'}$ | F | H | H |
| E2-20.5$^{B'}$ | Z20$^{B'}$ | $CH_2CH_3$ | H | H |
| E2-20.6$^{B'}$ | Z20$^{B'}$ | $CF_2H$ | H | H |
| E2-20.7$^{B'}$ | Z20$^{B'}$ | $CH_2F$ | H | H |
| E2-20.8$^{B'}$ | Z20$^{B'}$ | $CF_3$ | H | H |

TABLE 14.E2-continued (S)

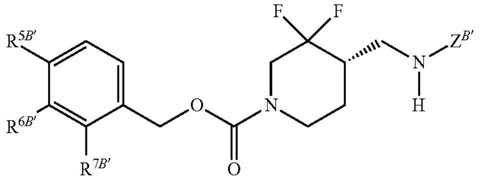

| compound | $Z^{B'}$ | $R^{5B'}$ | $R^{6B'}$ | $R^{7B'}$ |
|---|---|---|---|---|
| E2-20.9$^{B'}$ | Z20$^{B'}$ | $CF_2CH_3$ | H | H |
| E2-20.10$^{B'}$ | Z20$^{B'}$ | $CH_2CF_3$ | H | H |
| E2-20.11$^{B'}$ | Z20$^{B'}$ | cyclopropyl | H | H |
| E2-20.12$^{B'}$ | Z20$^{B'}$ | $OCF_3$ | H | H |
| E2-20.13$^{B'}$ | Z20$^{B'}$ | $OCF_2H$ | H | H |
| E2-20.14$^{B'}$ | Z20$^{B'}$ | Cl | H | F |
| E2-20.15$^{B'}$ | Z20$^{B'}$ | $CH_3$ | H | F |
| E2-20.16$^{B'}$ | Z20$^{B'}$ | $CH_3$ | F | H |
| E2-20.17$^{B'}$ | Z20$^{B'}$ | Cl | F | H |
| E2-20.18$^{B'}$ | Z20$^{B'}$ | F | F | H |
| E2-20.19$^{B'}$ | Z20$^{B'}$ | F | H | F |
| E2-20.20$^{B'}$ | Z20$^{B'}$ | F | H | Cl |
| E2-20.21$^{B'}$ | Z20$^{B'}$ | F | H | $CH_3$ |
| E2-20.22$^{B'}$ | Z20$^{B'}$ | Cl | H | $CH_3$ |
| E2-20.23$^{B'}$ | Z20$^{B'}$ | $SCH_3$ | H | H |
| E2-20.24$^{B'}$ | Z20$^{B'}$ | $SO_2CH_3$ | H | H |
| E2-20.25$^{B'}$ | Z20$^{B'}$ | ethynyl | H | H |
| E2-21.1$^{B'}$ | Z21$^{B'}$ | H | H | H |
| E2-21.2$^{B'}$ | Z21$^{B'}$ | $CH_3$ | H | H |
| E2-21.3$^{B'}$ | Z21$^{B'}$ | Cl | H | H |
| E2-21.4$^{B'}$ | Z21$^{B'}$ | F | H | H |
| E2-21.5$^{B'}$ | Z21$^{B'}$ | $CH_2CH_3$ | H | H |
| E2-21.6$^{B'}$ | Z21$^{B'}$ | $CF_2H$ | H | H |
| E2-21.7$^{B'}$ | Z21$^{B'}$ | $CH_2F$ | H | H |
| E2-21.8$^{B'}$ | Z21$^{B'}$ | $CF_3$ | H | H |
| E2-21.9$^{B'}$ | Z21$^{B'}$ | $CF_2CH_3$ | H | H |
| E2-21.10$^{B'}$ | Z21$^{B'}$ | $CH_2CF_3$ | H | H |
| E2-21.11$^{B'}$ | Z21$^{B'}$ | cyclopropyl | H | H |
| E2-21.12$^{B'}$ | Z21$^{B'}$ | $OCF_3$ | H | H |
| E2-21.13$^{B'}$ | Z21$^{B'}$ | $OCF_2H$ | H | H |
| E2-21.14$^{B'}$ | Z21$^{B'}$ | Cl | H | F |
| E2-21.15$^{B'}$ | Z21$^{B'}$ | $CH_3$ | H | F |
| E2-21.16$^{B'}$ | Z21$^{B'}$ | $CH_3$ | F | H |
| E2-21.17$^{B'}$ | Z21$^{B'}$ | Cl | F | H |
| E2-21.18$^{B'}$ | Z21$^{B'}$ | F | F | H |
| E2-21.19$^{B'}$ | Z21$^{B'}$ | F | H | F |
| E2-21.20$^{B'}$ | Z21$^{B'}$ | F | H | Cl |
| E2-21.21$^{B'}$ | Z21$^{B'}$ | F | H | $CH_3$ |
| E2-21.22$^{B'}$ | Z21$^{B'}$ | Cl | H | $CH_3$ |
| E2-21.23$^{B'}$ | Z21$^{B'}$ | $SCH_3$ | H | H |
| E2-21.24$^{B'}$ | Z21$^{B'}$ | $SO_2CH_3$ | H | H |
| E2-21.25$^{B'}$ | Z21$^{B'}$ | ethynyl | H | H |
| E2-21.26$^{B'}$ | 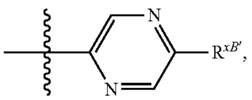 $R^{xB'}$ is $CH_3$ | $CH_3$ | H | H |
| E2-21.27$^{B'}$ | 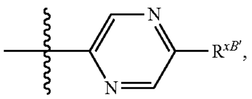 $R^{xB'}$ is Cl | $CH_3$ | H | H |
| E2-21.28$^{B'}$ | 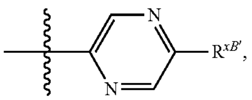 $R^{xB'}$ is F | $CH_3$ | H | H |

TABLE 14.E2-continued (S)

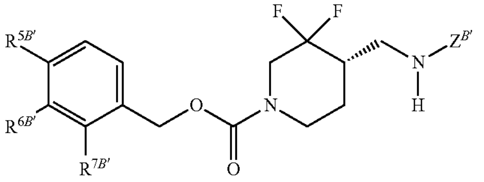

| compound | $Z^{B'}$ | $R^{5B'}$ | $R^{6B'}$ | $R^{7B'}$ |
|---|---|---|---|---|
| E2-21.29$^{B'}$ | 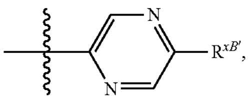 $R^{xB'}$ is $CF_3$ | $CH_3$ | H | H |
| E2-21.30$^{B'}$ | 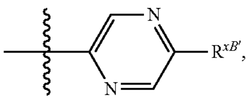 $R^{xB'}$ is CN | $CH_3$ | H | H |
| E2-21.31$^{B'}$ | 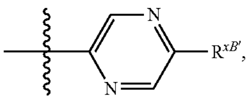 $R^{xB'}$ is $CH_3$ | H | H | H |
| E2-21.32$^{B'}$ | 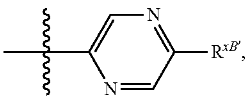 $R^{xB'}$ is $CH_3$ | $CH_3$ | H | H |
| E2-21.33$^{B'}$ | 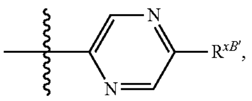 $R^{xB'}$ is $CH_3$ | Cl | H | H |
| E2-21.34$^{B'}$ | 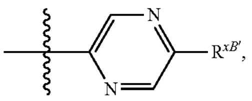 $R^{xB'}$ is $CH_3$ | F | H | H |
| E2-21.35$^{B'}$ | 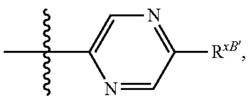 $R^{xB'}$ is $CH_3$ | $CH_2CH_3$ | H | H |
| E2-21.36$^{B'}$ | 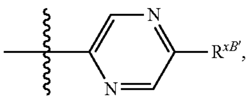 $R^{xB'}$ is $CH_3$ | $CF_2H$ | H | H |
| E2-22.1$^{B'}$ | Z22$^{B'}$ | H | H | H |
| E2-22.2$^{B'}$ | Z22$^{B'}$ | $CH_3$ | H | H |
| E2-22.3$^{B'}$ | Z22$^{B'}$ | Cl | H | H |
| E2-22.4$^{B'}$ | Z22$^{B'}$ | F | H | H |
| E2-22.5$^{B'}$ | Z22$^{B'}$ | $CH_2CH_3$ | H | H |
| E2-22.6$^{B'}$ | Z22$^{B'}$ | $CF_2H$ | H | H |
| E2-22.7$^{B'}$ | Z22$^{B'}$ | $CH_2F$ | H | H |

TABLE 14.E2-continued (S)

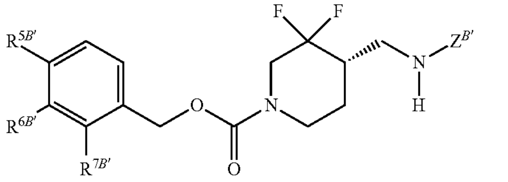

| compound | $Z^{B'}$ | $R^{5B'}$ | $R^{6B'}$ | $R^{7B'}$ |
|---|---|---|---|---|
| E2-22.8$^{B'}$ | Z22$^{B'}$ | $CF_3$ | H | H |
| E2-22.9$^{B'}$ | Z22$^{B'}$ | $CF_2CH_3$ | H | H |
| E2-22.10$^{B'}$ | Z22$^{B'}$ | $CH_2CF_3$ | H | H |
| E2-22.11$^{B'}$ | Z22$^{B'}$ | cyclopropyl | H | H |
| E2-22.12$^{B'}$ | Z22$^{B'}$ | $OCF_3$ | H | H |
| E2-22.13$^{B'}$ | Z22$^{B'}$ | $OCF_2H$ | H | H |
| E2-22.14$^{B'}$ | Z22$^{B'}$ | Cl | H | F |
| E2-22.15$^{B'}$ | Z22$^{B'}$ | $CH_3$ | H | F |
| E2-22.16$^{B'}$ | Z22$^{B'}$ | $CH_3$ | F | H |
| E2-22.17$^{B'}$ | Z22$^{B'}$ | Cl | F | H |
| E2-22.18$^{B'}$ | Z22$^{B'}$ | F | F | H |
| E2-22.19$^{B'}$ | Z22$^{B'}$ | F | H | F |
| E2-22.20$^{B'}$ | Z22$^{B'}$ | F | H | Cl |
| E2-22.21$^{B'}$ | Z22$^{B'}$ | F | H | $CH_3$ |
| E2-22.22$^{B'}$ | Z22$^{B'}$ | Cl | H | $CH_3$ |
| E2-22.23$^{B'}$ | Z22$^{B'}$ | $SCH_3$ | H | H |
| E2-22.24$^{B'}$ | Z22$^{B'}$ | $SO_2CH_3$ | H | H |
| E2-22.25$^{B'}$ | Z22$^{B'}$ | ethynyl | H | H |
| E2-22.26$^{B'}$ | 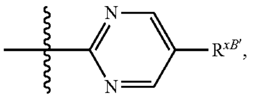 $R^{xB'}$ is $CH_3$ | $CH_3$ | H | H |
| E2-22.27$^{B'}$ | 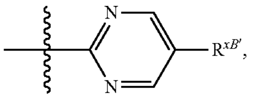 $R^{xB'}$ is Cl | $CH_3$ | H | H |
| E2-22.28$^{B'}$ | 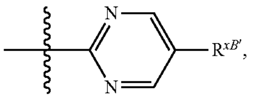 $R^{xB'}$ is F | $CH_3$ | H | H |
| E2-22.29$^{B'}$ | 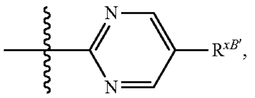 $R^{xB'}$ is $CF_3$ | $CH_3$ | H | H |
| E2-22.30$^{B'}$ | 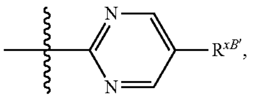 $R^{xB'}$ is CN | $CH_3$ | H | H |
| E2-23.1$^{B'}$ | Z23$^{B'}$ | H | H | H |
| E2-23.2$^{B'}$ | Z23$^{B'}$ | $CH_3$ | H | H |
| E2-23.3$^{B'}$ | Z23$^{B'}$ | Cl | H | H |
| E2-23.4$^{B'}$ | Z23$^{B'}$ | F | H | H |
| E2-23.5$^{B'}$ | Z23$^{B'}$ | $CH_2CH_3$ | H | H |
| E2-23.6$^{B'}$ | Z23$^{B'}$ | $CF_2H$ | H | H |
| E2-23.7$^{B'}$ | Z23$^{B'}$ | $CH_2F$ | H | H |
| E2-23.8$^{B'}$ | Z23$^{B'}$ | $CF_3$ | H | H |
| E2-23.9$^{B'}$ | Z23$^{B'}$ | $CF_2CH_3$ | H | H |
| E2-23.10$^{B'}$ | Z23$^{B'}$ | $CH_2CF_3$ | H | H |
| E2-23.11$^{B'}$ | Z23$^{B'}$ | cyclopropyl | H | H |

TABLE 14.E2-continued (S)

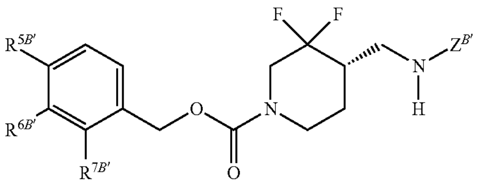

| compound | $Z^{B'}$ | $R^{5B'}$ | $R^{6B'}$ | $R^{7B'}$ |
|---|---|---|---|---|
| E2-23.12$^{B'}$ | Z23$^{B'}$ | $OCF_3$ | H | H |
| E2-23.13$^{B'}$ | Z23$^{B'}$ | $OCF_2H$ | H | H |
| E2-23.14$^{B'}$ | Z23$^{B'}$ | Cl | H | F |
| E2-23.15$^{B'}$ | Z23$^{B'}$ | $CH_3$ | H | F |
| E2-23.16$^{B'}$ | Z23$^{B'}$ | $CH_3$ | F | H |
| E2-23.17$^{B'}$ | Z23$^{B'}$ | Cl | F | H |
| E2-23.18$^{B'}$ | Z23$^{B'}$ | F | F | H |
| E2-23.19$^{B'}$ | Z23$^{B'}$ | F | H | F |
| E2-23.20$^{B'}$ | Z23$^{B'}$ | F | H | Cl |
| E2-23.21$^{B'}$ | Z23$^{B'}$ | F | H | $CH_3$ |
| E2-23.22$^{B'}$ | Z23$^{B'}$ | Cl | H | $CH_3$ |
| E2-23.23$^{B'}$ | Z23$^{B'}$ | $SCH_3$ | H | H |
| E2-23.24$^{B'}$ | Z23$^{B'}$ | $SO_2CH_3$ | H | H |
| E2-23.25$^{B'}$ | Z23$^{B'}$ | ethynyl | H | H |
| E2-23.26$^{B'}$ | 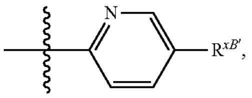 $R^{xB'}$ is $CH_3$ | $CH_3$ | H | H |
| E2-23.27$^{B'}$ | 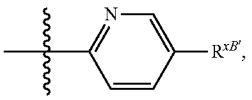 $R^{xB'}$ is Cl | $CH_3$ | H | H |
| E2-23.28$^{B'}$ | 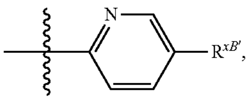 $R^{xB'}$ is F | $CH_3$ | H | H |
| E2-23.29$^{B'}$ | 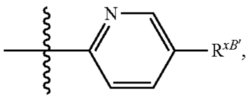 $R^{xB'}$ is $CF_3$ | $CH_3$ | H | H |
| E2-23.30$^{B'}$ | 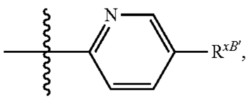 $R^{xB'}$ is CN | $CH_3$ | H | H |
| E2-23.31$^{B'}$ | 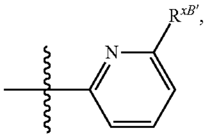 $R^{xB'}$ is $CH_3$ | H | H | H |

TABLE 14.E2-continued (S)

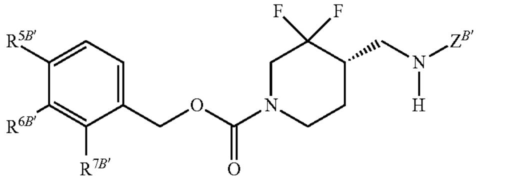

| compound | $Z^{B'}$ | $R^{5B'}$ | $R^{6B'}$ | $R^{7B'}$ |
|---|---|---|---|---|
| E2-23.32$^{B'}$ | 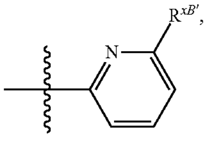 $R^{xB'}$ is $CH_3$ | $CH_3$ | H | H |
| E2-23.33$^{B'}$ | 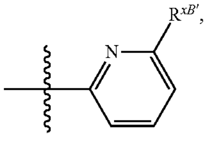 $R^{xB'}$ is $CH_3$ | Cl | H | H |
| E2-23.34$^{B'}$ | 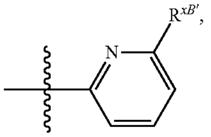 $R^{xB'}$ is $CH_3$ | F | H | H |
| E2-23.35$^{B'}$ | 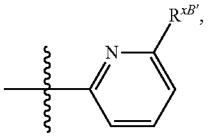 $R^{xB'}$ is $CH_3$ | $CH_2CH_3$ | H | H |
| E2-23.36$^{B'}$ | 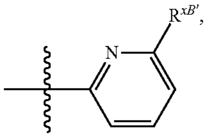 $R^{xB'}$ is $CH_3$ | $CF_2H$ | H | H |
| E2-24.1$^{B'}$ | Z24$^{B'}$ | H | H | H |
| E2-24.2$^{B'}$ | Z24$^{B'}$ | $CH_3$ | H | H |
| E2-24.3$^{B'}$ | Z24$^{B'}$ | Cl | H | H |
| E2-24.4$^{B'}$ | Z24$^{B'}$ | F | H | H |
| E2-24.5$^{B'}$ | Z24$^{B'}$ | $CH_2CH_3$ | H | H |
| E2-24.6$^{B'}$ | Z24$^{B'}$ | $CF_2H$ | H | H |
| E2-24.7$^{B'}$ | Z24$^{B'}$ | $CH_2F$ | H | H |
| E2-24.8$^{B'}$ | Z24$^{B'}$ | $CF_3$ | H | H |
| E2-24.9$^{B'}$ | Z24$^{B'}$ | $CF_2CH_3$ | H | H |
| E2-24.10$^{B'}$ | Z24$^{B'}$ | $CH_2CF_3$ | H | H |
| E2-24.11$^{B'}$ | Z24$^{B'}$ | cyclopropyl | H | H |
| E2-24.12$^{B'}$ | Z24$^{B'}$ | $OCF_3$ | H | H |
| E2-24.13$^{B'}$ | Z24$^{B'}$ | $OCF_2H$ | H | H |
| E2-24.14$^{B'}$ | Z24$^{B'}$ | Cl | H | F |
| E2-24.15$^{B'}$ | Z24$^{B'}$ | $CH_3$ | H | F |
| E2-24.16$^{B'}$ | Z24$^{B'}$ | $CH_3$ | F | H |
| E2-24.17$^{B'}$ | Z24$^{B'}$ | Cl | F | H |
| E2-24.18$^{B'}$ | Z24$^{B'}$ | F | F | H |
| E2-24.19$^{B'}$ | Z24$^{B'}$ | F | H | F |
| E2-24.20$^{B'}$ | Z24$^{B'}$ | F | H | Cl |

TABLE 14.E2-continued (S)

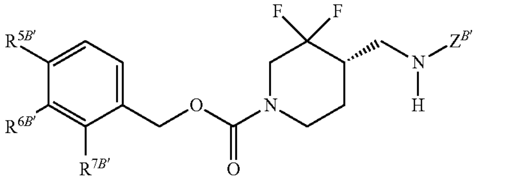

| compound | $Z^{B'}$ | $R^{5B'}$ | $R^{6B'}$ | $R^{7B'}$ |
|---|---|---|---|---|
| E2-24.21$^{B'}$ | Z24$^{B'}$ | F | H | $CH_3$ |
| E2-24.22$^{B'}$ | Z24$^{B'}$ | Cl | H | $CH_3$ |
| E2-24.23$^{B'}$ | Z24$^{B'}$ | $SCH_3$ | H | H |
| E2-24.24$^{B'}$ | Z24$^{B'}$ | $SO_2CH_3$ | H | H |
| E2-24.25$^{B'}$ | Z24$^{B'}$ | ethynyl | H | H |
| E2-24.26$^{B'}$ | 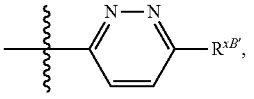 $R^{xB'}$ is $CH_3$ | $CH_3$ | H | H |
| E2-24.27$^{B'}$ | 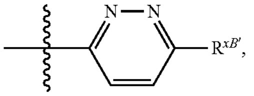 $R^{xB'}$ is Cl | $CH_3$ | H | H |
| E2-24.28$^{B'}$ | 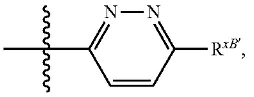 $R^{xB'}$ is F | $CH_3$ | H | H |
| E2-24.29$^{B'}$ | 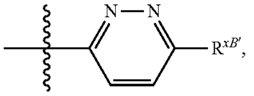 $R^{xB'}$ is $CF_3$ | $CH_3$ | H | H |
| E2-24.30$^{B'}$ | 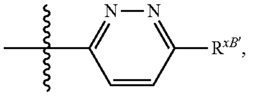 $R^{xB'}$ is CN | $CH_3$ | H | H |
| E2-25.1$^{B'}$ | Z25$^{B'}$, $R^{aB'}$ is H | H | H | H |
| E2-25.2$^{B'}$ | Z25$^{B'}$, $R^{aB'}$ is H | $CH_3$ | H | H |
| E2-25.3$^{B'}$ | Z25$^{B'}$, $R^{aB'}$ is H | Cl | H | H |
| E2-25.4$^{B'}$ | Z25$^{B'}$, $R^{aB'}$ is H | F | H | H |
| E2-25.5$^{B'}$ | Z25$^{B'}$, $R^{aB'}$ is H | $CH_2CH_3$ | H | H |
| E2-25.6$^{B'}$ | Z25$^{B'}$, $R^{aB'}$ is H | $CF_2H$ | H | H |
| E2-25.7$^{B'}$ | Z25$^{B'}$, $R^{aB'}$ is H | $CH_2F$ | H | H |
| E2-25.8$^{B'}$ | Z25$^{B'}$, $R^{aB'}$ is H | $CF_3$ | H | H |
| E2-25.9$^{B'}$ | Z25$^{B'}$, $R^{aB'}$ is H | $CF_2CH_3$ | H | H |
| E2-25.10$^{B'}$ | Z25$^{B'}$, $R^{aB'}$ is H | $CH_2CF_3$ | H | H |
| E2-25.11$^{B'}$ | Z25$^{B'}$, $R^{aB'}$ is H | cyclopropyl | H | H |
| E2-25.12$^{B'}$ | Z25$^{B'}$, $R^{aB'}$ is H | $OCF_3$ | H | H |
| E2-25.13$^{B'}$ | Z25$^{B'}$, $R^{aB'}$ is H | $OCF_2H$ | H | H |
| E2-25.14$^{B'}$ | Z25$^{B'}$, $R^{aB'}$ is H | Cl | H | F |
| E2-25.15$^{B'}$ | Z25$^{B'}$, $R^{aB'}$ is H | $CH_3$ | H | F |
| E2-25.16$^{B'}$ | Z25$^{B'}$, $R^{aB'}$ is H | $CH_3$ | F | H |
| E2-25.17$^{B'}$ | Z25$^{B'}$, $R^{aB'}$ is H | Cl | F | H |
| E2-25.18$^{B'}$ | Z25$^{B'}$, $R^{aB'}$ is H | F | F | H |
| E2-25.19$^{B'}$ | Z25$^{B'}$, $R^{aB'}$ is H | F | H | F |
| E2-25.20$^{B'}$ | Z25$^{B'}$, $R^{aB'}$ is H | F | H | Cl |
| E2-25.21$^{B'}$ | Z25$^{B'}$, $R^{aB'}$ is H | F | H | $CH_3$ |
| E2-25.22$^{B'}$ | Z25$^{B'}$, $R^{aB'}$ is H | Cl | H | $CH_3$ |
| E2-25.23$^{B'}$ | Z25$^{B'}$, $R^{aB'}$ is H | $SCH_3$ | H | H |
| E2-25.24$^{B'}$ | Z25$^{B'}$, $R^{aB'}$ is H | $SO_2CH_3$ | H | H |
| E2-25.25$^{B'}$ | Z25$^{B'}$, $R^{aB'}$ is H | ethynyl | H | H |

TABLE 14.E2-continued (S)

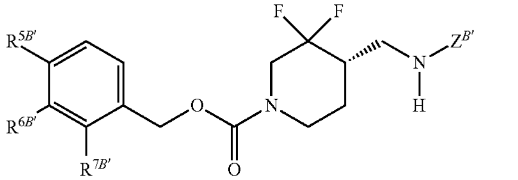

| compound | $Z^{B'}$ | $R^{5B'}$ | $R^{6B'}$ | $R^{7B'}$ |
|---|---|---|---|---|
| E2-25.26$^{B'}$ | 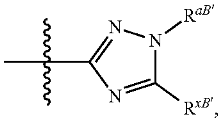 $R^{aB'}$ is H; $R^{xB'}$ is $CH_3$ | $CH_3$ | H | H |
| E2-25.27$^{B'}$ | 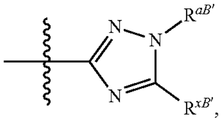 $R^{aB'}$ is H; $R^{xB'}$ is Cl | $CH_3$ | H | H |
| E2-25.28$^{B'}$ | 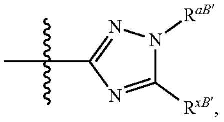 $R^{aB'}$ is H; $R^{xB'}$ is F | $CH_3$ | H | H |
| E2-25.29$^{B'}$ | 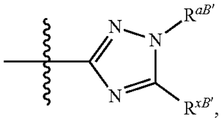 $R^{aB'}$ is H; $R^{xB'}$ is $CF_3$ | $CH_3$ | H | H |
| E2-25.30$^{B'}$ | 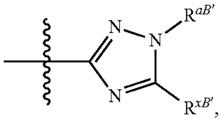 $R^{aB'}$ is H; $R^{xB'}$ is CN | $CH_3$ | H | H |
| E2-26.1$^{B'}$ | Z26$^{B'}$, $R^{aB'}$ is H | H | H | H |
| E2-26.2$^{B'}$ | Z26$^{B'}$, $R^{aB'}$ is H | $CH_3$ | H | H |
| E2-26.3$^{B'}$ | Z26$^{B'}$, $R^{aB'}$ is H | Cl | H | H |
| E2-26.4$^{B'}$ | Z26$^{B'}$, $R^{aB'}$ is H | F | H | H |
| E2-26.5$^{B'}$ | Z26$^{B'}$, $R^{aB'}$ is H | $CH_2CH_3$ | H | H |
| E2-26.6$^{B'}$ | Z26$^{B'}$, $R^{aB'}$ is H | $CF_2H$ | H | H |
| E2-26.7$^{B'}$ | Z26$^{B'}$, $R^{aB'}$ is H | $CH_2F$ | H | H |
| E2-26.8$^{B'}$ | Z26$^{B'}$, $R^{aB'}$ is H | $CF_3$ | H | H |
| E2-26.9$^{B'}$ | Z26$^{B'}$, $R^{aB'}$ is H | $CF_2CH_3$ | H | H |
| E2-26.10$^{B'}$ | Z26$^{B'}$, $R^{aB'}$ is H | $CH_2CF_3$ | H | H |
| E2-26.11$^{B'}$ | Z26$^{B'}$, $R^{aB'}$ is H | cyclopropyl | H | H |
| E2-26.12$^{B'}$ | Z26$^{B'}$, $R^{aB'}$ is H | $OCF_3$ | H | H |
| E2-26.13$^{B'}$ | Z26$^{B'}$, $R^{aB'}$ is H | $OCF_2H$ | H | H |
| E2-26.14$^{B'}$ | Z26$^{B'}$, $R^{aB'}$ is H | Cl | H | F |
| E2-26.15$^{B'}$ | Z26$^{B'}$, $R^{aB'}$ is H | $CH_3$ | H | F |
| E2-26.16$^{B'}$ | Z26$^{B'}$, $R^{aB'}$ is H | $CH_3$ | F | H |
| E2-26.17$^{B'}$ | Z26$^{B'}$, $R^{aB'}$ is H | Cl | F | H |
| E2-26.18$^{B'}$ | Z26$^{B'}$, $R^{aB'}$ is H | F | F | H |
| E2-26.19$^{B'}$ | Z26$^{B'}$, $R^{aB'}$ is H | F | H | F |
| E2-26.20$^{B'}$ | Z26$^{B'}$, $R^{aB'}$ is H | F | H | Cl |
| E2-26.21$^{B'}$ | Z26$^{B'}$, $R^{aB'}$ is H | F | H | $CH_3$ |
| E2-26.22$^{B'}$ | Z26$^{B'}$, $R^{aB'}$ is H | Cl | H | $CH_3$ |
| E2-26.23$^{B'}$ | Z26$^{B'}$, $R^{aB'}$ is H | $SCH_3$ | H | H |
| E2-26.24$^{B'}$ | Z26$^{B'}$, $R^{aB'}$ is H | $SO_2CH_3$ | H | H |

TABLE 14.E2-continued (S)

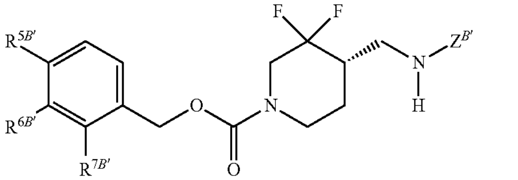

| compound | $Z^{B'}$ | $R^{5B'}$ | $R^{6B'}$ | $R^{7B'}$ |
|---|---|---|---|---|
| E2-26.25$^{B'}$ | Z26$^{B'}$, $R^{aB'}$ is H | ethynyl | H | H |
| E2-26.26$^{B'}$ | 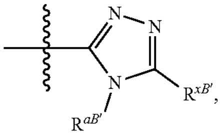 $R^{aB'}$ is H; $R^{xB'}$ is $CH_3$ | $CH_3$ | H | H |
| E2-26.27$^{B'}$ | 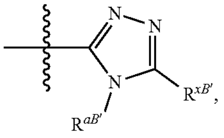 $R^{aB'}$ is H; $R^{xB'}$ is Cl | $CH_3$ | H | H |
| E2-26.28$^{B'}$ | 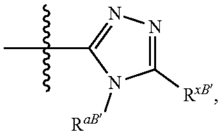 $R^{aB'}$ is H; $R^{xB'}$ is F | $CH_3$ | H | H |
| E2-26.29$^{B'}$ | 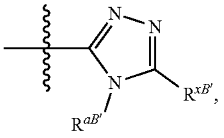 $R^{aB'}$ is H; $R^{xB'}$ is $CF_3$ | $CH_3$ | H | H |
| E2-26.30$^{B'}$ | 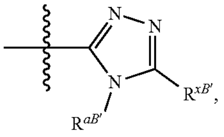 $R^{aB'}$ is H; $R^{xB'}$ is CN | $CH_3$ | H | H |
| E2-27.1$^{B'}$ | Z27$^{B'}$ | H | H | H |
| E2-27.2$^{B'}$ | Z27$^{B'}$ | $CH_3$ | H | H |
| E2-27.3$^{B'}$ | Z27$^{B'}$ | Cl | H | H |
| E2-27.4$^{B'}$ | Z27$^{B'}$ | F | H | H |
| E2-27.5$^{B'}$ | Z27$^{B'}$ | $CH_2CH_3$ | H | H |
| E2-27.6$^{B'}$ | Z27$^{B'}$ | $CF_2H$ | H | H |
| E2-27.7$^{B'}$ | Z27$^{B'}$ | $CH_2F$ | H | H |
| E2-27.8$^{B'}$ | Z27$^{B'}$ | $CF_3$ | H | H |
| E2-27.9$^{B'}$ | Z27$^{B'}$ | $CF_2CH_3$ | H | H |
| E2-27.10$^{B'}$ | Z27$^{B'}$ | $CH_2CF_3$ | H | H |
| E2-27.11$^{B'}$ | Z27$^{B'}$ | cyclopropyl | H | H |
| E2-27.12$^{B'}$ | Z27$^{B'}$ | $OCF_3$ | H | H |
| E2-27.13$^{B'}$ | Z27$^{B'}$ | $OCF_2H$ | H | H |
| E2-27.14$^{B'}$ | Z27$^{B'}$ | Cl | H | F |
| E2-27.15$^{B'}$ | Z27$^{B'}$ | $CH_3$ | H | F |
| E2-27.16$^{B'}$ | Z27$^{B'}$ | $CH_3$ | F | H |
| E2-27.17$^{B'}$ | Z27$^{B'}$ | Cl | F | H |
| E2-27.18$^{B'}$ | Z27$^{B'}$ | F | F | H |
| E2-27.19$^{B'}$ | Z27$^{B'}$ | F | H | F |
| E2-27.20$^{B'}$ | Z27$^{B'}$ | F | H | Cl |

TABLE 14.E2-continued (S)

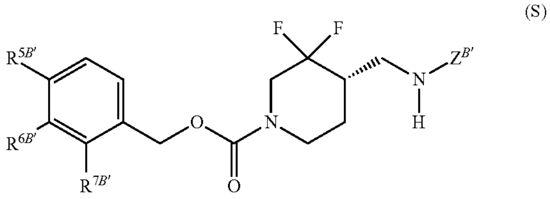

| compound | $Z^{B'}$ | $R^{5B'}$ | $R^{6B'}$ | $R^{7B'}$ |
|---|---|---|---|---|
| E2-27.21$^{B'}$ | Z27$^{B'}$ | F | H | $CH_3$ |
| E2-27.22$^{B'}$ | Z27$^{B'}$ | Cl | H | $CH_3$ |
| E2-27.23$^{B'}$ | Z27$^{B'}$ | $SCH_3$ | H | H |
| E2-27.24$^{B'}$ | Z27$^{B'}$ | $SO_2CH_3$ | H | H |
| E2-27.25$^{B'}$ | Z27$^{B'}$ | ethynyl | H | H |
| E2-27.26$^{B'}$ | 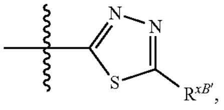 $R^{xB'}$ is $CH_3$ | $CH_3$ | H | H |
| E2-27.27$^{B'}$ | 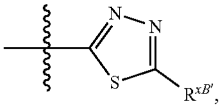 $R^{xB'}$ is Cl | $CH_3$ | H | H |
| E2-27.28$^{B'}$ | 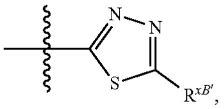 $R^{xB'}$ is F | $CH_3$ | H | H |
| E2-27.29$^{B'}$ | 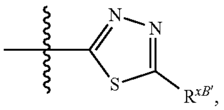 $R^{xB'}$ is $CF_3$ | $CH_3$ | H | H |
| E2-27.30$^{B'}$ | 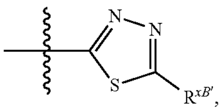 $R^{xB'}$ is CN | $CH_3$ | H | H |
| E2-28.1$^{B'}$ | Z28$^{B'}$ | H | H | H |
| E2-28.2$^{B'}$ | Z28$^{B'}$ | $CH_3$ | H | H |
| E2-28.3$^{B'}$ | Z28$^{B'}$ | Cl | H | H |
| E2-28.4$^{B'}$ | Z28$^{B'}$ | F | H | H |
| E2-28.5$^{B'}$ | Z28$^{B'}$ | $CH_2CH_3$ | H | H |
| E2-28.6$^{B'}$ | Z28$^{B'}$ | $CF_2H$ | H | H |
| E2-28.7$^{B'}$ | Z28$^{B'}$ | $CH_2F$ | H | H |
| E2-28.8$^{B'}$ | Z28$^{B'}$ | $CF_3$ | H | H |
| E2-28.9$^{B'}$ | Z28$^{B'}$ | $CF_2CH_3$ | H | H |
| E2-28.10$^{B'}$ | Z28$^{B'}$ | $CH_2CF_3$ | H | H |
| E2-28.11$^{B'}$ | Z28$^{B'}$ | cyclopropyl | H | H |
| E2-28.12$^{B'}$ | Z28$^{B'}$ | $OCF_3$ | H | H |
| E2-28.13$^{B'}$ | Z28$^{B'}$ | $OCF_2H$ | H | H |
| E2-28.14$^{B'}$ | Z28$^{B'}$ | Cl | H | F |
| E2-28.15$^{B'}$ | Z28$^{B'}$ | $CH_3$ | H | F |
| E2-28.16$^{B'}$ | Z28$^{B'}$ | $CH_3$ | F | H |
| E2-28.17$^{B'}$ | Z28$^{B'}$ | Cl | F | H |
| E2-28.18$^{B'}$ | Z28$^{B'}$ | F | F | H |
| E2-28.19$^{B'}$ | Z28$^{B'}$ | F | H | F |
| E2-28.20$^{B'}$ | Z28$^{B'}$ | F | H | Cl |
| E2-28.21$^{B'}$ | Z28$^{B'}$ | F | H | $CH_3$ |
| E2-28.22$^{B'}$ | Z28$^{B'}$ | Cl | H | $CH_3$ |

TABLE 14.E2-continued (S)

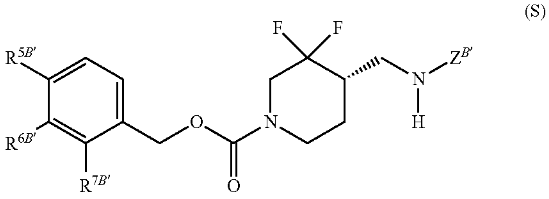

| compound | $Z^{B'}$ | $R^{5B'}$ | $R^{6B'}$ | $R^{7B'}$ |
|---|---|---|---|---|
| E2-28.23$^{B'}$ | Z28$^{B'}$ | $SCH_3$ | H | H |
| E2-28.24$^{B'}$ | Z28$^{B'}$ | $SO_2CH_3$ | H | H |
| E2-28.25$^{B'}$ | Z28$^{B'}$ | ethynyl | H | H |
| E2-28.26$^{B'}$ | 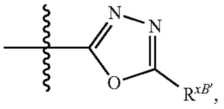 $R^{xB'}$ is $CH_3$ | $CH_3$ | H | H |
| E2-28.27$^{B'}$ | 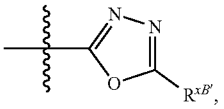 $R^{xB'}$ is Cl | $CH_3$ | H | H |
| E2-28.28$^{B'}$ | 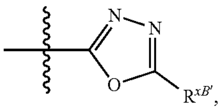 $R^{xB'}$ is F | $CH_3$ | H | H |
| E2-28.29$^{B'}$ | 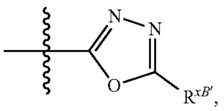 $R^{xB'}$ is $CF_3$ | $CH_3$ | H | H |
| E2-28.30$^{B'}$ | 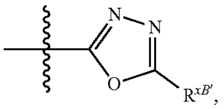 $R^{xB'}$ is CN | $CH_3$ | H | H |
| E2-29.1$^{B'}$ | Z29$^{B'}$ | H | H | H |
| E2-29.2$^{B'}$ | Z29$^{B'}$ | $CH_3$ | H | H |
| E2-29.3$^{B'}$ | Z29$^{B'}$ | Cl | H | H |
| E2-29.4$^{B'}$ | Z29$^{B'}$ | F | H | H |
| E2-29.5$^{B'}$ | Z29$^{B'}$ | $CH_2CH_3$ | H | H |
| E2-29.6$^{B'}$ | Z29$^{B'}$ | $CF_2H$ | H | H |
| E2-29.7$^{B'}$ | Z29$^{B'}$ | $CH_2F$ | H | H |
| E2-29.8$^{B'}$ | Z29$^{B'}$ | $CF_3$ | H | H |
| E2-29.9$^{B'}$ | Z29$^{B'}$ | $CF_2CH_3$ | H | H |
| E2-29.10$^{B'}$ | Z29$^{B'}$ | $CH_2CF_3$ | H | H |
| E2-29.11$^{B'}$ | Z29$^{B'}$ | cyclopropyl | H | H |
| E2-29.12$^{B'}$ | Z29$^{B'}$ | $OCF_3$ | H | H |
| E2-29.13$^{B'}$ | Z29$^{B'}$ | $OCF_2H$ | H | H |
| E2-29.14$^{B'}$ | Z29$^{B'}$ | Cl | H | F |
| E2-29.15$^{B'}$ | Z29$^{B'}$ | $CH_3$ | H | F |
| E2-29.16$^{B'}$ | Z29$^{B'}$ | $CH_3$ | F | H |
| E2-29.17$^{B'}$ | Z29$^{B'}$ | Cl | F | H |
| E2-29.18$^{B'}$ | Z29$^{B'}$ | F | F | H |
| E2-29.19$^{B'}$ | Z29$^{B'}$ | F | H | F |
| E2-29.20$^{B'}$ | Z29$^{B'}$ | F | H | Cl |
| E2-29.21$^{B'}$ | Z29$^{B'}$ | F | H | $CH_3$ |
| E2-29.22$^{B'}$ | Z29$^{B'}$ | Cl | H | $CH_3$ |
| E2-29.23$^{B'}$ | Z29$^{B'}$ | $SCH_3$ | H | H |
| E2-29.24$^{B'}$ | Z29$^{B'}$ | $SO_2CH_3$ | H | H |

TABLE 14.E2-continued

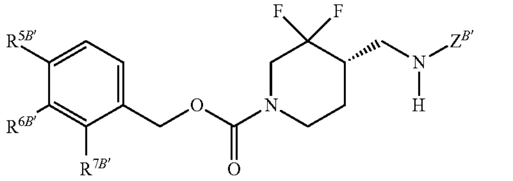

(S)

| compound | $Z^{B'}$ | $R^{5B'}$ | $R^{6B'}$ | $R^{7B'}$ |
|---|---|---|---|---|
| E2-29.25$^{B'}$ | Z29$^{B'}$ | ethynyl | H | H |
| E2-29.26$^{B'}$ | 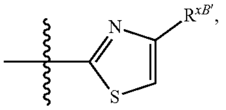 $R^{xB'}$ is $CH_3$ | $CH_3$ | H | H |
| E2-29.27$^{B'}$ | 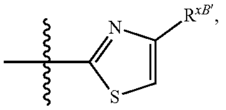 $R^{xB'}$ is Cl | $CH_3$ | H | H |
| E2-29.28$^{B'}$ | 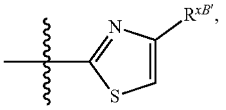 $R^{xB'}$ is F | $CH_3$ | H | H |
| E2-29.29$^{B'}$ | 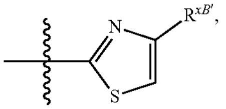 $R^{xB'}$ is $CF_3$ | $CH_3$ | H | H |
| E2-29.30$^{B'}$ | 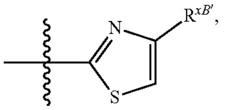 $R^{xB'}$ is CN | $CH_3$ | H | H |
| E2-29.31$^{B'}$ | 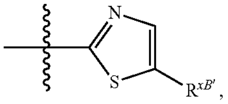 $R^{xB'}$ is $CH_3$ | $CH_3$ | H | H |
| E2-29.32$^{B'}$ | 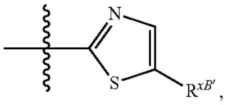 $R^{xB'}$ is Cl | $CH_3$ | H | H |
| E2-29.33$^{B'}$ | 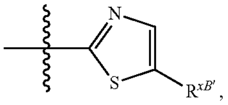 $R^{xB'}$ is F | $CH_3$ | H | H |

TABLE 14.E2-continued

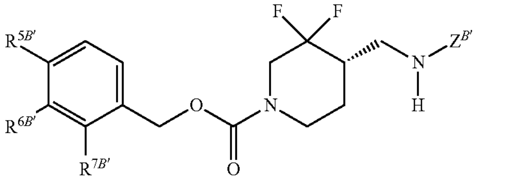

(S)

| compound | $Z^{B'}$ | $R^{5B'}$ | $R^{6B'}$ | $R^{7B'}$ |
|---|---|---|---|---|
| E2-29.34$^{B'}$ | 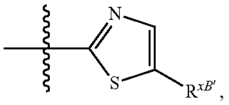 $R^{xB'}$ is $CF_3$ | $CH_3$ | H | H |
| E2-29.35$^{B'}$ | 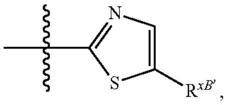 $R^{xB'}$ is CN | $CH_3$ | H | H |
| E2-30.1$^{B'}$ | Z30$^{B'}$ | H | H | H |
| E2-30.2$^{B'}$ | Z30$^{B'}$ | $CH_3$ | H | H |
| E2-30.3$^{B'}$ | Z30$^{B'}$ | Cl | H | H |
| E2-30.4$^{B'}$ | Z30$^{B'}$ | F | H | H |
| E2-30.5$^{B'}$ | Z30$^{B'}$ | $CH_2CH_3$ | H | H |
| E2-30.6$^{B'}$ | Z30$^{B'}$ | $CF_2H$ | H | H |
| E2-30.7$^{B'}$ | Z30$^{B'}$ | $CH_2F$ | H | H |
| E2-30.8$^{B'}$ | Z30$^{B'}$ | $CF_3$ | H | H |
| E2-30.9$^{B'}$ | Z30$^{B'}$ | $CF_2CH_3$ | H | H |
| E2-30.10$^{B'}$ | Z30$^{B'}$ | $CH_2CF_3$ | H | H |
| E2-30.11$^{B'}$ | Z30$^{B'}$ | cyclopropyl | H | H |
| E2-30.12$^{B'}$ | Z30$^{B'}$ | $OCF_3$ | H | H |
| E2-30.13$^{B'}$ | Z30$^{B'}$ | $OCF_2H$ | H | H |
| E2-30.14$^{B'}$ | Z30$^{B'}$ | Cl | H | F |
| E2-30.15$^{B'}$ | Z30$^{B'}$ | $CH_3$ | H | F |
| E2-30.16$^{B'}$ | Z30$^{B'}$ | $CH_3$ | F | H |
| E2-30.17$^{B'}$ | Z30$^{B'}$ | Cl | F | H |
| E2-30.18$^{B'}$ | Z30$^{B'}$ | F | F | H |
| E2-30.19$^{B'}$ | Z30$^{B'}$ | F | H | F |
| E2-30.20$^{B'}$ | Z30$^{B'}$ | F | H | Cl |
| E2-30.21$^{B'}$ | Z30$^{B'}$ | F | H | $CH_3$ |
| E2-30.22$^{B'}$ | Z30$^{B'}$ | Cl | H | $CH_3$ |
| E2-30.23$^{B'}$ | Z30$^{B'}$ | $SCH_3$ | H | H |
| E2-30.24$^{B'}$ | Z30$^{B'}$ | $SO_2CH_3$ | H | H |
| E2-30.25$^{B'}$ | Z30$^{B'}$ | ethynyl | H | H |
| E2-30.26$^{B'}$ | 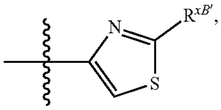 $R^{xB'}$ is $CH_3$ | $CH_3$ | H | H |
| E2-30.27$^{B'}$ | 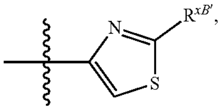 $R^{xB'}$ is Cl | $CH_3$ | H | H |
| E2-30.28$^{B'}$ | 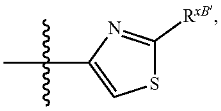 $R^{xB'}$ is F | $CH_3$ | H | H |

TABLE 14.E2-continued (S)

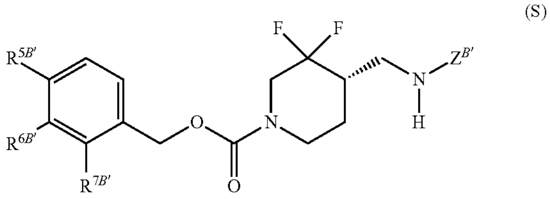

| compound | $Z^{B'}$ | $R^{5B'}$ | $R^{6B'}$ | $R^{7B'}$ |
|---|---|---|---|---|
| E2-30.29$^{B'}$ | 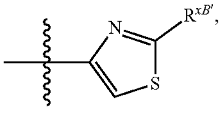 $R^{xB'}$ is $CF_3$ | $CH_3$ | H | H |
| E2-30.30$^{B'}$ | 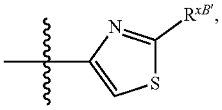 $R^{xB'}$ is CN | $CH_3$ | H | H |
| E2-30.31$^{B'}$ | 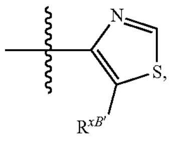 $R^{xB'}$ is $CH_3$ | $CH_3$ | H | H |
| E2-30.32$^{B'}$ | 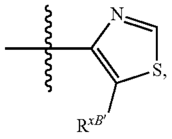 $R^{xB'}$ is Cl | $CH_3$ | H | H |
| E2-30.33$^{B'}$ | 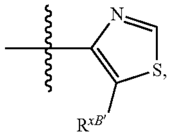 $R^{xB'}$ is F | $CH_3$ | H | H |
| E2-30.34$^{B'}$ | 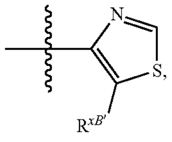 $R^{xB'}$ is $CF_3$ | $CH_3$ | H | H |
| E2-30.35$^{B'}$ | 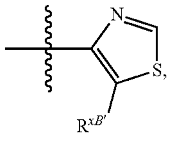 $R^{xB'}$ is CN | $CH_3$ | H | H |
| E2-31.1$^{B'}$ | Z31$^{B'}$ | H | H | H |
| E2-31.2$^{B'}$ | Z31$^{B'}$ | $CH_3$ | H | H |
| E2-31.3$^{B'}$ | Z31$^{B'}$ | Cl | H | H |
| E2-31.4$^{B'}$ | Z31$^{B'}$ | F | H | H |
| E2-31.5$^{B'}$ | Z31$^{B'}$ | $CH_2CH_3$ | H | H |
| E2-31.6$^{B'}$ | Z31$^{B'}$ | $CF_2H$ | H | H |

TABLE 14.E2-continued (S)

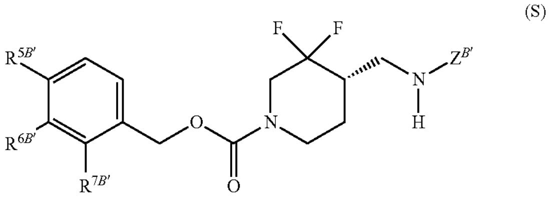

| compound | $Z^{B'}$ | $R^{5B'}$ | $R^{6B'}$ | $R^{7B'}$ |
|---|---|---|---|---|
| E2-31.7$^{B'}$ | Z31$^{B'}$ | $CH_2F$ | H | H |
| E2-31.8$^{B'}$ | Z31$^{B'}$ | $CF_3$ | H | H |
| E2-31.9$^{B'}$ | Z31$^{B'}$ | $CF_2CH_3$ | H | H |
| E2-31.10$^{B'}$ | Z31$^{B'}$ | $CH_2CF_3$ | H | H |
| E2-31.11$^{B'}$ | Z31$^{B'}$ | cyclopropyl | H | H |
| E2-31.12$^{B'}$ | Z31$^{B'}$ | $OCF_3$ | H | H |
| E2-31.13$^{B'}$ | Z31$^{B'}$ | $OCF_2H$ | H | H |
| E2-31.14$^{B'}$ | Z31$^{B'}$ | Cl | H | F |
| E2-31.15$^{B'}$ | Z31$^{B'}$ | $CH_3$ | H | F |
| E2-31.16$^{B'}$ | Z31$^{B'}$ | $CH_3$ | F | H |
| E2-31.17$^{B'}$ | Z31$^{B'}$ | Cl | F | H |
| E2-31.18$^{B'}$ | Z31$^{B'}$ | F | F | H |
| E2-31.19$^{B'}$ | Z31$^{B'}$ | F | H | F |
| E2-31.20$^{B'}$ | Z31$^{B'}$ | F | H | Cl |
| E2-31.21$^{B'}$ | Z31$^{B'}$ | F | H | $CH_3$ |
| E2-31.22$^{B'}$ | Z31$^{B'}$ | Cl | H | $CH_3$ |
| E2-31.23$^{B'}$ | Z31$^{B'}$ | $SCH_3$ | H | H |
| E2-31.24$^{B'}$ | Z31$^{B'}$ | $SO_2CH_3$ | H | H |
| E2-31.25$^{B'}$ | Z31$^{B'}$ | ethynyl | H | H |
| E2-31.26$^{B'}$ | 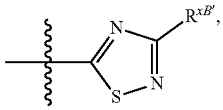 $R^{xB'}$ is $CH_3$ | $CH_3$ | H | H |
| E2-31.27$^{B'}$ | 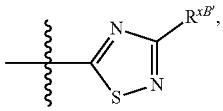 $R^{xB'}$ is Cl | $CH_3$ | H | H |
| E2-31.28$^{B'}$ | 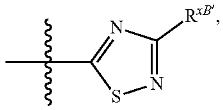 $R^{xB'}$ is F | $CH_3$ | H | H |
| E2-31.29$^{B'}$ | 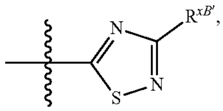 $R^{xB'}$ is $CF_3$ | $CH_3$ | H | H |
| E2-31.30$^{B'}$ | 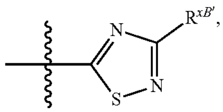 $R^{xB'}$ is CN | $CH_3$ | H | H |
| E2-32.1$^{B'}$ | Z32$^{B'}$ | H | H | H |
| E2-32.2$^{B'}$ | Z32$^{B'}$ | $CH_3$ | H | H |
| E2-32.3$^{B'}$ | Z32$^{B'}$ | Cl | H | H |
| E2-32.4$^{B'}$ | Z32$^{B'}$ | F | H | H |
| E2-32.5$^{B'}$ | Z32$^{B'}$ | $CH_2CH_3$ | H | H |
| E2-32.6$^{B'}$ | Z32$^{B'}$ | $CF_2H$ | H | H |
| E2-32.7$^{B'}$ | Z32$^{B'}$ | $CH_2F$ | H | H |
| E2-32.8$^{B'}$ | Z32$^{B'}$ | $CF_3$ | H | H |

TABLE 14.E2-continued (S)

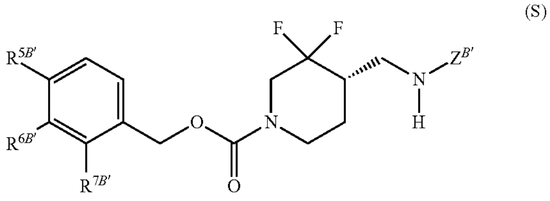

| compound | $Z^{B'}$ | $R^{5B'}$ | $R^{6B'}$ | $R^{7B'}$ |
|---|---|---|---|---|
| E2-32.9$^{B'}$ | Z32$^{B'}$ | $CF_2CH_3$ | H | H |
| E2-32.10$^{B'}$ | Z32$^{B'}$ | $CH_2CF_3$ | H | H |
| E2-32.11$^{B'}$ | Z32$^{B'}$ | cyclopropyl | H | H |
| E2-32.12$^{B'}$ | Z32$^{B'}$ | $OCF_3$ | H | H |
| E2-32.13$^{B'}$ | Z32$^{B'}$ | $OCF_2H$ | H | H |
| E2-32.14$^{B'}$ | Z32$^{B'}$ | Cl | H | F |
| E2-32.15$^{B'}$ | Z32$^{B'}$ | $CH_3$ | H | F |
| E2-32.16$^{B'}$ | Z32$^{B'}$ | $CH_3$ | F | H |
| E2-32.17$^{B'}$ | Z32$^{B'}$ | Cl | F | H |
| E2-32.18$^{B'}$ | Z32$^{B'}$ | F | F | H |
| E2-32.19$^{B'}$ | Z32$^{B'}$ | F | H | F |
| E2-32.20$^{B'}$ | Z32$^{B'}$ | F | H | Cl |
| E2-32.21$^{B'}$ | Z32$^{B'}$ | F | H | $CH_3$ |
| E2-32.22$^{B'}$ | Z32$^{B'}$ | Cl | H | $CH_3$ |
| E2-32.23$^{B'}$ | Z32$^{B'}$ | $SCH_3$ | H | H |
| E2-32.24$^{B'}$ | Z32$^{B'}$ | $SO_2CH_3$ | H | H |
| E2-32.25$^{B'}$ | Z32$^{B'}$ | ethynyl | H | H |
| E2-32.26$^{B'}$ | 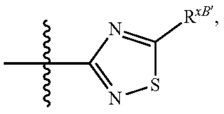 $R^{xB'}$ is $CH_3$ | $CH_3$ | H | H |
| E2-32.27$^{B'}$ | 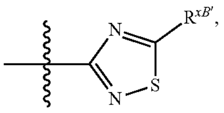 $R^{xB'}$ is Cl | $CH_3$ | H | H |
| E2-32.28$^{B'}$ | 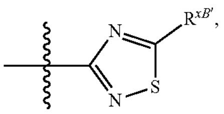 $R^{xB'}$ is F | $CH_3$ | H | H |
| E2-32.29$^{B'}$ | 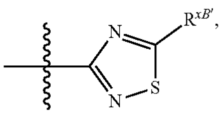 $R^{xB'}$ is $CF_3$ | $CH_3$ | H | H |
| E2-32.30$^{B'}$ | 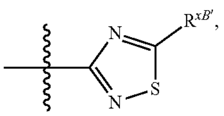 $R^{xB'}$ is CN | $CH_3$ | H | H |
| E2-33.1$^{B'}$ | Z33$^{B'}$ | H | H | H |
| E2-33.2$^{B'}$ | Z33$^{B'}$ | $CH_3$ | H | H |
| E2-33.3$^{B'}$ | Z33$^{B'}$ | Cl | H | H |
| E2-33.4$^{B'}$ | Z33$^{B'}$ | F | H | H |
| E2-33.5$^{B'}$ | Z33$^{B'}$ | $CH_2CH_3$ | H | H |
| E2-33.6$^{B'}$ | Z33$^{B'}$ | $CF_2H$ | H | H |
| E2-33.7$^{B'}$ | Z33$^{B'}$ | $CH_2F$ | H | H |
| E2-33.8$^{B'}$ | Z33$^{B'}$ | $CF_3$ | H | H |
| E2-33.9$^{B'}$ | Z33$^{B'}$ | $CF_2CH_3$ | H | H |
| E2-33.10$^{B'}$ | Z33$^{B'}$ | $CH_2CF_3$ | H | H |

TABLE 14.E2-continued (S)

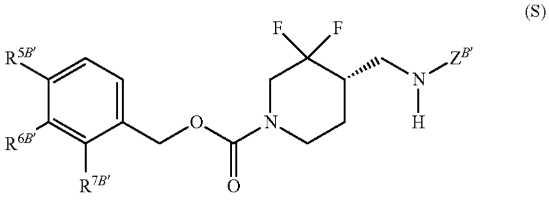

| compound | $Z^{B'}$ | $R^{5B'}$ | $R^{6B'}$ | $R^{7B'}$ |
|---|---|---|---|---|
| E2-33.11$^{B'}$ | Z33$^{B'}$ | cyclopropyl | H | H |
| E2-33.12$^{B'}$ | Z33$^{B'}$ | $OCF_3$ | H | H |
| E2-33.13$^{B'}$ | Z33$^{B'}$ | $OCF_2H$ | H | H |
| E2-33.14$^{B'}$ | Z33$^{B'}$ | Cl | H | F |
| E2-33.15$^{B'}$ | Z33$^{B'}$ | $CH_3$ | H | F |
| E2-33.16$^{B'}$ | Z33$^{B'}$ | $CH_3$ | F | H |
| E2-33.17$^{B'}$ | Z33$^{B'}$ | Cl | F | H |
| E2-33.18$^{B'}$ | Z33$^{B'}$ | F | F | H |
| E2-33.19$^{B'}$ | Z33$^{B'}$ | F | H | F |
| E2-33.20$^{B'}$ | Z33$^{B'}$ | F | H | Cl |
| E2-33.21$^{B'}$ | Z33$^{B'}$ | F | H | $CH_3$ |
| E2-33.22$^{B'}$ | Z33$^{B'}$ | Cl | H | $CH_3$ |
| E2-33.23$^{B'}$ | Z33$^{B'}$ | $SCH_3$ | H | H |
| E2-33.24$^{B'}$ | Z33$^{B'}$ | $SO_2CH_3$ | H | H |
| E2-33.25$^{B'}$ | Z33$^{B'}$ | ethynyl | H | H |
| E2-33.26$^{B'}$ | 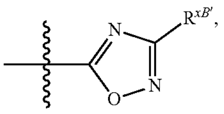 $R^{xB'}$ is $CH_3$ | $CH_3$ | H | H |
| E2-33.27$^{B'}$ | 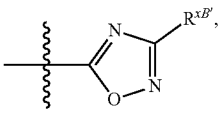 $R^{xB'}$ is Cl | $CH_3$ | H | H |
| E2-33.28$^{B'}$ | 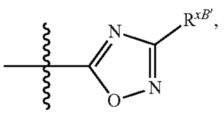 $R^{xB'}$ is F | $CH_3$ | H | H |
| E2-33.29$^{B'}$ | 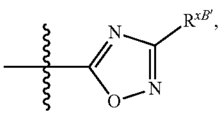 $R^{xB'}$ is $CF_3$ | $CH_3$ | H | H |
| E2-33.30$^{B'}$ | 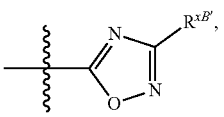 $R^{xB'}$ is CN | $CH_3$ | H | H |
| E2-34.1$^{B'}$ | Z34$^{B'}$ | H | H | H |
| E2-34.2$^{B'}$ | Z34$^{B'}$ | $CH_3$ | H | H |
| E2-34.3$^{B'}$ | Z34$^{B'}$ | Cl | H | H |
| E2-34.4$^{B'}$ | Z34$^{B'}$ | F | H | H |
| E2-34.5$^{B'}$ | Z34$^{B'}$ | $CH_2CH_3$ | H | H |
| E2-34.6$^{B'}$ | Z34$^{B'}$ | $CF_2H$ | H | H |
| E2-34.7$^{B'}$ | Z34$^{B'}$ | $CH_2F$ | H | H |
| E2-34.8$^{B'}$ | Z34$^{B'}$ | $CF_3$ | H | H |
| E2-34.9$^{B'}$ | Z34$^{B'}$ | $CF_2CH_3$ | H | H |
| E2-34.10$^{B'}$ | Z34$^{B'}$ | $CH_2CF_3$ | H | H |
| E2-34.11$^{B'}$ | Z34$^{B'}$ | cyclopropyl | H | H |
| E2-34.12$^{B'}$ | Z34$^{B'}$ | $OCF_3$ | H | H |

TABLE 14.E2-continued (S)

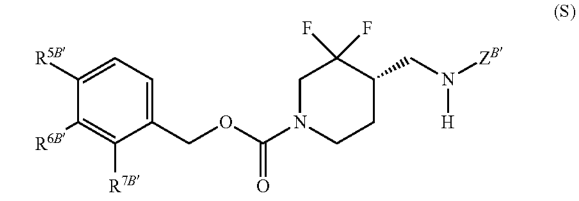

| compound | $Z^{B'}$ | $R^{5B'}$ | $R^{6B'}$ | $R^{7B'}$ |
|---|---|---|---|---|
| E2-34.13$^{B'}$ | Z34$^{B'}$ | $OCF_2H$ | H | H |
| E2-34.14$^{B'}$ | Z34$^{B'}$ | Cl | H | F |
| E2-34.15$^{B'}$ | Z34$^{B'}$ | $CH_3$ | H | F |
| E2-34.16$^{B'}$ | Z34$^{B'}$ | $CH_3$ | F | H |
| E2-34.17$^{B'}$ | Z34$^{B'}$ | Cl | F | H |
| E2-34.18$^{B'}$ | Z34$^{B'}$ | F | F | H |
| E2-34.19$^{B'}$ | Z34$^{B'}$ | F | H | F |
| E2-34.20$^{B'}$ | Z34$^{B'}$ | F | H | Cl |
| E2-34.21$^{B'}$ | Z34$^{B'}$ | F | H | $CH_3$ |
| E2-34.22$^{B'}$ | Z34$^{B'}$ | Cl | H | $CH_3$ |
| E2-34.23$^{B'}$ | Z34$^{B'}$ | $SCH_3$ | H | H |
| E2-34.24$^{B'}$ | Z34$^{B'}$ | $SO_2CH_3$ | H | H |
| E2-34.25$^{B'}$ | Z34$^{B'}$ | ethynyl | H | H |
| E2-34.26$^{B'}$ | 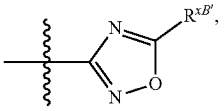 $R^{xB'}$ is $CH_3$ | $CH_3$ | H | H |
| E2-34.27$^{B'}$ | 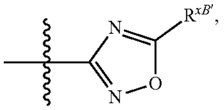 $R^{xB'}$ is Cl | $CH_3$ | H | H |
| E2-34.28$^{B'}$ | 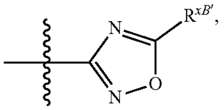 $R^{xB'}$ is F | $CH_3$ | H | H |
| E2-34.29$^{B'}$ | 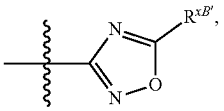 $R^{xB'}$ is $CF_3$ | $CH_3$ | H | H |
| E2-34.30$^{B'}$ | 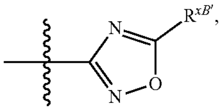 $R^{xB'}$ is CN | $CH_3$ | H | H |
| E2-35.1$^{B'}$ | Z35$^{B'}$, $R^{aB'}$ is H | H | H | H |
| E2-35.2$^{B'}$ | Z35$^{B'}$, $R^{aB'}$ is H | $CH_3$ | H | H |
| E2-35.3$^{B'}$ | Z35$^{B'}$, $R^{aB'}$ is H | Cl | H | H |
| E2-35.4$^{B'}$ | Z35$^{B'}$, $R^{aB'}$ is H | F | H | H |
| E2-35.5$^{B'}$ | Z35$^{B'}$, $R^{aB'}$ is H | $CH_2CH_3$ | H | H |
| E2-35.6$^{B'}$ | Z35$^{B'}$, $R^{aB'}$ is H | $CF_2H$ | H | H |
| E2-35.7$^{B'}$ | Z35$^{B'}$, $R^{aB'}$ is H | $CH_2F$ | H | H |
| E2-35.8$^{B'}$ | Z35$^{B'}$, $R^{aB'}$ is H | $CF_3$ | H | H |
| E2-35.9$^{B'}$ | Z35$^{B'}$, $R^{aB'}$ is H | $CF_2CH_3$ | H | H |
| E2-35.10$^{B'}$ | Z35$^{B'}$, $R^{aB'}$ is H | $CH_2CF_3$ | H | H |
| E2-35.11$^{B'}$ | Z35$^{B'}$, $R^{aB'}$ is H | cyclopropyl | H | H |
| E2-35.12$^{B'}$ | Z35$^{B'}$, $R^{aB'}$ is H | $OCF_3$ | H | H |
| E2-35.13$^{B'}$ | Z35$^{B'}$, $R^{aB'}$ is H | $OCF_2H$ | H | H |
| E2-35.14$^{B'}$ | Z35$^{B'}$, $R^{aB'}$ is H | Cl | H | F |

TABLE 14.E2-continued (S)

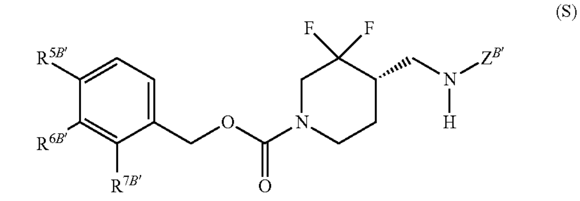

| compound | $Z^{B'}$ | $R^{5B'}$ | $R^{6B'}$ | $R^{7B'}$ |
|---|---|---|---|---|
| E2-35.15$^{B'}$ | Z35$^{B'}$, $R^{aB'}$ is H | $CH_3$ | H | F |
| E2-35.16$^{B'}$ | Z35$^{B'}$, $R^{aB'}$ is H | $CH_3$ | F | H |
| E2-35.17$^{B'}$ | Z35$^{B'}$, $R^{aB'}$ is H | Cl | F | H |
| E2-35.18$^{B'}$ | Z35$^{B'}$, $R^{aB'}$ is H | F | F | H |
| E2-35.19$^{aB'}$ | Z35$^{B'}$, $R^{aB'}$ is H | F | H | F |
| E2-35.20$^{B'}$ | Z35$^{B'}$, $R^{aB'}$ is H | F | H | Cl |
| E2-35.21$^{B'}$ | Z35$^{B'}$, $R^{aB'}$ is H | F | H | $CH_3$ |
| E2-35.22$^{B'}$ | Z35$^{B'}$, $R^{aB'}$ is H | Cl | H | $CH_3$ |
| E2-35.23$^{B'}$ | Z35$^{B'}$, $R^{aB'}$ is H | $SCH_3$ | H | H |
| E2-35.24$^{B'}$ | Z35$^{B'}$, $R^{aB'}$ is H | $SO_2CH_3$ | H | H |
| E2-35.25$^{B'}$ | Z35$^{B'}$, $R^{aB'}$ is H | ethynyl | H | H |
| E2-35.26$^{B'}$ | 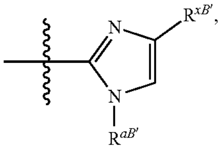 $R^{aB'}$ is H; $R^{xB'}$ is $CH_3$ | $CH_3$ | H | H |
| E2-35.27$^{B'}$ | 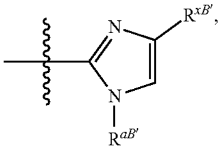 $R^{aB'}$ is H; $R^{xB'}$ is Cl | $CH_3$ | H | H |
| E2-35.28$^{B'}$ | 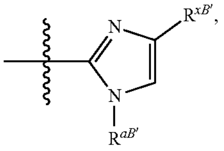 $R^{aB'}$ is H; $R^{xB'}$ is F | $CH_3$ | H | H |
| E2-35.29$^{B'}$ | 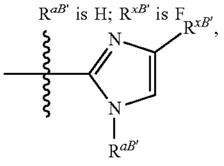 $R^{aB'}$ is H; $R^{xB'}$ is $CF_3$ | $CH_3$ | H | H |
| E2-35.30$^{B'}$ | 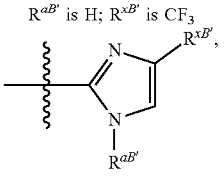 $R^{aB'}$ is H; $R^{xB'}$ is CN | $CH_3$ | H | H |
| E2-35.31$^{B'}$ | 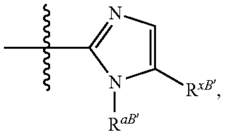 $R^{aB'}$ is H; $R^{xB'}$ is $CH_3$ | $CH_3$ | H | H |

(S)

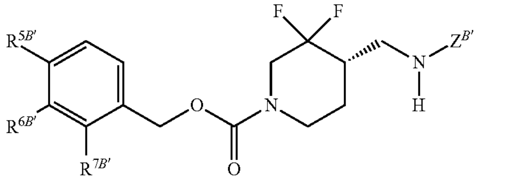

| compound | $Z^{B'}$ | $R^{5B'}$ | $R^{6B'}$ | $R^{7B'}$ |
|---|---|---|---|---|
| E2-35.32$^{B'}$ | 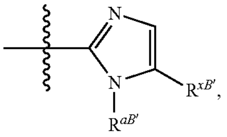 $R^{aB'}$ is H; $R^{xB'}$ is Cl | $CH_3$ | H | H |
| E2-35.33$^{B'}$ | 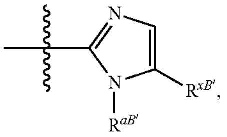 $R^{aB'}$ is H; $R^{xB'}$ is F | $CH_3$ | H | H |
| E2-35.34$^{B'}$ | 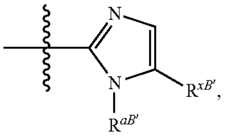 $R^{aB'}$ is H; $R^{xB'}$ is $CF_3$ | $CH_3$ | H | H |
| E2-35.35$^{B'}$ | 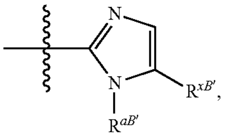 $R^{aB'}$ is H; $R^{xB'}$ is CN | $CH_3$ | H | H |
| E2-36.1$^{B'}$ | Z36$^{B'}$, $R^{aB'}$ is H | H | H | H |
| E2-36.2$^{B'}$ | Z36$^{B'}$, $R^{aB'}$ is H | $CH_3$ | H | H |
| E2-36.3$^{B'}$ | Z36$^{B'}$, $R^{aB'}$ is H | Cl | H | H |
| E2-36.4$^{B'}$ | Z36$^{B'}$, $R^{aB'}$ is H | F | H | H |
| E2-36.5$^{B'}$ | Z36$^{B'}$, $R^{aB'}$ is H | $CH_2CH_3$ | H | H |
| E2-36.6$^{B'}$ | Z36$^{B'}$, $R^{aB'}$ is H | $CF_2H$ | H | H |
| E2-36.7$^{B'}$ | Z36$^{B'}$, $R^{aB'}$ is H | $CH_2F$ | H | H |
| E2-36.8$^{B'}$ | Z36$^{B'}$, $R^{aB'}$ is H | $CF_3$ | H | H |
| E2-36.9$^{B'}$ | Z36$^{B'}$, $R^{aB'}$ is H | $CF_2CH_3$ | H | H |
| E2-36.10$^{B'}$ | Z36$^{B'}$, $R^{aB'}$ is H | $CH_2CF_3$ | H | H |
| E2-36.11$^{B'}$ | Z36$^{B'}$, $R^{aB'}$ is H | cyclopropyl | H | H |
| E2-36.12$^{B'}$ | Z36$^{B'}$, $R^{aB'}$ is H | $OCF_3$ | H | H |
| E2-36.13$^{B'}$ | Z36$^{B'}$, $R^{aB'}$ is H | $OCF_2H$ | H | H |
| E2-36.14$^{B'}$ | Z36$^{B'}$, $R^{aB'}$ is H | Cl | H | F |
| E2-36.15$^{B'}$ | Z36$^{B'}$, $R^{aB'}$ is H | $CH_3$ | H | F |
| E2-36.16$^{B'}$ | Z36$^{B'}$, $R^{aB'}$ is H | $CH_3$ | F | H |
| E2-36.17$^{B'}$ | Z36$^{B'}$, $R^{aB'}$ is H | Cl | F | H |
| E2-36.18$^{B'}$ | Z36$^{B'}$, $R^{aB'}$ is H | F | F | H |
| E2-36.19$^{B'}$ | Z36$^{B'}$, $R^{aB'}$ is H | F | H | F |
| E2-36.20$^{B'}$ | Z36$^{B'}$, $R^{aB'}$ is H | F | H | Cl |
| E2-36.21$^{B'}$ | Z36$^{B'}$, $R^{aB'}$ is H | F | H | $CH_3$ |
| E2-36.22$^{B'}$ | Z36$^{B'}$, $R^{aB'}$ is H | Cl | H | $CH_3$ |
| E2-36.23$^{B'}$ | Z36$^{B'}$, $R^{aB'}$ is H | $SCH_3$ | H | H |
| E2-36.24$^{B'}$ | Z36$^{B'}$, $R^{aB'}$ is H | $SO_2CH_3$ | H | H |
| E2-36.25$^{B'}$ | Z36$^{B'}$, $R^{aB'}$ is H | ethynyl | H | H |
| E2-36.26$^{B'}$ | 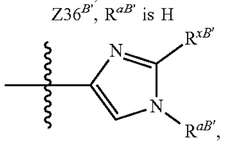 $R^{aB'}$ is H; $R^{xB'}$ is $CH_3$ | $CH_3$ | H | H |

(S)

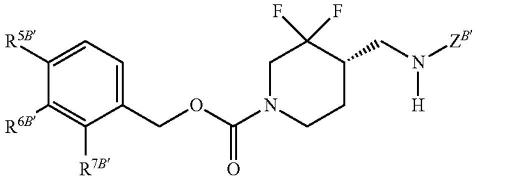

| compound | $Z^{B'}$ | $R^{5B'}$ | $R^{6B'}$ | $R^{7B'}$ |
|---|---|---|---|---|
| E2-36.27$^{B'}$ | 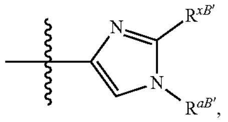 $R^{aB'}$ is H; $R^{xB'}$ is Cl | $CH_3$ | H | H |
| E2-36.28$^{B'}$ | 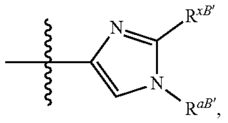 $R^{aB'}$ is H; $R^{xB'}$ is F | $CH_3$ | H | H |
| E2-36.29$^{B'}$ | 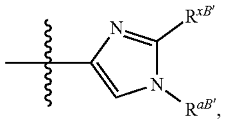 $R^{aB'}$ is H; $R^{xB'}$ is $CF_3$ | $CH_3$ | H | H |
| E2-36.30$^{B'}$ | 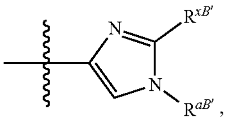 $R^{aB'}$ is H; $R^{xB'}$ is CN | $CH_3$ | H | H |
| E2-37.1$^{B'}$ | Z37$^{B'}$ | H | H | H |
| E2-37.2$^{B'}$ | Z37$^{B'}$ | $CH_3$ | H | H |
| E2-37.3$^{B'}$ | Z37$^{B'}$ | Cl | H | H |
| E2-37.4$^{B'}$ | Z37$^{B'}$ | F | H | H |
| E2-37.5$^{B'}$ | Z37$^{B'}$ | $CH_2CH_3$ | H | H |
| E2-37.6$^{B'}$ | Z37$^{B'}$ | $CF_2H$ | H | H |
| E2-38.1$^{B'}$ | Z38$^{B'}$ | H | H | H |
| E2-38.2$^{B'}$ | Z38$^{B'}$ | $CH_3$ | H | H |
| E2-38.3$^{B'}$ | Z38$^{B'}$ | Cl | H | H |
| E2-38.4$^{B'}$ | Z38$^{B'}$ | F | H | H |
| E2-38.5$^{B'}$ | Z38$^{B'}$ | $CH_2CH_3$ | H | H |
| E2-38.6$^{B'}$ | Z38$^{B'}$ | $CF_2H$ | H | H |
| E2-38.7$^{B'}$ | 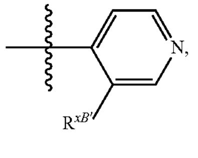 $R^{xB'}$ is F | H | H | H |
| E2-38.8$^{B'}$ | 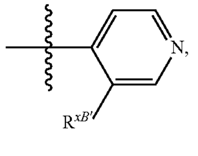 $R^{xB'}$ is F | $CH_3$ | H | H |

TABLE 14.E2-continued (S)

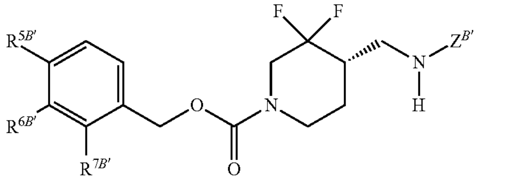

| compound | $Z^{B'}$ | $R^{5B'}$ | $R^{6B'}$ | $R^{7B'}$ |
|---|---|---|---|---|
| E2-38.9$^{B'}$ | 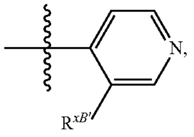 $R^{xB'}$ is F | Cl | H | H |
| E2-38.10$^{B'}$ | 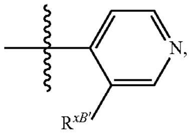 $R^{xB'}$ is F | F | H | H |
| E2-38.11$^{B'}$ | 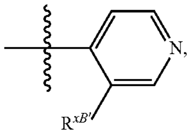 $R^{xB'}$ is F | $CH_3CH_3$ | H | H |
| E2-38.12$^{B'}$ | 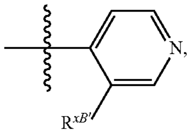 $R^{xB'}$ is F | $CF_2H$ | H | H |

TABLE 15.III-C

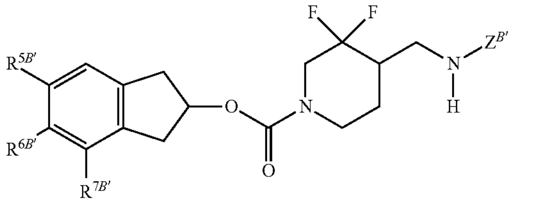

(racemic)

| compound | $Z^{B'}$ | $R^{5B'}$ | $R^{6B'}$ | $R^{7B'}$ |
|---|---|---|---|---|
| III-C-21.1$^{B'}$ | Z21$^{B'}$ | H | H | H |
| III-C-21.2$^{B'}$ | Z21$^{B'}$ | $CH_3$ | H | H |
| III-C-21.3$^{B'}$ | Z21$^{B'}$ | Cl | H | H |
| III-C-21.4$^{B'}$ | Z21$^{B'}$ | F | H | H |
| III-C-21.5$^{B'}$ | Z21$^{B'}$ | $CH_2CH_3$ | H | H |
| III-C-21.6$^{B'}$ | Z21$^{B'}$ | $CF_2H$ | H | H |
| III-C-22.1$^{B'}$ | Z22$^{B'}$ | H | H | H |
| III-C-22.2$^{B'}$ | Z22$^{B'}$ | $CH_3$ | H | H |
| III-C-22.3$^{B'}$ | Z22$^{B'}$ | Cl | H | H |
| III-C-22.4$^{B'}$ | Z22$^{B'}$ | F | H | H |
| III-C-22.5$^{B'}$ | Z22$^{B'}$ | $CH_2CH_3$ | H | H |
| III-C-22.6$^{B'}$ | Z22$^{B'}$ | $CF_2H$ | H | H |
| III-C-24.1$^{B'}$ | Z24$^{B'}$ | H | H | H |

TABLE 15.III-C-continued

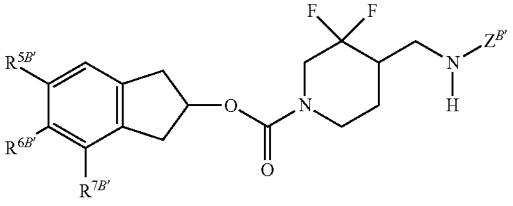

(racemic)

| compound | $Z^{B'}$ | $R^{5B'}$ | $R^{6B'}$ | $R^{7B'}$ |
|---|---|---|---|---|
| III-C-24.2$^{B'}$ | Z24$^{B'}$ | $CH_3$ | H | H |
| III-C-24.3$^{B'}$ | Z24$^{B'}$ | Cl | H | H |
| III-C-24.4$^{B'}$ | Z24$^{B'}$ | F | H | H |
| III-C-24.5$^{B'}$ | Z24$^{B'}$ | $CH_2CH_3$ | H | H |
| III-C-24.6$^{B'}$ | Z24$^{B'}$ | $CF_2H$ | H | H |
| III-C-37.1$^{B'}$ | Z37$^{B'}$ | H | H | H |
| III-C-37.2$^{B'}$ | Z37$^{B'}$ | $CH_3$ | H | H |
| III-C-37.3$^{B'}$ | Z37$^{B'}$ | Cl | H | H |
| III-C-37.4$^{B'}$ | Z37$^{B'}$ | F | H | H |
| III-C-37.5$^{B'}$ | Z37$^{B'}$ | $CH_2CH_3$ | H | H |
| III-C-37.6$^{B'}$ | Z37$^{B'}$ | $CF_2H$ | H | H |
| III-C-38.1$^{B'}$ | Z38$^{B'}$ | H | H | H |
| III-C-38.2$^{B'}$ | Z38$^{B'}$ | $CH_3$ | H | H |
| III-C-38.3$^{B'}$ | Z38$^{B'}$ | Cl | H | H |
| III-C-38.4$^{B'}$ | Z38$^{B'}$ | F | H | H |
| III-C-38.5$^{B'}$ | Z38$^{B'}$ | $CH_2CH_3$ | H | H |
| III-C-38.6$^{B'}$ | Z38$^{B'}$ | $CF_2H$ | H | H |

TABLE 16.III-E1

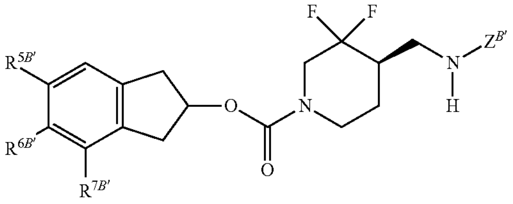

(R)

| compound | $Z^{B'}$ | $R^{5B'}$ | $R^{6B'}$ | $R^{7B'}$ |
|---|---|---|---|---|
| III-E1-21.1$^{B'}$ | Z21$^{B'}$ | H | H | H |
| III-E1-21.2$^{B'}$ | Z21$^{B'}$ | $CH_3$ | H | H |
| III-E1-21.3$^{B'}$ | Z21$^{B'}$ | Cl | H | H |
| III-E1-21.4$^{B'}$ | Z21$^{B'}$ | F | H | H |
| III-E1-21.5$^{B'}$ | Z21$^{B'}$ | $CH_2CH_3$ | H | H |
| III-E1-21.6$^{B'}$ | Z21$^{B'}$ | $CF_2H$ | H | H |
| III-E1-22.1$^{B'}$ | Z22$^{B'}$ | H | H | H |
| III-E1-22.2$^{B'}$ | Z22$^{B'}$ | $CH_3$ | H | H |
| III-E1-22.3$^{B'}$ | Z22$^{B'}$ | Cl | H | H |
| III-E1-22.4$^{B'}$ | Z22$^{B'}$ | F | H | H |
| III-E1-22.5$^{B'}$ | Z22$^{B'}$ | $CH_2CH_3$ | H | H |
| III-E1-22.6$^{B'}$ | Z22$^{B'}$ | $CF_2H$ | H | H |
| III-E1-24.1$^{B'}$ | Z24$^{B'}$ | H | H | H |
| III-E1-24.2$^{B'}$ | Z24$^{B'}$ | $CH_3$ | H | H |
| III-E1-24.3$^{B'}$ | Z24$^{B'}$ | Cl | H | H |
| III-E1-24.4$^{B'}$ | Z24$^{B'}$ | F | H | H |
| III-E1-24.5$^{B'}$ | Z24$^{B'}$ | $CH_2CH_3$ | H | H |
| III-E1-24.6$^{B'}$ | Z24$^{B'}$ | $CF_2H$ | H | H |
| III-E1-37.1$^{B'}$ | Z37$^{B'}$ | H | H | H |
| III-E1-37.2$^{B'}$ | Z37$^{B'}$ | $CH_3$ | H | H |
| III-E1-37.3$^{B'}$ | Z37$^{B'}$ | Cl | H | H |
| III-E1-37.4$^{B'}$ | Z37$^{B'}$ | F | H | H |
| III-E1-37.5$^{B'}$ | Z37$^{B'}$ | $CH_2CH_3$ | H | H |
| III-E1-37.6$^{B'}$ | Z37$^{B'}$ | $CF_2H$ | H | H |
| III-E1-38.1$^{B'}$ | Z38$^{B'}$ | H | H | H |
| III-E1-38.2$^{B'}$ | Z38$^{B'}$ | $CH_3$ | H | H |
| III-E1-38.3$^{B'}$ | Z38$^{B'}$ | Cl | H | H |
| III-E1-38.4$^{B'}$ | Z38$^{B'}$ | F | H | H |
| III-E1-38.5$^{B'}$ | Z38$^{B'}$ | $CH_2CH_3$ | H | H |
| III-E1-38.6$^{B'}$ | Z38$^{B'}$ | $CF_2H$ | H | H |

General Synthetic Methods

Compounds of formula $I^{A'}$ can be prepared, for example, by the methods described in WO2016/044323, published Mar. 24, 2016. Compounds of formula $I^{B''}$ can be prepared, for example, by the methods described in WO2016/196513, published Dec. 8, 2016.

Compounds of formula $I^{B'}$ can be synthesized according to Scheme 1 and/or using methods known in the art.

Scheme 1

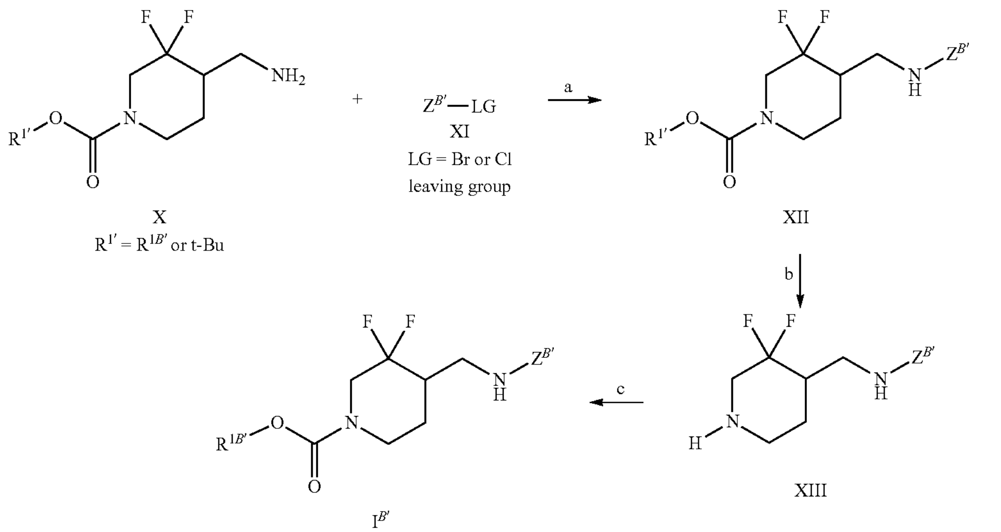

a. base (e.g., diisopropylethylamine), organic solvent (e.g., n-butanol), heat or Buchwald coupling conditions (e.g., Pd catalyst, base, organic solvent, heat). b. deprotection conditions (e.g., $CF_3CO_2H$ or HCl, room temperature when $R^{1'}$ = t-butyl). c. carbamate formation conditions (e.g., carbonyldiimidazole, $R^{1B'}$——OH, DMSO, room temperature).

In the method depicted in Scheme 1, in a first step, compounds of formula XII may be prepared by coupling of intermediates of formula X, wherein $R^{1'}=R^{1B'}$ or a protecting group (e.g., where $R^{1'}$ is t-butyl, the moiety $R^{1'}$—OC(O)— is a Boc group), with intermediates $Z^{B'}$-LG of formula XI. For compounds of formula XI the $Z^{B'}$ is a heterocyclic group as defined above and LG is a suitable group for the coupling reaction such as chlorine or bromine. In certain cases, the coupling reaction can be conducted as a base-mediated nucleophilic aromatic substitution reaction. In certain cases, the coupling reaction can be conducted as a Buchwald reaction mediated by palladium catalysis. Aromatic substitution coupling reactions can be conducted in suitable protic (e.g., isopropanol, n-butanol) or aprotic (e.g., $CH_2Cl_2$, DMF, DMSO, $CH_3CN$) solvents at temperatures from ambient to 160° C., for example, between 50° C. and 120° C. with intermediates of formula $Z^{B'}$—Cl in the presence of a suitable base (e.g., triethylamine, diisopropylethylamine). Buchwald coupling reactions (Buchwald and Muci *Top. Curr. Chem.* 2002, 219:133-209) can be conducted in suitable organic solvents (e.g., t-butanol, toluene, DMF, DMSO, $CH_3CN$) in the presence of a suitable palladium catalyst and phosphine ligand system (e.g., Brettphos/ Brettphos precatalyst, BINAP/$Pd_2(dba)_3$) at temperatures from 70° C. to 150° C., for example, between 80° C. and 130° C. with intermediates of formula $Z^{B'}$—Br, in the presence of a suitable base (e.g., $Cs_2CO_3$) under inert (e.g., nitrogen) atmosphere. In the case where $R^{1'}=R^{1B'}$, compounds of formula XII are equivalent to compounds of formula $I^{B'}$. In the case where $R^{1'}$ is a protecting group then intermediate compounds of formula XII can be converted to intermediate compounds of formula XIII using deprotection conditions known in the art. For example, when R" is a t-butyl group (i.e., where the R"-OC(O)— moiety is a Boc group), intermediate compounds of formula XII can be converted to intermediate compounds of formula XIII using a number of known methods. Typically, the Boc deprotection is conducted under acidic conditions using either HCl (e.g., 1-4 N HCl in ether or dioxane in a suitable organic solvent; e.g., dichloromethane, methanol, or THF) at temperatures between 0° C. and 50° C., or using trifluoroacetic acid in an aprotic solvent (e.g., dichloromethane) at temperatures between 0° C. and room temperature. The latter is particularly useful for compounds which are sensitive to chloride-mediated side reactions. Intermediate compounds of formula XIII can be converted to compounds of formula $I^{B'}$ by carbamoylation reaction with a carbamoylating reagent of formula $R^{1B'}OC(O)X$ wherein X is a suitable leaving group (e.g., Cl, imidazolyl, hydroxysuccinyl). Reagents of formula $R^{1B'}$ OC(O)X may be implemented in isolated form or generated in situ. For example, an alcohol of formula $R^{1B'}OH$ can be treated with carbonyldiimidazole in an aprotic organic solvent at between 0° C. and room temperature to first form the $R^{1B'}$ OC(O)imidazolyl carbamoylating reagent. In situ reaction of the $R^{1B'}OC(O)$imidazolyl carbamoylating reagent with intermediate compounds of formula XIII (in free base or acid addition salt form, at temperatures between 0° C. and 70° C.) in an aprotic solvent (e.g., DMSO) yields compounds of formula $I^{B'}$.

The heteroaryl chloride or bromide coupling reagents $Z^{B'}$-LG are either commercially available, can be prepared according to known literature procedures for the exact compound or can be prepared using methods known in the art for synthesizing heteroaryl chlorides and bromides. For example, the heteroaryl compound $Z^{B'}$—H can be brominated or chlorinated using methods known in the art (e.g. by treatment with bromine, N-bromosuccinimide, or another brominating reagent or treatment with a chlorinating reagent such as sulfuryl chloride) the desired $Z^{B'}$—Br or $Z^{B'}$—Cl heteroaryl coupling reagent can then be isolated by the appropriate procedure (e.g., by chromatography as needed to separate regioisomers). Heteroaryl coupling reagents $Z^{B'}$—

Cl wherein the chloro group is part of an iminochloride substructure can be prepared under standard conditions (e.g., using phosphorus oxychloride at elevated temperature as solvent itself or in a suitable aprotic organic solvent) from the corresponding $Z^{B'}$—OH starting material which has the corresponding amido tautomeric substructure. Other heteroaryl coupling reagents can be prepared from the corresponding $Z^{B'}$—$NH_2$ starting material under Sandmeyer reaction-type conditions which are well established in the art (i.e., diazotization reaction followed by chlorination or bromination with CuCl or CuBr). In some cases, the required $Z^{B'}$—H, $Z^{B'}$—OH, or $Z^{B'}$—$NH_2$ starting materials can be prepared using methods known in the art for synthesizing heteroaryl compounds.

Chemical entities of Formula $I^{B'}$ can be obtained as individual enantiomers from racemic mixtures using methods known in the art such as chiral chromatography or recrystallization of diastereomeric acid addition salts. Alternatively, chemical entities of Formula $I^{B'}$ can be obtained as individual enantiomers by asymmetric synthesis or from the corresponding individual enantiomer intermediates. For example, the individual enantiomers of chemical entities of Formula $I^{B'}$ can be prepared from enantiomers of the intermediates of formula X having the corresponding absolute stereochemical configuration at C-4 of the piperidine ring system. Intermediates of formula X can in turn be prepared by an asymmetric synthesis process as depicted in Scheme 2. In this process the known starting material XIV (Madaiah et al. *Tetrahedron Lett.* 2013, 54:1424-1427) is converted in three steps to an α,β-unsaturated acyl intermediate XV substituted with an optically pure R=(XVa) or S=(XVb) oxazolidinone chiral auxiliary system. In the case of XVa, with the R-absolute stereochemistry chiral auxiliary, standard catalytic hydrogenation using 10% Pd—C in ethyl acetate affords an approximate 5:1 mixture of diasteromeric products (R)-XVIa (major) and (S)-XVIa (minor). This mixture can be separated by standard chromatography over silica gel to give (R)-XVIa in pure form. As depicted in Scheme 2, hydrolysis of the chiral auxiliary of pure intermediate (R)-XVIa gives the pure enantiomer acid intermediate (R)-XVII. From (R)-XVII, a two-step Curtius reaction process gives the (−)-(R)—X enantiomer. The (+)-(S)—X enantiomer can be prepared in analogous fashion starting from intermediate XVb. Pure enantiomers of formula X may also be prepared from enantiomerically enriched or racemic mixtures by chiral acid addition salt formation and recrystallization (e.g., a chirally pure tartaric acid) using methods standard in the art.

Scheme 2

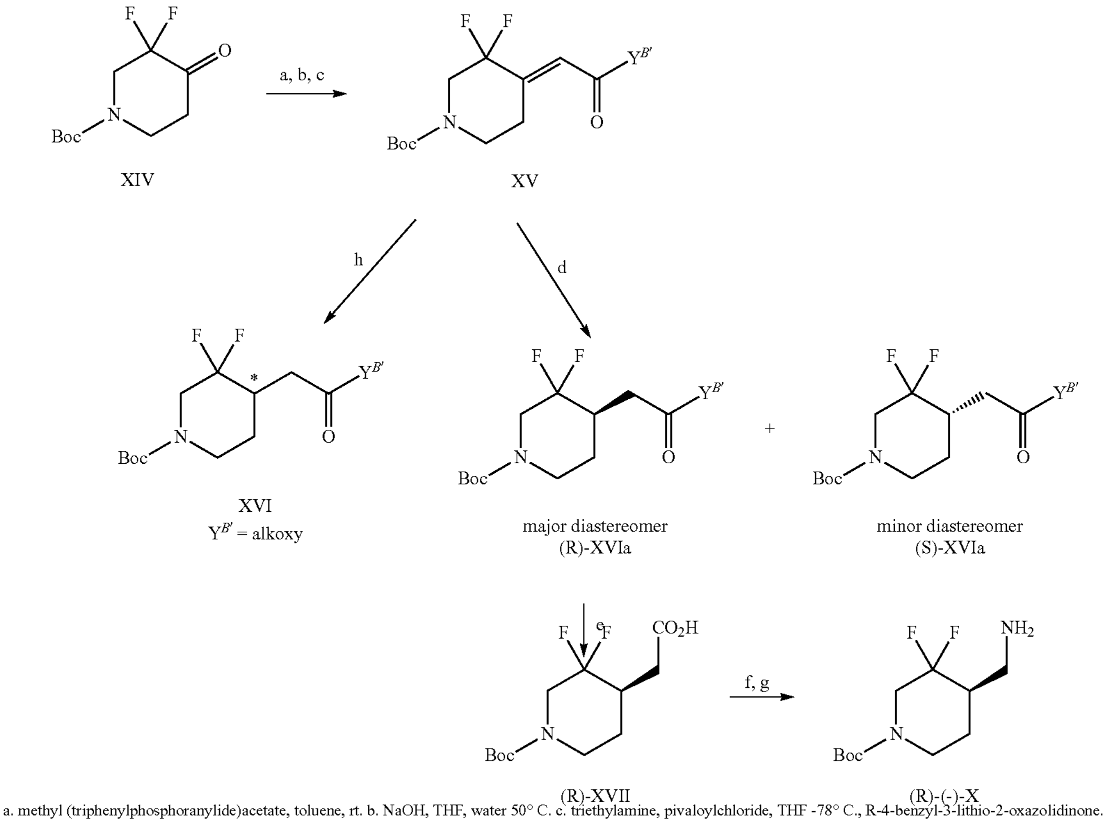

a. methyl (triphenylphosphoranylide)acetate, toluene, rt. b. NaOH, THF, water 50° C. c. triethylamine, pivaloylchloride, THF -78° C., R-4-benzyl-3-lithio-2-oxazolidinone. d. 10% Pd/C, $H_2$, ethyl acetate rt, separation of product diastereomers by column chromatography over silica gel. e. LiOH, 30% $H_2SO_2$, THF, 50° C. f. diphenylphosphorylazide, $PhCH_2OH$, trimethylamine, toluene, reflux. g. 10% Pd/C, $H_2$, ethyl acetate rt. h. asymmetric hydrogenation.

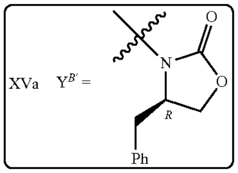

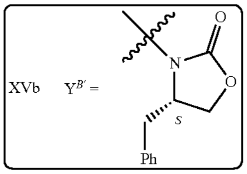

Enantiomer intermediates of formula XVI can also be prepared by catalytic asymmetric hydrogenation of the intermediates of formula XV wherein $Y^{B'}$ forms simple achiral ester group (e.g., $Y^{B'}$ =OMe, OEt). To this end chiral catalysts comprising a chiral phosphine ligand (e.g., Waldphos ligands) and a transition metal (e.g., Ir, Rh, or Ru) can be employed in asymmetric catalytic hydrogenation conditions at elevated temperature and pressure to give simple ester intermediates XVI of high enantiomeric purity. The latter can be converted to pure enantiomers of X using standard methods in the art such as those described above. Hydrogenation of α,β-unsaturated acid and ester systems have been reviewed by Tang et al. (*Chem. Rev.* 2003, 103:3029-3070), and additional useful catalytic asymmetric hydrogenation methods have been described by Krska et al. (*Tetrahedron* 2009, 65:8987-8994) and Tudge et al. (*Org. Process Res. Dev.* 2010, 14, 787-798).

Pure enantiomer intermediates for synthesizing enantiomers of compounds of Formula $I^{B'}$ may also be prepared by variants of the above methods using intermediates with alternative protecting groups or double bond isomers as exemplified in Scheme 3.

Scheme 3

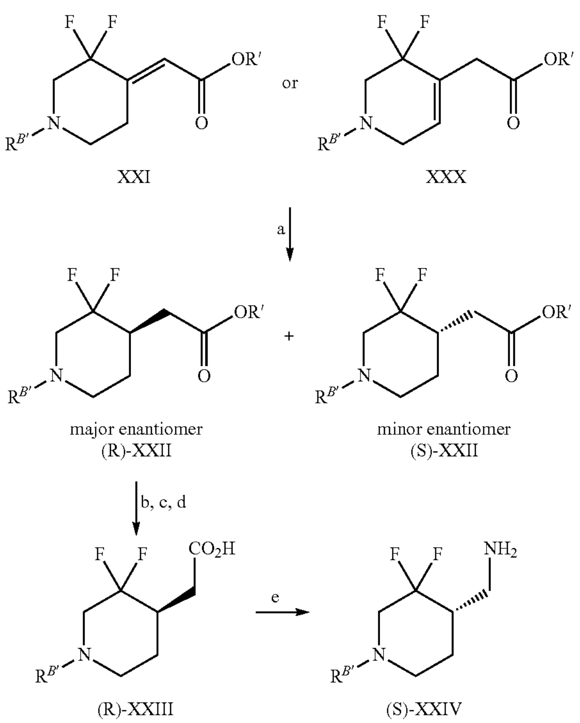

XXI or XXX major enantiomer (R)-XXII + minor enantiomer (S)-XXII (R)-XXIII (S)-XXIV a. $R^{B'}$ = $CH_2Ph$, R' = hydrogen or alkyl, (e.g., Me or Et), asymmetric catalytic hydrogenation. b. $H_2$ 10% Pd/C to remove benzyl protecting group to give $R^{B'}$ = H. c. carbamoylation, e.g., carbonyldiimidazole, $R^{1B'}$—OH, DMSO, to give R = $R^{1B'}$—OC(O)—. d. ester saponification, e.g., NaOH, THF. e. Hofmann degradation or Curtius rearrangement protocol.

For example, an intermediate of formula XXI wherein $R^{B'}$ =benzyl can be subjected to the above-described reduction processes (e.g., catalytic asymmetric hydrogenation) to generate intermediates of formula (R)-XXII that are chirally pure at the C-4 piperidine stereocenter. In subsequent steps the benzyl group can be removed and exchanged for another protecting group (e.g., Boc) or the $CO_2R^{1B'}$ group present in the compound of Formula $I^{B'}$. Alternatively, the same reaction scheme can be implemented via asymmetric hydrogenation of the double bond isomer starting material XXX.

Pharmacology

NMDA Receptors

The NMDA receptor is commonly found on the plasma membranes of neurons located in the central nervous system. This receptor is distinct in two ways: first, it is both ligand-gated and voltage-dependent; second, it requires co-activation by two ligands: glutamate and glycine. The voltage-dependent activation property of the NMDA receptor results from blockage of the ion channel by extracellular $Mg^{2+}$ ions. Removal of $Mg^{+2}$ from the ion channel brings about the flow of $Na^+$ and small amounts of $Ca^{2+}$ ions into neurons while $K^+$ flows out of the cells, resulting in voltage-dependent activation. Calcium flux through NMDA receptors on neural cells is thought be critical in synaptic plasticity, a cellular mechanism for learning and memory (Li and Tsien *N. Engl. J Med.* 2009, 361:302-303).

Structurally, NMDA receptors form a heterotetramer made up of two NR1 and two NR2 subunits. A related gene family of NR3A and B subunits has also been identified and appears to have an inhibitory effect on receptor activity. Multiple receptor isoforms with distinct brain distributions and functional properties arise by the selective splicing of NR1 transcripts and differential expression of NR2 subunits (Ishii et al. *J. Biol. Chem.* 1993, 268:2836-2843; Laurie et al. *Mol. Brain Res.* 1997, 51:23-32). The various resulting combinations produce a variety of NMDA receptors differing in physiological and pharmacological properties such as ion gating properties, magnesium sensitivity, pharmacological profile, as well as in anatomical distribution.

The NR2 NMDA subunit family is in turn divided into four subject subunit types: NR2A, NR2B, NR2C, and NR2D. These subunits contain binding sites for the neurotransmitter glutamate and each possesses a different intracellular C-terminal domain that can interact with different sets of intracellular signaling messengers (Ryan and Grant Nat. Rev. Neurosci. 2009, 10:701-712). Unlike NR1 subunits, NR2 subunits are expressed differentially across various cell types and control the electrophysiological properties of the NMDA receptor. One particular subunit, NR2B, is mainly present in immature neurons and in extrasynaptic locations. Whereas NR2B is predominantly expressed in the early postnatal brain, the number of NR2A subunits grows as the organism ages, and eventually NR2A subunit expression comes to predominate expression in NMDA receptors. Referred to as the "NR2B-NR2A developmental switch," the change in NR2 subunit expression is significant due to the differential kinetic properties each particular NR2 subunit lends to the receptor (Liu et al. *J. Neurosci.* 2004, 24(40):8885-8895). The NR2B and NR2A subunits each play different roles in mediating excitotoxic neuronal death with the developmental switch in subunit composition thought to explain developmental changes in NMDA neurotoxicity (Liu et al. *J. Neurosci.* 2007, 27(11):2846-2857); Zhou and Baudry *J. Neurosci.*, 2006, 26(11):2956-2963). NR2B gene disruption in mice results in perinatal lethality while deletion of the NR2A gene produces viable mice albeit with impaired hippocampal plasticity (Sprengel et al. Cell 1998, 92:279-289).

NR2B Subunit-Selective NMDA Receptor Antagonists

The NMDA receptor is an ionotropic receptor that facilitates the transfer of electrical signals between neurons in the central nervous system. For neural conduction of action potentials, the NMDA receptor is in an open or "activated" state. NMDA receptor activation occurs when glutamate and glycine bind to the NMDA receptor NR2 and NR1 subunits, respectively. NMDA receptor antagonist compounds inhibit or block the opening of the NMDA receptor channel thereby reducing or preventing glycine/glutamate-mediated excitatory postsynaptic potentials.

Described herein are certain NR2B subunit-selective NMDA antagonists. These antagonists selectively bind to the NR2B subunit and inhibit the activity of the NMDA receptor. In some embodiments, an antagonist described herein binds to the NR2B subunit of a human NMDA receptor. In some embodiments, an antagonist described herein inhibits the activity of a human NMDA receptor. In some embodiments, an antagonist described herein binds to the NR2B subunit of a non-human primate NMDA receptor. In some embodiments, an antagonist described herein inhibits the activity of a non-human primate NMDA receptor. In some embodiments, the non-human primate is a monkey. In some embodiments, an antagonist described herein binds to the NR2B subunit of a rodent NMDA receptor. In some embodiments, an antagonist described herein inhibits the activity of a rodent NMDA receptor. In some embodiments, the rodent is a mouse. In some embodiments, the rodent is a rat. In some embodiments, the precursor of the NR2B subunit comprises the amino acid sequence shown in GenBank accession number NP_000825.

In some embodiments, the NR2B subunit-selective NMDA antagonist is a chemical entity of formula $I^{A'}$:

IA'

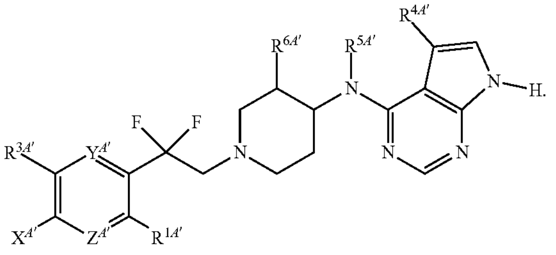

In some embodiments, the NR2B subunit-selective NMDA antagonist is a chemical entity of Formula $I^{B'}$.

IB'

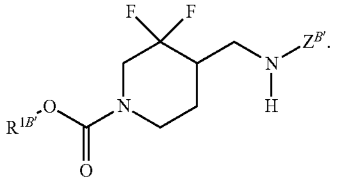

Mental Disorders

Autism Spectrum Disorders

Autism spectrum disorders constitute a range of multi-faceted neurodevelopmental disorders which are characterized by social impairments, communication difficulties, and restricted, repetitive, and stereotyped patterns of behavior (see DSM-5). ASD results from a failure to maintain neuronal homeostasis, leading to weakened synaptic flexibility, circuit dysfunction and, ultimately, abnormal behavior. This failure of neuronal adaptability can result from a myriad of pathologies including an unbalanced excitation/inhibition ratio, dysregulated transcriptional or translational control, impaired activity-dependent gene expression, or glial abnormalities.

Autistic disorder (a.k.a. "autism" or "classical ASD"), is the most severe form of ASD, while other conditions along the spectrum include a milder form known as Asperger's syndrome, and childhood disintegrative disorder and pervasive developmental disorder not otherwise specified (usually referred to as PDD-NOS). While ASD can differ significantly in character and severity depending on the subject, it is known to occur in all ethnic and socioeconomic groups and in all age groups. According to one estimate, 1 out of 88 children age 8 has an ASD (Centers for Disease Control and Prevention: Morbidity and Mortality Weekly Report, Mar. 30, 2012), with males more likely to have an ASD in comparison to females.

Subjects with ASDs commonly have difficulties in three key areas of development social interaction, language and behavior. However, due to the fact that ASD symptoms vary widely, two subjects with identical diagnoses may behave quite differently as outward manifestations of the condition. In many cases, however, the most severe cases of ASD are marked by the complete inability to communicate or interact with other people. Some subjects show signs of ASD in early infancy while others may develop normally for the first few months or years of life but then suddenly become withdrawn, aggressive or lose language skills that have been already acquired. Although each subject with autism is likely to exhibit a pattern of behavior unique to that subject, there are some common symptoms associated with ASDs, falling into categories of social skills, behavior, and language.

Social impairment and the failure to develop social relationships are hallmarks of ASDs. These can include a subject failing to respond to his or her name, inability to maintain eye contact with another person, inability to respond when another person is speaking to the subject, resistance to intimate parent-child behavior such as cuddling, hugging, or holding, inability to appreciate the feelings of others (i.e. lack of empathy), and a preference to be alone or to play alone.

Subjects with an ASD commonly exhibit one or more characteristic behaviors. These can include the performance of repetitive movements (such as rocking, spinning or hand-flapping), behavioral rigidity (such as the development and repetitive performance of specific routines or rituals as well as agitation upon the slightest change in these routines or rituals), constant movement, excessive lining up of toys or objects, lack of smiling, restricted patterns of interest that are abnormal in intensity or focus, unusual sensitivity to light, sound and touch, and obliviousness to pain. Additionally, subjects with ASDs often exhibit repetitive and disruptive behaviors which may result from exposure to novel or unexpected events and experiences, particularly ones which disrupt a set routine. Indeed, it is believed that novelty itself is disagreeable to subjects with ASDs and that novelty avoidance might cause attention impairments and, as a consequence, result in autistic characteristics (Dawson et al. *J. Autism and Dev. Disorders* 1998, 28:479-485).

Defects in language acquisition and communication are also characteristic symptoms of ASDs. These can include failure to acquire language (including no babbling or pointing by age 1, no use of single words by 16 months or use of two-word phrases by age 2), loss of previously acquired ability to use words or sentences, failure to make eye contact when making requests, speaking with an abnormal tone of voice or rhythm (such as a singsong voice or "robot-sounding" speech), inability to start a conversation or keep one going, repetition of words or phrases verbatim, but without the understanding of how to use them. Other symptoms of ASDs include inability to make friends with peers, absence or impairment of imaginative and social play, stereotyped or unusual use of language, and a preoccupation with particular objects or subjects.

Presently, there is no medical test that is capable of diagnosing ASDs. Accordingly, diagnosis of ASDs is based on behavior, not cause or mechanism (London, *Brain Pathol.* 2007, 17(4):408-411). The method of diagnosis varies, with some health care providers using available questionnaires or other screening instruments to gather information about a subject's development and behavior. For example, one commonly used screening device is known as "The Modified Checklist for Autism in Toddlers (M-CHAT™)" which is a scientifically validated tool for screening children between 16 and 30 months of age to assess their risk for ASD. Other screening devices rely solely on parental observations, while others rely on a combination of parent and doctor observations. If these screening instruments indicate the possibility of an ASD, a more comprehensive evaluation is typically undergone. A comprehensive evaluation usually employs several health care providers that can include psychologists, neurologists, psychiatrists, speech therapists and other professionals who diagnose children with ASDs and who conduct neurological assessments as well as cognitive and language testing.

Subjects exhibiting some symptoms of an ASD but lacking the number required to be diagnosed with classical autism are often diagnosed with pervasive developmental disorder not otherwise specified (PDD-NOS). Subjects with autistic behaviors and autistic impairments in social skills but who nevertheless have well-developed language skills are often diagnosed with Asperger's syndrome. Much rarer are children who may be diagnosed with childhood disintegrative disorder, in which they develop normally and then suddenly deteriorate between the ages of 3 to 10 years and show marked autistic behaviors.

Obsessive-Compulsive Disorder

Obsessive-compulsive disorder (OCD) is a disorder defined by pervasive and intrusive thoughts that produce discomfort, nervousness, fear, or anxiety, by repetitive and compulsive behaviors aimed at reducing the associated anxiety, or by a combination of such obsessions and compulsions. OCD is the fourth most common mental disorder and is believed to have a lifetime prevalence of about 2.5%, though other estimates of lifetime prevalence are generally in the range of 1.7-4%. (Karno et al. *Arch. Gen. Psychiatry* 1988, 45(12):1094-1099).

As noted above, OCD was previously grouped together with anxiety disorders; however, the DSM-5, includes a new chapter for OCD and related disorders, including body dysmorphic disorder (e.g. anorexia nervosa), hoarding disorder, trichotillomania, and excoriation disorder. The DSM-5 defines OCD as the presence of obsessions, compulsions, or both. OCD symptoms occur in response to cues that activate a normal, biologically primal motivational system that protects people from potential danger. However, security-related behaviors that for most people would readily shut down these primal concerns do not work well in people with OCD. Thus, from a pathophysiological perspective, OCD patients repeat these behaviors in an attempt to overcome their weak internal stop signal (Hinds et al. *PLoS ONE* 2012, 7(1): e30586). In particular, obsessions are characterized by repetitive or intrusive thoughts, impulses, or images that cause marked anxiety or distress. Compulsions, on the other hand, are considered to be repetitive and ritualistic behavior or mental acts that the subject feels compelled to accomplish, whose purpose is to reduce distress, but that are not realistically connected with that distress.

Subjects with OCD typically exhibit symptoms of both intrusive thoughts and compulsive behaviors. However, in the case of so-called "Purely Obsessional Obsessive-Compulsive Disorder" (a.k.a. OCD without overt compulsions or Primarily Obsessional OCD), the subject does not exhibit the compulsive behaviors normally observed in typical OCD. Nevertheless, even in this variant OCD disorder, ritualizing and neutralizing behaviors do take place, though they are almost entirely in the form of excessive repetitious thoughts (Toates and Coschug-Toates, *Obsessive compulsive disorder,* 2nd Ed., Class Publishing, London, 2000, pp. 111-128). The intrusive thoughts characteristic of subjects having or suspected of having OCD can take many varied forms, depending on the subject. These thoughts are usually involuntary in nature and consist of mental images and unpleasant ideas that are upsetting or distressing and which can be difficult to manage or eliminate. When occurring in OCD, subjects are less likely to be able to ignore these thoughts and end up paying excessive attention to them, resulting in the thoughts becoming ever more distressing and frequently occurring. In some subjects with OCD, these thoughts can be paralyzing, severe, and constantly present, and often center around inappropriately aggressive thoughts (e.g., violent obsessions about hurting themselves or other people), inappropriately sexual thoughts (e.g., intrusive thoughts or images of sexual activity and/or rape with strangers, friends, or family members as well as persistent thoughts relating to sexual orientation), or blasphemous thoughts pertaining to religious activities or subjects.

To be diagnosed with an anxiety disorder or OCD, typically a person must meet the particular diagnostic criteria described above and further outlined in the DSM-5. In most cases the symptoms must be present for weeks to months and cause significant disruption of the subject's normal functioning or wellness. Behaviors associated with anxiety or OCD generally must be out of proportion to the reported source of the worry and fear or the initial triggering event causing the problem. While there is no single medical test capable of diagnosing an anxiety disorder or OCD and identifying the specific subtype, diagnosis may be performed by a psychologist, psychiatrist, clinical social worker, or other licensed mental health professional. In some instances, rating scales are available (such as the Yale-Brown Obsessive Compulsive Scale ("Y—BOCS") for OCD or the Hamilton Anxiety Scale ("HAM-A") for GAD to assist the mental health professional in diagnosing the subject.

Anxiety Disorders

Anxiety disorders represent an array of psychiatric conditions characterized by excessive and debilitating worry or anxiousness over specific or non-specific life events or situations. These feelings often have notable physical manifestations, including particular panic or stress reactions. Subject anxiety disorders are sometimes defined by the specific source of the anxiety (e.g., post-traumatic stress disorder, social phobia, or specific phobia). Other classifications are based on the type of reaction (e.g., agoraphobia, panic disorder, generalized anxiety disorder). It is common for patients to experience a variety of symptoms and therefore be diagnosed with multiple types of anxiety disorders. Conventional treatment includes both psychotherapy and a subset of neuroactive drugs, including modulators of the serotonin or GABA receptor systems. Up to half of the patients do not respond adequately to treatment or cannot tolerate the side effects of drug therapy.

Agoraphobia and Panic Disorder

These types of anxiety disorders share the symptom of panic attack. Panic attack is characterized by discrete instances of intense fear or discomfort in the absence of any real danger (DSM-5). The attack is accompanied by at least 4 somatic or cognitive symptoms out a list of 13 (palpitations, pounding heart, or accelerated heart rate; sweating; trembling or shaking; sensations of shortness of breath or smothering; feeling of choking; chest pain or discomfort; nausea or abdominal distress; feeling dizzy, unsteady, lightheaded or faint; feelings of unreality (derealization) or being detached from oneself (depersonalization); fear of losing control or going crazy; fear of dying, numbness or tingling sensations (paresthesias); chills or hot flushes). The attacks have very sudden onset and peak quickly.

Agoraphobia is defined as worry or excessive avoidance of events, places or situations that might trigger a panic attack. This fear leads to pervasive avoidance behaviors of situations thought to trigger the panic attacks. Situations avoided can include being alone, being outside of home, traveling in cars or airplanes, or being in elevators or on bridges. The anxiety caused by fear of these situations can impair normal activities and cause substantial debilitation.

Panic disorder is defined as recurrent unexpected panic attacks and at least one of the attacks have been followed by 1 month (or more) of one (or more) of the following: the attacks are not due to the direct physiological effects of a substance (such as drug of abuse or a medication), or a general medical condition; the attacks are not better accounted for by another mental disorder, such as social phobia (such as occurring on exposure to feared social situations), specific phobia, post-traumatic stress disorder or separation anxiety disorder. Panic disorders can be present with or without agoraphobia and agoraphobia can occur without previous history of panic disorder. The prevalence of panic disorder with or without agoraphobia is thought to be approximately 1-2% with some evidence of a genetic or familial component in up to 25% of the cases.

Social Phobia

The primary characteristic of social phobia is marked fear of embarrassment in typical social or performance situations, including meeting new people, public speaking, group activities, or other common public activities. These situations routinely generate symptoms similar to those of panic attack with a range of severities, and subjects often avoid these situations or face them with substantial fear and worry. The fear and avoidance of these situations can interfere significantly with normal life activities, job or school performance, and personal relationships. The lifetime prevalence of social phobia meeting DSM-5 diagnostic criteria is thought to be around 2%. There is some evidence of genetic or familial association.

Post-Traumatic Stress Disorder

PTSD is characterized by chronic and repeated anxiety or fear generated by a previous, well-defined traumatic experience. The traumatic experience is severe in nature and typically entails an event that threatens death or serious injury either in the patient or a close relative or associate. The event elicits a response of fear, horror, or helplessness and generates an ongoing set of anxiety-like symptoms that are associated with disability and disruption to normal life experiences. Symptoms include persistent re-experiencing of the event, avoidance of stimuli associated with the traumatic event, numbing of general responsiveness, and increased arousal. Symptoms must persist for at least one month to meet diagnostic criteria. In most but not all cases, a major feature involves the patient going into a dissociative state lasting from seconds to days in which they relive the traumatic event or believe those events are happening again. These "flashbacks" are often triggered by stimuli that may resemble or remind the person of the original event. Thus, possible exposure to such stimuli are persistently and actively avoided causing significant degradation of quality-of-life. The lifetime prevalence of PTSD in the US is estimated to be 8% of the adult population. The propensity for suffering PTSD may have a familial or genetic component.

Generalized Anxiety Disorder

Generalized anxiety disorder is a type of anxiety disorder characterized by excessive anxiety and worry about multiple events or activities that occurs more days than not for at least 6 months. GAD has a lifetime prevalence of approximately 5% with an annual economic burden of $50 billion in the USA alone (Wittchen *Depress. Anxiety* 2002, 14:162-67). Approximately 25% of patients in anxiety disorder clinics have a presenting or comorbid diagnosis of GAD. Twin studies have shown a clear genetic association for the presence of GAD symptoms (Hettema et al. *Am. J. Psychiatry* 2001, 158:1568-1578; Chantarujikapong et al. *Psychiatry Res.* 2001, 103:133-145). GAD patients most often report they have felt anxious for most of their lives, that it fluctuates in severity but worsens during times of stress.

GAD patients show worry and anxiety that they are not able to control and are accompanied by at least three of the following symptoms: restlessness, being easily fatigued, difficulty concentrating, irritability, muscle tension, and disturbed sleep. The focus of the worry is generally everyday, routine life circumstances, and the intensity and duration are out of proportion to the impact or likelihood of the event. Subjects with GAD report subjective distress due to excessive worry that they cannot control, which impairs normal life activities such as social interactions and job.

Use, Formulation and Administration of NR2B Subunit-Selective NMDA Receptor Antagonists Uses of NR2B Subunit-Selective NMDA Receptor Antagonists and Pharmaceutically Acceptable Compositions The present invention provides methods for treating ASDs, OCD, and/or anxiety disorders by administering an effective amount of a described NR2B subunit-selective NMDA receptor antagonist ("antagonist"). The antagonist can be administered in any amount and using any route of administration effective for treating the disorders. In some embodiments, the antagonist is administered as a pharmaceutical composition, as described herein.

The effective amount required will vary from subject to subject, depending on the species, age, and general condition of the subject, the severity of the disorder, the particular agent, its mode of administration, and the like. The chemical entities of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the chemical entities and compositions of the present invention will be decided by the attending physician within the scope of sound medical judgment. The specific effective dose level for any particular patient or organism will depend upon a variety of factors including the disorder being treated and the severity of the disorder; the activity of the specific chemical entity employed; the specific composition employed; the age, body weight, general health, sex, and diet of the patient; the time of administration, route of administration, and rate of excretion of the specific chemical entity employed; the duration of the treatment; drugs used in combination or coincidental with the specific chemical entity employed, and like factors well known in the medical arts. The term "patient", as used herein, means an animal, preferably a mammal, and most preferably a human.

In some embodiments, administration may involve dosing that is intermittent (e.g., a plurality (i.e., at least two) of doses separated in time) and/or periodic (e.g., individual doses separated by a common period of time) dosing. In some embodiments, a dosing regimen for a particular active agent may involve intermittent or continuous administration, for example to achieve a particular desired pharmacokinetic profile or other pattern of exposure in one or more tissues or fluids of interest in the subject receiving therapy. In some embodiments, intermittent dosing may include dosing that occurs once a day, once every other day, once a week, once every two weeks, or once a month.

In some embodiments, administration may involve dosing that is titrated over time in order to reach a target dosage. In some embodiments, increases in dosing amount and/or schedule can occur at weekly intervals based on the subject's clinical response and tolerability.

In some embodiments, one or more features of a dosing regimen may be modified over time (e.g., increasing or decreasing amount of active in any individual dose, increasing or decreasing time intervals between doses, etc.), for example in order to optimize a desired therapeutic effect or response.

In some embodiments, pharmaceutically acceptable compositions of the present invention can be administered at periodic intervals, for example, once a week, once every other week, once a month, etc. In some embodiments, pharmaceutically acceptable compositions of the present invention can be administered once a week. In some embodiments, pharmaceutically acceptable compositions of the present invention can be administered once a day. In some embodiments, pharmaceutically acceptable compositions of the present invention can be administered twice a day. In some embodiments, pharmaceutically acceptable compositions of the present invention can be administered three times a day. In some embodiments, pharmaceutically acceptable compositions of the present invention can be administered with or without regard to food.

In some embodiments, pharmaceutically acceptable compositions of the present invention can be administered to treat acute conditions. Acute conditions may be sudden in onset. Acute condition symptoms may appear and change or worsen rapidly. In some embodiments, pharmaceutically acceptable compositions of the present invention can be administered to treat chronic conditions. Chronic conditions may be long-developing conditions. A chronic condition may develop and worsen over an extended period of time.

In some embodiments, compounds of the present invention improve social behavior (e.g., interpersonal relationships with peers, parent-child interactions, etc.). In some embodiments, the present invention provides a method of improving social behavior comprising administering a compound of the present invention.

Autism Spectrum Disorders

In some embodiments, the present invention provides a method for treating an autism spectrum disorder (ASD) in a subject in need thereof comprising administering an effective amount of a described NR2B subunit-selective NMDA receptor antagonist. The subject can be one diagnosed with an ASD or one suspected by a treating physician of having an ASD. In some embodiments, the subject is one diagnosed with an ASD. In some embodiments, the subject is a human. In some embodiments, compounds of the present invention reduce behaviors characteristic of ASD. In some such embodiments, the present invention provides a method for reducing one or more clinical signs of ASD such as repetitive or ritualistic behaviors, behavioral rigidity, constant movements, lack of social interaction, restricted patterns of interest that are abnormal in intensity or focus, or sensory abnormalities.

In some embodiments, the ASD is autism, Asperger's syndrome or pervasive developmental disorder not otherwise specified (PDD-NOS), and the antagonist is a chemical entity of formula $I^{A\prime}$:

IA′

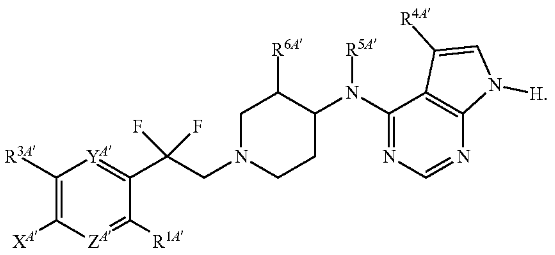

In some embodiments, the ASD is autism, Asperger's syndrome or pervasive developmental disorder not otherwise specified (PDD-NOS), and the antagonist is a chemical entity of Formula $I^{B\prime}$:

IB′

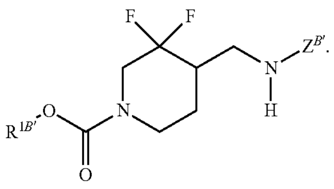

In some embodiments, the ASD is autism and the antagonist is a chemical entity of formula $I^{A\prime}$:

IA′

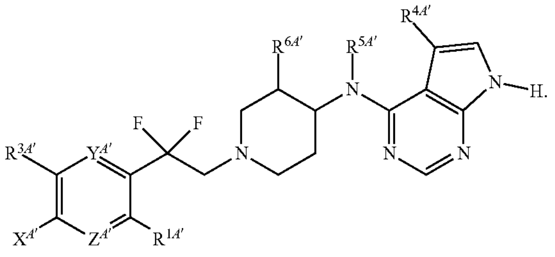

In some embodiments, the ASD is autism and the antagonist is a chemical entity of Formula $I^{B'}$:

IB′

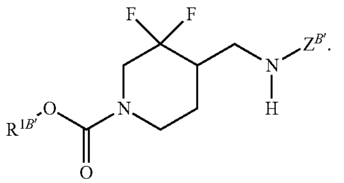

In some embodiments, the ASD is Asperger's syndrome and the antagonist is a chemical entity of formula $I^{A'}$:

IA′

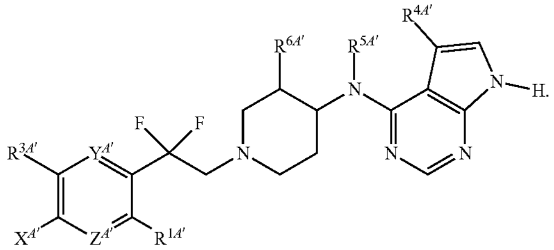

In some embodiments, the ASD is Asperger's syndrome and the antagonist is a chemical entity of Formula $I^{B'}$.

IB′

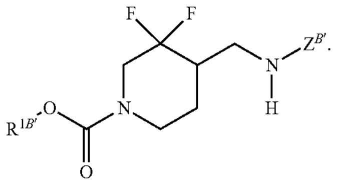

In some embodiments, the ASD is PDD-NOS and the antagonist is a chemical entity of formula $I^{A'}$:

IA′

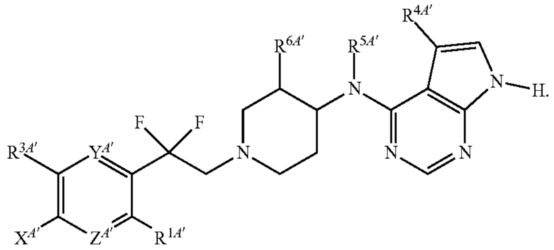

In some embodiments, the ASD is PDD-NOS and the antagonist is a chemical entity of Formula $I^{B'}$:

$I^{B'}$

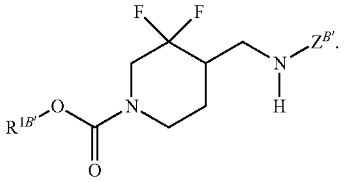

Obsessive-Compulsive Disorder

In some embodiments, the present invention provides a method for treating an obsessive-compulsive disorder (OCD) and related disorders in a subject in need thereof comprising administering an effective amount of a described NR2B subunit-selective NMDA receptor antagonist. The subject can be one diagnosed with an OCD and/or related disorders or one suspected by a treating physician of having an OCD and/or related disorders. In some embodiments, the subject is one diagnosed with an OCD and/or related disorders. In some embodiments, the subject is a human. In some embodiments, compounds of the present invention reduce behaviors characteristic of OCD and/or related disorders. In some such embodiments, the present invention provides a method for reducing one or more clinical signs of OCD and/or related disorders such as body dysmorphic disorder (e.g. anorexia nervosa), hoarding disorder, trichotillomania, and excoriation disorder.

In some embodiments, the NMDA-receptor-mediated disorder is obsessive-compulsive disorder and/or related disorders and the antagonist is a chemical entity of formula $I^{A'}$:

$I^{A'}$

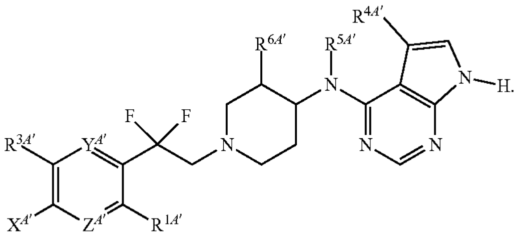

In some embodiments, the NMDA-receptor-mediated disorder is obsessive-compulsive disorder and/or related disorders and the antagonist is a chemical entity of Formula $I^{B'}$:

$I^{B'}$

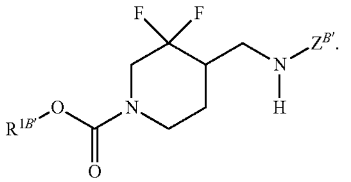

Anxiety Disorders

In some embodiments, the present invention provides a method for treating an anxiety disorder in a subject in need thereof comprising administering an effective amount of a described NR2B subunit-selective NMDA receptor antagonist. The subject can be one diagnosed with an anxiety disorder or one suspected by a treating physician of having an anxiety disorder. In some embodiments, the subject is one diagnosed with an anxiety disorder. In some embodiments, the subject is a human. In some embodiments, compounds of the present invention reduce behaviors characteristic of anxiety disorders. In some such embodiments, the present invention provides a method for reducing one or more clinical signs of anxiety disorders such as agoraphobia, panic disorders, social phobias, post-traumatic stress disorder, and generalized anxiety disorders.

In some embodiments, the anxiety disorder is generalized anxiety disorder, agoraphobia (with or without panic disorder), panic disorder, post-traumatic stress disorder or social anxiety disorder, and the antagonist is a chemical entity of formula $I^{A'}$:

$I^{A'}$

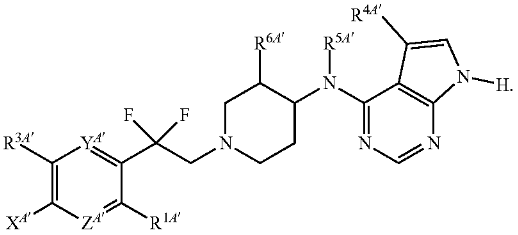

In some embodiments, the anxiety disorder is generalized anxiety disorder, agoraphobia (with or without panic disorder), panic disorder, post-traumatic stress disorder or social anxiety disorder, and the antagonist is a chemical entity of Formula $I^{B'}$:

$I^{B'}$

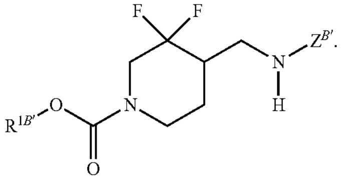

In some embodiments, the anxiety disorder is generalized anxiety disorder and the antagonist is a chemical entity of formula $I^{A'}$:

$I^{A'}$

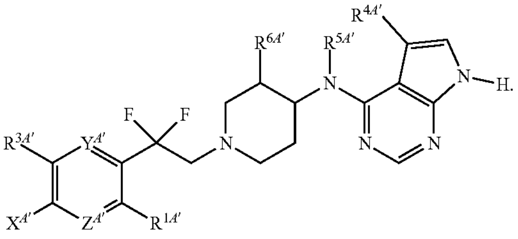

In some embodiments, the anxiety disorder is generalized anxiety disorder and the antagonist is a chemical entity of Formula $I^{B'}$:

$I^{B'}$

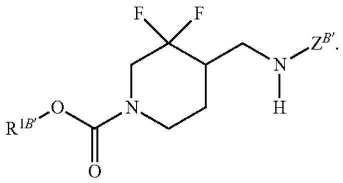

In some embodiments, the anxiety disorder is agoraphobia with panic disorder and the antagonist is a chemical entity of formula $I^{A'}$:

$I^{A'}$

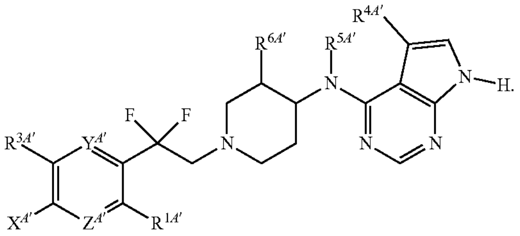

In some embodiments, the anxiety disorder is agoraphobia with panic disorder and the antagonist is a chemical entity of Formula $I^{B'}$:

$I^{B'}$

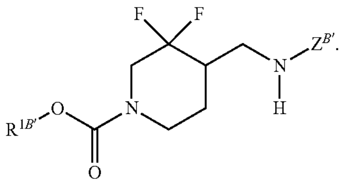

In some embodiments, the anxiety disorder is agoraphobia without panic disorder and the antagonist is a chemical entity of formula $I^{A'}$:

$I^{A'}$

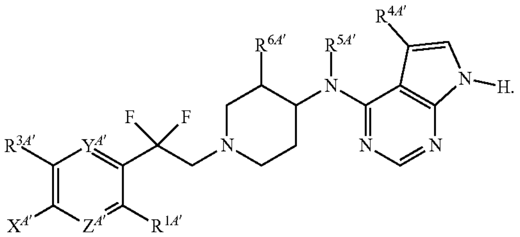

In some embodiments, the anxiety disorder is agoraphobia without panic disorder and the antagonist is a chemical entity of Formula $I^{B'}$:

$I^{B'}$

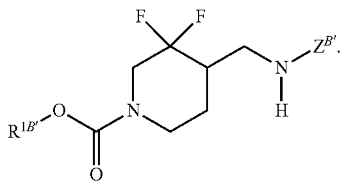

In some embodiments, the anxiety disorder is panic disorder and the antagonist is a chemical entity of formula $I^{A'}$.

$I^{A'}$

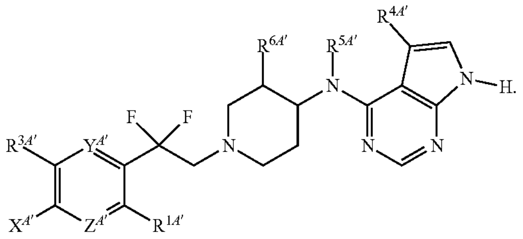

In some embodiments, the anxiety disorder is panic disorder and the antagonist is a chemical entity of Formula $I^{B'}$:

$I^{B'}$

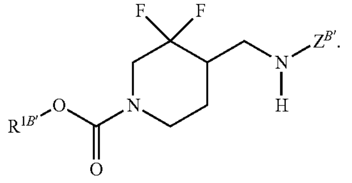

In some embodiments, the anxiety disorder is social anxiety disorder and the antagonist is a chemical entity of formula $I^{A'}$:

$I^{A'}$

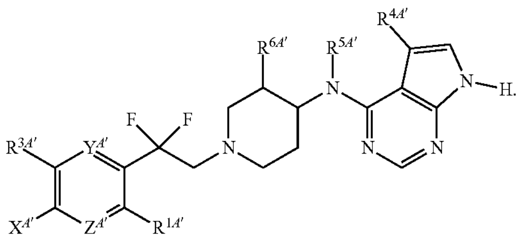

In some embodiments, the anxiety disorder is social anxiety disorder and the antagonist is a chemical entity of Formula $I^{B'}$:

$I^{B'}$

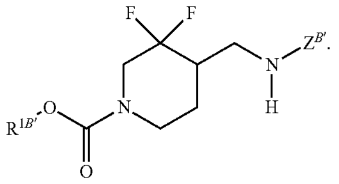

In some such embodiments, the chemical entity is selected from any of the Tables set forth herein.

Combinations

In some embodiments, a described NR2B subunit-selective NMDA receptor antagonist is administered with one or more therapeutic agents. Such therapeutic agents include agents for treating any of the symptoms of ASDs, such as those described herein, e.g., novelty phobia, behavioral rigidity as well as defects in social skills, behavior, and language use/acquisition. In some embodiments, a therapeutic agent useful for treating an ASD is a selective serotonin reuptake inhibitor, a typical antipsychotic, an atypical antipsychotic, a serotonin-norepinephrine reuptake inhibitor, a stimulant, a dopamine receptor agonist, secretin or oxytocin.

In some embodiments, a described NR2B subunit-selective NMDA receptor antagonist is administered in conjunction with electroconvulsive therapy or psychosurgery (e.g., deep brain stimulation or vagus nerve stimulation). Such therapies are particularly useful in severe and/or refractory cases of anxiety disorders.

In some embodiments, a described NR2B subunit-selective NMDA receptor antagonist is administered with one or more therapeutic agents useful for treating an anxiety disorder. Such therapeutic agents include agents for treating any of the symptoms of anxiety disorders, such as those described herein, e.g., excessive worry or anxiety. In some embodiments, a therapeutic agent useful for treating an anxiety disorder is a selective serotonin reuptake inhibitor, a tricyclic antidepressant, a benzodiazepine, an atypical antipsychotic or a serotonin-norepinephrine reuptake inhibitor.

In some embodiments, a described NR2B subunit-selective NMDA receptor antagonist is administered with one or more therapeutic agents. Examples of such therapeutic agents useful in the provided methods include selective serotonin reuptake inhibitors (such as Citalopram, Dapoxetine, Escitalopram, Fluoxetine, Fluvoxamine, Indalpine, Paroxetine, Sertraline, Vilazodone, and Zimelidine), tricyclic antidepressants (such as Amitriptyline, Amitriptylinoxide, Butriptyline, Clomipramine, Demexiptiline, Desipramine, Dibenzepin, Dimetacrine, Dosulepin/Dothiepin, Doxepin, Imipramine, Imipraminoxide, Lofepramine, Melitracen, Metapramine, Nitroxazepine, Nortriptyline, Noxiptiline, Pipofezine, Propizepine, Protriptyline, Quinupramine, Amineptine, Iprindole, Opipramol, Tianeptine, and Trimipramine), benzodiazepines (such as Alprazolam, Bretazenil, Bromazepam, Brotizolam, Chlordiazepoxide, Cinolazepam, Clonazepam, Clorazepate, Clotiazepam, Cloxazolam, Delorazepam, Diazepam, Estazolam, Etizolam, Flunitrazepam, Flurazepam, Flutoprazepam, Halazepam, Ketazolam, Loprazolam, Lorazepam, Lormetazepam, Medazepam, Midazolam, Nimetazepam, Nitrazepam, Nordazepam, Oxazepam, Phenazepam, Pinazepam, Prazepam, Premazepam, Quazepam, Temazepam, Tetrazepam, Triazolam, Clobazam, DMCM (methyl-6,7-dimethoxy-4-ethyl-beta-carboline-3-carboxylate), Zaleplon, Zolpidem, and Zopiclone), atypical antipsychotics (such as Amisulpride, Aripiprazole, Asenapine, Blonanserin, Clotiapine, Clozapine, Iloperidone, Llurasidone, Mosapramine, Olanzapine, Paliperidone, Perospirone, Quetiapine, Remoxipride, Risperidone, Sertindole, Sulpiride, Ziprasidone, Zotepine, Bifeprunox, Pimavanserin, and Vabicaserin), inositol, μ-Opioids (such as hydrocodone and tramadol), serotonin-norepinephrine reuptake inhibitors (such as venlafaxine and duloxetine), anticholinergics (such as Benztropine, Ispratropium, Oxitropium, Tiotropium, Glycopyrrolate, Oxybutinin, Tolterodine, Diphenhydramine, and Dimenhydrinate), nicotine, typical antipsychotics (such as Chlorpromazine, Thioridazine, Mesoridazine, Levomepromazine, Loxapine, Molindone, Perphenazine, Thiothixene, Trifluoperazine, Haloperidol, Fluphenazine, Droperidol, Zuclopenthixol, Flupentixol, and Prochlorperazine), anticonvulsants (such as Tegretol, Lamictal, Topamax, and Depakote), stimulants (such as Adderall, Concerta, Dexedrine, Focalin, Metadate, Methylin, Ritalin, and Vyvanse), dopamine receptor agonists (such as Aplindore, Apomorphine, Bromocriptine, Cabergoline, Ciladopa, Dihydroergocryptine, Lisuride, Pardoprunox, Pergolide, Piribedil, Pramipexole, Ropinirole, and Rotigotine), secretin and oxytocin.

In some embodiments, a described NR2B subunit-selective NMDA receptor antagonist is administered in conjunction with psychotherapy, such as a behavioral-based therapy, psychosocial-based therapy, psychological-based therapy or cognitive behavioral therapy.

In some embodiments, the present invention provides a method of treating ASD comprising administering a NR2B subunit-selective NMDA receptor antagonist as described herein is administered in conjunction with psychotherapy (e.g., a behavioral-based therapy, psychosocial-based therapy, psychological-based therapy or cognitive behavioral therapy). Intensive, sustained special education programs and behavioral therapy are commonly utilized to help subjects diagnosed with or suspected of having an ASD acquire self-care, social and job skills, improved functioning, and decreased symptom severity and maladaptive behavior. Examples of such behavioral-based, psychosocial-based, or psychological-based therapy for treatment of an ASD useful in the provided methods include behavior analysis, early intensive behavior intervention (EIBI; a.k.a. the LOVAAS method), pivotal response therapy, aversion therapy, the social communication, emotional regulation, transactional support (SCERTS) model, relationship development intervention, sensory integration, massage therapy, animal-assisted therapy, neurofeedback, patterning, packing, developmental model-based therapy, structured teaching, speech and language therapy, social skills therapy, and occupational therapy.

In some embodiments, the present invention provides a method of treating OCD comprising administering a NR2B subunit-selective NMDA receptor antagonist as described herein is administered in conjunction with psychotherapy (e.g., a behavioral-based therapy, psychosocial-based therapy, psychological-based therapy or cognitive behavioral therapy).

In some embodiments, the present invention provides a method of treating anxiety disorders comprising administering a NR2B subunit-selective NMDA receptor antagonist as described herein is administered in conjunction with psychotherapy (e.g., a behavioral-based therapy, psychosocial-based therapy, psychological-based therapy or cognitive behavioral therapy).

Formulation and Administration of NR2B Subunit-Selective NMDA Receptor Antagonists and Pharmaceutically Acceptable Compositions In some embodiments, the present invention provides administration of a composition comprising a described NR2B subunit-selective NMDA receptor antagonist ("antagonist") and a pharmaceutically acceptable carrier, adjuvant, or vehicle (together, an "antagonist composition") to a subject in need of such a composition. In some embodiments, the subject is a human. The administrations of an antagonist described herein are contemplated to include administration of an antagonist composition.

The term "pharmaceutically acceptable carrier, adjuvant, or vehicle" refers to a non-toxic carrier, adjuvant, or vehicle that does not destroy the pharmacological activity of the antagonist with which it is formulated. Pharmaceutically acceptable carriers, adjuvants, or vehicles that can be used in the antagonist compositions include ion exchangers, alumina, aluminum stearate, lecithin, serum proteins such as human serum albumin, buffer substances such as phosphates, glycine, sorbic acid, potassium sorbate, partial glyceride mixtures of saturated vegetable fatty acids, water, salts, or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

Antagonist compositions can be administered orally, parenterally, by inhalation spray, transdermal, rectally, nasally, buccally, vaginally, or via an implanted reservoir. The term "parenteral" as used herein includes subcutaneous, intravenous, intramuscular, intra-articular, intra-synovial, intrasternal, intrathecal, intrahepatic, intralesional, and intracranial injection or infusion techniques. In some embodiments, the antagonist compositions are administered orally. In some embodiments, the antagonist compositions are administered parenterally. In some embodiments, the antagonist compositions are administered intracranially (e.g., via intracerebral or intracerebroventricular injection) or intravenously. Sterile injectable forms of the compositions of this invention can be aqueous or oleaginous suspension. These suspensions can be formulated according to techniques known in the art using suitable dispersing or wetting agents and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are water, Hank's solution, Ringer's solution, and isotonic sodium chloride solution. In addition, sterile, fixed oils are conventionally employed as a solvent or suspending medium.

For this purpose, any bland fixed oil can be employed including synthetic mono- or di-glycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long-chain alcohol diluent or dispersant, such as carboxymethyl cellulose or similar dispersing agents that are commonly used in the formulation of pharmaceutically acceptable dosage forms, including emulsions and suspensions. Other commonly used surfactants, such as Tweens, Spans and other emulsifying agents or bioavailability enhancers which are commonly used in the manufacture of pharmaceutically acceptable solid, liquid, or other dosage forms can also be used for the purposes of formulation.

Antagonist compositions can be orally administered in any orally acceptable dosage form including capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents can also be added.

Antagonist compositions can be administered in the form of suppositories for rectal administration. These can be prepared by mixing the agent with a suitable non-irritating excipient that is solid at room temperature but liquid at rectal temperature and will therefore melt in the rectum to release the drug. Such materials include cocoa butter, beeswax, and polyethylene glycols.

Antagonist compositions can be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, fluorocarbons, and/or other conventional solubilizing or dispersing agents.

Antagonist compositions can be administered by oral administration. Such formulations can be administered with or without food. In some embodiments, antagonist compositions are administered without food. In some embodiments, antagonist compositions are administered with food.

In some embodiments, the amount of antagonist administered to the subject in one day is about 0.01 to about 20 mg/kg body weight, e.g., 0.05 to about 15 mg/kg, about 0.05 mg/kg, about 0.1 mg/kg, about 0.15 mg/kg, about 0.25 mg/kg, about 0.5 mg/kg, about 0.75 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg or about 15 mg/kg. In some embodiments, the antagonist is administered to the subject daily, every other day, once every three days, once every four days, once a week, once every other week, once a month, or once every other month. In some embodiments, the subunit-selective NMDA receptor antagonist is administered to the subject every day for at least 1, 2, 3, 4, 5, 6, 7, 8, 9, 10, 11, 12, 13, 14, 15, 20, 25, 30, 60, 90, 120, 150, 180, 210, 240, 270, 300, 330, or 360 days. In other embodiments, the antagonist is administered daily, every other day, once every three days, once every four days, once a week, once every other week, once a month, or once every other month for as long as administration of the antagonist is associated with reduction or inhibition of one or more symptoms associated with the disorder for which it is administered.

The amount of antagonist that can be combined with the carrier materials to produce a composition in a single dosage form will vary depending upon a variety of factors, including the host treated and the particular mode of administration. In some embodiments, antagonist compositions are formulated so that a dosage of about 0.01 to about 20 mg/kg body weight/day, e.g., about 0.05 to about 15 mg/kg body weight/day, of the antagonist can be administered to a patient receiving these compositions.

It should also be understood that a specific dosage and treatment regimen for any particular patient will depend upon a variety of factors, including the activity of the specific antagonist employed, the age, body weight, general health, sex, diet, time of administration, rate of excretion, drug combination, the judgment of the treating physician and the severity of the particular disorder being treated. The amount of a compound of antagonist in the composition will also depend upon the particular antagonist in the composition.

It should be appreciated that there may be considerable overlap in function of excipients used in the antagonist compositions described herein. Thus, any categorization of the above-listed excipients should be taken as merely exemplary of the types of excipients that are contemplated for inclusion in the antagonist compositions described herein. Further examples of pharmaceutical excipients suitable for use in the antagonist compositions can be found in the *United States Pharmacopeia* (*USP* 39)—*National Formulary* (*NF* 34), 2016, as well as in Rowe et al. *Handbook of Pharmaceutical Excipients,* 8th Ed., Pharmaceutical Press, London, 2016, and *Remington: The Science and Practice of Pharmacy,* 22nd Ed., Pharmaceutical Press, London, 2012, editor Loyd V. Allen, Jr., the applicable contents of which are hereby incorporated by reference herein.

Human Genetics of ASD, OCD, and Corresponding Transgenic Animal Models

Psychiatric drug discovery has been markedly enhanced by the development of animal models of ASD and OCD based on gene knockouts or related genetic manipulations (Fineberg et al. *Br. J. Pharmacol.* 2011, 164:1044-1061; Crawley *Dialogues Clin. Neurosci.* 2012, 14:293-305; Griebel and Holmes *Nat. Rev. Drug Disc.* 2013, 12:667-687). Such models provide an important link between the factors thought to cause human disease and in vivo preclinical testing that leads to new drug therapies. The present invention includes the development and characterization of mouse models that are specifically designed to investigate the underlying pathologies associated with ASD in the case of the Shank3 knockout mouse models and OCD in the case of the Sapap3 knockout mouse. The demonstrated ability of the described compounds to improve the behavioral deficits seen in these modified mice demonstrates that these compounds are capable of treating human patients suffering from ASD and OCD.

Recent human genetic and genomic studies have identified several candidate genes for ASDs, many of which encode glutamatergic synaptic proteins including SHANK3, Neuroligin-3, Neuroligin-4 and Neurexin-1. Among those candidate genes, SHANK3 showed the strongest genetic linkage with human ASD. Disruption of SHANK3 is believed to be the cause of the core neurodevelopmental and neurobehavioral deficits in Phelan-McDermid syndrome (PMS), a disorder in which subjects commonly display several autistic behaviors and symptoms (Wilson et al. *J. Med. Genet.* 2003, 40, 575-584). Recent genetic screens have identified mutations in the SHANK3 gene (including microdeletions, nonsense mutations, and recurrent breakpoints) in ASD patients not diagnosed with PMS (Durand et al. *Nat. Genet.* 2007, 39:25-27; Moessner et al. *Am. J. Hum. Genet.* 2007, 81:1289-1297; Gauthier et al. *Am. J. Med. Genet. B Neuropsychiatr. Genet.* 2009, 150B, 421-424). Consistent with human genetic studies, deletions of these synaptic genes in mice lead to autistic-like behaviors including repetitive behaviors, excessive self-grooming, social interaction deficits, phobic behaviors and anxiety. Notably, Shank3B knockout mice exhibit increased anxiety, reduced rearing and phobia of novel objects. Together these data suggest that Shank3B knockout mice (deletion of exons 13-16, resulting in absence of the Shank3b protein isoform) and the newly developed Shank3 complete knockout mice (deletion of exons 4-22, resulting in loss of Shank3 isoforms a-f) can serve as models of ASD with both construct and face validity (Peca et al. *Nature* 2011, 472(7344):437-442; Wang et al. *Nat. Commun.* 2016, 7:11459).

Like ASD, OCD has a strong genetic component. Recent human genetic studies also linked SAPAP3 to OCD and OCD-spectrum disorders (Züchner et al. *Mol. Psychiatry* 2009, 14:6-9; Bienvenu et al. *Am. J Med. Genet. B Neuropsychiatr. Genet.* 2009, 150B(5):710-720; Boardman et al. *Compr. Psychiatry* 2010, 52(2):181-187; Ryu et al. *Am. J. Med. Genet. B Neuropsychiatr. Genet.* 2011, 156B(8):949-959; Crane et al. *Am. J. Med. Genet. B Neuropsychiatr. Genet.* 2011, 156B(1):108-114). Mice with genetic deletion of the Sapap3 gene exhibit increased anxiety and compulsive grooming behavior leading to facial hair loss and skin lesions. Neurophysiological, biochemical and pharmacological studies of Sapap3 knockout mice demonstrated defects in the striatum, a key brain region that is dysfunctional in OCD patients. Together, these data support Sapap3 knockout mice as a disease model of OCD (Welch et al. *Nature* 2007, 448(7156):894-900).

Shank3 and Sapap3 are protein partners, and together with PSD95 they form a local scaffold, orchestrating the assembly of the macromolecular postsynaptic signaling complex at glutamatergic synapses. This complex plays important roles in targeting, anchoring, and dynamically regulating synaptic localization of glutamatergic receptors, including NMDA and AMPA receptors, as well as many other signaling molecules. Genetic deletion of the Shank3 and Sapap3 genes in mice results in reduced strength of synaptic connections and decreased efficiency of glutamatergic neurotransmission, which mirror the cellular mechanisms observed in subjects with ASD and OCD. Glutamatergic synapses contain two types of ionotropic glutamate receptors: AMPA receptors and NMDA receptors. AMPA receptors mediate fast synaptic transmission, whereas NMDA receptors play a critical role in regulating synaptic function and plasticity. Most native NMDA receptors are heterotetramers consisting of two obligatory NR1 subunits and two of the four NR2 subunits (NR2A-NR2D). Different NR2 subunits have different distribution patterns in the brain and confer distinct properties to the receptors. In much of the adult brain, typical mature synapses contain mainly NMDA receptors with NR2A subunits, while NR2B-containing NMDA receptors are common in the extrasynaptic membrane areas. The extrasynaptic NR2B NMDA receptor plays an important role in regulating synaptic strength and the trafficking of AMPA and NMDA receptors at the synapse.

Figure 1:
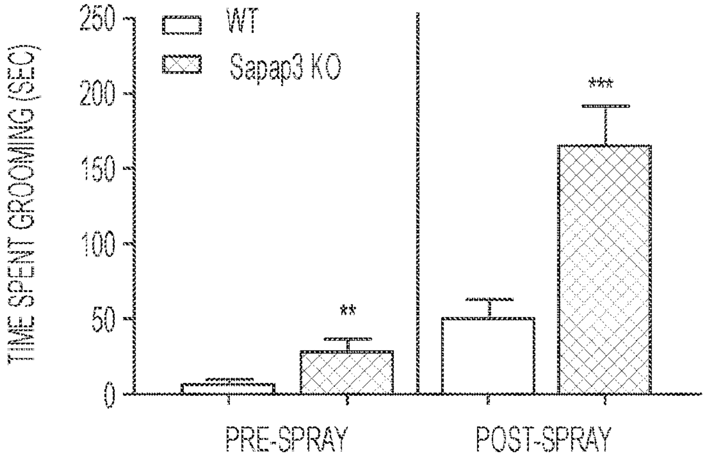
FIG. 1. Excessive self-grooming in Sapap3 knockout (KO) mice. Amount of time spent grooming (seconds) in an unfamiliar environment before and after being sprayed with water for Sapap3 knockout mice and littermate wild type (WT) controls. Significance comparing Sapap3 KO mice with WT littermates for either pre- or post-spray was determined by repeated measures analysis of variance followed by Bonferroni's post-hoc test; $^{}p<0.01$ and $^{*}p<0.001$. Sapap3 KO mice spent more time grooming than their WT littermates. N=7 mice per group.

In addition to excessive grooming, both Sapap3 and Shank3 knockout mice show excessive anxiety, especially toward novel objects or conspecific animals (Peca et al. *Nature* 2011, 472(7344):437-442; Wang et al. *Nat. Commun.* 2016, 7:11459; Welch et al. *Nature* 2007, 448(7156):894-900). In order to determine whether a given compound can address these deficits, the present invention provides the Grooming test, which involves measuring the amount of time spent self-grooming in an unfamiliar environment, with or without being lightly sprayed with water. Both Shank3B, Shank complete and Sapap3 knockout mice show significant deficits in this test compared to wild type littermates (Peca et al. *Nature* 2011, 472(7344):437-442; Wang et al. *Nat. Commun.* 2616, 7:11459; Welch et al. *Nature* 2007, 448(7156):894-900; see also FIG. 1 for Sapap3 knockout mice). This demonstrates that the increased anxiety, manifested as increased self-grooming, observed in these mice also generates behaviors resembling those seen in human conditions such as ASD and OCD.

Behavioral Animal Models of ASD, OCD, and Anxiety Disorders

The identification of compounds that are useful for treating human behavioral disorders, including ASD, OCD, and anxiety disorders is greatly facilitated by preclinical testing with appropriate animal models. In some aspects, the present invention encompasses the insight that the source of a problem encountered with other efforts to identify useful agents for the treatment of ASDs, OCD, and/or anxiety disorders is the use of a limited set of models for characterizing such agents. Among other things, the present disclosure demonstrates that the described compounds induce a particular activity spectrum in a combination of transgenic and wild type in vivo model test systems that quantitatively measure behaviors relevant to ASD, OCD, and various human anxiety disorders. This strategy includes use of genetic models of ASD and OCD, namely, Shank3B, Shank3 complete, and Sapap3 knockout mice, that have strong face and construct validity for their respective human diseases and show a clear component of anxiety.

The complete evaluation of relevant behaviors in these animals is further augmented by the grooming test provided herein that measures innate responses to stressful, anxiety-producing situations, i.e presence in an unfamiliar environment and in one version of the test also being lightly sprayed with water. Thus, among other things, the present disclosure defines and provides effective strategies for the identification and/or characterization of useful agents for the treatment of ASDs, OCD, and/or anxiety disorders. In some embodiments, such strategies include combinations of assays, for example both genetic and situational models.

In some embodiments of the present invention, behavioral testing in genetic models is supplemented with additional anxiety tests in wild type rodents as standard models of psychiatric disorders. Such tests have proven valuable for psychiatric drug discovery efforts targeted at treating behavioral deficits associated with a variety of psychiatric conditions, including those prominent in ASD, OCD, and anxiety disorders. Such symptoms, including heightened anxiety, repetitive behaviors, and social withdrawal or dysfunction, can be observed in certain wild type animal behavioral tests. However, this simple wild type animal behavioral model approach has recognized limitations in predicting human behaviors and drug efficacy in psychiatric disease (Moser *Psychopharmcology* (Berl.) 1989, 99(1):48-53; Silva and Brandao *Pharmacol. Biochem. Behav.* 2000, 65(2):209-216; Lucki et al., *Psychopharmacology* (*Berl.*) 2001, 155:315-322; Griebel and Holmes *Nat. Rev. Drug. Disc.* 2013, 12:667-687). Therefore, it is useful to assess a compound in multiple animal models of behavioral dysfunction to fully establish potential efficacy in human psychiatric disorders. Employing these wild type animal models in combination with the disease-focused genetic models provided herein mitigates the recognized limitations of the former in predicting drug efficacy in human psychiatric disease.

One standard model of anxiety and repetitive behavior is the Marble Burying Test (MBT) (Broekkamp et al. *Eur. J. Pharmacol.* 1986, 126: 223-229), often implemented as an acute single-administration experiment. Compounds that are active or efficacious in the MBT reduce the propensity of the mouse to bury marbles placed in its environment as anxietygenerating foreign objects. Because the mice spend much of the test period burying marbles, and in some cases reburying them, the test may also be a measure of repetitive behavior. Consequently, the MBT may predict efficacy in treating OCD patients as repetitive behaviors are a central component of the disease. For example, SSRIs approved to treat OCD have been found to be efficacious after acute administration in this test (Njung'e and Handley *Br. J. Pharmacol.* 1991, 104:105-112). This result is noteworthy as SSRIs demonstrate efficacy in human depression and OCD patients only after chronic administration (typically for 2-3 weeks).

There are reports in the literature of a positive effect of NR2B antagonists in the Marble Burying Test (Iijima et al. *Neuroscience,* 2010, 471:63-65; WO 2016/049048, published on Mar. 31, 2016). The NR2B antagonist, Ro25-6981, showed modest efficacy after a single subcutaneous administration (Iijima et al. *Neuroscience,* 2010, 471:63-65) at the highest dose tested. However, the study lacked a positive control arm, rendering interpretation of this effect incomplete. In contrast, it has been discovered that potent and selective NR2B antagonists described herein (e.g., chemical entities of Formula $I^{A'}$ and $I^{B'}$) are highly effective in the marble burying test (see Table 2.2.4).

Another model of anxiety is the novel phobia test, conducted as an acute study in wild type mice, but also an effective test in Sapap3 and Shank3B knockout mice. Novelty phobia is a key feature of anxiety, OCD and ASD in human patients, and this phenotype can be quantified in a mouse behavioral assay. In this behavioral assay, when a novel object is introduced into a mouse's home cage or assay chamber, some strains of wild type mice (e.g., C57Bl/6 mice) show hesitancy to approach and touch the object with their noses. By counting the number of bouts of nose touching of the object, the novelty phobia behavior of mice was quantitatively measured. It has been discovered that potent and selective NR2B antagonists described herein (e.g., chemical entities of Formula $I^{A'}$ and $I^{B'}$) are highly effective in the novel phobia test (see Table 2.2.5).

Transgenic+Behavioral Animal Models of ASD, OCD, and Anxiety Disorders

As noted above, the present disclosure provides, among other things, the insight that many wild type animal behavioral models are significantly limited and/or ineffective in predicting human behaviors and drug efficacy in psychiatric disease. Provided herein are disease-focused genetic models that mitigate these limitations. The predictive value of any single test in this battery is compromised by theoretical and empirical shortcomings. However, compounds that are robustly active across several tests in this series should be effective in treating the analogous constellation of symptoms that are routinely present in human ASD, OCD, and anxiety patients.

Transgenic Models and the Grooming Test

Excessive self-grooming is a key feature of OCD and ASD in human patients, and this phenotype can be quantified in a mouse behavioral assay. Sapap3, Shank3B, and Shank3 complete knockout mice also show excessive grooming behaviors relative to wild type mice; and this grooming often leads to facial lesions (Peca et al. *Nature* 2011, 472(7344):437-442; Wang et al. *Nat. Commun.* 2016, 7:11459; Welch et al. *Nature* 2007, 448(7156):894-900). The amount of time mice spent grooming in a novel environment was quantified in Sapap3 knockout mice and their wild type littermates. Sapap3 knockout mice groomed for longer than wild type littermates (see Example 2.2.1.1 and FIG. 1).

Figure 2:
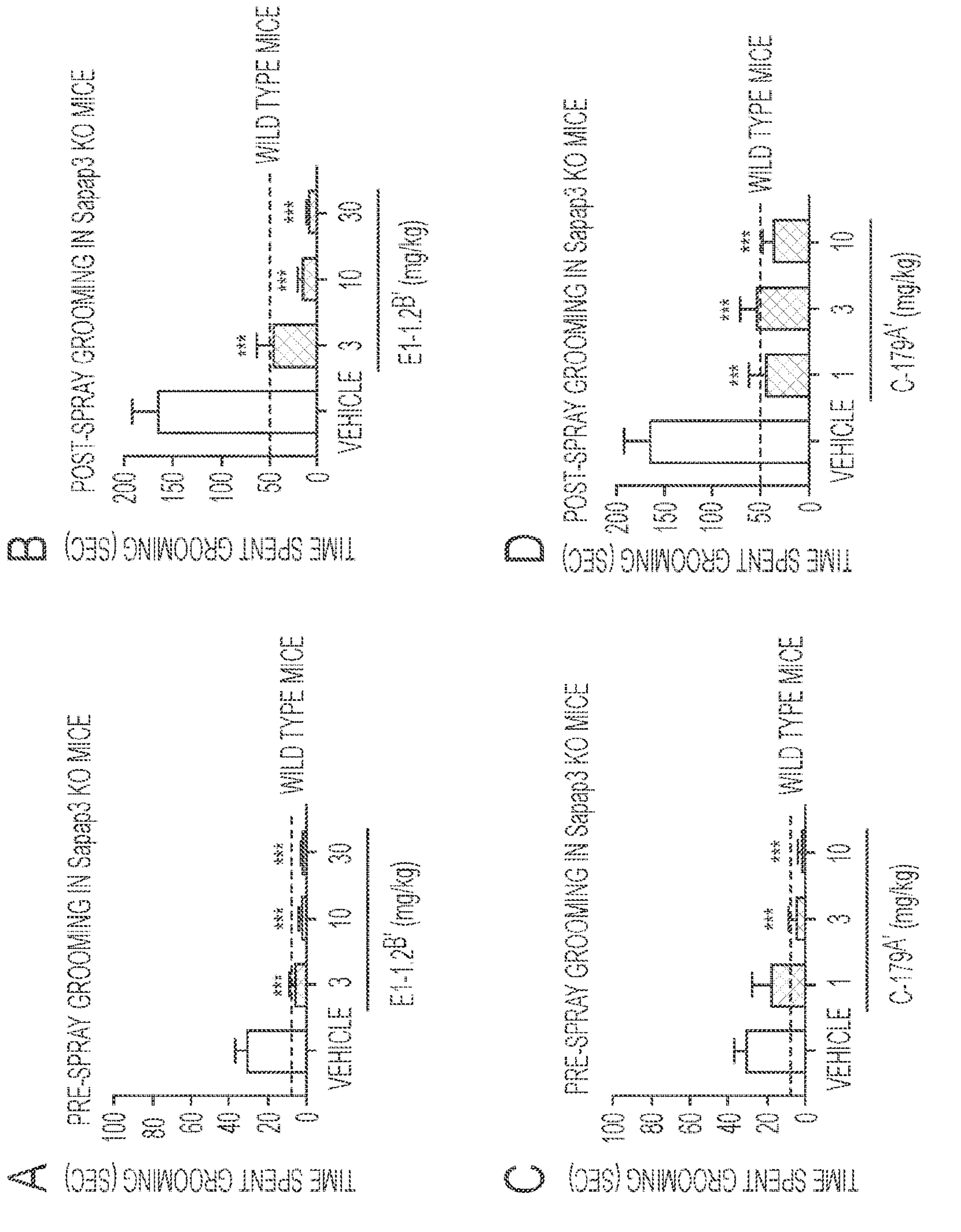
FIG. 2. Acute administration of NR2B antagonists reduces self-grooming in Sapap3 knockout (KO) mice. The effect of two NR2B antagonists administered intraperitoneally 20 minutes before testing on time spent grooming (seconds) in an unfamiliar environment before and after being sprayed with water for Sapap3 KO mice. The dotted line indicates the amount of time spent grooming by wild type littermates treated with vehicle. A, E1-1.2$^{B'}$, pre-spray; B, E1-1.2$^{B'}$, post-spray; C, C-179$^{A'}$, pre-spray; and D, C-179$^{A'}$, post-spray. Significance comparing compound treatments with vehicle for either pre- or post-spray was determined by repeated measures analysis of variance followed by Bonferroni's post-hoc test; ***p<0.001. The NR2B antagonists reduced the amount of grooming in Sapap3 KO mice to a level similar to that observed in wild type littermates. N=6-10 mice per group.

Administration of single intraperitoneal (IP) doses of two different NR2B subunit-selective NMDA antagonists, Compounds E1-1.2$^{B'}$, and C179$^{A'}$, significantly reduced the excessive grooming observed in Sapap3 knockout mice (see Example 2.2.1.1 and FIG. 2). The amount of self-grooming was similar to or less than the amount observed in vehicle-treated wild type littermates.

Figure 3:
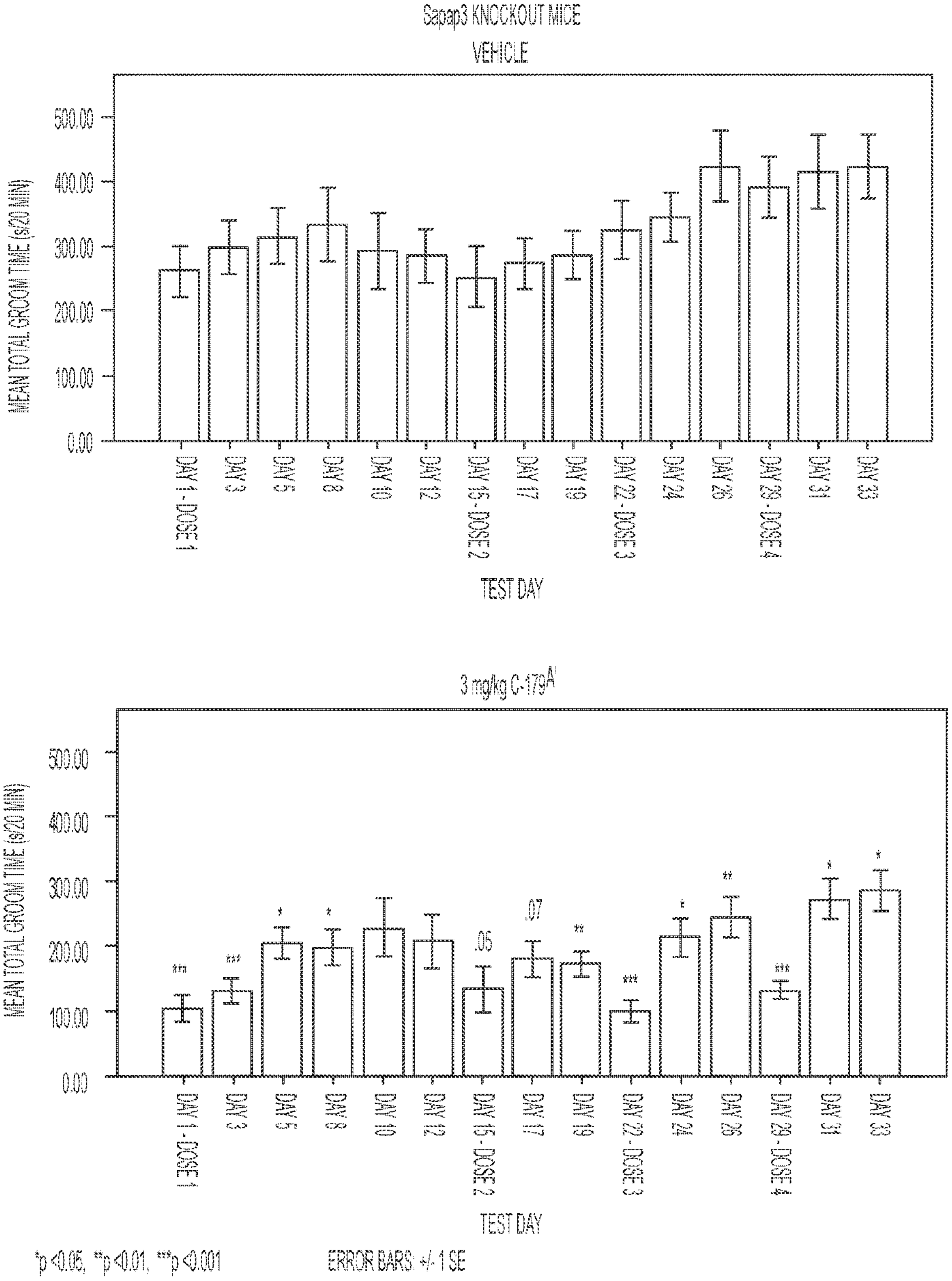
FIG. 3. Sustained effects of an NR2B antagonist on reducing self-grooming in Sapap3 knockout (KO) mice. The effect of 3 mg/kg C-179$^{A'}$, an NR2B antagonist, administered intraperitoneally 20 minutes before testing on Days 1, 15, 22, and 29 on time spent grooming (seconds) for Sapap3 KO mice. Significance comparing compound treatment and vehicle was determined by repeated measures analysis of variance followed by Bonferroni's post-hoc test; *p<0.05, p<0.01, and *p<0.001. Compound C-179$^{A'}$ reduced grooming for up to one week postdosing, despite the clearance of the compound from the plasma in about 8 hours. Furthermore, no tachyphylaxis developed over the 33 days of testing.

Another study was conducted with Compound C-179$^{A'}$ that addressed the question of whether efficacy in the Sapap3 knockout mouse grooming test was maintained beyond the duration of detectable plasma levels of the compound. Mice were dosed with 3 mg/kg of Compound C-179$^{A'}$ on Days 1, 15, 22, and 29, 20 minutes before testing. On Days 3, 5, 8, 10, 12, 15, 17, 19, 22, 24, 26, 29, 31, and 33, mice were tested in the Grooming Test (see Example 2.2.1.2 and FIG. 3).

Compound C-179$^{A'}$ was dosed on Day 1 and not again until Day 15. This portion of the study demonstrated that the effect of a single dose of 3 mg/kg Compound C-179$^{A'}$ resulted in sustained efficacy lasting for 1 week (see FIG. 3). Reductions in self-grooming were significant on Days 1, 3, 5, and 8, as a result of treatment with Compound C-179$^{A'}$ on Day 1. The effect of compound treatment was no longer significant during the second week post Day 1 dosing (e.g., Days 10 and 12). These data showed that a single dose of Compound C-179$^{A'}$ could have therapeutic effects well beyond the time period in which levels of compound could be detected in plasma.

Compound C-179$^{A'}$ was then administered weekly for an additional 3 weeks to evaluate the subacute effects of repeated dosing (i.e., to determine whether tachyphylaxis would occur). On each test day between Days 15 and 33, Compound C-179$^{A'}$ either significantly reduced or demonstrated a trend to reduce self-grooming compared with vehicle. Reductions in self-grooming were less on the $5^{th}$ day post each dose compared with the day of each dose, suggesting the maintenance of a pattern of the compound's efficacy wearing off in about one week that was observed in the first two weeks of the study. This phase of the study further substantiated the possibility of sustained therapeutic effects with intermittent dosing at weekly intervals and demonstrated that for one month, tachyphylaxis was not observed.

Acute and sustained effects of a single dose of several additional compounds were studied in the Sapap3 knockout and wild type littermate mice (see Example 2.2.1.3). In studies of Compound C-179$^{A'}$ at lower doses and of Compounds E1-21.26$^{B'}$, E1-22.2$^{B'}$, and E1-22.6$^{B'}$, the Sapap3 knockout mice showed excessive amounts of grooming compared with wild type mice on Day 1, the day of dosing (see FIG. 4). On Day 1, the compound treatments significantly reduced grooming in Sapap3 knockout mice as well as in wild type littermates in a dose-dependent manner.

Figure 5:
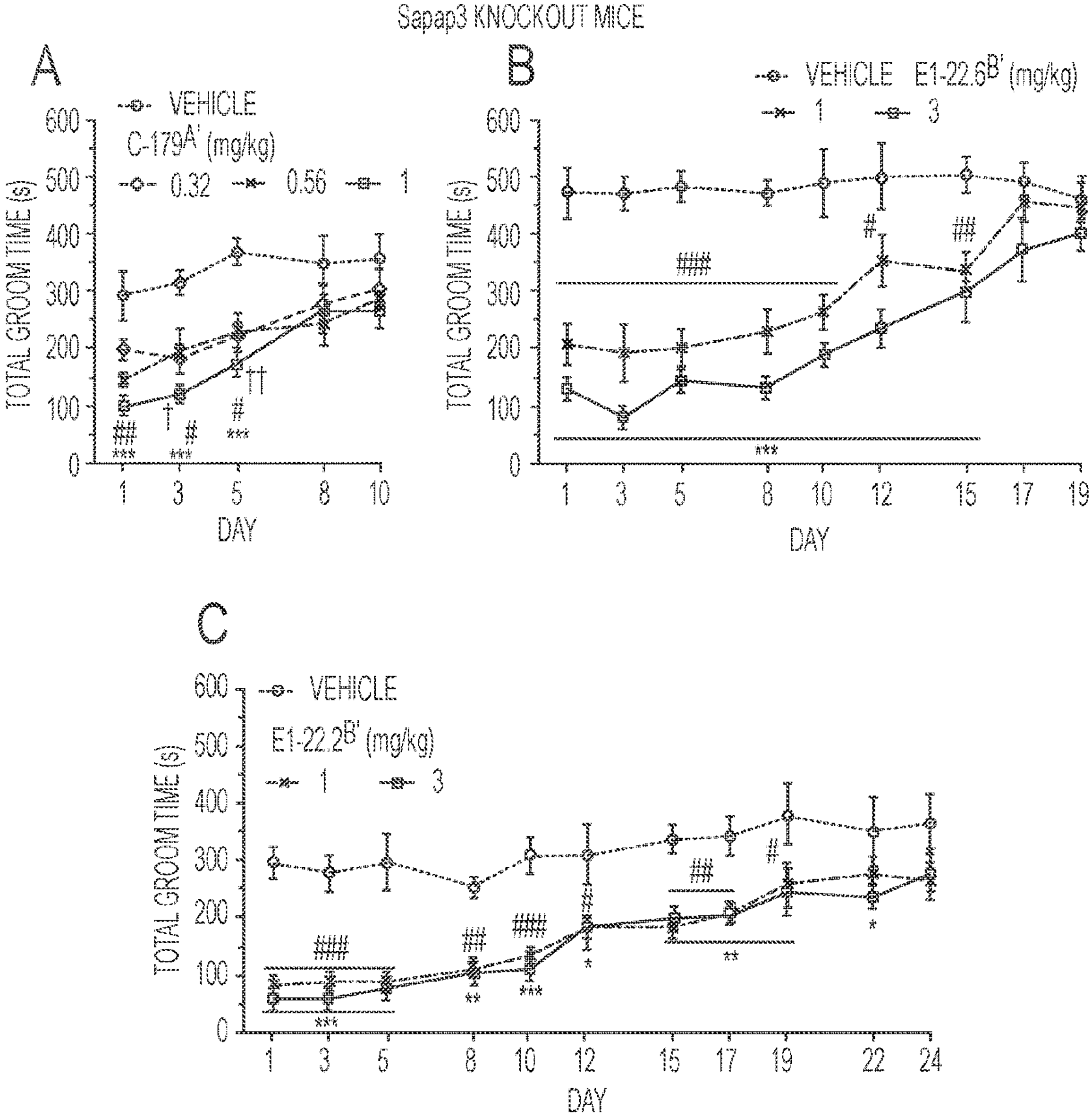
FIG. 5. Sustained effects of a single dose of an NR2B antagonist on reducing self-grooming in Sapap3 knockout mice. The effect of single doses of three NR2B antagonists administered intraperitoneally 20 minutes before testing on Day 1 on time spent grooming (seconds) for Sapap3 knockout mice. (See FIG. 4 for Day 1 data alone.) Significance comparing compound treatment and vehicle was determined by repeated measures analysis of variance followed by Bonferroni's post-hoc test. The repeated measure was test day. A, C-179$^{A'}$: 1 mg/kg, *p<0.001; 0.56 mg/kg, $^{\#}$p<0.05, and $^{\#\#}$p<0.01; and 0.32 mg/kg, $^{\dagger}$p<0.05 and $^{\dagger\dagger}$p<0.01. B, E1-22.6$^{B'}$: 3 mg/kg, *p<0.001; and 1 mg/kg, $^{\#}$p<0.05, $^{\#\#}$p<0.01, and $^{\#\#\#}$p<0.001. C, E1-22.2$^{B'}$:3 mg/kg, *p<0.05, p<0.01, and *p<0.001; and 1 mg/kg, #p<0.05, ##p<0.01, and ###p<0.001. Compound C-179$^{A'}$ at 0.32, 0.56, and 1 mg/kg reduced grooming through Day 5 postdosing; Compound E1-22.6$^{B'}$ at 1 and 3 mg/kg reduced grooming through Day 15; and Compound E1-22.2$^{B'}$ at 1 and 3 mg/kg reduced grooming through Days 19 and 22, respectively. All three compounds were cleared from plasma in about 8 hours. N=9-11 mice per group.

For Compounds C-179$^{A'}$, E1-22.2$^{B'}$, and E1-22.6$^{B'}$, the Sapap3 knockout mice were then retested on Days 3, 5, 8, 10, 12, 15, 17, 19, 22, and 24 without re-dosing, until there were no longer significant differences between vehicle and compound-treated groups in grooming (see FIG. 5). Sustained reductions in grooming lasted until Day 5 for Compound C-179$^{A'}$, until Days 19 or 22 for Compound E1-22.2$^{B'}$, and until Day 15 for Compound E1-22.6$^{B'}$.

Figure 6:
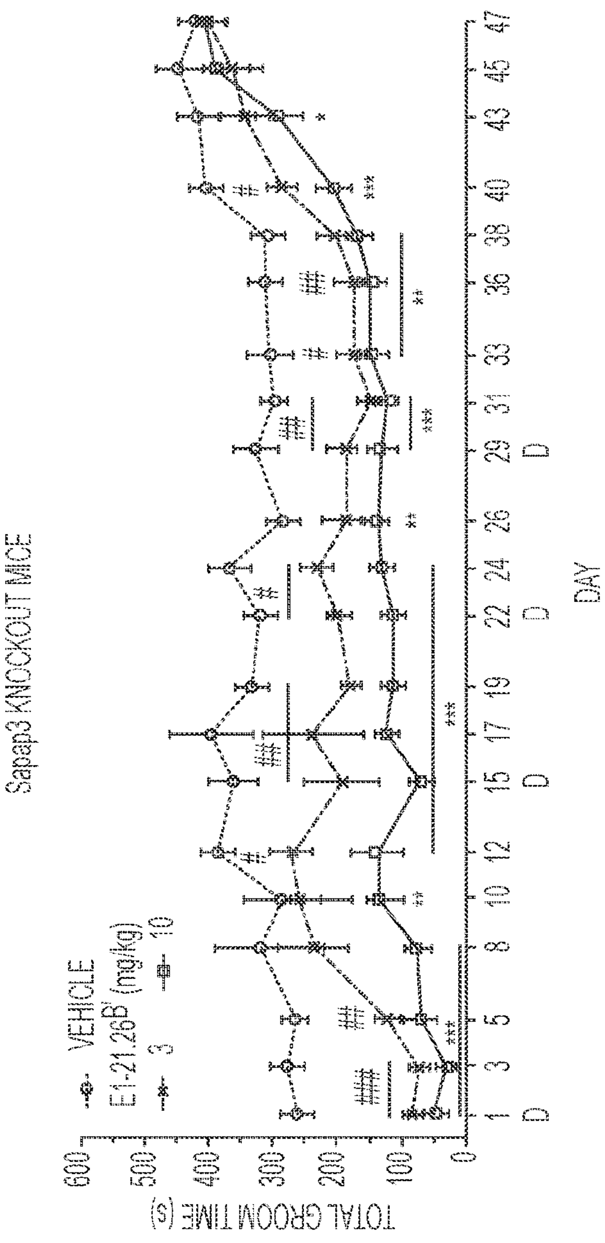
FIG. 6. Sustained effects of an NR2B antagonist on reducing self-grooming in Sapap3 knockout mice. The effects of 3 and 10 mg/kg E1-21.26$^{B'}$, an NR2B antagonist, administered intraperitoneally 20 minutes before testing on Days 1, 15, 22, and 29 on time spent grooming (seconds) for Sapap3 knockout mice. (See FIG. 4 for Day 1 data alone.) Significance comparing compound treatment and vehicle was determined by repeated measures analysis of variance followed by Bonferroni's post-hoc test. The repeated measure was test day. Compound E1-21.26$^{B'}$: 10 mg/kg, *p<0.05, p<0.01, and *p<0.001; and 3 mg/kg, $^{\#}$p<0.05, $^{\#\#}$p<0.01, and $^{\#\#\#}$p<0.001. Compound E1-21.26$^{B'}$ at 3 mg/kg reduced grooming through Day 5 after the first dose, while 10 mg/kg was efficacious through Day 12. Weekly redosing of Compound E1-21.26$^{B'}$ out to Day 29 produced sustained efficacy, without tachyphylaxis. The effect on grooming was no longer significant after Days 40 and 43 for 3 and 10 mg/kg, respectively. Compound E1-21.26$^{B'}$ was cleared from plasma in about 8 hours. N=9-10 mice per group. D=dosing day.

Compound E1-21.26$^{B'}$ was dosed on Days 1, 15, 22, and 29 to follow the effect of repeated weekly dosing and the length of time for the treatment effect to wear off in the Sapap3 knockout mice (see FIG. 6). The significant reduction in grooming wore off by Day 8 for the lower dose level, while the higher dose level remained effective through to the second dose on Day 15. Thereafter, repeated weekly dosing with Compound E1-21.26$^{B'}$ significantly reduced grooming. After the fourth and final dose on Day 29, the effects wore off, lasting through Days 40 or 43. These days corresponded to days 12 and 15, following the last dose. These additional studies show that multiple NR2B antagonists reduce grooming in Sapap3 knockout mice and produce sustained effects that may allow for intermittent dosing. Furthermore, the latter study also showed no tachyphylaxis with weekly dosing for up to one month.

Compounds have also been studied in the Shank3 complete knockout mice in the Grooming Test (see Example 2.2.1.4). Administration of single IP doses of two different NR2B subunit-selective NMDA antagonists, Compounds C-179$^{A'}$ and E1-22.2$^{B'}$, significantly reduced the excessive grooming observed in Shank3 complete knockout mice (see Example 2.2.1.4 and FIG. 7). The amount of self-grooming in the treated Shank3 complete knockout mice was similar to or less than the amount observed in vehicle-treated wild type littermates.

The Shank3 complete knockout mice were then retested on Days 3, 5, 8, 10, 12, 15, 17, 19, 22, 26, 29, 31, and 33 without redosing (see FIG. 8). Compounds C-179$^{A'}$ and E1-22.2$^{B'}$ significantly reduced grooming through Day 33. The wild type littermates of the Sapap3 knockout and Shank3 complete knockout mice were retested after Day 1 compound administration to determine whether the sustained effects were unique to the knockout mice (see Example 2.2.1.5 and FIG. 9). Compounds C-179$^{A'}$ and E1-22.2$^{B'}$ were tested in the wild type littermates of the Shank3 complete knockout mice; and Compound E1-22.6 was tested in the wild type littermates of the Sapap3 knockout mice. Mice were retested in the Grooming Test on Days 3, 5, 8, 10, and 12. The compounds had dose-dependent sustained effects on grooming in the wild type littermates that lasted shorter (only through Day 3) than in the knockout mice.

The Marble Burying Test in Wild Type Mice

In addition to measurement of grooming in transgenic animal models of OCD, the anxiolytic/OCD-mitigating effects of several compounds of the present invention were measured using the Marble Burying Test (see Example 2.2.4). Several compounds with NR2B antagonist activity dose-dependently reduced the number of marbles buried during the test, 20 minutes after IP or oral (PO) dosing (see Table 2.2.4). The compounds varied in the minimum effective dose in this test.

The Novelty Phobia Test in Wild Type Mice

Additional testing of compounds was performed in the Novelty Phobia Test in wild type mice (see Example 2.2.5). Most of the compounds significantly increased the number of bouts of nose touching of the novel object (see Table 2.2.5). In addition to variation in the minimum effective dose across the compounds, some compounds did not demonstrate efficacy, despite demonstrating efficacy in the Marble Burying Test, thereby demonstrating the utility of the test in distinguishing among compounds. Furthermore, while some compounds demonstrated dose-dependent increases in the number of bouts of nose touching of the novel object, the dose-response function for other compounds in this test was an inverted U-shaped curve. The minimum effective dose, as well as the pattern of the dose-response function, can be useful in compound selection of potentially effective clinical compounds.

EXAMPLES

Example 1. Assays

Example 1.1 NR2B Antagonist Activity

HEK293 cell lines stably expressing cloned human NR1/NR2B and NR1/NR2A, respectively, were established according to standard previously described methods (Hansen et al. *Comb. Chem High Throughput Screen.* 2008, 11:304-315). Activation of the NR2A or NR2B subtype of NMDA receptor with glutamate as an agonist and glycine co-agonist on these cells results in calcium influx, which can be monitored with fluorescent indicator Fluo-4. A cell-based assay has been implemented to evaluate the effect of a compound on NR2A and NR2B receptors by measuring the fluorescent changes (Hansen et al. *Comb. Chem High Throughput Screen.* 2008, 11:304-315).

HEK293 cells stably expressing NR2A or NR2B receptors were cultured at 37° C. in a humidified $CO_2$ incubator in DMEM supplemented with 10% fetal bovine serum (FBS) (Hyclone), 10 μM MK801 (Sigma-Aldrich) and 50 μM AP-5 (Tocris). For experiments, the cells were seeded onto poly-D-lysine-coated 96-well black plates with clear bottom (Corning) at a density of ~50,000 cells/well. After overnight culture, the growth medium was removed from the wells and the cells were incubated at 37° C. for 60 minutes in Hanks buffer containing 4 μM fluo-4-AM (Invitrogen) and 0.1% bovine serum albumin (BSA). After dye-loading, the cells were washed three times with Hanks buffer and incubated for 10 minutes at room temperature with various concentrations of test compounds prepared in Hanks buffer with 0.1% BSA. The cell plates were placed onto an FDSS Cell fluorescence reader (Hamamatsu). After 20 seconds of reading background fluorescence, agonist glutamate at final 100 M and co-agonist glycine at final 50 μM were added to the cells to activate the receptor, and the resulting fluorescence changes were recorded and quantified. Based on the changes in fluorescence intensity, the pharmacological effect of test compounds was analyzed and the $IC_{50}$ values derived from a non-linear least squares fitting of the concentration-dependent response to a standard logistic equation using Prism (Graphpad Software, Inc.):

$$\text{Amplitude}=\text{Max Amplitude}/(1+(IC_{50}/[\text{antagonist}])^n).$$

Results are shown in Table 1.1A and 1.1B below.

TABLE 1.1A

| Compound | Free Base Structure | NR2B $IC_{50}$ | NR2A $IC_{50}$ |
|---|---|---|---|
| C-2$^{A'}$ | 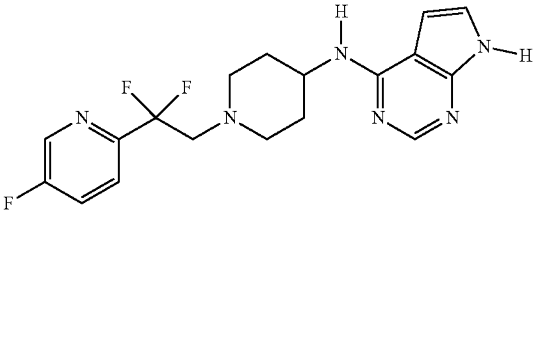 [SMILES: Fc1ccc(C(F)(F)CN2CCC(Nc3ncnc4[nH]ccc34)CC2)nc1] | 124 nM | >10 μM |

TABLE 1.1A-continued
| Compound | Free Base Structure | NR2B $IC_{50}$ | NR2A $IC_{50}$ |
|---|---|---|---|
| C-3[4'] | 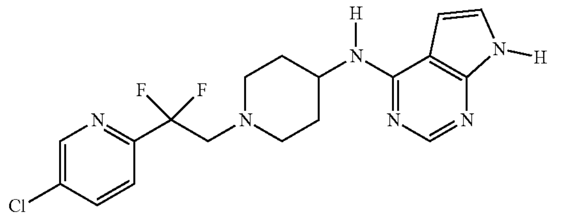 [SMILES: FC(F)(CN1CCC(Nc2ncnc3[nH]ccc23)CC1)c1ccc(Cl)cn1] | 22 nM | >10 μM |
| C-4[4'] | 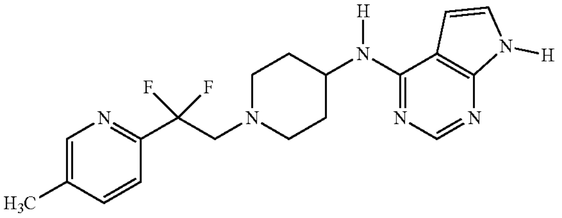 | 35 nM | >10 μM |
| C-5[4'] | 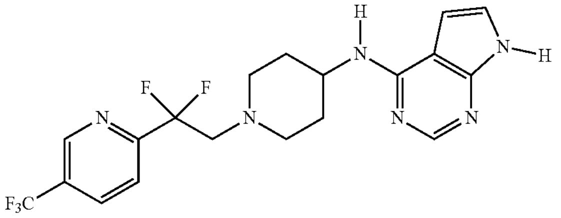 | 30 nM | >10 μM |
| C-16[4'] | 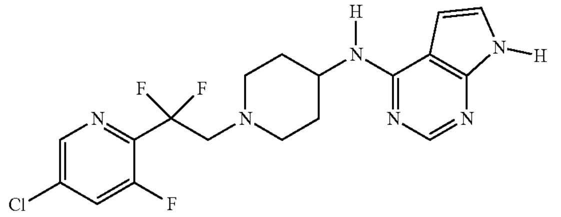 [SMILES: Fc1cc(Cl)cnc1C(F)(F)CN1CCC(Nc2ncnc3[nH]ccc23)CC1] | 47 nM | >10 μM |
| C-18[4'] | 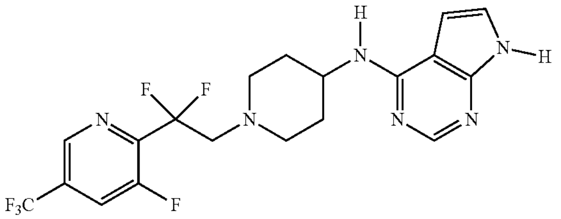 [SMILES: Fc1cc(C(F)(F)F)cnc1C(F)(F)CN1CCC(Nc2ncnc3[nH]ccc23)CC1] | 84 nM | >10 μM |
| C-17[4'] | 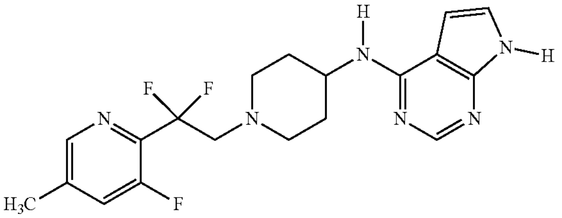 [SMILES: Cc1cnc(C(F)(F)CN2CCC(Nc3ncnc4[nH]ccc34)CC2)c(F)c1] | 44 nM | >10 μM |
| C-47[4'] | 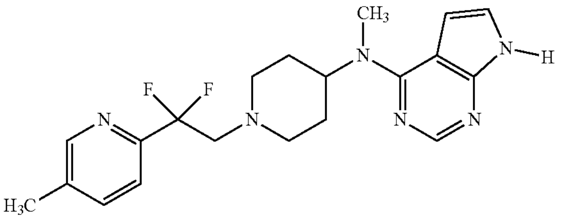 | 140 nM | >10 μM |

TABLE 1.1A-continued
| Compound | Free Base Structure | NR2B $IC_{50}$ | NR2A $IC_{50}$ |
|---|---|---|---|
| C-230[A'] | 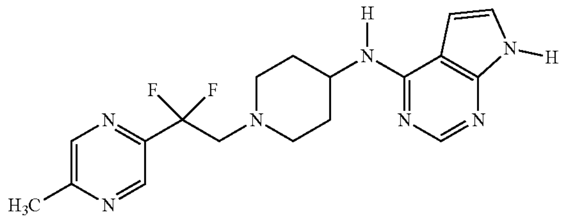 | 88 nM | >10 μM |
| C-1[A'] | 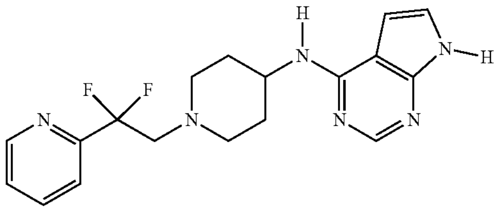 [SMILES: FC(F)(CN1CCC(Nc2ncnc3[nH]ccc23)CC1)c1ccccn1] | 159 nM | >10 μM |
| C-127[A'] | 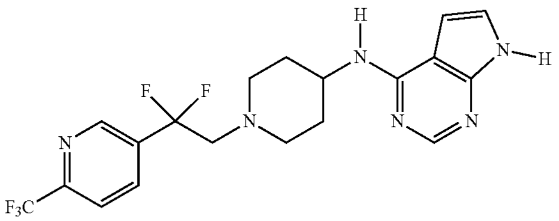 [SMILES: FC(F)(F)c1ccc(C(F)(F)CN2CCC(Nc3ncnc4[nH]ccc34)CC2)cn1] | 45 nM | >10 μM |
| C-128[A'] | 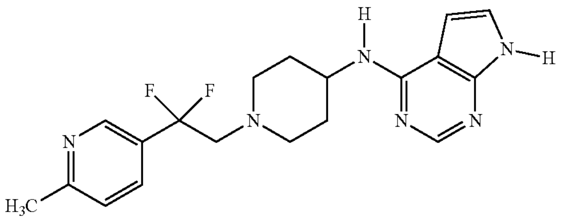 | 89 nM | >10 μM |
| C-6[A'] | 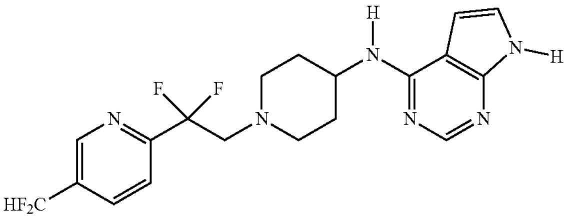 | 31 nM | >10 μM |
| C-7[A'] | 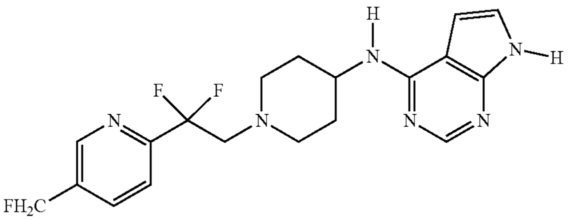 | 14 nM | >10 μM |
| C-11[A'] | 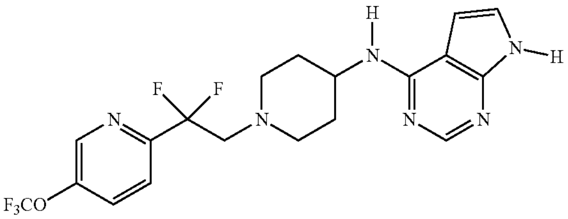 [SMILES: FC(F)(F)Oc1ccc(C(F)(F)CN2CCC(Nc3ncnc4[nH]ccc34)CC2)nc1] | 43 nM | >10 μM |

TABLE 1.1A-continued
| Compound | Free Base Structure | NR2B $IC_{50}$ | NR2A $IC_{50}$ |
|---|---|---|---|
| C-12[A'] | 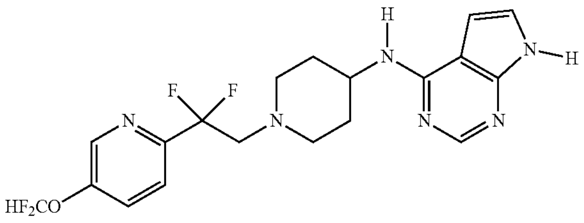 | 24 nM | >10 μM |
| C-178[A'] | 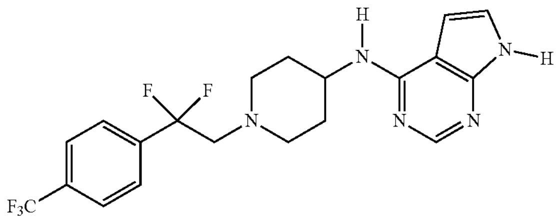 | 64 nM | >10 μM |
| C-179[A'] | 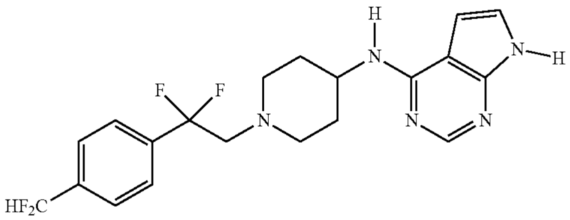 | 23 nM | >10 μM |
| C-175[A'] | 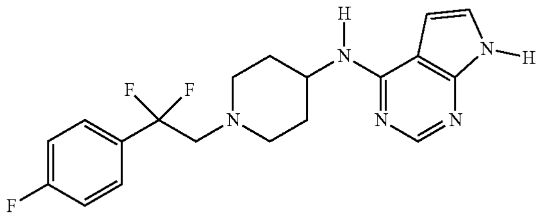 [SMILES: Fc1ccc(C(F)(F)CN2CCC(Nc3ncnc4[nH]ccc34)CC2)cc1] | 22 nM | >10 μM |
| C-176[A'] | 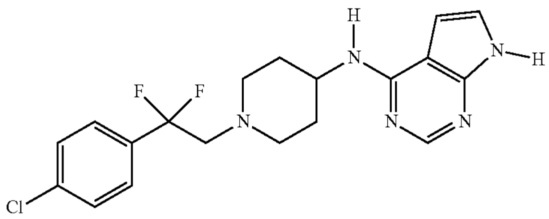 [SMILES: FC(F)(CN1CCC(Nc2ncnc3[nH]ccc23)CC1)c1ccc(Cl)cc1] | 26 nM | >10 μM |
| C-177[A'] | 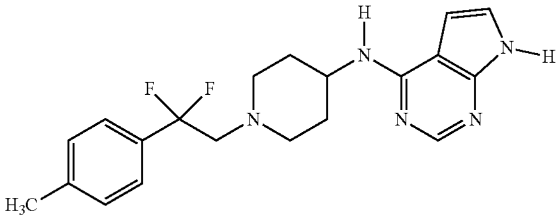 | 27 nM | >10 μM |
TABLE 1.1B
| Cmpd. No. | NR2B $IC_{50}$ (nM) | Number of Assays | NR2A $IC_{50}$ |
|---|---|---|---|
| E1-1.2[B'] | 20.7 | 3 | >10 μM |
| E2-1.2[B'] | 156 | 3 | >10 μM |
| E1-2.2[B'] | 10.4 | 2 | >10 μM |
| E1-9.2[B'] | 48.2 | 2 | >10 μM |
TABLE 1.1B-continued
| Cmpd. No. | NR2B $IC_{50}$ (nM) | Number of Assays | NR2A $IC_{50}$ |
|---|---|---|---|
| E1-8.2[B'] | 17.0 | 2 | >10 μM |
| E1-1.3[B'] | 14.8 | 2 | >10 μM |
| E1-1.4[B'] | 20.5 | 2 | >10 μM |
| E1-22.2[B'] | 11.0 | 2 | >10 μM |

TABLE 1.1B-continued

| Cmpd. No. | NR2B $IC_{50}$ (nM) | Number of Assays | NR2A $IC_{50}$ |
|---|---|---|---|
| E1-21.2[B'] | 13.9 | 2 | >10 μM |
| E1-21.26[B'] | 29.0 | 2 | >10 μM |
| E1-1.5[B'] | 9.6 | 2 | >10 μM |

Example 1.2 NR2B Radioligand Binding Assay

This example describes an NR2B receptor binding assay in rat brain using [$^3$H] (E)-N1-(2-methoxybenzyl)-cinnamidine (see below). The binding assay method was adapted from a previously described cellular human NR1a/NR2B cloned receptor assay (Kiss et al. *Neurochem. Internatl.* 2005, 46:453-464) to rat brain tissue. This assay serves as a selective measure of NR2B receptor binding activity in native rat brain receptors. Briefly, the brains of male Wistar rats were homogenized (Polytron) before centrifugation at 40,000×g for 15 minutes at 4° C. After 2 washes, the final pellet was homogenized and stored at −80° C. The protein concentration was determined by Bradford assay. [$^3$H] (E)-N1-(2-methoxybenzyl)-cinnamidine was used at 2 different concentrations, 0.5 and 30 nM, with 30 μg of membrane proteins. Non-specific binding was assessed in the presence of excess (10 μM) (E)-N1-(2-nethoxybenzyl)-cinnamidine. A high affinity site was identified, for which inhibition constant ($K_i$) values of 0.193, 0.176, 0.41, and 0.087 (mean=0.22) nM were determined in independent assays for (E)-N1-(2-methoxybenzyl)-cinnamidine. In cloned human NR1a/NR2B receptors, the $K_i$ values for (E)-N1-(2-methoxybenzyl)-cinnamidine were 1.0 nM and 0.7 nM using [$^3$H] (E)-N1-(2-methoxybenzyl)-cinnamidine and [$^3$H]-ifenprodil as the radioligands, respectively (Claiborne et al. *Bioorg. Med. Chem. Lett.* 2003, 13:697-700).

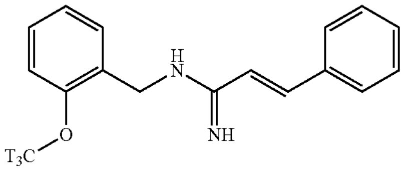

[$^3$H] (E)-N1-(2-methoxybenzyl)-cinnamidine

Test compounds were solubilized at 10 mM in DMSO. Then the dilutions were performed with a constant solvent concentration (1% DMSO) in the assay. After incubation for 4.5 hours at room temperature, the assays were filtered on GF/3 filters pretreated with 0.3% (v/v) polyethylenimine (PEI) with a Packard system. The experiment was performed in duplicate (n=2). The $K_i$ values for binding of compounds to native rat brain NR2B receptors are presented in Table 1.2.

TABLE 1.2

Inhibition Constant ($K_i$) in a Radioligand Binding Assay for Rat Brain NR2B Receptors %

| Compound | Structure | Arithmetic Mean $K_i$ (nM)[a] | Number of Assays |
|---|---|---|---|
| C-178[A'] | 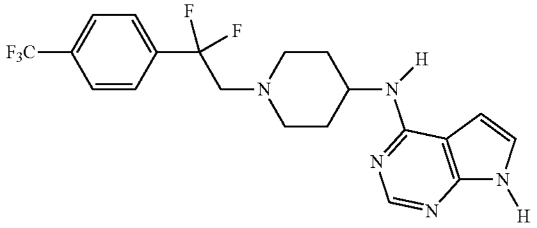 [SMILES: FC(F)(F)c1ccc(C(F)(F)CN2CCC(Nc3ncnc4[nH]ccc34)CC2)cc1] | 1.42 | 2 |
| C-127[A'] | 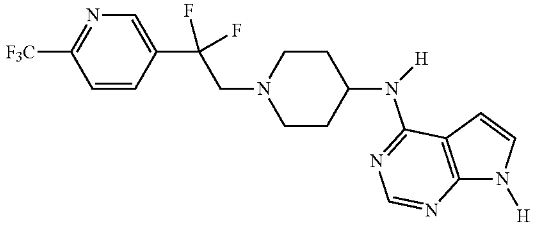 [SMILES: FC(F)(F)c1ccc(C(F)(F)CN2CCC(Nc3ncnc4[nH]ccc34)CC2)cn1] | 31.6 | 2 |
| C-179[A'] | 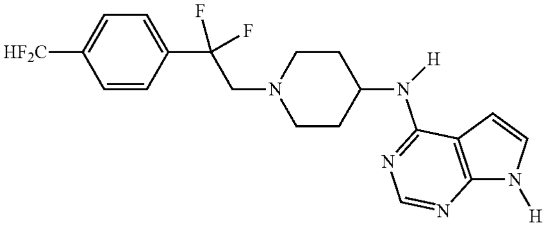 | 0.838 | 3 |

TABLE 1.2-continued
| Inhibition Constant ($K_i$) in a Radioligand Binding Assay for Rat Brain NR2B Receptors % | | | |
|---|---|---|---|
| Compound | Structure | Arithmetic Mean $K_i$ (nM)[a] | Number of Assays |
| C-5[A'] | 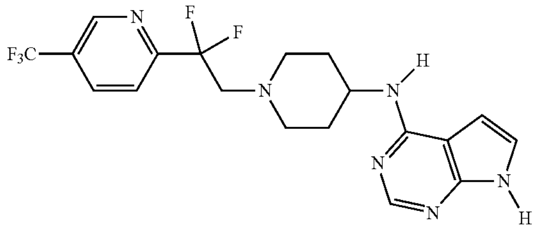 | 15.7 | 1 |
| C-11[A'] | 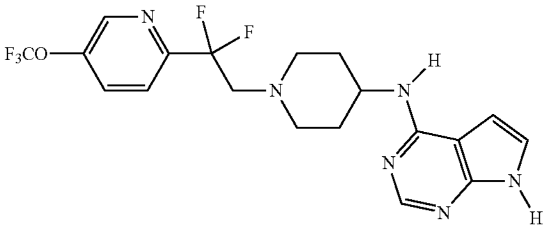 [SMILES: FC(F)(F)Oc1ccc(C(F)(F)CN2CCC(Nc3ncnc4[nH]ccc34)CC2)nc1] | 38.4 | 2 |
| E1-1.2[B'] | 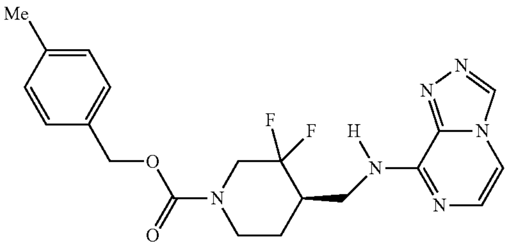 [SMILES: Cc1ccc(COC(=O)N2CC[C@H](CNc3nccn4cnnc34)C(F)(F)C2)cc1] | 4.81 | 3 |
| E2-1.2[B'] | 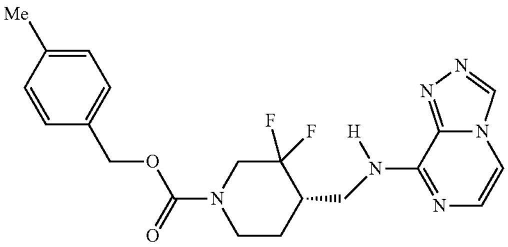 [SMILES: Cc1ccc(COC(=O)N2CC[C@@H](CNc3nccn4cnnc34)C(F)(F)C2)cc1] | 84.2 | 2 |
| E1-1.3[B'] | 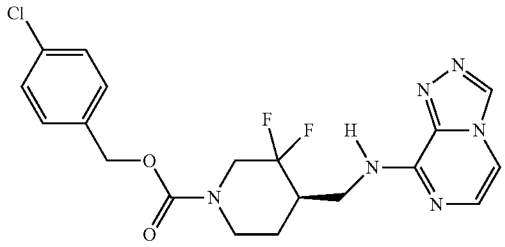 | 8.67 | 2 |
| E1-1.4[B'] | 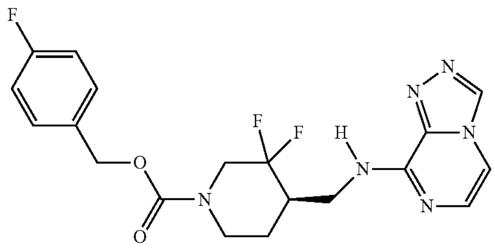 [SMILES: O=C(OCc1ccc(F)cc1)N1CC[C@H](CNc2nccn3cnnc23)C(F)(F)C1] | 18.2 | 1 |

TABLE 1.2-continued
| Inhibition Constant ($K_i$) in a Radioligand Binding Assay for Rat Brain NR2B Receptors % | | | |
|---|---|---|---|
| Compound | Structure | Arithmetic Mean $K_i$ (nM)[a] | Number of Assays |
| E1-1.5[B'] | 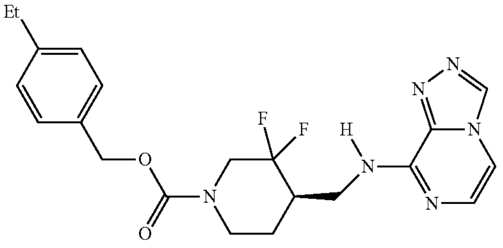 [SMILES: CCc1ccc(COC(=O)N2CC[C@H](CNc3nccn4cnnc34)C(F)(F)C2)cc1] | 2.55 | 3 |
| E1-8.2[B'] | 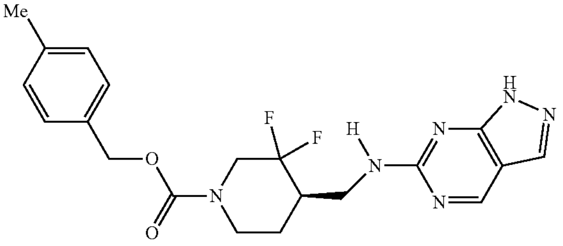 [SMILES: Cc1ccc(COC(=O)N2CC[C@H](CNc3ncc4cn[nH]c4n3)C(F)(F)C2)cc1] | 1.40 | 3 |
| E1-9.2[B'] | 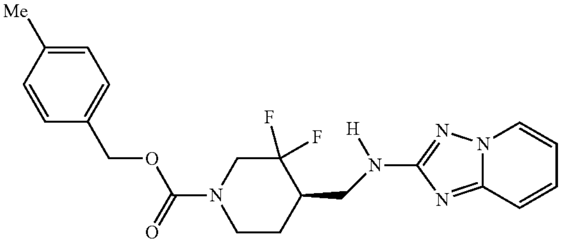 [SMILES: Cc1ccc(COC(=O)N2CC[C@H](CNc3nc4ccccn4n3)C(F)(F)C2)cc1] | 11.3 | 1 |
| E1-21.2[B'] | 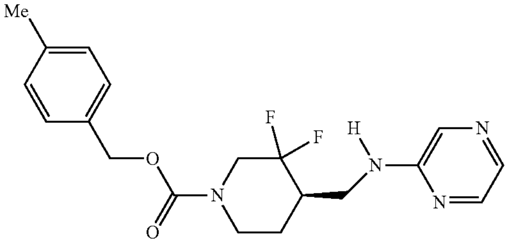 | 0.716 | 1 |
| E1-21.26[B'] | 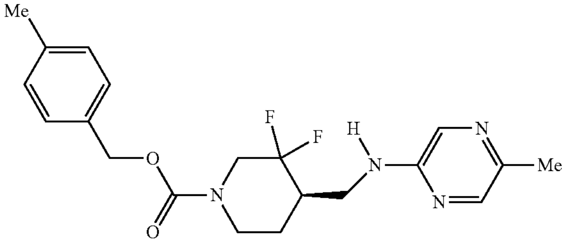 [SMILES: Cc1ccc(COC(=O)N2CC[C@H](CNc3cnc(C)cn3)C(F)(F)C2)cc1] | 1.02 | 2 |
| E1-22.26[B'] | 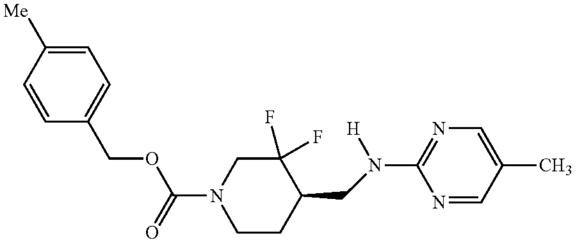 [SMILES: Cc1ccc(COC(=O)N2CC[C@H](CNc3ncc(C)cn3)C(F)(F)C2)cc1] | 3.4 | 1 |

TABLE 1.2-continued
| Compound | Structure | Arithmetic Mean $K_i$ (nM)[a] | Number of Assays |
|---|---|---|---|
| Inhibition Constant ($K_i$) in a Radioligand Binding Assay for Rat Brain NR2B Receptors % | | | |
| E1-22.29[B'] | 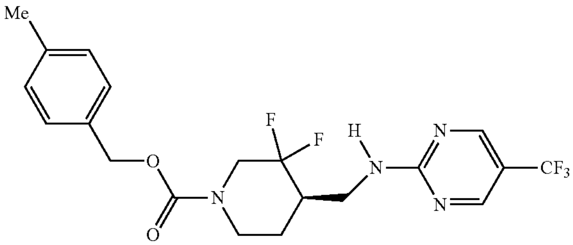 [SMILES: Cc1ccc(COC(=O)N2CC[C@H](CNc3ncc(C(F)(F)F)cn3)C(F)(F)C2)cc1] | >1000 | 1 |
| E1-22.5[B'] | 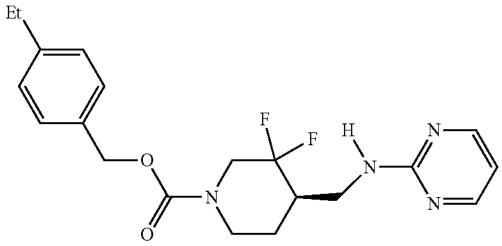 | 0.49, 0.55, Mean = 0.52 | 2 |
| E1-22.30[B'] | 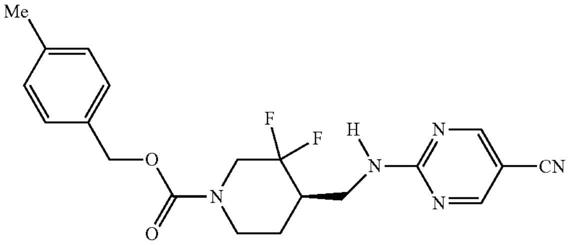 [SMILES: Cc1ccc(COC(=O)N2CC[C@H](CNc3ncc(C#N)cn3)C(F)(F)C2)cc1] | 2.6 | 1 |
| E1-22.2[B'] | 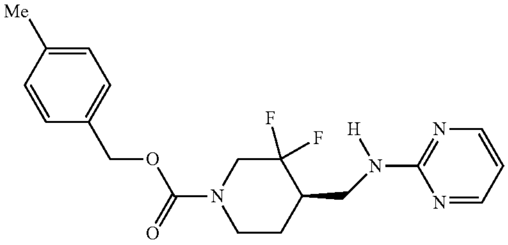 [SMILES: Cc1ccc(COC(=O)N2CC[C@H](CNc3ncccn3)C(F)(F)C2)cc1] | 0.413, 0.69, 0.68, Mean = 0.59 | 3 |
| E1-21.4[B'] | 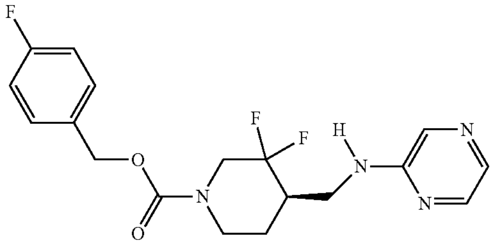 [SMILES: O=C(OCc1ccc(F)cc1)N1CC[C@H](CNc2cnccn2)C(F)(F)C1] | 1.3 | 1 |

TABLE 1.2-continued
Inhibition Constant ($K_i$) in a Radioligand Binding Assay for Rat Brain NR2B Receptors %
| Compound | Structure | Arithmetic Mean $K_i$ (nM)[a] | Number of Assays |
|---|---|---|---|
| E1-21.30[B'] | 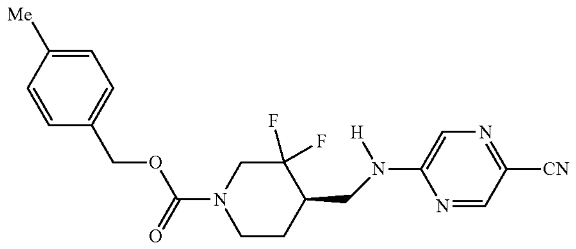 [SMILES: Cc1ccc(COC(=O)N2CC[C@H](CNc3cnc(C#N)cn3)C(F)(F)C2)cc1] | 31 | 1 |
| E1-21.34[B'] | 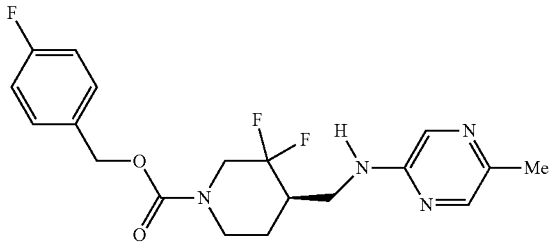 [SMILES: Cc1cnc(NC[C@H]2CCN(C(=O)OCc3ccc(F)cc3)CC2(F)F)cn1] | 16 | 1 |
| E1-21.33[B'] | 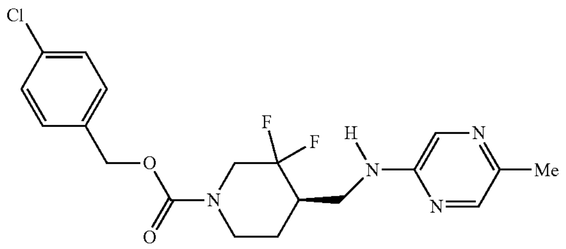 [SMILES: Cc1cnc(NC[C@H]2CCN(C(=O)OCc3ccc(Cl)cc3)CC2(F)F)cn1] | 11 | 1 |
| E1-22.3[B'] | 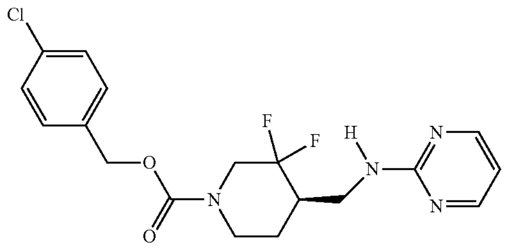 | 0.81 | 1 |
| E1-22.4[B'] | 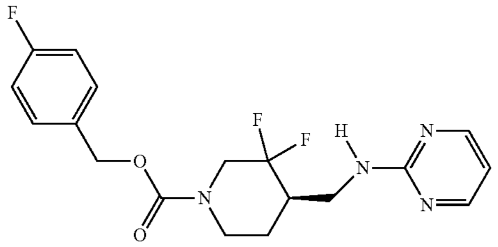 | 1.1, 1.7, Mean = 1.4 | 2 |

TABLE 1.2-continued
Inhibition Constant ($K_i$) in a Radioligand Binding Assay for Rat Brain NR2B Receptors %
| Compound | Structure | Arithmetic Mean $K_i$ (nM)[a] | Number of Assays |
|---|---|---|---|
| E1-22.6[B'] | 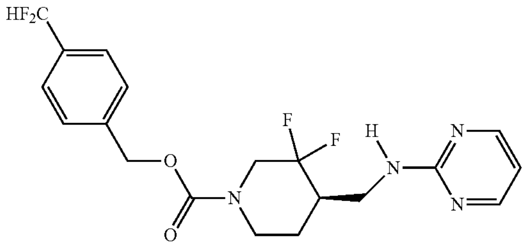 | 0.94. 0.79, 0.90 Mean = 0.88 | 3 |
| E1-22.28[B'] | 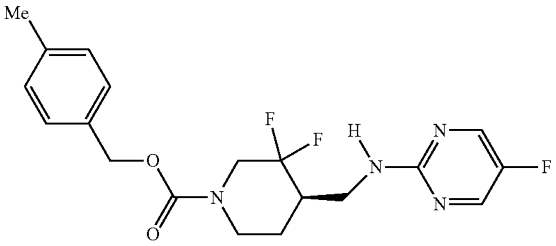 [SMILES: Cc1ccc(COC(=O)N2CC[C@H](CNc3ncc(F)cn3)C(F)(F)C2)cc1] | 1.6 | 1 |
| E1-23.2[B'] | 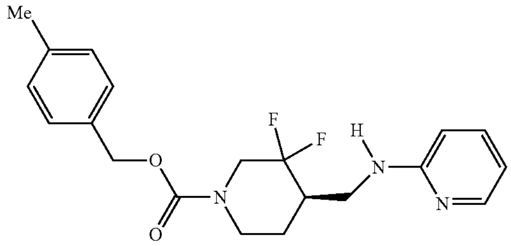 | 1.3, 1.4, Mean = 1.35 | 2 |
| E1-23.32[B'] | 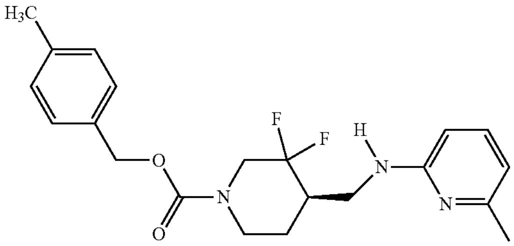 [SMILES: Cc1ccc(COC(=O)N2CC[C@H](CNc3cccc(C)n3)C(F)(F)C2)cc1] | 31 | 1 |
| E1-23.4[B'] | 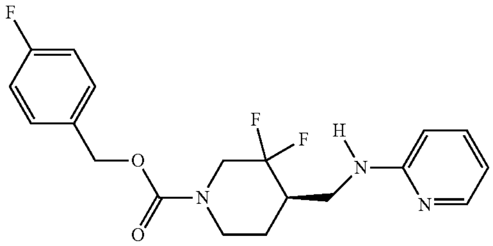 [SMILES: O=C(OCc1ccc(F)cc1)N1CC[C@H](CNc2ccccn2)C(F)(F)C1] | 7.8 | 1 |

TABLE 1.2-continued
| Inhibition Constant ($K_i$) in a Radioligand Binding Assay for Rat Brain NR2B Receptors % | | | |
|---|---|---|---|
| Compound | Structure | Arithmetic Mean $K_i$ (nM)[a] | Number of Assays |
| E1-23.26[B'] | 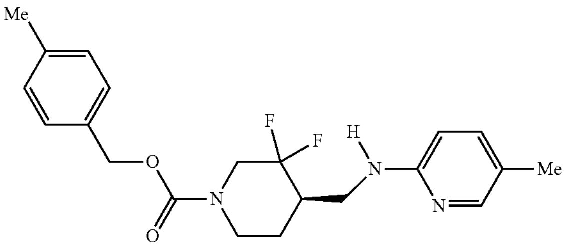 [SMILES: Cc1ccc(COC(=O)N2CC[C@H](CNc3ccc(C)cn3)C(F)(F)C2)cc1] | 6.5 | 1 |
| E1-24.2[B'] | 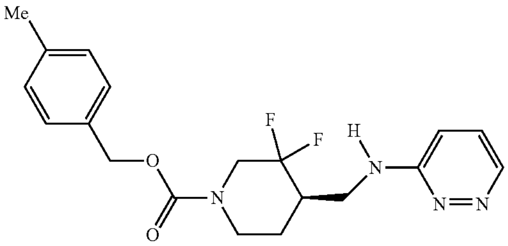 [SMILES: Cc1ccc(COC(=O)N2CC[C@H](CNc3cccnn3)C(F)(F)C2)cc1] | 2.1, 3.6, Mean = 2.85 | 2 |
| E1-24.4[B'] | 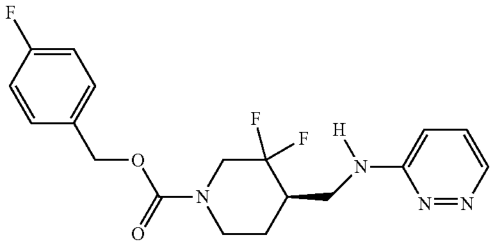 [SMILES: O=C(OCc1ccc(F)cc1)N1CC[C@H](CNc2cccnn2)C(F)(F)C1] | 10 | 1 |
| E1-24.6[B'] | 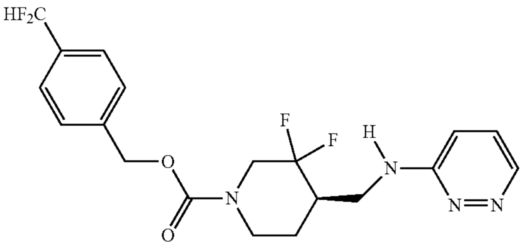 | 4.7 | 1 |
| E1-37.2[B'] | 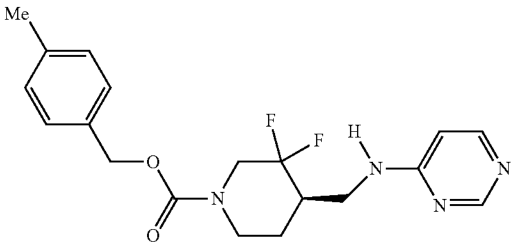 | 2.4 | 1 |

TABLE 1.2-continued
| Inhibition Constant ($K_i$) in a Radioligand Binding Assay for Rat Brain NR2B Receptors % | | | |
|---|---|---|---|
| Compound | Structure | Arithmetic Mean $K_i$ (nM)[a] | Number of Assays |
| E1-37.4[B'] | 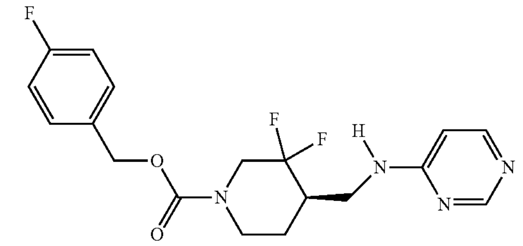 [SMILES: O=C(OCc1ccc(F)cc1)N1CC[C@H](CNc2ccncn2)C(F)(F)C1] | 4.7 | 1 |
| E1-37.6[B'] | 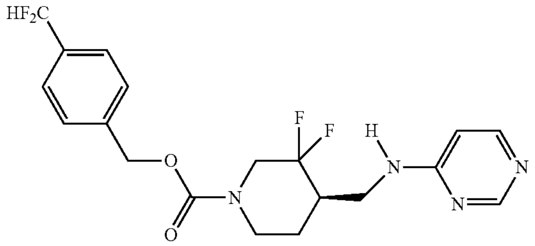 | 3.9 | 1 |
| E1-38.2[B'] | 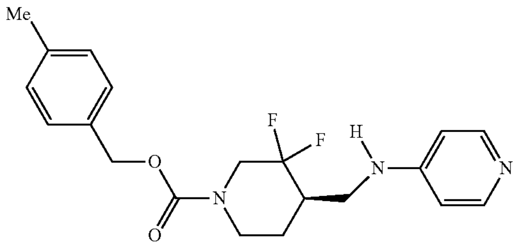 [SMILES: Cc1ccc(COC(=O)N2CC[C@H](CNc3ccncc3)C(F)(F)C2)cc1] | 0.18, 0.14, Mean = 0.16 | 2 |
| E1-38.4[B'] | 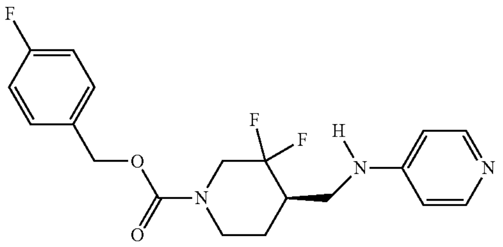 | 0.35 | 1 |
| E1-38.6[B'] | 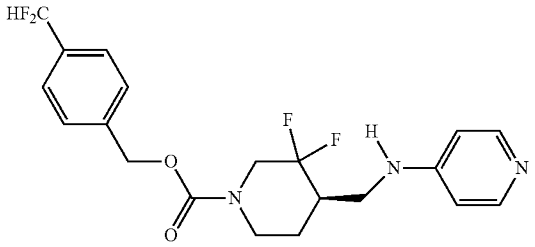 | 0.11 | 1 |

TABLE 1.2-continued
Inhibition Constant ($K_i$) in a Radioligand Binding Assay for Rat Brain NR2B Receptors %
| Compound | Structure | Arithmetic Mean $K_i$ (nM)[a] | Number of Assays |
|---|---|---|---|
| E1-38.8$^{B'}$ | 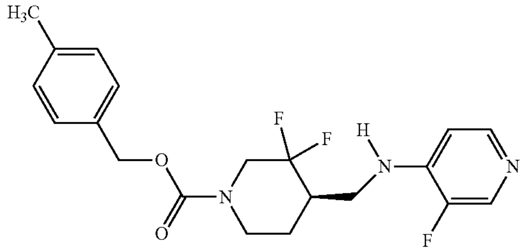 [SMILES: Cc1ccc(COC(=O)N2CC[C@H](CNc3ccncc3F)C(F)(F)C2)cc1] | 0.80 | 1 |
| E1-38.10$^{B'}$ | 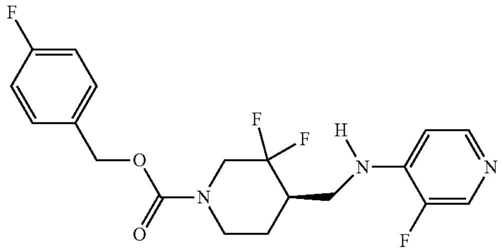 [SMILES: O=C(OCc1ccc(F)cc1)N1CC[C@H](CNc2ccncc2F)C(F)(F)C1] | 3.8 | 1 |
| III-E1-22.1$^{B'}$ | 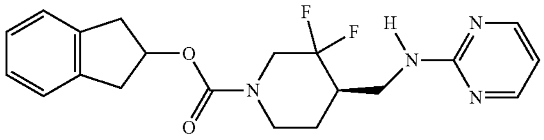 [SMILES: O=C(OC1Cc2ccccc2C1)N1CC[C@H](CNc2ncccn2)C(F)(F)C1] | 1.5 | 1 |
| III-E1-37.1$^{B'}$ | 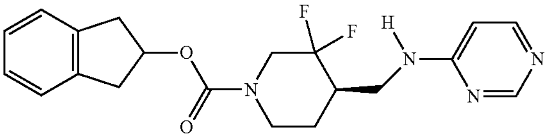 | 2.9 | 1 |
| III-E1-38.1$^{B'}$ | 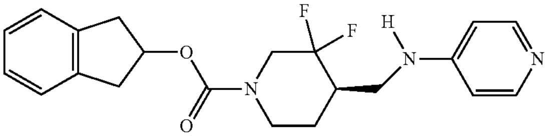 [SMILES: O=C(OC1Cc2ccccc2C1)N1CC[C@H](CNc2ccncc2)C(F)(F)C1] | 0.29 | 1 |
| E2-22.2$^{B'}$ | 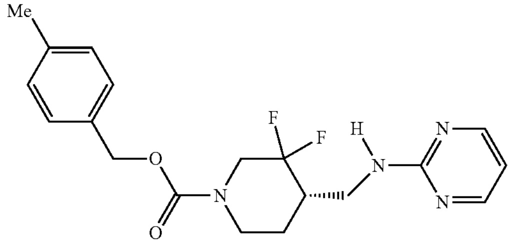 [SMILES: Cc1ccc(COC(=O)N2CC[C@@H](CNc3ncccn3)C(F)(F)C2)cc1] | 33 | 1 |
| E2-22.4$^{B'}$ | 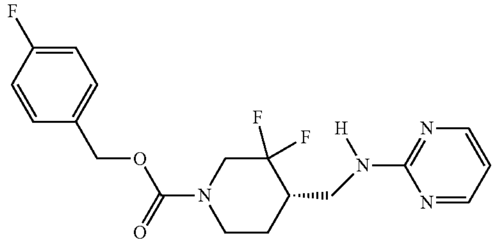 [SMILES: O=C(OCc1ccc(F)cc1)N1CC[C@@H](CNc2ncccn2)C(F)(F)C1] | 100 | 1 |

TABLE 1.2-continued

Inhibition Constant ($K_i$) in a Radioligand Binding Assay for Rat Brain NR2B Receptors %

| Compound | Structure | Arithmetic Mean $K_i$ (nM)[a] | Number of Assays |
|---|---|---|---|
| E2-22.6[B'] | 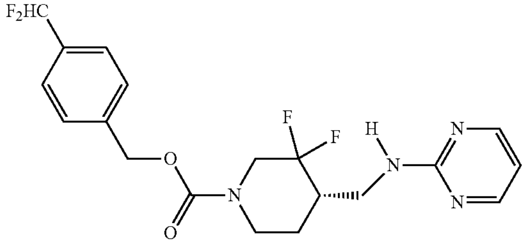 [SMILES: O=C(OCc1ccc(C(F)F)cc1)N1CC[C@@H](CNc2ncccn2)C(F)(F)C1] | 140 | 1 |
| E2-38.2[B'] | 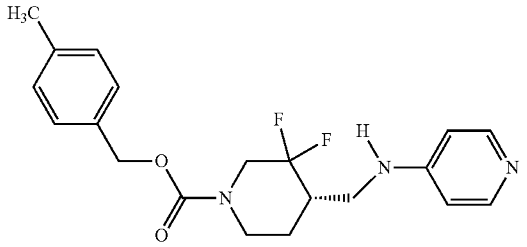 [SMILES: Cc1ccc(COC(=O)N2CC[C@@H](CNc3ccncc3)C(F)(F)C2)cc1] | 1.1 | 1 |

[a]Multiple values reflect the results from each assay. The last value is the arithmetic mean of the replicates. For some compounds, only the arithmetic mean value is shown.

Example 1.3. hERG Channel Inhibition

The assay was performed on hERG channel stably expressed in HEK293 cells. The cells were cultured at 37° C. in a humidified $CO_2$ incubator in the growth medium consisting of DMEM, 10% fetal bovine serum and antibiotics. Prior to the assay, the cells were seeded onto a 12-mm PDL-coated glass coverslip and cultured in a 35-mm Petri dish. After 16 to 40 hours culture, the coverslip was transferred into the chamber of OctaFlow perfusion system (ALA Instrument) and under a constant flow of extracellular solution (140 mM NaCl, 4 mM KCl, 1 mM $MgCl_2$, 2 mM $CaCl_2$, 10 mM HEPES, 10 mM D-glucose, pH 7.35, osmolarity 290). Whole cell patch clamping was performed with a glass micropipette filled with intracellular solution (120 mM KCl, 1.75 mM $MgCl_2$, 5.4 mM $CaCl_2$, 10 mM HEPES, 10 mM EGTA, and 4 mM ATP-$K_2$, pH 7.2, osmolarity 310). Giga-seal was maintained during the test. The voltage control and current measurement were carried out using Axon amplifier 700B, Digidata 1440A and CLAMPEX10 software (Molecular Devices). Whole-cell hERG currents were recorded following the Petroski protocol: the cell was held at −80 mV, and the voltage step jumped from −80 to 30 mV and stay for 2 seconds with a 20-millisecond prepulse at −40 mV. After depolarization, the voltage was decreased to −40 mV and stay for 2 seconds, and returned back to −80 mV. Test compound was applied by quartz capillary tubes tip (200 m inner diameter), and the flow rate was controlled at 2-3 mL/min with OctaFlow perfusion system. Different concentrations of the compound were applied to the cells for 5 minutes and the hERG current was measured three times before, during and after compound treatment. The data were analyzed using Clampfit 10 software (Molecular Devices) to generate $IC_{50}$ values. Results are shown in the Tables 1.3A and 1.3B below.

TABLE 1.3A

| Compound | Structure | hERG $IC_{50}$ | hNR2B $IC_{50}$ |
|---|---|---|---|
| C-3[A'] | 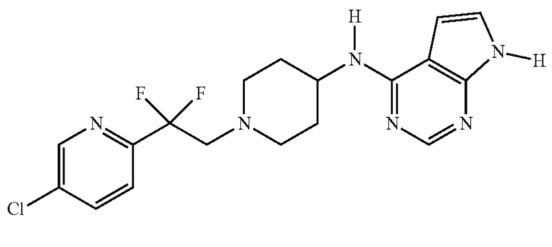 | 7.0 μM | 22 nM |

TABLE 1.3A-continued
| Compound | Structure | hERG $IC_{50}$ | hNR2B $IC_{50}$ |
|---|---|---|---|
| C-4[A'] | 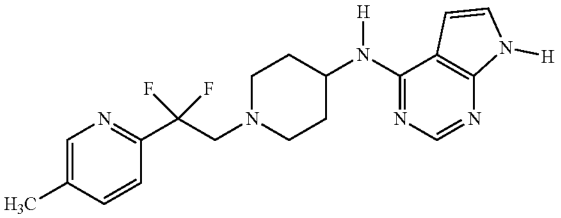 | 11.4 μM | 35 nM |
| C-5[A'] | 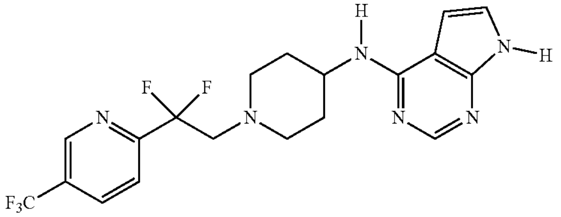 [SMILES: FC(F)(F)c1ccc(C(F)(F)CN2CCC(Nc3ncnc4[nH]ccc34)CC2)nc1] | 9.5 μM | 30 nM |
| C-230[A'] | 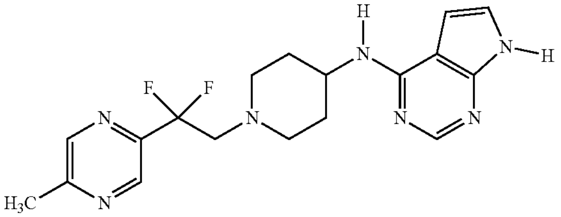 | 13.8 μM | 88 nM |
| C-127[A'] | 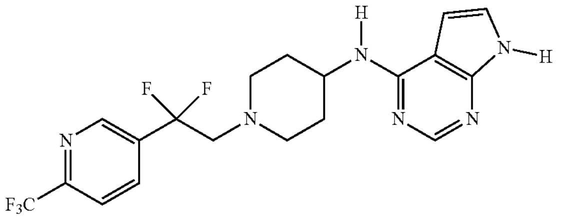 | 6 μM | 45 nM |
| C-128[A'] | 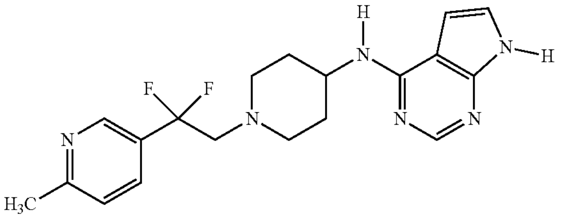 | 28 μM | 89 nM |
| C-175[A'] | 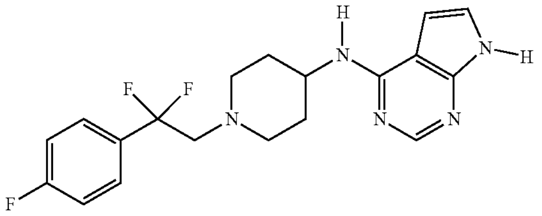 | 4.5 μM | 22 nM |
| C-16[A'] | 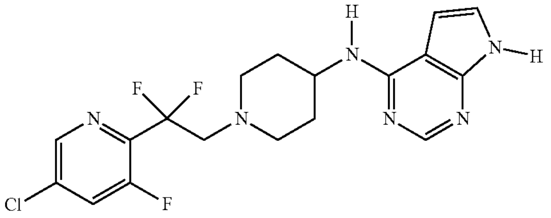 | 60 μM | 47 nM |

TABLE 1.3A-continued

| Compound | Structure | hERG $IC_{50}$ | hNR2B $IC_{50}$ |
|---|---|---|---|
| C-178[A'] | 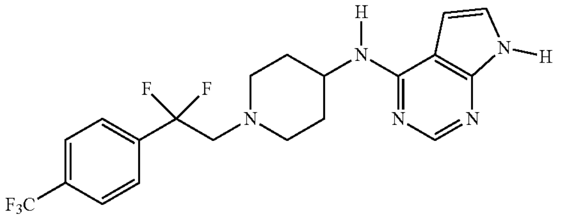 | 1.6 μM | 64 nM |
| C-179[A'] | 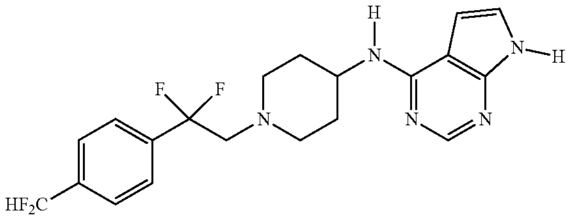 | 1.4 μM | 23 nM |
| C-11[A'] | 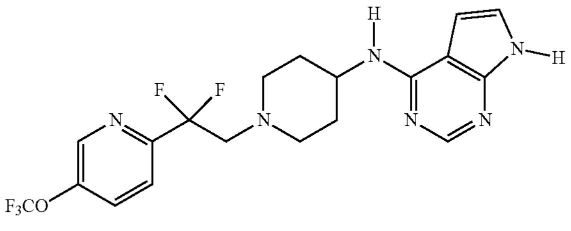 [SMILES: FC(F)(F)Oc1ccc(C(F)(F)CN2CCC(Nc3ncnc4[nH]ccc34)CC2)nc1] | 3.8 μM | 43 nM |
| C-6[A'] | 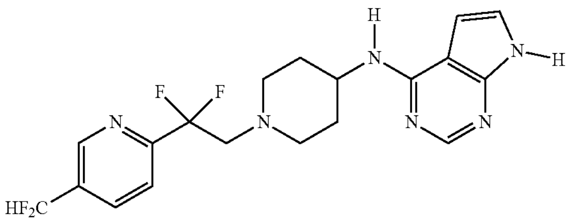 | 6.9 μM | 31 nM |

TABLE 1.3B

| Compound | NR2B $IC_{50}$ (nM) | hERG $IC_{50}$ (μM) | hERG Inhibition at 10 μM (%) |
|---|---|---|---|
| E1-1.2[B'] | 20.7 | 40 | 17 |
| E2-1.2[B'] | 156 | | 22 |
| E1-2.2[B'] | 10.4 | | 32 |
| E1-9.2[B'] | 48.2 | | 38 |
| E1-8.2[B'] | 17.0 | 6.8 | 57 |
| E1-1.3[B'] | 14.8 | | 19 |
| E1-1.4[B'] | 20.5 | | 11 |
| E1-22.2[B'] | 42.4 | >10 | |
| E1-21.2[B'] | 13.9 | | 27 |
| E1-21.26[B'] | 29.0 | | 39 |
| E1-1.5[B'] | 9.6 | | 46 |
| E1-22.5[B'] | | 9.2 | |
| E1-22.2[B'] | | 17 | |
| E1-22.4[B'] | | 39 | |
| E1-22.6[B'] | | 7.3 | |
| E1-23.2[B'] | | 5.6 | |
| E1-24.2[B'] | | 25 | |
| E1-38.2[B'] | | 2.9 | |
| III-E1-22.1[B'] | | 35 | |

Example 1.4. CYP P450 Enzyme Inhibition

Inhibitory activities of test compounds on 5 major isoforms of CYP P450 were evaluated by using pooled human liver microsome (HLM, purchased from BD Gentest) and selective substrates for those isoforms. Those CYP isoforms and their corresponding probe substrates are as follows: CYP1A2 (phenacetin, 30 μM), CYP2C9 (tolutamide, 100 μM), CYP2C19 (S-mephenytoin, 40 μM), CYP2D6 (dextromethorphan, 5 μM), and CYP3A4 (midazolam, 1 μM). All probe substrates were used at concentrations near or below their $K_{ms}$. A reaction mixture of test compound at 10 μM or in serial dilution, CYP probe substrate described above and 0.2 mg/mL pooled HLM in phosphate buffer, pH 7.4 in a final volume of 200 μL was pre-incubated at 37° C. for 10 minutes in triplicate. The reaction was initiated by addition of NADPH at final concentration of 1 mM. The reaction was terminated after 10 minutes (CYP1A2, CYP2D6, and CYP3A4) or 30 minutes (CYP2C9 and CYP2C19) by addition of 100 μL ice-cold acetonitrile with internal standard (IS). The samples were then centrifuged at 13,000 rpm and the supernatants were injected to an LC-MS/MS (Agilent Technologies) to quantify the concentration of the specific metabolites of the probe substrates formed by individual CYP450 isoforms. The inhibition ratio is calculated as:

$$(M_t-M_0)/M_{water}\times100\%$$

in which $M_t$ and $M_0$ represent the concentrations of the specific probe substrate metabolite, which was formed by individual CYP450 isoform, at the beginning and end of the reaction in the presence of test compound; while $M_{water}$ represents the concentration of the specific metabolite at the end of the reaction in the absence of test compound. Test compound concentration-dependent response studies were performed in triplicate. Mean CYP2D6 $IC_{50}$ values were derived from non-linear, least-squares fitting of dose-dependent response data to a standard logistic equation (Prism, GraphPad Software, Inc.) to generate the CYP2D6 $IC_{50}$ results shown in the Tables 1.4A and 1.4B below.

TABLE 1.4A

| Compound | Free Base Structure | CYP2D6 $IC_{50}$ | NR2B $IC_{50}$ |
|---|---|---|---|
| C-3[A'] | 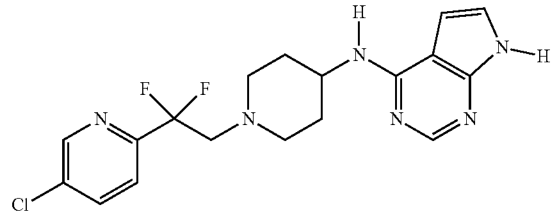 [SMILES: FC(F)(CN1CCC(Nc2ncnc3[nH]ccc23)CC1)c1ccc(Cl)cn1] | 12 μM | 22 nM |
| C-5[A'] | 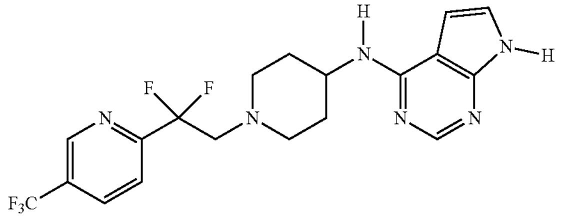 | 33 μM | 30 nM |
| C-127[A'] | 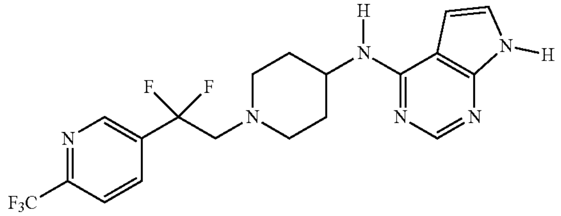 | 11 μM | 45 nM |
| C-178[A'] | 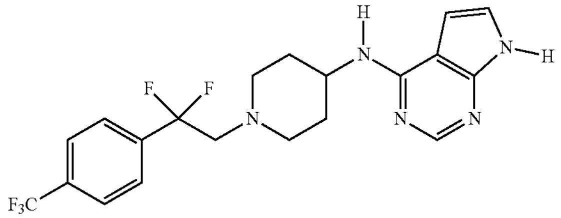 | 6.7 μM | 64 nM |
| C-179[A'] | 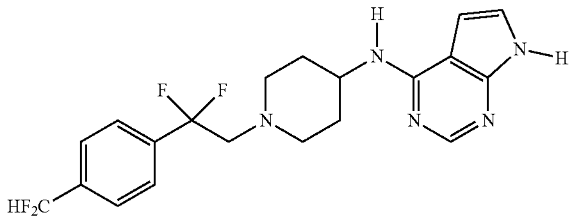 | 4.9 μM | 23 nM |
| C-175[A'] | 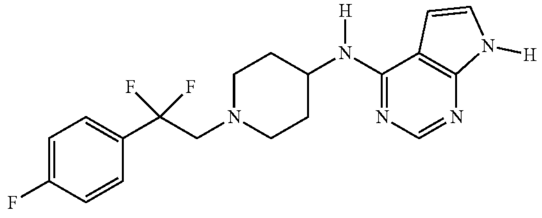 | 2.3 μM | 22 nM |

TABLE 1.4B

| Cmpd. No. | NR2B $IC_{50}$ (nM) | CYP2D6 $IC_{50}$ (μM) | CYP2D6 Inhibiton at 10 μM (%) |
|---|---|---|---|
| E1-1.2$^{B'}$ | 20.7 | | 14 |
| E2-1.2$^{B'}$ | 156 | | |
| E1-2.2$^{B'}$ | 10.4 | | 18 |
| E1-9.2$^{B'}$ | 48.2 | | 14 |
| E1-8.2$^{B'}$ | 17.0 | 5.9 | 83 |
| E1-1.3$^{B'}$ | 14.8 | | 37 |
| E1-1.4$^{B'}$ | 20.5 | | 19 |
| E1-22.2$^{B'}$ | 11.0 | | |
| E1-21.2$^{B'}$ | 13.9 | | 97 |
| E1-21.26$^{B'}$ | 29.0 | | 32 |
| E1-1.5$^{B'}$ | 9.6 | | 28 |
| E1-22.5$^{B'}$ | | 29 | |
| E1-22.2$^{B'}$ | | >50 | |
| E1-22.4$^{B'}$ | | >50 | |
| E1-22.6$^{B'}$ | | 41 | |
| E1-23.2$^{B'}$ | | 18 | |
| E1-23.26$^{B'}$ | | 9.7 | |
| E1-24.2$^{B'}$ | | 15 | |
| E1-37.2$^{B'}$ | | 0.20 | |
| E1-38.2$^{B'}$ | | 1.49 | |
| III-E1-22.1$^{B'}$ | | >50 | |

Example 2. Behavioral Assays

Several behavioral assays were performed in genetic animal models of OCD and ASD in Sapap3, Shank3B and Shank3 complete knockout mice and in standard models of anxiety in wild type mice using tests that are predictive of the anxiolytic effects of compounds.

Example 2.2.1. Grooming Test in Sapap3 and Shank3 Complete Knockout Mice

Animals. The breeding conditions and genotyping methods for Sapap3 and Shank3 complete knockout mice were the same as described in Welch et al. (*Nature* 2007, 448 (7156):894-900) and in Wang et al. (*Nat. Commun.* 2016, 7:11459), respectively. Homozygous knockout mice and littermate wild type mice of both genders were used at 4 to 8 weeks of age.

Compound formulation. The test compounds were dissolved in a small volume of dimethyl sulfoxide (DMSO) and diluted in an aqueous solution of 2-hydroxypropyl-beta-cyclodextrin (HP-β-CD) and administered IP. Dosing volume was 10 mL/kg. At 20 minutes after dosing, the mice were subjected to the behavioral test as described below.

Testing room and apparatus. The test room was maintained under the same conditions as the colony rooms, except the mice were housed in conventional shoe-box cages with food, water, and nesting materials. Animals were housed in the test room 48-72 hours prior to testing, in order to permit the mice to fully acclimate to the test room and conventional housing cages before testing. Tests were conducted in white polyvinyl-fluoride hard-sided foam test arenas (20×20×12 cm). The arenas were indirectly illuminated by dimmable LED light bars placed level with the arena floor and 30 cm away from the external wall of the test arena. This permitted the internal area of the arena to be evenly illuminated at approximately 40 lux. The illumination levels where the mice were housed before testing were about 80-100 lux.

Testing procedure. Mice were carefully placed into the test arenas 20 minutes after compound administration. Animals were given free exploration of the arena for 10 minutes, after which they were gently sprayed with 4 quick pumps of a water mist (total water volume approximated 1.5-1.7 mL). Mice were then allowed an additional 10 minutes to self-groom and engage in other behaviors before being removed from the arena. All tests were videotaped using cameras mounted above the testing arena and were saved to digital media format using Noldus Media Player software (Noldus Information Technologies, Leesburg, Va.). The mice were only tested once in the acute studies and were repeatedly tested in the sustained effect studies.

Quantitation of grooming bouts. Analyses of the video recordings were conducted with TopScan behavioral recognition software (Cleversys Inc, Reston, Va.). Configurations were made which scored time spent in grooming. For TopScan, the settings for grooming had a maximum cycle of 30, with motion greater than 0.04, variance from 2.5-20, high frequency moving pixels greater than 3%, and a grooming fraction set to 0.8. These settings permitted automated scoring of grooming by TopScan that corresponded well to manual-scoring of these behaviors by a trained blinded observer using Noldus Observer XT9 (Noldus Information Technologies), with an average corrected kappa of 0.925 (range 0.807-0.983).

Statistical analyses. Data are presented as means and standard error of the means (SEMs). Analyses were conducted using SPSS 23 (IBM SPSS Statistics, Chicago, Ill.). Time spent in grooming behavior (seconds) over the 10-minute pre- and post-spray time blocks were analyzed with repeated measures analyses of variance (RMANOVA). The pre- and post-spray times were used for the within subject effects and the genotype and compound treatment condition were used as the between subject effects. In sustained effect studies, days were also used for a within subject effect. Some analyses of total groom time were performed in Prism 7.01 (GraphPad Software, La Jolla, Calif.), with one-way ANOVAs to compare genotypes on Day 1 or with RMANOVAs to compare treatment groups within the same genotype across days. Treatments with compounds were compared independently with the vehicle. All post-hoc comparisons were performed with Bonferroni corrections for multiple comparisons to avoid a Type I error. In all cases, a $p<0.05$ was considered significant.

Example 2.2.1.1. Acute Effects in the Grooming Test in Sapap3 Knockout Mice The initial analysis in the Sapap3 knockout mice determined that the genetic model of OCD did indeed demonstrate excessive self-grooming relative to wild type littermates. The amount of time mice spent grooming in a novel environment was quantified in Sapap3 knockout mice and their wild type littermates for 10 minutes and then mice were lightly sprayed with water and grooming behavior was quantified for another 10 minutes (n=7). Sapap3 knockout mice groomed for longer both pre- and post-spray than wild type littermates (see FIG. 1). Pre-spray, Sapap3 knockout mice groomed for 31 seconds compared to 8 seconds for wild type mice ($p=0.007$). Post-spray, both genotypes increased grooming, but the difference between the genotypes was maintained (Sapap3 knockout mice, 167 seconds vs. wild type mice, 52 seconds; $p=0.001$).

Next, the effect of two subunit-selective NR2B antagonists administered as a single IP dose and assessed 20 minutes postdose was studied in the Sapap3 knockout mice (n=6-10 mice per treatment group). Compounds E1-1.2$^{B'}$ (see FIGS. 2A and B) and C-179$^{A'}$ (see FIGS. 2C and D) markedly reduced excessive self-grooming, such that the time spent grooming was similar to or less than the amount observed in vehicle-treated wild type littermates (dotted horizontal line in each graph). For Compound E1-1.2$^{B'}$, the magnitude of the reduction was similar for the pre- and post-spray conditions (70%-80% for 3 mg/kg and >90% for 10 and 30 mg/kg). All dose levels of E1-1.2$^{B'}$ were highly significantly different from the Sapap3 knockout vehicle-treated group ($p<0.001$). For Compound C-179$^{A'}$, the magnitude of the reduction in self-grooming was dose-dependent for the pre-spray condition, i.e., 43.6%, 80.5%, and 91.7% for 1, 3 and 10 mg/kg, respectively. In the pre-spray condition, the 3 and 10 mg/kg dose levels achieved significance ($p<0.001$) compared with Sapap3 knockout vehicle-treated mice. In the post-spray condition, the dose levels of Compound C-179$^{A'}$ showed similar reductions in self-grooming, on the order of 66.9% to 77.6%. All groups treated with Compound C-179$^{A'}$ were highly significantly different ($p<0.001$) from the vehicle-treated group in the post-spray condition.

Example 2.2.1.2. Sustained Effects in the Grooming Test in Sapap3 Knockout Mice Sapap3 knockout mice were treated with 3 mg/kg of Compound C-179$^{A'}$ or vehicle and wild type littermates with vehicle 20 minutes before testing on Day 1 of the study. Compared with wild type littermates, the Sapap3 knockout mice showed excessive amounts of grooming both pre- and post-spray ($p<0.029$ and $p<0.006$, respectively) and confirmed the baseline OCD-like behavior of the Sapap3 knockout mice. Only the Sapap3 knockout mice were continued for the sustained effect portion of the study. Mice were dosed with 3 mg/kg of Compound C-179$^{A'}$ on Days 1, 15, 22, and 29, 20 minutes before testing. On Days 3, 5, 8, 10, 12, 15, 17, 19, 22, 24, 26, 29, 31, and 33, mice were tested in the Grooming Test, both pre- and post-spray. One group of C-179$^{A'}$-treated mice was administered vehicle on days when they were not dosed with compound. Because this group did not differ significantly from the C-179$^{A'}$-treated mice that only received compound on dosed days, the groups were combined for presentation and analysis. Furthermore, because similar effects were observed pre- and post-spray, the results were combined into a single grooming time in this study.

Compound C-179$^{A'}$ was dosed on Day 1 and not again until Day 15. This portion of the study demonstrated that the effect of a single dose of 3 mg/kg Compound C-179$^{A'}$ resulted in sustained efficacy lasting for 1 week (see FIG. 3). Reductions in self-grooming were highly significant ($p<0.001$) on Days 1 and 3 and remained significant on Days 5 and 8 ($p<0.05$), as a result of treatment with Compound C-179$^{A'}$ on Day 1. The effect of compound treatment was no longer significant during the second week post Day 1 dosing (e.g., Days 10 and 12; p=NS). These data showed that a single dose of Compound C-179$^{A'}$ could have therapeutic effects well beyond the time period in which levels of compound could be detected in plasma (e.g., a maximum of about 8 hours at a dose level of 3 mg/kg, IP).

Compound C-179$^{A'}$ was then administered weekly for an additional 3 weeks to evaluate the subacute effects of repeated dosing (i.e., to determine whether tachyphylaxis would occur). On each test day between Days 15 and 33, Compound C-179$^{A'}$ either significantly reduced or demonstrated a trend to reduce self-grooming compared with vehicle. Reductions in self-grooming were less on the 5$^{th}$ day post each dose compared with the day of each dose, suggesting the maintenance of a pattern of the compound's efficacy wearing off in about one week that was observed in the first two weeks of the study. This phase of the study further substantiated the possibility of sustained therapeutic effects with intermittent dosing at weekly intervals and demonstrated that tachyphylaxis was not observed for one month.

Example 2.2.1.3. Acute and Sustained Effects in the Grooming Test in Sapap3 Knockout Mice Acute and sustained effects of a single dose of several compounds were studied in the Sapap3 knockout and wild type littermate mice. Sapap3 knockout mice and wild type littermates were treated with compounds or vehicle 20 minutes before testing on Day 1. For these studies, the total groom time, combining the pre- and post-spray testing periods, is presented. Compound C-179$^{A'}$ was administered at 0.32, 0.56 or 1 mg/kg; Compound E1-21.26$^{B'}$ was administered at 3 and 10 mg/kg; and Compounds E1-22.2$^{B'}$ and E1-22.6$^{B'}$ were administered at 1 and 3 mg/kg.

Figure 4:
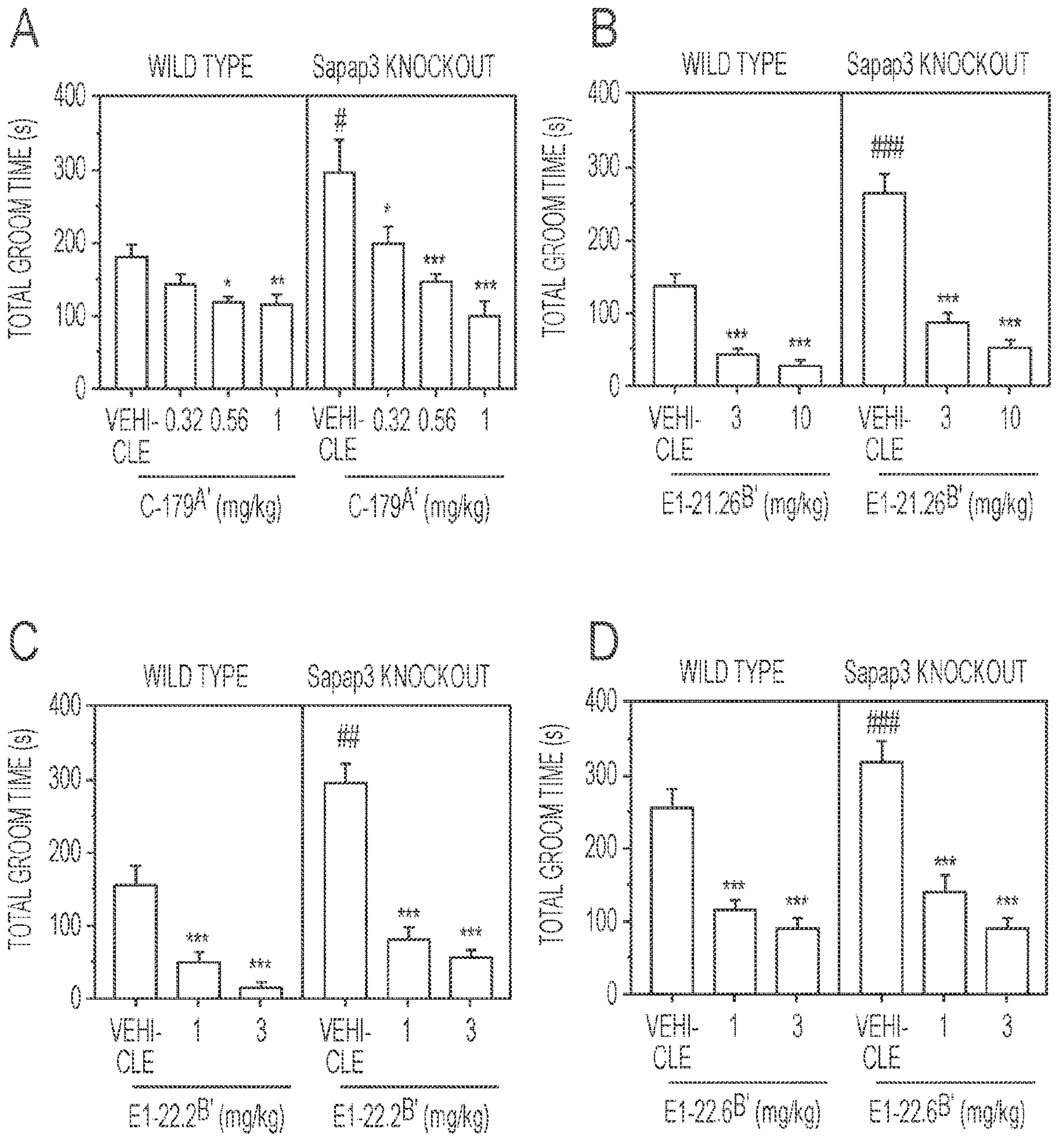
FIG. 4. Acute administration of NR2B antagonists reduces self-grooming in Sapap3 knockout mice and their wild type littermates. The effect of C-179$^{A'}$ at lower doses than presented in FIG. 2 and of three other NR2B antagonists administered intraperitoneally 20 minutes before testing on time spent grooming (seconds) in an unfamiliar environment for the entire 20-minute test period (before and after being sprayed with water midway through the test period). A, C-179$^{A'}$; B, E1-21.26$^{B'}$; C, E1-22.2$^{B'}$; and D, E1-22.6$^{B'}$. Significance comparing compound treatments with vehicle within each genotype was determined by one-way analysis of variance followed by Bonferroni's post-hoc test; *p<0.05, p<0.01, and *p<0.001. Significance comparing vehicle-treated Sapap3 knockout and wild type mice was determined by repeated measures analysis of variance followed by Bonferroni's post-hoc test; #p<0.05, ##p<0.01, and ###p<0.001. The within-subjects measure was pre- vs. post-spray periods. The NR2B antagonists reduced the amount of grooming in Sapap3 knockout mice to a level similar to or below that observed in the vehicle-treated wild type littermates. The NR2B antagonists also reduced the amount of grooming in wild type mice. N=9-11 mice per group.

On Day 1, compared with wild type littermates, the Sapap3 knockout mice treated with vehicle showed excessive amounts of grooming in each study (see FIG. 4; $^{\#}p<0.05$, $^{\#\#}p<0.01$, $^{\#\#\#}p<0.001$). Compound treatments significantly reduced grooming in Sapap3 knockout mice as well as in wild type littermates in a dose-dependent manner (see FIG. 4; *p<0.05, p<0.01, *p<0.001).

The Sapap3 knockout mice were then retested on Days 3, 5, 8, 10, 12, 15, 17, 19, 22, and 24, until there were no longer significant differences between vehicle and compound-treated groups in grooming. No treatments were administered before the mice were tested in the Grooming Test on these re-test days (see FIG. 5). Compound C-179$^{A'}$ at the 3 doses tested (0.32, 0.56 and 1 mg/kg) significantly reduced grooming through Day 5. The higher dose of Compound C-179$^{A'}$ (3 mg/kg) resulted in significant reductions in grooming through Day 8 (see FIG. 3). Compound E1-22.2$^{B'}$ at 1 and 3 mg/kg significantly reduced grooming through Days 19 and 22, respectively; and Compound E1-22.6$^{B'}$ at 1 and 3 mg/kg significantly reduced grooming through Day 15 (see FIG. 5).

Compound E1-21.26$^{B'}$ was dosed on Days 1, 15, 22, and 29 to follow the effect of repeated weekly dosing and the length of time for the treatment effect to wear off in the Sapap3 knockout mice (see FIG. 6). Following the first dose of 3 mg/kg, the significant reduction in grooming wore off by Day 8, although 10 mg/kg remained effective through to the second dose on Day 15. Thereafter, repeated weekly dosing with Compound E1-21.26$^{B'}$ significantly reduced grooming at both 3 and 10 mg/kg. After the fourth and final dose on Day 29, the effects wore off, lasting through Days 40 and 43 for 3 and 10 mg/kg, respectively. These days corresponded to days 12 and 15, following the last dose of Compound E1-21.26$^{B'}$.

Example 2.2.1.4. Acute and Sustained Effects in the Grooming Test in Shank3 Complete Knockout Mice The amount of time mice spent grooming in a novel environment was quantified in Shank3 complete knockout mice (Wang et al. *Nat. Commun.* 2016, 7:11459) and their wild type littermates for 10 minutes. Mice are then lightly sprayed with water and grooming behavior was quantified for another 10 minutes. For these studies, the total groom time, combining the pre- and post-spray testing periods, is presented. Shank3 complete knockout mice treated with vehicle 20 minutes before the Grooming Test showed significantly more grooming than the wild type littermates ($^{\#\#}$p<0.002, see FIG. 7).

Next, the effect of subunit-selective NR2B antagonists administered as a single IP dose and assessed 20 minutes postdose was studied in the Shank3 complete knockout and wild type littermate mice. Mice were treated with Compound C-179$^{A'}$ at 1 or 3 mg/kg, Compound E1-22.2$^{B'}$ at 3 mg/kg, or vehicle on Day 1. The compound treatments significantly reduced grooming in Shank3 complete knockout mice to levels at or below the groom time in vehicle-treated wild type mice (see FIG. 7, *p<0.001). Furthermore, 3 mg/kg of either Compound C-179$^{A'}$ or Compound E1-22.2$^{B'}$ significantly reduced grooming in the wild type littermates (p<0.01).

The Shank3 complete knockout mice were then retested on Days 3, 5, 8, 10, 12, 15, 17, 19, 22, 24, 26, 29, 31, and 33. No treatments were administered before the mice were tested in the Grooming Test on these re-test days (see FIG. 8). Compound C-179$^{A'}$ (1 and 3 mg/kg) and Compound E1-22.2$^{B'}$ (3 mg/kg) significantly reduced grooming through Day 33.

Example 2.2.1.5. Sustained Effects in the Grooming Test in Wild Type Mice

The wild type littermates of the Sapap3 knockout and Shank3 complete knockout mice were retested after Day 1 compound administration to determine whether the sustained effects were unique to the knockout mice. Compound C-179$^{A'}$ (1 and 3 mg/kg) and Compound E1-22.2$^{B'}$ (3 mg/kg) were tested in the wild type littermates of the Shank3 complete knockout mice (see Example 2.2.1.4 for Day 1 results); and Compound E1-22.6$^{B'}$ (1 and 3 mg/kg) was tested in the wild type littermates of the Sapap3 knockout mice (see Example 2.2.1.3 for Day 1 results). Mice were retested in the Grooming Test on Days 3, 5, 8, 10, and 12. The compounds had dose-dependent sustained effects on grooming in the wild type littermates that lasted shorter than in the knockout mice (see FIG. 9). Compound C-179$^{A'}$ (3 mg/kg), Compound E1-22.2$^{B'}$ (3 mg/kg) and Compound E1-22.6$^{B'}$ (3 mg/kg) significantly reduced grooming on Day 3, as well as on Day 1. By Day 5, Compound C-179$^{A'}$ (3 mg/kg) and Compound E1-22.2$^{B'}$ (3 mg/kg) showed levels of grooming that were comparable to the level in the vehicle-treated group.

Compound E1-22.6$^{B'}$ (3 mg/kg) on Day 5 significantly increased grooming, with grooming behavior returning to the vehicle level by Day 8. Compound E1-22.6$^{B'}$ (1 mg/kg), although showing significant reduction in grooming on Day 1, did not show an effect on Day 3.

Example 2.2.2. Grooming Test in Shank3B Knockout Mice

Animals. Heterozygous breeding pairs of Shank3B mice (B6.129-Shank3$^{tm2gfmg}$/J model; Peca et al. *Nature* 2011, 472(7344):437-442) are purchased from the Jackson Laboratory (Bar Harbor, Me.). The breeding conditions and genotyping methods are as described in Peca et al. (*Nature* 2011, 472(7344):437-442). Shank3B knockout mice and littermate wild type mice of both genders are used.

Compound formulation. The test compounds are prepared in a vehicle of 0.5% DMSO and 4% HP-β-CD, and administered IP. The test compounds or vehicle are administered 20 minutes before the behavioral test described below.

Testing procedure. Behaviors are recorded over a one-hour test session, in which individual mice are videotaped in a clean empty standard mouse cage. Well-trained raters, blind to genotype and drug treatment, score each video using Noldus Observer event recording software. Time spent engaged in grooming follows criteria previously published by the Crawley lab (e.g. Silverman et al. *Sci. Transl. Med.* 2012, 4(131):131ra51; Silverman et al. *Neuropsychopharmacology* 2015, 40(9):2228-2239). Scoring is initially conducted in 10-minute time blocks across the 60-minute session. Amount time spent self-grooming is compared between the first 10 minutes versus subsequent 10-minute blocks, to determine the optimum length of scoring time.

Example 2.2.3. Adult Social Interaction Test in Shank3B Knockout Mice

Animals. Heterozygous breeding pairs of Shank3B mice (B6.129-Shank3$^{tm2gfmg}$/J model; Peca et al., *Nature* 2011, 472(7344):437-442) are purchased from the Jackson Laboratory (Bar Harbor, Me.). The breeding conditions and genotyping methods are as described in Peca et al. (*Nature* 2011, 472(7344):437-442). Male Shank3B knockout mice and littermate wild type mice are used.

Compound formulation. The test compounds are prepared in a vehicle of 0.5% DMSO and 4% HP-β-CD, and administered IP. The test compounds or vehicle are administered 20 minutes before the behavioral test described below.

Testing procedure. Behaviors are videorecorded and audiorecorded over a five-minute test session, in which a male wild type or Shank3B knockout mouse is placed in a clean empty standard mouse cage within a soundproofed chamber, equipped with a videocamera and an Avisoft ultrasonic microphone. Well-trained raters, blind to genotype and drug treatment, score each video using Noldus Observer event recording software, and calculate the number of calls emitted using Avisoft software. Social parameters and vocalization scoring follow criteria previously published by the Crawley lab (e.g. Brielmaier et al. *PLoS ONE* 2012, 7(7):e40914; Silverman et al. *Sci. Transl. Med.* 2012, 4(131):131ra51; Silverman et al. *Neuropsychopharmacology* 2015, 40(9):2228-2239).

Example 2.2.4. Marble Burying Test in Wild Type Mice

Animals. Male NMRI mice (20-30 g body weight) were obtained from Janvier Labs (Le Genest-Saint Isle, France) and allowed to acclimate to the animal facility for at least 5 days. Twelve mice were studied per treatment group.

Compound formulation. The test compounds were prepared in a vehicle of 0.5% DMSO and 4% HP-β-CD, and administered orally (PO) or IP. The test compounds or vehicle were administered 20 minutes before the behavioral test described below. Clobazam (8 mg/kg IP), administered 30 minutes before the test, was used as the positive reference compound.

Clobazam was dispersed in 0.2% hydroxypropylmethylcellulose (HPMC) in physiological saline. Dosing volume was 10 mL/kg.

Testing procedure. The Marble Burying Test was conducted as previously described by Broekkamp et al. (*Eur. J. Pharmacol.* 1986, 126:223-229). Mice exposed to small novel objects (marbles) will bury them in the sawdust floor covering. Anxiolytics decrease the number of marbles buried at non-sedating doses. Mice were individually placed in transparent plastic cages (33×21×18 cm) with 5 cm of sawdust on the floor and 25 marbles grouped in the center of the cage. The cage was covered with an inverted plastic cage. Each test cage, together with the marbles, was impregnated with mouse odor before-hand by leaving 10 mice in the cage for 15 minutes. These mice then played no further role in the experiment. The number of marbles covered by sawdust (⅔ or more) was counted at the end of the 30-minute test. The test was performed blind (compounds versus vehicle).

Statistical analyses. Data were analyzed by comparing test compound-treated groups with the vehicle control group using the Kruskal-Wallis test followed by post-hoc Mann-Whitney U tests. Data comparing the reference compound with the vehicle were analyzed using the Mann-Whitney U test. A p value<0.05 was considered significant.

Eleven compounds were tested in the MBT, either IP, PO, or both. The compounds dose-dependently reduced the number of marbles buried by wild type mice (see Table 2.2.4). Table 2.2.4 shows the percent change from the vehicle group in marbles buried and the level of statistical significance for each dose level. For most compounds, one or more dose level produced a maximal response (i.e., >90% reduction in marbles buried). In each study, clobazam also significantly reduced the number of buried marbles (data not shown), indicating that the test was effectively detecting anxiolytic-like activity in each study. The compounds demonstrated varying minimum effective doses, ranging from Compounds E1-22.2$^{B'}$ and E1-22.5$^{B'}$ (fully efficacious at the lowest test concentration of 1 mg/kg, IP) to Compound C-11$^{A'}$ (partially efficacious at the highest test concentration of 60 mg/kg, IP).

TABLE 2.2.4

Percent Inhibition of Marble Burying Relative to Vehicle Control in Wild Type Mice

| Compound | Structure | Route of Administration | Dose (mg/kg) | Percent Change |
|---|---|---|---|---|
| C-127$^{A'}$ | 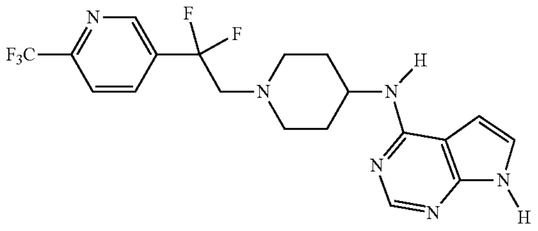 [SMILES: FC(F)(F)c1ccc(C(F)(F)CN2CCC(Nc3ncnc4[nH]ccc34)CC2)cn1] | IP | 1 | +15 |
| | | | 3 | −27* |
| | | | 10 | −98*** |
| C-179$^{A'}$ | 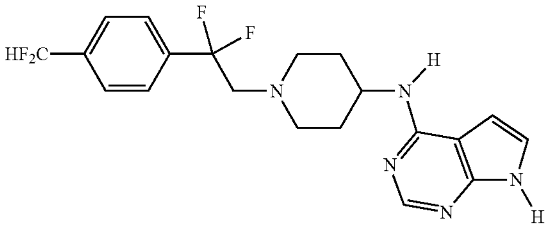 | PO | 0.562 | −3 |
| | | | 1 | −1.1 |
| | | | 1.78 | −81*** |
| | | | 3 | −81*** |
| | | | 5.62 | −99*** |
| | | | 10 | −99*** |
| | | IP | 0.316 | +9 |
| | | | 0.562 | −27 |
| | | | 1 | −69*** |
| | | | 1 | −56*** |
| | | | 3 | −96*** |
| | | | 10 | −94*** |
| C-5$^{A'}$ | 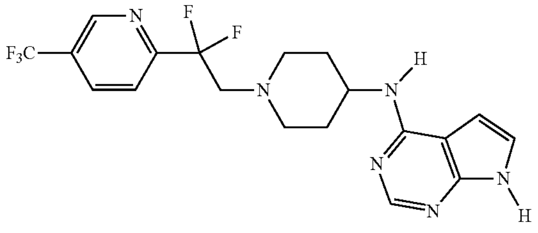 [SMILES: FC(F)(F)c1ccc(C(F)(F)CN2CCC(Nc3ncnc4[nH]ccc34)CC2)nc1] | IP | 3 | +2 |
| | | | 10 | −50* |
| | | | 30 | −98*** |
| C-6$^{A'}$ | 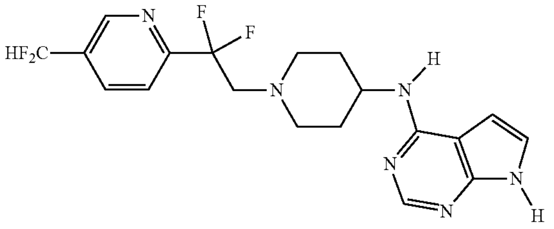 | IP | 3 | −23* |
| | | | 10 | −62* |
| | | | 30 | −100*** |

TABLE 2.2.4-continued
Percent Inhibition of Marble Burying Relative to Vehicle Control in Wild Type Mice
| Compound | Structure | Route of Administration | Dose (mg/kg) | Percent Change |
|---|---|---|---|---|
| C-11[A'] | 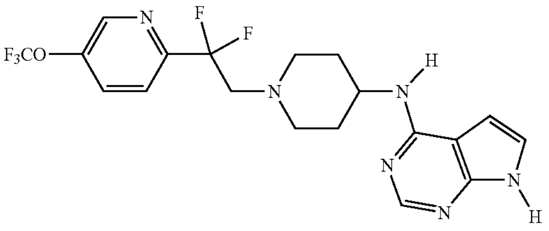 [SMILES: FC(F)(F)Oc1ccc(C(F)(F)CN2CCC(Nc3ncnc4[nH]ccc34)CC2)nc1] | IP | 1 | +10 |
| | | | 3 | +3 |
| | | | 10 | −26 |
| | | IP | 10 | −18 |
| | | | 30 | −44* |
| | | | 60 | −58** |
| C-12[A'] | 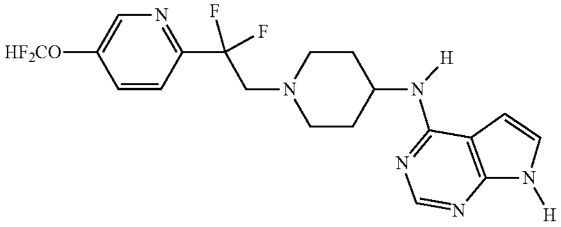 | IP | 3 | −14 |
| | | | 10 | −56* |
| | | | 30 | −100*** |
| E1-1.2[B'] | 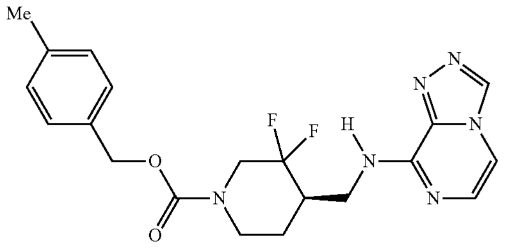 [SMILES: Cc1ccc(COC(=O)N2CC[C@H](CNc3nccn4cnnc34)C(F)(F)C2)cc1] | PO | 1 | −5 |
| | | | 3 | −56*** |
| | | | 10 | −99*** |
| | | PO | 1 | −9 |
| | | | 3 | −68*** |
| | | | 10 | −95*** |
| E1-21.26[B'] | 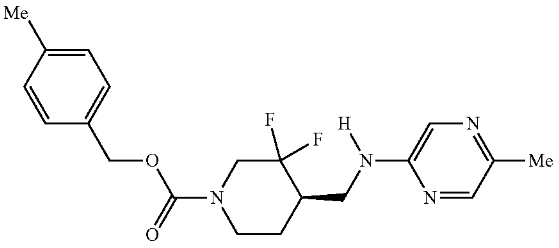 [SMILES: Cc1ccc(COC(=O)N2CC[C@H](CNc3cnc(C)cn3)C(F)(F)C2)cc1] | PO | 1 | +8 |
| | | | 3 | −41* |
| | | | 10 | −78*** |
| | | IP | 0.316 | −14 |
| | | | 0.562 | −30* |
| | | | 1 | −29** |
| | | | 1 | −44** |
| | | | 3 | −97*** |
| | | | 10 | −96*** |
| E1-22.26[B'] | 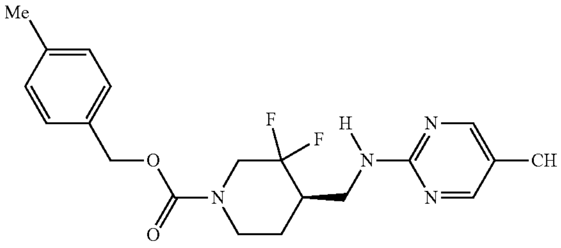 [SMILES: Cc1ccc(COC(=O)N2CC[C@H](CNc3ncc(C)cn3)C(F)(F)C2)cc1] | IP | 1 | −12 |
| | | | 3 | −23 |
| | | | 10 | −96*** |
| E1-22.5[B'] | 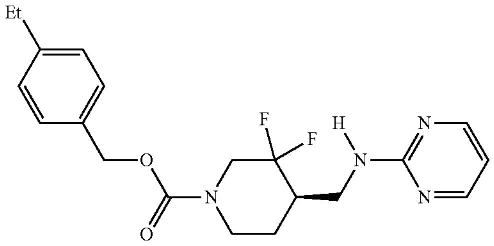 [SMILES: CCc1ccc(COC(=O)N2CC[C@H](CNc3ncccn3)C(F)(F)C2)cc1] | PO | 0.3 | −11 |
| | | | 1 | −15 |
| | | | 3 | −76*** |
| | | IP | 0.1 | −9 |
| | | | 0.3 | +8* |
| | | | 1 | −75*** |
| | | | 1 | −97*** |
| | | | 3 | −100*** |
| | | | 10 | −100*** |

TABLE 2.2.4-continued

Percent Inhibition of Marble Burying Relative to Vehicle Control in Wild Type Mice

| Compound | Structure | Route of Administration | Dose (mg/kg) | Percent Change |
|---|---|---|---|---|
| E1-22.6[B'] | 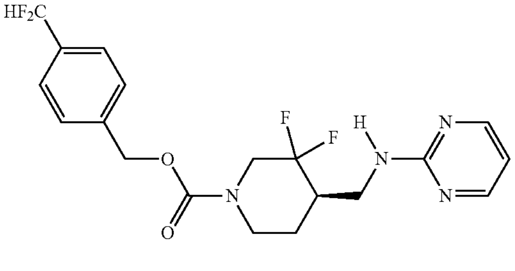 | IP | 0.1 | −30* |
| | | | 0.3 | −95*** |
| | | | 1 | −100*** |
| | | | 1 | −98*** |
| | | | 3 | −98*** |
| | | | 10 | −100*** |
| E1-22.2[B'] | 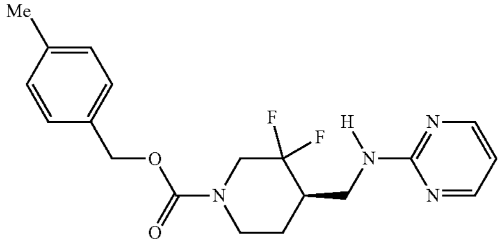 [SMILES: Cc1ccc(COC(=O)N2CC[C@H](CNc3ncccn3)C(F)(F)C2)cc1] | PO | 0.1 | +14 |
| | | | 0.3 | +16 |
| | | | 1 | −93*** |
| | | | 1 | −83*** |
| | | | 3 | −88*** |
| | | | 10 | −99*** |
| | | IP | 0.03 | −9 |
| | | | 0.1 | −13 |
| | | | 0.3 | −92*** |
| | | | 0.316 | −68*** |
| | | | 0.562 | −92*** |
| | | | 1 | −95*** |
| | | | 1 | −96*** |
| | | | 3 | −93*** |
| | | | 10 | −97*** |
| E1-38.2[B'] | 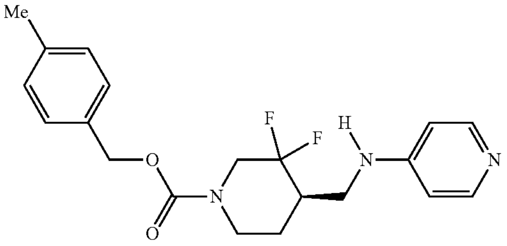 [SMILES: Cc1ccc(COC(=O)N2CC[C@H](CNc3ccncc3)C(F)(F)C2)cc1] | IP | 0.3 | +4 |
| | | | 1 | −18 |
| | | | 3 | −76*** |
| E1-24.2[B'] | 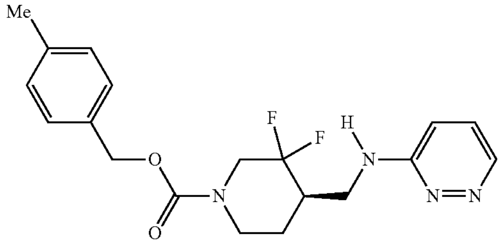 [SMILES: Cc1ccc(COC(=O)N2CC[C@H](CNc3cccnn3)C(F)(F)C2)cc1] | IP | | −100*** |
| | | | | −100*** |
| | | | | −100*** |
| E1-22.4[B'] | 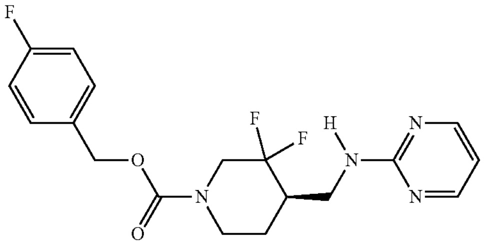 [SMILES: O=C(OCc1ccc(F)cc1)N1CC[C@H](CNc2ncccn2)C(F)(F)C1] | IP | 0.3 | −6 |
| | | | 0.562 | −55** |
| | | | 1 | −56*** |
| | | | 1 | −83*** |
| | | | 1.78 | −97*** |
| | | | 3 | −99*** |

Abbreviations: IP, intraperitoneal, Mol. Wt., molecular weight; PO, oral by gavage.

Notes:

Statistical significance determined by Kruskal-Wallis nonparametric analysis of variance, followed by Mann-Whitney post-hoc tests compared with vehicle (*p < 0 .05, p < 0.01, and *p < 0.001).

Example 2.2.5. Novelty Phobia Test in Wild Type Mice

Animals. Male C57Bl/6 mice (18-30 g body weight; 6-8 weeks of age) were obtained from Slaccas (Shanghai, China) and allowed to acclimate to the animal facility for 7 days. Mice were group housed in plastic cages (no more than 4 animals per cage) on wood shavings with nesting material. All animals had free access to food (M01-F, Slaccas) and water. The animal facility was maintained under artificial lighting between 7:00 AM and 7:00 PM in a controlled ambient temperature of 22-24° C. and relative humidity between 50-60%.

Compound formulation. The test compounds were prepared in a vehicle of DMSO and HP-β-CD, and administered IP or PO. The test compounds or vehicle were administered at various times (10-20 minutes) before the behavioral test described below. Dosing volume was 10 mL/kg. Methodological details for each study are presented in Table 2.2.5.

Testing procedure. The behavioral testing apparatus was a rectangular black Plexiglas, 2-chambered box, with no top or bottom (50 cm long, 26 cm wide and 15 cm tall) and allowed for the simultaneous testing of 2 mice. The box was placed on a laboratory bench. The chambers of the testing box were cleaned and fresh paper chip bedding was added between tests. Mice were brought to the experiment room in their home cages on the day of testing. Behavioral tests were conducted between 10:00 AM and 1:00 PM in dim light. After drug administration, a mouse was placed into a test chamber and allowed to explore for 10 minutes. After this habituation period, a novel object (e.g., a toy ball of 3 cm in diameter with spikes) was introduced to the center of the chamber for 5 minutes. For the entire 15-minute test period, video was recorded for offline analysis with Any-maze Video Tracking software (Stoelting Co., Wood Dale, Ill.). The total distance traveled during the entire 15 minutes and the number of bouts that each mouse touched the novel object during the last 5 minutes were measured.

Statistical analyses. Data are presented as means and SEMs. Data were analyzed using one-way analysis of variance (ANOVA; Prism, GraphPad Software Inc., San Diego, Calif.), followed by the post-hoc Dunnett's test to compare test compound-treated groups with the vehicle control. A p value<0.05 was considered significant.

Compounds were tested in the Novelty Phobia Test following TP administration, and for one compound (Compound C-$11^{A'}$), also following PO administration. Significant increases in bouts of nose touching of the novel object (i.e., reductions in novelty phobia) were observed for most of the compounds over a range of minimum effective doses (see Table 2.2.5). Noteworthy exceptions were Compounds C-$5^{A'}$ and C-$12^{A'}$. While these compounds demonstrated efficacy in the Marble Burying Test, similar doses in the Novelty Phobia Test were not efficacious (compare Table 2.2.4 and Table 2.2.5). Some of the compounds demonstrated dose-dependent increases in bouts of nose touching of the novel object (e.g., Compounds C-$178^{A'}$, C-$127^{A'}$, E1-$1.2^{B'}$, and E1-$21.26^{B'}$), while others demonstrated an inverted U-shaped dose-response function C-$18^{A'}$ DMS (e.g., Compounds C-$175^{A'}$, C-$179^{A'}$, and C-$11^{A'}$). The lack of efficacy for some compounds and the inverted U-shaped dose-response function for others in the Novelty Phobia Test, when all compounds demonstrated dose-dependent efficacy, albeit at varying minimum effective doses, in the Marble Burying Test illustrates the utility of incorporating multiple behavioral tests in the process of selecting potential clinical candidates.

TABLE 2.2.5

Percent Change in Novel Object Number of Nose Touches in the Novelty Phobia Test Relative to Vehicle Control in Wild Type Mice

| Compound | Structure | Summary of Methods | Dose (mg/kg) | Percent Change |
| --- | --- | --- | --- | --- |
| C-$178^{A'}$ | 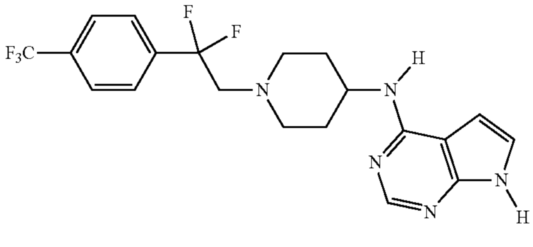 [SMILES: FC(F)(F)c1ccc(C(F)(F)CN2CCC(Nc3ncnc4[nH]ccc34)CC2)cc1] | Route: IP<br>Pre-test time: 20 min<br>Vehicle: 1% DMSO + 4% HP-β-CD<br>n = 8 per group | 0.3<br>1<br>3 | −4.12<br>50.3<br>110*** |
| C-$175^{A'}$ | 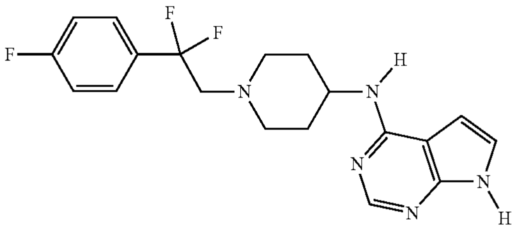 [SMILES: Fc1ccc(C(F)(F)CN2CCC(Nc3ncnc4[nH]ccc34)CC2)cc1] | Route: IP<br>Pre-test time: 10 min<br>Vehicle: 2% DMSO + 4% HP-β-CD<br>n = 8 per group | 3<br>10<br>30 | 25.1<br>139***<br>−88.1††† |

TABLE 2.2.5-continued

Percent Change in Novel Object Number of Nose Touches in the Novelty Phobia Test Relative to Vehicle Control in Wild Type Mice

| Compound | Structure | Summary of Methods | Dose (mg/kg) | Percent Change |
|---|---|---|---|---|
| C-127[A'] | 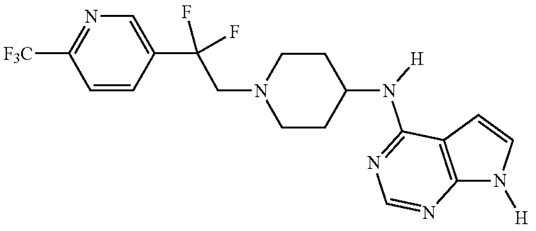 [SMILES: FC(F)(F)c1ccc(C(F)(F)CN2CCC(Nc3ncnc4[nH]ccc34)CC2)cn1] | Route: IP<br>Pre-test time: 15 min<br>Vehicle: 2% DMSO + 4% HP-β-CD<br>n = 8 per group | 3<br>10<br>30<br>3<br>10<br>30 | 68.4<br>142**<br>160***<br>30.6<br>51.3<br>145*** |
| | | Route: IP<br>Pre-test time: 15 min<br>Vehicle: 2% DMSO + 4% HP-β-CD<br>n = 8 per group | 10<br>20<br>30 | 94.1***<br>120***<br>156*** |
| C-179[A'] | 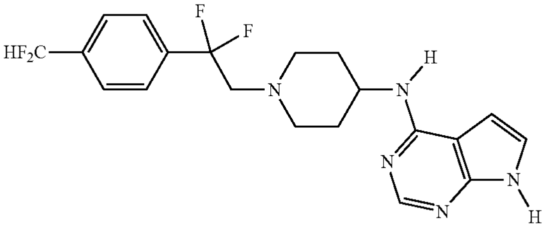 | Route: IP<br>Pre-test time: 15 min<br>Vehicle: 2% DMSO + 4% HP-β-CD<br>n = 8 per group | 1<br>3<br>10<br>30 | 64.7<br>123**<br>74.8<br>28.0 |
| | | Route: IP<br>Pre-test time: 15 min<br>Vehicle: 1% DMSO + 4% HP-β-CD<br>n = 8 per group | 0.3<br>1<br>3<br>10 | −12.0<br>78.6*<br>97.1*<br>152*** |
| | | Route: IP<br>Pre-test time: 20 min<br>Vehicle: 1% DMSO + 4% HP-β-CD<br>n = 7-8 per group | 0.3<br>1<br>3 | 51.7<br>139***<br>164*** |
| C-5[A'] | 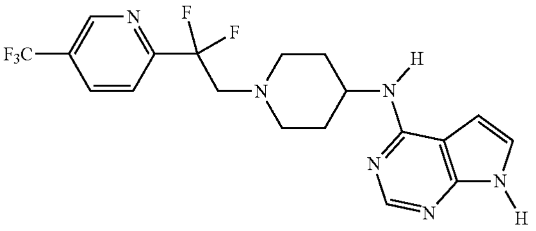 [SMILES: FC(F)(F)c1ccc(C(F)(F)CN2CCC(Nc3ncnc4[nH]ccc34)CC2)nc1] | Route: IP<br>Pre-test time: 10 min<br>Vehicle: 2% DMSO + 4% HP-β-CD<br>n = 11-12 per group | 10<br>30<br>60 | 70.8<br>42.4<br>−36.9 |

TABLE 2.2.5-continued

Percent Change in Novel Object Number of Nose Touches in the Novelty Phobia Test Relative to Vehicle Control in Wild Type Mice

| Compound | Structure | Summary of Methods | Dose (mg/kg) | Percent Change |
| --- | --- | --- | --- | --- |
| C-11[A'] | 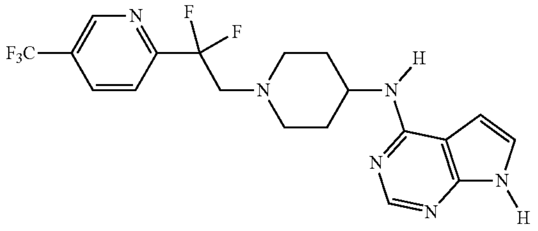 [SMILES: FC(F)(F)c1ccc(C(F)(F)CN2CCC(Nc3ncnc4[nH]ccc34)CC2)nc1] | Route: IP<br>Pre-test time:<br>10 min<br>Vehicle: 1% DMSO + 4% HP-β-CD<br>n = 7-8 per group | 3<br>10<br>30 | 36.3<br>15.2<br>60.3 |
| | | Route: IP<br>Pre-test time:<br>10 min<br>Vehicle: 1% DMSO + 4% HP-β-CD<br>n = 12 per group | 30 | 207*** |
| | | Route: PO<br>Pre-test time:<br>10 min<br>Vehicle: 2% DMSO + 8% HP-β-CD<br>n = 12 per group | 30<br>60<br>100 | 123**<br>99.0*<br>−2.05 |
| | | Route: IP<br>Pre-test time:<br>10 min<br>Vehicle: 1% DMSO + 4% HP-β-CD<br>n = 18 per group | 30 | 37.2* |
| | | Route: IP<br>Pre-test time:<br>20 min<br>Vehicle: 25% HP-β-CD<br>n = 8 per group | 3<br>10<br>30 | 16.9<br>37.5<br>79.7*** |
| C-12[A'] | 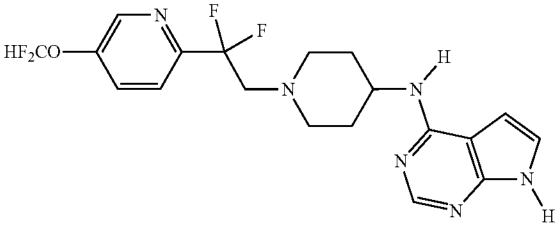 | Route: IP<br>Pre-test time:<br>20 min<br>Vehicle: 1% DMSO + 4% HP-β-CD<br>n = 6-8 per group | 3<br>10<br>30<br>3<br>10<br>30 | 1.27<br>3.82<br>−10.8<br>8.01<br>25.9<br>−51.8[††] |
| E1-1.2[B'] | 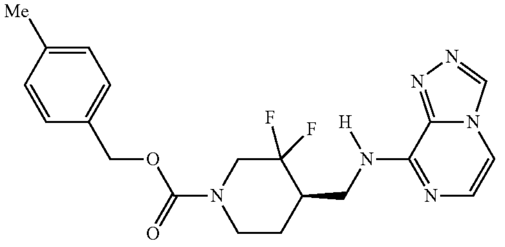 [SMILES: Cc1ccc(COC(=O)N2CC[C@H](CNc3nccn4cnnc34)C(F)(F)C2)cc1] | Route: IP<br>Pre-test time:<br>10 min<br>Vehicle: 1% DMSO + 4% HP-β-CD<br>n = 8 per group | 1<br>3<br>1<br>3 | 3.83<br>67.8**<br>51.5<br>120*** |

TABLE 2.2.5-continued

Percent Change in Novel Object Number of Nose Touches in the Novelty Phobia Test Relative to Vehicle Control in Wild Type Mice

| Compound | Structure | Summary of Methods | Dose (mg/kg) | Percent Change |
|---|---|---|---|---|
| | | Route: IP<br>Pre-test time:<br>10 min<br>Vehicle: 1%<br>DMSO +<br>4% HP-β-<br>CD<br>n = 12 per<br>group | 0.3<br>1<br>3<br>10 | 16.1<br>92.9***<br>123***<br>218*** |
| E1-21.26$^{B'}$ | 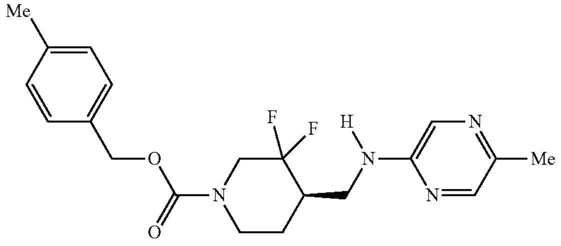 [SMILES: Cc1ccc(COC(=O)N2CC[C@H](CNc3cnc(C)cn3)C(F)(F)C2)cc1] | Route: IP<br>Pre-test time:<br>20 min<br>Vehicle: 2%<br>DMSO +<br>8% HP-P-<br>CD<br>n = 8 per<br>group | 3<br>10<br>30 | 141***<br>149***<br>171 *** |
| E1-22.2$^{B'}$ | 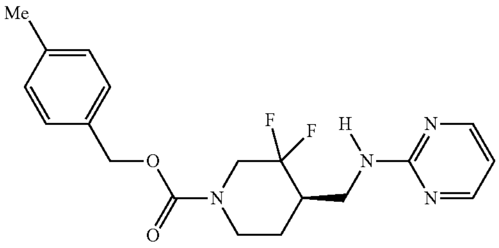 [SMILES: Cc1ccc(COC(=O)N2CC[C@H](CNc3ncccn3)C(F)(F)C2)cc1] | Route: IP<br>Pre-test time:<br>20 min<br>Vehicle: 1%<br>DMSO +<br>4% HP-β-<br>CD<br>n = 8 per<br>group | 3<br>10<br>30 | 163***<br>115*<br>98.9* |

Abbreviations: DMSO, dimethyl sulfoxide; HP-β-CD, 2-hydroxypropyl-beta-cyclodextrin; IP, intraperitoneal, Mol. Wt., molecular weight; PO, oral by gavage.

Notes:

Statistical significance determined by one-way analysis of variance, followed by Dunnett's multiple comparison post-hoc test compared with vehicle for studies with multiple compound treatment groups and by Student's t-test for studies with 1compound treatment group (efficacious response: *$p < 0.05$, $p < 0.01$, and *$p < 0.001$ and impaired response: ††$p < 0.01$ and †††$p < 0.001$).

Example 3. Chemical Entities

As depicted in the Examples below, in certain exemplary embodiments, chemical entities are prepared according to the following procedures. It will be appreciated that, although the general methods depict the synthesis of certain chemical entities of the present invention, the following methods, and other methods known to persons skilled in the art, can be applied to all chemical entities and subclasses and species of each of these chemical entities, as described herein.

Temperatures are given in degrees centigrade. If not mentioned otherwise, all evaporations are performed under reduced pressure, preferably between 15 mmHg and 100 mmHg. The structures of intermediates and final products are confirmed by standard analytical methods, for example, mass spectrometry and NMR spectroscopy. Optical rotations are measured at the sodium D line and given in degrees. Enantiomeric excess can be determined via chiral HPLC methods (e.g., using CHIRALPAK AD-H4.6*150 mm, 5 m columns and suitable mobile phase selection, e.g., hexane/isopropanol (80:20), and flow rates, e.g., 1.5 mL/min).

Abbreviations:

| | |
|---|---|
| aq | aqueous |
| BINAP | 2,2'-bis(diphenylphosphino)-1,1'-binaphthalene |
| Boc | t-butoxycarbonyl |
| Brettphos | 2-(dicyclohexylphosphino)-3,6-dimethoxy-2',4',6'-triisopropyl-1,1'-biphenyl |
| Brettphos precatalyst | chloro[2-(dicyclohexylphosphino)-3,6-dimethoxy-2',4',6'-triisopropyl-1,1'-biphenyl][2-(2-aminoethyl)phenyl]-palladium(II) |
| *n*BuOH | n-butanol |
| Cbz | benzyloxycarbonyl |
| CDI | carbonyldiimidazole |
| DAST | diethylamino sulfur trifluoride |
| dba | dibenylideneacetone |
| DCE | 1,2-dichloroethane |
| DCM | dichloromethane |
| DIPEA | N,N-diisopropylethylamine |
| DMAP | dimethylaminopyridine |
| DMF | N,N-dimethylformamide |
| DMSO | dimethyl sulfoxide |
| ee | enantiomeric excess |
| Et | ethyl |
| $Et_2O$ | diethyl ether ("ether") |
| EtOAc | ethyl acetate |
| EtOH | ethanol |
| eq | equivalents |
| HPLC | high performance liquid chromatography |

-continued

| | |
|---|---|
| LC | liquid chromatography |
| Me | methyl |
| Ms | methanesulfonyl |
| MsCl | methanesulfonylchloride |
| MS | mass spectrometry |
| MS (ESI) | mass spectrometry electrospray ionization |
| MTBE | methyl t-butyl ether |
| NMP | N-methyl-2-pyrrolidone |
| m/z | mass-to-charge ratio |
| NMR | nuclear magnetic resonance |
| Pd/C | palladium supported on carbon |
| Pd-G1 | 2-dicyclohexylphoshpino-2',4',6'-trisisopropyl-1,1'-biphenyl)[2-(2-aminoethyl)phenyl)]palladium(II) chloride |
| rt | room temperature |
| TEA | triethylamine |
| TFA | trifluoroacetic acid |
| THF | tetrahydrofuran |
| TLC | thin layer chromatography |
| Ts | p-toluenesulfonyl |

Example 3A. Chiral Purity (Ee) and Chiral HPLC Purity Analysis

Chiral HPLC enantiomeric purity analyses were conducted using CHIRALPAK® HPLC columns (e.g. CHIRALPAK® IC™) from Diacel Corporation (www.diacel.com). To determine optical purity, chiral HPLC separation methods were developed for the corresponding compound racemic mixture in which the enantiomers were well resolved to enable precise quantitation of optical purity or enantiomer excess (e.e.). The preparation and chiral purity of the enantiomeric intermediates (R)-tert-butyl 4-((((benzyloxy)carbonyl)amino)methyl)-3, 3-difluoropiperidine-11-carboxylate and (S)-tert-butyl 4-((((benzyloxy)carbonyl)amino)methyl)-3,3-difluoropiperidine-11-carboxylate is described below. The chiral center in these intermediates is considered non-racemizable and the syntheses described from the R and S intermediates assigned to yield R or S enantiomer intermediates and final example products generally. Chiral HPLC purity analyses for certain specific example compounds confirming the chiral purity were in correspondence to the chiral purity of the enantiomerically pure intermediate.

Example 3B. Intermediates

Example 3B.1. (R)-tert-butyl 4-((((benzyloxy)carbonyl)amino)methyl)-3,3-difluoropiperidine-1-carboxylate

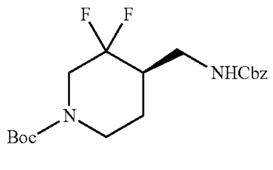 [SMILES: CC(C)(C)OC(=O)N1CC[C@H](CNC(=O)OCc2ccccc2)C(F)(F)C1]

Step 1: tert-butyl 3,3-difluoro-4,4-dihydroxypiperidine-1-carboxylate

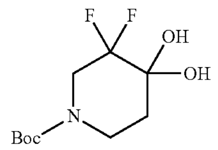

To a solution of 1-benzyl-3,3-difluoropiperidine-4,4-diol (100.0 g, 412 mmol) in ethanol (1850 mL) was added 10% Pd/C (10.0 g) and HCl (6.0 M, 69 mL, 414 mmol). The mixture was purged with $H_2$ three times and hydrogenated at room temperature under atmospheric pressure. After the starting material was consumed, the mixture was filtered through celite and the filter pad was extracted with EtOH. The combined filtrates were concentrated under reduced pressure and the crude 3,3-difluoropiperidine-4,4-diol hydrochloride product was used directly in the next step without purification. A stirred solution of the crude product 3,3-difluoropiperidine-4,4-diol hydrochloride (78 g) in water (1000 mL) and acetone (500 mL) was basified by $Na_2CO_3$ to pH 9. Di-tert-butyl dicarbonate (98.9 g, 453 mmol) was then added and the mixture was stirred at rt for 4 hours. The mixture was concentrated under reduced pressure to remove the acetone cosolvent. The resulting mixture was extracted with EtOAc. The combined organic layers were dried over $Na_2SO_4$ and concentrated to afford the crude product as a brown oil. The oil was treated with hexane and the precipitated solid material was triturated and filtered to give the title compound as a white powder (94.3 g, 90% overall). $^1H$ NMR (400 MHz, $CD_3OD$) δ 3.72 (t, J=11.6 Hz, 2H), 3.56-3.46 (m, 2H), 1.83-1.77 (m, 2H), 1.42 (s, 9H).

Step 2: tert-butyl 3,3-difluoro-4-(2-methoxy-2-oxoethylidene)piperidine-1-carboxylate

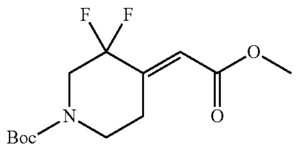 [SMILES: COC(=O)/C=C1\CCN(C(=O)OC(C)(C)C)CC1(F)F]

To a stirred solution of tert-butyl 3,3-difluoro-4,4-dihydroxypiperidine-1-carboxylate (80.0 g, 314 mmol) in toluene (1000 mL) was added methyl (triphenylphosphoranylidene)acetate (126 g, 377 mmol) and the reaction mixture was stirred at room temperature for 4 hours. The reaction mixture was concentrated in vacuo and the residue was purified by column chromatography over silica gel (EtOAc/hexane=1:5) to afford the title compound as a colorless oil (79.6 g, 87%). $^1H$ NMR (400 MHz, $CDCl_3$) δ 6.23 (s, 1H), 3.83-3.71 (m, 2H), 3.76 (s, 3H), 3.58-3.47 (m, 2H), 3.13-3.05 (m, 2H), 1.48 (s, 9H).

Step 3: tert-butyl 3,3-difluoro-4-(2-methoxy-2-oxoethyl)piperidine-1-carboxylate

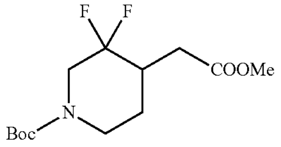 [SMILES: COC(=O)CC1CCN(C(=O)OC(C)(C)C)CC1(F)F]

To a stirred solution in tert-butyl 3,3-difluoro-4-(2-methoxy-2-oxoethylidene)piperidine-1-carboxylate (78.5 g, 269.49 mmol) in methanol was added 10% Pd/C (3.5 g). The stirred suspension was hydrogenated at atmospheric pressure at room temperature overnight. The starting material was consumed, and the reaction mixture was filtered to remove Pd/C. The filtrate was concentrated under reduced pressure to afford the crude title compound as a light brown oil (75.2 g, 95%). $^1$H NMR (400 MHz, $CDCl_3$) δ 4.30-4.13 (m, 1H), 4.10-4.01 (m, 1H), 5.69 (s, 3H), 3.25-3.05 (m, 1H), 3.00-2.80 (m, 1H), 2.78-2.70 (m, 1H), 2.55-2.40 (m, 1H), 2.31-2.24 (m, 1H), 1.91-1.82 (m, 1H), 1.50-1.40 (m, 1H), 1.46 (s, 9H).

Step 4: 2-(1-(tert-butoxycarbonyl)-3,3-difluoropiperidin-4-yl)acetic acid

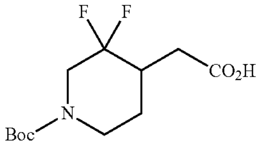 [SMILES: CC(C)(C)OC(=O)N1CCC(CC(=O)O)C(F)(F)C1]

To a stirred solution of tert-butyl 3,3-difluoro-4-(2-methoxy-2-oxoethyl)piperidine-1-carboxylate (35.5 g, 115 mol) in THF (220 mL) was added 1.0 M aqueous NaOH (231 mL, 231 mmol) at room temperature. After stirring overnight, the starting material was consumed, and the THF was removed by concentration under reduced pressure. The aqueous concentrate was extracted with ethyl acetate and acidified to pH 5 with 4.0 M aqueous HCl under ice-water bath cooling. The aqueous phase was extracted with ethyl acetate three times. The combined organic phases were washed with water, brine, dried over $Na_2SO_4$, and concentrated under reduced pressure. The residue was triturated with hexane and the suspension was filtered to afford the title product as an off-white powder (24.58 g, 76%). $^1$H NMR (400 MHz, DMSO-$d_6$) δ 12.99 (s, 1H), 6.11 (s, 1H), 3.81 (t, J=11.6 Hz, 2H), 3.50-3.42 (m, 2H), 2.94-2.88 (m, 2H), 1.42 (s, 9H).

Step 5: (R)-2-(1-(tert-butoxycarbonyl)-3,3-difluoropiperidin-4-yl)acetate (R)-α-methyl benzylamine salt

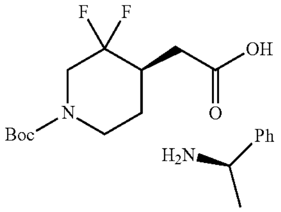

To a stirred solution of 2-(1-(tert-butoxycarbonyl)-3,3-difluoropiperidin-4-yl)acetic acid (95.17 g, 340.76 mmol) in isopropanol (900 mL) was added (R)-α-methyl benzylamine (41.29 g, 340.76 mmol) in isopropanol (50 mL). After stirring for 2 hours, the mixture was cooled to ice bath temperature, and then stirred overnight. The resulting white suspension was filtered to afford the title salt as a white powder (44.73 g). The R-enantiomer enriched salt was recrystallized three times from isopropanol to afford the title salt as a white powder (23.25 g) which was demonstrated to be of high enantiomeric purity from the chiral HPLC purity determination for the subsequent intermediate (R)-tert-butyl 4-((((benzyloxy)carbonyl)amino)methyl)-3,3-difluoropiperidine-1-carboxylate.

Step 6: (R)-2-(1-(tert-butoxycarbonyl)-3,3-difluoropiperidin-4-yl)acetic acid

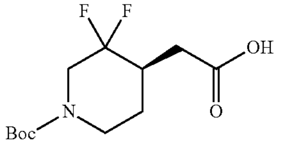 [SMILES: CC(C)(C)OC(=O)N1CC[C@H](CC(=O)O)C(F)(F)C1]

The (R)-2-(1-(tert-butoxycarbonyl)-3,3-difluoropiperidin-4-yl)acetate (R)-α-methyl benzylamine (15.64 g) was suspended in water (100 mL), and then acidified with 3 M aqueous HCl. The aqueous phase was extracted with ethyl acetate three times. The combined organic phases were washed with brine, dried over $Na_2SO_4$ and concentrated under reduced pressure to afford the title compound as a colorless oil (10.31 g, 94%) which formed a white solid upon standing. $^1$H NMR (400 MHz, DMSO-$d_6$) δ 12.39 (br, 1H), 4.18-3.97 (m, 1H), 3.95-3.80 (m, 1H), 3.29-3.06 (m, 1H), 3.05-2.78 (m, 1H), 2.60-2.58 (m, 1H), 2.48-2.36 (m, 1H), 2.19-2.11 (m, 1H), 1.85-1.75 (m, 1H), 1.39 (s, 9H), 1.37-1.26 (m, 1H).

Step 7: (R)-tert-butyl 4-((((benzyloxy)carbonyl)amino)methyl)-3,3-difluoropiperidine-1-carboxylate

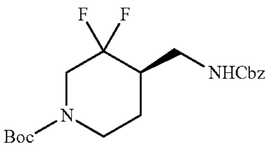 [SMILES: CC(C)(C)OC(=O)N1CC[C@H](CNC(=O)OCc2ccccc2)C(F)(F)C1]

To a solution of (R)-2-(1-(tert-butoxycarbonyl)-3,3-difluoropiperidin-4-yl)acetic acid (45.1 g, 161.4 mmol) in toluene (450 mL) was added triethyl amine (33.6 mL, 242.1 mmol) at room temperature. Then dipenylphosphoyryl azide (48.85 g, 177.5 mmol) was added under nitrogen atmosphere. The resulting mixture was heated to 80° C. After stirring for 20 minutes, benzyl alcohol (18.3 g, 169.5 mmol) was added. The mixture thus obtained was heated to 100° C. and stirred overnight. After cooling to room temperature, the mixture was washed with water, brine, dried over $Na_2SO_4$ and the organic phase was concentrated under reduced pressure. The concentrate was suspended in hexane and ethyl acetate (10:1, 550 mL), and then heated to reflux to afford a clear brown solution. The solution was slowly cooled down to room temperature under stirring. The resulting suspension was filtered to afford the title compound as a light brown solid (55.4 g, 89%). Chiral HPLC purity >99% ee (CHIRALPAK® IC™ column, 4.6×150 mm, particle size 5 μm, hexane/ethanol 80:20 v/v, flow rate: 1.5 mL/min, UV detection λ=214 nm, retention time=3.10 minutes). $^1$H NMR (400 MHz, $CDCl_3$) δ 7.39-7.29 (m, 5H), 5.13-5.07 (m, 2H), 5.04-4.96 (m, 1H), 4.41-4.01 (m, 1H), 3.55-3.45 (m, 1H), 3.37-3.26 (m, 1H), 3.03-2.65 (m, 2H), 2.18-2.00 (m, 1H), 1.80-1.71 (m, 1H), 1.58-1.46 (m, 1H), 1.46 (s, 9H).

Example 3B.2. (S)-tert-butyl 4-((((benzyloxy)carbonyl)amino)methyl)-3,3-difluoropiperidine-1-carboxylate

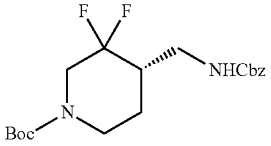 [SMILES: CC(C)(C)OC(=O)N1CC[C@@H](CNC(=O)OCc2ccccc2)C(F)(F)C1]

Step 1: (S)-2-(1-(tert-butoxycarbonyl)-3,3-difluoropiperidin-4-yl)acetic acid

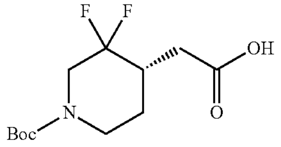 [SMILES: CC(C)(C)OC(=O)N1CC[C@@H](CC(=O)O)C(F)(F)C1]

(S)-2-(1-(tert-butoxycarbonyl)-3,3-difluoropiperidin-4-yl)acetate (S)-α-methyl benzylamine salt was prepared in analogous fashion to the corresponding (R)-2-(1-(tert-butoxycarbonyl)-3,3-difluoropiperidin-4-yl)acetate (R)-α-methyl benzylamine salt as described herein above. The salt formed from one equivalent of (S)-α-methyl benzylamine and racemic 2-(1-(tert-butoxycarbonyl)-3,3-difluoropiperidin-4-yl)acetic acid in isopropanol was recrystallized repeatedly to obtain the pure (S)-2-(1-(tert-butoxycarbonyl)-3,3-difluoropiperidin-4-yl)acetate (S)-α-methyl benzylamine salt salt. The (S)-2-(1-(tert-butoxycarbonyl)-3,3-difluoropiperidin-4-yl)acetate (S)-1-phenylethanamine salt (49.0 g, 122.5 mmol) was suspended in water (400 mL), and then basified with 2.0 M aqueous NaOH (70 mL). The aqueous phase was extracted with ethyl acetate. Then the aqueous phase was acidified with 2.0M aqueous HCl (120 mL), and then extracted with ethyl acetate. The combined organic phases were washed with brine, dried over $Na_2SO_4$ and concentrated under reduced pressure to afford the title compound as a clear colorless oil (33.15 g, 97%), which formed a white solid upon standing. $^1$H NMR (400 MHz, $CDCl_3$) δ 4.52-4.40 (m, 2H), 3.10-2.72 (m, 3H), 2.46-2.26 (m, 2H), 1.95-1.86 (m, 1H), 1.58-1.47 (m, 1H), 1.46 (s, 9H).

Step 2: (S)-tert-butyl 4-((((benzyloxy)carbonyl)amino)methyl)-3,3-difluoropiperidine-1-carboxylate

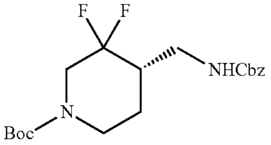 [SMILES: CC(C)(C)OC(=O)N1CC[C@@H](CNC(=O)OCc2ccccc2)C(F)(F)C1]

(S)-2-(1-(tert-butoxycarbonyl)-3,3-difluoropiperidin-4-yl)acetic acid (33.2 g, 118.8 mmol) was dissolved in toluene (300 mL), and then triethyl amine (26.9 mL, 193.5 mmol) and diphenylphosphoryl azide (39.0 g, 141.9 mmol) were added consecutively. The resulting mixture was heated to 80° C. under nitrogen atmosphere. After the emission of bubble ceased, benzyl alcohol (14.6 g, 135.5 mmol) was added slowly. The mixture thus obtained was heated to 100° C. and stirred overnight. After cooling down to room temperature, the mixture was washed with water several times, brine, dried over $Na_2SO_4$ and concentrated under reduced pressure. The concentrate was suspended in hexane and ethyl acetate (8:1, 500 mL), and then heated to reflux to afford a clear solution. The mixture was slowly cooled down to room temperature under fierce stirring to afford an off-white suspension which was filtered to yield the title product as an off-white solid (36.31 g, 72%). Chiral HPLC purity >99% ee (CHIRALPAK® IC™ column, 4.6×150 mm, particle size 5 μm, hexane/ethanol 80:20 v/v, flow rate: 1.5 mL/min, UV detection λ=214 nm, retention time=7.89 minutes). $^1$H NMR (400 MHz, $CDCl_3$) δ 7.39-7.30 (m, 5H), 5.10 (s, 2H), 5.03-4.96 (m, 1H), 4.45-4.00 (m, 2H), 3.55-3.56 (m, 2H), 3.05-2.64 (m, 2H), 2.18-2.03 (m, 1H), 1.81-1.72 (m, 1H), 1.59-1.48 (m, 1H), 1.46 (s, 9H).

Example 3B.3. (difluoromethyl)benzil (2,5-dioxopyrrolidin-1-yl)carbonate

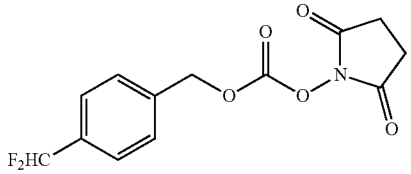 [SMILES: O=C(OCc1ccc(C(F)F)cc1)ON1C(=O)CCC1=O]

Step 1: methyl 4-(difluoromethyl)benzoate

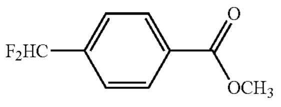

To a solution of methyl 4-formylbenzoate (79.50 g, 0.48 mol) in DCM (800 mL) was added diethylaminosulfur trifluoride (96 mL, 0.73 mol) dropwise at 0-5° C. The reaction mixture was then allowed to warm to 40° C. and stirred at 40° C. for 4 hours. The mixture was poured into ice-water and diluted with ethyl acetate. The organic layer was washed with saturated $NaHCO_3$, brine, dried over $Na_2SO_4$ and concentrated under reduced pressure to afford the crude title compound as an off-white solid (98.00 g). The crude product was used in the next step without further purification.

Step 2: (4-(difluoromethyl)phenyl)methanol

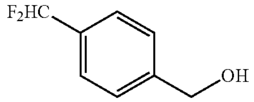 [SMILES: OCc1ccc(C(F)F)cc1]

To a stirred suspension of lithium borohydride (21.10 g, 0.97 mol) in THE (900 mL) was added methyl 4-(difluoromethyl)benzoate (98.00 g, 0.48 mol) in THE (200 mL) dropwise at 0-5° C. The reaction mixture was then warmed to 60° C. and stirred at 60° C. for 4 hours. After the reaction was completed, the mixture was quenched with 2 M aqueous HCl and diluted with ethyl acetate. The organic layer was washed with saturated $NaHCO_3$, brine, dried over $Na_2SO_4$, and concentrated under reduced pressure to afford the crude product, which was purified by distillation under reduced pressure pump to afford the title compound as a colorless oil (65.50 g, 85%). $^1$H NMR (400 MHz, $CDCl_3$) δ 7.51 (d, J=8.0 Hz, 2H), 7.46 (d, J=8.0 Hz, 2H), 6.65 (t, J=56.4 Hz, 1H), 4.76 (d, J=5.2 Hz, 2H), 1.74 (t, J=5.8 Hz, 1H).

Step 3: 4-(difluoromethyl)benzyl (2,5-dioxopyrrolidin-1-yl) carbonate

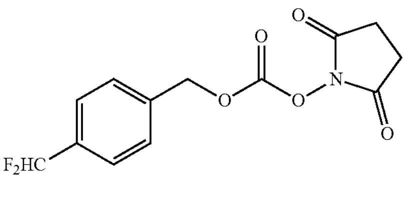 [SMILES: O=C(OCc1ccc(C(F)F)cc1)ON1C(=O)CCC1=O]

To a solution of (4-(difluoromethyl)phenyl)methanol (65.40 g, 0.41 mol) in dichloromethane (600 mL) and MeCN (600 mL) was added bis(2,5-dioxopyrrolidin-1-yl) carbonate (106.0 g, 0.41 mol) in one portion and DMAP (25.30 g, 0.21 mol) in one portion while the inner temperature was kept <5° C. After stirring at 0-5° C. for 3 hours, the reaction mixture was concentrated in vacuo. The concentrate was diluted with dichloromethane (1000 mL), washed with water (300 mL×5), brine, dried over $Na_2SO_4$ and the organic phase was concentrated in vacuo. Then the concentrate was triturated with hexane/ethyl acetate (2:1) to afford the title compound as a white solid (105.5 g, 85%). $^1$H NMR (400 MHz, $CDCl_3$) δ 7.55 (d, J=8.0 Hz, 2H), 7.49 (d, J=8.0 Hz, 2H), 6.66 (t, J=56.4 Hz, 1H), 5.35 (s, 2H), 2.84 (s, 4H).

Example 3B.4. 2,3-dihydro-1H-inden-2-yl (2,5-dioxopyrrolidin-1-yl) carbonate

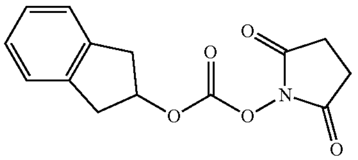 [SMILES: O=C(OC1Cc2ccccc2C1)ON1C(=O)CCC1=O]

To a solution of 2,3-dihydro-1H-inden-2-ol (5.0 g, 37.3 mmol) in DCM (50 mL) and MeCN (50 mL) was added bis(2,5-dioxopyrrolidin-1-yl) carbonate (9.6 g, 37.3 mmol) and DMAP (2.3 g, 18.6 mmol) at 0° C. After stirring for 3 hours at 0° C., the reaction mixture was concentrated under reduced pressure. The concentrate was dissolved in DCM, washed with water, brine, dried over $Na_2SO_4$, and concentrated under reduced pressure. The crude product was triturated with hexane and ethyl acetate (5:1, 50 mL) to give the title compound as a brown solid (7.0 g, 70%). $^1$H NMR (400 MHz, $CDCl_3$): δ 7.27-7.20 (m, 4H), 5.59-5.54 (m, 1H), 3.41-3.35 (m, 2H), 3.23-3.18 (m, 2H), 2.81 (s, 4H).

Example 3B.5. (2,5-dioxopyrrolidin-1-yl)methyl 4-fluorobenzyl carbonate

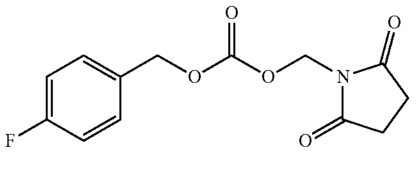 [SMILES: O=C(OCc1ccc(F)cc1)OCN1C(=O)CCC1=O]

To a solution of (4-fluorophenyl)methanol (8.52 g, 67.53 mmol) in DCM (80 mL) and acetonitrile (80 mL) at 0° C. was added bis(2,5-dioxopyrrolidin-1-yl) carbonate (5.73 g, 22.36 mmol) and DMAP (1.37 g, 11.18 mmol). The resulting mixture was allowed to warm up to room temperature. After stirring for 3 hours, the reaction mixture was concentrated under reduced pressure. The concentrate was dissolved in DCM, washed with water, brine, dried over $Na_2SO_4$ and concentrated under reduced pressure. The crude product was triturated with EtOAc and hexane (1:4, 35 mL) to afford the title product as a white solid (14.0 g, 77%). $^1$H NMR (400 MHz, $CDCl_3$): δ 7.42-7.36 (m, 2H), 7.12-7.05 (m, 2H), 5.28 (s, 2H), 2.84 (s, 4H).

Example 3B.6. 4-chlorobenzyl (2,5-dioxopyrrolidin-1-yl) carbonate

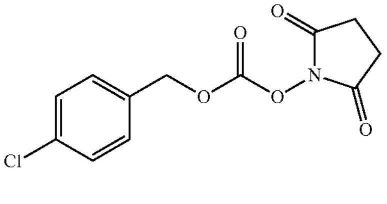 [SMILES: O=C(OCc1ccc(Cl)cc1)ON1C(=O)CCC1=O]

To a solution of (4-chlorophenyl)methanol (2.00 g, 14.03 mmol) in DCM/MeCN (1:1, 20 mL) was added bis(2,5-dioxopyrrolidin-1-yl) carbonate (3.59 g, 14.03 mmol) and DMAP (858 mg, 7.02 mmol) at ice-bath temperature. The reaction mixture was slowly warmed to room temperature. After stirring for 2 hours, the mixture was concentrated under reduced pressure. The residue was dissolved in ethyl acetate, washed with brine, dried over sodium sulfate, and the organic phase was concentrated under reduced pressure. The concentrate was triturated with hexane/ethyl acetate (2:1, v/v) to afford the compound as a white power (3.10 g, 78%). $^1$H NMR (400 MHz, $CDCl_3$) δ 7.39-7.33 (m, 4H), 5.28 (s, 2H), 2.84 (s, 4H).

Example 3B.7. 2,5-dioxopyrrolidin-1-yl 4-ethylbenzyl carbonate

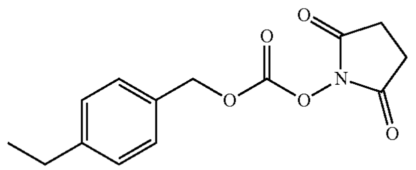 [SMILES: CCc1ccc(COC(=O)ON2C(=O)CCC2=O)cc1]

To a solution of (4-ethylphenyl)methanol (4.0 g, 29 mmol) in DCM (40 mL) and MeCN (40 mL) were added bis(2,5-dioxopyrrolidin-1-yl) carbonate (7.5 g, 29 mmol) and DMAP (1.8 mg, 15 mmol) sequentially at room temperature. After stirring for 3 hours, the reaction mixture was concentrated in vacuo. The concentrate was dissolved in ethyl acetate and then washed with water. The organic phase was dried over $Na_2SO_4$ and concentrated under reduced pressure. The residue was triturated with hexane and ethyl acetate (3:1, 80 mL) to give the title compound as a white solid (3.3 g, 40%).

Example 3B.8. 2,5-dioxopyrrolidin-1-yl 4-methylbenzyl carbonate

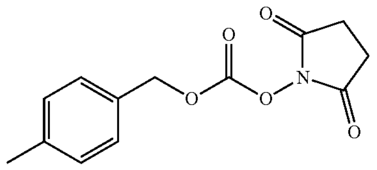 [SMILES: Cc1ccc(COC(=O)ON2C(=O)CCC2=O)cc1]

To a stirred solution of p-tolylmethanol (70.0 g, 570 mmol) in DCM/MeCN (1:1, v/v, 1400 mL) was added bis(2,5-dioxopyrrolidin-1-yl) carbonate (146.8 g, 570 mmol) and DMAP (35.0 g, 285 mmol) at 0-5° C. The mixture was allowed to warm up to room temperature. After stirring at room temperature for 3 hours, the mixture was concentrated under reduced pressure. The residue was dissolved in DCM (1500 mL), washed with water, brine, dried over sodium sulfate, and the organic phase was concentrated under reduced pressure. The concentrate was triturated with hexane/ethyl acetate (2:1, v/v) to afford the title compound as a white solid (120 g, 80%). $^1$H NMR (400 MHz, $CDCl_3$) δ 7.29 (d, J=8.0 Hz, 2H), 7.20 (d, J=8.0 Hz, 2H), 5.27 (s, 2H), 2.81 (s, 4H), 2.36 (s, 3H).

Example 3.1. (S)-4-methylbenzyl 3,3-difluoro-4-((pyrimidin-2-ylamino)methyl)piperidine-1-carboxylate mesylate (E2-22.2$^{B'}$)

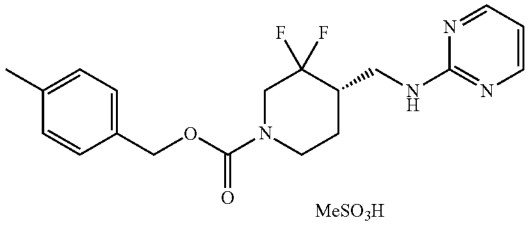 [SMILES: "MeSO3H" ; Cc1ccc(COC(=O)N2CC[C@@H](CNc3ncccn3)C(F)(F)C2)cc1]

Step 1: (S)-tert-butyl 4-(aminomethyl)-3,3-difluoropiperidine-1-carboxylate

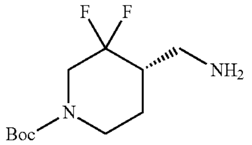 [SMILES: CC(C)(C)OC(=O)N1CC[C@@H](CN)C(F)(F)C1]

To a solution of (S)-tert-butyl 4-((((benzyloxy)carbonyl)amino)methyl)-3,3-difluoropiperidine-1-carboxylate (36.21 g, 94.29 mmol) in methanol (150 mL) was added 10% Pd/C (3.0 g). The suspension was degassed three times under hydrogen gas atmosphere, and stirred overnight under balloon hydrogen gas pressure. After the starting material was consumed, the Pd/C was filtered off and the filtrate was concentrated under reduced pressure to afford the title compounds as a yellow oil (23.48 g, 91%). $^1$H NMR (400 MHz, $CDCl_3$) δ 4.45-3.95 (m, 2H), 3.17-3.10 (m, 1H), 3.05-2.70 (m, 2H), 2.70-2.63 (m, 1H), 1.95-1.80 (m, 2H), 1.56-4.45 (m, 1H), 1.45 (s, 9H).

Step 2: (S)-tert-butyl 3,3-difluoro-4-((pyrimidin-2-ylamino)methyl)piperidine-1-carboxylate

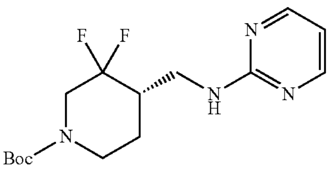 [SMILES: CC(C)(C)OC(=O)N1CC[C@@H](CNc2ncccn2)C(F)(F)C1]

A suspension of (S)-tert-butyl 4-(aminomethyl)-3,3-difluoropiperidine-1-carboxylate (3.00 g, 11.98 mmol), 2-chloropyrimidine (1.65 g, 14.38 mmol) and DIPEA (2.9 mL, 17.4 mmol) in n-BuOH (40 mL) was heated to 110° C. After stirring overnight, the solvent was removed under reduced pressure. The concentrate was purified by column purification over silica gel (eluent: hexane/ethyl acetate=2:1) to afford the title compound as an off-white solid (2.85 g, 72%). MS (ESI) calculated for $C_{15}H_{22}F_2N_4O_2$: 328.2 m/z; found: 329.4 m/z [M+H]. $^1$H NMR (400 MHz, $CDCl_3$) δ 8.27 (d, J=4.8 Hz, 2H), 6.54 (t, J=4.8 Hz, 1H), 5.39-5.32 (m, 1H), 4.50-4.00 (m, 2H), 3.82-3.74 (m, 1H), 3.58-3.48 (m, 1H), 3.07-2.65 (m, 2H), 2.31-2.15 (m, 1H), 1.88-1.79 (m, 1H), 1.63-1.51 (m, 1H), 1.46 (s, 9H).

Step 3: (S)—N-((3,3-difluoropiperidin-4-yl)methyl) pyrimidin-2-amine trifluoroacetate

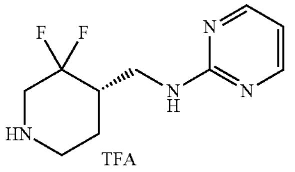 [SMILES: FC1(F)CNCC[C@H]1CNc1ncccn1]

(S)-tert-butyl 3,3-difluoro-4-((pyrimidin-2-ylamino) methyl)piperidine-1-carboxylate (2.85 g, 8.69 mmol) was dissolved in DCM (30 mL), and then trifluoroacitic acid (15 mL) was added at room temperature. After stirring for one hour, the starting material was consumed, and the volatiles were removed under reduced pressure to yield the crude title compound as a brown oil (6.6 g) which was directly used in the next step. MS (ESI) calculated for $C_{10}H_{14}F_2N_4$: 228.1 m/z; found: 229.1 m/z [M+H].

Step 4: (S)-4-methylbenzyl 3,3-difluoro-4-((pyrimidin-2-ylamino)methyl)piperidine-1-carboxylate

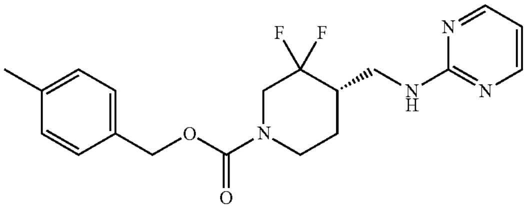 [SMILES: Cc1ccc(COC(=O)N2CC[C@@H](CNc3ncccn3)C(F)(F)C2)cc1]

The crude (S)—N-((3,3-difluoropiperidin-4-yl)methyl) pyrimidin-2-amine trifluoroactetate (2.2 g) from last step was dissolved in MeCN (15 mL), and then triethyl amine (2.0 mL, 14.5 mmol) was added at room temperature. After the mixture was cooled down to room temperature, 2,5-dioxopyrrolidin-1-yl 4-methylbenzyl carbonate (840 mg, 3.19 mmol) was added in one portion. The resulting mixture was stirred for 2 hours at ambient temperature. After the starting material was consumed, the solvent was concentrated. The concentrate was dissolved in ethyl acetate, washed with water for several times, brine, dried over $Na_2SO_4$ and the organic phase was concentrated under reduced pressure. The concentrate was purified by column purification over silica gel (eluent: hexane/DCM/ethyl acetate=2:2:1) to afford the title product as a white solid (780 mg, 71% overall yield over two steps). Chiral HPLC purity >99% ee (CHIRALPAK® H™ column, 4.6×150 mm, particle size 5 μm, hexane/ethanol 80:20 v/v, flow rate: 1.5 mL/min, UV detection λ=256 nm, retention time=14.54 minutes). MS (ESI) calculated for $C_{19}H_{22}F_2N_4O_2$: 376.2 m/z; found: 377.4 m/z [M+H]. $^1$H NMR (400 MHz, $CDCl_3$) δ 8.27 (d, J=4.8 Hz, 2H), 7.25 (d, J=8.0 Hz, 2H), 7.17 (d, J=7.6 Hz, 2H), 6.55 (d, J=4.8 Hz, 1H), 5.36-5.30 (m, 1H), 5.15-5.05 (m, 2H), 4.53-4.10 (m, 2H), 3.84-3.74 (m, 1H), 3.57-3.48 (m, 1H), 3.11-2.91 (m, 1H), 2.90-2.75 (m, 1H), 2.35 (s, 3H), 2.33-2.18 (m, 1H), 1.91-1.79 (m, 1H), 1.63-1.52 (m, 1H).

Step 5: (S)-4-methylbenzyl 3,3-difluoro-4-((pyrimidin-2-ylamino)methyl)piperidine-1-carboxylate mesylate

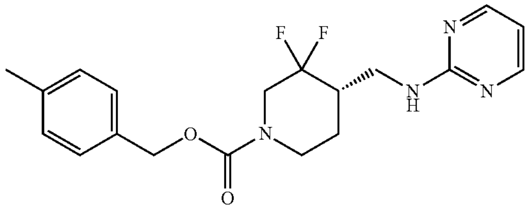

$MeSO_3H$ (S)-4-methylbenzyl 3,3-difluoro-4-((pyrimidin-2-ylamino)methyl)piperidine-1-carboxylate (780 mg, 2.07 mmol) was dissolved in DCM/MeOH (3:1, 12 mL), and then 1.0 M methanesulfonic acid in methanol (2.07 mL, 2.07 mmol) was added. The resulting solution was stirred for 30 minutes at room temperature and then concentrated under reduced pressure. The concentrate was triturated with ether to afford the title product as a white powder (951 mg, 97%). MS (ESI) calculated for $C_{19}H_{22}F_2N_4O_2$: 376.2 m/z; found: 377.5 m/z [M+H]. $^1$H NMR (400 MHz, $CD_3OD$) δ 8.88-8.77 (m, 2H), 7.24 (d, J=7.6 Hz, 2H), 7.17 (d, J=8.0 Hz, 2H), 7.03 (t, J=5.4 Hz, 1H), 5.09 (s, 2H), 4.40-4.25 (m, 1H), 4.22-4.12 (m, 1H), 3.97-3.89 (m, 1H), 3.62-3.54 (m, 1H), 3.28-3.09 (m, 1H), 3.05-2.87 (m, 1H), 2.72 (s, 3H), 2.55-2.39 (m, 1H), 2.33 (s, 3H), 1.97-1.88 (m, 1H), 1.59-1.46 (m, 1H).

Example 3.2. (R)-4-(difluoromethyl)benzyl 3,3-difluoro-4-((pyrimidin-2-ylamino)methyl)piperidine-1-carboxylate mesylate (E1-22.6[B'])

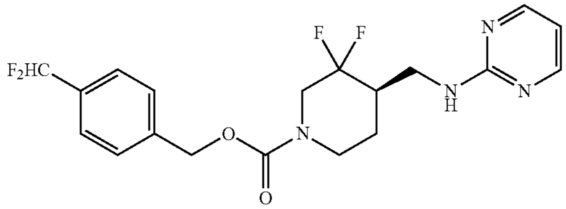

$MeSO_3H$

Step 1: (R)-tert-butyl 4-(aminomethyl)-3,3-difluoropiperidine-1-carboxylate

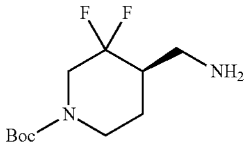 [SMILES: CC(C)(C)OC(=O)N1CC[C@H](CN)C(F)(F)C1]

A mixture of (R)-tert-butyl 4-((((benzyloxy)carbonyl) amino)methyl)-3,3-difluoropiperidine-1-carboxylate (150.0 g, 0.39 mol) and 10% Pd/C (7.5 g) in methanol (1500 mL)

was stirred at room temperature overnight under hydrogen atmosphere. The mixture was filtered and the filter cake was washed with methanol. The combined filtrates were concentrated to afford the crude title compound as a pale yellow oil (97.7 g) which was used directly without further purification. $^1H$ NMR (400 MHz, $CDCl_3$) δ 4.37-4.01 (m, 2H), 3.14 (dd, J=5.2, 13.2 Hz, 1H), 3.06-2.71 (m, 2H), 2.67 (dd, J=6.8, 13.2 Hz, 1H), 1.94-1.81 (m, 2H), 1.55-1.48 (m, 1H), 1.46 (s, 9H).

Step 2: (R)-tert-butyl 3,3-difluoro-4-((pyrimidin-2-ylamino)methyl)piperidine-1-carboxylate

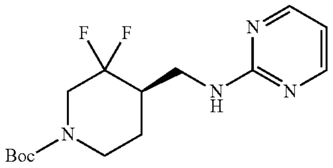

To a solution of (R)-tert-butyl 4-(aminomethyl)-3,3-difluoropiperidine-1-carboxylate (97.7 g, 0.39 mol) in n-butanol (1000 mL) was added 2-chloropyrimidine (67.1 g, 0.58 mol) and DIPEA (135 mL, 0.78 mol). The reaction mixture was degassed three times under $N_2$ atmosphere and heated to 100° C. After stirring at 100° C. for 18 hours, the mixture was cooled down to room temperature and concentrated under reduced pressure. The concentrate was diluted with ethyl acetate, washed with water, brine, dried over $Na_2SO_4$, and concentrated in vacuo. The crude product was recrystallized from ethyl acetate/hexane (160 mL/160 mL) to afford the title compound as an off-white solid (94.70 g, 74%). MS (ESI) calculated for $C_{15}H_{22}F_2N_4O_2$: 328.2 m/z; found: 329.4 m/z [M+H]. $^1H$ NMR (400 MHz, $CDCl_3$) δ 8.27 (d, J=4.80 Hz, 2H), 6.54 (t, J=4.80 Hz, 1H), 5.37-5.34 (m, 1H), 4.47-3.98 (m, 2H), 3.82-3.75 (m, 1H), 3.57-3.50 (m, 1H), 3.04-2.68 (m, 2H), 2.31-2.16 (m, 1H), 1.85-1.82 (m, 1H), 1.62-1.52 (m, 1H), 1.46 (s, 9H).

Step 3: (R)—N-((3,3-difluoropiperidin-4-yl)methyl)pyrimidin-2-amine trifluoroacetate

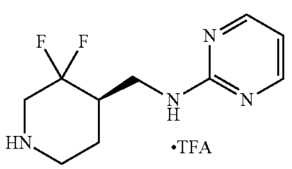 [SMILES: FC1(F)CNCC[C@@H]1CNc1ncccn1]

•TFA

To a solution of (R)-tert-butyl 3,3-difluoro-4-((pyrimidin-2-ylamino)methyl)piperidine-1-carboxylate (80.1 g, 0.24 mol) in dichloromethane (530 mL) was added TFA (270 mL) at room temperature. After stirring for 3 hours, the reaction mixture was concentrated in vacuo to afford the crude TFA salt as a yellow oil (217 g), which was used in the next step without further purification. MS (ESI) calculated for $C_{15}H_{22}F_2N_4O_2$: 228.1 m/z; found: 229.1 m/z [M+H].

Step 4: (+)-(R)-4-(difluoromethyl)benzyl 3,3-difluoro-4-((pyrimidin-2-ylamino)methyl)piperidine-1-carboxylate

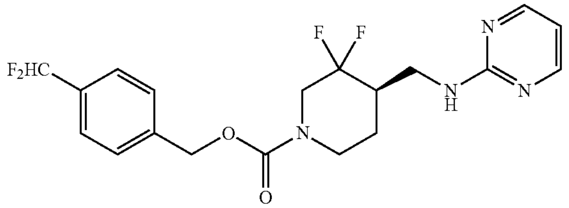 [SMILES: O=C(OCc1ccc(C(F)F)cc1)N1CC[C@H](CNc2ncccn2)C(F)(F)C1]

To a solution of crude (R)—N-((3,3-difluoropiperidin-4-yl)methyl)pyrimidin-2-amine trifluoroacetate (217.0 g, 0.24 mol) in $CH_3CN$ (800 mL) was added triethylamine (200 mL, 1.46 mol) slowly. After the mixture was cooled down to room temperature, 4-(difluoromethyl)benzyl (2,5-dioxopyrrolidin-1-yl) carbonate (73.0 g, 0.24 mol) was added slowly. After stirring at room temperature overnight, the solvent was evaporated under reduced pressure and the concentrate was diluted with ethyl acetate (800 mL). The organic layer was washed with water (300 mL), and the aqueous layer was with ethyl acetate (250 mL×2). The combined organic layers were washed with water (450 mL×5), 1 M HCl (400 mL×2), saturated $NaHCO_3$ (400 mL), brine, dried over $Na_2SO_4$ and concentrated in vacuo. The residue was recrystallized from hexane/ethyl acetate (1:1, 400 mL) to afford the title compound as an off-white solid (81.00 g, 80%). MS (ESI) calculated for $C_{19}H_{20}F_4N_4O_2$: 412.2 m/z; found: 413.5 m/z [M+H]. $[\alpha]^{30}_{\lambda}$=+16° (c: 10 mg/mL, ethanol). $^1H$ NMR (400 MHz, $CDCl_3$) δ 8.27 (d, J=4.8 Hz, 2H), 7.51 (d, J=8.0 Hz, 2H), 7.43 (d, J=8.0 Hz, 2H), 6.64 (t, J=56.4 Hz, 1H), 6.55 (t, J=4.8 Hz, 1H), 5.41 (m, 1H), 5.22-5.14 (m, 2H), 4.51-4.11 (m, 2H), 3.83-3.77 (m, 1H), 3.57-3.50 (m, 1H), 3.13-2.80 (m, 2H), 2.35-2.21 (m, 1H), 1.90-1.86 (m, 1H), 1.65-1.55 (m, 1H).

Step 5: (+)-(R)-4-(difluoromethyl)benzyl 3,3-difluoro-4-((pyrimidin-2-ylamino)methyl)piperidine-1-carboxylate mesylate

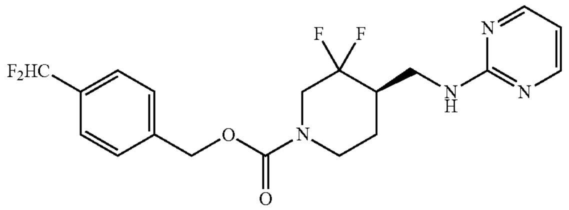

$MeSO_3H$

To a solution of (R)-4-(difluoromethyl)benzyl 3,3-difluoro-4-((pyrimidin-2-ylamino)methyl)piperidine-1-carboxylate (326.16 g, 0.791 mol) in DCM/MeOH (2 L/1 L, v/v) was added 1.0 M methanesulfonic acid solution in methanol (791 mL, 0.791 mol) at room temperature. After stirring for 30 minutes, the solvent was removed under reduced pressure. The salt was recrystallized from isopropanol/MTBE (1:1, v/v) to afford the title product as a white solid (382.8 g, 95%). Chiral HPLC purity >99% ee (CHIRALPAK® IC™ column, 4.6×150 mm, particle size 5 μm, hexane/ethanol 85:15 v/v, flow rate: 1.5 mL/min, UV detection λ=254 nm, retention time=21.09 minutes). $[\alpha]^{30}_{k}$=+3.2° (c: 10 mg/mL, ethanol). MS (ESI) calculated for $C_{19}H_{20}F_4N_4O_2$: 412.2 m/z; found: 413.5 m/z [M+H]. $^1H$ NMR (400 MHz, $CD_3OD$) δ 8.82-8.40 (m, 2H), 7.54 (d, J=8.4 Hz, 2H), 7.48 (d, J=8.0 Hz, 2H), 7.02 (t, J=5.4 Hz, 1H), 6.76 (t, J=56.4 Hz, 1H), 5.24-5.16 (m, 2H), 4.40-4.30 (m, 1H), 4.23-4.14 (m, 1H), 3.96-3.89 (m, 1H), 3.62-3.55 (m, 1H), 3.28-3.10 (m, 1H), 3.07-2.89 (m, 1H), 2.71 (s, 3H), 2.55-2.40 (m, 1H), 1.98-1.89 (m, 1H), 1.60-1.48 (m, 1H).

Example 3.3. (S)-4-(difluoromethyl)benzyl 3,3-difluoro-4-((pyrimidin-2-ylamino)methyl)piperidine-1-carboxylate mesylate (E2-22.6$^{B'}$)

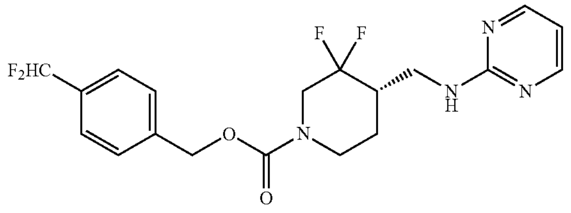

$MeSO_3H$

Step 1: (S)-4-(difluoromethyl)benzyl 3,3-difluoro-4-((pyrimidin-2-ylamino)methyl)piperidine-1-carboxylate

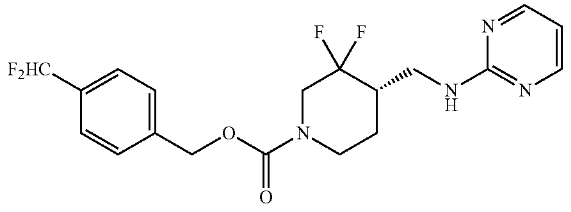

Crude (S)—N-((3,3-difluoropiperidin-4-yl)methyl)pyrimidin-2-amine trifluoroactetate (2.2 g) was dissolved in MeCN (15 mL), and then triethylamine (2.0 mL, 14.5 mmol) was added at room temperature. After the mixture was cooled down to room temperature, 4 (difluoromethyl)benzyl (2,5-dioxopyrrolidin-1-yl) carbonate (954 mg, 3.19 mmol) was added in one portion. The resulting clear solution was stirred for 2 hours at room temperature and the mixture was concentrated under reduced pressure. The concentrate was dissolved in ethyl acetate, washed with water, brine, dried over $Na_2SO_4$ and the organic phase was concentrated under reduced pressure. The concentrate was purified by column purification over silica gel (eluent: hexane/DCM/ethyl acetate, 2:2:1) to afford the title compound as a white solid (740 mg, 61% overall yield over two steps). MS (ESI) calculated for $C_{19}H_{20}F_4N_4O_2$: 412.2 m/z; found: 413.5 m/z [M+H]. $^1H$ NMR (400 MHz, $CDCl_3$) δ 8.27 (d, J=4.8 Hz, 2H), 7.51 (d, J=8.0 Hz, 2H), 7.43 (d, J=8.0 Hz, 2H), 6.65 (t, J=56.4 Hz, 1H), 6.55 (t, J=4.8 Hz, 1H), 5.37-5.31 (m, 1H), 5.22-5.13 (m, 2H), 4.51-4.02 (m, 2H), 3.84-3.75 (m, 1H), 3.59-3.49 (m, 1H), 3.15-2.77 (m, 2H), 2.36-2.19 (m, 1H), 1.92-1.83 (m, 1H), 1.64-1.54 (m, 1H).

Step 2: (S)-4-(difluoromethyl)benzyl 3,3-difluoro-4-((pyrimidin-2-ylamino)methyl)piperidine-1-carboxylate mesylate

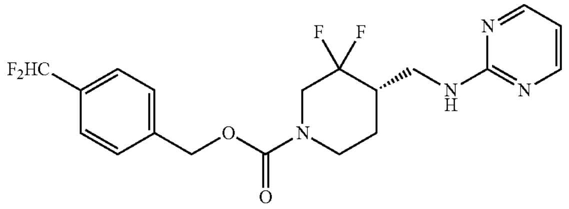 [SMILES: O=C(OCc1ccc(C(F)F)cc1)N1CC[C@@H](CNc2ncccn2)C(F)(F)C1]

$MeSO_3H$ (S)-4-(difluoromethyl)benzyl 3,3-difluoro-4-((pyrimidin-2-ylamino)methyl)piperidine-1-carboxylate (730 mg, 1.77 mmol) was dissolved in DCM/MeOH (3:1, v/v, 12 mL), and then 1.0 M methanesulfonic acid in methanol (1.77 mL, 1.77 mmol) was added. The resulting solution was stirred for 30 minutes at room temperature, and then concentrated under reduced pressure. The concentrate was triturated with ether to afford the title product as a white powder (871 mg, 97%). Chiral HPLC purity >99% ee (CHIRALPAK® IC™ column, 4.6×150 mm, particle size 5 μm, hexane/ethanol 85:15 v/v, flow rate: 1.5 mL/min, UV detection λ=254 nm, retention time=14.98 minutes). MS (ESI) calculated for $C_{19}H_{20}F_4N_4O_2$: 412.2 m/z; found: 413.5 m/z [M+H]. $^1H$ NMR (400 MHz, $CD_3OD$) δ 8.85-8.40 (m, 2H), 7.55 (d, J=8.0 Hz, 2H), 7.48 (d, J=8.0 Hz, 2H), 7.03 (t, J=5.4 Hz, 1H), 6.77 (t, J=56.0 Hz, 1H), 5.25-5.15 (m, 2H), 4.40-4.30 (m, 1H), 4.24-4.15 (m, 1H), 3.97-3.90 (m, 1H), 3.62-3.55 (m, 1H), 3.28-3.10 (m, 1H), 3.09-2.90 (m, 1H), 2.72 (s, 3H), 2.56-2.40 (m, 1H), 1.97-1.90 (m, 1H), 1.61-1.48 (m, 1H).

Example 3.4. (R)-4-chlorobenzyl 3,3-difluoro-4-((pyrimidin-2-ylamino)methyl)piperidine-1-carboxylate methanesulfonate (E1-22.3$^{B'}$)

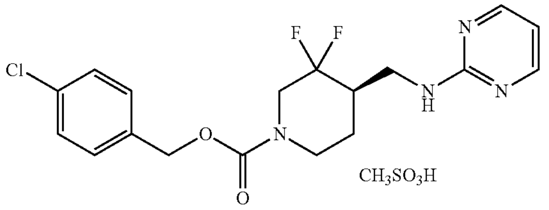

$CH_3SO_3H$

Step 1: (R)-4-chlorobenzyl 3,3-difluoro-4-((pyrimidin-2-ylamino)methyl)piperidine-1-carboxylate

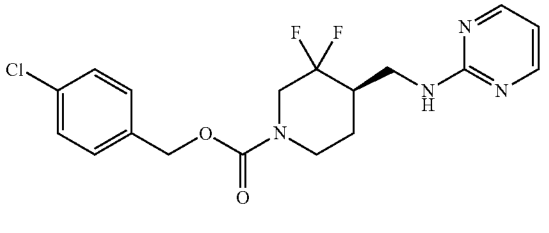 [SMILES: O=C(OCc1ccc(Cl)cc1)N1CC[C@H](CNc2ncccn2)C(F)(F)C1]

To a stirred solution of crude (R)—N-((3,3-difluoropiperidin-4-yl)methyl)pyrimidin-2-amine trifluoroacetate (1.80 g, 7.89 mmol) and triethylamine (5.5 mL, 39.5 mmol) in MeCN (20 mL) was added 4-chlorobenzyl (2,5-dioxopyrrolidin-1-yl) carbonate (2.23 g, 7.89 mmol) at room temperature. After stirring for 3 hours, the reaction mixture was concentrated under reduced pressure. The residue was dissolved in ethyl acetate, water, brine, dried over $Na_2SO_4$, and the organic phase was concentrated under reduced pressure. The concentrate was purified by column chromatography over silica gel (eluent: ethyl acetate/DCM=1:15 to ethyl acetate gradient), and further recrystallized from ethyl acetate/hexane (8 mL/9 mL, v/v) to afford the title compound as a white power (2.05 g, 66%). MS (ESI) calculated for $C_{18}H_{19}ClF_2N_4O_2$: 396.1 m/z; found: 397.5 m/z [M+H]. $^1H$ NMR (400 MHz, $CDCl_3$) δ 8.27 (d, J=4.8 Hz, 2H), 7.33 (d, J=8.4 Hz, 2H), 7.28 (d, J=8.4 Hz, 2H), 6.55 (t, J=4.8 Hz, 1H), 5.36-5.29 (m, 1H), 5.14-5.07 (m, 2H), 4.45-4.14 (m, 2H), 3.82-3.76 (m, 1H), 3.57-3.50 (m, 1H), 3.11-2.79 (m, 2H), 2.34-2.20 (m, 1H), 1.89-1.85 (m, 1H), 1.58-1.54 (m, 1H).

Step 2: (R)-4-chlorobenzyl 3,3-difluoro-4-((pyrimidin-2-ylamino)methyl)piperidine-1-carboxylate methanesulfonate

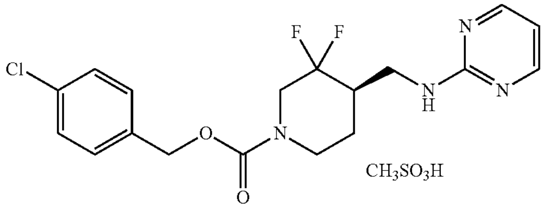

To a solution of (R)-4-chlorobenzyl 3,3-difluoro-4-((pyrimidin-2-ylamino)methyl)piperidine-1-carboxylate (1.05 g, 2.52 mmol) in DCM/methanol (1:1, 20 mL) was added 1 M methanesulfonic acid in methanol (2.52 mL, 2.52 mmol). After stirring at room temperature for 30 minutes, the reaction mixture was concentrated in vacuo and triturated with ether to afford the title compound as a white powder (1.24 g, 99%). MS (ESI) calculated for $C_{18}H_{19}ClF_2N_4O_2$: 396.1 m/z; found: 397.4 m/z [M+H]. $^1H$ NMR (400 MHz, $CD_3OD$) δ 8.78-8.46 (m, 2H), 7.38-7.34 (m, 4H), 7.04-7.02 (t, J=5.2 Hz, 1H), 5.16-5.09 (m, 2H), 4.37-4.29 (m, 1H), 4.19-4.15 (m, 1H), 3.96-3.91 (m, 1H), 3.61-3.56 (m, 1H), 3.24-2.91 (m, 2H), 2.72 (s, 3H), 2.55-2.40 (m, 1H), 1.95-1.92 (m, 1H), 1.59-1.48 (m, 1H).

Example 3.5. (R)-4-fluorobenzyl 3,3-difluoro-4-((pyrimidin-2-ylamino)methyl)piperidine-1-carboxylate methanesulfonate (E1-22.$4^{B'}$)

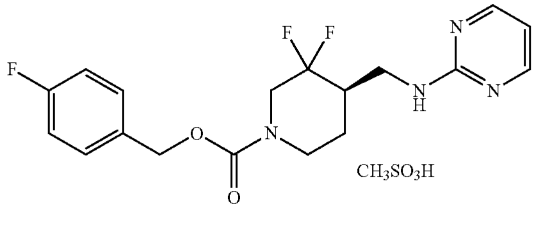

Step 1: (R)-4-fluorobenzyl 3,3-difluoro-4-((pyrimidin-2-ylamino)methyl)piperidine-1-carboxylate

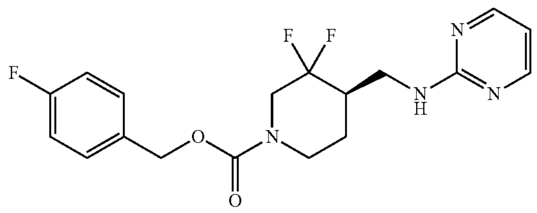 [SMILES: O=C(OCc1ccc(F)cc1)N1CC[C@H](CNc2ncccn2)C(F)(F)C1]

To a stirred solution of crude (R)—N-((3,3-difluoropiperidin-4-yl)methyl)pyrimidin-2-amine trifluoroacetate (1.80 g, approximately 7.9 mmol) and triethylamine (5.5 mL, 40 mmol) in MeCN (30 mL) was added 2,5-dioxopyrrolidin-1-yl 4-fluorobenzyl carbonate (2.10 g, 7.9 mmol) at room temperature. The mixture was allowed to warm to room temperature. After stirring at room temperature overnight, the reaction mixture was concentrated under reduced pressure. The residue was dissolved in ethyl acetate, washed with water, brine, dried over $Na_2SO_4$, and the organic phase was concentrated under reduced pressure. The concentrate was purified by column chromatography over silica gel (gradient eluent: ethyl acetate/DCM=15:1 v/v to 100% ethyl acetate), and the solid was further recrystallized from ethyl acetate/hexane (2 mL/7 mL, v/v) to afford the title compound as a white solid (2.49 g, 83%). MS (ESI) calculated for $C_{18}H_{19}F_3N_4O_2$: 380.2 m/z; found: 381.5 m/z [M+H]. $^1H$ NMR (400 MHz, $CD_3OD$) δ 8.26 (d, J=4.8 Hz, 2H), 7.42-7.37 (m, 2H), 7.12-7.05 (m, 2H), 6.60 (t, J=4.8 Hz, 1H), 5.14-5.08 (m, 2H), 4.33-4.20 (m, 1H), 4.16-4.09 (m, 1H), 3.81-3.75 (m, 1H), 3.42-3.35 (m, 1H), 3.24-3.07 (m, 1H), 3.03-2.85 (m, 1H), 2.46-2.31 (m, 1H), 1.94-1.85 (m, 1H), 1.55-1.42 (m, 1H).

Step 2: (R)-4-fluorobenzyl 3,3-difluoro-4-((pyrimidin-2-ylamino)methyl)piperidine-1-carboxylate methanesulfonate

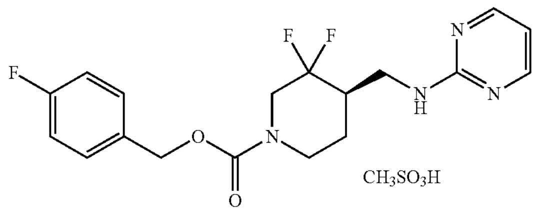

To a solution of (R)-4-fluorobenzyl 3,3-difluoro-4-((pyrimidin-2-ylamino)methyl)piperidine-1-carboxylate (2.49 g, 6.55 mmol) in DCM/methanol (2:1, v/v, 30 mL) was added 1 M methanesulfonic acid in methanol (6.55 mL, 6.55 mmol). After stirring at room temperature for 30 minutes, the reaction mixture was concentrated in vacuo and triturated with ether to afford the title compound as a white solid (2.70 g, 86%). MS (ESI) calculated for $C_{18}H_{19}F_3N_4O_2$: 380.2 m/z; found: 381.5 m/z [M+H]. $^1H$ NMR (400 MHz, $CD_3OD$) δ 8.82-8.38 (m, 2H), 7.42-7.38 (m, 2H), 7.11-7.05 (m, 2H), 7.02 (t, J=5.4 Hz, 1H), 5.16-5.08 (m, 2H), 4.38-4.27 (m, 1H), 4.21-4.13 (m, 1H), 3.96-3.89 (m, 1H), 3.61-

3.54 (m, 1H), 3.23-3.09 (m, 1H), 3.04-2.89 (m, 1H), 2.71 (s, 3H), 2.54-2.39 (m, 1H), 1.97-1.88 (m, 1H), 1.59-1.46 (m, 1H).

Example 3.6. (S)-4-fluorobenzyl 3,3-difluoro-4-((pyrimidin-2-ylamino)methyl)piperidine-1-carboxylate mesylate (E2-22.4[B'])

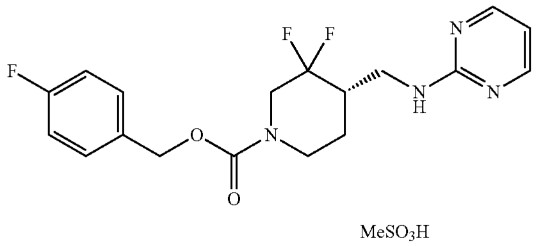 [SMILES: "MeSO3H" ; O=C(OCc1ccc(F)cc1)N1CC[C@@H](CNc2ncccn2)C(F)(F)C1]

Step 1: (S)-4-fluorobenzyl 3,3-difluoro-4-((pyrimidin-2-ylamino)methyl)piperidine-1-carboxylate

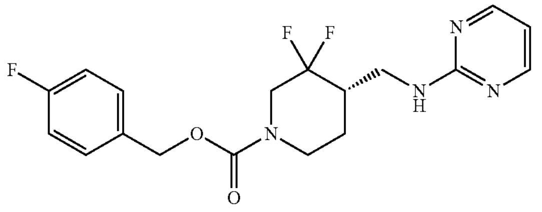 [SMILES: O=C(OCc1ccc(F)cc1)N1CC[C@@H](CNc2ncccn2)C(F)(F)C1]

Crude (S)—N-((3,3-difluoropiperidin-4-yl)methyl)pyrimidin-2-amine trifluoroactetate (2.2 g) was dissolved in MeCN (15 mL), and then triethylamine (2.0 mL, 14.5 mmol) was added at room temperature. After the mixture was cooled down to room temperature, 2,5-dioxopyrrolidin-1-yl 4-fluorobenzyl carbonate (851 mg, 3.19 mmol) was added in one portion. The resulting mixture was stirred for 2 hours at ambient temperature and the mixture was concentrated under reduced pressure. The concentrate was dissolved in ethyl acetate, washed with water, brine, dried over $Na_2SO_4$ and the organic phase was concentrated under reduced pressure. The concentrate was purified by column chromatography over silica gel (eluent: hexane/DCM/ethyl acetate=2:2:1) to afford the title compound as a white solid (860 mg, 71%). MS (ESI) calculated for $C_{18}H_{19}F_3N_4O_2$: 380.2; found: 381.5 [M+H]. $^1$H NMR (400 MHz, $CDCl_3$) δ 8.27 (d, J=4.8 Hz, 2H), 7.35-7.30 (m, 2H), 7.08-7.01 (m, 2H), 6.55 (t, J=4.8 Hz, 1H), 6.37-6.31 (m, 1H), 5.15-5.05 (m, 2H), 4.50-4.10 (m, 2H), 3.83-3.75 (m, 1H), 3.58-3.47 (m, 1H), 3.12-2.92 (m, 1H), 2.91-2.75 (m, 1H), 2.35-2.17 (m, 1H), 1.91-1.81 (m, 1H), 1.65-1.51 (m, 1H).

Step 2: (S)-4-fluorobenzyl 3,3-difluoro-4-((pyrimidin-2-ylamino)methyl)piperidine-1-carboxylate mesylate

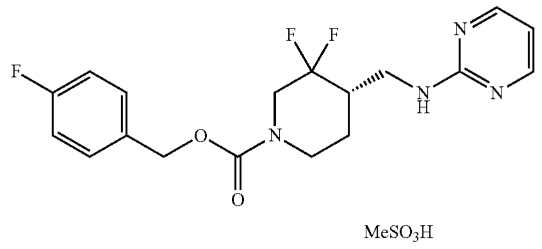 [SMILES: "MeSO3H" ; O=C(OCc1ccc(F)cc1)N1CC[C@@H](CNc2ncccn2)C(F)(F)C1]

(S)-4-fluorobenzyl 3,3-difluoro-4-((pyrimidin-2-ylamino)methyl)piperidine-1-carboxylate (800 mg, 2.10 mmol) was dissolved in DCM/MeOH (3:1, v/v, 12 mL) and then 1.0 M methanesulfonic acid in methanol (2.10 mL, 2.10 mmol) was added. The resulting solution was stirred for 30 minutes at room temperature, and then concentrated under reduced pressure.

The concentrate was triturated with ether to afford the title product as a white powder (966 mg, 97%). MS (ESI) calculated for $C_{18}H_{19}F_3N_4O_2$: 380.2 m/z; found: 381.5 m/z [M+H]. $^1$H NMR (400 MHz, $CD_3OD$) δ 8.88-8.38 (m, 2H), 7.43-7.37 (m, 2H), 7.13-7.06 (m, 2H), 7.03 (t, J=5.4 Hz, 1H), 5.16-5.08 (m, 2H), 4.38-4.26 (m, 1H), 4.21-4.13 (m, 1H), 3.96-3.89 (m, 1H), 3.61-3.54 (m, 1H), 3.29-3.08 (m, 1H), 3.05-2.88 (m, 1H), 2.72 (s, 3H), 2.55-2.39 (m, 1H), 1.97-1.88 (m, 1H), 1.59-1.46 (m, 1H).

Example 3.7. (R)-4-ethylbenzyl 3,3-difluoro-4-((pyrimidin-2-ylamino)methyl)piperidine-1-carboxylate methanesulfonate (E1-22.5[B'])

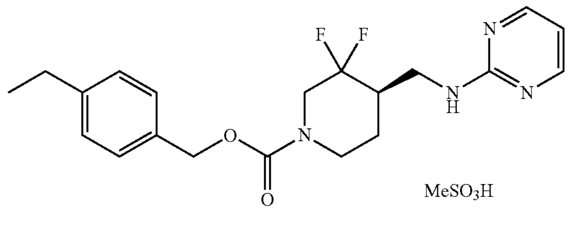 [SMILES: "MeSO3H" ; CCc1ccc(COC(=O)N2CC[C@H](CNc3ncccn3)C(F)(F)C2)cc1]

Step 1: (R)-4-ethylbenzyl 3,3-difluoro-4-((pyrimidin-2-ylamino)methyl)piperidine-1-carboxylate

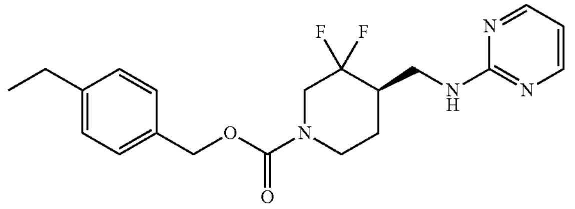 [SMILES: CCc1ccc(COC(=O)N2CC[C@H](CNc3ncccn3)C(F)(F)C2)cc1]

To a solution of crude (R)—N-((3,3-difluoropiperidin-4-yl)methyl)pyrimidin-2-amine trifluoroacetate (2.72 g, approximately 12 mmol) in $CH_3CN$ (30 mL) was added TEA (8.3 mL, 60 mmol) and 2,5-dioxopyrrolidin-1-yl 4-ethylbenzyl carbonate (3.3 g, 12 mmol) at room temperature. After stirring for 3 hours, the solvent was removed, and the concentrate was dissolved in ethyl acetate. The organic phase was washed with water, brine, dried over $Na_2SO_4$ and concentrated in vacuo. The concentrate was purified by column chromatography over silica gel (eluent: DCM/ethyl acetate=10:1 to 3:1 v/v) to give the title compound as a white solid (3.80 g, 71%). MS (ESI) calculated for $C_{20}H_{24}F_2N_4O_2$: 390.2 m/z; found: 391.5 m/z [M+H]. $^1H$ NMR (400 MHz, $CDCl_3$) δ 8.27 (d, J=4.8 Hz, 2H), 7.27 (d, J=8.0 Hz, 2H), 7.20 (d, J=8.0 Hz, 2H), 6.55 (t, J=4.80 Hz, 1H), 5.36-5.29 (m, 1H), 5.13-5.08 (m, 2H), 4.55-4.16 (m, 2H), 3.83-3.75 (m, 1H), 3.57-3.49 (m, 1H), 3.11-2.91 (m, 1H), 2.89-2.74 (m, 1H), 2.65 (q, J=7.6 Hz, 2H), 2.35-2.19 (m, 1H), 1.92-1.79 (m, 1H), 1.65-1.52 (m, 1H), 1.24 (t, J=8.0 Hz, 3H).

Step 2: (R)-4-ethylbenzyl 3,3-difluoro-4-((pyrimidin-2-ylamino)methyl)piperidine-1-carboxylate methanesulfonate

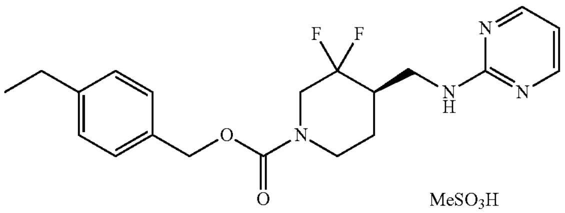 [SMILES: "MeSO3H" ; CCc1ccc(COC(=O)N2CC[C@H](CNc3ncccn3)C(F)(F)C2)cc1]

To a solution of (R)-4-ethylbenzyl 3,3-difluoro-4-((pyrimidin-2-ylamino)methyl)piperidine-1-carboxylate (3.80 g, 9.74 mmol) in DCM and MeOH (10:1, 44 mL) was added 1.0 M $CH_3SO_3H$ in methanol (9.75 mL, 9.75 mmol) at room temperature. After stirring for 30 minutes, the reaction mixture was concentrated in vacuo and triturated with $Et_2O$ to give the desired salt as a white solid (4.02 g, 85%). MS (ESI) calculated for $C_{20}H_{24}F_2N_4O_2$: 390.2 m/z; found: 391.5 m/z [M+H]. $^1H$ NMR (400 MHz, $CD_3OD$) δ 8.86-8.36 (m, 2H), 7.23 (d, J=8.0 Hz, 2H), 7.16 (d, J=8.0 Hz, 2H), 6.98 (t, J=5.6 Hz, 1H), 5.06 (s, 2H), 4.38-4.26 (m, 1H), 4.21-4.13 (m, 1H), 3.96-3.87 (m, 1H), 3.61-3.54 (m, 1H), 3.26-3.08 (m, 1H), 3.05-2.87 (m, 1H), 2.71 (s, 3H), 2.64 (q, J=7.6 Hz, 2H), 2.50-2.39 (m, 1H), 1.97-1.87 (m, 1H), 1.59-1.47 (m, 1H), 1.18.

Example 3.8. (R)-2,3-dihydro-1H-inden-2-yl 3,3-difluoro-4-((pyrimidin-2-ylamino)methyl)piperidine-1-carboxylate methanesulfonate (III-E1-22.$1^{B'}$)

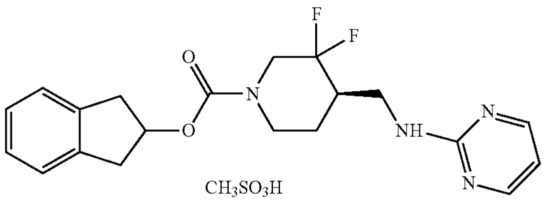

Step 1: (R)-2,3-dihydro-1H-inden-2-yl 3,3-difluoro-4-((pyrimidin-2-ylamino)methyl)piperidine-1-carboxylate

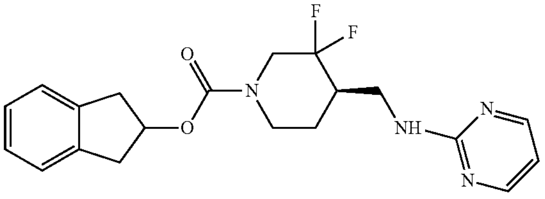 [SMILES: O=C(OC1Cc2ccccc2C1)N1CC[C@H](CNc2ncccn2)C(F)(F)C1]

To a solution of (R)—N-((3,3-difluoropiperidin-4-yl)methyl) pyrimidin-2-amine trifluoroacetate salt (crude, 8.5 g, 25 mmol) in $CH_3CN$ (82 mL) was added triethylamine (20 mL) and 2,3-dihydro-1H-inden-2-yl (2,5-dioxopyrrolidin-1-yl) carbonate (6.9 g, 25 mmol). The resulting mixture was stirred at room temperature. After stirring for 3 hours, the solvent was removed under reduced pressure. The concentrate was dissolved in ethyl acetate, washed with water, brine, dried over $Na_2SO_4$ and the organic phase was concentrated under reduced pressure. The residue was purified by column chromatography over silica gel (eluent: ethyl acetate/DCM=1:10 to 1:4 v/v) to afford the title compound as a light brown solid (8.3 g, 86%). MS (ESI) calculated for $C_{20}H_{22}F_2N_4O_2$: 388.2 m/z; found: 389.4 m/z [M+H]. $^1H$ NMR (400 MHz, $CDCl_3$): δ 8.27 (d, J=4.8 Hz, 2H), 7.23-7.17 (m, 4H), 6.54 (d, J=4.8 Hz, 1H), 6.52-6.47 (m, 1H), 5.37-5.34 (m, 1H), 4.49-3.98 (m, 2H), 3.81-3.74 (m, 1H), 3.55-3.48 (m, 1H), 3.36-3.30 (m, 2H), 3.06-3.02 (m, 2H), 2.98-2.90 (m, 1H), 2.82-2.75 (m, 1H), 2.28-2.19 (m, 1H), 1.87-1.77 (m, 1H), 1.63-1.51 (m, 1H).

Step 2: (R)-2,3-dihydro-1H-inden-2-yl 3,3-difluoro-4-((pyrimidin-2-ylamino) methyl) piperidine-1-carboxylate methanesulfonate

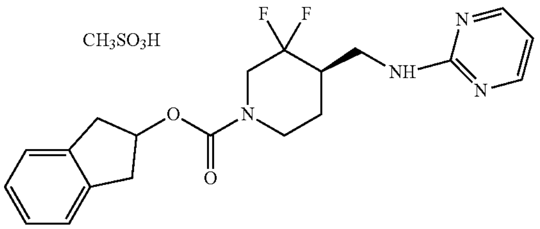 [SMILES: O=C(OC1Cc2ccccc2C1)N1CC[C@H](CNc2ncccn2)C(F)(F)C1 ; "CH3SO3H"]

To a solution of (R)-2,3-dihydro-1H-inden-2-yl 3,3-difluoro-4-((pyrimidin-2-ylamino)methyl)piperidine-1-carboxylate (6.2 g, 16 mmol) in DCM/methanol (2:1 v/v, 60 mL) was added 1.0 M methanesulfonic acid in methanol (16 mL, 16 mmol) at room temperature. After stirring for 30 minutes, the reaction mixture was concentrated in vacuo and triturated with $Et_2O$ to afford the title compound as a white solid (7.2 g, 93%). MS (ESI) calculated for $C_{20}H_{22}F_2N_4O_2$: 388.2 m/z; found: 389.5 m/z [M+H]. $^1H$ NMR (400 MHz, $CD_3OD$) δ 8.82-8.37 (m, 2H), 7.23-7.21 (m, 2H), 7.17-7.13 (m, 2H), 7.02 (d, J=5.2 Hz, 1H), 5.45-5.40 (m, 1H), 4.38-3.96 (m, 2H), 3.93-3.88 (m, 1H), 3.59-3.53 (m, 1H), 3.33-3.27 (m, 2H), 3.18-3.08 (m, 1H), 3.02-3.01 (m, 1H), 2.98-2.97 (m, 1H), 2.94-2.88 (m, 1H), 2.71 (s, 3H), 2.49-2.36 (m, 1H), 1.94-1.84 (m, 1H), 1.57-1.39 (m, 1H).

Example 3.9. (R)-4-methylbenzyl 3,3-difluoro-4-((pyridin-4-ylamino)methyl)piperidine-1-carboxylate methanesulfonate (E1-38.2[B'])

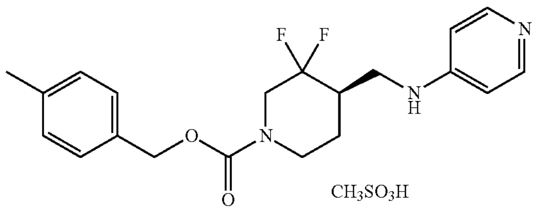

Step 1: (R)-tert-butyl 3,3-difluoro-4-((pyridin-4-ylamino)methyl)piperidine-1-carboxylate

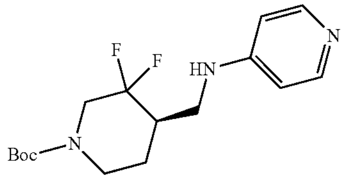 [SMILES: CC(C)(C)OC(=O)N1CC[C@H](CNc2ccncc2)C(F)(F)C1]

To a suspension of (R)-tert-butyl 4-(aminomethyl)-3,3-difluoropiperidine-1-carboxylate (5.00 g, 20.0 mmol), 4-bromopyridine hydrochloride (4.27 g, 22.0 mmol) and $Cs_2CO_3$ (13.0 g, 40.0 mmol) in 1.4-dioxane (80 mL) was added Pd-G1 (160 mg, 0.2 mmol) and Brettphos (160 mg, 0.3 mmol) consecutively under $N_2$ atmosphere. The mixture was stirred at 100° C. for 4 hours and allowed to cool to room temperature. The mixture was concentrated under reduced pressure, diluted with ethyl acetate, washed with water, brine, dried over $Na_2SO_4$, and the organic phase was concentrated under reduced pressure. The concentrate was purified by column chromatography over silica gel (gradient eluent: acetone/hexane) to afford the title compound as a yellow solid (1.83 g, 28%). MS (ESI) calculated for $C_{16}H_{23}F_2N_3O_2$: 327.2 m/z; found: 328.4 m/z [M+H]. $^1H$ NMR (400 MHz, $CDCl_3$) δ 8.20 (d, J=6.0 Hz, 2H), 6.45 (d, J=6.4 Hz, 2H), 4.48-4.40 (m, 1H), 4.40-4.05 (m, 2H), 3.67-3.58 (m, 1H), 3.24-3.13 (m, 1H), 3.06-2.65 (m, 2H), 2.22-2.06 (m, 1H), 1.87-1.80 (m, 1H), 1.62-1.52 (m, 1H), 1.47 (s, 9H).

Step 2: (R)—N-((3,3-difluoropiperidin-4-yl)methyl)pyridin-4-amine trifluoroacetate

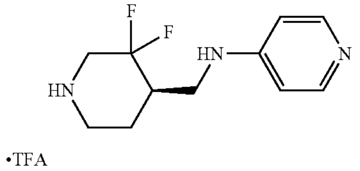 [SMILES: FC1(F)CNCC[C@@H]1CNc1ccncc1]

A mixture of (R)-tert-butyl 3,3-difluoro-4-((pyridin-4-ylamino)methyl)piperidine-1-carboxylate (1.83 g, 5.59 mmol) and trifluoroacetic acid (10 mL) in DCM (20 mL) was stirred at room temperature for one hour. The mixture was concentrated under reduced pressure to afford the crude title compound as a yellow oil, which was used in the next step without further purification.

Step 3: (R)-4-methylbenzyl 3,3-difluoro-4-((pyridin-4-ylamino)methyl)piperidine-1-carboxylate

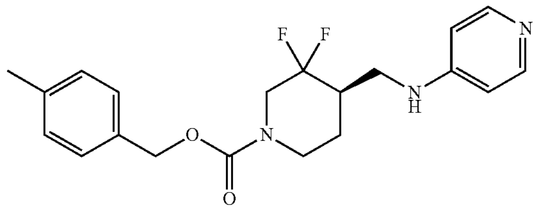 [SMILES: Cc1ccc(COC(=O)N2CC[C@H](CNc3ccncc3)C(F)(F)C2)cc1]

To a stirred solution of crude (R)—N-((3,3-difluoropiperidin-4-yl)methyl)pyridin-4-amine trifluoroacetate (approximately 5.59 mmol) in MeCN (20 mL) was added triethylamine (4.0 mL, 28.0 mmol). Then, 2,5-dioxopyrrolidin-1-yl 4-methylbenzyl carbonate (1.47 g, 5.59 mmol) was added at 0-5° C. The mixture was allowed to warm up to room temperature. After stirring at room temperature for 3 hours, the reaction mixture was concentrated under reduced pressure. The residue was dissolved in ethyl acetate, washed with brine, water, dried over $Na_2SO_4$, and the organic phase concentrated under reduced pressure. The concentrate was purified by column chromatography over silica gel (eluent: DCM/methanol=20:1 to 10:1 v/v) to afford the title compound as a white solid (1.05 g, 50%). MS (ESI) calculated for $C_{20}H_{23}F_2N_3O_2$: 375.2 m/z; found: 376.5 m/z [M+H]. $^1H$ NMR (400 MHz, $CD_3OD$) δ 8.06 (d, J=7.2 Hz, 2H), 7.26 (d, J=8.0 Hz, 2H), 7.19 (d, J=8.0 Hz, 2H), 6.84 (d, J=7.2 Hz, 2H), 5.12-5.06 (m, 2H), 4.42-4.28 (m, 1H), 4.23-4.16 (m, 1H), 3.76-3.69 (m, 1H), 3.37-3.33 (m, 1H), 3.26-3.09 (m, 1H), 3.06-2.89 (m, 1H), 2.44-2.36 (m, 1H), 2.33 (s, 3H), 1.95-1.91 (m, 1H), 1.58-1.48 (m, 1H).

Step 4: (R)-4-methylbenzyl 3,3-difluoro-4-((pyridin-4-ylamino)methyl)piperidine-1-carboxylate methanesulfonate

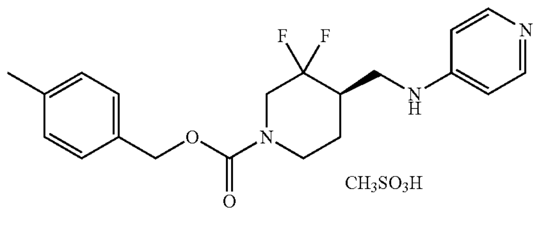

To a solution of (R)-4-methylbenzyl 3,3-difluoro-4-((pyridin-4-ylamino)methyl)piperidine-1-carboxylate (1.05 g, 2.80 mmol) in DCM/methanol (2:1, v/v 10 mL) was added 1 M methanesulfonic acid in methanol (2.8 mL, 2.80 mmol). After stirring at room temperature for 30 minutes, the reaction mixture was concentrated in vacuo and triturated with ether to afford the title compound as an off-white solid (1.00 g, 77%). MS (ESI) calculated for $C_{20}H_{23}F_2N_3O_2$: 375.2 m/z; found: 376.3 m/z [M+H]. $^1H$ NMR (400 MHz, $CD_3OD$) 8.15 (d, J=7.2 Hz, 1H), 8.01 (d, J=7.2 Hz, 1H), 7.24 (d, J=8.0 Hz, 2H), 7.17 (d, J=8.0 Hz, 2H), 6.94-6.88 (m, 2H), 5.12-5.06 (m, 2H), 4.40-4.27 (m, 1H), 4.22-4.14 (m, 1H), 3.76-3.70 (m, 1H), 3.40-3.35 (m, 1H), 3.24-3.08 (m, 1H), 3.04-2.90 (m, 1H), 2.71 (s, 3H), 2.45-2.35 (m, 1H), 2.33 (s, 3H), 1.97-1.89 (m, 1H), 1.59-1.49 (m, 1H).

Example 3.10. (R)-4-fluorobenzyl 3,3-difluoro-4-((pyridin-4-ylamino)methyl)piperidine-1-carboxylate mesylate (E1-38.4[B'])

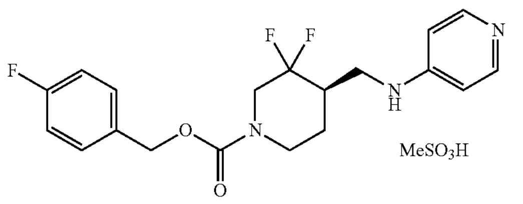 [SMILES: "MeSO3H" ; O=C(OCc1ccc(F)cc1)N1CC[C@H](CNc2ccncc2)C(F)(F)C1]

Step 1: (R)-4-fluorobenzyl 3,3-difluoro-4-((pyridin-4-ylamino)methyl)piperidine-1-carboxylate

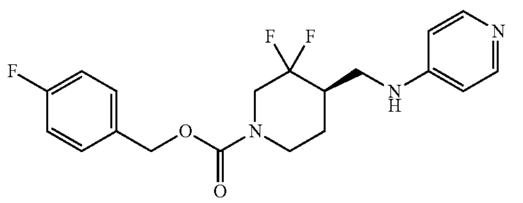 [SMILES: O=C(OCc1ccc(F)cc1)N1CC[C@H](CNc2ccncc2)C(F)(F)C1]

To a stirred solution of crude (R)—N-((3,3-difluoropiperidin-4-yl)methyl)pyridin-4-amine trifluoroacetate (6.10 mmol) and triethylamine (4 mL) in acetonitrile (20 mL) was added 2,5-dioxopyrrolidin-1-yl 4-fluorobenzyl carbonate (1.64 g, 6.10 mmol) at room temperature. After stirring at room temperature for 2 hours, the reaction mixture was concentrated under reduced pressure. The residue was dissolved in ethyl acetate, washed with water, brine, dried over $Na_2SO_4$, and the organic phase was concentrated to afford the crude product. The crude product was purified by chromatography over silica gel (ethyl acetate/methanol=10:1 v/v with 5% TEA) to afford the title compound as an off-white solid (2.03 g, 88%). MS (ESI) calculated for $C_{19}H_{20}F_3N_3O_2$: 379.4 m/z; found: 380.5 m/z [M+H]. $^1H$ NMR (400 MHz, $CD_3OD$) δ 8.01 (d, J=6.8 Hz, 2H), 7.42-7.38 (m, 2H), 7.11-7.07 (m, 2H), 6.61 (d, J=6.4 Hz, 2H), 5.15-5.09 (m, 2H), 4.37-4.25 (m, 1H), 4.19-4.12 (m, 1H), 3.65-3.61 (m, 1H), 3.24-3.10 (m, 2H), 3.04-2.87 (m, 1H), 2.38-2.24 (m, 1H), 1.98-1.89 (m, 1H), 1.55-1.45 (m, 1H).

Step 2: (R)-4-fluorobenzyl 3,3-difluoro-4-((pyridin-4-ylamino)methyl)piperidine-1-carboxylate mesylate

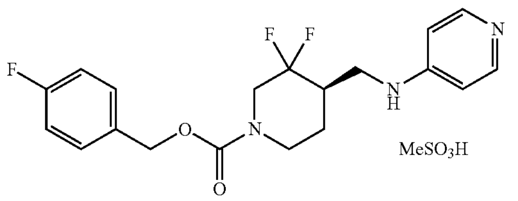 [SMILES: "MeSO3H" ; O=C(OCc1ccc(F)cc1)N1CC[C@H](CNc2ccncc2)C(F)(F)C1]

To a solution of (R)-4-fluorobenzyl 3,3-difluoro-4-((pyridin-4-ylamino)methyl)piperidine-1-carboxylate (2.03 g, 5.37 mmol) in DCM/MeOH (1:1, 10 mL) was added 1.0 M methanesulfonic acid in methanol (5.37 mL, 5.37 mmol) at room temperature. After stirring for 30 minutes, the solvent was removed under reduced pressure, and the concentrate was treated with diethyl ether to afford the title product as an off-white solid (2.41 g, 95%). MS (ESI) calculated for $C_{19}H_{20}F_3N_3O_2$: 379.4 m/z; found: 380.5 m/z [M+H]. $^1H$ NMR (400 MHz, $CD_3OD$) δ 8.15 (d, J=7.2 Hz, 1H), 8.01 (d, J=6.8 Hz, 1H), 7.43-7.37 (m, 2H), 7.13-7.05 (m, 2H), 6.95-6.88 (m, 1H), 5.16-5.08 (m, 2H), 4.40-4.27 (m, 1H), 4.22-4.14 (m, 1H), 3.76-3.70 (m, 1H), 3.41-3.34 (m, 1H), 3.26-3.09 (m, 1H), 3.07-2.88 (m, 1H), 2.71 (s, 3H), 2.47-2.31 (m, 1H), 1.98-1.89 (m, 1H), 1.60-1.47 (m, 1H).

Example 3.11. (S)-4-methylbenzyl 3,3-difluoro-4-((pyridin-4-ylamino)methyl)piperidine-1-carboxylate mesylate (E2-38.2[B'])

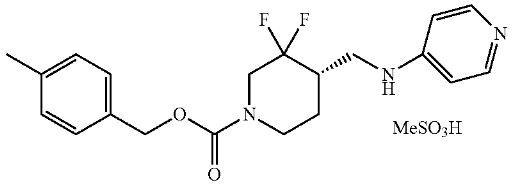 [SMILES: "MeSO3H" ; Cc1ccc(COC(=O)N2CC[C@@H](CNc3ccncc3)C(F)(F)C2)cc1]

Step 1: (S)-tert-butyl 3,3-difluoro-4-((pyridin-4-ylamino)methyl)piperidine-1-carboxylate

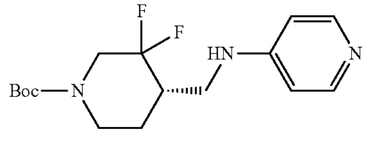 [SMILES: CC(C)(C)OC(=O)N1CC[C@@H](CNc2ccncc2)C(F)(F)C1]

To a suspension of (S)-tert-butyl 4-(aminomethyl)-3,3-difluoropiperidine-1-carboxylate (2.0 g, 8.0 mmol), 4-bromopyridine hydrochloride (1.9 g, 9.6 mmol), sodium sulfate (3.7 g) and $Cs_2CO_3$ (6.5 g, 20 mmol) in 1,4-dioxane (20 mL) was added Pd-G1 (128 mg, 0.16 mmol) and Brettphos (129 mg, 0.24 mmol) consecutively under $N_2$ atmosphere. The mixture was stirred at 110° C. for 23 hours, allowed to cool to room temperature and filtered. The filtrate was concentrated under reduced pressure. The crude product was purified by column chromatograph over silica gel (eluent:

EtOAc/MeOH 20:1 v/v with 5% TEA) to afford the title compound as a yellow solid (0.95 g, 36%). MS (ESI) calculated for $C_{16}H_{23}F_2N_3O_2$: 327.4 m/z; found: 328.4 m/z [M+H]. $^1H$ NMR (400 MHz, $CDCl_3$) δ 8.220 (d, J=6.4 Hz, 2H), 6.44 (d, J=6.4 Hz, 2H), 4.45-4.37 (m, 1H), 4.37-4.10 (m, 2H), 3.66-3.60 (m, 1H), 3.24-3.14 (m, 1H), 3.06-2.65 (m, 2H), 2.22-2.06 (m, 1H), 1.88-1.80 (m, 1H), 1.64-1.51 (m, 1H), 1.47 (s, 9H).

Step 2: (S)—N-((3,3-difluoropiperidin-4-yl)methyl) pyridin-4-amine trifluoroacetate

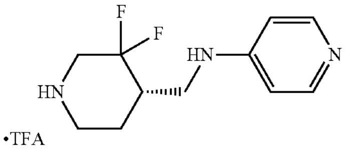 [SMILES: FC1(F)CNCC[C@H]1CNc1ccncc1]

•TFA

A mixture of (S)-tert-butyl 3,3-difluoro-4-((pyridin-4-ylamino)methyl)piperidine-1-carboxylate (950 mg, 2.90 mmol) and trifluoroacetic acid (5 mL) in DCM (10 mL) was stirred at room temperature for one hour. The mixture was concentrated under reduced pressure to afford the crude title compound as a yellow oil, which was used in the next step without further purification.

Step 3: (S)-4-methylbenzyl 3,3-difluoro-4-((pyridin-4-ylamino)methyl)piperidine-1-carboxylate

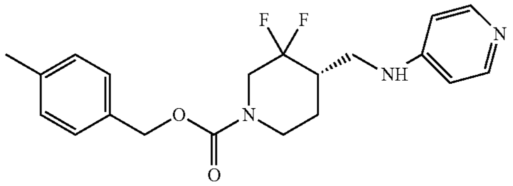 [SMILES: Cc1ccc(COC(=O)N2CC[C@@H](CNc3ccncc3)C(F)(F)C2)cc1]

To a stirred solution of the above crude (S)—N-((3,3-difluoropiperidin-4-yl)methyl)pyridin-4-amine trifluoroacetate (approximately 2.90 mmol) and triethylamine (2.0 mL, 14.5 mmol) in acetonitrile (10 mL) was added 2,5-dioxopyrrolidin-1-yl 4-methylbenzyl carbonate (764 mg, 2.90 mmol) at room temperature. After stirring at room temperature overnight, the reaction mixture was concentrated under reduced pressure. The residue was dissolved in ethyl acetate, washed with water, half-brine, dried over sodium sulfate, and the organic phase was concentrated under reduced pressure. The crude product was purified by column chromatograph on silica gel (eluent: EtOAc/MeOH 15:1 v/v with 5% TEA) to give a solid which was further triturated with hexane to afford the title compound as an off-white solid (265 mg, 26%). MS (ESI) calculated for $C_{20}H_{23}F_2N_3O_2$: 375.4 m/z; found: 376.5 m/z [M+H]. $^1H$ NMR (400 MHz, $CD_3OD$) δ 7.99 (d, J=6.8 Hz, 2H), 7.24 (d, J=8.0 Hz, 2H), 7.17 (d, J=8.0 Hz, 2H), 6.55 (d, J=6.4 Hz, 2H), 5.12-5.06 (m, 2H), 4.36-4.23 (m, 1H), 4.19-4.11 (m, 1H), 3.64-3.58 (m, 1H), 3.25-3.08 (m, 2H), 3.01-2.85 (m, 1H), 2.33 (s, 3H), 2.32-2.21 (m, 1H), 1.98-1.89 (m, 1H), 1.54-1.44 (m, 1H).

Step 4: (S)-4-methylbenzyl 3,3-difluoro-4-((pyridin-4-ylamino)methyl)piperidine-1-carboxylate mesylate

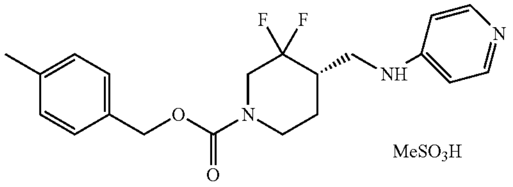 [SMILES: "MeSO3H" ; Cc1ccc(COC(=O)N2CC[C@@H](CNc3ccncc3)C(F)(F)C2)cc1]

$MeSO_3H$

To a solution of (S)-4-methylbenzyl 3,3-difluoro-4-((pyridin-4-ylamino)methyl)piperidine-1-carboxylate (265 mg, 0.71 mmol) in DCM/MeOH (1:1, 6 mL) was added 1.0 M methanesulfonic acid in methanol (0.71 mL, 0.71 mmol) at room temperature. After stirring for 30 minutes, the solvent was concentrated under reduced pressure. The concentrate was treated with diethyl ather to afford the title product as an off-white powder (323 mg, 97%). MS (ESI) calculated for $C_{20}H_{23}F_2N_3O_2$: 375.4 m/z; found: 376.5 m/z [M+H]. $^1H$ NMR (400 MHz, $CD_3OD$) δ 8.15 (d, J=7.2 Hz, 1H), 8.00 (d, J=7.2 Hz, 1H), 7.24 (d, J=8.0 Hz, 2H), 7.17 (d, J=8.0 Hz, 2H), 6.95-6.87 (m, 1H), 5.13-5.06 (m, 2H), 4.41-4.26 (m, 1H), 4.22-4.14 (m, 1H), 3.77-3.70 (m, 1H), 3.41-3.34 (m, 1H), 3.25-3.09 (m, 1H), 3.06-2.88 (m, 1H), 2.70 (s, 3H), 2.46-2.34 (m, 1H), 2.33 (s, 3H), 1.97-1.88 (m, 1H), 1.60-1.48 (m, 1H).

Example 3.11. (R)-2,3-dihydro-1H-inden-2-yl 3,3-difluoro-4-((pyridin-4-ylamino)methyl)piperidine-1-carboxylate mesylate (III-E1-38.1$^{B'}$)

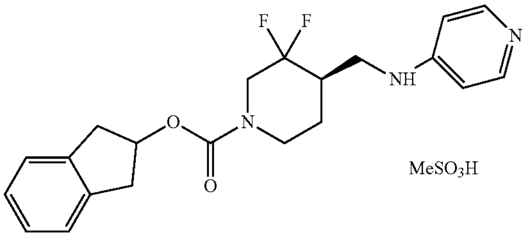 [SMILES: "MeSO3H" ; O=C(OC1Cc2ccccc2C1)N1CC[C@H](CNc2ccncc2)C(F)(F)C1]

$MeSO_3H$

Step 1: (R)—N-((3,3-difluoropiperidin-4-yl)methyl) pyridin-4-amine trifluoroacetate

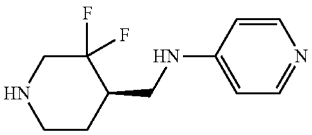

TFA

A solution of (R)-tert-butyl 3,3-difluoro-4-((pyridin-4-ylamino)methyl)piperidine-1-carboxylate (2.02 g, 6.20 mmol) and TFA (10 mL) in DCM (20 mL) was stirred at room temperature for 2 hours. The mixture was concentrated under reduced pressure to afford the crude TFA salt as a yellow oil, which was used in the next step without further purification.

Step 2: (R)-2,3-dihydro-1H-inden-2-yl 3,3-difluoro-4-((pyridin-4-ylamino)methyl)piperidine-1-carboxylate

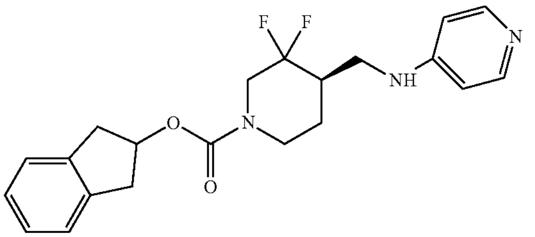 [SMILES: O=C(OC1Cc2ccccc2C1)N1CC[C@H](CNc2ccncc2)C(F)(F)C1]

To a stirred solution of the crude (R)—N-((3,3-difluoropiperidin-4-yl)methyl)pyridin-4-amine trifluoroacetate (approximately 6.2 mmol) and triethylamine (5.0 mL, 31 mmol) in acetonitrile (26 mL) was added 2,3-dihydro-1H-inden-2-yl (2,5-dioxopyrrolidin-1-yl) carbonate (1.70 g, 6.2 mmol) at room temperature. After stirring at room temperature for 3 hours, the reaction mixture was concentrated under reduced pressure. The residue was dissolved in ethyl acetate, washed with water, brine, dried over $Na_2SO_4$, and the organic phase was concentrated under reduced pressure. The crude product was purified by column chromatograph on silica gel (eluent: EtOAc/MeOH=15:1 v/v containing 5% TEA) to afford the title compound as an off-white solid (1.01 g, 42%). MS (ESI) calculated for $C_{21}H_{23}F_2N_3O_2$: 387.4 m/z; found: 388.5 m/z [M+H]. $^1H$ NMR (400 MHz, $CD_3OD$) δ 7.99 (d, J=6.4 Hz, 2H), 7.24-7.20 (m, 2H), 7.18-7.13 (m, 2H), 6.54 (d, J=6.4 Hz, 2H), 5.46-5.41 (m, 1H), 4.36-3.93 (m, 2H), 3.62-3.56 (m, 1H), 3.34-3.25 (m, 2H), 3.19-3.06 (m, 2H), 3.04-2.96 (m, 2H), 2.92-2.84 (m, 1H), 2.34-2.17 (m, 1H), 1.97-1.81 (m, 1H), 1.55-1.36 (m, 1H).

Step 3: (R)-2,3-dihydro-1H-inden-2-yl 3,3-difluoro-4-((pyridin-4-ylamino)methyl)piperidine-1-carboxylate mesylate

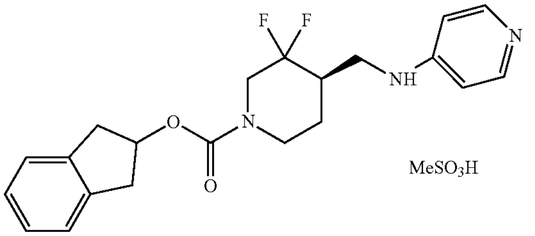 [SMILES: "MeSO3H" ; O=C(OC1Cc2ccccc2C1)N1CC[C@H](CNc2ccncc2)C(F)(F)C1]

To a solution of (R)-2,3-dihydro-1H-inden-2-yl 3,3-difluoro-4-((pyridin-4-ylamino)methyl)piperidine-1-carboxylate (1.01 g, 2.61 mmol) in DCM/MeOH (1:1, 10 mL) was added 1.0 M methanesulfonic acid in methanol (2.61 mL, 2.61 mmol) at room temperature. After stirring for 30 minutes, the solvent was concentrated under reduced pressure. The concentrate was treated with diethyl ether to afford the title product as an off-white solid (1.04 g, 83%). MS (ESI) calculated for $C_{21}H_{23}F_2N_3O_2$: 387.4 m/z; found: 388.5 m/z [M+H]. $^1H$ NMR (400 MHz, $CD_3OD$) δ 8.14 (d, J=7.2 Hz, 1H), 8.00 (d, J=7.2 Hz, 1H), 7.25-7.20 (m, 2H), 7.18-7.13 (m, 2H), 6.94-6.86 (m, 2H), 5.46-5.41 (m, 1H), 4.42-3.95 (m, 2H), 3.75-3.68 (m, 1H), 3.40-3.34 (m, 1H), 3.30-3.25 (m, 2H), 3.22-3.07 (m, 1H), 3.04-2.86 (m, 3H), 2.70 (s, 3H), 2.43-2.27 (m, 1H), 1.98-1.80 (m, 1H), 1.60-1.40 (m, 1H).

Example 3.12. (R)-4-(difluoromethyl)benzyl 3,3-difluoro-4-((pyridin-4-ylamino)methyl)piperidine-1-carboxylate mesylate (E1-38.6$^{B'}$)

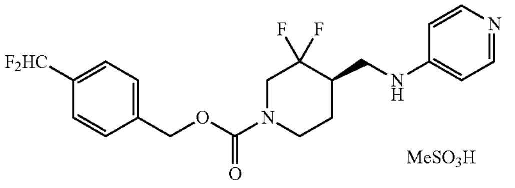 [SMILES: "MeSO3H" ; O=C(OCc1ccc(C(F)F)cc1)N1CC[C@H](CNc2ccncc2)C(F)(F)C1]

Step 1: (R)—N-((3,3-difluoropiperidin-4-yl)methyl)pyridin-4-amine trifluoroacetate

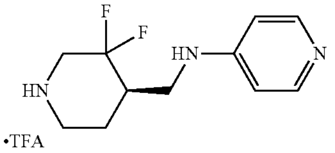 [SMILES: FC1(F)CNCC[C@@H]1CNc1ccncc1]

A solution of (R)-tert-butyl 3,3-difluoro-4-((pyridin-4-ylamino)methyl)piperidine-1-carboxylate (1.30 g, 4.0 mmol) and trifluoroacetic acid (6 mL) in DCM (13 mL) was stirred at room temperature for one hour. The mixture was concentrated under reduced pressure to afford the crude title compound as a yellow oil, which was used in the next step without further purification.

Step 3: (R)-4-(difluoromethyl)benzyl 3,3-difluoro-4-((pyridin-4-ylamino)methyl)piperidine-1-carboxylate

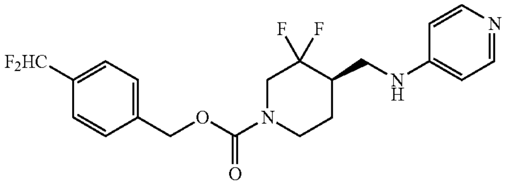 [SMILES: O=C(OCc1ccc(C(F)F)cc1)N1CC[C@H](CNc2ccncc2)C(F)(F)C1]

To a stirred solution of the above crude (R)—N-((3,3-difluoropiperidin-4-yl)methyl)pyridin-4-amine trifluoroacetate (ca. 4.0 mmol) in acetonitrile (13 mL) was added triethylamine (2.5 mL, 20 mmol). Then 4-(difluoromethyl)benzyl (2,5-dioxopyrrolidin-1-yl) carbonate (1.2 g, 4.0 mmol) was also added at room temperature. After stirring at room temperature overnight, the reaction mixture was concentrated under reduced pressure. The residue was diluted with ethyl acetate, washed with water, brine, dried over $Na_2SO_4$, and the organic phase was concentrated under reduced pressure. The crude product was purified by column chromatograph over silica gel (eluent: EtOAc/MeOH=15:1 v/v containing 5% TEA) to afford the title compound as an off-white solid (1.28 g, 78%). MS (ESI) calculated for $C_{20}H_{21}F_4N_3O_2$: 411.4 m/z; found: 412.4 m/z [M+H]. $^1$H NMR (400 MHz, $CD_3OD$) δ 8.01 (d, J=6.8 Hz, 2H), 7.54 (d, J=8.4 Hz, 2H), 7.48 (d, J=8.4 Hz, 2H), 6.76 (d, J=56.0 Hz, 1H), 6.60 (d, J=6.4 Hz, 2H), 5.24-5.17 (m, 2H), 4.37-4.30 (m, 1H), 4.22-4.14 (m, 1H), 3.66-3.61 (m, 1H), 3.26-3.11 (m, 2H), 3.06-2.89 (m, 1H), 2.39-2.25 (m, 1H), 1.99-1.91 (m, 1H), 1.57-1.46 (m, 1H).

Step 4: (R)-4-(difluoromethyl)benzyl 3,3-difluoro-4-((pyridin-4-ylamino)methyl)piperidine-1-carboxylatemesylate

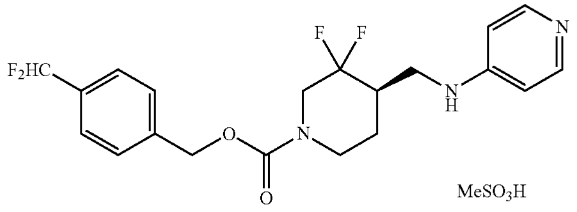 [SMILES: "MeSO3H" ; O=C(OCc1ccc(C(F)F)cc1)N1CC[C@H](CNc2ccncc2)C(F)(F)C1]

To a solution of (R)-4-(difluoromethyl)benzyl 3,3-difluoro-4-((pyridin-4-ylamino)methyl)piperidine-1-carboxylate (1.28 g, 3.11 mmol) in DCM/MeOH (1:1, 10 mL) was added 1.0 M methanesulfonic acid in methanol (3.11 mL, 3.11 mmol) at room temperature. After stirring for 30 minutes, the solvent was removed under reduced pressure. The concentrate was treated with diethyl ather to afford the title product as a white solid (1.49 g, 94%). MS (ESI) calculated for $C_{20}H_{21}F_4N_3O_2$: 411.4 m/z; found: 412.4 m/z [M+H]. $^1$H NMR (400 MHz, $CD_3OD$) δ 8.15 (d, J=7.2 Hz, 1H), 8.01 (d, J=7.2 Hz, 1H), 7.54 (d, J=8.0 Hz, 2H), 7.48 (d, J=8.0 Hz, 2H), 6.96-6.88 (m, 2H), 6.77 (t, J=56.0 Hz, 1H), 5.25-5.16 (m, 2H), 4.41-4.32 (m, 1H), 4.25-4.16 (m, 1H), 3.77-3.71 (m, 1H), 3.42-3.35 (m, 1H), 3.29-3.11 (m, 1H), 3.09-2.90 (m, 1H), 2.70 (s, 3H), 2.48-2.32 (m, 1H), 1.99-1.91 (m, 1H), 1.62-1.50 (m, 1H).

Example 3.13. (R)-4-methylbenzyl 3,3-difluoro-4-(((5-fluoropyrimidin-2-yl)amino)methyl)piperidine-1-carboxylate methanesulfonate (E1-22.28$^{B'}$)

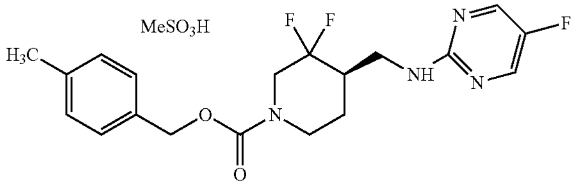 [SMILES: "MeSO3H" ; Cc1ccc(COC(=O)N2CC[C@H](CNc3ncc(F)cn3)C(F)(F)C2)cc1]

Step 1: (R)-tert-butyl 3,3-difluoro-4-(((5-fluoropyrimidin-2-yl)amino)methyl)piperidine-1-carboxylate

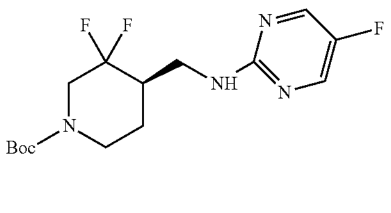 [SMILES: CC(C)(C)OC(=O)N1CC[C@H](CNc2ncc(F)cn2)C(F)(F)C1]

To a stirred mixture of (R)-tert-butyl 4-(aminomethyl)-3,3-difluoropiperidine-1-carboxylate (1.2 g, 4.8 mmol), 2-chloro-5-fluoropyrimidine (0.76 g, 5.8 mmol), and $Cs_2CO_3$ (3.9 g, 12 mmol) in t-butanol (12 mL) was added Pd-G1 (77 mg, 0.01 mmol) and Brettphos (77 mg, 0.14 mmol) consecutively under $N_2$ atmosphere. The mixture was heated to 80° C., and stirred for 23 hours. The mixture was filtered and the filtrate was concentrated under reduced pressure. The concentrate was purified by column chromatography over silica gel (eluent: hexane/ethyl acetate=3:1, v/v) to afford the title compound as a yellow solid (1.06 g, 64%). MS (ESI) calculated for $C_{15}H_{21}F_3N_4O_2$: 346.4 m/z; found: 347.1 m/z [M+H]. $^1$H NMR (400 MHz, $CDCl_3$) δ 8.17 (s, 2H), 5.31-5.25 (m, 1H), 4.45-4.00 (m, 2H), 3.79-3.71 (m, 1H), 3.53-3.43 (m, 1H), 3.05-2.88 (m, 1H), 2.81-2.66 (m, 1H), 2.30-2.14 (m, 1H), 1.86-1.78 (m, 1H), 1.62-1.50 (m, 1H), 1.46 (s, 9H).

Step 2: (R)—N-((3,3-difluoropiperidin-4-yl)methyl)-5-fluoropyrimidin-2-amine trifluoroacetate

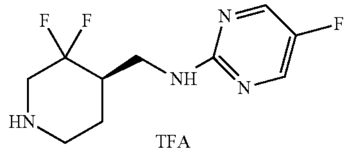 [SMILES: Fc1cnc(NC[C@H]2CCNCC2(F)F)nc1]

To a solution of (R)-tert-butyl 3,3-difluoro-4-(((5-fluoropyrimidin-2-yl)amino)methyl)piperidine-1-carboxylate (1.06 g, 3.06 mmol) in DCM (6 mL) was added trifluoroacetic acid (4 mL) at room temperature. After stirring for 2.5 hours, the mixture was concentrated under reduced pressure to give the crude title compound as a yellow oil (2.9 g). The crude title compound was used in the next step without further purification. MS (ESI) calculated for $C_{10}H_{13}F_3N_4$: 246.2 m/z; found: 247.1 m/z [M+H].

Step 3: (R)-4-methylbenzyl 3,3-difluoro-4-(((5-fluoropyrimidin-2-yl)amino)methyl)piperidine-1-carboxylate

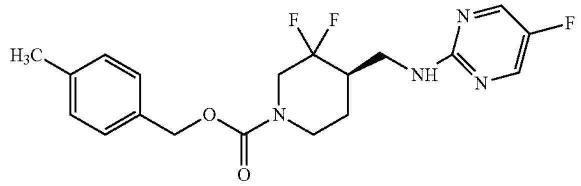 [SMILES: Cc1ccc(COC(=O)N2CC[C@H](CNc3ncc(F)cn3)C(F)(F)C2)cc1]

To a solution of crude (R)—N-((3,3-difluoropiperidin-4-yl)methyl)-5-fluoropyrimidin-2-amine trifluoroacetate (2.9 g, ca. 3.06 mmol) in acetonitrile (11 mL) was added triethylamine (4 mL, 29 mmol) and 2,5-dioxopyrrolidin-1-yl 4-methylbenzyl carbonate (0.81 g, 3.06 mmol) at room temperature. After stirring for 3 hours, the mixture was concentrated under reduced pressure. The concentrate was dissolved in DCM, washed with water, brine, dried over $Na_2SO_4$ and the organic phase concentrated in vacuo. The crude product was purified by column chromatography over silica gel (eluent: DCM/EtOAc=1:1, acetone/hexane=1:1) to give the title compound as an off-white solid (2.65 g, 83%).

MS (ESI) calculated for $C_{19}H_{21}F_3N_4O_2$: 394.4 m/z; found: 395.3 m/z [M+H]. $^1H$ NMR (400 MHz, $CDCl_3$) δ 8.17 (s, 1H), 7.25 (d, J=7.6 Hz, 2H), 7.17 (d, J=7.6 Hz, 2H), 5.30-5.24 (m, 1H), 5.13-5.07 (m, 2H), 4.50-4.10 (m, 2H), 3.79-3.71 (m, 1H), 3.52-3.44 (m, 1H), 3.09-2.93 (m, 1H), 2.87-2.76 (m, 1H), 2.35 (s, 3H), 2.31-2.17 (m, 1H), 1.88-1.77 (m, 1H).

Step 4: (R)-4-methylbenzyl 3,3-difluoro-4-(((5-fluoropyrimidin-2-yl)amino)methyl)piperidine-1-carboxylate methanesulfonate

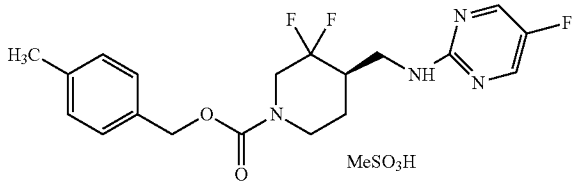 [SMILES: "MeSO3H" ; Cc1ccc(COC(=O)N2CC[C@H](CNc3ncc(F)cn3)C(F)(F)C2)cc1]

To a solution of (R)-4-methylbenzyl 3,3-difluoro-4-(((5-fluoropyrimidin-2-yl)amino)methyl)piperidine-1-carboxylate (402 mg, 1.02 mmol) in DCM/MeOH (1:1, 4 mL) was added 1.0 M methanesulfonic acid in methanol (1.02 mL, 1.02 mmol). After stirring at room temperature for 30 min, the reaction mixture was concentrated in vacuo and triturated with ether to afford the title compound as an off-white solid (450 mg, 99%). MS (ESI) calculated for $C_{19}H_{21}F_3N_4O_2$: 394.4 m/z; found: 395.3 m/z [M+H]. $^1H$ NMR (400 MHz, $CDOD_3$) δ 8.62 (s, 1H), 7.24 (d, J=8.0 Hz, 2H), 7.17 (d, J=8.0 Hz, 2H), 5.12-5.05 (m, 2H), 4.36-4.24 (m, 1H), 4.19-4.12 (m, 1H), 3.89-3.83 (m, 1H), 3.51-3.44 (m, 1H), 3.25-3.08 (m, 1H), 3.03-2.87 (m, 1H), 2.72 (s, 3H), 2.49-2.35 (m, 1H), 2.33 (s, 3H), 1.95-1.86 (s, 1H), 1.56-1.44 (m, 1H).

Example 3.14. (R)-4-methylbenzyl 3,3-difluoro-4-(((5-(trifluoromethyl)pyrimidin-2-yl)amino)methyl)piperidine-1-carboxylate methanesulfonate (E1-22.29$^{B'}$)

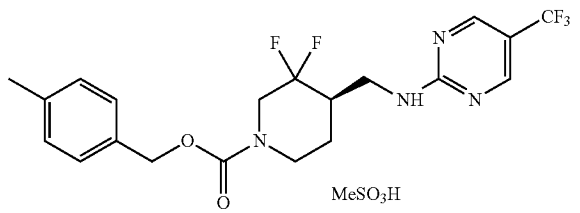 [SMILES: "MeSO3H" ; Cc1ccc(COC(=O)N2CC[C@H](CNc3ncc(C(F)(F)F)cn3)C(F)(F)C2)cc1]

Step 1: (R)-tert-butyl 3,3-difluoro-4-(((5-(trifluoromethyl)pyrimidin-2-yl)amino)methyl)piperidine-1-carboxylate

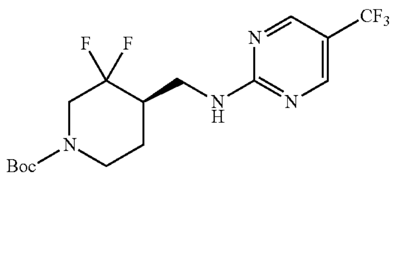 [SMILES: CC(C)(C)OC(=O)N1CC[C@H](CNc2ncc(C(F)(F)F)cn2)C(F)(F)C1]

To a solution of (R)-tert-butyl 4-(aminomethyl)-3,3-difluoropiperidine-1-carboxylate (2.00 g, 8.00 mmol) in n-BuOH (20 mL) was added 2-chloro-5-(trifluoromethyl)pyrimidine (1.48 g, 8.80 mmol) and $Cs_2CO_3$ (3.90 g, 12.00 mmol). The reaction mixture was stirred at 90° C. under $N_2$ atmosphere. After stirring for 24 hours, the reaction mixture was concentrated under reduced pressure to give the crude product, which was purified by column chromatography over silica gel (eluent: hexane/EtOAc=10:1 to 3:1, v/v) to give the title compound as a white solid (2.20 g, 69%). MS (ESI) calculated for $C_{16}H_{21}F_5N_4O_2$: 396.2 m/z; found: 397.2 m/z [M+H]. $^1H$ NMR (400 MHz, $CDCl_3$) δ 8.52-8.41 (m, 2H), 5.78-5.70 (m, 1H), 4.50-4.40 (m, 2H), 3.85-3.77 (m, 1H), 3.65-3.55 (m, 1H), 3.06-2.67 (m, 2H), 2.31-2.15 (m, 1H), 1.85-1.77 (m, 1H), 1.63-1.52 (m, 1H), 1.46 (s, 9H).

Step 2: (R)—N-((3,3-difluoropiperidin-4-yl)methyl)-5-(trifluoromethyl)pyrimidin-2-amine trifluoroacetate

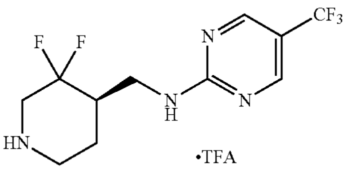 [SMILES: FC(F)(F)c1cnc(NC[C@H]2CCNCC2(F)F)nc1]

To a solution of (R)-tert-butyl 3,3-difluoro-4-(((5-(trifluoromethyl)pyrimidin-2-yl)amino)methyl)piperidine-1-carboxylate (2.20 g, 5.55 mmol) in DCM (10 mL) was added TFA (10 mL) at room temperature. After stirring for 3 hours, the reaction mixture was concentrated under reduced pressure to give the crude title compound as a yellow oil (2.50 g).

Step 3: (R)-4-methylbenzyl 3,3-difluoro-4-(((5-(trifluoromethyl)pyrimidin-2-yl)amino)methyl)piperidine-1-carboxylate

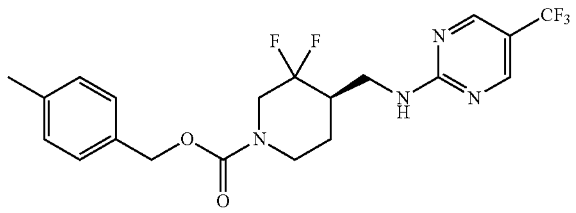 [SMILES: Cc1ccc(COC(=O)N2CC[C@H](CNc3ncc(C(F)(F)F)cn3)C(F)(F)C2)cc1]

To a solution of the above crude (R)—N-((3,3-difluoropiperidin-4-yl)methyl)-5-(trifluoromethyl)pyrimidin-2-amine trifluoroacetate (2.50 g, approximately 5.55 mmol) in $CH_3CN$ (20 mL) was added TEA (3.9 mL, 28 mmol) and 2,5-dioxopyrrolidin-1-yl 4-methylbenzyl carbonate (1.46 g, 5.55 mmol) at room temperature. After stirring for 2 hours, the reaction mixture was concentrated under reduced pressure. The residue was dissolved in ethyl acetate, washed with $H_2O$, dried over $Na_2SO_4$ and the organic phase was concentrated under reduced pressure. The crude product was purified by column chromatography over silica gel (eluent: DCM/ethyl acetate=15:1 to 10:1, v/v) to afford the title compound as a white solid (1.48 g, 60%). MS (ESI) calculated for $C_{20}H_{21}F_5N_4O_2$: 444.2 m/z; found: 445.4 m/z

[M+H]. $^1$H NM/R (400 MHz, $CDCl_3$) δ 8.48 (br, 2H), 7.25 (d, J=8.0 Hz, 2H), 7.17 (d, J=8.0 Hz, 2H), 5.78-5.70 (m, 1H), 5.14-5.07 (m, 2H), 4.56-4.12 (m, 2H), 3.85-3.77 (m, 1H), 3.65-3.55 (m, 1H), 3.10-2.76 (m, 2H), 2.35 (s, 3H), 2.32-2.19 (m, 1H), 1.88-1.78 (m, 1H), 1.65-1.52 (in, 1H).

Step 4: (R)-4-methylbenzyl 3,3-difluoro-4-(((5-(trifluoromethyl)pyrimidin-2-yl)amino)methyl)piperidine-1-carboxylate methanesulfonate

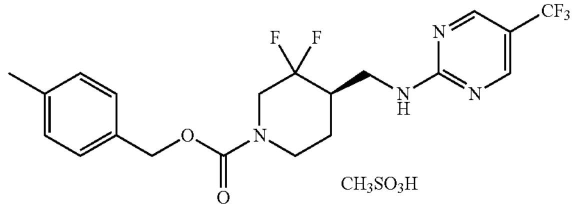

To a solution of (R)-4-methylbenzyl 3,3-difluoro-4-(((5-(trifluoromethyl)pyrimidin-2-yl)amino)methyl)piperidine-1-carboxylate (1.48 g, 3.33 mmol) in DCM/MeOH (10 mL/5 mL) was added 1.0 M methanesulfonic acid (3.33 mL, 3.33 mmol) in methanol at room temperature. After stirring at room temperature for 20 minutes, the solvent was removed and the residue was treated with ether/DCM to afford the title compound as a white powder (1.51 g, 83%). MS (ESI) calculated for $C_{20}H_{21}F_5N_4O_2$: 444.2 m/z; found: 445.4 m/z [M+H]. $^1$H NMR (400 MHz, $CD_3OD$) δ 8.82-8.62 (m, 2H), 7.24 (d, J=8.0 Hz, 2H), 7.17 (d, J=8.0 Hz, 2H), 5.12-5.06 (m, 2H), 4.36-4.24 (m, 1H), 4.18-4.11 (m, 1H), 3.90 (dd, J=5.6, 14.0 Hz, 1H), 3.52 (dd, J=5.6, 14.0 Hz, 1H), 3.29-3.07 (m, 1H), 3.03-2.86 (m, 1H), 2.73 (s, 3H), 2.51-2.36 (m, 1H), 2.33 (s, 3H), 1.95-1.85 (m, 1H), 1.57-1.45 (m, 1H).

Example 3.15. (R)-4-methylbenzyl 3,3-difluoro-4-(((5-methylpyrimidin-2-yl)amino)methyl)piperidine-1-carboxylate mesylate (E1-22.26$^{B'}$)

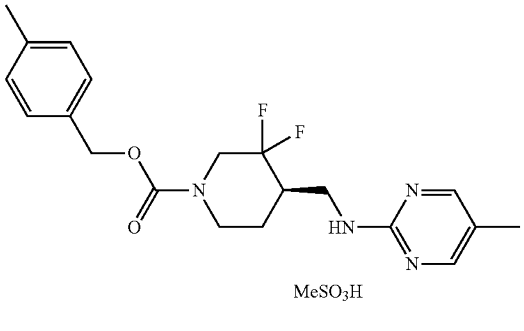 [SMILES: "MeSO3H" ; Cc1ccc(COC(=O)N2CC[C@H](CNc3ncc(C)cn3)C(F)(F)C2)cc1]

Step 1: (R)-tert-butyl 3,3-difluoro-4-(((5-methylpyrimidin-2-yl)amino)methyl)piperidine-1-carboxylate

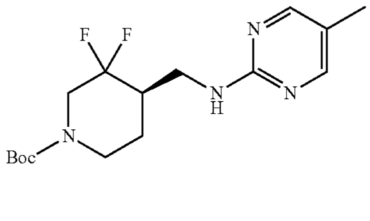 [SMILES: Cc1cnc(NC[C@H]2CCN(C(=O)OC(C)(C)C)CC2(F)F)nc1]

To a suspension of (R)-tert-butyl 4-(aminomethyl)-3,3-difluoropiperidine-1-carboxylate (3.31 g, 13.2 mmol) and 2-chloro-5-methylpyrimidine (2.21 g, 17.2 mmol) in n-BuOH (40 mL) was added DIPEA (6.5 mL, 40 mmol). The resulting mixture was heated to 100° C. under nitrogen atmosphere. After stirring at 100° C. for 2 days, the mixture was concentrated under reduced pressure. The residue was purified by column chromatography over silica gel (gradient eluent: hexane/ethyl acetate, 3:1, v/v, then DCM/ethyl acetate, 2:1, v/v) to afford the title product as a dark brown solid (1.91 g, 42%). MS (ESI) calculated for $C_{16}H_{24}F_2N_4O_2$: 342.2 m/z; found: 343.2 m/z [M+H]. $^1$H NMR (400 MHz, $CDCl_3$) δ 8.12 (s, 2H), 5.20-5.14 (m, 1H), 4.45-4.05 (m, 2H), 3.80-3.72 (m, 1H), 3.55-3.45 (m, 1H), 3.06-2.65 (m, 2H), 2.30-2.14 (m, 1H), 2.12 (s, 3H), 1.87-1.78 (m, 1H), 1.62-1.50 (m, 1H), 1.46 (s, 9H).

Step 2: (R)—N-((3,3-difluoropiperidin-4-yl)methyl)-5-methylpyrimidin-2-amine trifluoroacetate

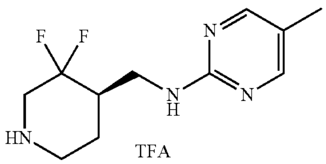 [SMILES: Cc1cnc(NC[C@H]2CCNCC2(F)F)nc1]

To a solution of (R)-tert-butyl 3,3-difluoro-4-(((5-methylpyrimidin-2-yl)amino)methyl)piperidine-1-carboxylate (7.08 g, 20.7 mmol) in DCM (50 mL) was added trifluoroacetic acid (25 mL) at room temperature. After stirring for 3 hours, the starting material the mixture was concentrated to afford the crude product as a dark brown oil, which was directly taken into the next step without further purification.

Step 3: (R)-4-methylbenzyl 3,3-difluoro-4-(((5-methylpyrimidin-2-yl)amino)methyl)piperidine-1-carboxylate

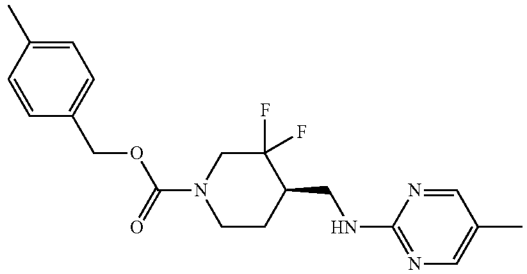 [SMILES: Cc1ccc(COC(=O)N2CC[C@H](CNc3ncc(C)cn3)C(F)(F)C2)cc1]

The crude (R)—N-((3,3-difluoropiperidin-4-yl)methyl)-5-methylpyrimidin-2-amine trifluoroacetate from above was dissolved in MeCN (60 mL), and TEA (14.5 mL) was added. After the mixture was cooled down to room temperature, 2,5-dioxopyrrolidin-1-yl 4-methylbenzyl carbonate (5.44 g, 20.7 mmol) was added in one portion. The mixture thus obtained was stirred for 3 hours, and then concentrated under reduced pressure. The concentrate was dissolved in ethyl acetate, washed with water, brine, dried over $Na_2SO_4$ and the organic phase was concentrated under reduced pressure. The concentrate was purified by column chromatography over silica gel (gradient eluent: DCM/ethyl acetate, 20:1 to 5:1) to afford the product as an off-white solid (4.94 g, 61%). MS (ESI) calculated for $C_{20}H_{24}F_2N_4O_2$: 390.2 m/z; found: 391.5 m/z [M+H]. $^1H$ NMR (400 MHz, $CDCl_3$) δ 8.12 (s, 2H), 7.25 (d, J=8.0 Hz, 2H), 7.17 (d, J=8.0 Hz, 2H), 5.19-5.14 (m, 1H), 5.12-5.07 (m, 2H), 4.50-4.09 (m, 2H), 3.81-3.72 (m, 1H), 3.55-3.45 (m, 1H), 3.11-2.91 (m, 1H), 2.90-2.75 (m, 1H), 2.05 (s, 3H), 2.32-2.17 (m, 1H), 2.12 (s, 3H), 1.90-1.79 (m, 1H), 1.65-1.51 (m, 1H).

Step 4: (R)-4-methylbenzyl 3,3-difluoro-4-(((5-methylpyrimidin-2-yl)amino)methyl)piperidine-1-carboxylate mesylate

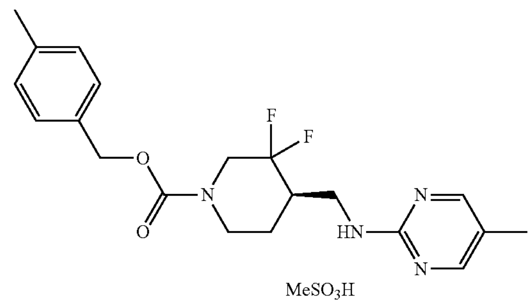 [SMILES: "MeSO3H" ; Cc1ccc(COC(=O)N2CC[C@H](CNc3ncc(C)cn3)C(F)(F)C2)cc1]

To a solution of (R)-4-methylbenzyl 3,3-difluoro-4-(((5-methylpyrimidin-2-yl)amino)methyl)piperidine-1-carboxylate (4.94 g, 12.7 mmol) in DCM (60 mL) was added 1.0 M methanesulfonic acid in methanol (12.7 mL, 12.7 mmol) at room temperature. After stirring for 30 minutes, the solvent was removed under reduced pressure, and the concentrate was triturated with ether to afford the title product as an off-white solid (5.81 g, 94%). MS (ESI) calculated for $C_{20}H_{24}F_2N_4O_2$: 390.2 m/z; found: 391.5 m/z [M+H]. $^1H$ NMR (400 MHz, $CD_3OD$) δ 8.50 (brs, 2H), 7.26 (d, J=8.0 Hz, 2H), 7.19 (d, J=8.0 Hz, 2H), 5.14-5.07 (m, 2H), 4.40-4.25 (m, 1H), 4.22-4.14 (m, 1H), 3.96-3.88 (m, 1H), 3.61-3.54 (m, 1H), 3.30-3.09 (m, 1H), 3.06-2.88 (m, 1H), 2.73 (s, 3H), 2.54-2.38 (m, 1H), 2.35 (s, 3H), 2.28 (s, 3H), 1.98-1.88 (m, 1H), 1.60-1.47 (m, 1H).

Example 3.16. (R)-4-methylbenzyl 3,3-difluoro-4-((pyridazin-3-ylamino)methyl)piperidine-1-carboxylate (E1-24.2$^{B'}$)

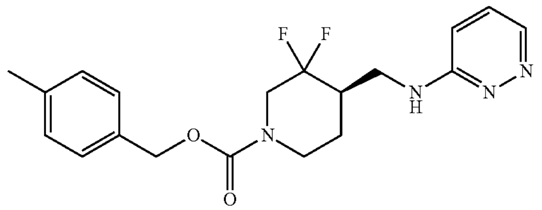 [SMILES: Cc1ccc(COC(=O)N2CC[C@H](CNc3cccnn3)C(F)(F)C2)cc1]

Step 1: (R)-tert-butyl 3,3-difluoro-4-((pyridazin-3-ylamino)methyl)piperidine-1-carboxylate

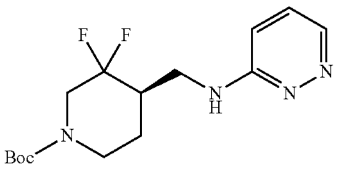 [SMILES: CC(C)(C)OC(=O)N1CC[C@H](CNc2cccnn2)C(F)(F)C1]

To a solution of (R)-tert-butyl 4-(aminomethyl)-3,3-difluoropiperidine-1-carboxylate (4.75 g, 19.0 mmol) in dioxane (50 mL) was added 3-bromopyridazine (2.5 g, 16 mmol), $Pd_2(dba)_3$ (145 mg, 0.16 mmol), Xantphos (137 mg, 0.24 mmol) and $Cs_2CO_3$ (8.25 g, 25.3 mmol). The reaction mixture was stirred at 100° C. under $N_2$ atmosphere for 4 hours. The mixture was allowed to cool to room temperature, filtered and filtrate was concentrated in vacuo. The concentrate was purified by column chromatography over silica gel (eluent: DCM/acetone=5:1 to 4:1, v/v) to give the title compound as a dark solid (693 mg, 13%). MS (ESI) calculated for $C_{15}H_{22}F_2N_4O_2$: 328.2 m/z; found: 329.4 m/z [M+H]. $^1H$ NMR (400 MHz, $CDCl_3$) δ 8.55 (dd, J=4.8, 1.2 Hz, 1H), 7.17 (dd, J=9.2, 4.8 Hz, 1H), 6.64 (dd, J=9.2, 1.2 Hz, 1H), 4.94-4.88 (m, 1H), 4.45-4.00 (m, 2H), 3.80-3.55 (m, 2H), 3.05-2.65 (m, 2H), 2.44-2.28 (m, 1H), 1.92-1.83 (m, 1H), 1.72-1.50 (m, 1H), 1.46 (s, 9H).

Step 2: (R)—N-((3,3-difluoropiperidin-4-yl)methyl)pyridazin-3-amine

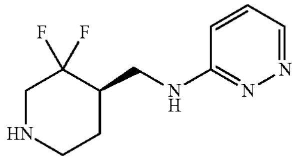 [SMILES: FC1(F)CNCC[C@@H]1CNc1cccnn1]

To a solution of (R)-tert-butyl 3,3-difluoro-4-((pyridazin-3-ylamino)methyl)piperidine-1-carboxylate (970 mg, 3.0 mmol) in DCM (10 mL) was added 2.5 M HCl (in dioxane, 22 mL) at room temperature. After stirring for 2 hours, the reaction mixture was concentrated in vacuo. Then the residue was basified with 1.0 M aq NaOH and extracted with ethyl acetate. The combined organic phases were dried and concentrated in vacuo to give the title product as an off-white powder (524 mg, 77%) which was used directly in the next step without further purification.

Step 3: (R)-4-methylbenzyl 3,3-difluoro-4-((pyridazin-3-ylamino)methyl)piperidine-1-carboxylate

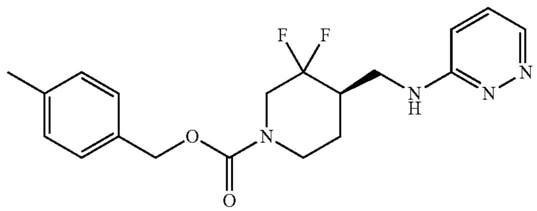 [SMILES: Cc1ccc(COC(=O)N2CC[C@H](CNc3cccnn3)C(F)(F)C2)cc1]

To a solution of (R)—N-((3,3-difluoropiperidin-4-yl)methyl)pyridazin-3-amine (524 mg, 2.3 mmol) in $CH_3CN$ (10 mL) was added TEA (1.6 mL, 12 mmol) and 2,5-dioxopyrrolidin-1-yl 4-methylbenzyl carbonate (605 mg, 2.29 mmol). The reaction mixture was stirred at room temperature. After stirring for 16 hours, the reaction mixture was concentrated in vacuo, and then dissolved in ethyl acetate. The organic phase washed with $H_2O$, brine, dried over $Na_2SO_4$ and concentrated in vacuo. The concentrate was purified by column chromatography over silica gel (gradient eluent: acetone/hexane=1:2 to 2:1, v/v) to give the title compound as a dark brown oil (372 mg, 43%). MS (ESI) calculated for $C_{19}H_{22}F_2N_4O_2$: 376.2 m/z; found: 377.2 m/z [M+H]. $^1$H NMR (400 MHz, $CD_3OD$) δ 8.37 (dd, J=4.4, 1.2 Hz, 1H), 7.27 (dd, J=9.2, 4.4 Hz, 1H), 7.24 (d, J=8.0 Hz, 2H), 7.17 (d, J=7.6 Hz, 2H), 6.88 (dd, J=9.2, 1.2 Hz, 1H), 5.11-5.07 (m, 2H), 4.34-4.21 (m, 1H), 4.17-4.10 (m, 1H), 3.85-3.79 (m, 1H), 3.46-3.38 (m, 1H), 3.29-3.06 (m, 1H), 3.03-2.87 (m, 1H), 2.53-2.37 (m, 1H), 2.33 (s, 3H), 1.97-1.88 (m, 1H), 1.56-1.44 (m, 1H).

Example 3.17. (R)-4-fluorobenzyl 3,3-difluoro-4-((pyridazin-3-ylamino)methyl)piperidine-1-carboxylate methanesulfonate (E1-24.4$^{B'}$)

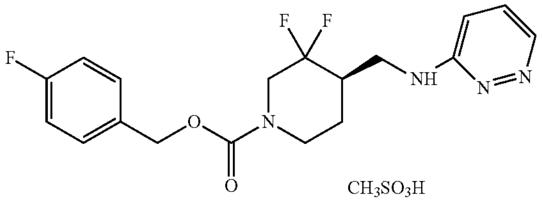

Step 1: (R)-4-fluorobenzyl 3,3-difluoro-4-((pyridazin-3-ylamino)methyl)piperidine-1-carboxylate

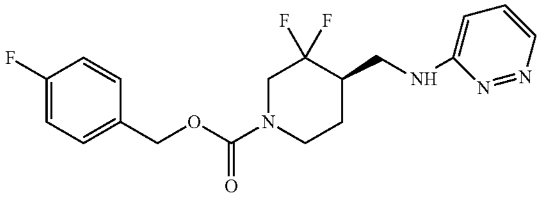 [SMILES: O=C(OCc1ccc(F)cc1)N1CC[C@H](CNc2cccnn2)C(F)(F)C1]

To a solution of (R)—N-((3,3-difluoropiperidin-4-yl)methyl)pyridazin-3-amine (1.26 g, 5.51 mmol) in acetonitrile (15 mL) was added triethylamine (3 mL, 22 mmol) and (2,5-dioxopyrrolidin-1-yl)methyl 4-fluorobenzyl carbonate (1.47 g, 5.51 mmol) at room temperature. After stirring for 3 hours, the solvent was removed under reduced pressure. The concentrate was dissolved in DCM, washed with water, brine, dried over $Na_2SO_4$ and concentrated in vacuo. The crude product was purified by column chromatography over silica gel (gradient eluent: EtOAc/DCM=50% to 100%) to give the title compound as an off-white solid (1.88 g, 90%). MS (ESI) calculated for $C_{18}H_{19}F_3N_4O_2$: 380.4 m/z; found: 381.5 m/z [M+H]. $^1$H NMR (400 MHz, $CDCl_3$): δ 8.55 (d, J=4.4 Hz, 1H), 7.36-7.30 (m, 2H), 7.15 (dd, J=4.4, 8.8 Hz, 1H), 7.08-7.01 (m, 2H), 6.63 (dd, J=1.2, 8.8 Hz, 1H), 5.15-5.05 (m, 2H), 4.91-4.84 (m, 1H), 4.53-4.10 (m, 1H), 3.81-3.58 (m, 2H), 3.10-2.76 (m, 2H), 2.49-2.33 (m, 1H), 1.95-1.85 (m, 1H), 1.64-1.50 (m, 1H).

Step 2: (R)-4-fluorobenzyl 3,3-difluoro-4-((pyridazin-3-ylamino)methyl)piperidine-1-carboxylate methanesulfonate

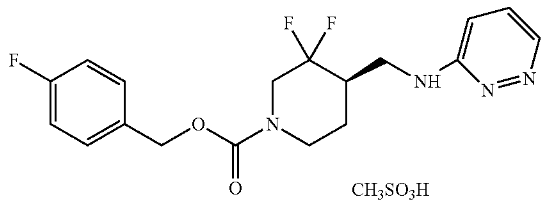

To a solution of (R)-4-fluorobenzyl 3,3-difluoro-4-((pyridazin-3-ylamino)methyl)piperidine-1-carboxylate (1.50 g, 3.94 mmol) in DCM/MeOH (1:1, v/v, 16 mL) was added 1.0 M methanesulfonic acid in methanol (3.94 mL, 3.94 mmol). After stirring at room temperature for 30 minutes, the reaction mixture was concentrated in vacuo and triturated with ether to afford the title compound as an off-white solid (1.95 g, 99%). MS (ESI) calculated for $C_{18}H_{19}F_3N_4O_2$: 380.4 m/z; found: 381.4 m/z [M+H]. $^1$H NMR (400 MHz, $CD_3OD$): δ 8.56-8.51 (m, 1H), 7.83-7.78 (m, 1H), 7.62-7.55 (m, 1H), 7.44-7.37 (m, 2H), 7.13-7.06 (m, 2H), 5.16-5.04 (m, 2H), 4.41-4.29 (m, 1H), 4.23-4.16 (m, 1H), 3.86-3.77 (m, 1H), 3.49-3.42 (m, 1H), 3.27-3.11 (m, 1H), 3.08-2.91 (m, 1H), 2.70 (s, 3H), 2.56-2.40 (m, 1H), 2.02-1.98 (m, 1H), 1.61-1.49 (m, 1H).

Example 3.18. (R)-4-methylbenzyl 4-(((5-cyanopyrimidin-2-yl)amino)methyl)-3,3-difluoropiperidine-1-carboxylate methanesulfonate (E1-22.30$^{B'}$)

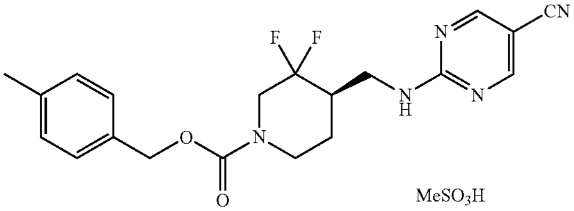 [SMILES: "MeSO3H" ; Cc1ccc(COC(=O)N2CC[C@H](CNc3ncc(C#N)cn3)C(F)(F)C2)cc1]

Step 1: (R)-tert-butyl 4-(((5-cyanopyrimidin-2-yl)amino)methyl)-3,3-difluoropiperidine-1-carboxylate

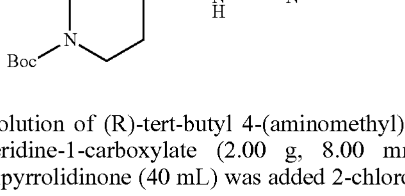

To a solution of (R)-tert-butyl 4-(aminomethyl)-3,3-difluoropiperidine-1-carboxylate (2.00 g, 8.00 mmol) in N-methylpyrrolidinone (40 mL) was added 2-chloropyrimidine-5-carbonitrile (1.23 g, 8.80 mmol) and $Cs_2CO_3$ (3.90 g, 12.00 mmol). The reaction mixture was stirred at 90° C. under $N_2$ atmosphere for 16 hours. The reaction mixture was cooled down to room temperature, and diluted with ethyl acetate, washed with $H_2O$, brine, dried over $Na_2SO_4$ and the organic phase was concentrated in vacuo. The concentrate was purified by column chromatography over silica gel (gradient eluent: hexane/ethyl acetate=8:1 to 3:1, v/v) to give the title compound as an off-yellow oil (2.28 g, 81%). MS (ESI) calculated for $C_{16}H_{21}F_2N_5O_2$: 353.2 m/z; found: 298.3 m/z [M-55]. $^1H$ NMR (400 MHz, DMSO-$d_6$) δ 8.74 (d, J=2.8 Hz, 1H), 8.65 (d, J=2.8 Hz, 1H), 8.40 (t, J=6.0 Hz, 1H), 4.16-3.95 (m, 1H), 3.94-3.82 (m, 1H), 3.76-3.68 (m, 1H), 3.30-3.06 (m, 2H), 2.97-2.72 (m, 1H), 2.42-2.22 (m, 1H), 1.83-1.75 (m, 1H), 1.39 (s, 9H), 1.35-1.24 (m, 1H).

Step 2: (R)-2-(((3,3-difluoropiperidin-4-yl)methyl) amino)pyrimidine-5-carbonitrile

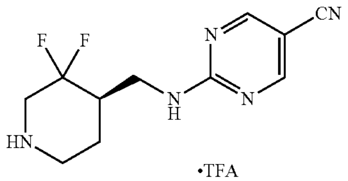 [SMILES: N#Cc1cnc(NC[C@H]2CCNCC2(F)F)nc1]

•TFA

To a solution of (R)-tert-butyl 4-(((5-cyanopyrimidin-2-yl)amino)methyl)-3,3-difluoropiperidine-1-carboxylate (2.28 g, 6.46 mmol) in DCM (10 mL) was added TFA (15 mL) at room temperature. After stirring for 5 hours, the reaction mixture was concentrated in vacuo to give the crude title compound as a brown oil.

Step 3: (R)-4-methylbenzyl 4-(((5-cyanopyrimidin-2-yl)amino)methyl)-3,3-difluoropiperidine-1-carboxylate

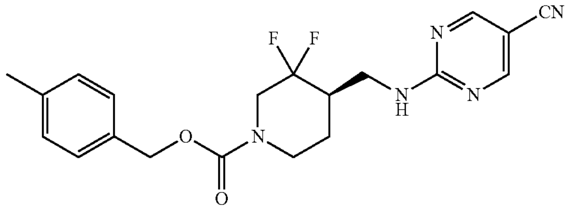 [SMILES: Cc1ccc(COC(=O)N2CC[C@H](CNc3ncc(C#N)cn3)C(F)(F)C2)cc1]

To a solution of crude (R)-2-(((3,3-difluoropiperidin-4-yl)methyl)amino)pyrimidine-5-carbonitrile trifluoroacetate (9.12 g, 6.46 mmol) in $CH_3CN$ (20 mL) was added TEA (4.5 mL, 32 mmol) and 2,5-dioxopyrrolidin-1-yl 4-methylbenzyl carbonate (1.70 g, 4.06 mmol). The reaction mixture was stirred at room temperature. After stirring for 3 hours, the reaction mixture was concentrated in vacuo. The concentrate was dissolved in ethyl acetate, washed with $H_2O$, brine, dried over $Na_2SO_4$ and the organic phase was concentrated in vacuo. The residue was triturated with hexane/ethyl acetate (2:1) to give the title compound as a white solid (1.99 g, 77%). MS (ESI) calculated for $C_{20}H_{21}F_2N_5O_2$: 401.2 m/z; found: 402.4 m/z [M+H]. $^1H$ NMR (400 MHz, $CDCl_3$) δ 8.55-8.45 (m, 2H), 7.25 (d, J=8.0 Hz, 2H), 7.17 (d, J=8.0 Hz, 2H), 5.90-5.85 (m, 1H), 5.12-5.08 (m, 2H), 4.58-4.14 (m, 2H), 3.85-3.76 (m, 1H), 3.66-3.58 (m, 1H), 3.10-2.75 (m, 2H), 2.35 (s, 3H), 2.32-2.15 (m, 1H), 1.87-1.74 (m, 1H).

Step 4: (R)-4-methylbenzyl 4-(((5-cyanopyrimidin-2-yl)amino)methyl)-3,3-difluoropiperidine-1-carboxylate methanesulfonate

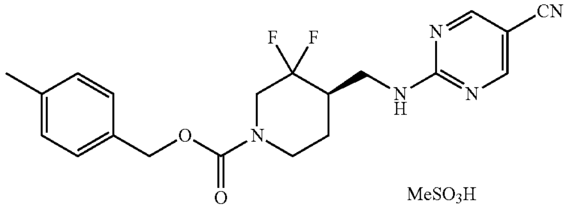 [SMILES: "MeSO3H" ; Cc1ccc(COC(=O)N2CC[C@H](CNc3ncc(C#N)cn3)C(F)(F)C2)cc1]

$MeSO_3H$

To a solution of (R)-4-methylbenzyl 4-(((5-cyanopyrimidin-2-yl)amino)methyl)-3,3-difluoropiperidine-1-carboxylate (1.99 g, 5.00 mmol) in DCM/MeOH (10:1, v/v, 22 mL) was added 1.0 M $CH_3SO_3H$ in methanol (5.0 mL, 5.0 mmol) at room temperature. After stirring for 30 minutes the reaction mixture was concentrated in vacuo and triturated with $Et_2O$ to give the title compound as a white solid (1.97 g, 79%). MS (ESI) calculated for $C_{20}H_{21}F_2N_5O_2$: 401.2 m/z; found: 402.4 m/z [M+H]. $^1H$ NMR (400 MHz, $CD_3OD$) δ 8.65-8.53 (m, 2H), 7.23 (d, J=8.0 Hz, 2H), 7.17 (d, J=8.0 Hz, 2H), 5.12-5.05 (m, 2H), 4.34-4.21 (m, 1H), 4.17-4.08 (m, 1H), 3.88-3.82 (m, 1H), 3.48-3.41 (m, 1H), 3.25-2.85 (m, 2H), 2.72 (s, 3H), 2.46-2.34 (m, 1H), 2.33 (s, 3H), 1.91-1.83 (m, 1H), 1.54-1.43 (m, 1H), 1.37-1.28 (m, 1H).

Example 3.19. (R)-4-methylbenzyl 3,3-difluoro-4-((pyridin-2-ylamino)methyl)piperidine-1-carboxylate (E1-23.$2^{B'}$)

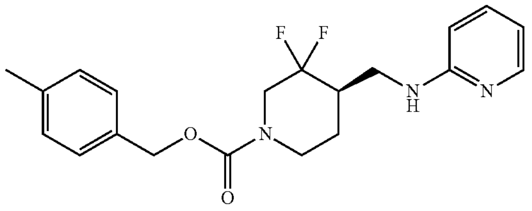 [SMILES: Cc1ccc(COC(=O)N2CC[C@H](CNc3ccccn3)C(F)(F)C2)cc1]

Step 1: (R)-tert-butyl 3,3-difluoro-4-((pyridin-2-ylamino)methyl)piperidine-1-carboxylate

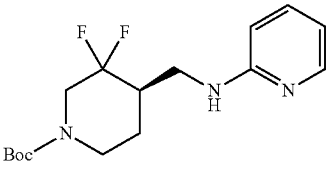 [SMILES: CC(C)(C)OC(=O)N1CC[C@H](CNc2ccccn2)C(F)(F)C1]

To a solution of (R)-tert-butyl 4-(aminomethyl)-3,3-difluoropiperidine-1-carboxylate (10.02 g, 40.0 mmol) in dioxane (100 mL) was added 2-chloropyridine (3.76 g, 33.3 mmol), Pd-G1 (26 mg, 0.33 mmol), Brettphos (27 mg, 0.50 mmol) and $Cs_2CO_3$ (17.4 g, 53 mmol). The reaction mixture was stirred at 100° C. under $N_2$ atmosphere. After stirring for 3 hours, the reaction mixture was filtered and the filtrate was concentrated in vacuo. The concentrate was purified by column chromatography over silica gel (gradient eluent: hexane/ethyl acetate=4:1 to 2:1, v/v) to give the title product as a yellow oil (5.30 g, 49%). MS (ESI) calculated for $C_{16}H_{23}F_2N_3O_2$: 327.2 m/z; found: 328.4 m/z [M+H]. $^1$H NMR (400 MHz, DMSO-$d_6$) δ 8.08 (d, J=4.8 Hz, 1H), 7.44-7.38 (m, 1H), 6.60-6.56 (m, 1H), 6.40 (d, J=8.4 Hz, 1H), 4.68-4.61 (m, 1H), 4.45-4.00 (m, 2H), 3.74-3.66 (m, 1H), 3.48-3.36 (m, 1H), 3.06-2.66 (m, 2H), 2.29-2.13 (m, 1H), 1.91-1.83 (m, 1H), 1.62-1.51 (m, 1H), 1.47 (s, 9H).

Step 2: (R)—N-((3,3-difluoropiperidin-4-yl)methyl) pyridin-2-amine

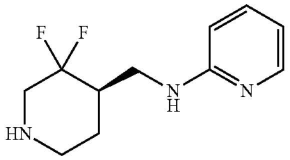 [SMILES: FC1(F)CNCC[C@@H]1CNc1ccccn1]

To a solution of (R)-tert-butyl 3,3-difluoro-4-((pyridin-2-ylamino)methyl)piperidine-1-carboxylate (5.30 g, 16.2 mmol) in DCM (30 mL) was added 2.5 M HCl (in dioxane, 30 mL) at room temperature. After stirring for 3 hours, the reaction mixture was concentrated in vacuo, and the concentrate was suspended in ethyl acetate. The organic phase was basified with 1.0 M aq NaOH and extracted with ethyl acetate. The combined organic phases were dried over $Na_2SO_4$ and concentrated in vacuo to give the crude title product as a pale brown solid.

Step 3: (R)-4-methylbenzyl 3,3-difluoro-4-((pyridin-2-ylamino)methyl)piperidine-1-carboxylate

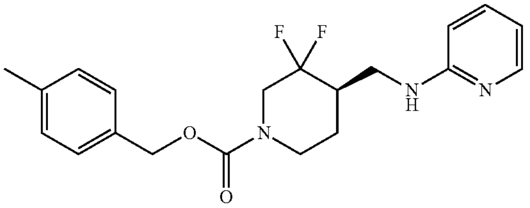 [SMILES: Cc1ccc(COC(=O)N2CC[C@H](CNc3ccccn3)C(F)(F)C2)cc1]

To a solution of the above crude (R)—N-((3,3-difluoropiperidin-4-yl)methyl)pyridin-2-amine (3.68 g, approximately 16 mmol) in $CH_3CN$ (40 mL) was added TEA (11 mL) and 2,5-dioxopyrrolidin-1-yl 4-methylbenzyl carbonate (4.26 g, 16.2 mmol). The reaction mixture was stirred at room temperature for 2 hours and the reaction mixture was concentrated in vacuo. The concentrate was dissolved in ethyl acetate and then washed with $H_2O$. The organic phase was dried and concentrated in vacuo and then purified by column chromatography over silica gel (eluent: DCM/ethyl acetate=15:1 to 10:1, v/v) to give the title compound as a white powder (4.10 g, 67%). MS (ESI) calculated for $C_{20}H_{23}F_2N_3O_2$: 375.2 m/z; found: 376.5 m/z [M+H]. $^1$H NMR (400 MHz, $CDCl_3$) δ 8.08 (d, J=4.8 Hz, 1H), 7.44-7.37 (m, 1H), 7.25 (d, J=8.0 Hz, 2H), 7.17 (d, J=7.6 Hz, 2H), 6.60-6.55 (m, 1H), 6.39 (d, J=8.4 Hz, 1H), 5.13-5.07 (m, 2H), 4.65-4.58 (m, 1H), 4.52-4.12 (m, 2H), 3.74-3.66 (m, 1H), 3.47-3.37 (m, 1H), 3.09-2.93 (m, 1H), 2.87-2.75 (m, 1H), 2.35 (s, 3H), 2.30-2.15 (m, 1H), 1.93-1.83 (m, 1H), 1.61-1.50 (m, 1H).

Step 4: (R)-4-methylbenzyl 3,3-difluoro-4-((pyridin-2-ylamino)methyl)piperidine-1-carboxylate fumarate

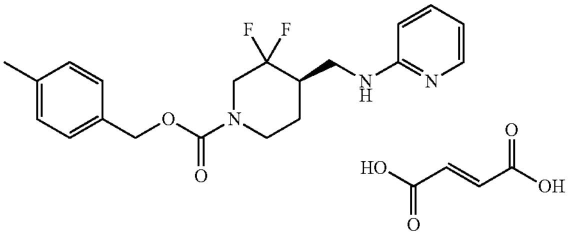 [SMILES: Cc1ccc(COC(=O)N2CC[C@H](CNc3ccccn3)C(F)(F)C2)cc1 ; O=C(O)/C=C/C(=O)O]

To a solution of (R)-4-methylbenzyl 3,3-difluoro-4-((pyridin-2-ylamino)methyl)piperidine-1-carboxylate (1.00 g, 2.67 mmol) in methanol (10 mL) was added 1 M fumaric acid in methanol (2.67 mL, 2.67 mmol). After stirring at room temperature for 30 minutes, the reaction mixture was concentrated in vacuo and triturated with ether (50° C.) to afford the title compound as an off-white powder (918 mg, 70%). MS (ESI) calculated for $C_{20}H_{23}F_2N_3O_2$: 375.2 found m z: 376.4 m/z [M+H]. $^1$H NMR (400 MHz, $CD_3OD$) δ 7.90 (d, J=5.2 Hz, 1H), 7.61-7.56 (m, 1H), 7.24 (d, J=8.0 Hz, 2H), 7.17 (d, J=8.0 Hz, 2H), 6.74 (s, 2H), 6.71-6.65 (m, 2H), 5.09 (s, 2H), 4.30 (brs, 1H), 4.17-4.14 (m, 1H), 3.74-3.68 (m, 1H), 3.36-3.33 (m, 1H), 3.25-3.09 (m, 1H), 3.01-2.89 (m, 1H), 2.44-2.35 (m, 1H), 2.33 (s, 3H), 1.96-1.92 (m, 1H), 1.56-1.45 (m, 1H).

Example 3.20. (R)-4-fluorobenzyl 3,3-difluoro-4-((pyridin-2-ylamino)methyl)piperidine-1-carboxylate (E1-23.4$^{B'}$)

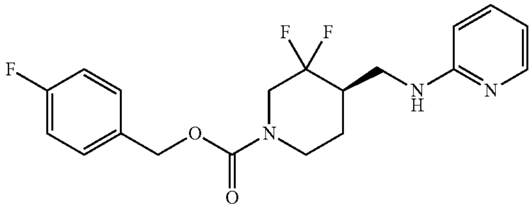 [SMILES: O=C(OCc1ccc(F)cc1)N1CC[C@H](CNc2ccccn2)C(F)(F)C1]

To a solution of (R)—N-((3,3-difluoropiperidin-4-yl)methyl)pyridin-2-amine (2.01 g, 8.81 mmol) in $CH_3CN$ (20 mL) was added TEA (6.1 mL, 44 mmol) and 2,5-dioxopyrrolidin-1-yl 4-fluorobenzyl carbonate (2.35 g, 8.82 mmol) at room temperature. After stirring for 16 hours, the reaction mixture was concentrated in vacuo, and the concentrate was dissolved in ethyl acetate. The organic phase was washed with $H_2O$, brine dried over $Na_2SO_4$ and concentrated in vacuo. The residue was purified by column chromatography over silica gel (gradient eluent: DCM/ethyl acetate=5:1 to 3:1, v/v) to give the title compound as an off-white powder (2.11 g, 63%). MS (ESI) calculated for $C_{20}H_{23}F_2N_3O_2$: 379.2 m/z; found: 380.5 m/z [M+H]. $^1$H NMR (400 MHz, $CDCl_3$) δ 8.08 (dd, J=5.2, 1.2 Hz, 1H), 7.43-7.38 (m, 1H), 7.35-7.30 (m, 2H), 7.08-7.01 (m, 2H), 6.58 (dd, J=6.4, 5.2 Hz, 1H), 6.39 (d, J=8.4 Hz, 1H), 5.12-5.08 (m, 2H), 4.64-4.58 (m, 1H), 4.50-4.10 (m, 2H), 3.73-3.67 (m, 1H), 3.50-3.37 (m, 1H), 3.12-2.76 (m, 2H), 2.32-2.16 (m, 1H), 1.95-1.84 (m, 1H).

Example 3.21. (R)-4-methylbenzyl 3,3-difluoro-4-(((5-methylpyridin-2-yl)amino)methyl)piperidine-1-carboxylate (E1-23.26[B'])

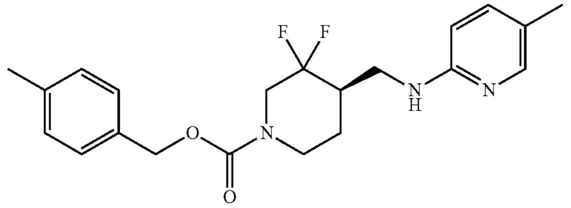

Step 1: (R)-tert-butyl 3,3-difluoro-4-(((5-methylpyridin-2-yl)amino)methyl)piperidine-1-carboxylate

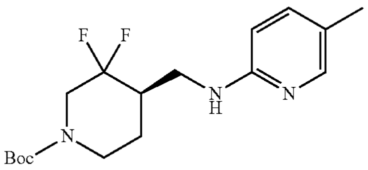

To a solution of (R)-tert-butyl 4-(aminomethyl)-3,3-difluoropiperidine-1-carboxylate (8.01 g, 32.0 mmol) in dioxane (80 mL) was added 2-bromo-5-methylpyridine (4.56 g, 26.7 mmol), Pd-G1 (215 mg, 0.27 mmol), Brettphos (217 mg, 0.41 mmol) and $Cs_2CO_3$ (13.9 g, 42.6 mmol). The reaction mixture was stirred at 100° C. under $N_2$ atmosphere. After stirring for 3 hours, the reaction mixture was filtered and filtrate was concentrated in vacuo. The concentrate was purified by column chromatography over silica gel (gradient eluent: hexane/ethyl acetate=4:1 to 1:1, v/v) to give the title compound as a yellow oil (4.47 g, 49%). MS (ESI) calculated for $C_{17}H_{25}F_2N_3O_2$: 341.2 m/z; found: 342.4 m/z [M+H]. $^1H$ NMR (400 MHz, $CDCl_3$) δ 7.91 (s, 1H), 7.26-7.23 (m, 1H), 6.34 (d, J=8.4 Hz, 1H), 4.52-4.46 (m, 1H), 4.33-4.11 (m, 2H), 3.70-3.63 (m, 1H), 3.46-3.32 (m, 1H), 3.06-2.65 (m, 2H), 2.25-2.10 (m, 4H), 1.90-1.82 (m, 1H), 1.59-1.48 (m, 1H), 1.46 (s, 9H).

Step 2: (R)—N-((3,3-difluoropiperidin-4-yl)methyl)-5-methylpyridin-2-amine

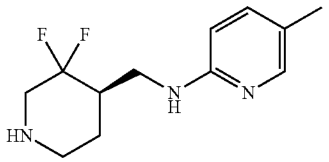 [SMILES: Cc1ccc(NC[C@H]2CCNCC2(F)F)nc1]

To a solution of (R)-tert-butyl 3,3-difluoro-4-(((5-methylpyridin-2-yl)amino)methyl)piperidine-1-carboxylate (4.47 g, 13.1 mmol) in DCM (20 mL) was added 2.5 M HCl in dioxane (30 mL) at room temperature. After stirring for 2 hours, the reaction mixture was concentrated in vacuo. Then the concentrate was suspended in water, basified with 1.0 aq NaOH, and extracted with ethyl acetate. The combined organic phases were dried and concentrated in vacuo to give the title product as an off-white powder which was used directly in the next step without further purification.

Step 3: (R)-4-methylbenzyl 3,3-difluoro-4-(((5-methylpyridin-2-yl)amino)methyl)piperidine-1-carboxylate

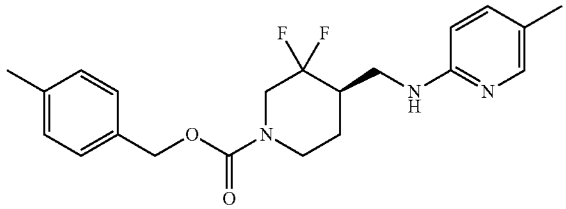

To a solution of the above (R)—N-((3,3-difluoropiperidin-4-yl)methyl)-5-methylpyridin-2-amine (approximately 13.10 mmol) in $CH_3CN$ (40 mL) was added TEA (9.1 mL) and 2,5-dioxopyrrolidin-1-yl 4-methylbenzyl carbonate (3.45 g, 13.10 mmol). The reaction mixture was stirred at room temperature. After stirring for 2 hours, the reaction mixture was concentrated in vacuo, and then dissolved in ethyl acetate. The organic phase was washed with $H_2O$, brine, dried over $Na_2SO_4$ and concentrated in vacuo. The concentrate was purified by column chromatography over silica gel (gradient eluent: DCM/ethyl acetate=15:1 to 3:1) to give the title product as an off-white solid (3.07 g, 60%). MS (ESI) calculated for $C_{21}H_{25}F_2N_3O_2$: 389.2 m/z; found: 390.5 m/z [M+H]. $^1H$ NMR (400 MHz, $CD_3OD$) δ 7.90 (s, 1H), 7.26-7.24 (m, 3H), 7.17 (d, J=8.0 Hz, 2H), 6.33 (d, J=8.4 Hz, 1H), 5.13-5.07 (m, 2H), 4.51-4.44 (m, 1H), 4.39-4.10 (m, 2H), 3.71-3.63 (m, 1H), 3.44-3.33 (m, 1H), 3.10-2.72 (m, 2H), 2.35 (s, 3H), 2.29-2.15 (m, 1H), 2.17 (s, 3H), 1.93-1.82 (m, 1H), 1.63-1.48 (m, 1H).

Example 3.22. (+)-(R)-4-methylbenzyl 3,3-difluoro-4-(((6-methylpyridin-2-yl)amino)methyl)piperidine-1-carboxylate (E1-23.32[B'])

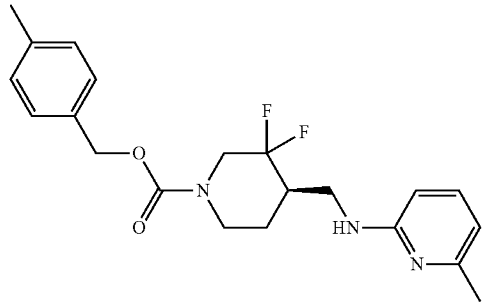 [SMILES: Cc1ccc(COC(=O)N2CC[C@H](CNc3cccc(C)n3)C(F)(F)C2)cc1]

Step 1: (R)-tert-butyl 3,3-difluoro-4-(((6-methylpyridin-2-yl)amino)methyl)piperidine-1-carboxylate

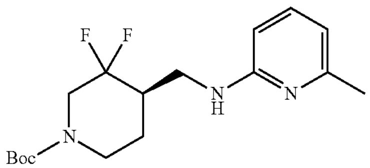 [SMILES: Cc1cccc(NC[C@H]2CCN(C(=O)OC(C)(C)C)CC2(F)F)n1]

To a stirred suspension of (R)-tert-butyl 4-(aminomethyl)-3,3-difluoropiperidine-1-carboxylate (705 mg, 2.82 mmol) and 2-chloro-6-methylpyridine (300 mg, 2.35 mmol) in toluene (8 mL) was added $Pd_2(dba)_3$ (215 mg, 0.235 mmol), BINAP (293 mg, 0.47 mmol) and t-BuONa (452 mg, 4.7 m mmol) sequentially under nitrogen atmosphere. The resulting mixture was heated to 100° C. overnight and allowed to cool to room temperature. The mixture was partitioned into ethyl acetate and water. The organic phase was washed with brine, dried over $Na_2SO_4$ and concentrated under reduced pressure. The residue was purified by column chromatography over silica gel (gradient eluent: hexane/ethyl acetate=2:1, v/v) to afford the title product as a yellow oil (412 mg, 42%). MS (ESI) calculated for $C_{17}H_{25}F_2N_3O_2$: 341.2 m/z; found: 342.6 m/z [M+H]. $^1$H NMR (400 MHz, $CD_3OD$) δ 7.33 (dd, J=7.4, 8.0 Hz, 1H), 6.43 (d, J=7.2, 8.0 Hz, 1H), 6.31 (d, J=8.4 Hz, 1H), 4.28-4.12 (m, 1H), 4.12-4.03 (m, 1H), 3.72-3.65 (m, 1H), 3.31-3.23 (m, 1H), 3.22-2.77 (m, 2H), 2.39-2.22 (m, 1H), 2.31 (s, 3H), 1.95-1.87 (m, 1H), 1.54-1.41 (m, 1H), 1.46 (s, 9H).

Step 2: (R)—N-((3,3-difluoropiperidin-4-yl)methyl)-6-methylpyridin-2-amine trifluoroacetate

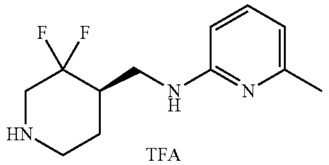 [SMILES: Cc1cccc(NC[C@H]2CCNCC2(F)F)n1]

To a solution of (R)-tert-butyl 3,3-difluoro-4-(((6-methylpyridin-2-yl)amino)methyl)piperidine-1-carboxylate (341 mg, 1.20 mmol) in DCM (8 mL) was added trifluoroacetic acid (3 mL) at room temperature. After stirring for one hour, the mixture was concentrated to afford the crude title compound as a dark brown oil, which was directly taken into the next step without further purification.

Step 3: (+)-(R)-4-methylbenzyl 3,3-difluoro-4-(((6-methylpyridin-2-yl)amino)methyl)piperidine-1-carboxylate

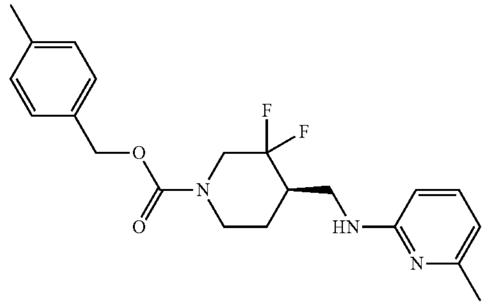 [SMILES: Cc1ccc(COC(=O)N2CC[C@H](CNc3cccc(C)n3)C(F)(F)C2)cc1]

The crude (R)—N-((3,3-difluoropiperidin-4-yl)methyl)-6-methylpyridin-2-amine trifluoroacetate from above was dissolved in MeCN (8 mL), and TEA (2.0 mL) was added followed by 2,5-dioxopyrrolidin-1-yl 4-methylbenzyl carbonate (348 mg, 1.32 mmol) in one portion at room temperature. The mixture was stirred for 3 hours and then concentrated under reduced pressure. The concentrate was dissolved in ethyl acetate, washed with water, brine, dried over $Na_2SO_4$ and the organic phase was concentrated under reduced pressure. The concentrate was purified by column chromatography over silica gel (eluent: hexane/ethyl acetate=3:1, v/v) to afford the title compound as an off-white solid 313 mg, 62% over two steps). MS (ESI) calculated for $C_{21}H_{25}F_2N_3O_2$: 389.2 m/z; found: 390.6 m/z [M+H]. Optical rotation: $[\alpha]^{30}_{\lambda}$=+6.8° (c: 10 mg/mL, methanol). $^1$H NMR (400 MHz, $CDOD_3$) δ 7.33 (dd, J=7.4, 8.2 Hz, 1H), 7.24 (d, J=8.0 Hz, 1H), 7.17 (d, J=8.0 Hz, 1H), 6.42 (d, J=7.2 Hz, 1H), 6.30 (d, J=8.4 Hz, 1H), 5.12-5.06 (m, 2H), 4.33-4.20 (m, 1H), 4.16-4.08 (m, 1H), 3.72-3.65 (m, 1H), 3.30-3.23 (m, 1H), 3.23-2.85 (m, 2H), 2.40-2.25 (m, 1H), 2.33 (s, 3H), 2.31 (s, 3H), 1.97-1.88 (m, 1H), 1.56-1.42 (m, 1H).

Example 3.23. (R)-2,3-dihydro-1H-inden-2-yl 3,3-difluoro-4-((pyrimidin-4-ylamino)methyl)piperidine-1-carboxylate methanesulfonate (III-E1-37.1$^{B'}$)

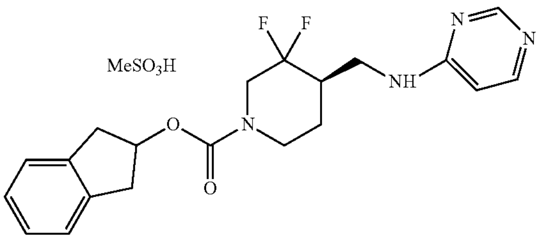 [SMILES: "MeSO3H" ; O=C(OC1Cc2ccccc2C1)N1CC[C@H](CNc2ccncn2)C(F)(F)C1]

Step 1: (R)-2,3-dihydro-1H-inden-2-yl 3,3-difluoro-4-((pyrimidin-4-ylamino)methyl)piperidine-1-carboxylate

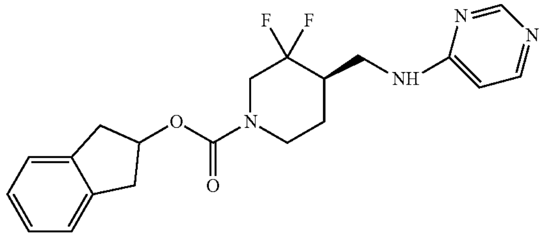 [SMILES: O=C(OC1Cc2ccccc2C1)N1CC[C@H](CNc2ccncn2)C(F)(F)C1]

To a solution of crude (R)—N-((3,3-difluoropiperidin-4-yl)methyl)pyrimidin-4-amine TFA salt (5.0 g, 6.4 mmol) in acetonitrile (25 mL) was added triethylamine (5.0 mL, 36 mmol) and 2,3-dihydro-1H-inden-2-yl (2,5-dioxopyrrolidin-1-yl) carbonate (1.8 g, 6.4 mmol) at room temperature. After stirring at room temperature for 3 hours, the mixture was concentrated under reduced pressure. The concentrate was dissolved in DCM, washed with water, brine, dried over $Na_2SO_4$ and the organic layer was concentrated under reduced pressure. The residue was purified by column chromatography over silica gel (eluent: DCM/EtOAc=1:1, v/v then acetone/hexane=1:1 v/v) to give the title compound as an off-white solid (2.0 g, 80%). MS (ESI) calculated for $C_{20}H_{22}F_2N_4O_2$: 388.2 m/z; found: 389.5 m/z [M+H]. $^1H$ NMR (400 MHz, $CDCl_3$): δ 8.56 (s, 1H), 8.15 (d, J=5.6 Hz, 1H), 7.26-7.16 (m, 4H), 6.35-6.31 (m, 1H), 5.53-5.47 (m, 1H), 5.14-5.04 (s, 1H), 4.55-3.98 (m, 2H), 3.74-3.65 (m, 1H), 3.59-3.45 (m, 1H), 3.37-3.29 (m, 2H), 3.08-2.99 (m, 2H), 2.99-2.88 (m, 1H), 2.83-2.74 (m, 1H), 2.29-2.12 (m, 1H), 1.90-1.75 (m, 1H), 1.66-1.45 (m, 1H).

Step 2: (R)-2,3-dihydro-1H-inden-2-yl 3,3-difluoro-4-((pyrimidin-4-ylamino)methyl)piperidine-1-carboxylate methanesulfonate

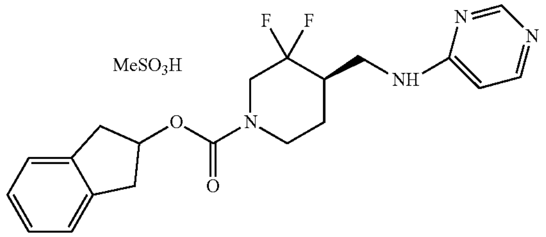 [SMILES: "MeSO3H" ; O=C(OC1Cc2ccccc2C1)N1CC[C@H](CNc2ccncn2)C(F)(F)C1]

To a solution of (R)-2,3-dihydro-1H-inden-2-yl 3,3-difluoro-4-((pyrimidin-4-ylamino)methyl)piperidine-1-carboxylate (1.5 g, 3.9 mmol) in DCM/MeOH (1:1, v/v, 16 mL) was added 1.0 M methanesulfonic acid in methanol (3.9 mL, 3.9 mmol). After stirring at room temperature for 30 minutes, the reaction mixture was concentrated in vacuo and triturated with ether to afford the title compound as an off-white solid (1.9 g, 98%). MS (ESI) calculated for $C_{20}H_{22}F_2N_4O_2$: 388.2 m/z; found: 389.5 m/z [M+H]. $^1H$ NMR (400 MHz, $CD_3OD$): δ 8.70 (s, 1H), 8.08-8.04 (m, 1H), 7.26-7.20 (m, 2H), 7.18-7.13 (m, 2H), 6.79 (d, J=7.6 Hz, 1H), 5.46-5.40 (m, 1H), 4.40-3.97 (m, 2H), 3.93 (d, J=5.6, 14.0 Hz, 1H), 3.97-3.90 (m, 1H), 3.65-3.58 (m, 1H), 3.35-3.25 (m, 1H), 3.20-3.05 (m, 1H), 3.04-2.96 (m, 2H), 2.95-2.86 (m, 1H), 2.70 (s, 3H), 2.48-2.32 (m, 1H), 1.94-1.76 (m, 1H), 1.56-1.37 (m, 1H).

Example 3.24. (R)-4-fluorobenzyl 3,3-difluoro-4-((pyrimidin-4-ylamino)methyl)piperidine-1-carboxylate mesylate (E1-37.4[B'])

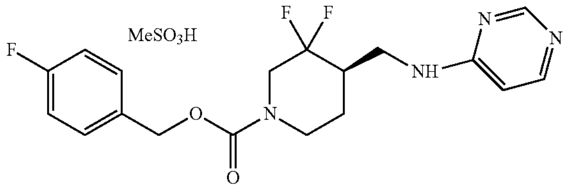 [SMILES: "MeSO3H" ; O=C(OCc1ccc(F)cc1)N1CC[C@H](CNc2ccncn2)C(F)(F)C1]

Step 1: (R)-tert-butyl 3,3-difluoro-4-((pyrimidin-4-ylamino)methyl)piperidine-1-carboxylate

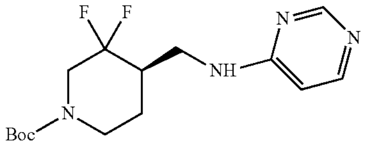 [SMILES: CC(C)(C)OC(=O)N1CC[C@H](CNc2ccncn2)C(F)(F)C1]

To a stirred solution of (R)-tert-butyl 4-(aminomethyl)-3,3-difluoropiperidine-1-carboxylate (6.3 g, 25 mmol) and 4-chloropyrimidine hydrochloride (4.6 g, 30 mmol) in n-butanol (70 mL) was added DIPEA (12.5 mL, 75.6 mmol). The mixture was heated to 60° C. under $N_2$ atmosphere. After stirring at 60° C. overnight, the mixture was concentrated under reduced pressure. The residue was purified by column chromatography over silica gel (eluent: acetone/hexane, 1:1 v/v to 100% acetone) to afford the title compound as a light yellow solid (6.1 g, 72%). MS (ESI) calculated for $C_{15}H_{22}F_2N_4O_2$: 328.4 m/z; found: 329.4 m/z [M+H]. $^1H$ NMR (400 MHz, $CDCl_3$): δ 8.57 (s, 1H), 8.16 (d, J=6.0 Hz, 1H), 6.34 (d, J=6.0 Hz, 1H), 5.16-5.06 (m, 1H), 4.45-4.10 (m, 2H), 3.75-3.66 (m, 1H), 3.59-3.44 (m, 1H), 3.05-2.86 (m, 1H), 2.82-2.67 (m, 1H), 2.29-2.13 (m, 1H), 1.87-1.78 (m, 1H), 1.63-1.50 (m, 1H), 1.46 (s, 9H).

Step 2: (R)—N-((3,3-difluoropiperidin-4-yl)methyl)pyrimidin-4-aminetrifluoroacetate

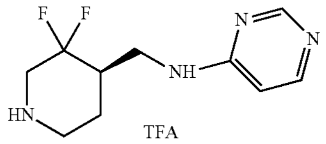 [SMILES: FC1(F)CNCC[C@@H]1CNc1ccncn1]

To a solution of (R)-tert-butyl 3,3-difluoro-4-((pyrimidin-4-ylamino)methyl)piperidine-1-carboxylate (3.65 g, 11.1 mmol) in DCM (27 mL) was added TFA (14 mL) at room temperature. After stirring at room temperature for 2.5 hours, the mixture was concentrated under reduced pressure to give crude title compound as a light oil (8.0 g). MS (ESI) calculated for $C_{10}H_{14}F_2N_4$: 228.2 m/z; found: 229.1 m/z [M+H].

Step 3: (R)-4-fluorobenzyl 3,3-difluoro-4-((pyrimidin-4-ylamino)methyl)piperidine-1-carboxylate

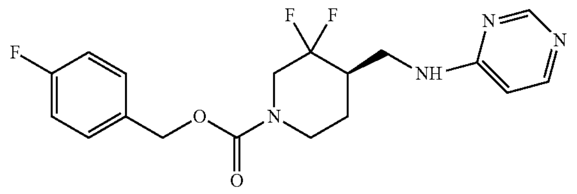 [SMILES: O=C(OCc1ccc(F)cc1)N1CC[C@H](CNc2ccncn2)C(F)(F)C1]

To a solution of crude (R)—N-((3,3-difluoropiperidin-4-yl)methyl)pyrimidin-4-amine trifluoroacetate (8.0 g, approximately 11 mmol) in acetonitrile (40 mL) was added triethylamine (11 mL, 79 mmol) and (2,5-dioxopyrrolidin-1-yl)methyl 4-fluorobenzyl carbonate (3.0 g, 11 mmol) at room temperature. After stirring for 3 hours, the solvent was removed under reduced pressure. The concentrate was diluted with DCM, washed with water, brine, dried over $Na_2SO_4$ and the organic phase was concentrated in vacuo. The concentrate was purified by column chromatograph over silica gel (eluent: MeOH/DCM=95:5 to 90:10 v/v gradient) to give the title compound as an off-white solid (3.6 g, 85%). MS (ESI) calculated for $C_{18}H_{19}F_3N_4O_2$: 380.2 m/z; found: 381.4 m/z [M+H]. $^1H$ NMR (400 MHz, $CDCl_3$): δ 8.57 (s, 1H), 8.16 (d, J=5.6 Hz, 1H), 7.36-7.30 (m, 2H), 7.08-7.01 (m, 2H), 6.34 (d, J=6.0 Hz, 1H), 5.15-5.02 (m, 3H), 4.55-4.17 (m, 2H), 3.75-3.67 (m, 1H), 3.60-3.45 (m, 1H), 3.11-2.75 (m, 2H), 2.31-2.16 (m, 1H), 1.90-1.81 (m, 1H), 1.63-1.57 (m, 1H).

Step 4: (R)-4-fluorobenzyl 3,3-difluoro-4-((pyrimidin-4-ylamino)methyl)piperidine-1-carboxylate mesylate

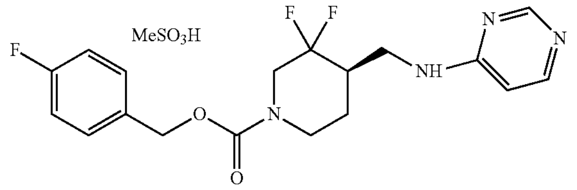 [SMILES: "MeSO3H" ; O=C(OCc1ccc(F)cc1)N1CC[C@H](CNc2ccncn2)C(F)(F)C1]

To a solution of (R)-4-fluorobenzyl 3,3-difluoro-4-((pyrimidin-4-ylamino)methyl)piperidine-1-carboxylate (3.24 g, 8.52 mmol) in DCM/MeOH (1:1, 30 mL) was added 1.0 M methanesulfonic acid in methanol (8.52 mL, 8.52 mmol). After stirring at room temperature for 30 minutes, the reaction mixture was concentrated in vacuo and triturated with ether to afford the title compound as an off-white solid (3.9 g, 96%). MS (ESI) calculated for $C_{18}H_{19}F_3N_4O_2$: 380.2 m/z; found: 381.4 m/z [M+H]. $^1H$ NMR (400 MHz, $CD_3OD$): δ 8.71 (s, 1H), 8.07 (dd, J=1.4, 7.6 Hz, 1H), 7.43-7.37 (m, 2H), 7.13-7.05 (m, 2H), 6.80 (d, J=7.6 Hz, 1H), 5.16-5.08 (m, 2H), 4.38-4.25 (m, 1H), 4.20-4.12 (m, 1H), 3.99-3.91 (m, 1H), 3.68-3.60 (m, 1H), 3.28-3.07 (m, 1H), 3.05-2.86 (m, 1H), 2.70 (s, 3H), 2.51-2.36 (m, 1H), 1.93-1.84 (m, 1H), 1.58-1.45 (m, 1H).

Example 3.25. (R)-4-methylbenzyl 3,3-difluoro-4-((pyrimidin-4-ylamino)methyl)piperidine-1-carboxylate methanesulfonate (E1-37.2$^{B'}$)

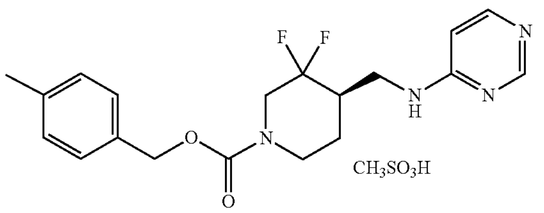

Step 1: (R)-4-methylbenzyl 3,3-difluoro-4-((pyrimidin-4-ylamino)methyl)piperidine-1-carboxylate

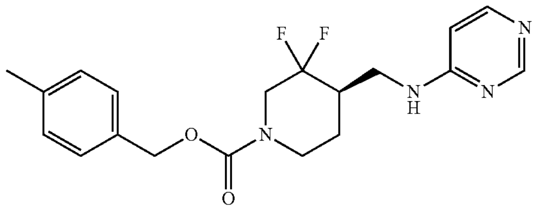 [SMILES: Cc1ccc(COC(=O)N2CC[C@H](CNc3ccncn3)C(F)(F)C2)cc1]

To a stirred solution of crude (R)—N-((3,3-difluoropiperidin-4-yl)methyl)pyrimidin-2-amine trifluoroacetate (approximately 11.1 mmol) in MeCN (50 mL) was added triethylamine (7.7 mL, 55 mmol) at room temperature followed by 2,5-dioxopyrrolidin-1-yl 4-methylbenzyl carbonate (2.92 g, 11.1 mmol). After stirring at room temperature overnight, the reaction mixture was concentrated under reduced pressure. The residue was dissolved in ethyl acetate, washed with water, brine, dried over sodium sulfate, and the organic phase was concentrated under reduced pressure. The concentrate was purified by column chromatography over silica gel (gradient eluent: DCM/ethyl acetate=1:2, v/v, then DCM/methanol=20:1, v/v), and the resulting solid was recrystallized from ethyl acetate/hexane to afford the title compound as a white solid (2.44 g, 58%). MS (ESI) calculated for $C_{19}H_{22}F_2N_4O_2$: 376.2 m/z; found: 377.5 m/z [M+H]. $^1H$ NMR (400 MHz, $CD_3OD$) δ 8.39 (s, 1H), 7.98 (s, 1H), 7.24 (d, J=8.0 Hz, 2H), 7.17 (d, J=8.0 Hz, 2H), 6.50 (d, J=6.0 Hz, 1H), 5.12-5.06 (m, 2H), 4.35-4.21 (m, 1H), 4.17-4.10 (m, 1H), 3.82-3.73 (m, 1H), 3.45-3.33 (m, 1H), 3.24-3.06 (m, 1H), 3.02-2.86 (m, 1H), 2.45-2.35 (m, 1H), 2.33 (s, 3H), 1.92-1.83 (m, 1H), 1.54-1.42 (m, 1H).

Step 2: (R)-4-methylbenzyl 3,3-difluoro-4-((pyrimidin-4-ylamino)methyl)piperidine-1-carboxylate methanesulfonate

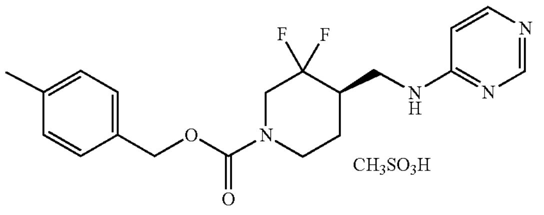

To a solution of (R)-4-methylbenzyl 3,3-difluoro-4-((pyrimidin-4-ylamino)methyl)piperidine-1-carboxylate (2.44 g, 6.5 mmol) in DCM/methanol (2:1, v/v, 30 mL) was added 1 M methanesulfonic acid in methanol (6.5 mL, 6.5 mmol). After stirring at room temperature for 30 minutes, the reaction mixture was concentrated in vacuo to afford the title compound as a yellow solid (3.00 g, 98%). MS (ESI) calculated for $C_{19}H_{22}F_2N_4O_2$: 376.2 m/z; found: 377.2 m/z [M+H]. $^1$H NMR (400 MHz, $CD_3OD$) δ 8.71 (s, 1H), 8.06 (dd, J=1.4, 7.4 Hz, 1H), 7.24 (d, J=8.0 Hz, 2H), 7.17 (d, J=8.0 Hz, 2H), 6.79 (d, J=7.2 Hz, 1H), 5.12-5.06 (m, 2H), 4.38-4.26 (m, 1H), 4.20-4.12 (m, 1H), 3.98-3.92 (m, 1H), 3.67-3.60 (m, 1H), 3.23-3.12 (m, 1H), 3.02-2.88 (m, 1H), 2.70 (s, 3H), 2.49-2.37 (m, 1H), 2.33 (s, 3H), 1.92-1.83 (m, 1H), 1.58-1.46 (m, 1H).

Example 3.26. (R)-4-(difluoromethyl)benzyl 3,3-difluoro-4-((pyrimidin-4-ylamino)methyl)piperidine-1-carboxylate hydrochloride (E1-37.6B)

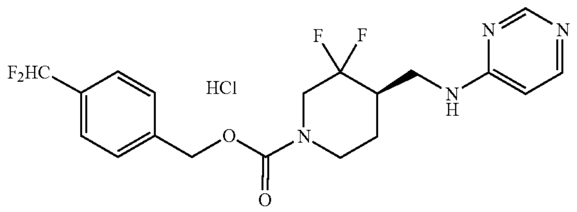 [SMILES: O=C(OCc1ccc(C(F)F)cc1)N1CC[C@H](CNc2ccncn2)C(F)(F)C1 ; Cl]

Step 1: (R)-4-(difluoromethyl)benzyl 3,3-difluoro-4-((pyrimidin-4-ylamino)methyl)piperidine-1-carboxylate

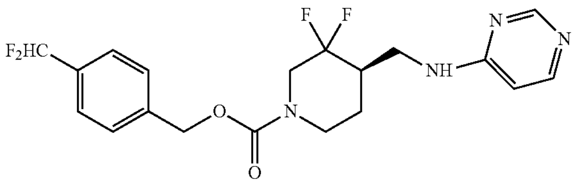 [SMILES: O=C(OCc1ccc(C(F)F)cc1)N1CC[C@H](CNc2ccncn2)C(F)(F)C1]

To a solution of crude (R)—N-((3,3-difluoropiperidin-4-yl)methyl)pyrimidin-4-amine trifluoroacetate (5.6 g, 7.8 mmol) in acetonitrile (25 mL) was added triethylamine (8.0 mL) and 4-(difluoromethyl)benzyl (2,5-dioxopyrrolidin-1-yl) carbonate (2.4 g, 7.8 mmol) at room temperature. After stirring for 3 hours, the mixture was concentrated. The concentrate was dissolved in DCM, washed with water, brine, dried over $Na_2SO_4$ and the organic phase was concentrated under reduced pressure. The crude product was purified by column chromatography over silica gel (eluent: DCM/EtOAc, 1:1, v/v, then acetone/hexane, 1:1, v/v) to give the title compound as an off-white solid (2.65 g, 83%). MS (ESI) calculated for $C_{19}H_{20}F_4N_4O_2$: 412.4 m/z; found: 413.5 m/z [M+H]. $^1$H NMR (400 MHz, $CDCl_3$): δ 8.57 (s, 1H), 8.16 (d, J=5.6 Hz, 1H), 7.51 (d, J=8.0 Hz, 2H), 7.43 (d, J=8.0 Hz, 2H), 6.65 (t, J=56.4 Hz, 1H), 6.34 (d, J=6.0 Hz, 1H), 5.23-5.14 (m, 2H), 5.11-5.03 (m, 1H), 4.55-4.15 (m, 2H), 3.76-3.68 (m, 1H), 3.61-3.47 (m, 1H), 3.14-2.77 (m, 2H), 2.33-2.18 (m, 1H), 1.91-1.83 (m, 1H), 1.65-1.52 (m, 1H).

Step 2: (R)-4-(difluoromethyl)benzyl 3,3-difluoro-4-((pyrimidin-4-ylamino)methyl)piperidine-1-carboxylate hydrochloride

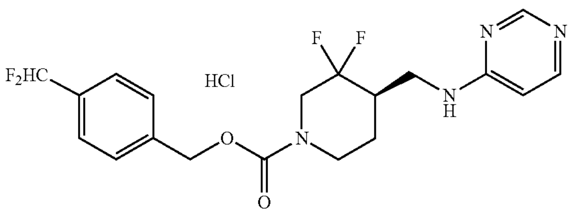 [SMILES: O=C(OCc1ccc(C(F)F)cc1)N1CC[C@H](CNc2ccncn2)C(F)(F)C1 ; Cl]

To a solution of (R)-4-(difluoromethyl)benzyl 3,3-difluoro-4-((pyrimidin-4-ylamino)methyl)piperidine-1-carboxylate (2.41 g, 5.84 mmol) in DCM and methanol (2:1, 24 mL) was added 1.0 M HCl in methanol (5.85 mL, 5.85 mmol) at room temperature. After stirring for 30 minutes, the solvent was concentrated and the residue was triturated with ether to afford the title compound as a white powder (2.12 g, 80%). MS (ESI) calculated for $C_{19}H_{20}F_4N_4O_2$: 412.4 m/z; found: 413.5 m/z [M+H]. $^1$H NMR (400 MHz, $CD_3OD$): δ 8.59 (s, 1H), 8.07-8.01 (m, 1H), 7.54 (d, J=8.0 Hz, 2H), 7.48 (d, J=8.4 Hz, 2H), 6.74 (t, J=56.0 Hz, 1H), 6.70 (d, J=6.8 Hz, 1H), 5.25-5.16 (m, 2H), 4.38-4.28 (m, 1H), 4.22-4.13 (m, 2H), 3.94-3.88 (m, 1H), 3.61-3.50 (m, 1H), 3.29-2.88 (m, 2H), 2.50-2.34 (m, 1H), 1.94-1.86 (m, 1H), 1.59-1.46 (m, 1H).

Example 3.27. (R)-4-fluorobenzyl 3,3-difluoro-4-((pyrazin-2-ylamino)methyl)piperidine-1-carboxylate mesylate (E1-21.4$^{B'}$)

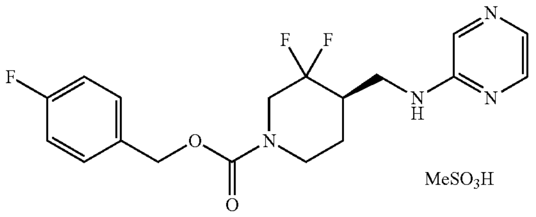 [SMILES: "MeSO3H" ; O=C(OCc1ccc(F)cc1)N1CC[C@H](CNc2cnccn2)C(F)(F)C1]

Step 1: (R)-tert-butyl 3,3-difluoro-4-((pyrazin-2-ylamino)methyl)piperidine-1-carboxylate

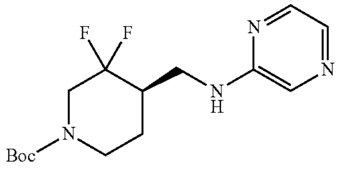 [SMILES: CC(C)(C)OC(=O)N1CC[C@H](CNc2cnccn2)C(F)(F)C1]

To a solution of (R)-tert-butyl 4-(aminomethyl)-3,3-difluoropiperidine-1-carboxylate (5.01 g, 20 mmol) and 2-chloropyrazine (2.98 g, 26 mmol) in dioxane (50 mL) was added Pd-G1 (160 mg, 0.2 mmol), Brettphos (160 mg, 0.3 mmol) and $Cs_2CO_3$ (10.4 g, 32 mmol) under nitrogen atmosphere. The resulting mixture was heated to 100° C. and stirred at 100° C. for 5 hours. The mixture was allowed to cool to room temperature, diluted with ethyl acetate, and filtered through celite. The filtrate was concentrated under reduced pressure. The residue was purified by column chromatography over silica gel (gradient eluent: hexane/ethyl acetate=3:1 to 100% ethyl acetate) to afford the title product as a light yellow oil (1.91 g, 29%). MS (ESI) calculated for $C_{15}H_{22}F_2N_4O_2$: 328.2 m/z; found: 329.3 m/z [M+H]. $^1H$ NMR (400 MHz, $CDCl_3$) δ 7.99-7.97 (m, 1H), 7.91-7.88 (m, 1H), 7.82-7.79 (m, 1H), 4.81-4.74 (m, 1H), 4.58-4.03 (m, 2H), 3.76-3.68 (m, 1H), 3.57-3.47 (m, 1H), 3.06-2.66 (m, 2H), 2.31-2.16 (m, 1H), 1.87-1.79 (m, 1H), 1.62-1.51 (m, 1H), 1.46 (s, 9H).

Step 2: (R)—N-((3,3-difluoropiperidin-4-yl)methyl) pyrazin-2-amine trifluoroacetate

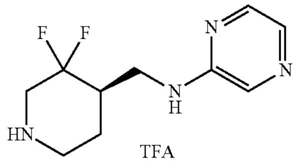 [SMILES: FC1(F)CNCC[C@@H]1CNc1cnccn1]

TFA

To a solution of (R)-tert-butyl 3,3-difluoro-4-((pyrazin-2-ylamino)methyl)piperidine-1-carboxylate (1.91 g, 5.8 mmol) in DCM (13 mL) was added trifluoroacetic acid (6.0 mL) at room temperature. After stirring for 40 minutes, the starting material the mixture was concentrated under reduced pressure to yield the crude title compound as a brown oil which was directly used in the next step.

Step 3: (R)-4-fluorobenzyl 3,3-difluoro-4-((pyrazin-2-ylamino)methyl)piperidine-1-carboxylate

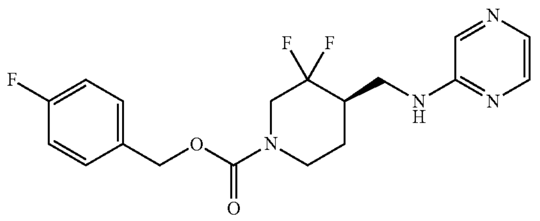

The crude (R)—N-((3,3-difluoropiperidin-4-yl)methyl) pyrazin-2-amine trifluoroacetate from above (approximately 5.8 mmol) was dissolved in MeCN (15 mL), and TEA (3.4 mL, 24 mmol) was added at room temperature followed by, 2,5-dioxopyrrolidin-1-yl 4-fluorobenzyl carbonate (1.55 g, 5.8 mmol). The resulting mixture was stirred for 2 hours, and then concentrated under reduced pressure. The residue was purified by column chromatography over silica gel (gradient eluent: DCM/EtOAc, 8:1 to 2:1, v/v) to afford the title product as a light yellow oil (1.1 g, 50% over two steps). MS (ESI) calculated for $C_{18}H_{19}F_3N_4O_2$: 380.2 m/z; found: 381.2 m/z [M+H]. $^1H$ NMR (400 MHz, $CDCl_3$) δ 7.99-7.96 (m, 1H), 7.90-7.87 (m, 1H), 7.82-7.79 (m, 1H), 7.36-7.30 (m, 2H), 7.08-7.01 (m, 1H), 5.15-5.05 (m, 2H), 4.81-4.741 (m, 1H), 4.54-4.10 (m, 2H), 3.77-3.68 (m, 1H), 3.58-3.46 (m, 1H), 3.12-2.75 (m, 2H), 2.35-2.18 (m, 1H), 1.91-1.80 (m, 1H), 1.63-1.51 (m, 1H).

Step 4: (R)-4-fluorobenzyl 3,3-difluoro-4-((pyrazin-2-ylamino)methyl)piperidine-1-carboxylate mesylate

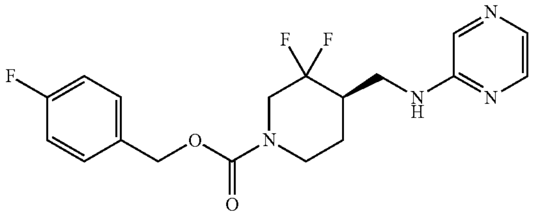 [SMILES: O=C(OCc1ccc(F)cc1)N1CC[C@H](CNc2cnccn2)C(F)(F)C1]

$MeSO_3H$

To a solution of (R)-4-fluorobenzyl 3,3-difluoro-4-((pyrazin-2-ylamino)methyl)piperidine-1-carboxylate (1.18 g, 3.6 mmol) in DCM/MeOH (1:1, v/v, 10 mL) was added 1.0 M methanesulfonic acid in methanol (3.6 mL, 3.6 mmol) at room temperature. After stirring for 30 minutes, the solvent was evaporated under reduced pressure, and the resulting solid triturated with ether to afford the title product as a white solid (1.32 g, 90%). MS (ESI) calculated for $C_{18}H_{19}F_3N_4O_2$: 380.2 m/z; found: 381.4 m/z [M+H]. $^1H$ NMR (400 MHz, $CD_3OD$) δ 8.29-8.26 (m, 1H), 8.26-8.24 (m, 1H), 7.87-7.85 (m, 1H), 7.43-7.37 (m, 2H), 7.12-7.06 (m, 2H), 5.16-5.07 (m, 2H), 4.38-4.27 (m, 1H), 4.21-4.14 (m, 1H), 3.88-3.81 (m, 1H), 3.52-3.45 (m, 1H), 3.30-3.09 (m, 1H), 3.07-2.89 (m, 1H), 2.71 (s, 3H), 2.55-2.39 (m, 1H), 2.00-1.92 (m, 1H), 1.59-1.47 (m, 1H).

Example 3.28. (R)-4-chlorobenzyl 3,3-difluoro-4-(((5-methylpyrazin-2-yl)amino)methyl)piperidine-1-carboxylate mesylate (E1-21.33[B'])

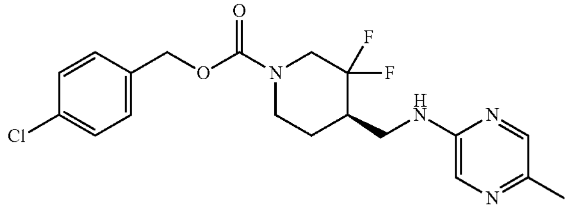

$CH_3SO_3H$

Step 1: (R)—N-((3,3-difluoropiperidin-4-yl) methyl)-5-methylpyrazin-2-amine trifluoroacetate

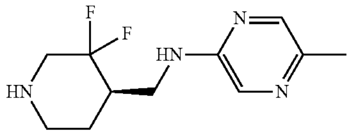

TFA

To a solution of (R)-tert-butyl 3,3-difluoro-4-(((5-methylpyrazin-2-yl)amino)methyl)piperidine-1-carboxylate (500 mg, 1.46 mmol) in DCM (4 mL) was added trifluoracetic acid (2 mL) at room temperature. After stirring for one hour, the mixture was concentrated under reduced pressure. The concentrate as a light brown oil (415 mg, crude) was directly used in the next step without further purification.

Step 2: (R)-4-chlorobenzyl 3,3-difluoro-4-(((5-methylpyrazin-2-yl)amino)methyl)piperidine-1-carboxylate

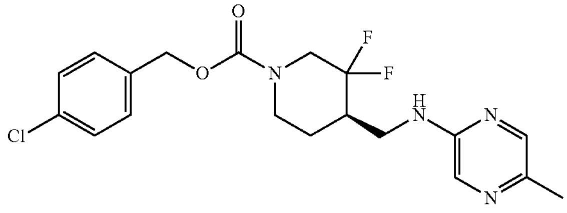

To a solution of the above crude (R)—N-((3,3-difluoropiperidin-4-yl)methyl)-5-methylpyrazin-2-amine trifluoroacetate (415 mg) and TEA (1.1 mL, 7.3 mmol) in MeCN (10 mL) was added 4-chlorobenzyl (2,5-dioxopyrrolidin-1-yl) carbonate (413 mg, 1.46 mmol) at room temperature. The resulting dark brown mixture was stirred overnight, and then concentrated under reduced pressure. The residue was dissolved in ethyl acetate, washed with water, brine, dried over $Na_2SO_4$ and the organic phase was concentrated under reduced pressure.

The concentrate was purified by column chromatography over silica gel (gradient eluent: DCM/EtOAc=3:1 to 2:1, v/v) to afford the title product as a white solid (510 mg, 85% over two steps). MS (ESI) calculated for $C_{19}H_{21}ClF_2N_4O_2$: 410.1 m/z; found: 411.5 m/z [M+H]. $^1H$ NMR (400 MHz, $CD_3OD$) δ 7.85 (s, 1H), 7.79 (s, 1H), 7.38-7.33 (m, 4H), 5.16-5.08 (m, 2H), 4.32-4.23 (m, 1H), 4.16-4.09 (m, 1H), 3.77-3.71 (m, 1H), 3.36-3.31 (m, 1H), 3.28-2.85 (m, 2H), 2.43-2.33 (m, 1H), 2.31 (s, 3H), 1.95-1.86 (m, 1H), 1.55-1.42 (m, 1H).

Step 3: (R)-4-chlorobenzyl 3,3-difluoro-4-(((5-methylpyrazin-2-yl)amino)methyl)piperidine-1-carboxylate mesylate

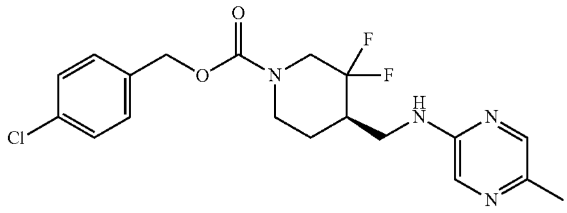 [SMILES: Cc1cnc(NC[C@H]2CCN(C(=O)OCc3ccc(Cl)cc3)CC2(F)F)cn1]

$CH_3SO_3H$

To a solution of (R)-4-chlorobenzyl 3,3-difluoro-4-(((5-methylpyrazin-2-yl)amino)methyl)piperidine-1-carboxylate (190 mg, 0.46 mmol) in methanol (4 mL) was added 1.0 M methanesulfonic acid in methanol (0.46 mL, 0.46 mmol) at room temperature. After stirring for 30 minutes, the solvent was removed under reduced pressure, and the concentrate was treated with diethyl ether to afford the title product as a yellow solid (211 mg, 90%). MS (ESI) calculated for $C_{19}H_{21}ClF_2N_4O_2$: 410.1 m/z; found: 411.1 m/z [M+H]. $^1H$ NMR (400 MHz, $CD_3OD$) δ 8.20 (s, 1H), 8.07 (s, 1H), 7.39-7.33 (m, 4H), 5.17-5.09 (m, 2H), 4.37-4.28 (m, 1H), 4.21-4.13 (m, 1H), 3.85-3.78 (m, 1H), 3.49-3.42 (m, 1H), 3.28-2.85 (m, 2H), 2.70 (s, 3H), 2.48 (s, 3H), 2.47-2.35 (m, 1H), 1.98-1.90 (m, 1H), 1.59-1.47 (m, 1H).

Example 3.29. (R)-4-fluorobenzyl 3,3-difluoro-4-(((5-methylpyrazin-2-yl)amino)methyl)piperidine-1-carboxylate mesylate (E1-21.34[B'])

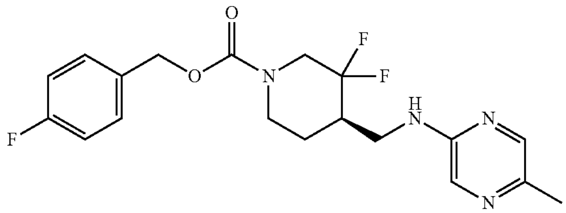

$CH_3SO_3H$

Step 1: (R)—N-((3,3-difluoropiperidin-4-yl)methyl)-5-methylpyrazin-2-amine trifluoroacetate

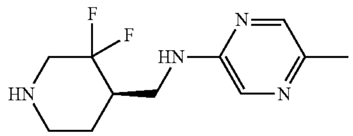

TFA

To a solution of (R)-tert-butyl 3,3-difluoro-4-(((5-methylpyrazin-2-yl)amino)methyl)piperidine-1-carboxylate (200 mg, 0.58 mmol) in DCM (4 mL) was added trifluoracetic acid (2 mL) at room temperature. After stirring for 2.5 hours, the solvent was removed under reduced pressure to afford the crude title compound as a light brown oil, which was directly used in the next step.

Step 2: (R)-4-fluorobenzyl 3,3-difluoro-4-(((5-methylpyrazin-2-yl)amino)methyl)piperidine-1-carboxylate

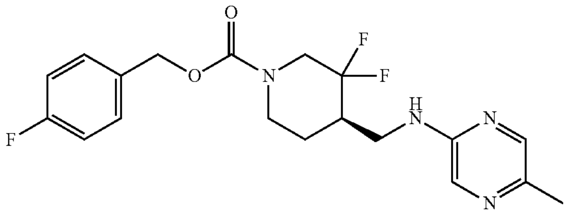 [SMILES: Cc1cnc(NC[C@H]2CCN(C(=O)OCc3ccc(F)cc3)CC2(F)F)cn1]

Crude (R)—N-((3,3-difluoropiperidin-4-yl)methyl)-5-methylpyrazin-2-amine trifluoroacetate (approximately 0.58 mmol) was dissolved in MeCN (3 mL), and TEA (0.40 mL) was added followed by 2,5-dioxopyrrolidin-1-yl 4-fluorobenzyl carbonate (156 mg, 0.58 mmol).

The mixture was stirred at room temperature for 3 hours, and then concentrated under reduced pressure. The residue was dissolved in ethyl acetate, washed with water, brine, dried over $Na_2SO_4$ and the organic phase was concentrated under reduced pressure. The residue was purified by column chromatography over silica gel (eluent: EtOAc/DCM, 1:1, v/v)) to afford the title product as an off-white solid (140 mg, 61%). MS (ESI) calculated for $C_{19}H_{21}F_3N_4O_2$: 394.2 m/z; found: 395.5 m/z [M+H]. $^1$H NMR (400 MHz, $CD_3OD$) δ 7.85 (s, 1H), 7.80-7.78 (m, 1H), 7.42-7.37 (m, 2H), 7.12-7.05 (m, 2H), 5.15-5.08 (m, 2H), 4.33-4.21 (m, 1H), 4.16-4.08 (m, 1H), 3.77-3.71 (m, 1H), 3.36-3.31 (m, 1H), 3.26-3.05 (m, 1H), 3.02-2.85 (m, 1H), 2.43-2.32 (m, 1H), 2.31 (s, 3H), 1.94-1.86 (m, 1H), 1.54-1.42 (m, 1H).

Step 3: (R)-4-fluorobenzyl 3,3-difluoro-4-(((5-methylpyrazin-2-yl)amino)methyl)piperidine-1-carboxylate mesylate

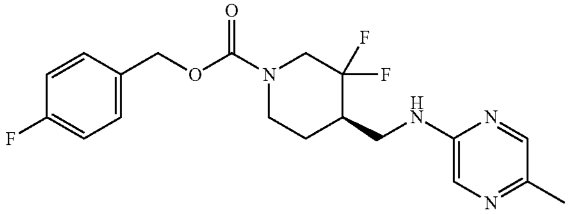

$CH_3SO_3H$

To a solution of (R)-4-fluorobenzyl 3,3-difluoro-4-(((5-methylpyrazin-2-yl)amino)methyl)piperidine-1-carboxylate (140 mg, 0.35 mmol) in methanol (4 mL) was added 1.0 M methanesulfonic acid in methanol (0.35 mL, 0.35 mmol) at room temperature. After stirring for 30 minutes, the solvent was evaporated under reduced pressure, and the residue was triturated with ether to afford the title product as a white solid (85 mg, 49%). MS (ESI) calculated for $C_{19}H_{21}F_3N_4O_2$: 394.2 m/z; found: 395.5 m/z [M+H]. $^1$H NMR (400 MHz, $CD_3OD$) δ 8.20 (s, 1H), 8.07-8.05 (m, 1H), 7.42-7.37 (m, 2H), 7.12-7.05 (m, 2H), 5.16-5.08 (m, 2H), 4.38-4.25 (m, 1H), 4.20-4.13 (m, 1H), 3.85-3.78 (m, 1H), 3.49-3.42 (m, 1H), 3.28-3.10 (m, 1H), 3.05-2.88 (m, 1H), 2.70 (s, 3H), 2.47 (s, 3H), 2.45-2.35 (m, 1H), 1.97-1.88 (m, 1H), 1.59-1.46 (m, 1H).

Example 3.30. (R)-4-methylbenzyl 4-(((5-cyanopyrazin-2-yl)amino)methyl)-3,3-difluoropiperidine-1-carboxylate (E1-21.30$^{B'}$)

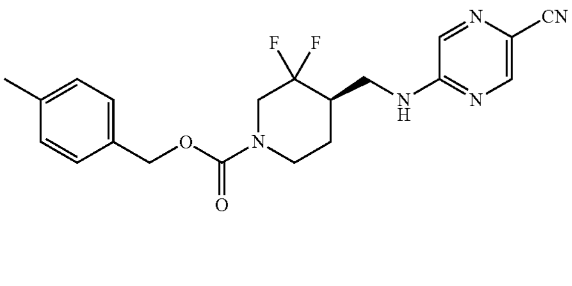 [SMILES: Cc1ccc(COC(=O)N2CC[C@H](CNc3cnc(C#N)cn3)C(F)(F)C2)cc1]

Step 1: (R)-tert-butyl 4-(((5-cyanopyrazin-2-yl)amino)methyl)-3,3-difluoropiperidine-1-carboxylate

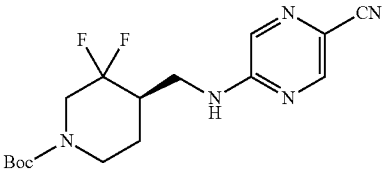 [SMILES: CC(C)(C)OC(=O)N1CC[C@H](CNc2cnc(C#N)cn2)C(F)(F)C1]

To a solution of (R)-tert-butyl 4-(aminomethyl)-3,3-difluoropiperidine-1-carboxylate (680 mg, 2.72 mmol) and 5-bromopyrazine-2-carbonitrile (500 mg, 2.72 mmol) in dioxane (20 mL) was added Pd-G1 (43 mg, 0.05 mmol), Brettphos (44 mg, 0.05 mmol) and $Cs_2CO_3$ (1.40 g, 4.35 mmol) sequentially under nitrogen atmosphere. The resulting suspension was heated to 100° C. with stirring at 100° C. for 5 hours. The mixture was cooled to room temperature and filtered through celite. The filtrate was concentrated under reduced pressure and purified by column chromatography over silica gel (eluent: DCM/EtOAc, 6:1, v/v) to afford the title compound as a dark gray solid (240 mg, 25%). MS (ESI) calculated for $C_{16}H_{21}F_2N_5O_2$: 353.2 m/z; found: 354.2 m/z [M+H]. $^1$HNMR (400 MHz, $CD_3OD$) δ 8.34 (d, J=1.2 Hz, 1H), 7.92 (d, J=1.2 Hz, 1H), 4.28-4.16 (m, 1H), 4.11-4.04 (m, 1H), 3.86-3.79 (m, 1H), 3.47-3.40 (m, 1H), 3.23-2.78 (m, 2H), 2.44-2.28 (m, 1H), 1.90-1.82 (m, 1H), 1.53-1.41 (m, 1H), 1.46 (s, 9H).

Step 2: (R)-5-(((3,3-difluoropiperidin-4-yl)methyl)amino)pyrazine-2-carbonitrile trifluoroacetate

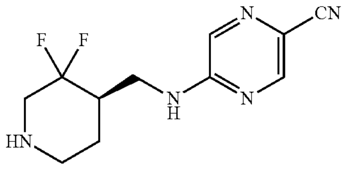

TFA

To a solution of (R)-tert-butyl 4-(((5-cyanopyrazin-2-yl)amino)methyl)-3,3-difluoropiperidine-1-carboxylate (240 g, 0.68 mmol) in DCM (2 mL) was added trifluoracetic acid (2 mL) at room temperature. After stirring for one hour, the mixture was concentrated under reduced pressure. The concentrate was portioned into ethyl acetate and saturated aq sodium bicarbonate. The aqueous phase was extracted with ethyl acetate. The combined organic phases were washed with brine, dried over $Na_2SO_4$ and concentrated under reduced pressure to afford the crude title compound as a light yellow solid (190 mg), which was used into the next without further purification.

Step 3: (R)-4-methylbenzyl 4-(((5-cyanopyrazin-2-yl)amino)methyl)-3,3-difluoropiperidine-1-carboxylate

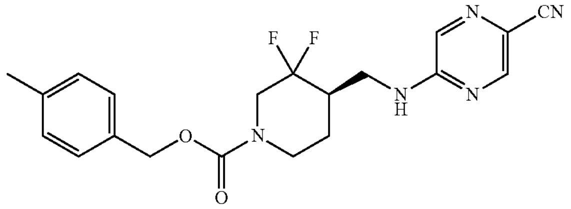 [SMILES: Cc1ccc(COC(=O)N2CC[C@H](CNc3cnc(C#N)cn3)C(F)(F)C2)cc1]

To a stirred solution of the crude (R)-5-(((3,3-difluoropiperidin-4-yl)methyl)amino)pyrazine-2-carbonitrile trifluoroacetate (190 mg) from above and TEA (0.21 mL) in MeCN (4 mL) was added 2,5-dioxopyrrolidin-1-yl 4-methylbenzyl carbonate (203 mg, 0.77 mmol) at room temperature. The mixture was stirred overnight at room temperature and concentrated under reduced pressure. The residue was dissolved in ethyl acetate, washed with water, brine, dried over $Na_2SO_4$ and the organic phase was concentrated under reduced pressure. The concentrate was purified by preparative HPLC to afford the title product as a light yellow solid (38 mg, 12%). MS (ESI) calculated for $C_{20}H_{21}F_2N_5O_2$: 401.2 m/z; found: 402.2 m/z [M+H]. $^1H$ NMR (400 MHz, $CD_3OD$) δ 8.56 (d, J=0.8 Hz, 1H), 7.83 (d, J=1.2 Hz, 1H), 7.24 (d, J=8.0 Hz, 2H), 7.17 (d, J=8.0 Hz, 2H), 5.12-5.05 (m, 2H), 4.34-4.22 (m, 1H), 4.17-4.09 (m, 1H), 3.85-3.77 (m, 1H), 3.46-3.38 (m, 1H), 3.28-2.85 (m, 2H), 2.48-2.34 (m, 1H), 2.33 (s, 3H), 1.93-1.85 (m, 1H), 1.55-1.43 (m, 1H).

Example 3.31. (R)-4-methylbenzyl 3,3-difluoro-4-(((3-fluoropyridin-4-yl)amino)methyl)piperidine-1-carboxylate hydrochloride (E1-38.8$^{B'}$)

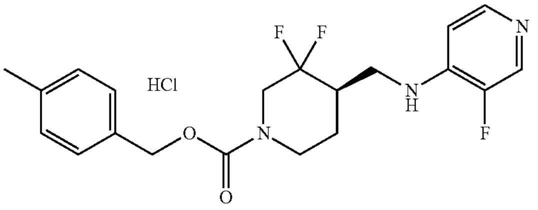 [SMILES: Cc1ccc(COC(=O)N2CC[C@H](CNc3ccncc3F)C(F)(F)C2)cc1 ; Cl]

Step 1: (R)-tert-butyl 3,3-difluoro-4-(((3-fluoropyridin-4-yl)amino)methyl)piperidine-1-carboxylate

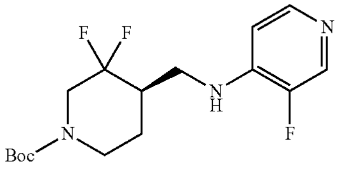 [SMILES: CC(C)(C)OC(=O)N1CC[C@H](CNc2ccncc2F)C(F)(F)C1]

To a stirred solution of (R)-tert-butyl 4-(aminomethyl)-3,3-difluoropiperidine-1-carboxylate (1.02 g, 4.1 mmol) and 4-bromo-3-fluoropyridine hydrochloride (1.05 g, 4.9 mmol) in dioxane (15 mL) was added Pd-G1 (67 mg, 0.08 mmol), Brettphos (67 mg, 0.12 mmol) and $Cs_2CO_3$ (3.4 g, 10.3 mmol) under nitrogen atmosphere. The resulting mixture was heated to 110° C. and stirred at 110° C. overnight. The mixture allowed to cool to room temperature and was diluted with ethyl acetate and filtered through celite. The filtrate was concentrated under reduced pressure. The residue was purified by column chromatography over silica gel (eluent: hexane/ethyl acetate=2:1) to afford the title product as a light brown solid (1.53 g, 55%). MS (ESI) calculated for $C_{16}H_{22}F_3N_3O_2$: 345.2 m/z; found: 346.2 m/z [M+H]. $^1H$ NMR (400 MHz, $CDCl_3$) δ 8.14 (d, J=3.2 Hz, 1H), 8.10 (d, J=5.6 Hz, 1H), 6.58 (dd, J=5.6, 7.6 Hz, 1H), 4.66-4.58 (m, 1H), 4.53-4.05 (m, 2H), 3.71-3.63 (m, 1H), 3.28-3.19 (m, 1H), 3.07-2.65 (m, 2H), 2.24-2.03 (m, 1H), 1.91-1.82 (m, 1H), 1.66-1.53 (m, 1H), 1.47 (s, 9H).

Step 2: (R)—N-((3,3-difluoropiperidin-4-yl)methyl)-3-fluoropyridin-4-amine trifluoroacetate

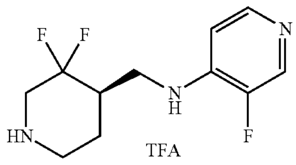 [SMILES: Fc1cnccc1NC[C@H]1CCNCC1(F)F]

To a solution of (R)-tert-butyl 3,3-difluoro-4-(((3-fluoropyridin-4-yl)amino)methyl)piperidine-1-carboxylate (670 mg, 1.94 mmol) in DCM (6 mL) was added trifluoroacetic acid (3 mL) at room temperature. After stirring for 40 minutes, the mixture was concentrated under reduced pressure to afford the crude title compound as a brown oil, which was directly used in the next step.

Step 3: (R)-4-methylbenzyl 3,3-difluoro-4-(((3-fluoropyridin-4-yl)amino)methyl)piperidine-1-carboxylate

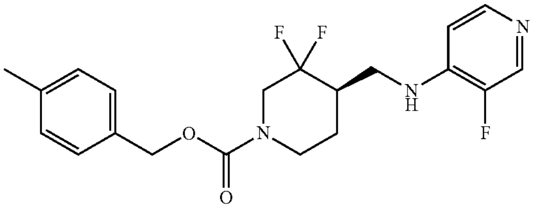 [SMILES: Cc1ccc(COC(=O)N2CC[C@H](CNc3ccncc3F)C(F)(F)C2)cc1]

The above crude (R)—N-((3,3-difluoropiperidin-4-yl)methyl)-3-fluoropyridin-4-amine trifluoroacetate was dissolved in MeCN (5 mL), and TEA (1.4 mL, 10 mmol) was added followed by 2,5-dioxopyrrolidin-1-yl 4-methylbenzyl carbonate (511 mg, 1.94 mmol). The resulting mixture was stirred for 2 hours at room temperature and then concentrated under reduced pressure. The residue was purified by column chromatography over silica gel (gradient eluent: EtOAc/hexane=30% to 100% EtOAc) to afford the title product as an off-white solid (580 mg, 78% over two steps). MS (ESI) calculated for $C_{20}H_{22}F_3N_3O_2$: 393.2 m/z; found: 394.5 m/z [M+H]. $^1H$ NMR (400 MHz, $CDCl_3$) δ 8.15 (d, J=3.2 Hz, 1H), 8.10 (d, J=5.6 Hz, 1H), 7.25 (d, J=8.0 Hz, 2H), 7.18 (d, J=8.0 Hz, 2H), 6.57 (dd, J=5.6, 7.2 Hz, 1H), 5.15-5.07 (m, 2H), 4.66-4.58 (m, 1H), 4.55-4.15 (m, 2H), 3.71-3.63 (m, 1H), 3.28-3.19 (m, 1H), 3.11-2.72 (m, 2H), 2.36 (s, 3H), 2.25-2.09 (m, 1H), 1.95-1.80 (m, 1H), 1.68-1.52 (m, 1H).

Step 4: (R)-4-methylbenzyl 3,3-difluoro-4-(((3-fluoropyridin-4-yl)amino)methyl)piperidine-1-carboxylate hydrochloride

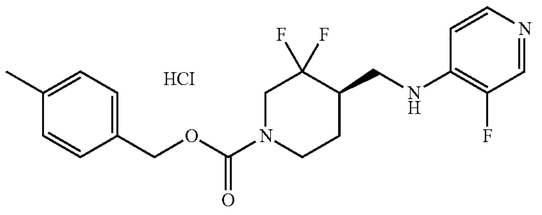

To a solution of (R)-4-methylbenzyl 3,3-difluoro-4-(((3-fluoropyridin-4-yl)amino)methyl)piperidine-1-carboxylate (287 mg, 0.73 mmol) in DCM/MeOH (1:1, 3 mL) was added 1.0 M HCl in methanol (0.73 mL, 0.73 mmol) at room temperature. After stirring for 30 minutes, the solvent was evaporated under reduced pressure, and then triturated with ether to afford the title product as a white solid (215 mg, 68%). MS (ESI) calculated for $C_{20}H_{22}F_3N_3O_2$: 393.2 m/z; found: 394.5 m/z [M+H]. $^1H$ NMR (400 MHz, $CD_3OD$) δ 8.36 (d, J=6.0 Hz, 1H), 8.14 (d, J=6.8 Hz, 1H), 7.24 (d, J=8.0 Hz, 2H), 7.17 (d, J=8.0 Hz, 2H), 7.12 (t, J=7.4 Hz, 1H), 5.13-5.05 (m, 2H), 4.41-4.27 (m, 1H), 4.22-4.14 (m, 1H), 3.87-3.80 (m, 1H), 3.48-3.41 (m, 1H), 3.28-3.07 (m, 1H), 3.04-2.86 (m, 1H), 2.57-2.37 (m, 1H), 2.33 (s, 3H), 1.97-1.88 (m, 1H), 1.60-1.48 (m, 1H).

Example 3.32. (R)-4-fluorobenzyl 3,3-difluoro-4-(((3-fluoropyridin-4-yl)amino)methyl)piperidine-1-carboxylate mesylate (E1-38.10$^{B'}$)

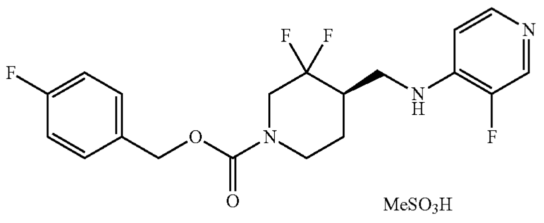 [SMILES: "MeSO3H" ; O=C(OCc1ccc(F)cc1)N1CC[C@H](CNc2ccncc2F)C(F)(F)C1]

Step 1: (R)—N-((3,3-difluoropiperidin-4-yl)methyl)-3-fluoropyridin-4-amine trifluoroacetate

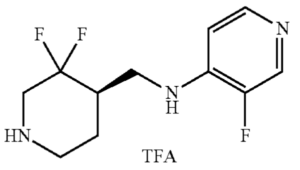 [SMILES: Fc1cnccc1NC[C@H]1CCNCC1(F)F ; "TFA"]

To a solution of (R)-tert-butyl 3,3-difluoro-4-(((3-fluoropyridin-4-yl)amino)methyl)piperidine-1-carboxylate (680 mg, 1.97 mmol) in DCM (6 mL) was added trifluoroacetic acid (3 mL) at room temperature. After stirring for 40 minutes, the mixture was concentrated under reduced pressure to afford the crude title compound as a brown oil, which was directly used in the next step.

Step 2: (R)-4-fluorobenzyl 3,3-difluoro-4-(((3-fluoropyridin-4-yl)amino)methyl)piperidine-1-carboxylate

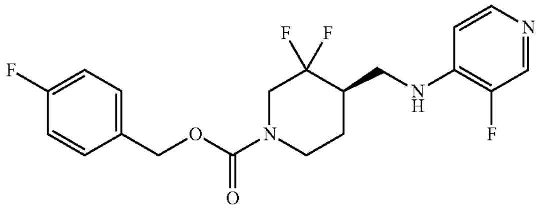 [SMILES: O=C(OCc1ccc(F)cc1)N1CC[C@H](CNc2ccncc2F)C(F)(F)C1]

The above crude (R)—N-((3,3-difluoropiperidin-4-yl)methyl)-3-fluoropyridin-4-amine trifluoroacetate was dissolved in MeCN (5 mL), and TEA (1.4 mL, 10 mmol) was added followed by, 2,5-dioxopyrrolidin-1-yl 4-fluorobenzyl carbonate (526 mg, 1.97 mmol). The resulting mixture was stirred for 2 hours at room temperature and then concentrated under reduced pressure. The residue was purified by column chromatography over silica gel (gradient eluent: EtOAc/hexane=30% to 100% EtOAc) to afford the title product as an off-white solid (585 mg, 74% over two steps). MS (ESI) calculated for $C_{19}H_{19}F_4N_3O_2$: 397.1 m/z; found: 398.5 m/z [M+H]. $^1H$ NMR (400 MHz, $CD_3OD$) δ 8.39 (d, J=6.0 Hz, 1H), 8.16 (d, J=7.6 Hz, 1H), 7.43-7.37 (m, 2H), 7.18-7.06 (m, 2H), 5.16-5.08 (m, 2H), 4.41-4.27 (m, 1H), 4.22-4.14 (m, 1H), 3.88-3.80 (m, 1H), 3.50-3.42 (m, 1H), 3.26-2.87 (m, 2H), 2.70 (s, 3H), 2.54-2.37 (m, 1H), 1.97-1.88 (m, 1H), 1.60-1.47 (m, 1H).

Step 3: (R)-4-fluorobenzyl 3,3-difluoro-4-(((3-fluoropyridin-4-yl)amino)methyl)piperidine-1-carboxylate mesylate

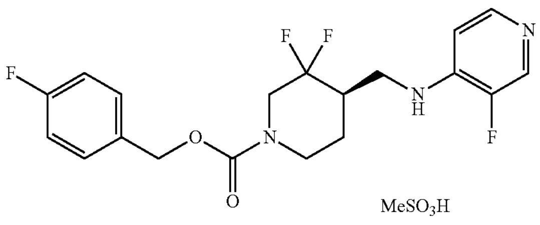 [SMILES: "MeSO3H" ; O=C(OCc1ccc(F)cc1)N1CC[C@H](CNc2ccncc2F)C(F)(F)C1]

To a solution of (R)-4-fluorobenzyl 3,3-difluoro-4-(((3-fluoropyridin-4-yl)amino)methyl)piperidine-1-carboxylate (585 mg, 1.47 mmol) in DCM/MeOH (1:1, 6 mL) was added 1.0 M methanesulfonic acid in methanol (1.47 mL, 1.47 mmol) at room temperature. After stirring for 30 minutes, the solvent was removed under reduced pressure. The concentrate was triturated with diethyl ether to afford the title product as an off-white solid (680 mg, 94%). MS (ESI) calculated for $C_{19}H_{19}F_4N_3O_2$: 397.1 m/z; found: 398.5 m/z [M+H]. $^1H$ NMR (400 MHz, $CD_3OD$) δ 8.39 (d, J=6.0 Hz, 1H), 8.16 (d, J=7.2 Hz, 1H), 7.44-2.37 (m, 2H), 7.15 (t, J=7.2 Hz, 1H), 7.12-7.05 (m, 2H), 5.16-5.08 (m, 2H), 4.41-4.28 (m, 1H), 4.22-4.14 (m, 1H), 3.88-3.80 (m, 1H), 3.50-3.41 (m, 1H), 3.26-2.87 (m, 2H), 2.70 (s, 3H), 2.54-2.38 (m, 1H), 1.98-1.89 (m, 1H), 1.80-1.47 (m, 1H).

Example 3.33. (R)-4-(difluoromethyl)benzyl 3,3-difluoro-4-((pyridazin-3-ylamino)methyl)piperidine-1-carboxylate hydrochloride (E1-24.6[B'])

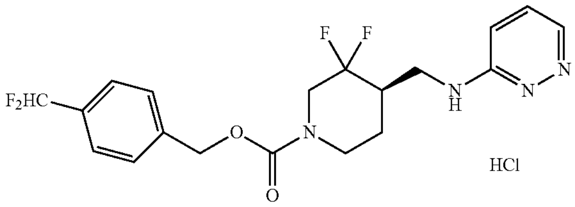 [SMILES: O=C(OCc1ccc(C(F)F)cc1)N1CC[C@H](CNc2cccnn2)C(F)(F)C1 ; Cl]

Step 1: (R)-tert-butyl 3,3-difluoro-4-((pyridazin-3-ylamino)methyl)piperidine-1-carboxylate

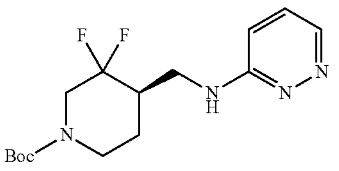 [SMILES: CC(C)(C)OC(=O)N1CC[C@H](CNc2cccnn2)C(F)(F)C1]

To a stirred mixture of (R)-tert-butyl 4-(aminomethyl)-3,3-difluoropiperidine-1-carboxylate (10.44 g, 41.7 mmol), 3-bromopyridazine (5.52 g, 34.77 mmol) and cesium carbonate (17.0 g, 52.2 mmol) in dioxane (120 mL) was added $Pd_2(dba)_3$ (720 mg, 0.69 mmol) and xantphos (604 mg, 1.04 mmol) consecutively under $N_2$ atmosphere. The mixture was heated to 100° C. and stirred overnight. The mixture was filtered and the filtrate was concentrated under reduced pressure. The concentrate was purified by column chromatography over silica gel (eluent: DCM/MeOH=60:1) to afford the title compound as a yellow solid (3.24 g, 28%). MS (ESI) calculated for $C_{15}H_{22}F_2N_4O_2$: 328.4 m/z; found: 329.3 m/z [M+H]. $^1H$ NMR (400 MHz, DMSO-$d_6$): δ 8.55 (dd, J=1.2, 4.4 Hz, 1H), 7.15 (dd, J=4.4, 8.4 Hz, 1H), 6.64 (dd, J=1.2, 8.4 Hz, 1H), 5.02-4.94 (m, 1H), 4.45-4.00 (m, 2H), 3.81-3.52 (m, 1H), 3.05-2.67 (m, 2H), 2.45-2.27 (m, 1H), 1.92-1.84 (m, 1H), 1.62-1.50 (m, 1H), 1.46 (s, 9H).

Step 2: (R)—N-((3,3-difluoropiperidin-4-yl)methyl)pyridazin-3-amine

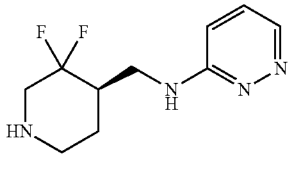 [SMILES: FC1(F)CNCC[C@@H]1CNc1cccnn1]

To a solution of (R)-tert-butyl 3,3-difluoro-4-((pyridazin-3-ylamino)methyl)piperidine-1-carboxylate (13.1 g, 39.9 mmol) in DCM (200 mL) was added trifluoracetic acid (80 mL) at room temperature. After stirring for one hour, the mixture was concentrated under reduced pressure. The residue was diluted with MeCN and basified with solid $K_2CO_3$. The resulting suspension was filtered, and the filtrate was concentrated under reduced pressure. The concentrate was purified by column chromatography over silica gel (eluent: DCM/EtOAc/MeOH/TEA=20:20:5:1) to afford the title compound as a brown solid (12.45 g). MS (ESI) calculated for $C_{10}H_{14}F_2N_4$: 228.2 m/z; found: 229.1 m/z [M+H]. $^1H$ NMR (400 MHz, $CDCl_3$): δ 8.54 (dd, J=1.2, 4.4 Hz, 1H), 7.15 (dd, J=4.6, 9.0 Hz, 1H), 6.64 (dd, J=1.2, 9.2 Hz, 1H), 5.10-5.00 (m, 1H), 3.76-3.68 (m, 1H), 3.66-3.58 (m, 1H), 3.23-3.14 (m, 1H), 3.11-3.03 (m, 1H), 2.83-2.70 (m, 1H), 2.65-2.56 (m, 1H), 2.40-2.24 (m, 1H), 1.95-1.88 (m, 1H), 1.55-1.43 (m, 1H).

Step 3: (R)-4-(difluoromethyl)benzyl 3,3-difluoro-4-((pyridazin-3-ylamino)methyl)piperidine-1-carboxylate

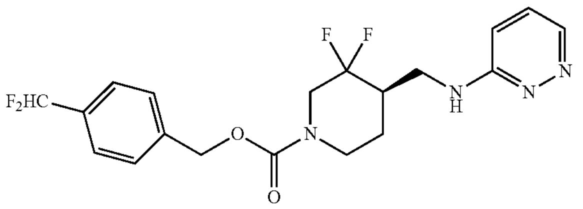 [SMILES: O=C(OCc1ccc(C(F)F)cc1)N1CC[C@H](CNc2cccnn2)C(F)(F)C1]

To a solution of (R)—N-((3,3-difluoropiperidin-4-yl)methyl)pyridazin-3-amine (5.32 g, 23.3 mmol) in MeCN (50 mL) was added TEA (10.0 mL) and 4-(difluoromethyl)benzyl (2,5-dioxopyrrolidin-1-yl) carbonate (6.98 g, 23.3 mmol) sequentially at room temperature. The resulting dark gray mixture was stirred for 2 hours, and then concentrated under reduced pressure. The residue was dissolved in ethyl acetate, washed with water, brine, dried over $Na_2SO_4$ and concentrated under reduced pressure. The residue was purified by column chromatography over silica gel (eluent: hexane/EtOAc/MeOH=5:5:1) to afford the title product as a light gray solid (5.8 g, 60%). MS (ESI) calculated for $C_{19}H_{20}F_4N_4O_2$: 412.2 m/z; found: 413.5 m/z [M+H]. $^1H$ NMR (400 MHz, $CDCl_3$) δ 8.52 (dd, J=0.8, 8.4 Hz, 1H), 7.51 (d, J=8.0 Hz, 2H), 7.43 (d, J=8.0 Hz, 2H), 7.15 (dd, J=4.4, 8.8 Hz, 1H), 6.65 (t, J=56.4 Hz, 1H), 6.62 (d, J=1.2 Hz, 1H), 5.23-5.13 (m, 2H), 4.93-4.86 (m, 1H), 4.55-4.12 (m, 2H), 3.82-3.58 (m, 2H), 3.13-2.76 (m, 2H), 2.52-2.33 (m, 1H), 1.96-1.87 (m, 1H), 1.65-1.52 (m, 1H).

Step 4: (R)-4-(difluoromethyl)benzyl 3,3-difluoro-4-((pyridazin-3-ylamino)methyl)piperidine-1-carboxylate hydrochloride

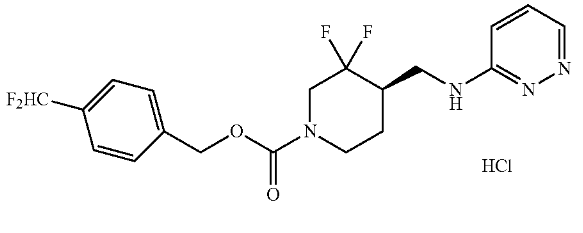 [SMILES: O=C(OCc1ccc(C(F)F)cc1)N1CC[C@H](CNc2cccnn2)C(F)(F)C1 ; Cl]

To a solution of (R)-4-(difluoromethyl)benzyl 3,3-difluoro-4-((pyridazin-3-ylamino)methyl)piperidine-1-carboxylate (5.38 g, 13.05 mmol) in DCM/MeOH (1:1, 50 mL)

was added 2.0 M HCl in methanol (6.50 mL, 13.0 mmol) at room temperature. After stirring for 30 minutes, the solvent was evaporated under reduced pressure, and the resulting solid was triturated with ether to afford the title product as a white solid (5.08 g, 86%). MS (ESI) calculated for $C_{19}H_{20}F_4N_4O_2$: 412.2 m/z; found: 413.4 m/z [M+H]. $^1H$ NMR (400 MHz, $CD_3OD$) δ 8.48 (d, J=4.0 Hz, 1H), 7.62 (dd, J=4.4, 9.2 Hz, 1H), 7.54 (d, J=8.0 Hz, 2H), 7.48 (d, J=8.0 Hz, 2H), 7.35 (d, J=9.6 Hz, 1H), 6.77 (t, J=56.4 Hz, 1H), 5.26-5.15 (m, 2H), 4.40-4.30 (m, 1H), 4.24-4.15 (m, 1H), 3.85-3.79 (m, 1H), 3.49-3.41 (m, 1H), 3.29-3.11 (m, 1H), 3.10-2.91 (m, 1H), 2.57-2.40 (m, 1H), 2.02-1.93 (m, 1H), 1.61-1.49 (m, 1H).

Example 3.34. (R)-2,3-dihydro-1H-inden-2-yl 3,3-difluoro-4-((pyridazin-3-ylamino)methyl)piperidine-1-carboxylate-hydrochloride (III-E1-24.1$^{B'}$)

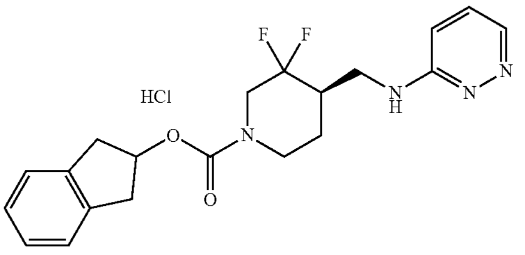 [SMILES: O=C(OC1Cc2ccccc2C1)N1CC[C@H](CNc2cccnn2)C(F)(F)C1 ; Cl]

Step 1: (R)-2,3-dihydro-1H-inden-2-yl 3,3-difluoro-4-((pyridazin-3-ylamino)methyl)piperidine-1-carboxylate

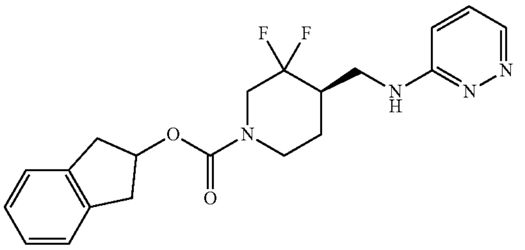 [SMILES: O=C(OC1Cc2ccccc2C1)N1CC[C@H](CNc2cccnn2)C(F)(F)C1]

To a solution of (R)—N-((3,3-difluoropiperidin-4-yl)methyl)pyridazin-3-amine (5.02 g, 22 mmol) in MeCN (50 mL) was added TEA (9.1 mL) and 2,3-dihydro-1H-inden-2-yl (2,5-dioxopyrrolidin-1-yl) carbonate (6.06 g, 22 mmol). The mixture was stirred for 2 hours, and then concentrated under reduced pressure. The residue was dissolved in ethyl acetate, washed with water, brine, dried over $Na_2SO_4$ and the organic phase was concentrated under reduced pressure. The residue was purified by column chromatography over silica gel (gradient eluent: EtOAc/DCM) to afford the title product as an off-white solid (5.1 g, 59%). MS (ESI) calculated for $C_{20}H_{22}F_2N_4O_2$: 388.2 m/z; found: 389.5 m/z [M+H]. $^1H$ NMR (400 MHz, $CDCl_3$) δ 8.54 (dd, J=0.8, 4.4 Hz, 1H), 7.25-7.12 (m, 5H), 6.63 (dd, J=1.0, 9.0 Hz, 1H), 5.53-5.46 (m, 1H), 4.96-4.90 (m, 1H), 4.55-3.95 (m, 2H), 3.79-3.55 (m, 2H), 3.37-3.28 (m, 2H), 3.08-3.00 (m, 2H), 3.00-2.86 (m, 1H), 2.83-2.73 (m, 1H), 2.46-2.28 (m, 1H), 1.95-1.85 (m, 1H), 1.65-1.45 (m, 1H).

Step 2: (R)-2,3-dihydro-1H-inden-2-yl 3,3-difluoro-4-((pyridazin-3-ylamino)methyl)piperidine-1-carboxylate hydrochloride

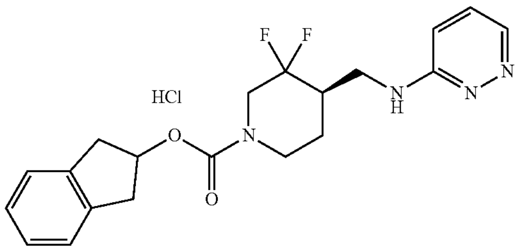 [SMILES: O=C(OC1Cc2ccccc2C1)N1CC[C@H](CNc2cccnn2)C(F)(F)C1 ; Cl]

To a solution of (R)-2,3-dihydro-1H-inden-2-yl 3,3-difluoro-4-((pyridazin-3-ylamino)methyl)piperidine-1-carboxylate (4.38 g, 11.3 mmol) in DCM (55 mL) was added 2.0 M HCl in methanol (5.65 mL, 11.30 mmol) at room temperature. After stirring for 30 minutes, the solvent was evaporated under reduced pressure, and then the residue was triturated with ether to afford the title product as a white solid (4.45 g, 92%). MS (ESI) calculated for $C_{20}H_{22}F_2N_4O_2$: 388.2 m/z; found: 389.4 m/z [M+H]. $^1H$ NMR (400 MHz, $CD_3OD$) δ 8.47 (d, J=4.0 Hz, 1H), 7.62 (dd, J=4.4, 9.6 Hz, 1H), 7.35 (d, J=9.2 Hz, 1H), 7.25-7.20 (m, 2H), 7.18-7.13 (m, 2H), 5.46-5.40 (m, 1H), 4.40-3.92 (m, 2H), 3.83-3.76 (m, 1H), 3.46-3.39 (m, 1H), 3.35-3.26 (m, 2H), 3.22-3.07 (m, 1H), 3.04-2.96 (m, 2H), 2.96-2.87 (m, 1H), 2.52-2.31 (m, 1H), 2.01-1.82 (m, 1H), 1.61-1.37 (m, 1H).

What is claimed is:

1. The chemical entity of formula:

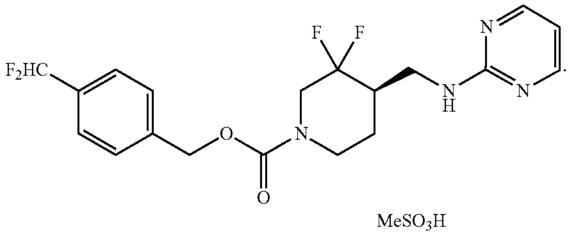 [SMILES: "MeSO3H" ; O=C(OCc1ccc(C(F)F)cc1)N1CC[C@H](CNc2ncccn2)C(F)(F)C1]

2. A pharmaceutical composition comprising the chemical entity of claim 1 and a pharmaceutically acceptable carrier.

3. A method of treating an NMDA receptor-mediated disorder in a subject in need thereof, comprising administering to the subject an effective amount of the pharmaceutical composition of claim 2, wherein the NMDA-receptor mediated disorder is selected from (i) an obsessive-compulsive disorder (OCD) and/or related disorder, (ii) an autism spectrum disorder (ASD), or (iii) an anxiety disorder.

4. The method according to claim 3, wherein the NMDA receptor-mediated disorder is an obsessive-compulsive disorder (OCD) and/or related disorder.

5. The method according to claim 3, wherein the NMDA receptor-mediated disorder is an autism spectrum disorder (ASD).

6. The method according to claim 3, wherein the NMDA receptor-mediated disorder is an anxiety disorder.

7. The method according to claim 4, wherein the OCD and/or related disorder is selected from body dysmorphic disorder (e.g., anorexia nervosa), hoarding disorder, trichotillomania and excoriation disorder.

8. The method according to claim 5, wherein the ASD is characterized by one or more of repetitive or ritualistic behaviors, behavioral rigidity, constant movements, lack of social interaction, restricted patterns of interest that are abnormal in intensity or focus, or sensory abnormalities.

9. The method of claim 5, wherein the autism spectrum disorder is autism, Asperger's syndrome, or pervasive developmental disorder not otherwise specified (PDD-NOS).

10. The method of claim 6, wherein the anxiety disorder is generalized anxiety disorder.

11. The method of claim 6, wherein the anxiety disorder is agoraphobia with panic disorder.

12. The method of claim 6, wherein the anxiety disorder is agoraphobia without panic disorder.

13. The method of claim 6, wherein the anxiety disorder is panic disorder.

14. The method of claim 6, wherein the anxiety disorder is post-traumatic stress disorder.

15. The method of claim 6, wherein the anxiety disorder is social anxiety disorder.

16. The method of claim 3, wherein the NR2B subunit-selective NMDA antagonist is administered intravenously or intracranially.

17. The method of claim 3, further comprising administering to the subject an effective amount of a therapeutic agent useful for treating an anxiety disorder.

18. The method of claim 17, wherein the therapeutic agent is a selective serotonin reuptake inhibitor, a tri-cyclic antidepressant, a benzodiazepine, an atypical antipsychotic or a serotonin-norepinephrine reuptake inhibitor.

19. The method of claim 3, wherein the chemical entity is administered in conjunction with behavioral therapy, electroconvulsive therapy, deep brain stimulation, or vagus nerve stimulation.

20. The method of claim 3, further comprising administering to the subject an effective amount of a therapeutic agent useful for treating an autism spectrum disorder.

21. The method of claim 20, wherein the therapeutic agent is an atypical antipsychotic, a dopamine receptor agonist, a selective serotonin reuptake inhibitor, an atypical antipsychotic, a serotonin-norepinephrine reuptake inhibitor, a stimulant, secretin, oxytocin, or a typical antipsychotic.

22. The method of claim 3, wherein the chemical entity is administered in conjunction with behavioral therapy, electroconvulsive therapy, or hyperbaric oxygen therapy.

23. The method of claim 3, wherein the subject is a human.

* * * * *